United States Patent
Tchoryk, Jr. et al.

(10) Patent No.: US 9,086,488 B2
(45) Date of Patent: Jul. 21, 2015

(54) ATMOSPHERIC MEASUREMENT SYSTEM AND METHOD

(75) Inventors: Peter Tchoryk, Jr., Ann Arbor, MI (US); David Michael Zuk, Dexter, MI (US); David Keith Johnson, Canton, MI (US); Charles J. Richey, San Francisco, CA (US); Parviz Tayebati, Sherborn, MA (US)

(73) Assignee: Michigan Aerospace Corporation, Ann Arbor, MI (US)

( * ) Notice: Subject to any disclaimer, the term of this patent is extended or adjusted under 35 U.S.C. 154(b) by 333 days.

(21) Appl. No.: 13/983,511

(22) PCT Filed: Feb. 2, 2011

(86) PCT No.: PCT/US2011/023516
§ 371 (c)(1),
(2), (4) Date: Aug. 2, 2013

(87) PCT Pub. No.: WO2012/105973
PCT Pub. Date: Aug. 9, 2012

(65) Prior Publication Data
US 2013/0314694 A1    Nov. 28, 2013

Related U.S. Application Data

(63) Continuation-in-part of application No. PCT/US2010/062111, filed on Dec. 24, 2010, which is a continuation-in-part of application No. PCT/US2010/043801, filed on Jul. 29, 2010, which is
(Continued)

(51) Int. Cl.
*G01S 17/95* (2006.01)
*G01S 17/58* (2006.01)
(Continued)

(52) U.S. Cl.
CPC ............ *G01S 17/95* (2013.01); *G01N 21/45* (2013.01); *G01N 21/538* (2013.01); *G01S 17/003* (2013.01); *G01S 17/58* (2013.01)

(58) Field of Classification Search
CPC ..... G01N 21/538; G01S 7/4972; G01S 17/95; G01C 3/08
USPC ............ 356/3.01–3.15, 4.01–4.1, 5.01–5.15, 356/6–22, 28, 28.5
See application file for complete search history.

(56) References Cited

U.S. PATENT DOCUMENTS 4,483,614 A   11/1984 Rogers
7,106,447 B2   9/2006 Hays
(Continued)

OTHER PUBLICATIONS

P. B. Hays and R. G. Roble, "A Technique for Recovering Doppler Line Profiles from Fabry-Perot Interferometer Fringes of Very Low Intensity", Applied Optics, Jan. 1971, vol. 10, No. 1, pp. 193-200.
(Continued)

*Primary Examiner* — Luke Ratcliffe
(74) *Attorney, Agent, or Firm* — Juan Carlos A. Marquez; Bacon & Thomas PLLC

(57) ABSTRACT

One of first and second beams (28) of corresponding first and second light (13) are projected into an atmosphere (20) and at least one physical property of the atmosphere (20) is detected from the interference pattern (47) generated from the resulting scattered light (30). The first and second beams (20) are selected responsive to either a detected signal-to-noise ratio (SNR) or a detected aerosol-to-molecular ratio (AMR). The wavelength (740) of the first light (13) provides for either molecular or aerosol scattering, whereas the wavelength (738) of the second light (13) provides for primarily only aerosol scattering. In accordance with a second aspect, scattered light (30) from one or more beams (28) of substantially monochromatic light (13) projected into the atmosphere (20) and received from a plurality of interaction regions (17) or measurement volumes (52) provides for determining wind power (P*) within a region of the atmosphere (20).

27 Claims, 107 Drawing Sheets

Related U.S. Application Data a continuation-in-part of application No. 12/780,895, filed on May 15, 2010, now Pat. No. 8,427,649, which is a continuation-in-part of application No. PCT/US2010/031695, filed on Apr. 21, 2010.

(51) Int. Cl.
*G01N 21/45* (2006.01)
*G01N 21/53* (2006.01)
*G01S 17/00* (2006.01)

(56) References Cited

U.S. PATENT DOCUMENTS 7,495,774 B2 * 2/2009 Hays et al. .................. 356/519
7,580,127 B1   8/2009 Mayor et al.
8,269,950 B2 * 9/2012 Spinelli et al. ............... 356/4.01

OTHER PUBLICATIONS

Christoph R. Englert et al., "Doppler Asymmetric Spatial Heterodyne Spectroscopy (DASH): Concept and Experimental Demonstration", Applied Optics, Oct. 10, 2007, vol. 46, No. 29, pp. 7297-7307.

Timothy L. Killeen and P. B. Hays, "Doppler Line Profile Analysis for a Multichannel Fabry-Perot Interferometer", Applied Optics, Feb. 15, 1984, vol. 23, No. 4, pp. 612-620.

G. Hernandez, "Fabry-Perot Interferometers", Cambridge University Press 1986, 2 cover pages and pp. 8-23.

Robert A. Brown, "Fluid Mechanics of the Atmosphere", Academic Press, Inc., 1991, vol. 47 in the International Geophysics Series, 2 cover pages and pp. 74-77.

G. Fiocco and J. B. DeWolf, "Frequency Spectrum of Laser Echoes from Atmospheric Constituents and Determination of the Aerosol Content of Air", Journal of the Atmospheric Sciences, Aug. 25, 1967, vol. 25, pp. 488-496.

G. Benedetti-Michelangeli et al., "Measurement of Aerosol Motion and Wind Velocity in the Lower Troposphere by Doppler Optical Radar", Journal of the Atmospheric Sciences, Mar. 6, 1972, vol. 29, pp. 906-910.

Ian Powell and Pavel Cheben, "Modeling of the Generic Spatial Heterodyne Spectrometer and Comparison with Conventional Spectrometer", Applied Optics, Dec. 20, 2006, vol. 45, No. 36, pp. 9079-9086.

Jorge Nocedal and Stephen J. Wright, "Numerical Optimization", Springer Series in Operations Research, 1999 Springer-Verlag New York, Inc., 1999, 2 cover pages, and Chapter 8, pp. 194-201.

David G. Luenberger, "Optimization by Vector Space Methods", John Wiley & Sons, Inc., 1969, 2 cover pages and pp. 84-87.

John M. Harlander, et al. "Spatial Heterodyne Spectroscopy for High Spectral Resolution Space-Based Remote Sensing", Optics & Photonics News, Jan. 2004, cover page and pp. 47-51.

J. M. Vaughan et al., "The Fabry-Perot interferometer, History, Theory, Practice and Applications", The Adam Hilger Series on Optics and Optoelectronics, 1989, 2 cover sheets and pp. 89-103.

Extended European Search Report in corresponding European application 11 857 829.3 mailed Dec. 19, 2014, 7 pp.

\* cited by examiner

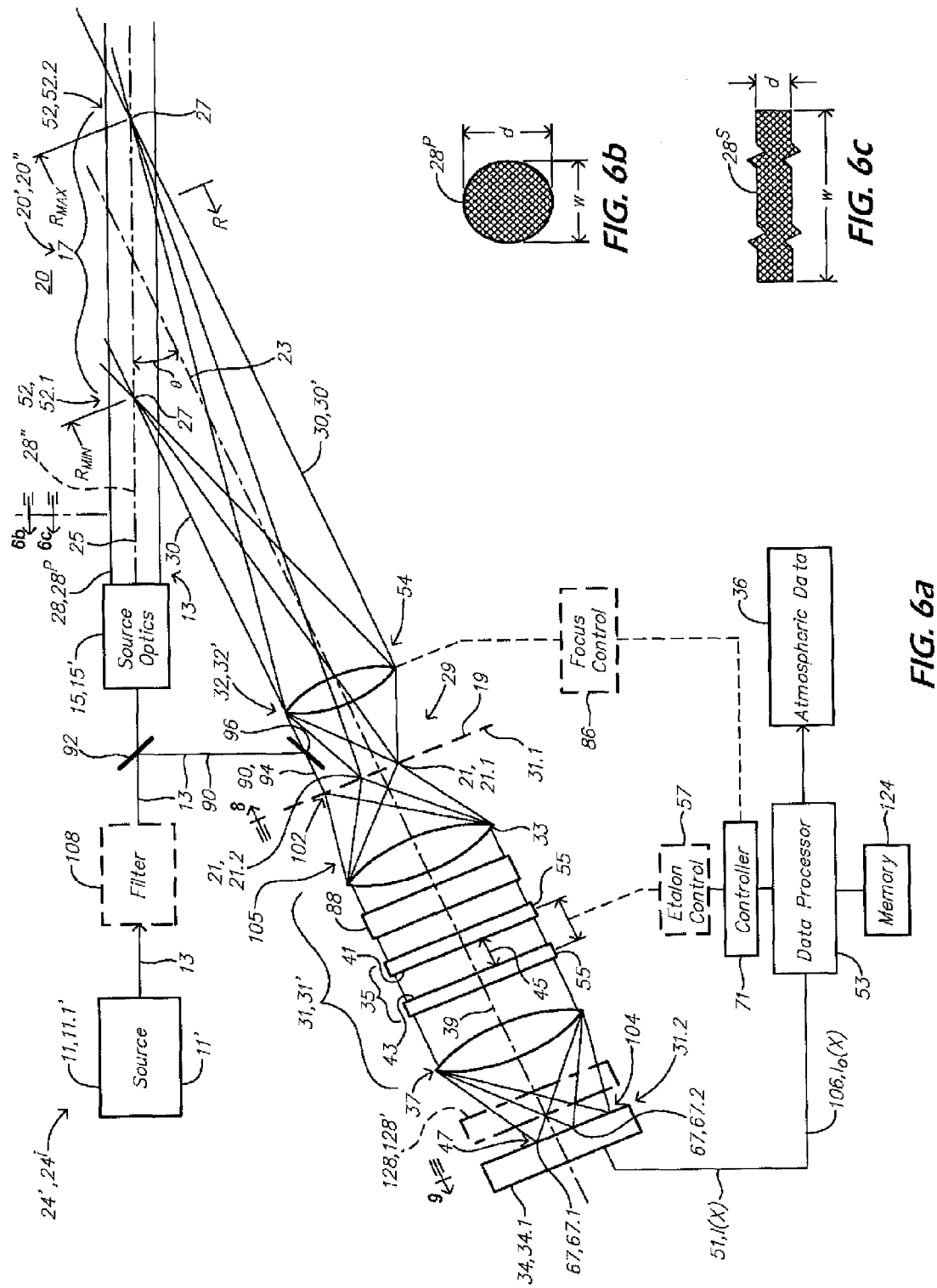

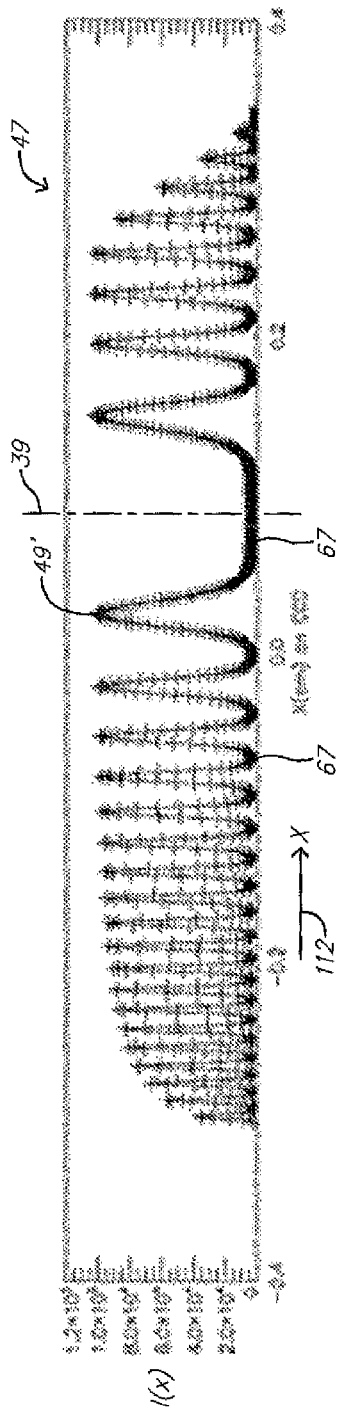
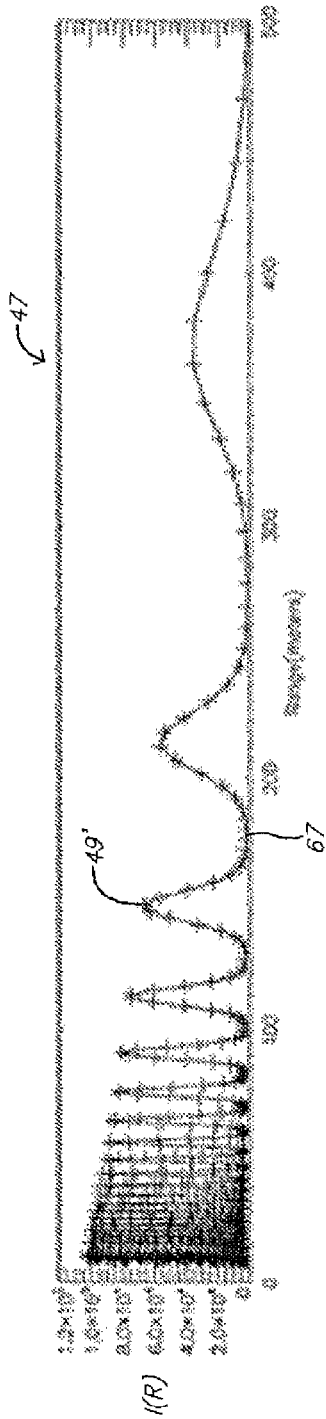
FIG. 10a
FIG. 10b

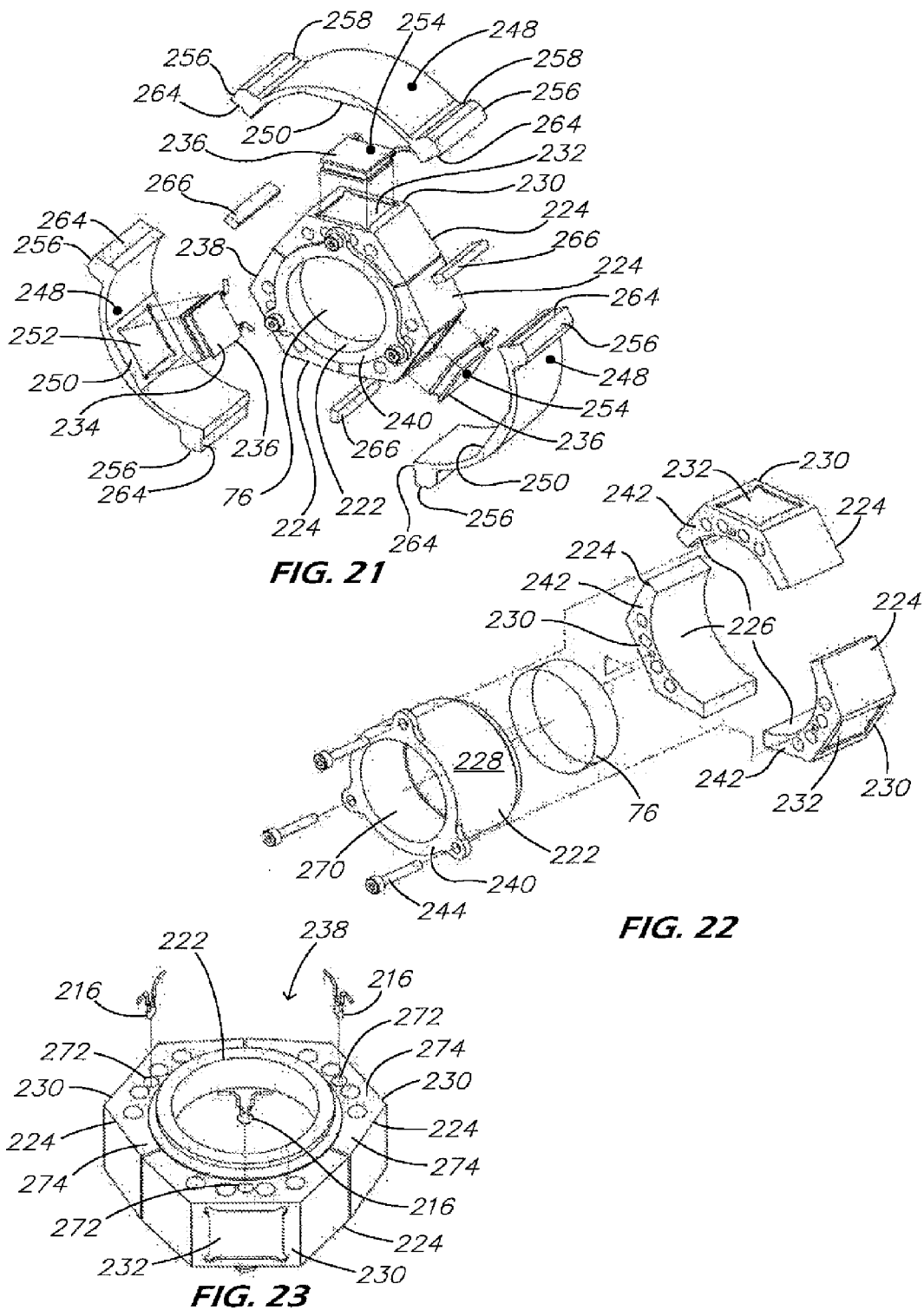

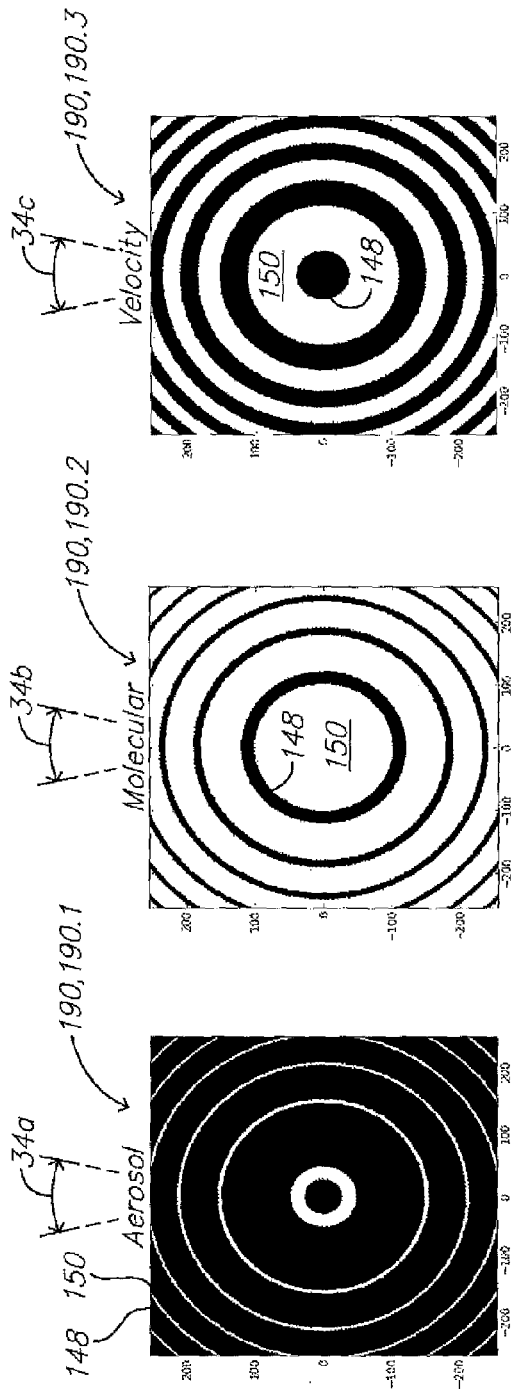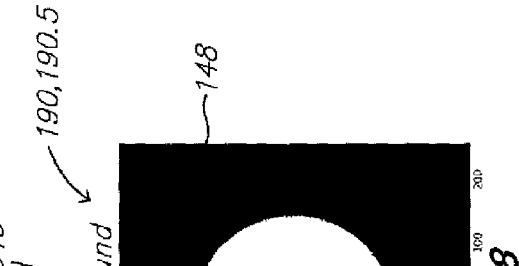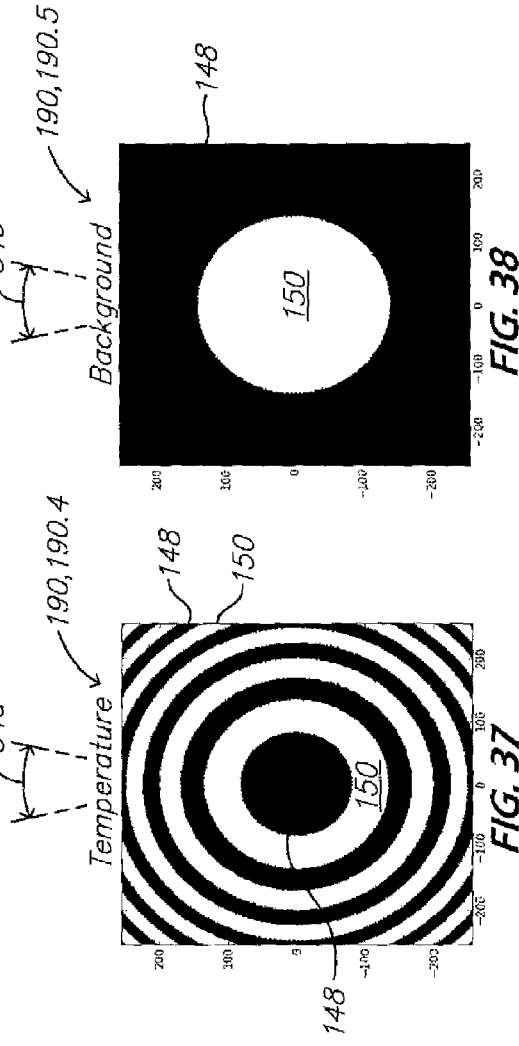

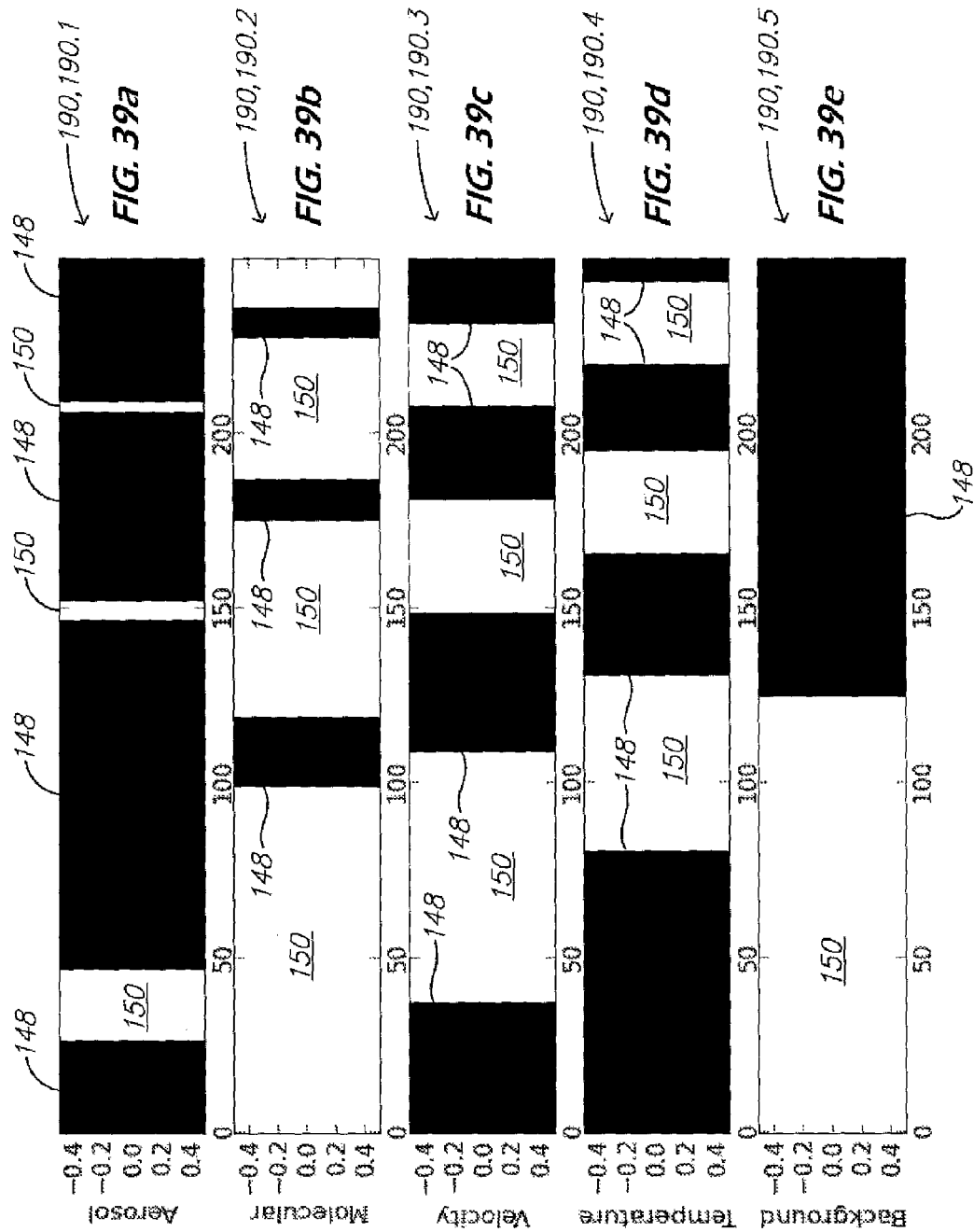

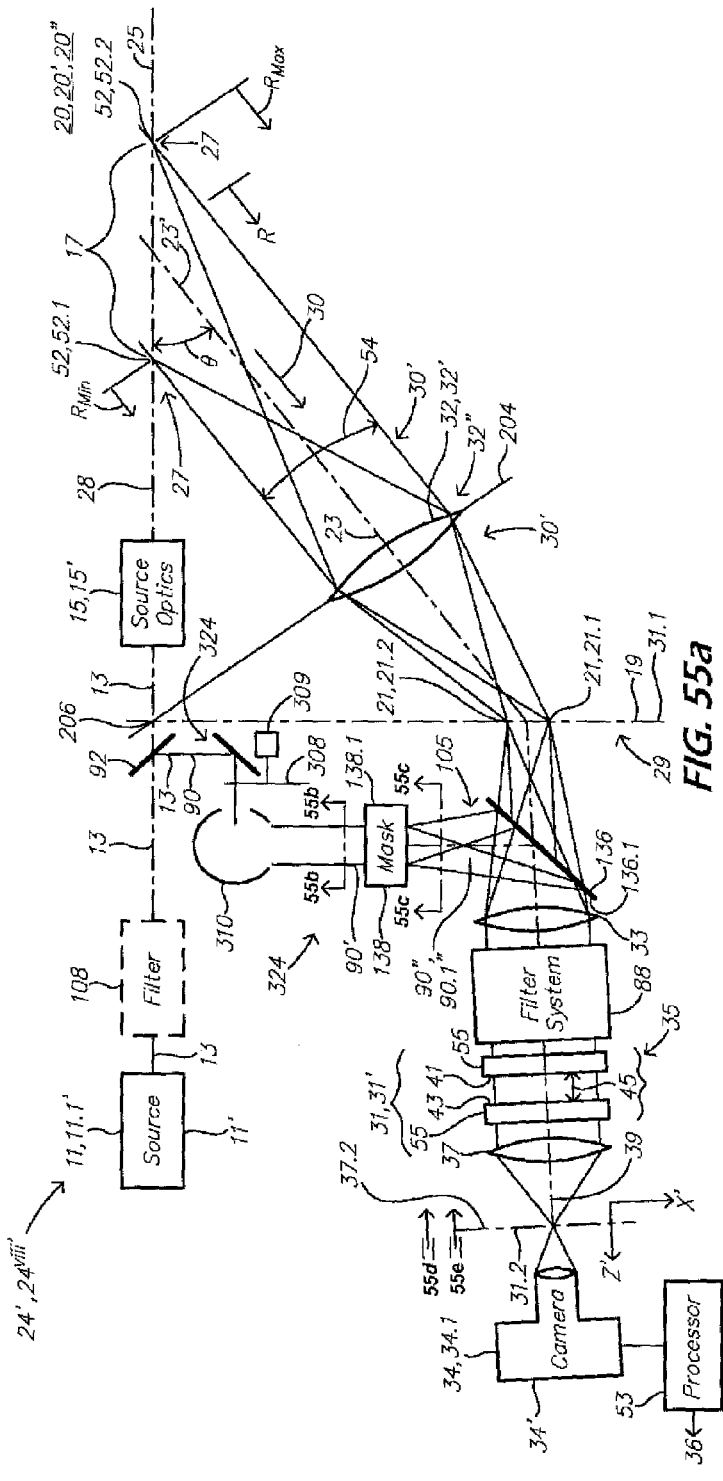
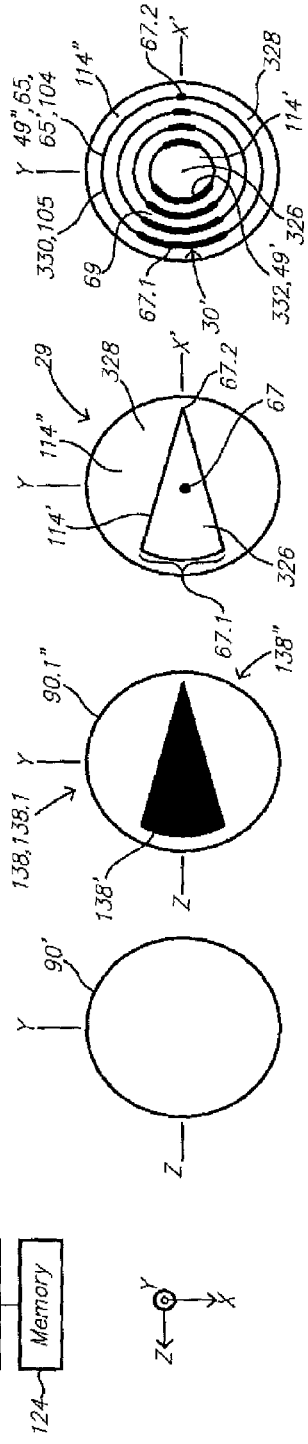
FIG. 55a
FIG. 55b
FIG. 55c
FIG. 55d
FIG. 55e

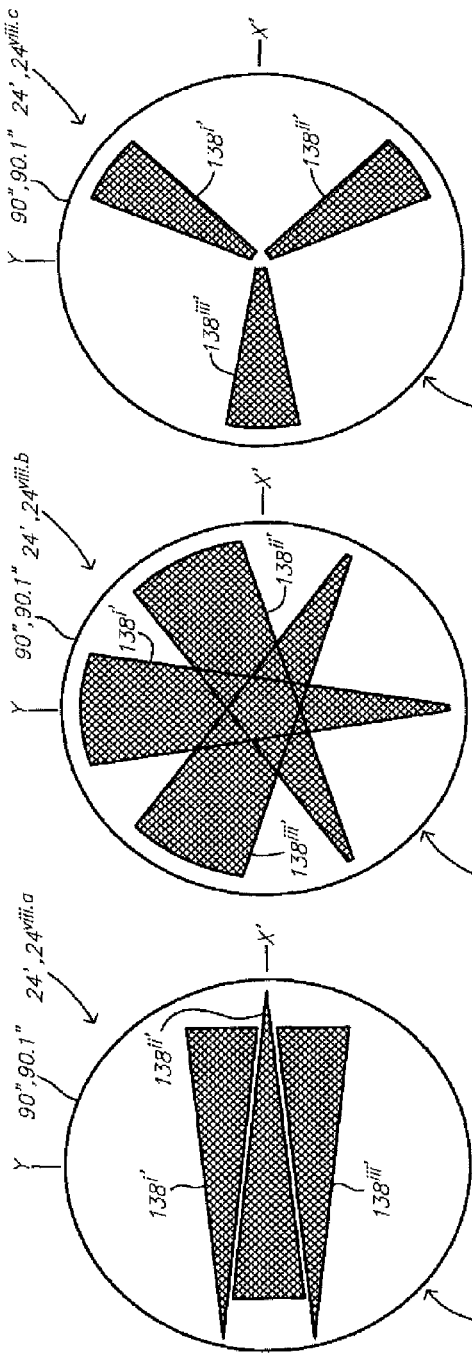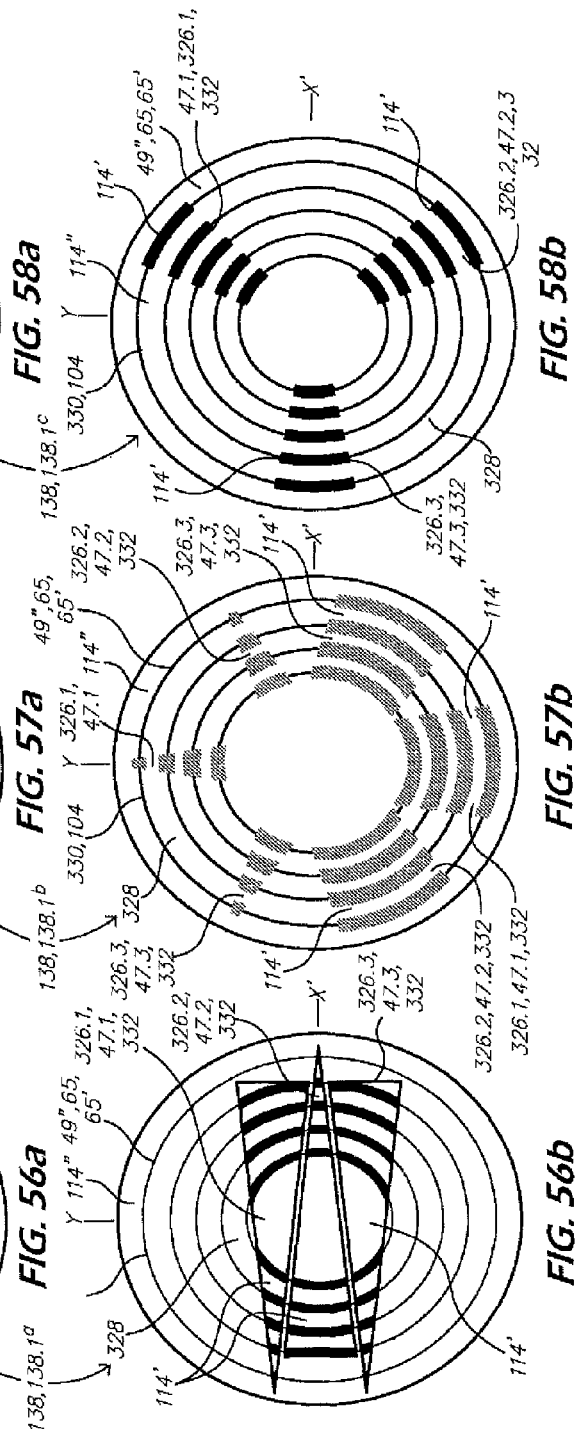

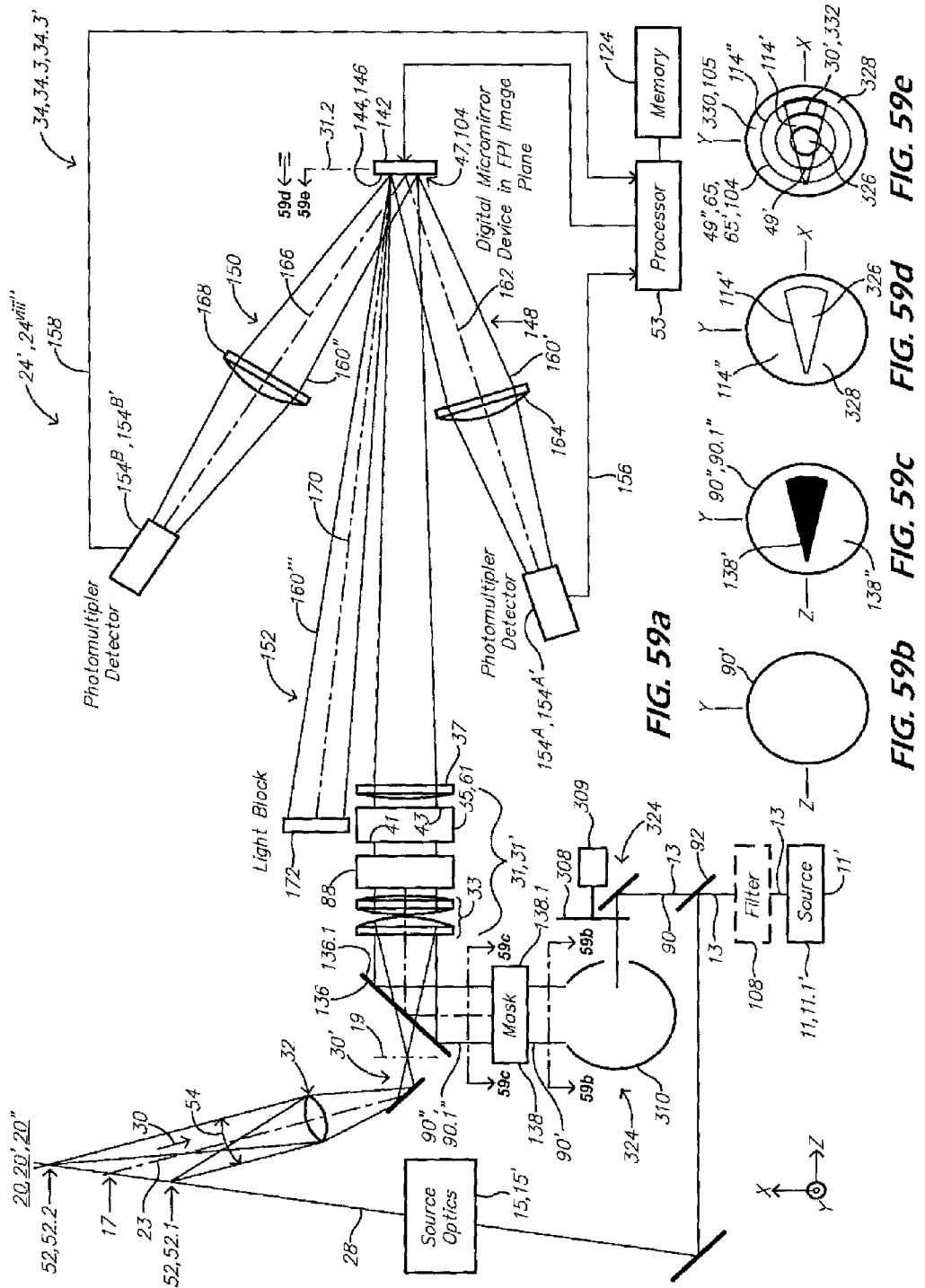

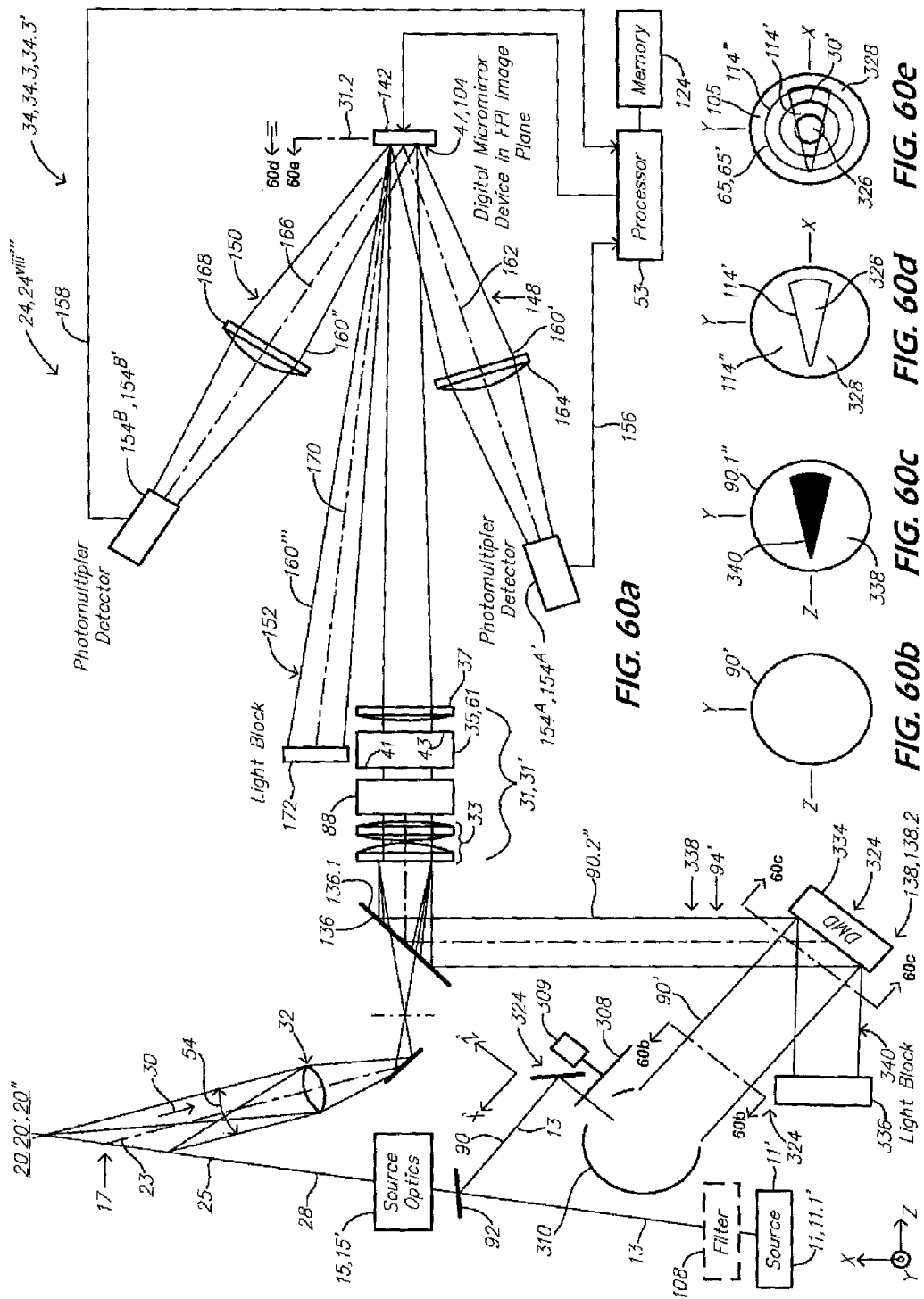

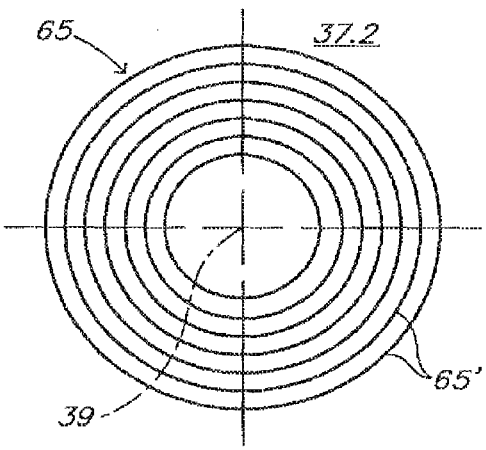
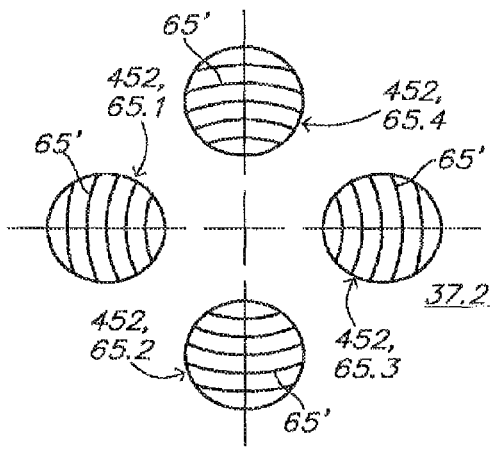
FIG. 69a  FIG. 69b
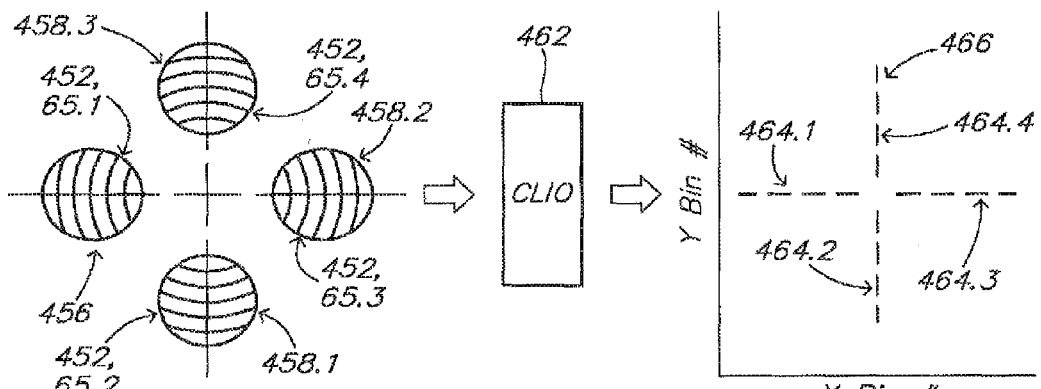
FIG. 70
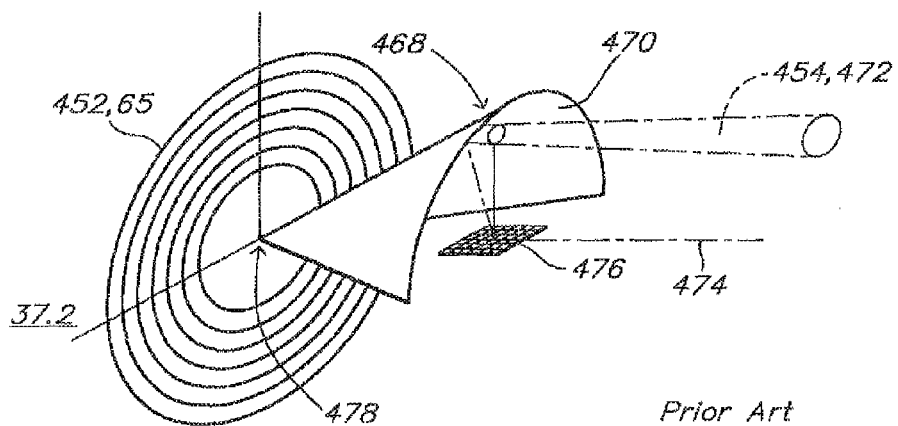
Prior Art
FIG. 71

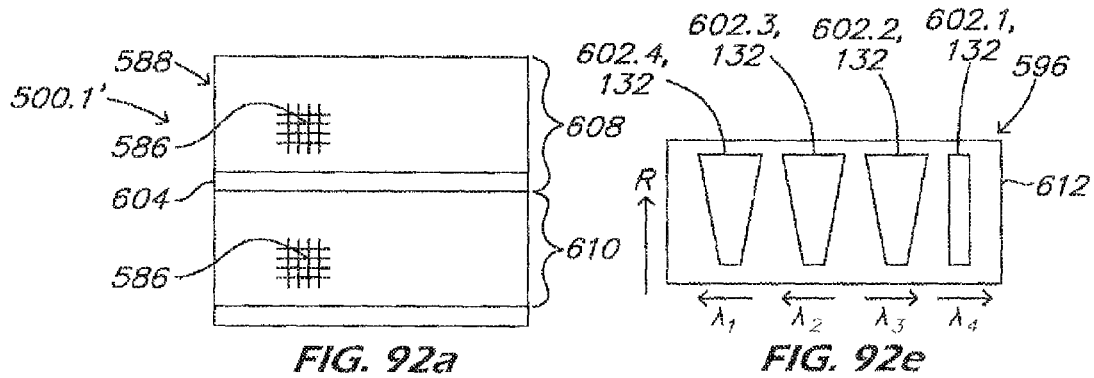
FIG. 92a
FIG. 92e
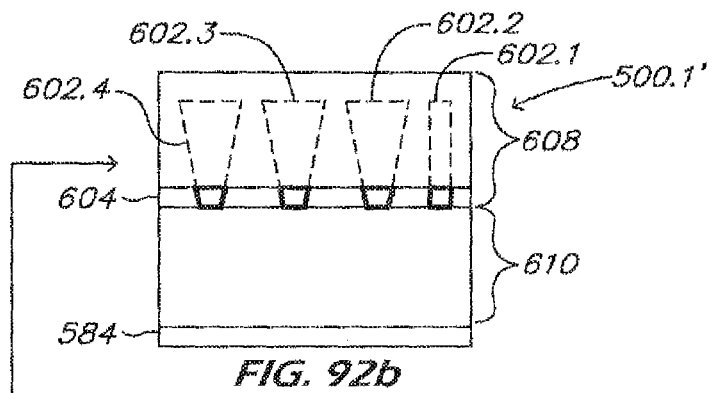
FIG. 92b
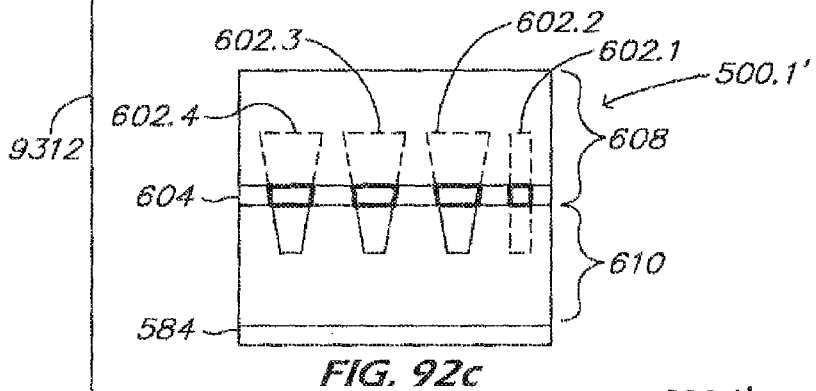
FIG. 92c
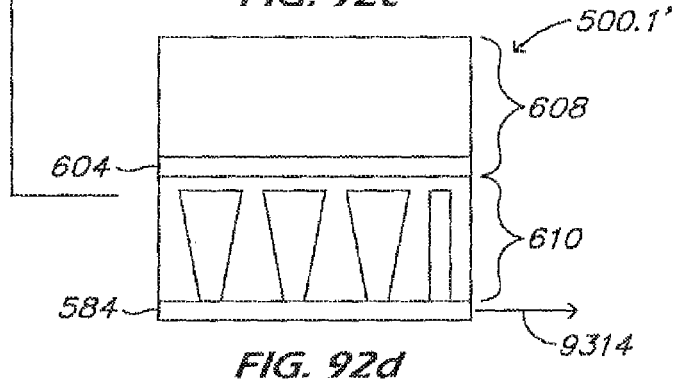
FIG. 92d

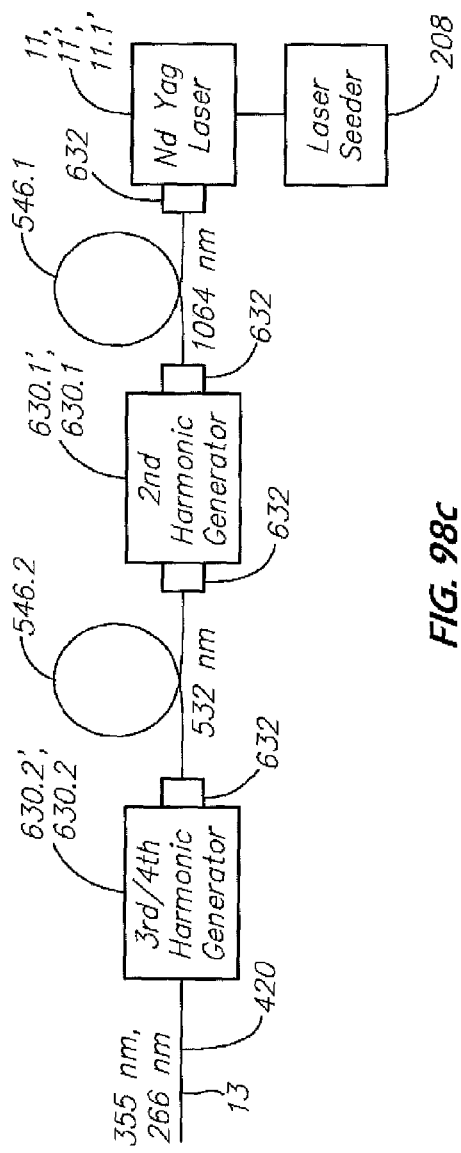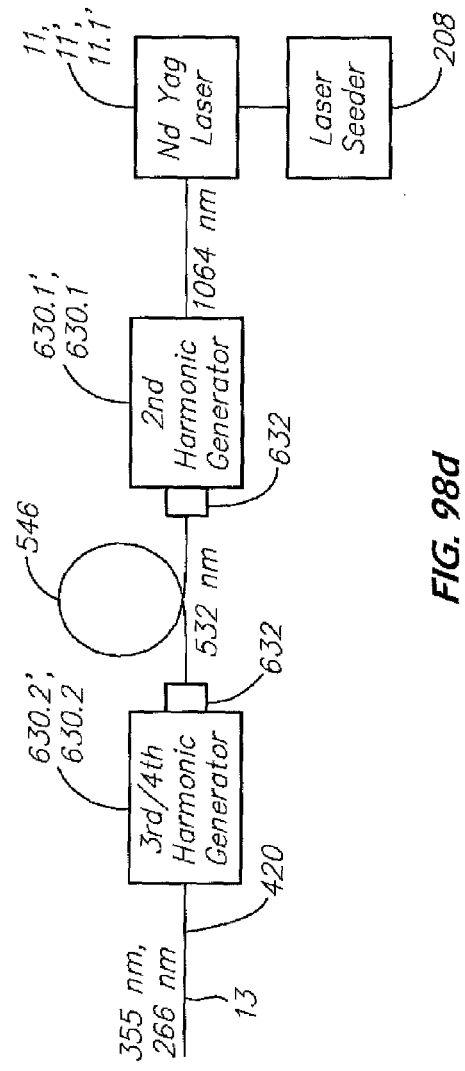
FIG. 98c
FIG. 98d

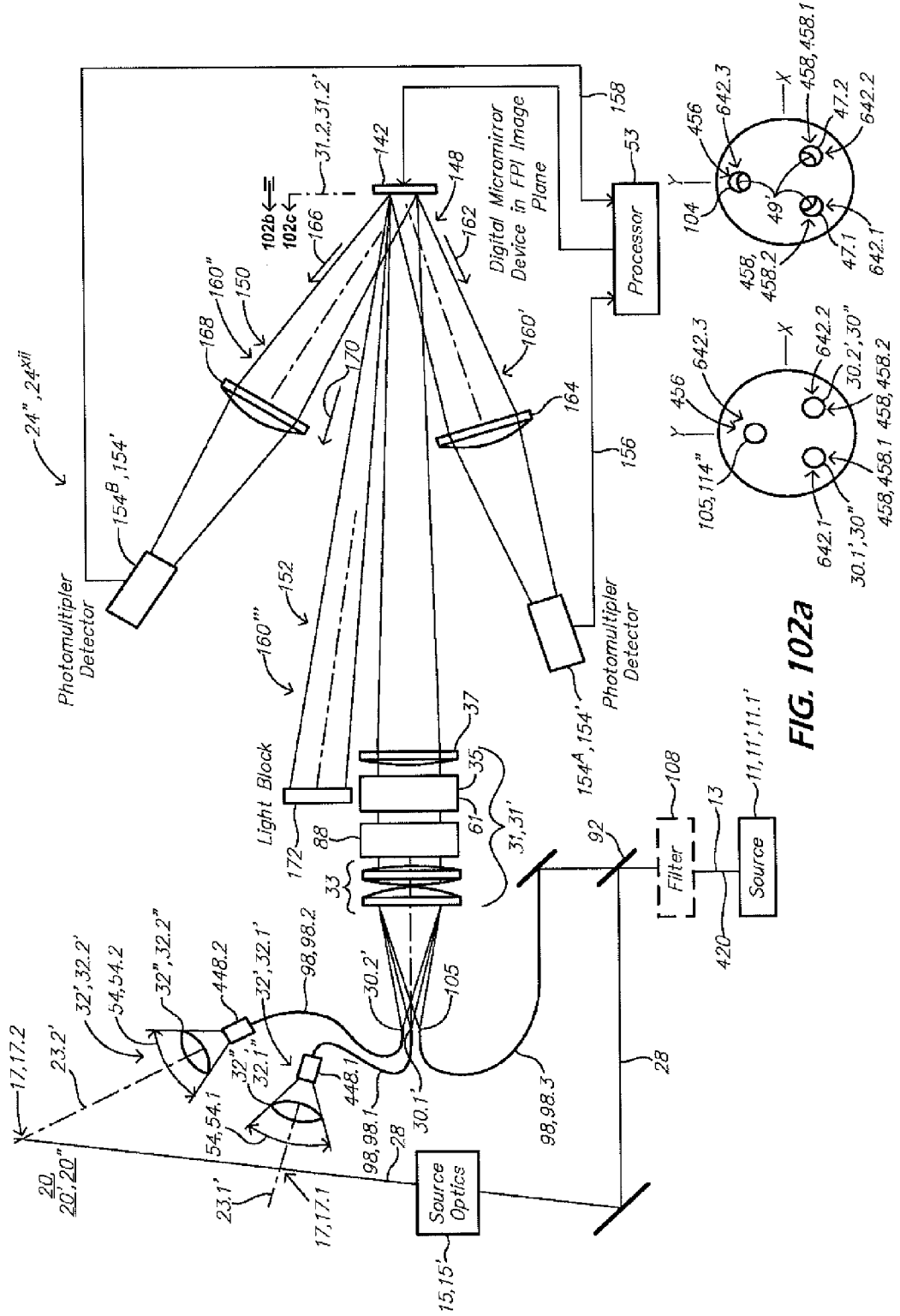

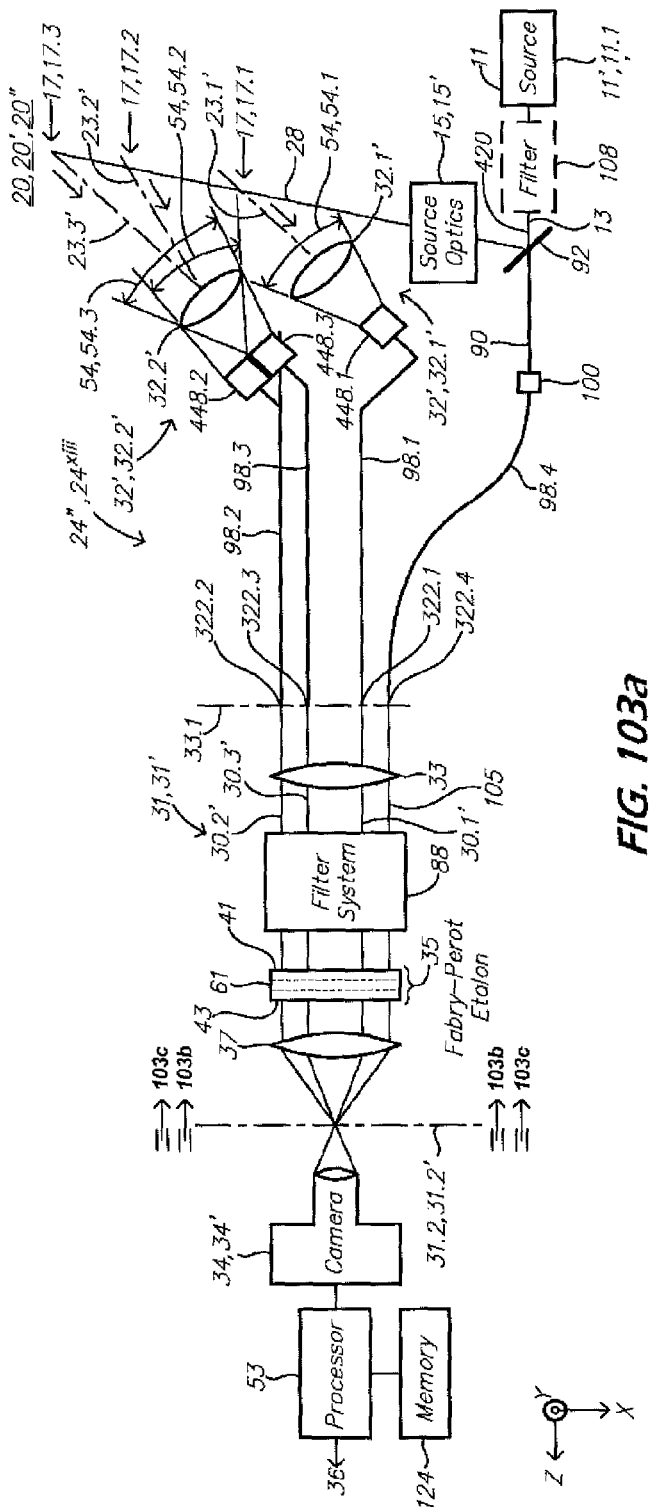
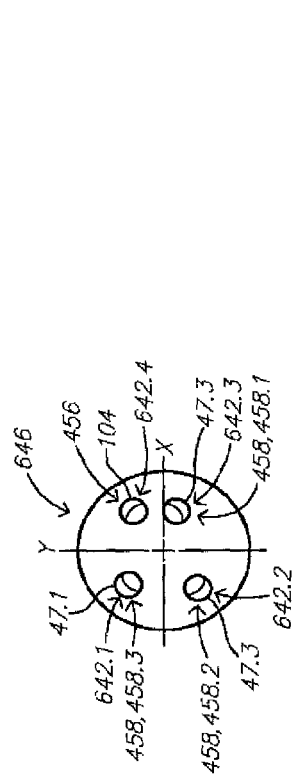
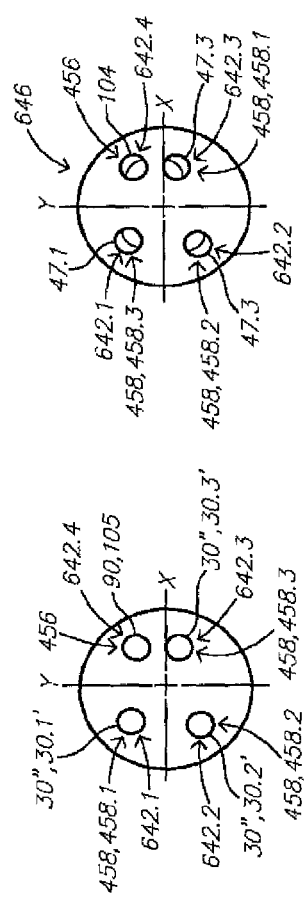
FIG. 103a
FIG. 103c
FIG. 103b

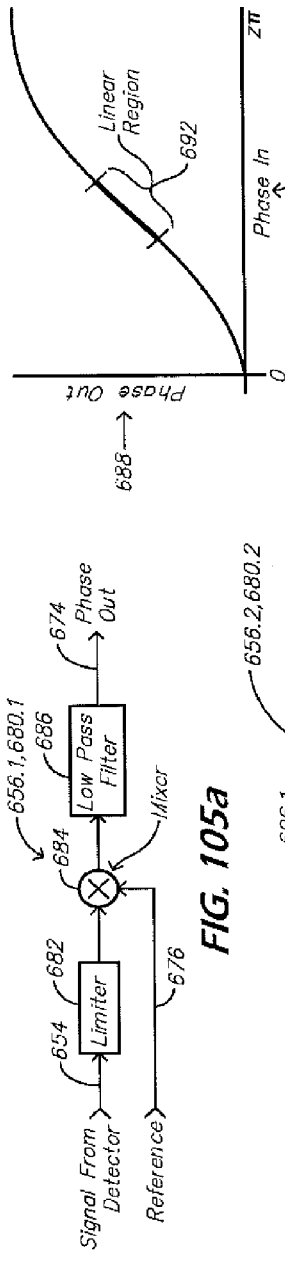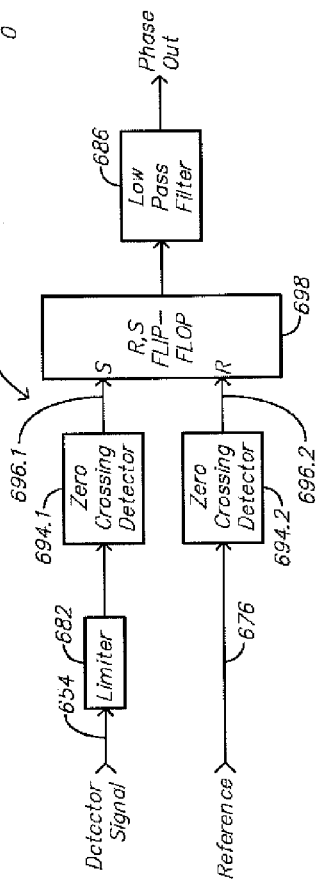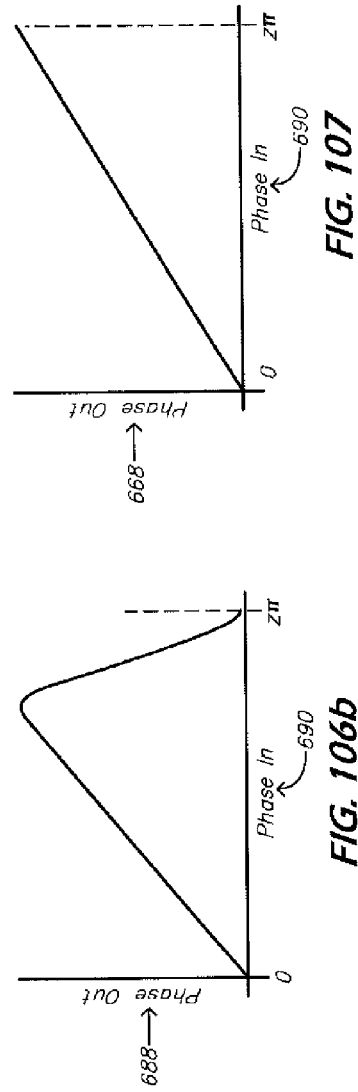

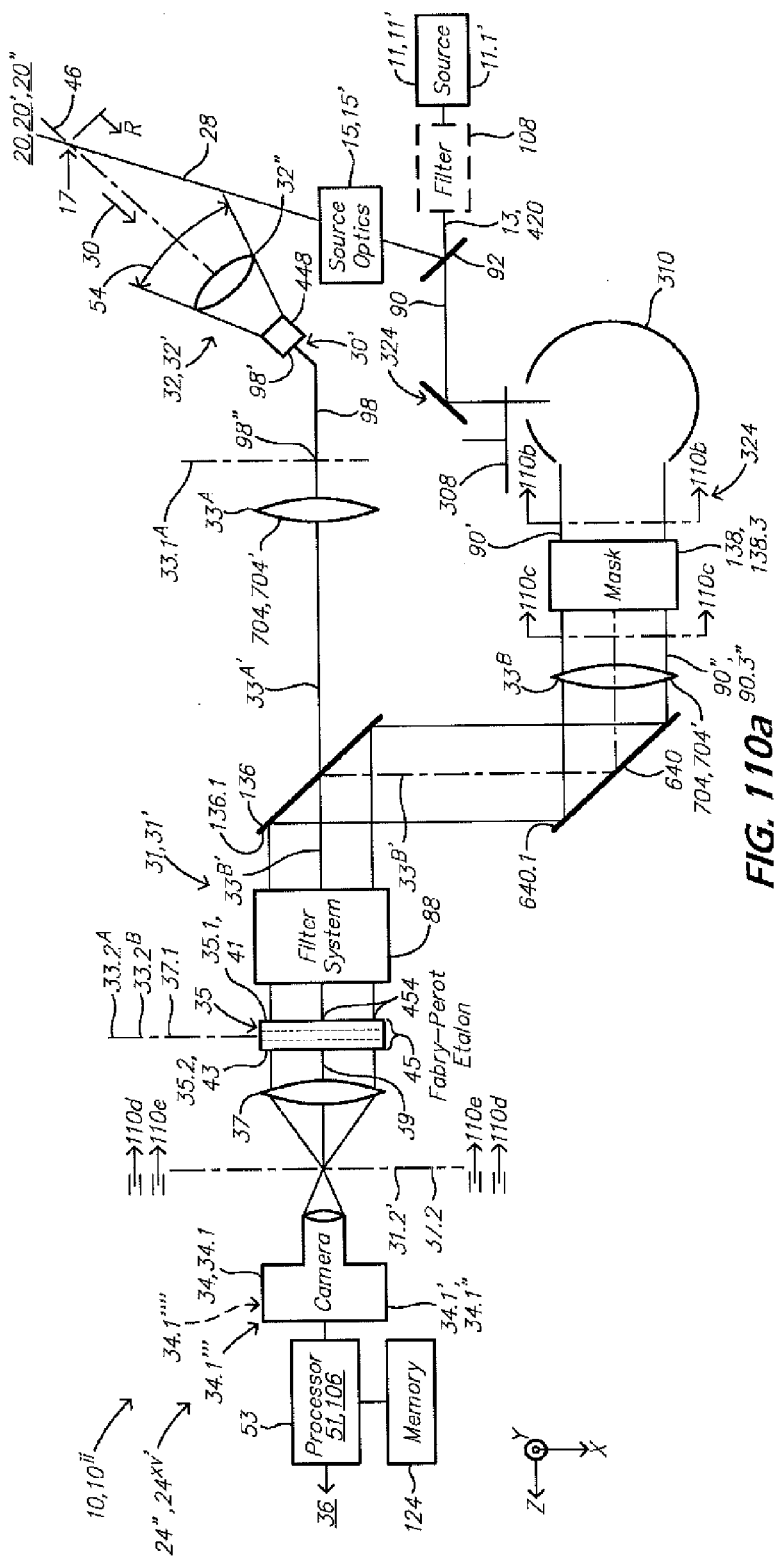

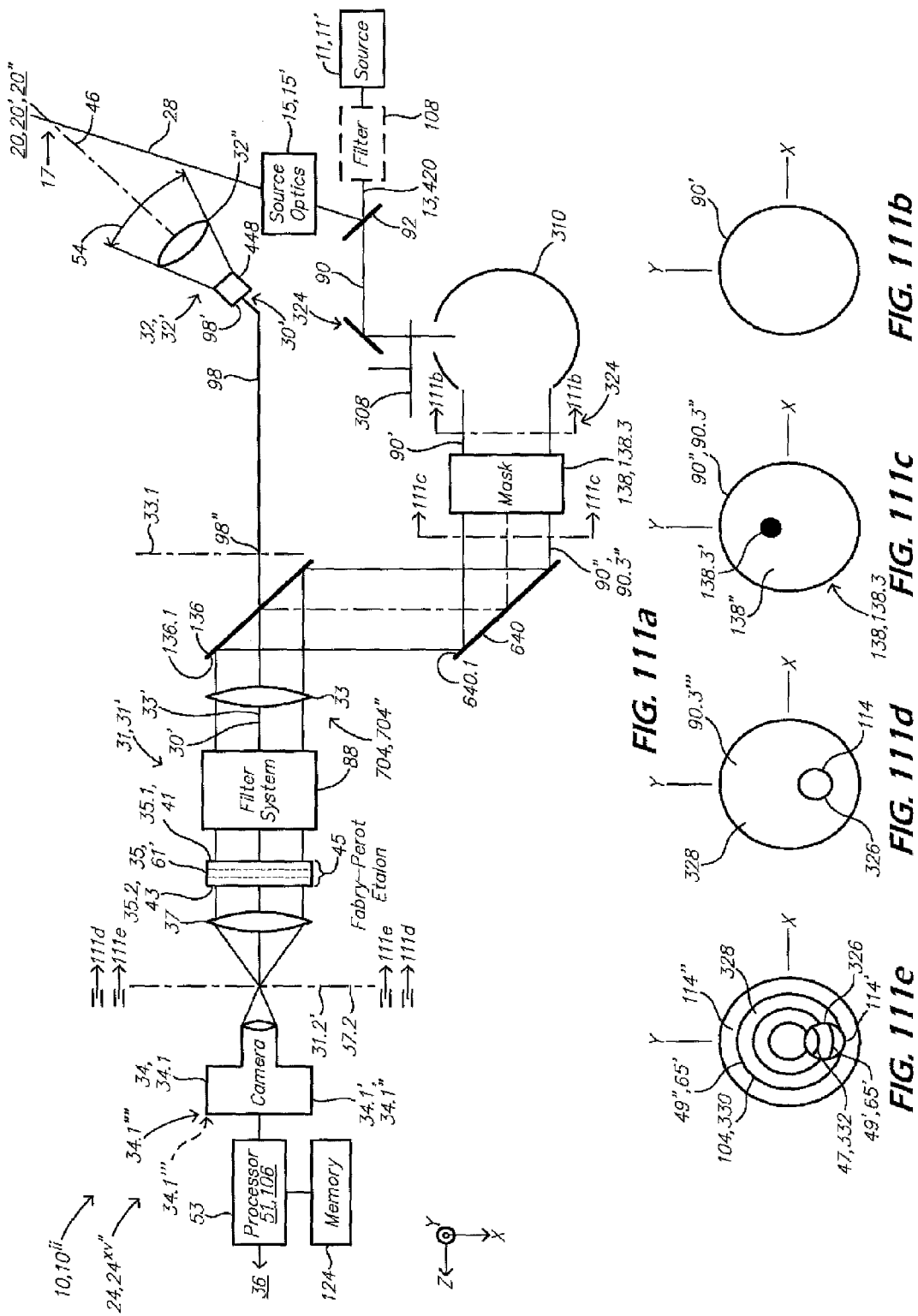

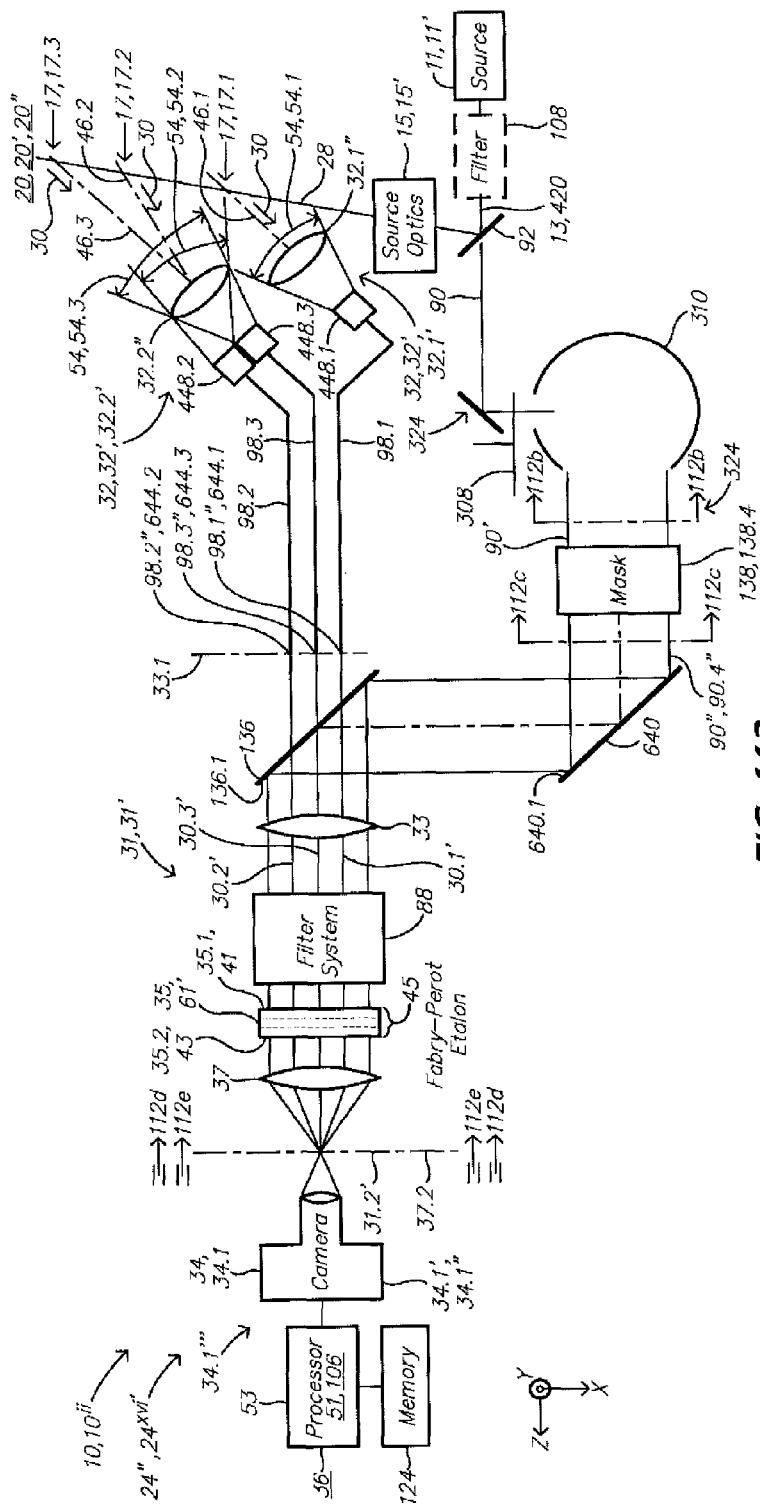
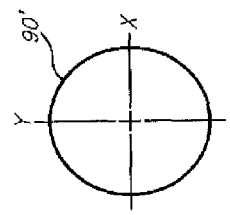
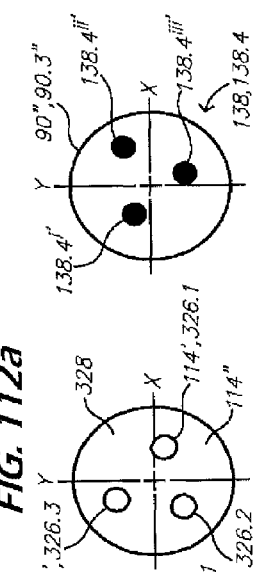
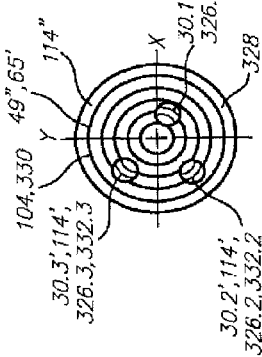
FIG. 112a
FIG. 112b
FIG. 112c
FIG. 112d
FIG. 112e

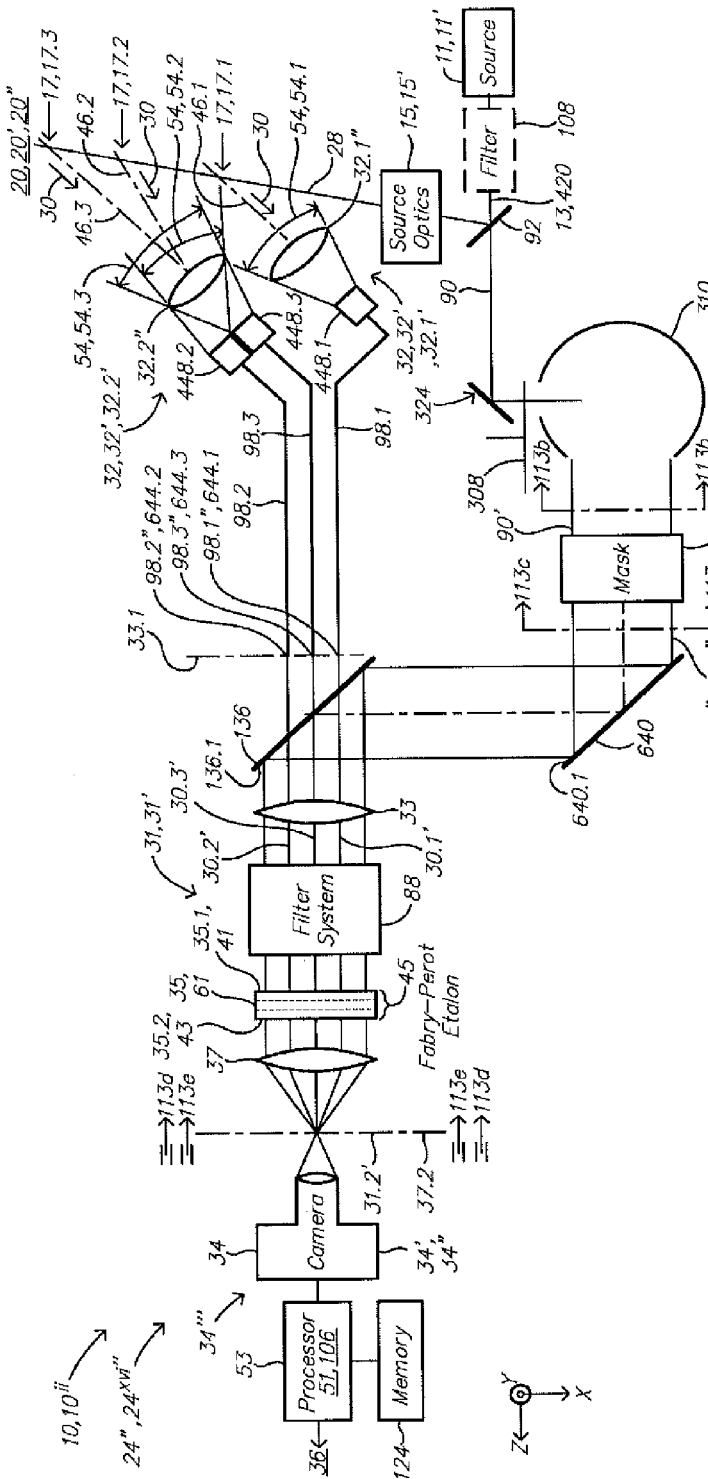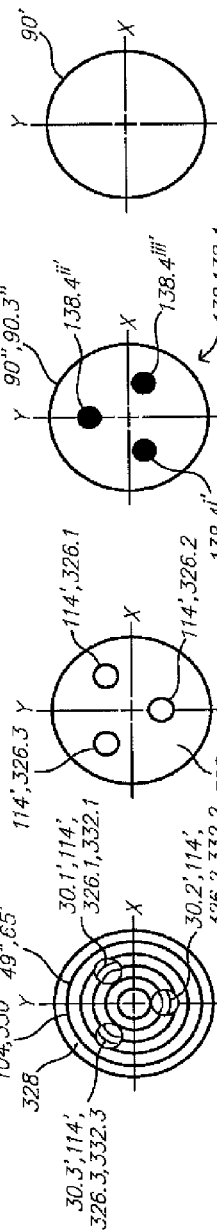
FIG. 113a
FIG. 113b
FIG. 113c
FIG. 113d
FIG. 113e

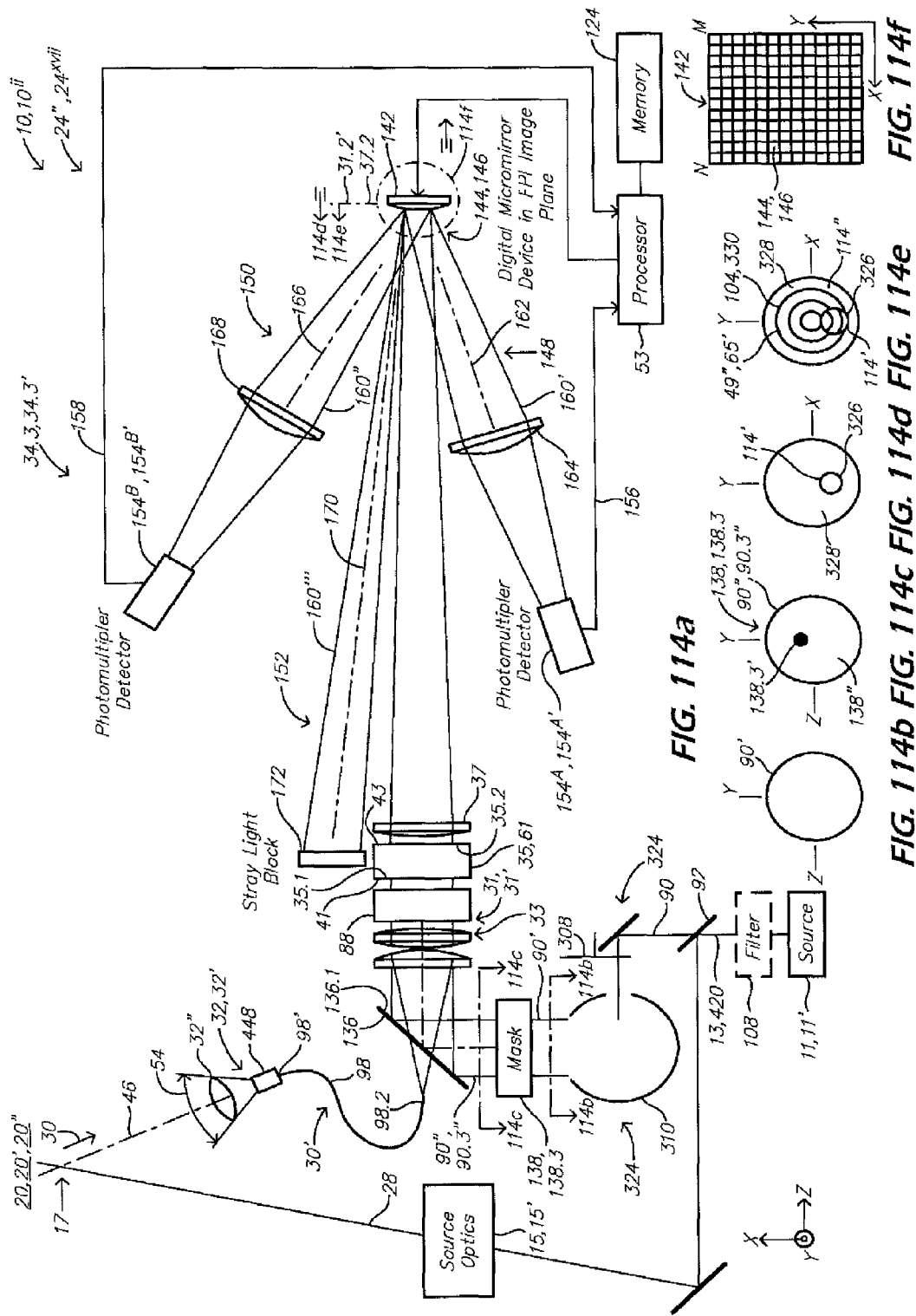

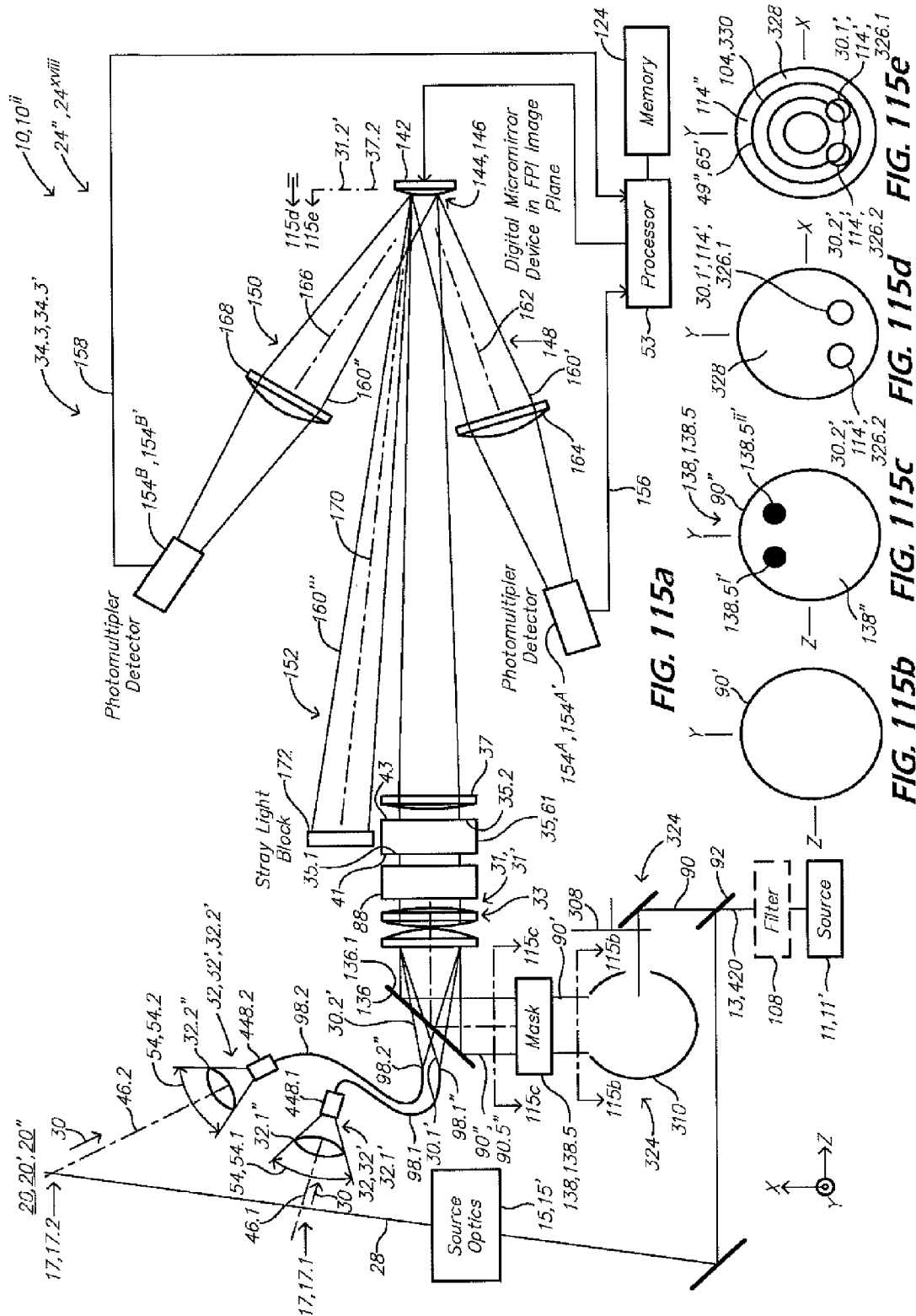

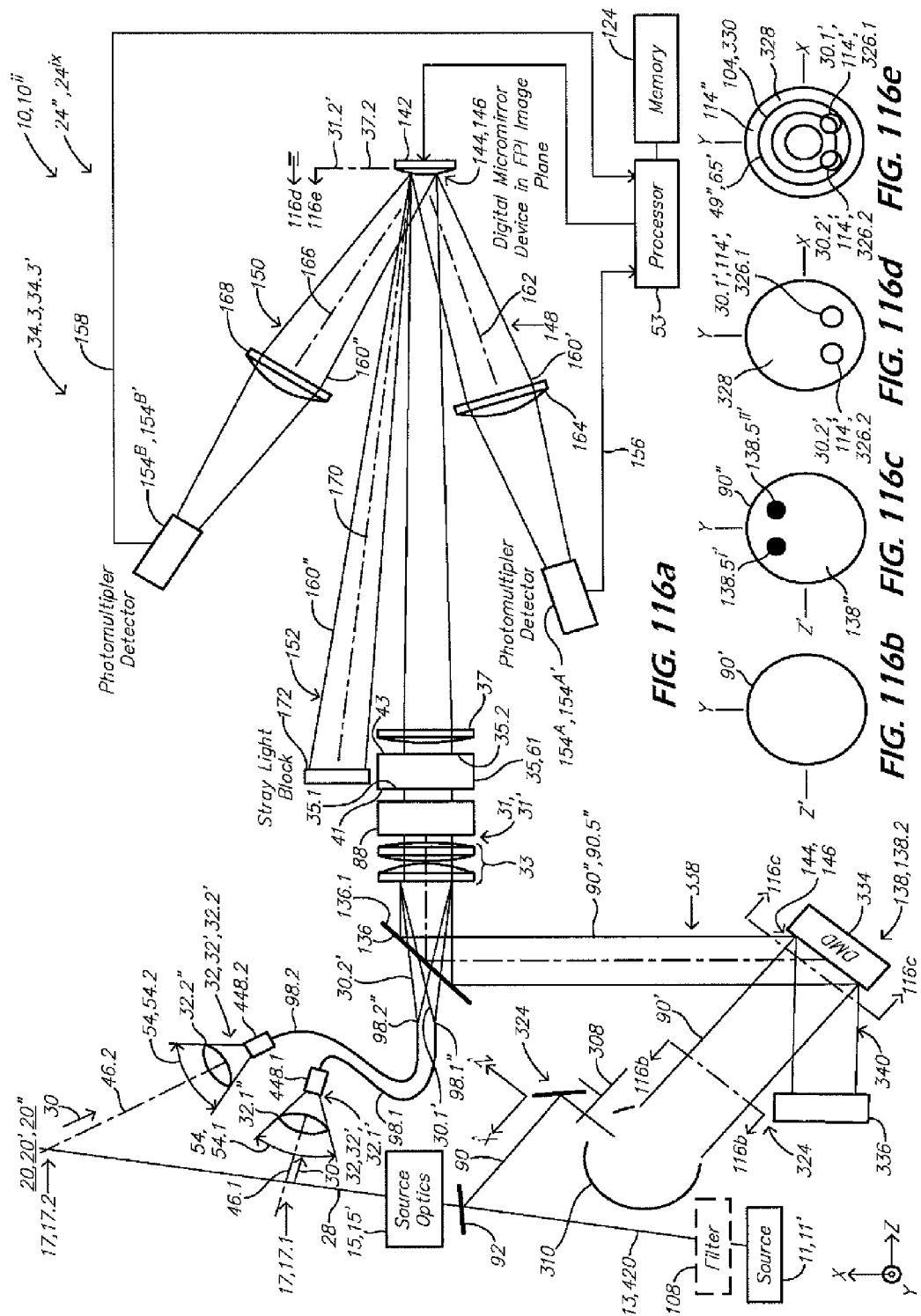

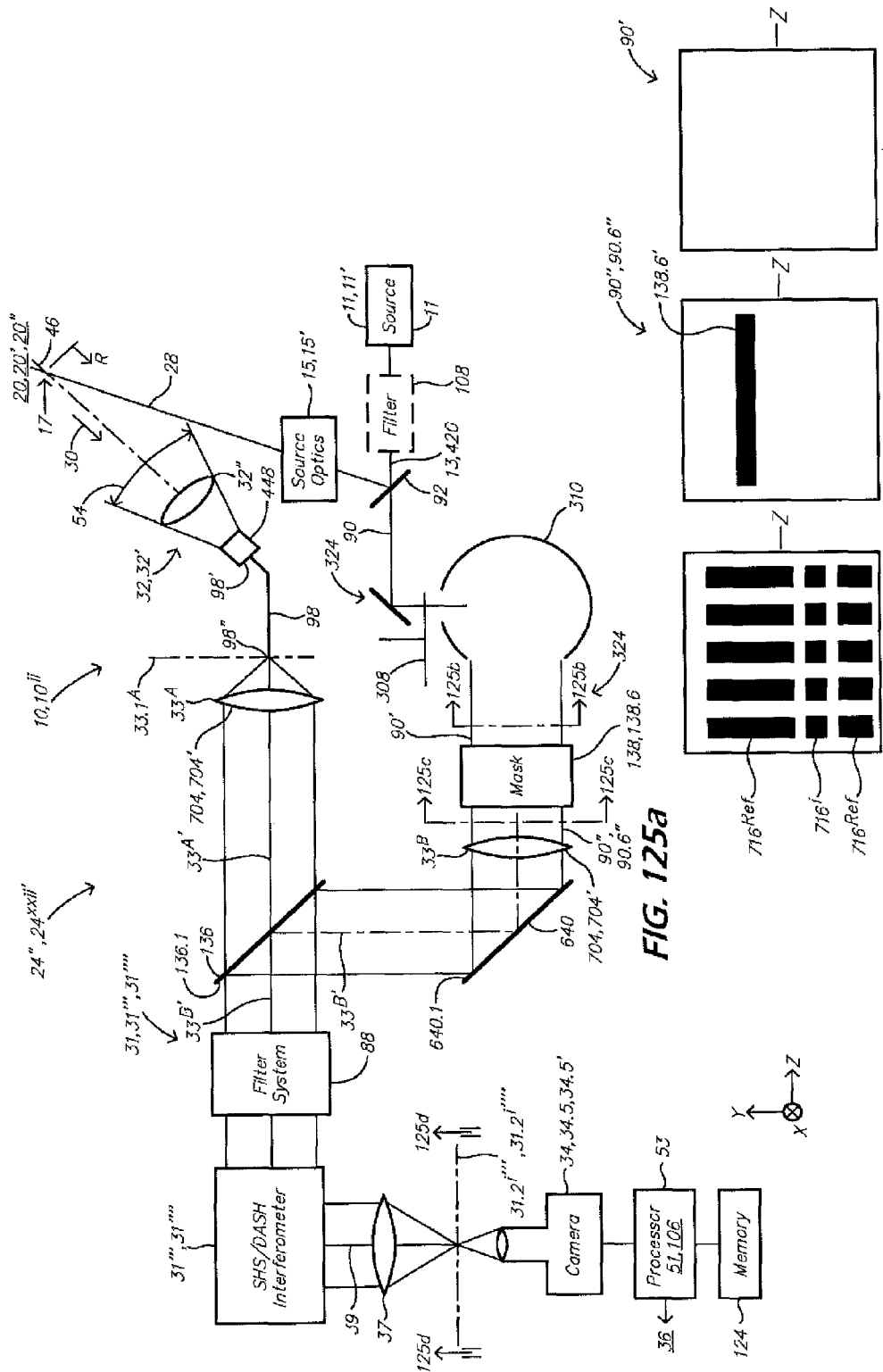

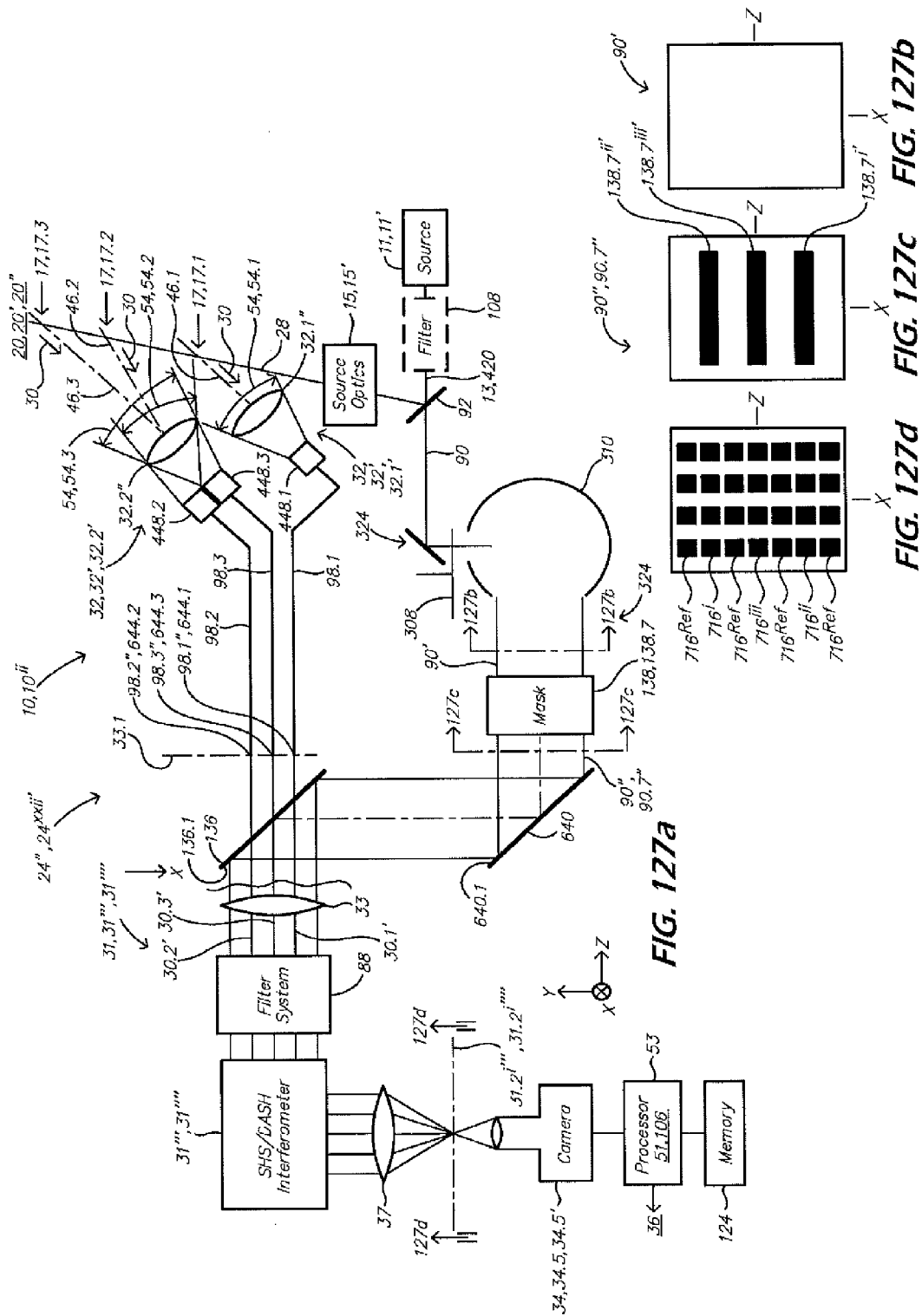

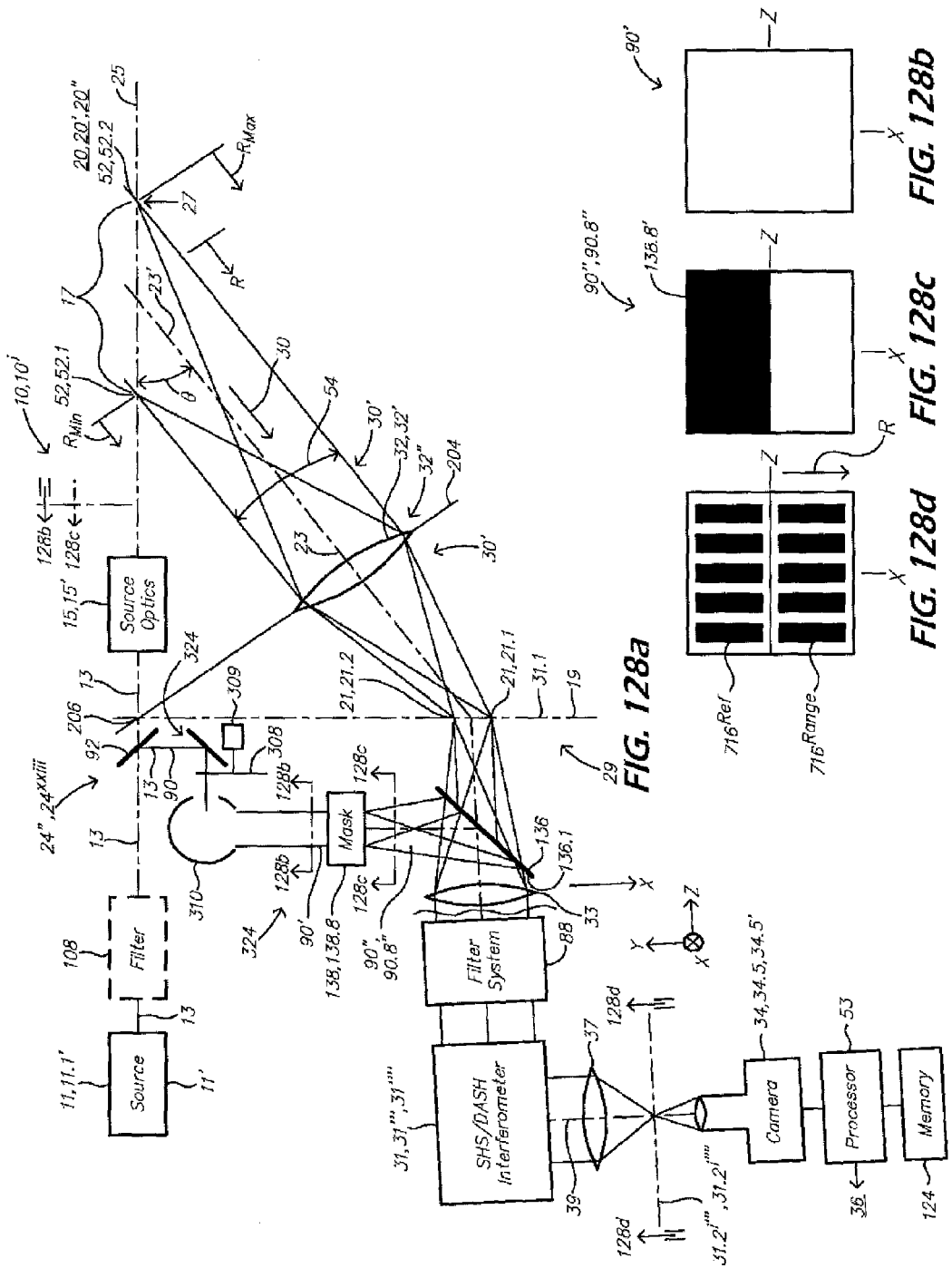

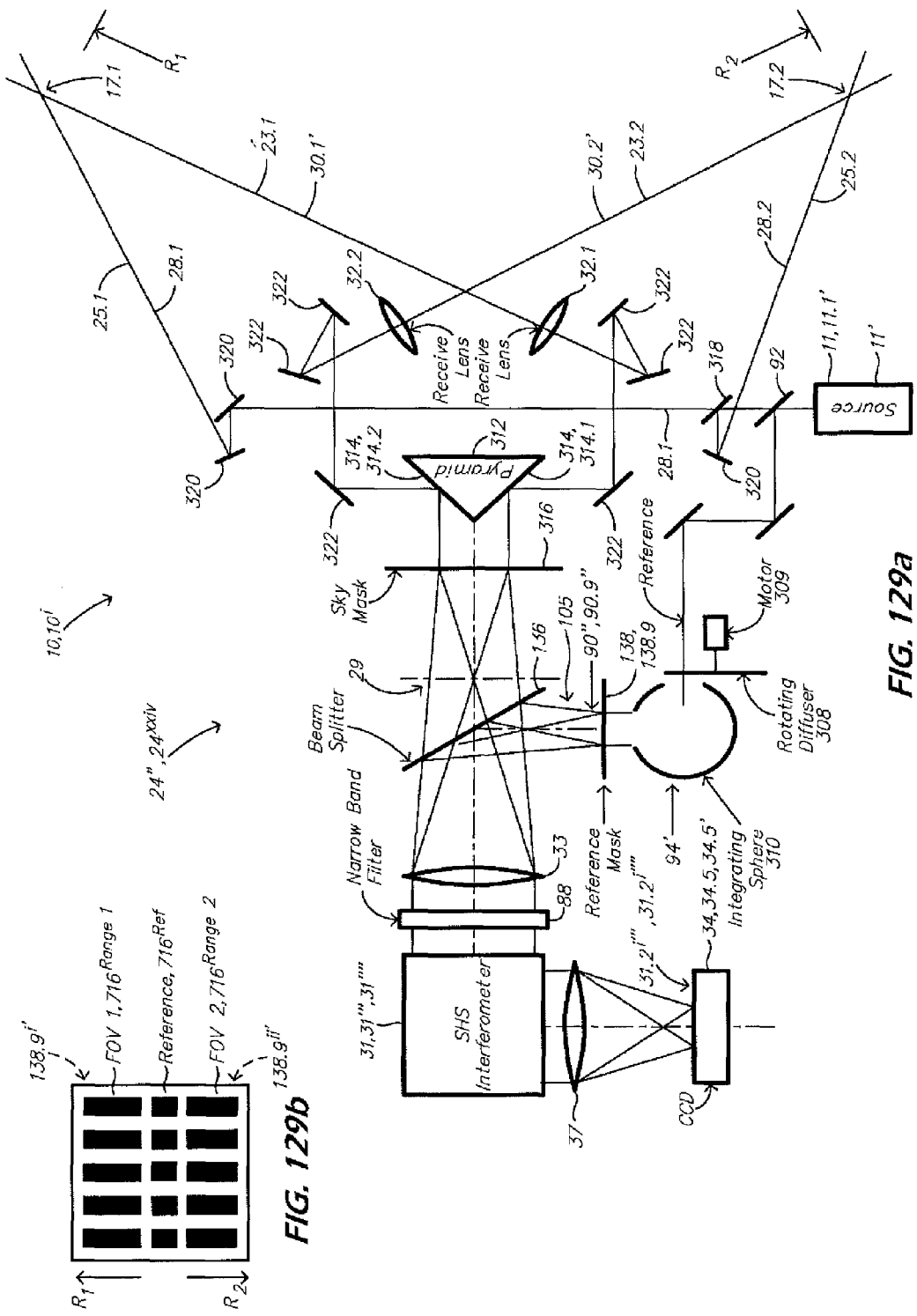

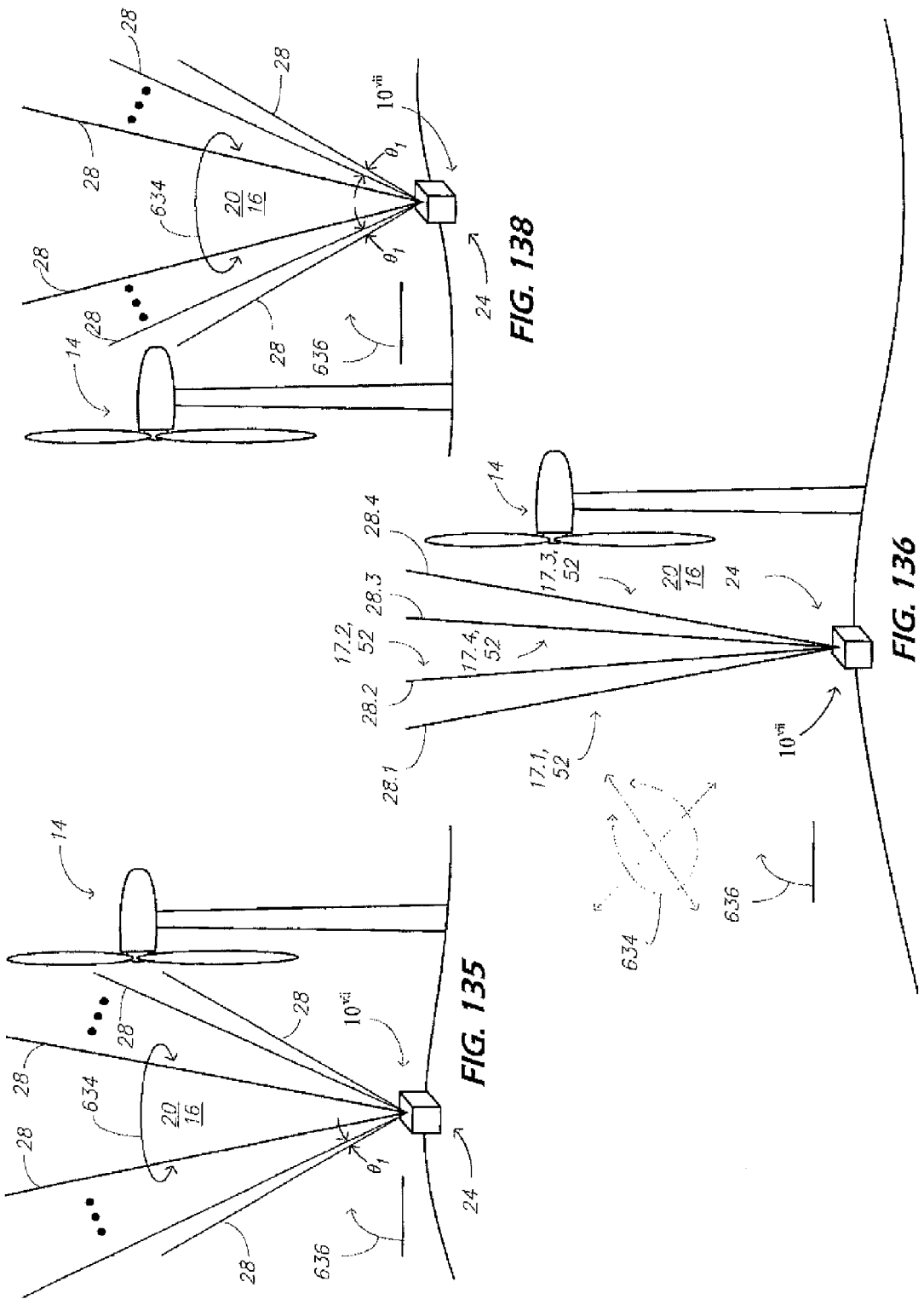

ATMOSPHERIC MEASUREMENT SYSTEM AND METHOD

CROSS-REFERENCE TO RELATED APPLICATIONS

The instant application is a continuation-in-part of International Application No. PCT/US10/62111 filed on 24 Dec. 2010, which claims benefit of priority of U.S. Provisional Application No. 61/290,004 filed on 24 Dec. 2009. The instant application is also a continuation-in-part of International Application No. PCT/US10/43801 filed on 29 Jul. 2010 which claims benefit of the following U.S. Provisional Application Nos. 61/229,608 filed on 29 Jul. 2009, 61/266,916 filed on 4 Dec. 2009, and 61/290,004 filed on 24 Dec. 2009. The instant application is also a continuation-in-part of U.S. application Ser. No. 12/780,895 15 filed on May 2010 which claims benefit of the following U.S. Provisional Application Nos. 61/178,550 filed on 15 May 2009, and 61/290,004 filed on 24 Dec. 2009. The instant application is also a continuation-in-part of International Application No. PCT/US10/31965 filed on 21 Apr. 2010 which claims benefit of the following U.S. Provisional Application Nos. 61/171,080 filed on 21 Apr. 2009, 61/178,550 filed on 15 May 2009, and 61/290,004 filed on 24 Dec. 2009.

BRIEF DESCRIPTION OF THE DRAWINGS

FIG. 6a illustrates a first set of embodiments of a first aspect of a range-imaging LIDAR system incorporated in a first aspect of an atmospheric measurement system;

FIG. 6b illustrates a transverse cross-section of a first embodiment of a beam of light;

FIG. 6c illustrates a transverse cross-section of a second embodiment of a beam of light;

FIG. 8 illustrates an example of a composite of an image of scattered light from an interaction region and an associated reference beam, as input to a Fabry-Pérot interferometer of the first aspect of the range-imaging LIDAR system illustrated in FIG. 6a;

FIG. 10a illustrates a plot of signal intensity as a function of image distance of the fringe pattern illustrated in FIG. 9;

FIG. 10b illustrates a plot of signal intensity as a function of range from the LIDAR system to the interaction region, corresponding to the plot illustrated in FIG. 10a;

FIG. 14b illustrates an alternate decision block of the first aspect of a circular binning process illustrated in FIG. 14a;

FIG. 21 illustrates a first exploded view of a core assembly incorporated in the thermal chamber assembly illustrated in FIG. 20;

FIG. 22 illustrates a second exploded view of the core assembly incorporated in the thermal chamber assembly illustrated in FIG. 20;

FIG. 23 illustrates a third exploded view of the core assembly incorporated in the thermal chamber assembly illustrated in FIG. 20;

FIG. 29a illustrates a first embodiment of a third aspect of an associated detection system of a range-imaging LIDAR system;

FIG. 29b illustrates a plan view of a digital micromirror device (DVD) used in the embodiments illustrated in FIG. 29a.

FIG. 32 illustrates a partial derivative with respect to velocity of the intensity distribution of FIG. 16a;

FIG. 33 illustrates a partial derivative with respect to temperature of the intensity distribution of FIG. 16a;

FIG. 34 illustrates a set of complementary reflection patterns of a digital micromirror device programmed to gather associated complementary aerosol signal components;

FIG. 35 illustrates a set of complementary reflection patterns of a digital micromirror device programmed to gather associated complementary molecular signal components;

FIG. 36 illustrates a set of complementary reflection patterns of a digital micromirror device programmed to gather associated complementary velocity signal components;

FIG. 37 illustrates a set of complementary reflection patterns of a digital micromirror device programmed to gather associated complementary temperature signal components;

FIG. 38 illustrates a set of complementary reflection patterns of a digital micromirror device programmed to gather associated complementary background signal components;

FIGS. 39a-e illustrate radial cross-sections through the complementary reflection patterns illustrated in FIGS. 34-38, respectively;

FIG. 55a illustrates a first embodiment of an eighth aspect of a range-imaging LIDAR system incorporating a first aspect of the associated mask system and the first aspect of an associated detection system;

FIG. 55b illustrates a transverse cross-section of an expanded reference beam of light associated with the range-imaging LIDAR system illustrated in FIG. 55a;

FIG. 55c illustrates a transverse cross-section of the expanded reference beam of light after passing through a mask associated with the range-imaging LIDAR system illustrated in FIG. 55a;

FIG. 55d illustrates an image that would be produced by a Fabry-Pérot interferometer of the range-imaging LIDAR system illustrated in FIG. 55a if the associated Fabry-Pérot etalon were removed therefrom, corresponding to an image of the light signals entering the Fabry-Pérot interferometer;

FIG. 55e illustrates an image from the Fabry-Pérot interferometer of the range-imaging LIDAR system illustrated in FIG. 55a;

FIG. 56a illustrates a transverse cross-section of an expanded reference beam of light after passing through a mask associated with a first aspect of plural fringe patterns generated by a first variation of the eighth aspect of a range-imaging LIDAR system used to process light signals from plurality of associated regions of interest;

FIG. 56b illustrates an image from the Fabry-Pérot interferometer of the range-imaging LIDAR system associated with the image illustrated in FIG. 56a;

FIG. 57a illustrates a transverse cross-section of an expanded reference beam of light after passing through a mask associated with a second aspect of plural fringe patterns generated by a second variation of the eighth aspect of a range-imaging LIDAR system used to process light signals from plurality of associated regions of interest;

FIG. 57b illustrates an image from the Fabry-Pérot interferometer of the range-imaging LIDAR system associated with the image illustrated in FIG. 57a;

FIG. 58a illustrates a transverse cross-section of an expanded reference beam of light after passing through a mask associated with a third aspect of plural fringe patterns generated by a third variation of the eighth aspect of a range-imaging LIDAR system used to process light signals from plurality of associated regions of interest;

FIG. 58b illustrates an image from the Fabry-Pérot interferometer of the range-imaging LIDAR system associated with the image illustrated in FIG. 58a;

FIG. 59a illustrates a second embodiment of the eighth aspect of a range-imaging LIDAR system incorporating the first aspect of the associated mask system and the third aspect of an associated detection system;

FIG. 59b-e illustrate various images associated with the second embodiment of the eighth aspect of a range-imaging LIDAR system corresponding to corresponding images of FIG. 55d-g for the first embodiment of the eighth aspect;

FIG. 60a-e illustrates a third embodiment of the eighth aspect of a range-imaging LIDAR system incorporating a second aspect of the associated mask system and the third aspect of an associated detection system;

FIG. 69a illustrates fringes from a fully-illuminated Fabry-Pérot etalon;

FIG. 69b illustrates fringes from a Fabry-Pérot etalon illuminated with four fiber input channels;

FIG. 70 illustrates four channels of fringes being collapsed by a quad circle-to-line interferometer optic (quad-CLIO) to four lines in the shape of a cross-pattern on an opto-electric detector;

FIG. 71 illustrates a prior art circle-to-line interferometer optic (CLIO);

FIG. 92a illustrates a plan view of a CCD detector in an initial state;

FIG. 92b illustrates a plan view of the CCD detector at the beginning stage of an image recording cycle;

FIG. 92c illustrates a plan view of the CCD detector at an intermediate stage of the image recording cycle;

FIG. 92d illustrates a plan view of the CCD detector at a final stage of the image recording cycle;

FIG. 92e illustrates an image transferred from the CCD detector;

FIG. 98a illustrates a first embodiment of a laser coupled with a fiber optic to a plurality of harmonic generators in series for generating a fourth harmonic;

FIG. 98b illustrates a second embodiment of a laser coupled with a fiber optic to a plurality of harmonic generators in series for generating a third harmonic;

FIG. 98c illustrates a third embodiment of a laser coupled with a first fiber optic to a first harmonic generator, the latter of which is connected to a second harmonic generator with a second fiber optic;

FIG. 98d illustrates a fourth embodiment of a laser coupled to a first harmonic generator, the latter of which is connected to a second harmonic generator with a fiber optic;

FIG. 99 illustrates a gimbal mechanism operatively associated with an optical air data system;

FIG. 100 illustrates a schematic block diagram of a tenth aspect of a LIDAR system;

FIG. 101 illustrates a schematic block diagram of an eleventh aspect of a LIDAR system;

FIG. 102a illustrates a schematic block diagram of a twelfth aspect of a LIDAR system;

FIG. 102b illustrates an image in the output focal plane of the Fabry-Pérot interferometer incorporated in the twelfth aspect of the LIDAR system illustrated in FIG. 102a, absent the associated Fabry-Pérot etalon;

FIG. 102c illustrates an image in the output focal plane of the Fabry-Pérot interferometer incorporated in the twelfth aspect of the LIDAR system illustrated in FIG. 102a, with the associated Fabry-Pérot etalon in place;

FIG. 103a illustrates a schematic block diagram of a thirteenth aspect of a LIDAR system;

FIG. 103b illustrates an image in the output focal plane of the Fabry-Pérot interferometer incorporated in the thirteenth aspect of the LIDAR system illustrated in FIG. 103a, absent the associated Fabry-Pérot etalon;

Figure 104:
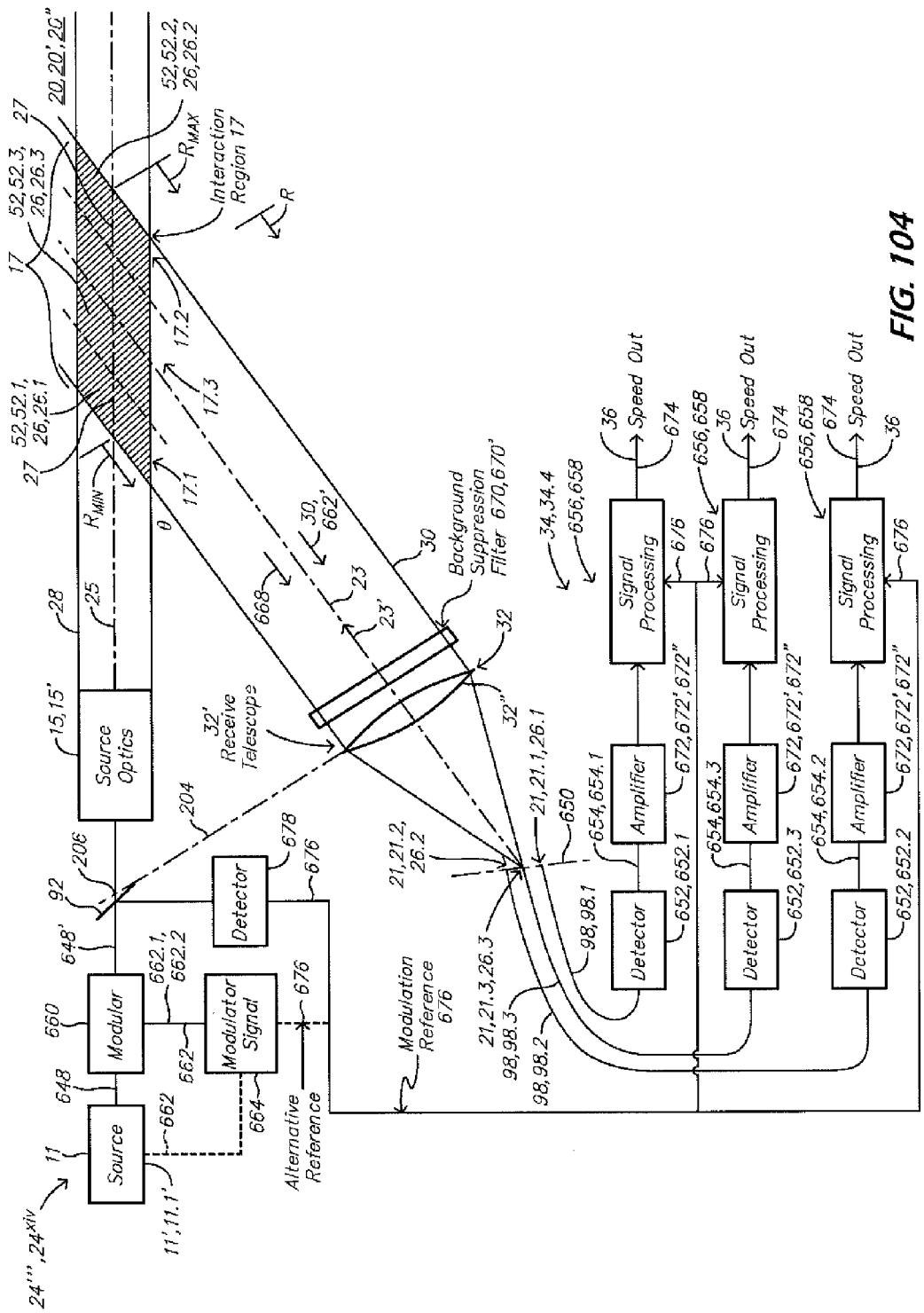
Figure 108:
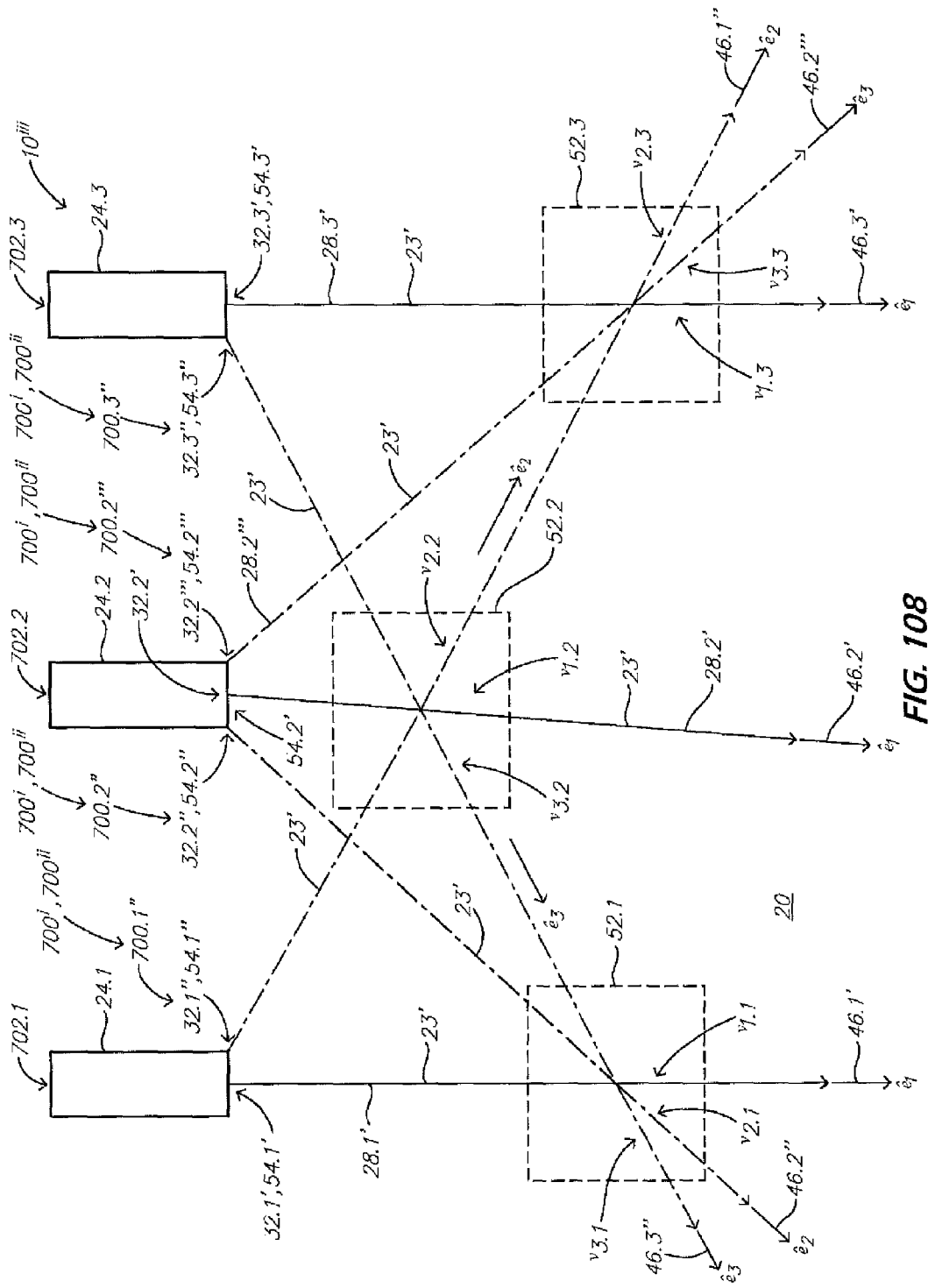
Figure 109:
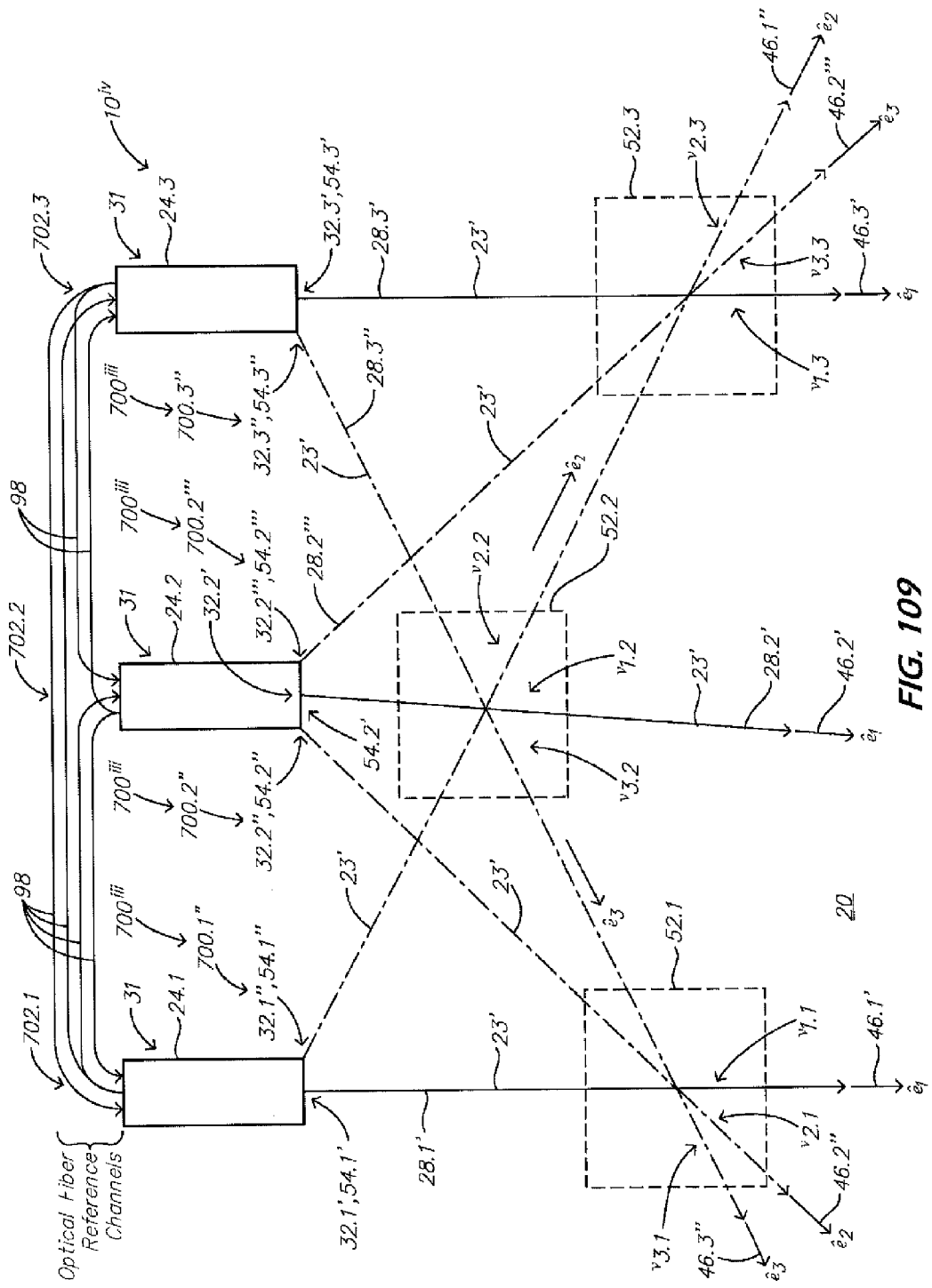

FIG. 103c illustrates an image in the output focal plane of the Fabry-Pérot interferometer incorporated in the thirteenth aspect of the LIDAR system illustrated in FIG. 103a, with the associated Fabry-Pérot etalon in place;

FIG. 104 illustrates a generalized embodiment a direct detection LIDAR system in accordance with a fourteenth aspect of a LIDAR system incorporated in a third aspect of an atmospheric measurement system;

FIG. 105a illustrates a first embodiment of an analog phase detector;

FIG. 105b illustrates an operating characteristic of the first embodiment of the analog phase detector illustrated in FIG. 105a;

FIG. 106a illustrates a second embodiment of an analog phase detector;

FIG. 106b illustrates an operating characteristic of the second embodiment of the analog phase detector illustrated in FIG. 106a;

FIG. 107 illustrates an operating characteristic of a digital phase detector;

FIG. 108 illustrates a fourth aspect of an atmospheric measurement system;

FIG. 109 illustrates a fifth aspect of an atmospheric measurement system;

FIG. 110a illustrates a first embodiment of a fifteenth aspect of a LIDAR system incorporated in the second aspect of an atmospheric measurement system that provides for processing backscattered light from a single range cell using a LIDAR system incorporating a second aspect of an associated mask system, a first aspect of an associated collimation system and a first aspect of an associated detection system;

FIG. 110b illustrates a transverse cross-section of an expanded reference beam of light associated with the atmospheric measurement system illustrated in FIG. 110a;

FIG. 110c illustrates a transverse cross-section of the expanded reference beam of light after passing through a mask associated with the atmospheric measurement system illustrated in FIG. 110a;

FIG. 110d illustrates an image that would be produced by a Fabry-Pérot interferometer of the LIDAR system illustrated in FIG. 110a if the associated Fabry-Pérot were removed therefrom, corresponding to an image of the light signals entering the Fabry-Pérot interferometer;

FIG. 110e illustrates an image from the Fabry-Pérot interferometer of the LIDAR system illustrated in FIG. 110a;

FIGS. 111a-111e illustrate a second embodiment of the fifteenth aspect of a LIDAR system incorporated in the second aspect of an atmospheric measurement system and various images associated therewith, corresponding to the first embodiment illustrated in FIGS. 110a-110e except that the second embodiment incorporates a second embodiment of an associated collimation system;

FIGS. 112a-112e illustrate a first embodiment of a sixteenth aspect of a LIDAR system incorporated in the second aspect of an atmospheric measurement system and various images associated therewith, corresponding to the second embodiment of the fifteenth aspect illustrated in FIGS. 111a-111e except that the first embodiment the sixteenth aspect provides for processing a plurality of associated range cells, wherein the associated backscatter light signals are not all radially aligned with a common set of fringes of the associated Fabry-Pérot interferometer;

FIGS. 113a-113e illustrate a second embodiment of the sixteenth aspect of a LIDAR system incorporated in the second aspect of an atmospheric measurement system and various images associated therewith, corresponding to the first embodiment illustrated in FIGS. 112a-112e except that the associated backscatter light signals are all radially aligned with a common set of fringes of the associated Fabry-Pérot interferometer;

FIGS. 114a-114f illustrate a seventeenth aspect of a LIDAR system incorporated in the second aspect of an atmospheric measurement system and various images associated therewith, corresponding to the second embodiment of the fifteenth aspect illustrated in FIGS. 111a-111e except that the seventeenth aspect incorporates a second embodiment of an associated detection system;

FIGS. 115a-115e illustrate an eighteenth aspect of a LIDAR system incorporated in the second aspect of an atmospheric measurement system and various images associated therewith, corresponding to the seventeenth aspect illustrated in FIGS. 114a-114e except that the eighteenth aspect provides for processing a plurality of associated range cells; and FIGS. 116a-116e illustrate a nineteenth aspect of a LIDAR system incorporated in the second aspect of an atmospheric measurement system and various images associated therewith, corresponding to the eighteenth aspect illustrated in FIGS. 115a-115e except that the nineteenth aspect incorporates the second aspect of an associated mask system.

Figure 1:
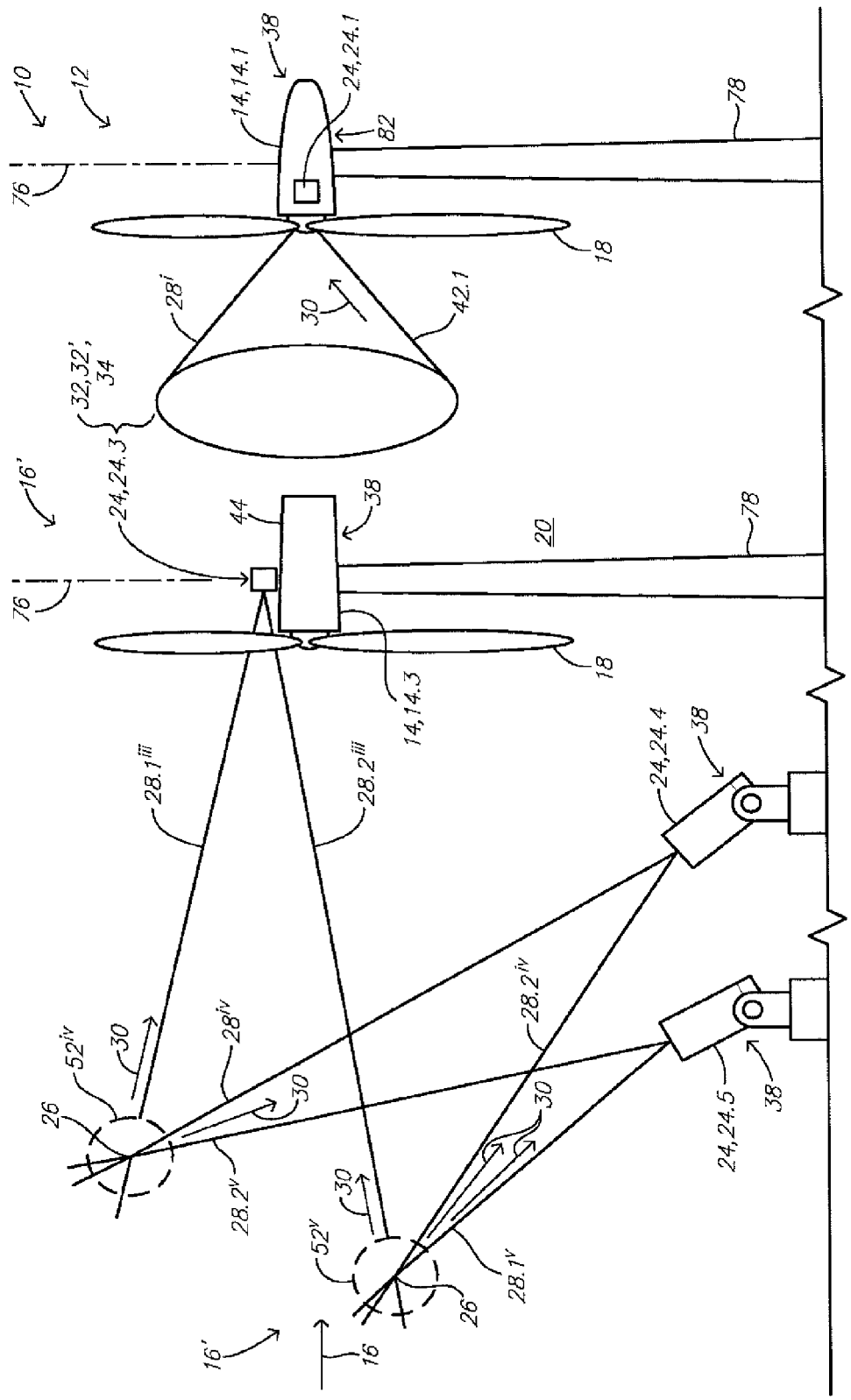
FIG. 1 illustrates a side view of a portion of a wind farm in association with an atmospheric measurement system.
Figure 52:
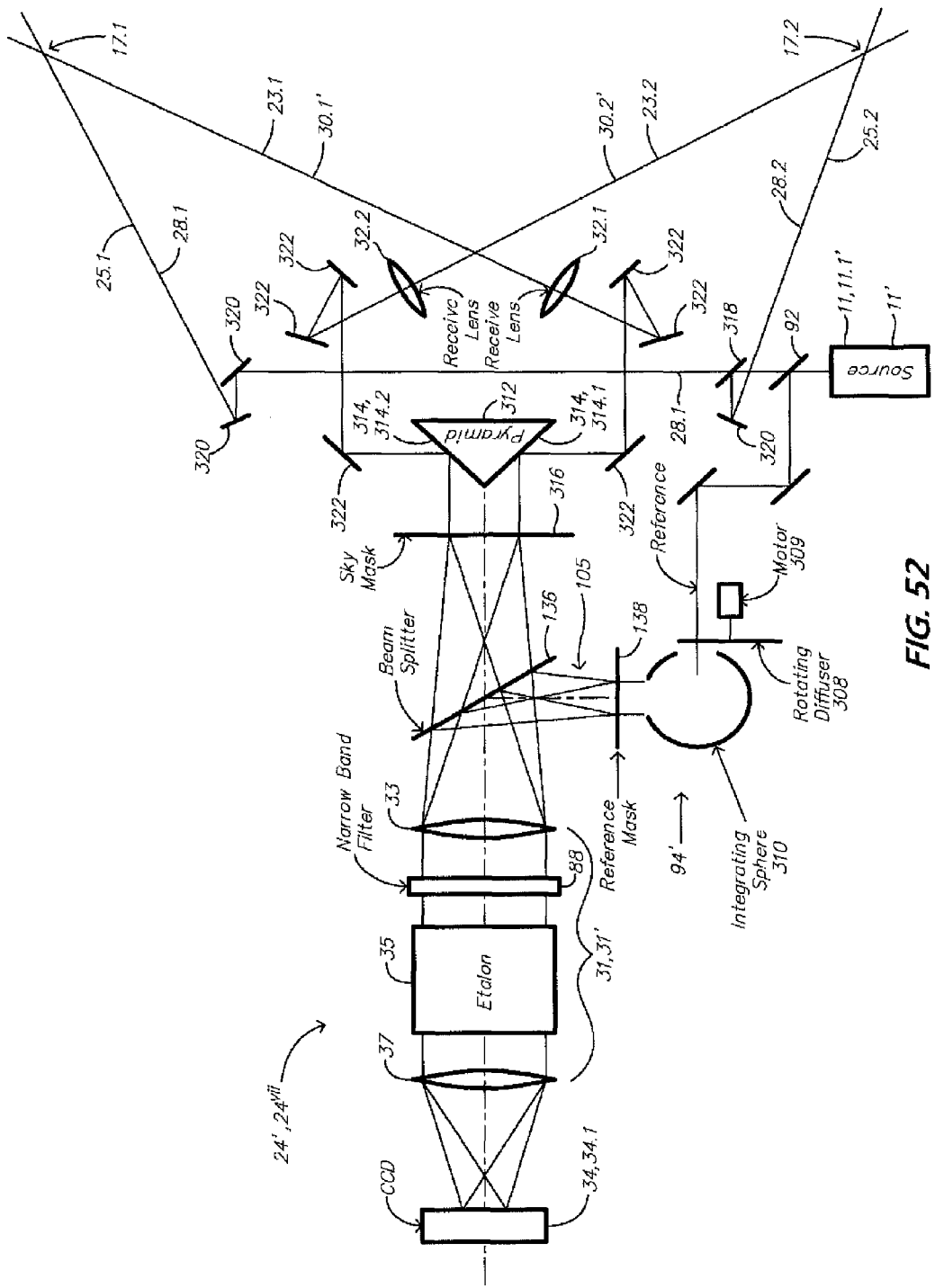
FIG. 52 illustrates an embodiment of a seventh aspect of a range-imaging LIDAR system.
Figure 64:
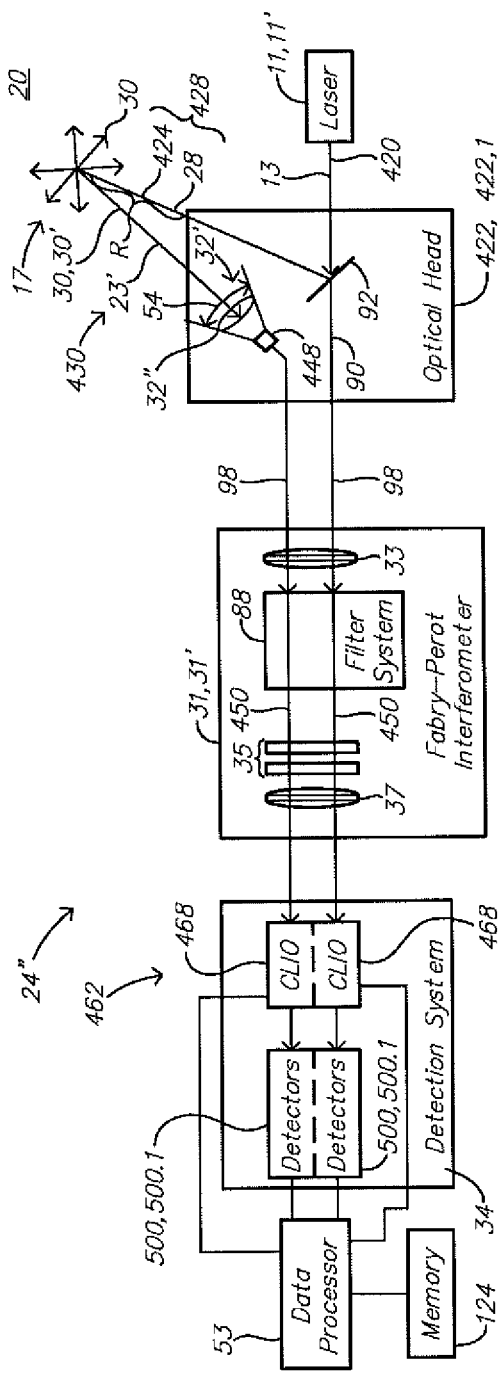
FIG. 64 illustrates a schematic block diagram of a ninth aspect of a LIDAR system incorporated in a second aspect of an atmospheric measurement system.
Figure 117:
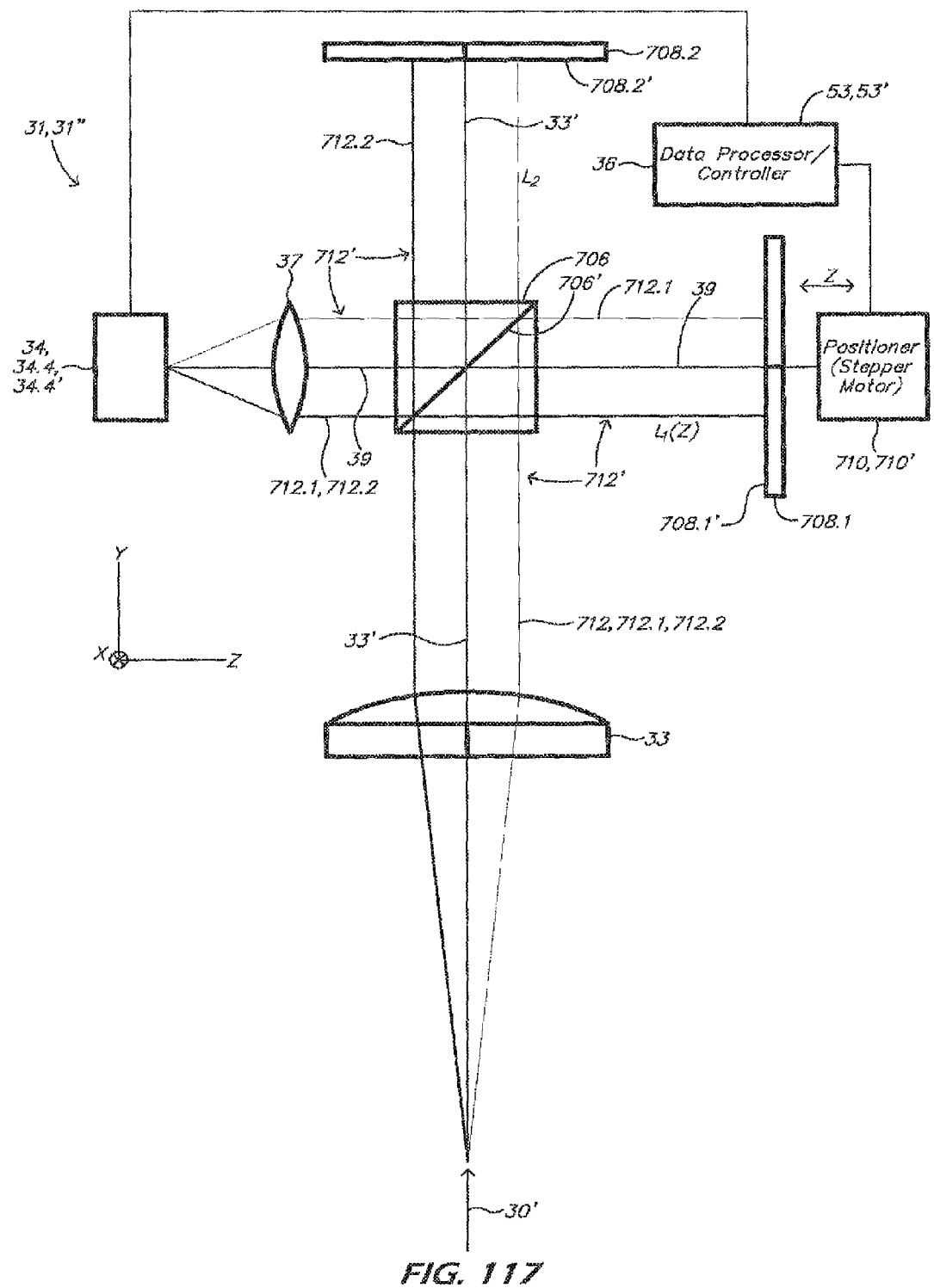
Figure 118A:
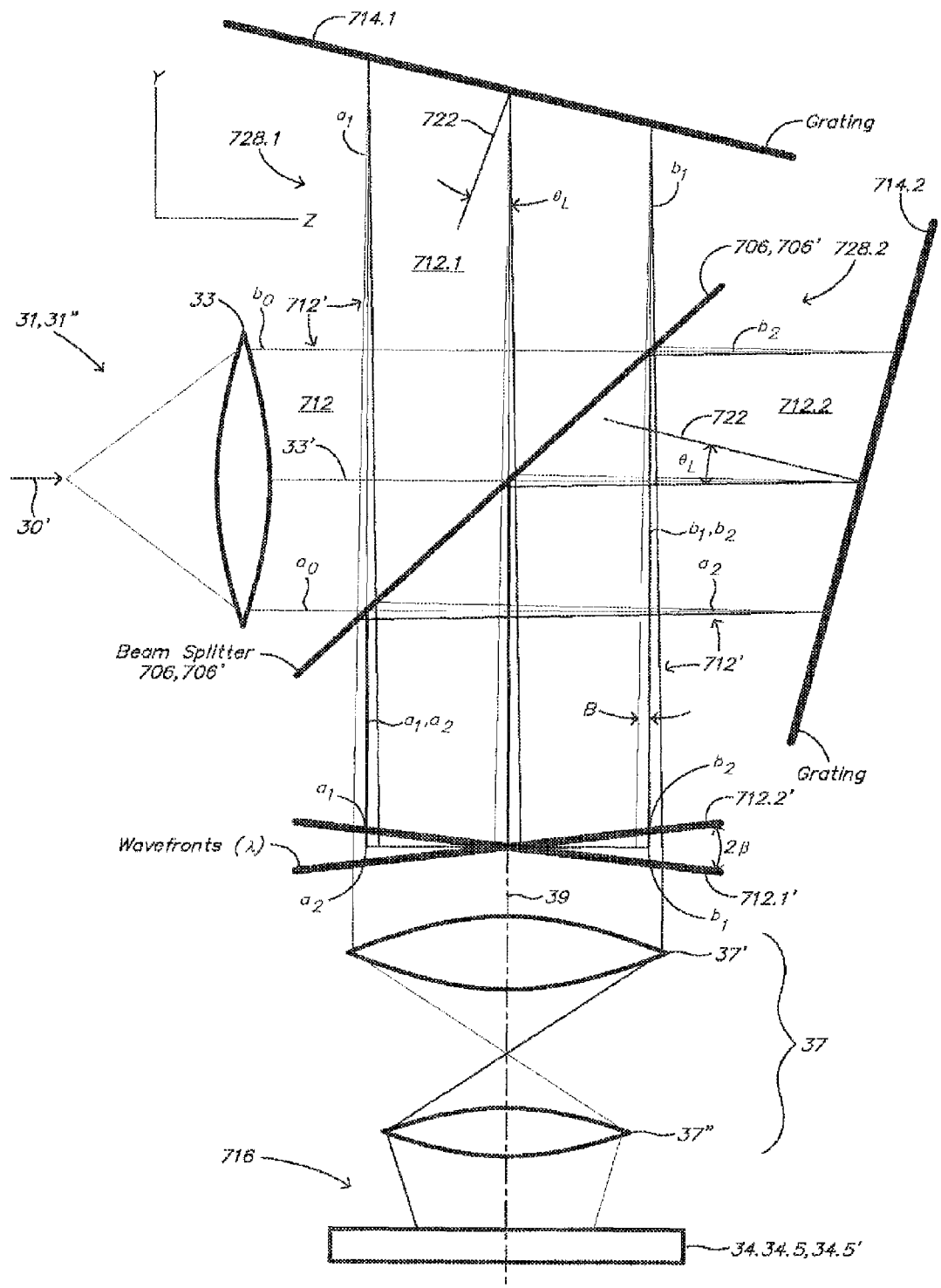
Figure 118B:
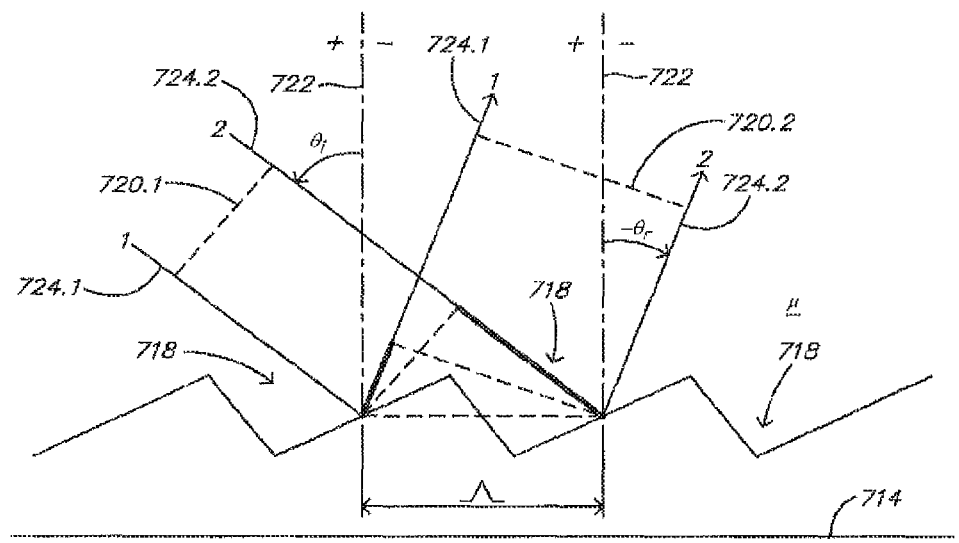
Figure 119:
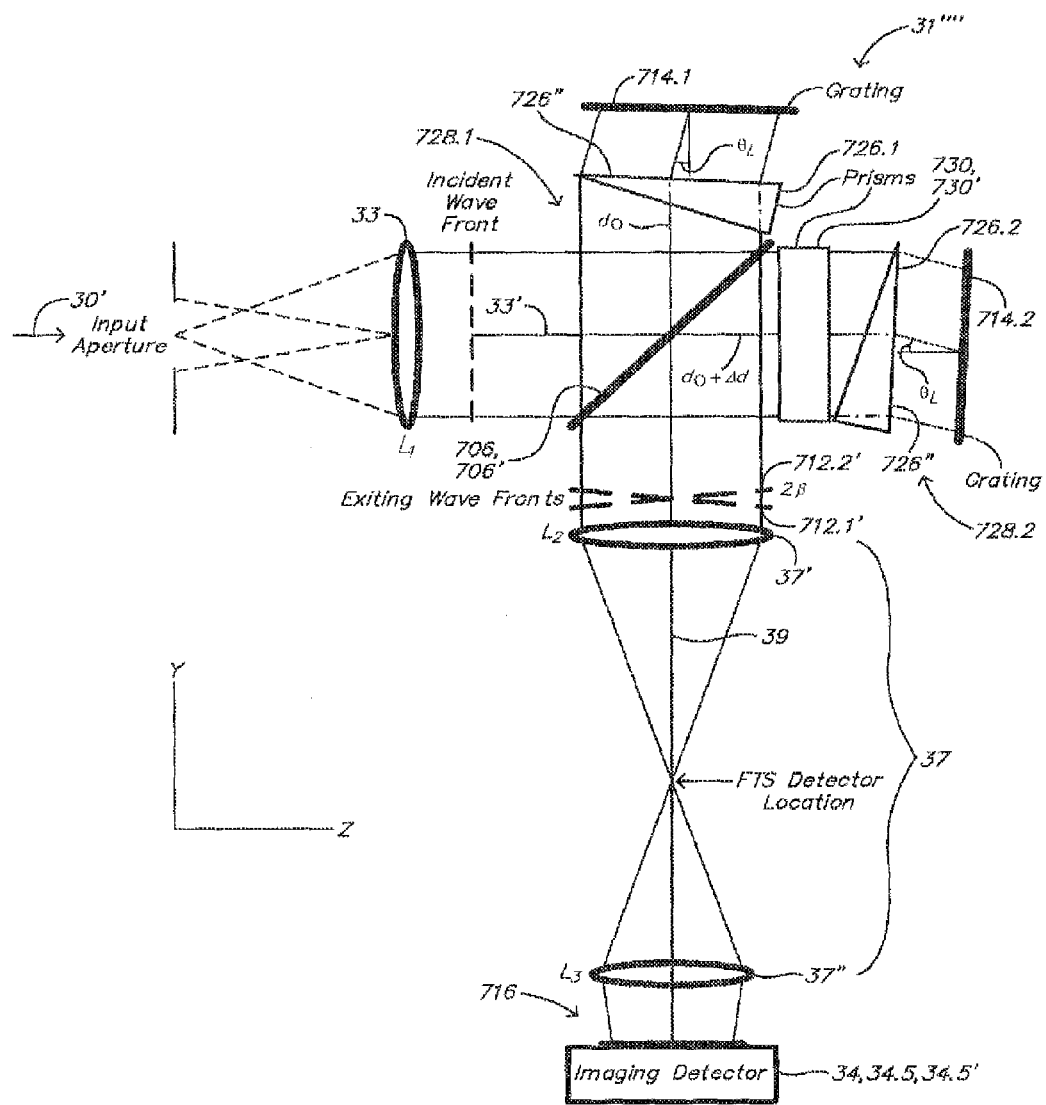
Figure 120:
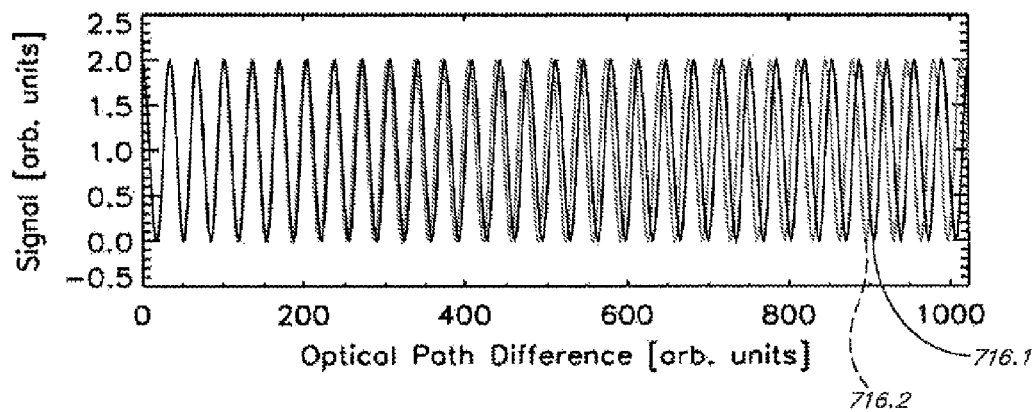
Figure 121:
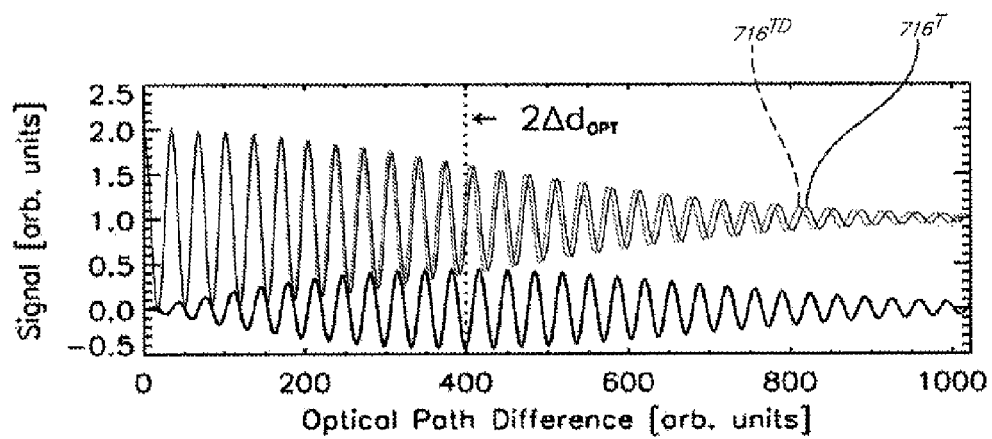
Figure 122A:
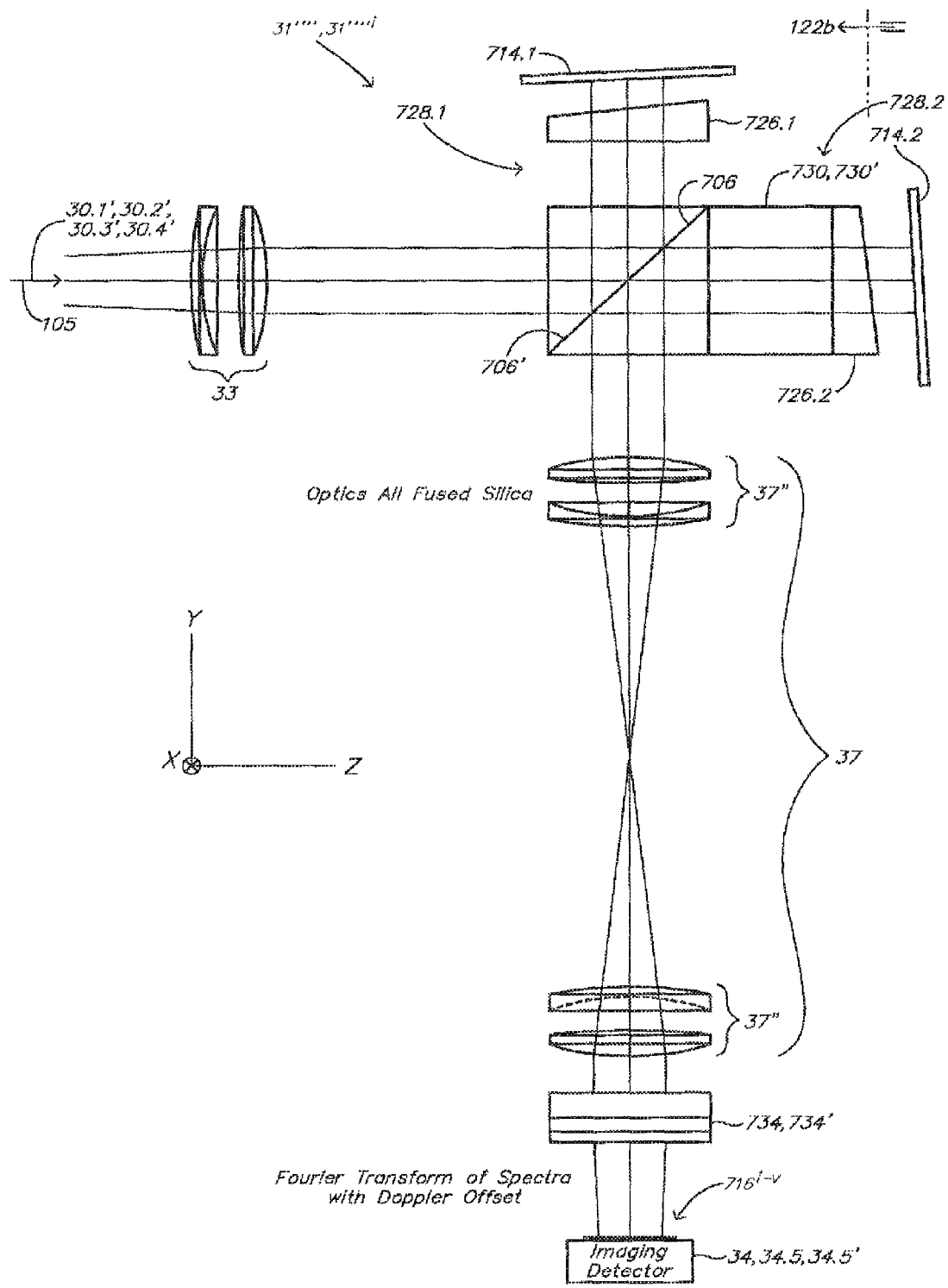
Figures 122B, 122C:
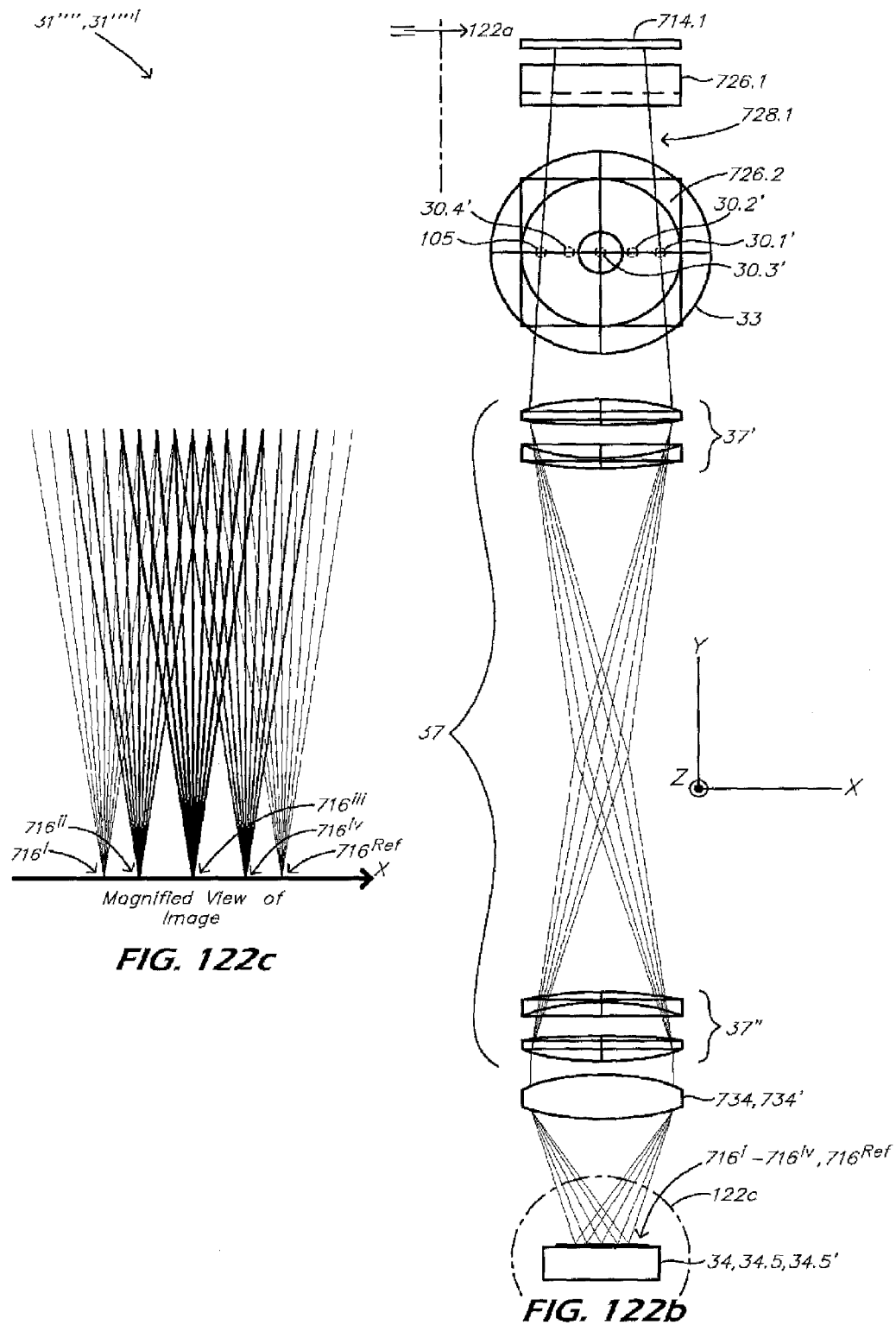
Figures 123A, 123B:
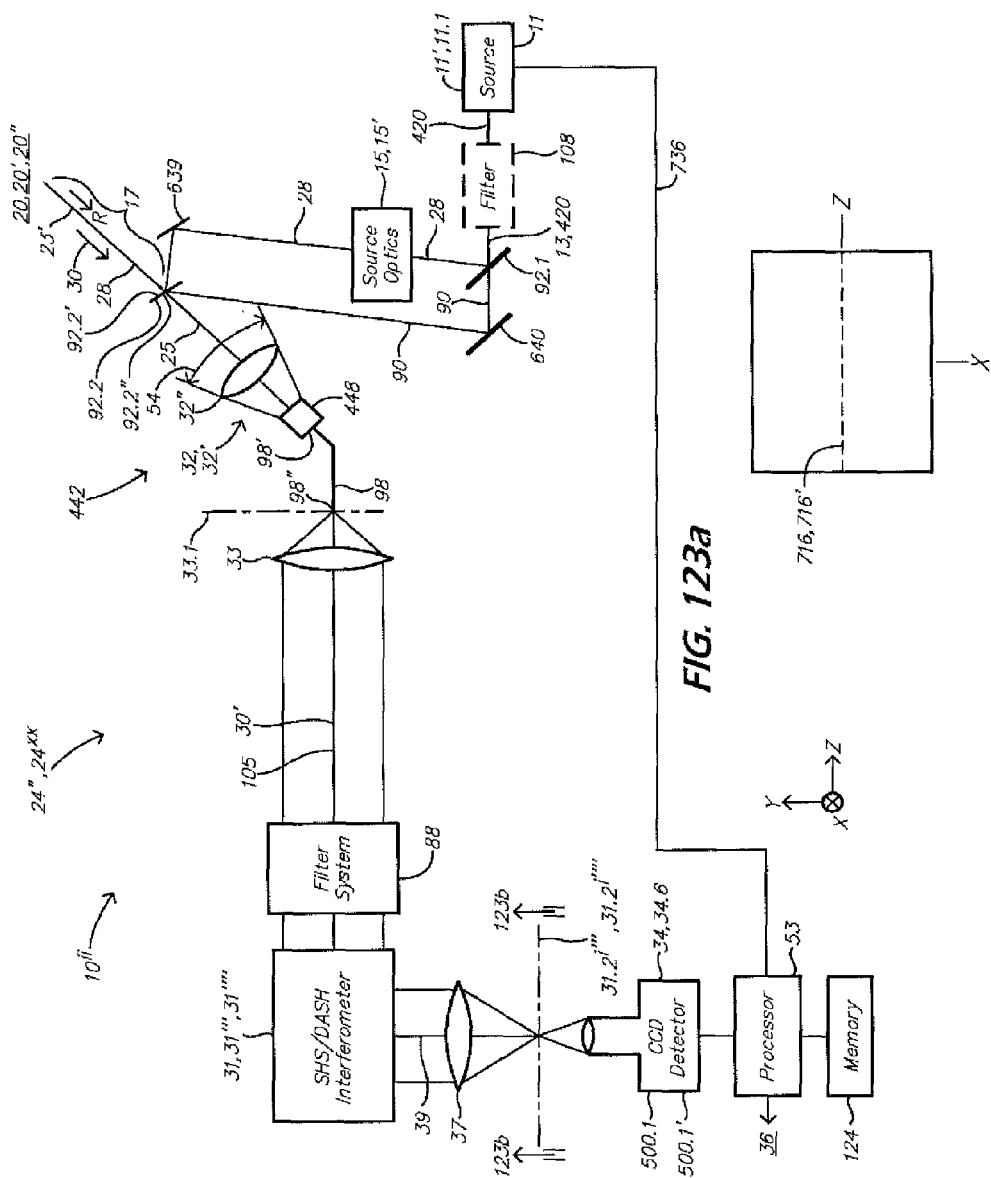
Figure 124A:
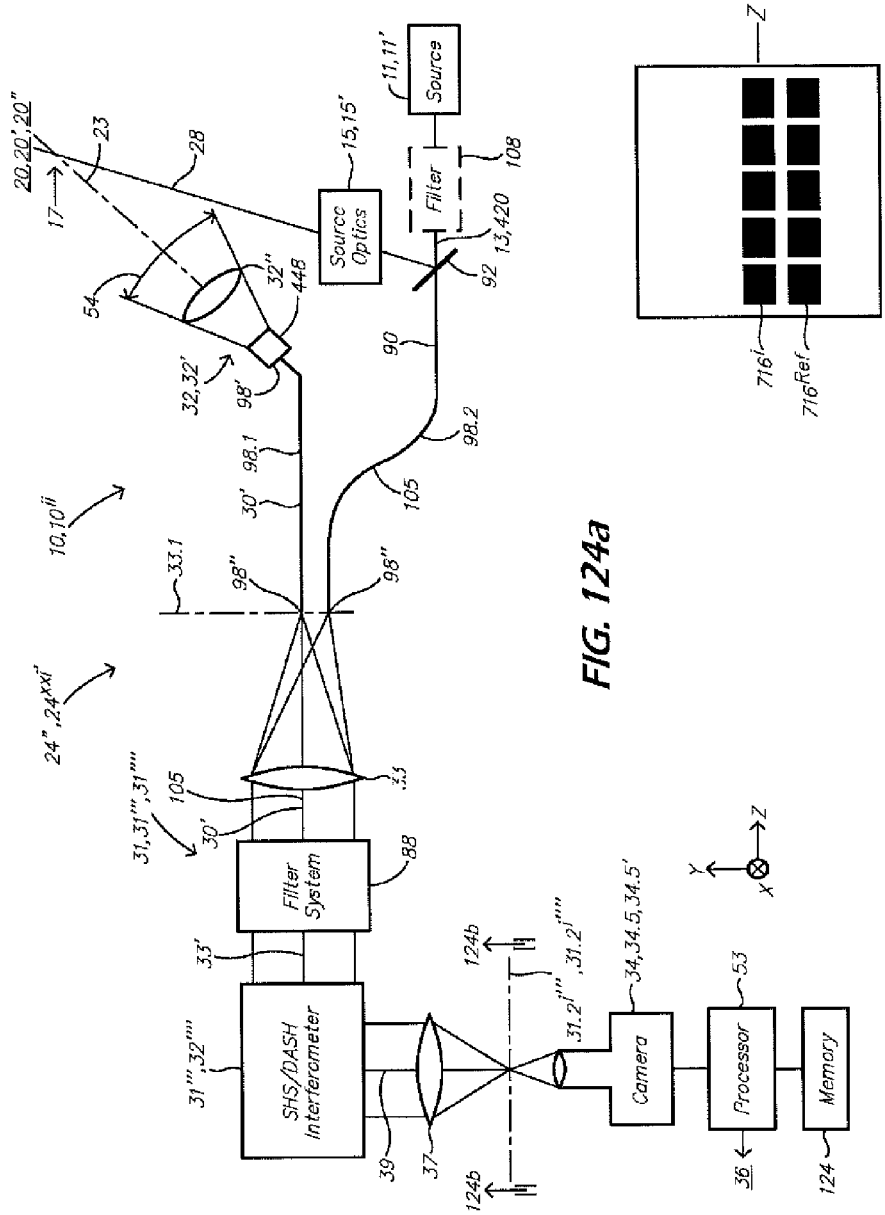
Figure 124B:
Figures 126A, 126B:
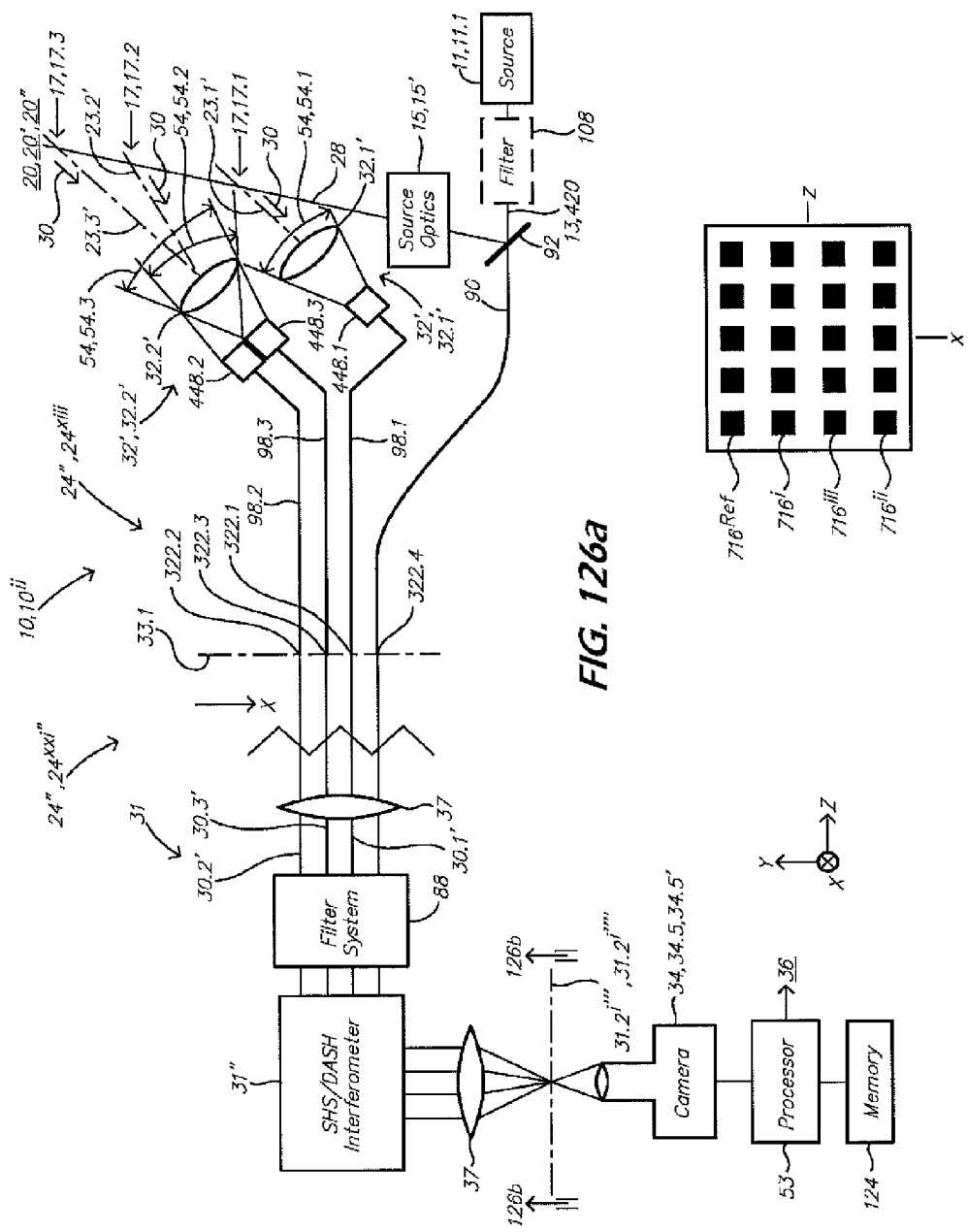
Figure 130:
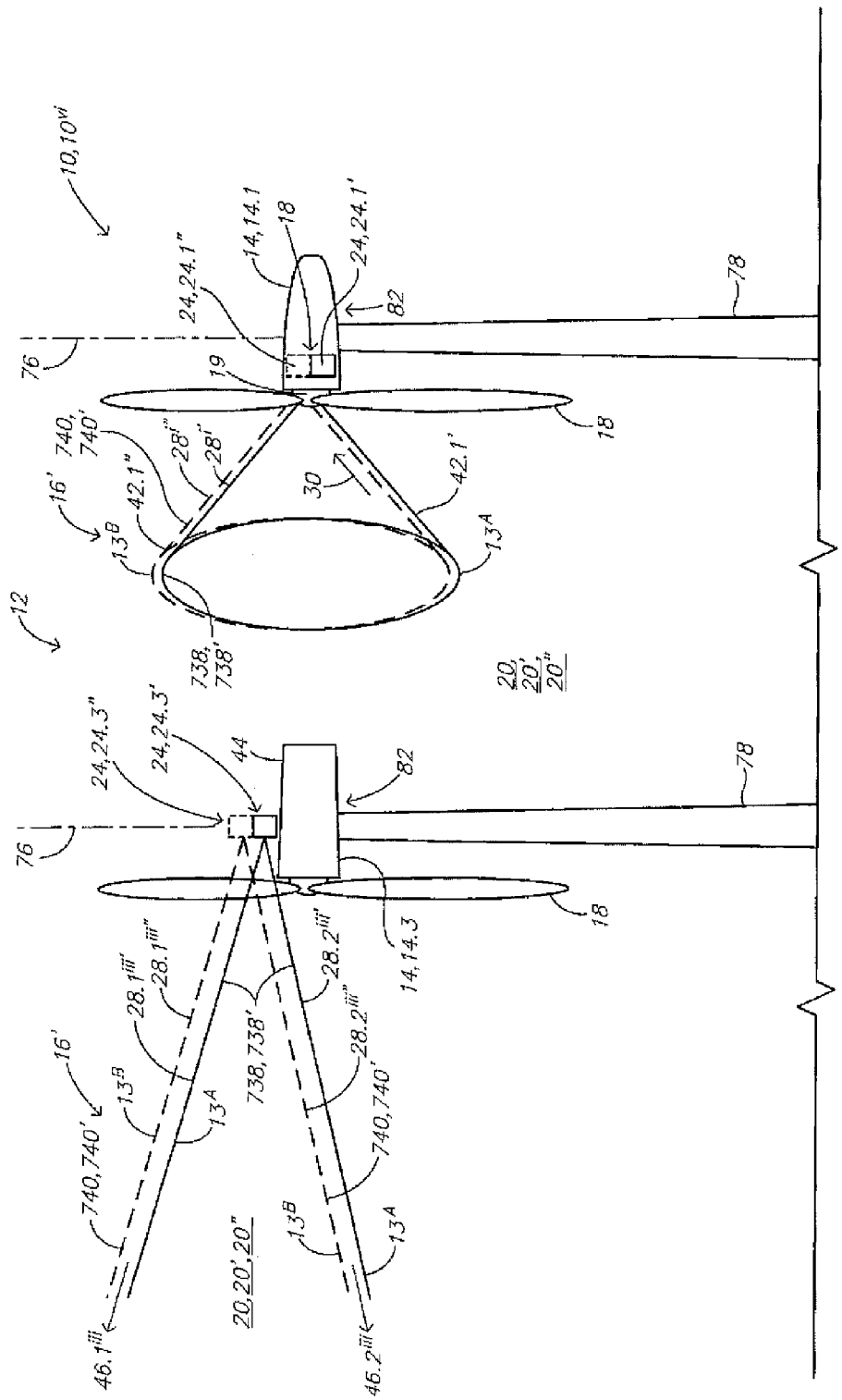
Figure 131:
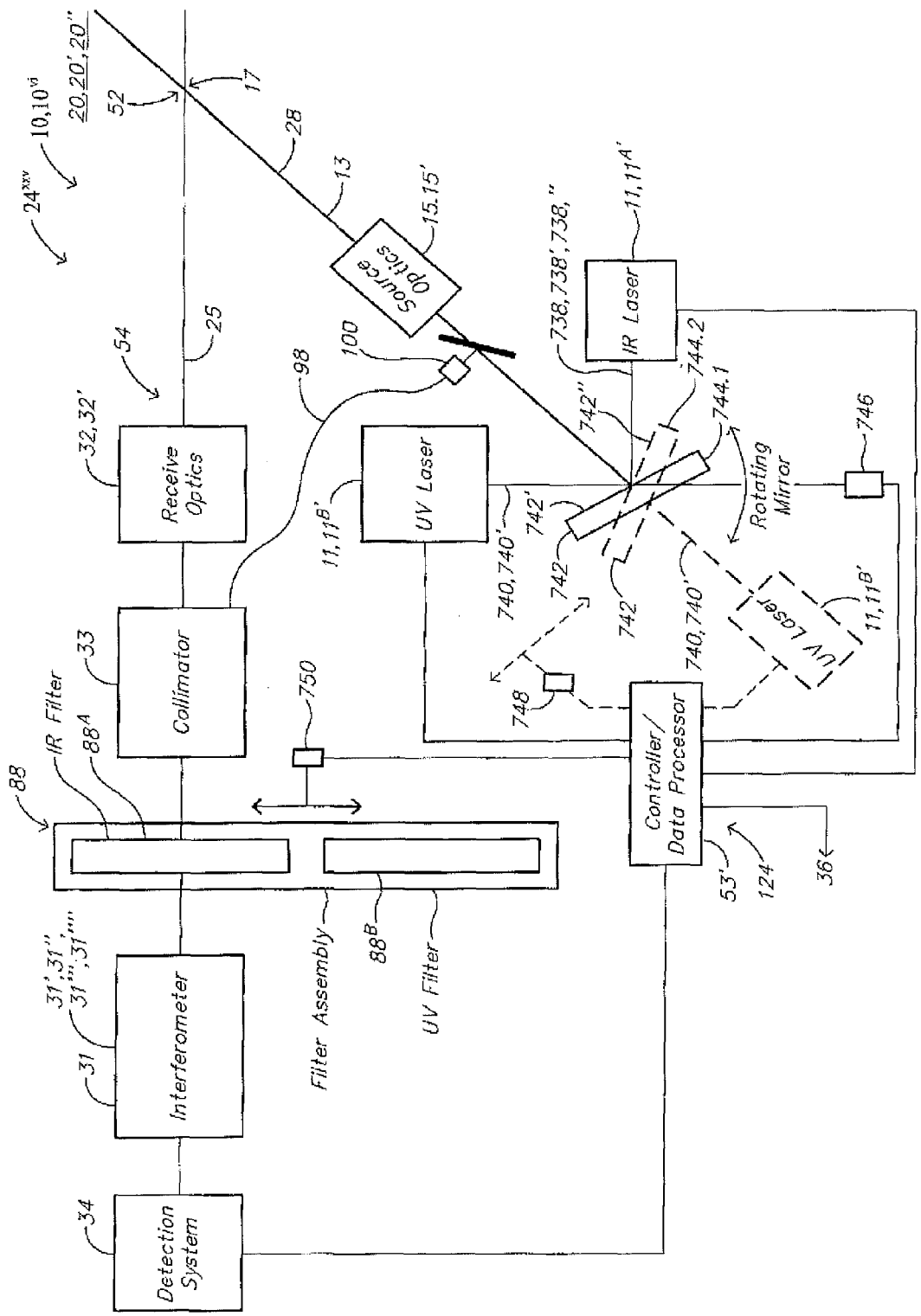
Figure 132:
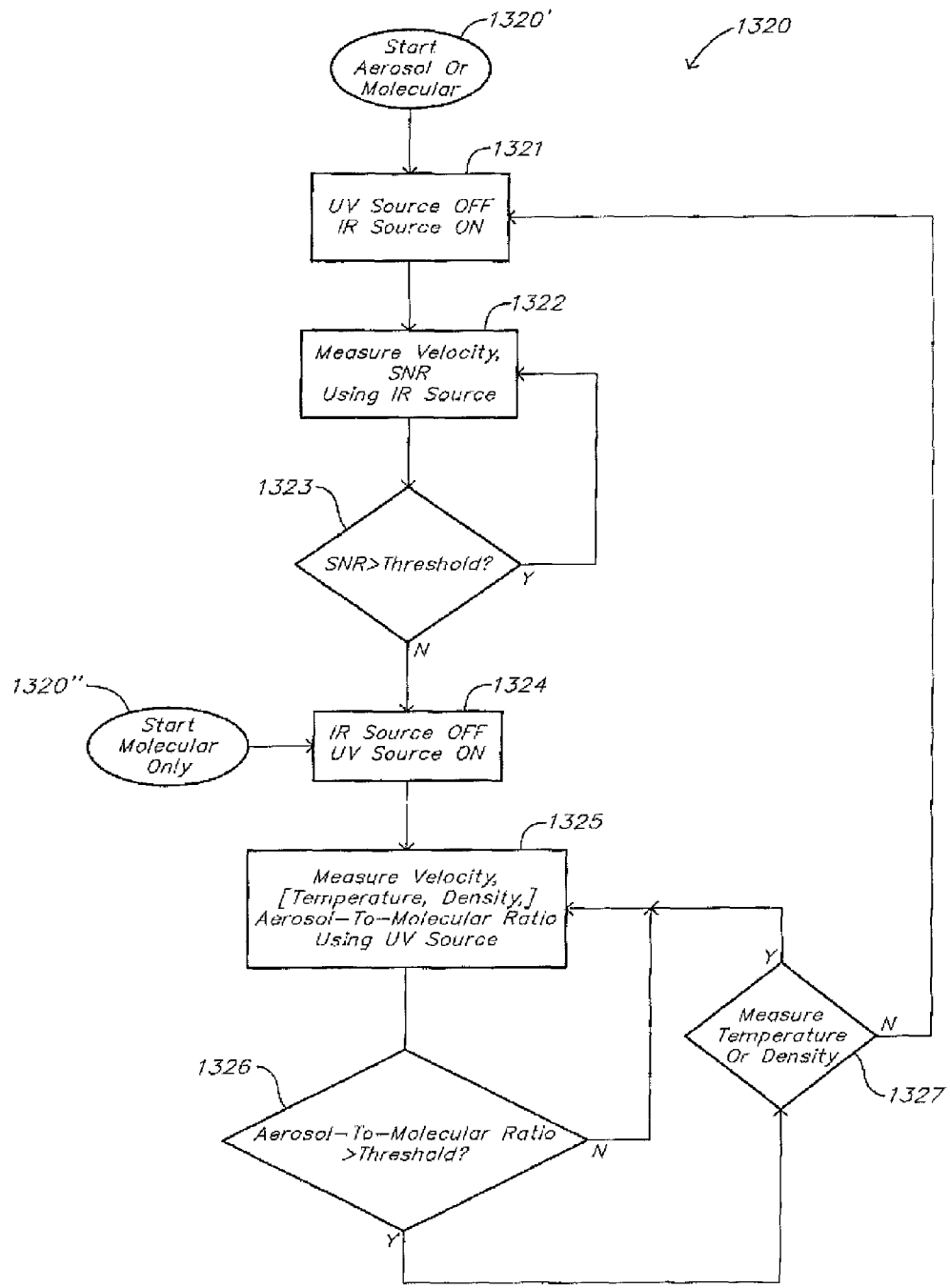
Figure 133:
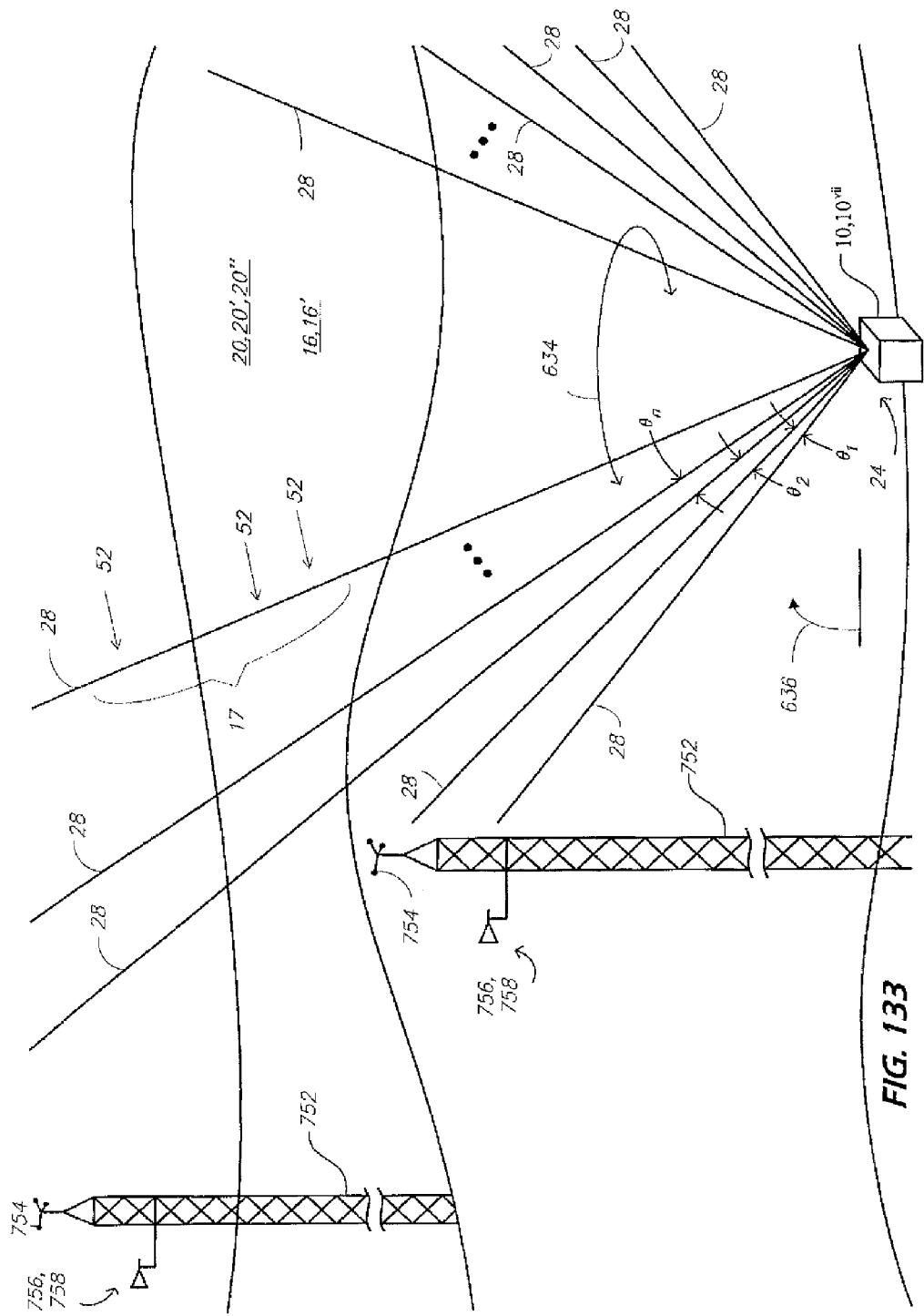
Figure 134:
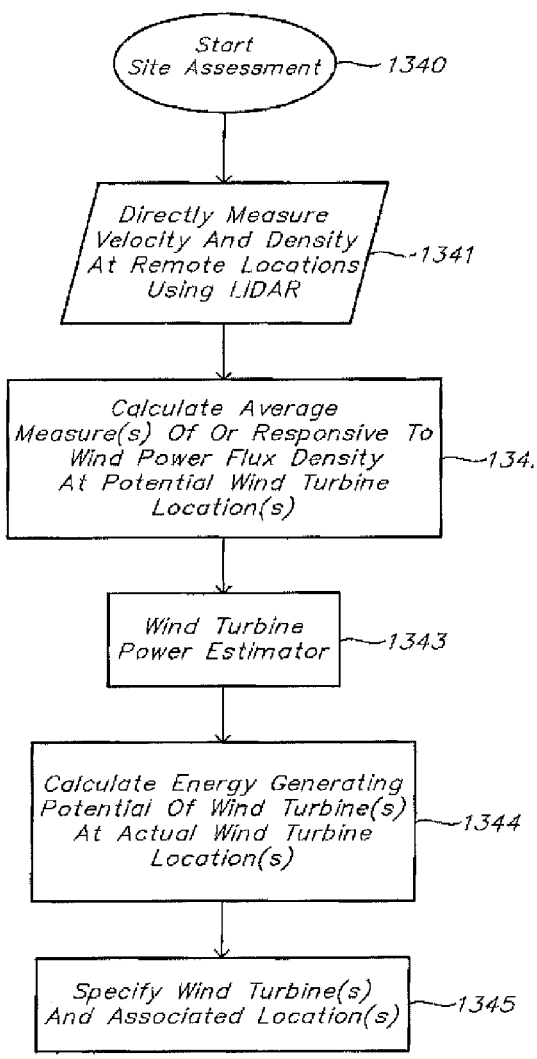
Figure 137:
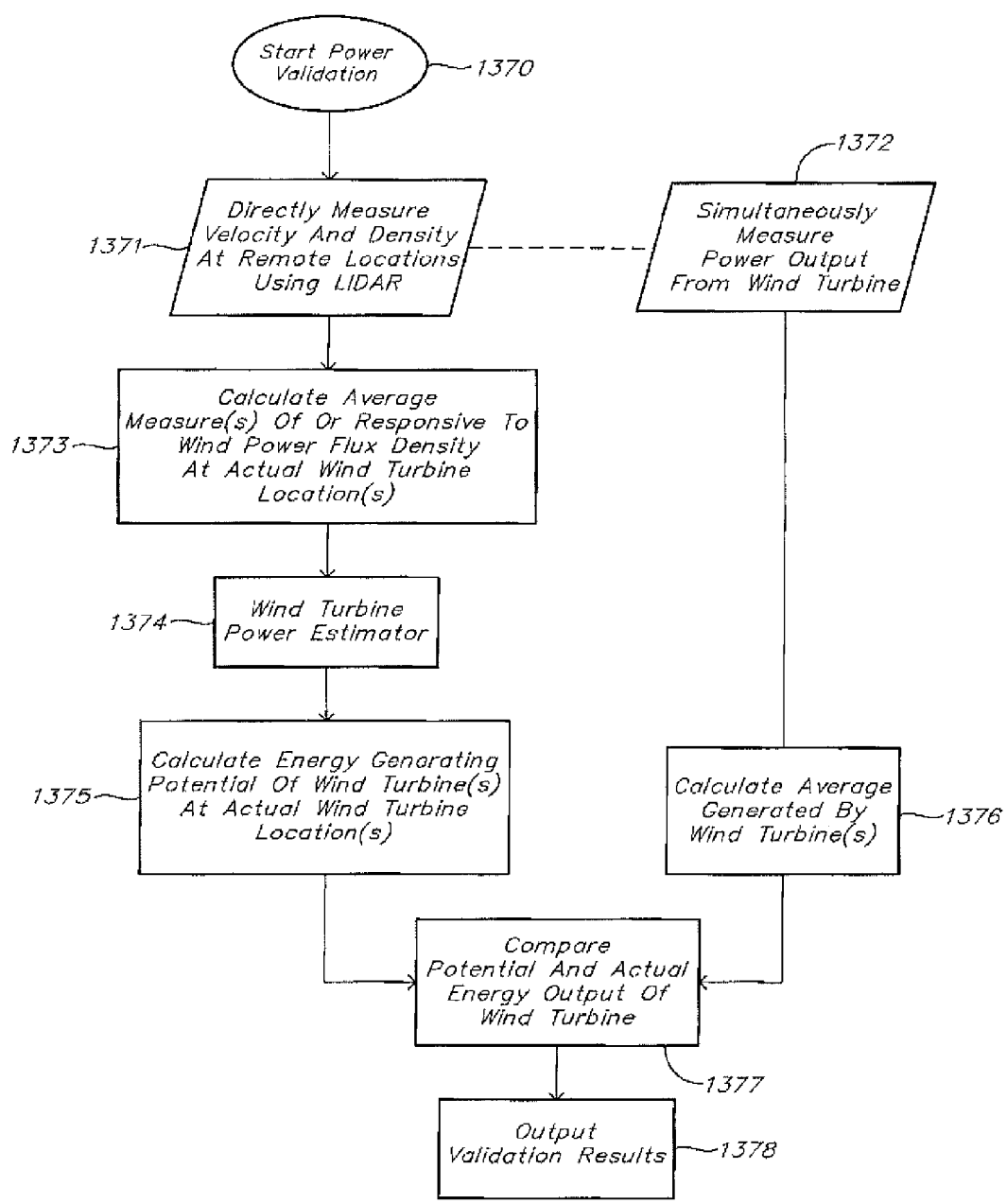

FIG. 117 illustrates a second aspect of an interferometer comprising a Michelson interferometer configured as Fourier Transform Spectrometer, used in cooperation with a fourth aspect of an associated detection system;

FIG. 118a illustrates a third aspect of an interferometer comprising a Spatial Heterodyne Spectrometer (SHS) used in cooperation with a fifth aspect of an associated detection system;

FIG. 118b illustrates the operation of each diffraction grating that is incorporated in the Spatial Heterodyne Spectrometer illustrated in FIG. 118a;

FIG. 119 illustrates a fourth aspect of an interferometer comprising a Doppler Asymmetric Spatial Heterodyne (DASH) Spectrometer used in cooperation with the fifth aspect of an associated detection system;

FIG. 120 illustrates output images of the fourth aspect of the interferometer illustrated in FIG. 119, for corresponding inputs comprising two light signals, one substantially monochromatic, and the other slightly Doppler-shifted with respect thereto;

FIG. 121 illustrates the output image of the fourth aspect of the interferometer illustrated in FIG. 119, for corresponding inputs comprising two light signals, one a temperature-broadened scattered light signal, the other slightly Doppler-shifted with respect thereto, together with a plot of the difference therebetween;

FIG. 122a illustrates a top view of an embodiment of the fourth aspect of the interferometer, portions of which are otherwise shown schematically in FIG. 119;

FIG. 122b illustrates a side view of the embodiment of the fourth aspect of the interferometer illustrated in FIG. 122a;

FIG. 122c illustrates a magnified view of the formation of the image illustrated in FIG. 122b;

FIGS. 123a and 123b illustrate a twentieth aspect of a LIDAR system incorporated in a second aspect of an atmospheric measurement system and an image associated therewith;

FIGS. 124a and 124b illustrate a first embodiment of a twenty-first aspect of a LIDAR system incorporated in a second aspect of an atmospheric measurement system and various images associated therewith, corresponding to the ninth aspect of the LIDAR system illustrated in FIG. 64 but with either a third or fourth aspect of the associated interferometer;

FIGS. 125a-125d illustrates a first embodiment of a twenty-second aspect of a LIDAR system incorporated in a second aspect of an atmospheric measurement system and various images associated therewith, corresponding to the fifteenth aspect of the LIDAR system illustrated in FIGS. 110a-110c and 110e but with either a third or fourth aspect of the associated interferometer;

FIGS. 126a and 126b illustrate a second embodiment of the twenty-first aspect of a LIDAR system incorporated in a second aspect of an atmospheric measurement system and various images associated therewith, corresponding to the thirteenth aspect of the LIDAR system illustrated in FIGS. 103a and 103c but with either a third or fourth aspect of the associated interferometer;

FIGS. 127a-127d illustrate a second embodiment of the twenty-second aspect of a LIDAR system incorporated in a second aspect of an atmospheric measurement system and various images associated therewith, corresponding to the sixteenth aspect of the LIDAR system illustrated in FIGS. 112a-112c and 112e and 113a-113c and 113e but with either a third or fourth aspect of the associated interferometer;

FIGS. 128a-128d illustrate a twenty-third aspect of a range-imaging LIDAR system incorporated in a first aspect of an atmospheric measurement system and various images associated therewith, corresponding to the eighth aspect of the LIDAR system illustrated in FIGS. 55a-55c and 55e but with either a third or fourth aspect of the associated interferometer;

FIGS. 129a and 129b illustrate a twenty-forth aspect of a range-imaging LIDAR system incorporated in a first aspect of an atmospheric measurement system and an image associated therewith, corresponding to the seventh aspect of the LIDAR system illustrated in FIG. 52 but with either a third or fourth aspect of the associated interferometer;

FIG. 130 illustrates a side view of a portion of the wind farm corresponding to FIG. 1, but illustrating two embodiments of a sixth aspect of an associated atmospheric measurement system, each embodiment incorporating a pair of LIDAR systems;

FIG. 131 illustrates a twenty-fifth aspect of a LIDAR system in accordance with an embodiment of the sixth aspect of the atmospheric measurement system providing for operation at a plurality of different wavelengths;

FIG. 132 illustrates a flow chart of an atmospheric measurement process using a dual-wavelength atmospheric measurement system;

FIG. 133 illustrates the application of a first embodiment of a seventh aspect of an atmospheric measurement system to wind turbine site assessment for purposes of determining a location for one or more wind turbines;

FIG. 134 illustrates a flow chart of a wind turbine site assessment process;

FIG. 135 illustrates the application of the first embodiment of the seventh aspect of an atmospheric measurement system to either wind turbine control or wind turbine power validation;

FIG. 136 illustrates the application of a second embodiment of the seventh aspect of an atmospheric measurement system to either wind turbine control or wind turbine power validation;

FIG. 137 illustrates a flow chart of a wind turbine power validation process; and FIG. 138 illustrates the application of the first embodiment of the seventh aspect of an atmospheric measurement system to the characterization of wake flow behind a wind turbine.

DESCRIPTION OF EMBODIMENT(S)

Figure 2:
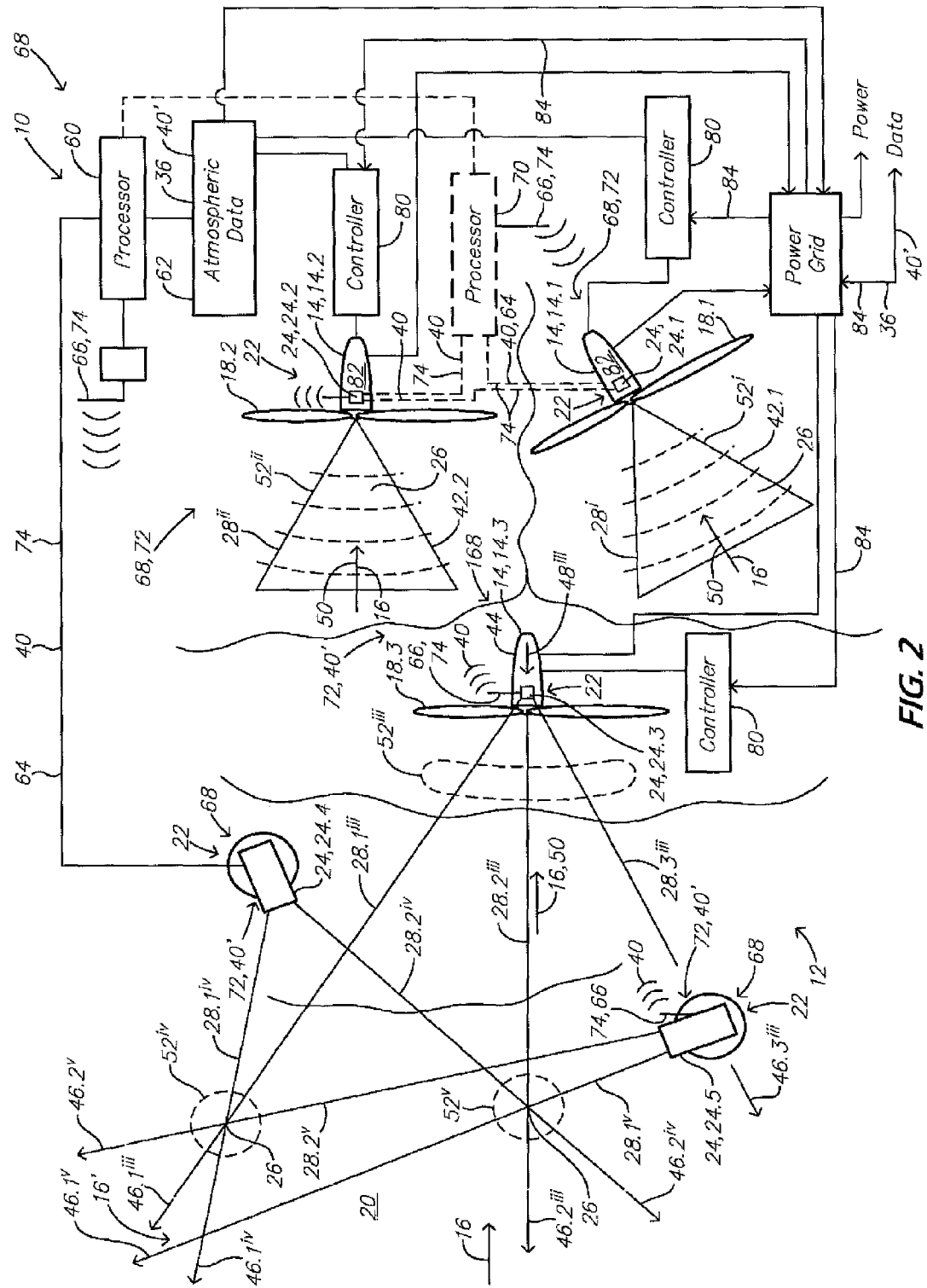
FIG. 2 illustrates a top view of the wind farm and associated atmospheric measurement system illustrated in FIG. 1.

Referring to FIGS. 1 and 2, an atmospheric measurement system 10 is illustrated in association with a wind farm 12 comprising a plurality of wind turbines 14 that are used to generate power, e.g. electrical power, from the wind 16.

For each wind turbine 14, the theoretical upper limit to the amount of wind power P* available for conversion to mechanical or electrical power is given by Betz' Law, i.e.

$$P^* = 0.5 * \rho * v^3 * A \qquad (1)$$

wherein the wind power P* is the power in units of watts of the wind 16 flowing at an effective wind speed v through the area A swept by the rotor 18 of the wind turbine 14, $\rho$ is the density of the atmosphere 20 in units of [kg m$^{-3}$], the effective wind speed v of the wind 16 is in units of [m s$^{-1}$], and the swept area A of the rotor 18 is in units of [m$^2$], with the wind 16 flowing in a direction normal to the swept area A.

More generally, for an arbitrary direction of wind 16 relative to the swept area A, the corresponding upper limit of wind power $\overline{P}$ flowing through the area A swept by the rotor 18 of the wind turbine 14 is given by the dot product of the wind power flux density $\overline{\psi}$ and the area vector $\overline{A}$ of the swept area A of the rotor 18 of the wind turbine 14, or $$P^* \overline{\psi} \cdot \overline{A} \qquad (2)$$

wherein the wind power flux density $\overline{\psi}$ is a vector pointing in the direction of the wind 16, having a magnitude of:

$$\|\overline{\psi}\| = 0.5 * \rho * v^3 \qquad (3)$$

with units of [watt m$^{-2}$], and the area vector $\overline{A}$ is a vector pointing in a direction that is normal to, and having a magnitude equal to, the swept area A of the rotor 18, wherein the associated wind power flux propagates in the direction of the wind power flux density $\overline{\psi}$ vector.

The direction and magnitude of wind power flux density $\overline{\psi}$ are a function of spatial coordinates, which can be expressed with respect to any suitable coordinate system, for example, Cartesian coordinates, i.e. $\overline{\psi}(x, y, z)$; spherical coordinates centered about the Earth i.e. $\overline{\psi}(r, \phi, \theta)$ with r being the distance from the center of the earth, $\phi$ being the angle of longitude, and $\theta$ being the angle of latitude; or ellipsoidal or oblate spheroidal coordinates that might better account for the shape of Earth's surface.

The atmospheric measurement system 10 provides for generating a measure of wind power flux density $\overline{\psi}$ over the geographic area of the wind farm 12, which can be used to predict an upper bound on power generating capability of each of the wind turbines 14 thereof, and which can accordingly be used for controlling the wind turbines 14 responsive thereto. More particularly, the atmospheric measurement system 10 comprises a network 22 of LIDAR systems 24, each of which provide for remotely sensing atmospheric data including wind speed v and atmospheric density ρ at one or more different range bins 26 along one or more associated beams of light 28 projected into the atmosphere 20, from scattered light 30 scattered by the atmosphere 20 from within the range bins 26 and received by associated receive optics 32, e.g. one or more telescopes 32', of each LIDAR system 24 that cooperate with one or more associated detection systems 34. For example, each LIDAR system 24 may be constructed and operated in accordance with the teachings of any of the following: U.S. patent application Ser. No. 11/460,603 filed on 27 Jul. 2006 that issued as U.S. Pat. No. 7,495,774 on 24 Feb. 2009, entitled Optical Air Data System; International Application Serial No. PCT/US10/31965 filed on 21 Apr. 2010, entitled Atmospheric measurement system; U.S. application Ser. No. 12/780,895 filed on 15 May 2010, entitled Range imaging LIDAR U.S. Provisional Patent Application Ser. No. 61/266,916, filed on Dec. 4, 2009, entitled Direct Detection LIDAR; and U.S. Provisional Patent Application Ser. No. 61/290,004, filed on Dec. 24, 2009, entitled LIDAR Signal Processing System and Method, all of which above-identified patents and patent applications are incorporated herein by reference in their entirety.

For each beam of light 28, and within each associated range bin 26 thereof, the associated LIDAR system 24 provides for measuring corresponding atmospheric data 36, including a component of wind speed v in a direction along the beam of light 28 responsive to a Doppler shift in the frequency of the scattered light 30 by either or both molecular or aerosol components of the atmosphere 20, and including associated atmospheric data scalars of atmospheric temperature T, atmospheric density ρ, molecular counts $N_M$, aerosol counts $N_A$ and background counts $N_B$ at a given sampling times, wherein the particular sampling times $t_i$ are also measured, for example, using an associated GPS receiver 38 that provides a corresponding universal time reference, so as to provide for accounting for the dynamic behavior of the associated atmospheric data. Accordingly, in an atmospheric measurement system 10 adapted to generate a measure of wind power flux density $\overline{\psi}$ over a geographic area, each associated LIDAR system 24 provides for generating an atmospheric measurement record 40 for each range bin 26 at each sampling time $t_i$ that includes at least an identification or nominal location of the associated range bin 26, the extent, e.g. length, of the range bin 26, the sampling time $t_i$, the magnitude and direction of the component of wind speed v in the direction along the beam of light 28, the local density ρ of the atmosphere 20, and may also include measurements of the other atmospheric data scalars identified herein, for example, temperature. As another example, in some embodiments, water vapor is also measured and the measurement of water vapor is also included in the atmospheric measurement record 40.

In the example of the atmospheric measurement system 10 and wind farm 12 illustrated in FIGS. 1 and 2, two of the wind turbines 14.1, 14.2 are illustrated with associated LIDAR systems 24.1, 24.2 incorporating corresponding beams of light $28^i$, $28^{ii}$ that emanate from a central region of the rotors 18 of the associated wind turbines 14.1, 14.2—for example, from the hubs 19 thereof—and that rotate therewith so that the respective associated beams of light 28 sweep out corresponding conical surfaces of revolution 42.1, 42.2, wherein different wind turbines 14.1, 14.2 are illustrated pointing in different directions, for example, responsive to spatial variations of the associated wind field 16', with the associated conical surfaces of revolution 42.1, 42.2 aligned with the associated rotors 18.1, 18.2 pointing in the corresponding different directions. The LIDAR system 24 can also be decoupled from the hub 19, providing fixed beams of light 28 pointing in different directions. Anywhere from one to six beams of light 28 would be typical. In one embodiment, a single beam of light 28 is aligned with the axis of rotation of the wind turbine. The beam of light 28 can be either aligned with and along the axis of rotation or transversely offset relative thereto. A third wind turbine 14.3 is illustrated with an associated LIDAR system 24.3 relatively fixed to the nacelle 44 thereof and incorporating three associated fixed beams of light $28.1^{iii}$, $28.2^{iii}$, $28.3^{iii}$ directed in three corresponding different directions $46.1^{iii}$, $46.2^{iii}$, $46.3^{iii}$, wherein the beams of light $28.1^{iii}$, $28.2^{iii}$, $28.3^{iii}$ along the associated directions $46.1^{iii}$, $46.2^{iii}$, $46.3^{iii}$ turn with the nacelle 44 as the direction $48^{iii}$ of the nacelle 44 is changed to accommodate changes in the local direction 50 of the wind 16. The atmospheric measurement system 10 is also illustrated with additional LIDAR systems 24.4, 24.5 that are separate from the wind farm 12, for example, upstream thereof in the associated wind field 16' so as to provide associated atmospheric data 36 of wind 16 in advance of the interaction thereof with the wind turbines 14.1, 14.2, 14.3 located downstream thereof. For example, a fourth LIDAR system 24.4 is illustrated incorporating two associated beams of light $28.1^{iv}$, $28.2^{iv}$ in two corresponding different directions $46.1^{iv}$, $46.2^{iv}$, and a fifth LIDAR system 24.5 is illustrated also incorporating two associated beams of light $28.1^{v}$, $28.2^{v}$ in two corresponding different directions $46.1^{v}$, $46.2^{v}$.

Generally, the determination of wind direction and the total magnitude of wind speed v requires at least three measures of associated wind speed v in three linearly independent directions. This can be provided either by a single LIDAR system 24 with an associated beam or beams of light 28 and associated receive optics 32 looking in at least three linearly independent directions, or a plurality of different LIDAR system 24 that collectively incorporate associated beams of light 28 and associated receive optics 32 collectively looking in at least three linearly independent directions, such that the wind field 16' being measured by the LIDAR system or systems 24 is assumed to be relatively uniform for each group of separate associated measurements, for example, each group of three measurements in three associated linearly independent directions.

Figure 3:
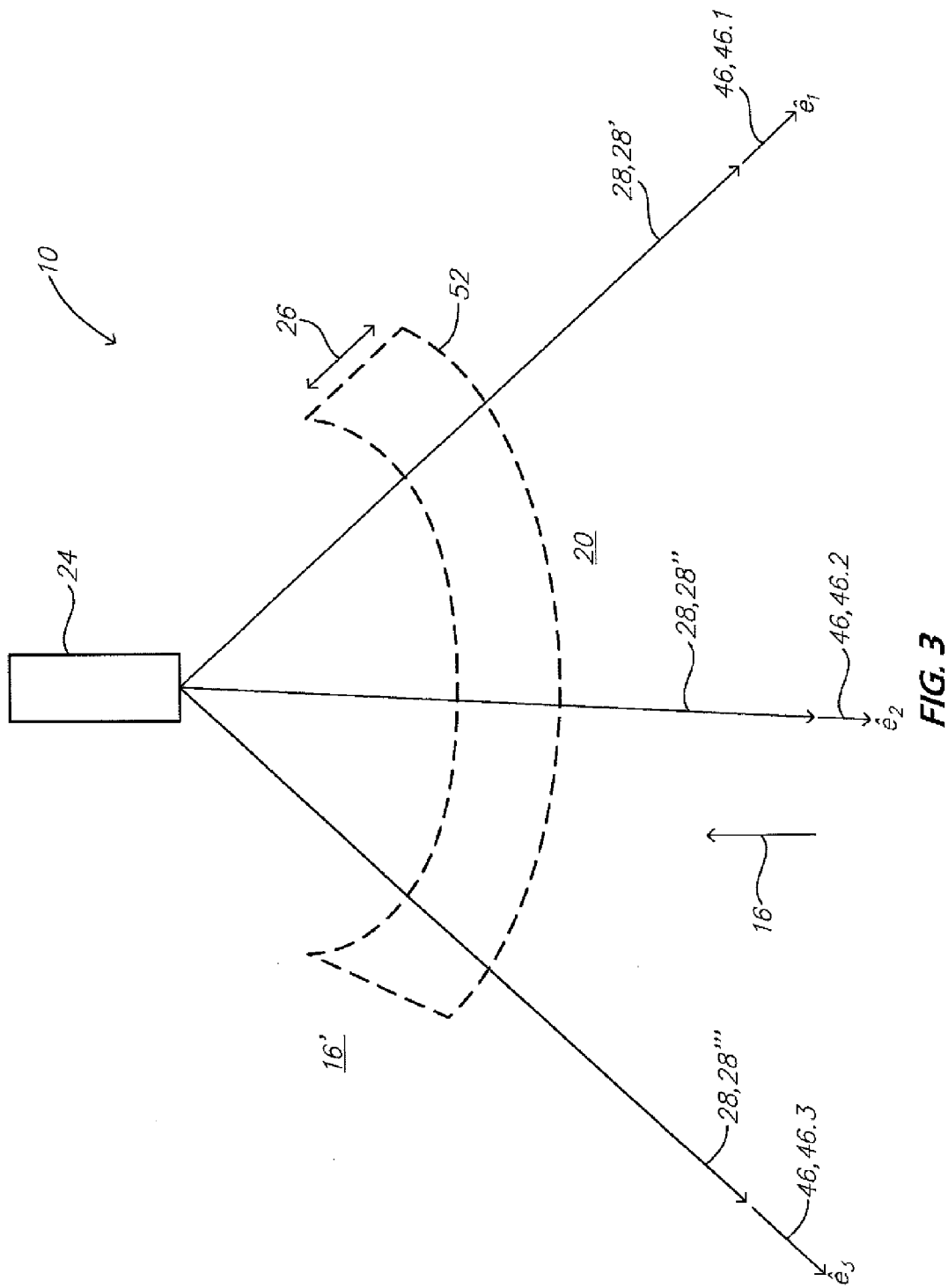
FIG. 3 illustrates a LIDAR system of an atmospheric measurement system, and an associated measurement volume.

For example, in accordance with a first aspect, referring to FIGS. 1, 2 and 3, for a single LIDAR system 24 with either a single beam of light 28 projected into the atmosphere 20 at three different times in three different linearly independent directions 46, or three separate beams of light 28', 28", 28''' projected into the atmosphere 20 substantially simultaneously in three different linearly independent directions 46.1, 46.2, 46.3, the resulting three measurements of wind speed v for the associated range bin 26 can be combined to provide a vector measure of wind velocity $\overline{v}$ for the associated measurement volume 52 if the wind field 16' is relatively uniform within measurement volume 52 during the period of time over which the associated measurements are made with the LIDAR system 24. For example, the first aspect illustrated in FIG. 3 is representative of the measurement volumes $52^i$, $52^{ii}$, $52^{iii}$ associated with the first 24.1, second 24.2 and third 24.3 LIDAR systems illustrated in FIGS. 1 and 2, wherein for the first 24.1 and second 24.2 LIDAR systems the three separate beams of light 28', 28", 28''' illustrated in FIG. 3 correspond to the respective single beams of light $28^i$, $28^{ii}$ illustrated in FIGS. 1 and 2 at three distinct points in time corresponding to three distinct rotational angles of the corresponding rotors 18 of the corresponding wind turbines 14.1, 14.2; and for the third LIDAR system 24.3, the three separate beams of light 28', 28", 28'" illustrated in FIG. 3 correspond to the respective associated three separate beams of light $28.1^{iii}$, $28.2^{iii}$, $28.3^{iii}$ illustrated in FIGS. 1 and 2 at a substantially common point in time. The resolution and accuracy of the resulting measure of wind velocity $\overline{v}$ will depend upon the relative separation and independence of the associated directions 46.1, 46.2, 46.3 of the beams of light 28', 28", 28'" from which the measurement is derived. For example, to be independent, the three beams of light 28', 28", 28'" cannot all lie in the same plane. The resulting measure of wind velocity $\overline{v}$ is improved with increasing mutual angles of separation of the associated beams of light 28', 28", 28'". The resolution and accuracy of the resulting measure of wind velocity $\overline{v}$ will also depend upon the variation of actual wind velocity $\overline{v}$ within the measurement volume 52 during the associated measurement interval. For example, for the first 24.1 and second 24.2 LIDAR systems, this is dependent both upon the spatial extent of the associated conical surfaces of revolution 42.1, 42.2, and the temporal extent between the first and last rotational positions of the associated rotors 18 and associated respective beams of light $28^i$, $28^{ii}$ associated with the corresponding beams of light 28', 28", 28'" for which the measurements of wind speed v are made, and upon the associated change in wind velocity $\overline{v}$ over both these associated spatial and temporal extents.

With three separate beams of light 28', 28", 28'" emanating from a common LIDAR system 24, the spatial extent of the measurement volume 52 and the associated separation between wind speed v measurements grows with range from the LIDAR system 24, thereby increasing the prospects for variation in associated actual wind velocity $\overline{v}$ within the measurement volume 52 with increasing range, which could thereby reduce the accuracy of a resulting associated measurement of wind velocity $\overline{v}$ from the associated wind speed v measurements. For example, it is not uncommon to have a substantial variation of actual wind speed v between the top and bottom of the path of the associated rotor 18 during the rotation thereof.

Figure 4:
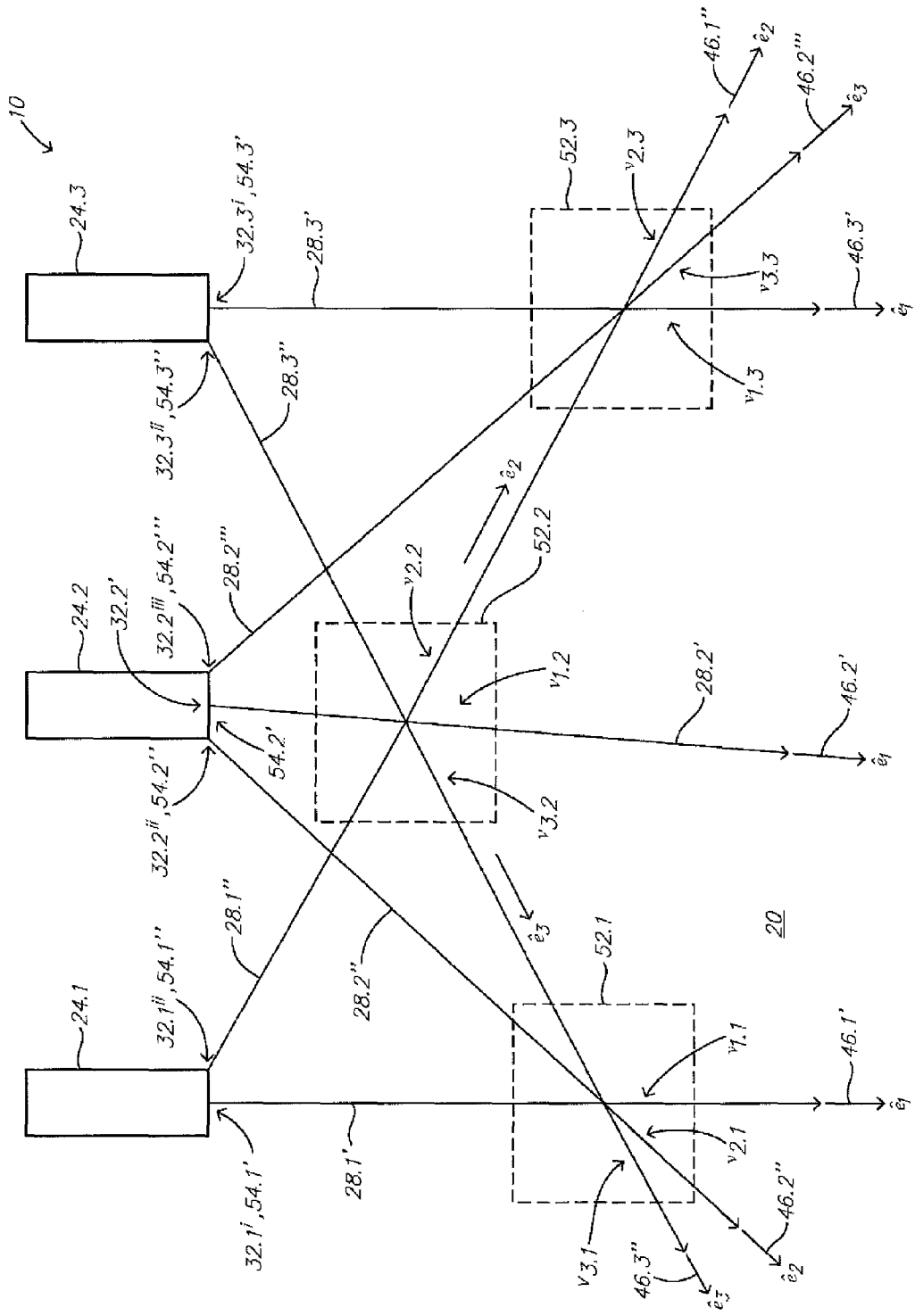
FIG. 4 illustrates a plurality of LIDAR systems of an atmospheric measurement system, and a plurality of associated measurement volumes in common therewith.

In accordance with a second aspect, referring to FIGS. 1, 2 and 4, the LIDAR systems 24 may be used in cooperation with one another so as to provide for a plurality of different beams of light 28', 28", 28'" in different directions from different LIDAR systems 24.1, 24.2, 24.3 directed through a common measurement volume 52, and with associated receive optics 32 of the different LIDAR systems 24.1, 24.2, 24.3 having associated different fields-of-view 54.1, 54.2, 54.3 (with different superscripts ', ", and '" associated with different beams of light 28', 28", 28'" from each of the LIDAR systems 24.1, 24.2, 24.3) that each intersect one another within the common measurement volume 52 so as to receive scattered light 30 therefrom, and thereby collectively provide for generating three different corresponding measures of wind speed $v_1$, $v_2$, $v_3$ from three different associated directions 46.1, 46.2, 46.3 for the common measurement volume 52, from which an associated wind velocity $\overline{v}$ can be determined that is substantially unaffected by either spatial or temporal variations in actual wind velocity $\overline{v}$ if the measures of wind speed $v_1$, $v_2$, $v_3$ are sufficiently simultaneous relative to any temporal variation of the wind field 16' within the measurement volume 52. The size of the common measurement volume 52, and therefore the spatial resolution of the resulting measurement of wind velocity $\overline{v}$, depends upon the extent to which the different beams of light 28', 28", 28'" and the associated different fields-of-view 54.1, 54.2, 54.3 of the associated receive optics 32 intersect one another, and the relative angles thereof, within the common measurement volume 52.

To the extent that the different beams of light 28', 28", 28'" or the associated different fields-of-view 54.1, 54.2, 54.3 of the associated receive optics 32 do not all intersect one another within the common measurement volume 52, or to the extent that all of the associated measures of wind speed $v_1$, $v_2$, $v_3$ are not generated simultaneously, then the accuracy of the resulting measure of wind velocity $\overline{v}$ as determined from the measures of wind speed $v_1$, $v_2$, $v_3$ will be affected by both the spatial and temporal variation of actual wind velocity $\overline{v}$ from an assumed uniform common actual wind velocity $\overline{v}$ that is otherwise assumed to be associated with the measures of wind speed $v_1$, $v_2$, $v_3$.

Referring in particular to FIG. 4, there is illustrated a group of three LIDAR systems 24.1, 24.2, 24.3 in cooperation with one another so as to provide for generating three different measures of wind velocity $\overline{v}_1$, $\overline{v}_2$, $\overline{v}_3$ from three corresponding different measurement volumes 52.1, 52.2, 52.3, substantially independent of spatial and temporal variations of the associated wind field 16'. More particularly, each of the LIDAR systems 24.1, 24.2, 24.3 respectively projects a corresponding respective first beam of light 28.1', 28.2', 28.3' into the respective corresponding measurement volume 52.1, 52.2, 52.3 substantially in front of the corresponding respective LIDAR system 24.1, 24.2, 24.3, and each LIDAR system 24.1, 24.2, 24.3 incorporates a respective corresponding first set of receive optics $32.1^i$, $32.2^i$, $32.3^i$, each having a respective corresponding associated, fields-of-view 54.1', 54.2', 54.3' that intersect the respective corresponding first beam of light 28.1', 28.2', 28.3' within the respective corresponding measurement volume 52.1, 52.2, 52.3 so as to provide for measuring a respective corresponding first component of wind speed $v_{1.1}$, $v_{1.2}$, $v_{1.3}$ therewithin along a respective corresponding first direction 46.1', 46.2', 46.3'. The first LIDAR system 24.1 also projects a second beam of light 28.1" through the second 52.2 and third 52.3 measurement volumes, and incorporates a second set of receive optics $32.1^{ii}$ having associated fields-of-view 54.1" that intersect the second beam of light 28.1" within the second 52.2 and third 52.3 measurement volumes so as to provide for measuring respective corresponding second components of wind speed $v_{2.2}$, $v_{2.3}$ therewithin along a corresponding second direction 46.1". The second LIDAR system 24.2 also projects a second beam of light 28.2" through the first measurement volume 52.1 and incorporates a second set of receive optics $32.2^{ii}$ having an associated field-of-view 54.2" that intersects the second beam of light 28.2" within the first measurement volume 52.1 so as to provide for measuring a corresponding second component of wind speed $v_{2.1}$ therewithin along a corresponding second direction 46.2". Furthermore, the second LIDAR system 24.2 also projects a third beam of light 28.2'" through the third measurement volume 52.3, and incorporates a third set of receive optics $32.2^{iii}$ having an associated field-of-view 54.2'" that intersects the third beam of light 28.2'" within the third measurement volume 52.3 so as to provide for measuring a corresponding third component of wind speed $v_{3.3}$ therewithin along a corresponding third direction 46.2'". The third LIDAR system 24.3 also projects a second beam of light 28.3" through the second 52.2 and first 52.1 measurement volumes, and incorporates a second set of receive optics $32.3^{ii}$ having associated fields-of-view 54.3" that intersect the second beam of light 28.3" within the second 52.2 and first 52.1 measurement volumes so as to provide for measuring respective corresponding third components of wind speed $v_{3.2}$, $v_{3.3}$ therewithin along a corresponding second direction 46.3". The associated beams of light 28.1', 28.2", 28.2', 28.2", 28.3''', 28.3', 28.3" are configured so that the associated directions 46.1', 46.2" and 46.3" are linearly independent (i.e. not all in the same plane) within the first measurement volume 52.1, the associated directions 46.2', 46.1" and 46.3" are linearly independent (i.e. not all in the same plane) within the second measurement volume 52.2, and the associated directions 46.3', 46.1" and 46.2''' are linearly independent (i.e. not all in the same plane) within the third measurement volume 52.3, so as to provide for determining a first measure of wind velocity $\bar{v}_1$ from the first $v_{1.1}$, second $v_{2.1}$ and third $v_{3.1}$ components of wind speed within the first measurement volume 52.1, determining a second measure of wind velocity $\bar{v}_2$ from the first $v_{1.2}$, second $v_{2.2}$ and third $v_{3.2}$ components of wind speed within the second measurement volume 52.2, and determining a third measure of wind velocity $\bar{v}_3$ from the first $v_{1.3}$, second $v_{2.3}$ and third $v_{3.3}$ components of wind speed within the third measurement volume 52.3. For example, the second aspect illustrated in FIG. 4 is representative of the measurement volumes $52^{iv}$, $52^{v}$ associated with the third 24.3, fourth 24.4 and fifth 24.5 LIDAR systems illustrated in FIGS. 1 and 2.

Generally, each LIDAR system 24 may provide for one or more beams of light 28 and associated fields-of-view 54, and any number of distinct beams of light 28 and associated fields-of-view 54 from different LIDAR systems 24 may be associated with each measurement volume 52. The configurations illustrated in FIGS. 1-4 are not intended to be limiting. For example, the a particular LIDAR systems 24.3, 24.4, 24.5 illustrated in FIGS. 1 and 2, or the LIDAR systems 24.1, 24.2, 24.3 illustrated in FIG. 4, with associated distinct beams of light 28 could each incorporated more than three distinct fields-of-view 54, for example, using the same number of fixed beams of light 28 or a fewer number of beams of light 28 whose position or direction is varied over time. Furthermore, there could be more than three associated fields-of-view 54 associated with any of the associated measurement volumes $52^{iii}$, $52^{iv}$, $52^{v}$, 52.1, 52.2, 52.3. As a further example, for either the first 14.1 or second 14.2 wind turbine illustrated in FIGS. 1 and 2, the beams of light 28 associated therewith could be adapted to sweep out a plurality of conical surfaces of revolution 42, or a more general pattern, by varying the angle of the beam of light 28 relative to the axis of rotation of the associated wind turbine 14. Furthermore, the associated LIDAR systems 24 of the atmospheric measurement system 10 may incorporate, or be incorporated in, a variety of platforms, including, but not limited to fixed, portable, or mobile platforms, the latter of which include land vehicles, aircraft, balloons and satellites, wherein for each platform, the associated one or more beams of light 28 of the associated LIDAR system 24 may be either fixed or positionable relative to the associated platform, the latter of which includes either positioning at discrete orientations or continuous scanning.

The location of a particular measurement volume 52 and the value of the associated measure of wind velocity $\bar{v}$ collectively depend upon the locations of the associated LIDAR systems 24 and the associated directions 46.1, 46.2, 46.3 of the associated beams of light 28 and the directions of the fields-of-view 54 of the associated receive optics 32. Accordingly, the accuracy to which the locations of the associated LIDAR systems 24, the directions 46.1, 46.2, 46.3 of the associated beams of light 28, and the directions of the fields-of-view of the 54 of the associated receive optics 32 are known or measured, and the variability thereof, will affect the accuracy and variability of the resulting calculated location of the associated measurement volume 52 and the resulting calculated measure of wind velocity $\bar{v}$ associated therewith.

When a plurality of different LIDAR systems 24 are associated with a particular measurement volume 52, then the resulting accuracy and variability of the associated calculated location of the associated measurement volume 52 and the calculated measure of wind velocity $\bar{v}$ associated therewith will depend upon the collective accuracy and variability of the underlying locations and directions of the associated plural LIDAR systems 24, wherein for a given level of accuracy and variability, the resulting level of accuracy needed for each associated LIDAR system 24 decreases as the number of associated LIDAR systems 24 is increased.

Depending upon the underlying structure to which the LIDAR system 24 is mounted, the location of the LIDAR system 24 can be influenced by the local winds. For example, although commercial wind turbines 14 can be impressive structures, they should not necessarily be considered to be stationary. Large wind loads can cause the associated towers to bend and sway, thereby changing the associated LIDAR look angles and location, respectively, of an associated LIDAR system 24 mounted thereon. Changes in the LIDAR look angle(s) will produce errors in reporting the measurement vector resulting in relatively larger altitude errors at relatively longer ranges. Sway of the LIDAR system 24 causes an error in the resulting measure of wind velocity $\bar{v}$.

However, these errors may be accounted for by measuring the motion of each LIDAR system 24 with associated sensors responsive to bending and swaying of the underlying platform. The selection of the sensors will depend upon the dynamics of the particular platform. For example, for a mobile platform, an Inertial Measurement Unit, IMU, might be required to provide the necessary platform orientation, location and velocity information. In other situations, such as a portable or stationary scenario, a simple tilt sensor coupled with a compass or some other method of determining an azimuth might be sufficient. There are entire suites of sensors and techniques that may be used depending upon the platform dynamics and the required measurement accuracy. The associated measurements from each LIDAR system 24 can then be corrected to account the underlying movement thereof, for example, by transforming the locations of the associated measurements to locations in either an absolute coordinate system or an earth-fixed coordinate system responsive to measurements of the motion of the underlying platform.

Given a measure of three independent wind speed $v_1$, $v_2$, $v_3$ components of a common wind velocity $\bar{v}$ within a particular measurement volume 52 along respective directions 46.1, 46.2, 46.3 represented by associated respective unit vectors $\hat{e}_1$, $\hat{e}_2$, $\hat{e}_3$, the corresponding wind velocity $\bar{v}$ is given by:

$$\bar{v} = \begin{bmatrix} \hat{e}_1 \\ \hat{e}_2 \\ \hat{e}_3 \end{bmatrix}^{-1} \cdot \begin{bmatrix} v_1 \\ v_2 \\ v_3 \end{bmatrix} \qquad (4)$$

If more than three wind speed v measurements are available for a particular measurement volume 52—for at least three linearly independent directions 46, i.e. not all in the same plane—then the corresponding wind velocity $\bar{v}$ can be solved therefrom, for example, using linear regression.

The LIDAR systems 24 provide for determining wind velocity $\bar{v}$ at each of the associated measurement volumes 52 from a combination of measurements along separate directions 46; and for determining a measure of atmospheric density $\rho$ associated with each measurement within each measurement volume 52, which can be averaged to provide for a single associated averaged measure of atmospheric density ρ for each measurement volume 52. Accordingly, the LIDAR systems 24 provide for determining the associated wind power flux density $\overline{\psi}$, the magnitude of which is given by Equation (3), the direction of which is given by that of the associated wind velocity $\overline{v}$, i.e.:

$$\overline{\psi}^* = 0.5 * \rho * v^2 \cdot \overline{v} \tag{5}$$

where:

$$v = \|\overline{v}\| \tag{6}$$

In addition to vector measures of wind velocity $\overline{v}$ and wind power flux density $\overline{\psi}$, and the associated scalar magnitudes thereof, and the atmospheric data scalar atmospheric density ρ, the associated LIDAR systems 24 provide for generating measures of atmospheric data scalars of atmospheric temperature T, molecular counts $N_M$, aerosol counts $N_A$ and background counts $N_B$, which, together with a measure of the associated sampling times $t_i$, for example, using an associated GPS receiver 38, can be stored for each measurement volume 52 so as to provide for a map of atmospheric data over space and time, which can be used for anticipatory control of the associated wind farm 12 and the associated power grid 56 supplied therefrom, or for other applications, such as weather forecasting. Depending upon the location, size and number of measurement volumes 52, the associated atmospheric measurement system 10 can provide for detecting associated atmospheric turbulence so as to provide for warning if turbulence—for example, as a from an approaching boundary layer interface 58—exceeds or is expected to exceed acceptable associated turbine-dependent threshold levels for the wind turbines 14 of the wind farm 12, so as to prevent turbulence-induced fatigue or damage to the wind turbines 14.

Figure 5:
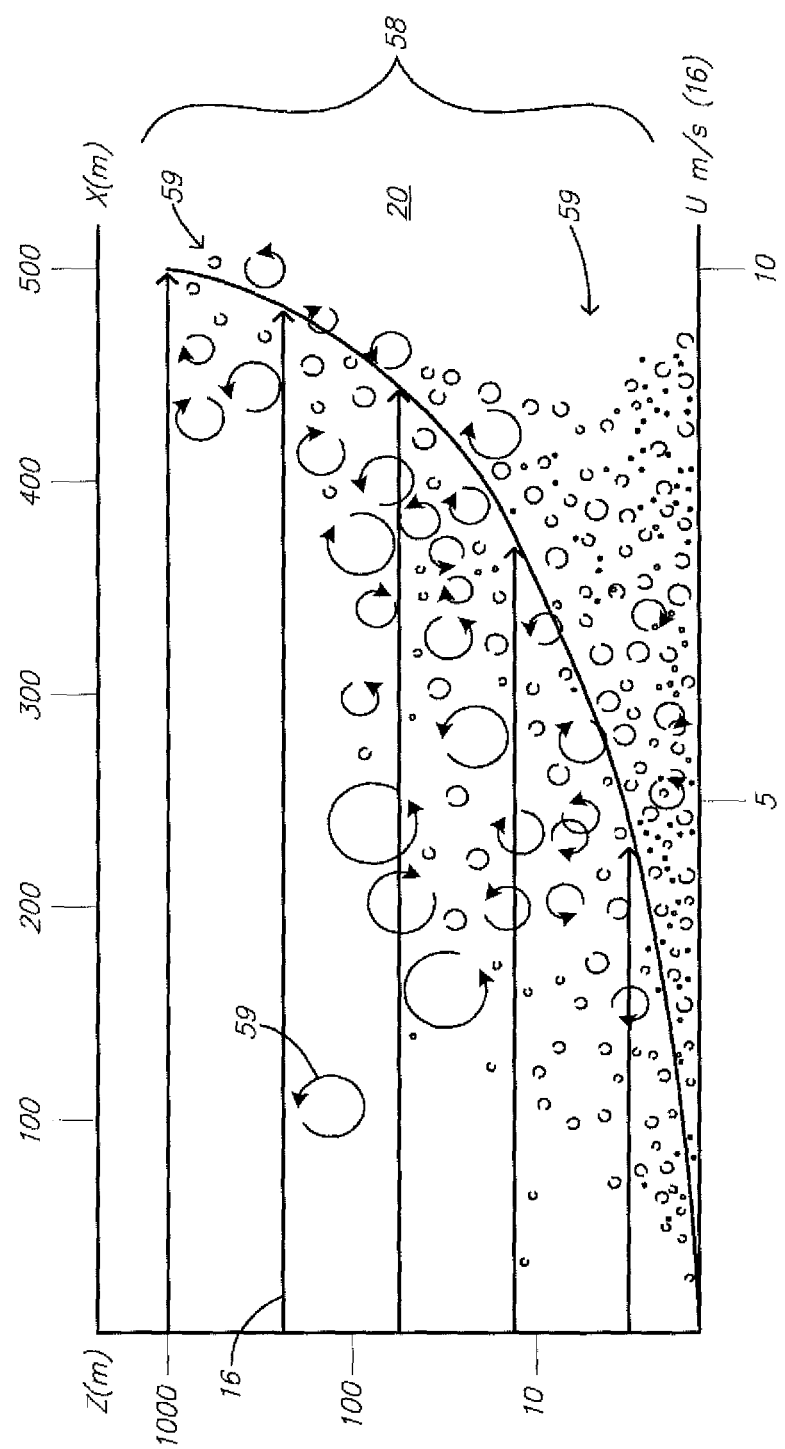
FIG. 5 illustrates a planetary boundary layer containing turbulent eddies generated either by associated surface roughness or by thermal gradients.

Referring to FIG. 5, from Robert A. Brown, *Fluid Mechanics of the Atmosphere*, Academic Press, Inc., New York, 1991, which is incorporated herein by reference, turbulence is a random velocity fluctuation from the mean wind speed and direction, wherein associated turbulent elements are vortex elements of variable size and strength and associated turbulent eddies 59 provide for transporting fluid properties in random motion and associated properties are exchanged by rapid mixing.

In general, wind turbines 14 are pointed in a direction 48 to receive the main flow of wind 16 from the associated wind field 16', so that an associated LIDAR system 24 mounted on a wind turbine 14 and looking towards incoming the wind 16 is positioned optimally to measure the wind speed v directed at the wind turbine 14. However, turbulence or a velocity component that is perpendicular to the main flow could potentially damage the wind turbine 14, but might not be detectable by a LIDAR system 24 mounted on a wind turbine 14 and looking towards incoming the wind 16. The atmospheric measurement system 10 can incorporate additional LIDAR systems 24 that provide for detecting this turbulence so as to provide for protecting the associated wind turbines 14 from turbulence-induced fatigue or damage. More particularly, with a sufficient number and density of associated measurement volumes 52, the atmospheric measurement system 10 can provide sufficient resolution to detect turbulent eddies 59, vortices and billows within the atmosphere 20, and to provide an indication when changes in wind velocity $\overline{v}$ or wind power flux density $\overline{\psi}$ are sufficiently large to possibly damage one or more wind turbines 14.

More particularly, the atmospheric measurement system 10 can provide for measuring the uniformity or non-uniformity of the wind field 16' from spatially-distributed measurements of the wind velocity $\overline{v}$ field from the spatially-distributed LIDAR systems 24 so as to provide for characterizing either turbulence or wind shear. These measurements can include approximations of the vorticity on several different length scales that are important to wind turbines 14.

Measurements of an associated temperature structure parameter $C_T^2$ can also be used to identify areas where significant turbulence is occurring. A time series of temperature T may be used to compute its power spectral density for the $C_T^2$.

Kolmogorov theory provides the tools necessary to convert the series of temperature measurements into the power spectral density. Recall that each temperature measurement is the temperature of the air mass that was moving through the LIDAR field-of-view (FOV) during the measurement interval. The LIDAR system 24 provides the velocity (speed and direction) so that measurements made at particular times represent different samples in space.

Simplifying the power spectral density, $S_T(K)$, for a single dimension is given by the following:

$$S_T(K) = 0.25 C_T^2 K^{-\frac{5}{3}} \tag{7}$$

The power spectral density may be obtained by taking the Fourier transform of the temperature differences as illustrated in the following equation.

$$S_T(K) = F\{T(t)\}(K) \tag{8}$$

where F{ } is the Fourier transform of the Temperature data, T, collected at time T, but presented in spatial terms via the time samples and the measured velocity.

The level at which the power spectrum becomes an issue depends upon the scenario. In the case of a wind turbine, power spectral density for spatial wave numbers on the order of the turbine blade diameter or larger are of interest. Changes at higher frequencies are not as damaging as they don't contain the same energy as the larger structures.

Another potential indicator of turbulence is the boundary layer interface 58. Turbulence usually occurs at the boundary layer interface 58, so that the location of that interface can be used to predict impending turbulence. The boundary layer starts out low and may reach only a few tens of meters in the morning. As solar heating warms the terrain, the boundary layer will rise and may reach altitudes of 1 km to 2 km. In the evening, the boundary layer will decrease and can fall to the point where the associated turbulence will interact with wind turbines.

In accordance with a first method, the derivative of the rate of change of atmospheric temperature T as a function of altitude—based upon measurements of temperature T at different altitudes from the LIDAR systems 24—can be used to measure the extent of the boundary layer interface 58. For example, the partial derivative of temperature T with respect to time can be given by:

$$\frac{\partial T(z,t)}{\partial t} = \sum a_i \vartheta_i(z,t) \tag{9}$$

and partial derivative with respect to altitude of this time rate of change of temperature T is then given by:

$$\frac{\partial^2 T(z,t)}{\partial z \partial t} = \sum a_i \frac{\partial \theta_i(z,t)}{\partial z} \quad (10)$$

Wherein in equations (9) and (10), θ(z,t) are interpolation functions for example B-spline and a is a weight determined by fitting the data.

In accordance with a second method, because aerosol concentration is significantly reduced above the boundary layer interface 58, a change in aerosol content detected by the LIDAR systems 24 responsive to a measures of aerosol counts $N_A$ and molecular counts $N_M$, can be used to estimate the location of the boundary layer interface 58.

The atmospheric measurement system 10 can further provide for generating a measure of wind shear from measurements of wind speed v at different ranges and at different pointing angles. For example, in one embodiment, wind shear is characterized by a wind shear exponent α given from the following power law equation:

$$\frac{v(z)}{v_0(z_0)} = \left(\frac{z}{z_0}\right)^\alpha \quad (11)$$

or, $$\alpha = \frac{\ln(v) - \ln(v_0)}{\ln(z) - \ln(z_0)} \quad (12)$$

where v(z) is the total wind speed at altitude z, and $v_0(z_0)$ is the total wind speed at altitude $z_0$, wherein the altitudes z, $z_0$ are measured above ground level.

The above measures of turbulence and wind shear are based upon measurements along the associated beams of light 28 that are generally angled with respect to horizontal and vertical, with associated distances being with respect to the associated light source 11. These distances may be either transformed to corresponding altitudes for purposes of determining the above measures of turbulence and wind shear. Alternatively, the above measures of turbulence and wind shear may be made with respect to an associated slant range. Generally, at least three different beams of light 28 would be used, with at least two of those beams of light 28 at an angle with respect to horizontal. Generally the aerosol to molecular ratio could be measured along each beam that has an angle with respect to the horizontal.

There are no absolute requirements on the spacing of measurements in either space or time. One could determine turbulence with a single measurement, or one could use a time series of measurements to determine turbulence. If the aerosol to molecular ratio changes suddenly with respect to altitude within a single measurement, that could be an indicator of turbulence. Similarly, turbulence could be determined by using a time series for each altitude.

The threshold values can be determined based on the measurement precision and the characteristics of the wind turbine, with different wind turbines having different thresholds. The measurement precision defines a lower bound based on probability. Generally, the false alarm rate would also be considered along with the probability of detection.

Referring to FIG. 2, the atmospheric measurement system 10 provides for either communication between the LIDAR systems 24 and a central, network or cloud processor 60, or for communication amongst the associated LIDAR systems 24, so as to provide for exchanging pertinent data as necessary to construct a map, model or database 62 of the associated atmospheric data with respect to space and time. For example, the communication can be by either a wire or fiber-optic communication channel 64 or by a wireless communication channel 66, using either direct or networked interconnections. For example, among other techniques, data may be communicated wirelessly via either a satellite or ground-based transponder, and networked communications may use an Ethernet protocol.

For example, in a centralized, hierarchical system 68, the separate LIDAR systems 24 provide their measurements to the central, network or cloud processor 60 which then calculates the associated wind velocity $\bar{v}$ and wind power flux density $\bar{\psi}$ for the various measurement volume 52, possibly using measurements from separate associated LIDAR systems 24, and combines these calculated vector measures with the associated atmospheric data scalars in the map, model or database 62 that can then be distributed to the various wind turbines 14 for control thereof. The centralized, hierarchical system 68 can include various sub-processors 70 that interface with subsets of associated LIDAR systems 24 and communicate the information therefrom to the central, network or cloud processor 60 while also possible combining measurements from the associated LIDAR systems 24 in communication therewith so as to provide for determining the necessary local set of atmospheric data needed for local control of the associated wind turbines 14.

As another example, in a decentralized system 72, each particular LIDAR system 24 provides for communicating with other LIDAR systems 24 so as to acquire the data therefrom as necessary to determine the corresponding atmospheric data for the measurement volume 52 or measurement volumes 52 associated with that particular LIDAR system 24. For example, referring to FIG. 2, the third LIDAR system 24.3 could communicate with the fourth 24.4 and fifth 24.5 LIDAR systems so as to obtain the associated measures of wind speed v as necessary to determine the associated wind velocity $\bar{v}$ for the measurement volumes $52^{iv}$, $52^v$ associated therewith. Generally, the measurement volumes 52 of different LIDAR systems 24 may overlap, in which case the LIDAR systems 24 associated with the overlapping measurement volumes 52 could each generate their own associated localized map, model or database 62 as the associated atmospheric data that can be used by the wind turbine 14 or wind turbines 14 associated with each LIDAR system 24. For example, similar to the third LIDAR system 24.3, the fourth LIDAR system 24.4 could communicate with the third 24.3 and fifth 24.5 LIDAR systems, and the fifth LIDAR system 24.5 could communicate with the third 24.3 and fourth 24.4 LIDAR systems, so as to obtain the associated measures of wind speed v as necessary to determine the associated wind velocity $\bar{v}$ for the same measurement volumes $52^{iv}$, $52^v$.

A decentralized system 72 can be operated in either a request mode or a broadcast mode, depending upon the nature of the communication between LIDAR systems 24. In accordance with the request mode of operation, a particular LIDAR system 24 sends out a request for atmospheric measurement records 40 for information associated with particular measurement volumes 52, or within a particular geographic regions, and other LIDAR systems 24 in communication therewith that can provide atmospheric data for the specified location or geographic criteria then return the requested atmospheric measurement records 40. In a broadcast mode, each particular LIDAR system 24 broadcasts its atmospheric measurement records 40 to the associated communication network 74, from which other LIDAR systems 24 can then select and use those atmospheric measurement records 40, for example, to calculate a composite atmospheric measurement record 40' for one or more common measurement volumes 52, or for compiling a local map, model or database 62. A decentralized system 72 can provide for improved fault tolerance, reliability and robustness by distributing information and associated decision processes amongst a group of associated, or all, LIDAR systems 24, thereby avoiding the prospect of single-point failure that might otherwise be possible with some embodiments of a centralized, hierarchical system 68.

Generally, each LIDAR system 24 could have a pre-assigned measurement volume 52 over which to perform associated data analysis, wherein external data that is within that measurement volume 52 is incorporated in the generation of a local atmospheric map, model or database 62, for example of wind power flux density $\overline{\psi}$, wind velocity $\overline{v}$, atmospheric density $\rho$, atmospheric temperature T, and the ratio of molecular county $N_M$ to aerosol counts $N_A$. Each atmospheric measurement record 40 could first be filtered to determine if it is within the assigned measurement volume 52. Atmospheric measurement records 40 from measurements located within the assigned measurement volume 52 could then be processed further to determine the relative proximity thereof by computing the relative distances between the locations associated therewith. For a given set of measurements of wind speed $v_1$, $v_2$, $v_3$ for a given associated measurement volume 52, the associated measurement direction vectors, for example, the associated unit vectors $\hat{e}_1$, $\hat{e}_2$, $\hat{e}_3$, are examined to insure that the look directions provide the diversity necessary to produce reasonable orthogonal measurement components, for example, so that resulting wind velocity $\overline{v}$ calculated therefrom is sufficiently accurate. For example, in one embodiment, the following metric $\eta$, having a value between zero and unity, may be used to evaluate the diversity or relative orthogonality of the associated measurement direction vectors:

$$\eta = \hat{e}_1 \times \hat{e}_2 \cdot \hat{e}_3 \quad (13)$$

Atmospheric measurement records 40 that are deemed to be sufficiently close in space and time and are associated with sufficient diversity in pointing angle are combined into a single composite atmospheric measurement record 40' that includes the associated averaged values of location and sampling time $t_i$, averaged values of the associated atmospheric data scalars, and the calculated values of associated wind velocity $\overline{v}$ and wind power flux density $\overline{\psi}$ and the associated magnitudes thereof.

The vector measures of wind velocity $\overline{v}$ and wind power flux density $\overline{\psi}$ from each LIDAR system 24, and the locations of the associated measurement volumes 52, are referenced to a particular coordinate system, and these measures can be transformed as necessary so that the corresponding measures in the map, model or database 62 are referenced to a common coordinate system. For example, for the first 24.1, second 24.2 and third 24.3 LIDAR systems, the wind velocity $\overline{v}$ and wind power flux density $\overline{\psi}$ might be based on measurements of wind speed $v_1$, $v_2$, $v_3$ along corresponding directions 46.1, 46.2, 46.3 with respect to a first local spherical coordinate system referenced to the nacelle 44 of the associated wind turbines 14.1, 14.2, 14.3 oriented in a second local cylindrical coordinate system aligned with the corresponding vertical axes of rotation 76 about which the nacelle 44 can rotate with respect to the associated towers 78 so as to provide for aligning the associated rotors 18.1, 18.2, 18.3 with the local direction 50 of the wind field 16', wherein the towers 78 of the wind turbines 14.1, 14.2, 14.3 can be located on the Earth with respect to a central Earth-referenced spherical, oblate-spherical or ellipsoidal coordinate system. Accordingly, if the vector measures in the map, model or database 62 are expressed with respect to this central Earth-referenced coordinate system, then the wind velocity $\overline{v}$ and wind power flux density $\overline{\psi}$ from each LIDAR system 24, and the locations of the associated measurement volumes 52, could be transformed from the associated local coordinate systems to coordinate system of the map, model or database 62 before inclusion therein.

Measurements of atmospheric data from the atmospheric measurement system 10 made with respect to a diversity of spatial coordinate systems and temporal resolutions using associated various LIDAR systems 24 can be input to relatively high-resolution computational fluid dynamics (CFD) simulations of the associated wind field 16' to help understand realistic wind 16 patterns at a particular site and to which a prospective one or wind turbines 14 located thereat would be subjected. For example, a CFD simulation can characterize the role and impact of turbulence induced by the local topographical thermal-fluid environment, wherein turbulence can be modeled using either a Reynolds Averaged Navier Stokes (RANS) approach, Large Eddy Simulations (LES); Detached Eddy Simulations (DES) or Direct Numerical Simulation (DNS), depending on factors related to geometry and flow conditions. Direct Numerical Simulation (DNS) can be used to build new turbulence models but is more computationally expensive than the other approaches. Atmospheric data from associated LIDAR systems 24 of the atmospheric measurement system 10 can be used to provide for defining initial and boundary conditions for the wind field 16' being simulated, and to provide statistics for choosing and using the correct turbulence model to be used in the simulation. The spatial diversity of the atmospheric data from associated LIDAR systems 24 of the atmospheric measurement system 10 provides for resolving the turbulent boundary layer interface 58, and the corresponding temporal resolution of this atmospheric data provides for estimating the associated turbulent kinetic energy. The results of CFD simulations can be used as input to the design of wind turbines 14, the identification of wind turbine sites, the placement of wind turbines 14 at the site, the affects of wind turbine wake on other wind turbines 14 in proximity thereto, and the design of wind turbine control systems.

Atmospheric data from the atmospheric measurement system 10 can be used for controlling the wind turbines 14 of an associated wind farm 12—or of a plurality of wind farms 12 within the geographic extent of the associated map, model or database 62 compiled by the atmospheric measurement system 10—or the power grid 56 supplied therefrom. The associated LIDAR systems 24 need not be located exclusively at wind sites or with overlapping fields-of-view 54 in order to provide useful information to the wind farm 12. Furthermore, as illustrated in FIGS. 1 and 2, The LIDAR systems 24 need not necessarily be mounted on associated wind turbines 14. For example, LIDAR systems 24 located kilometers away from the wind farm 12 can make atmospheric measurements that can be combined with measurements from other LIDAR systems 24 within the region of the wind farm 12 so as to provide a larger scale estimation of wind energy potential in an approaching air mass. At longer ranges, small scale turbulences are not necessarily as important because they may dissipate by the time they reach the wind farm 12. Although a map, model or database 62 of atmospheric data for the wind field 16' local to a particular wind turbine 14 can be useful for immediate control of the particular wind turbine 14, a map, model or database 62 of atmospheric data for the wind field 16' over and upstream of the entire wind farm 12 provide for a coordinated control of the associated wind turbines 14 and the associated power grid 56 so as to provide for extracting as much power as either possible or necessary from the wind field 16' while protecting the associated wind turbines 14 from damage, for example, as a result of excessive wind speed v or turbulence. A regional or global map, model or database 62 of atmospheric data could be provided by a centralized, hierarchical system 68, or could be compiled from separate maps, models or databases 62 that are separately generated by the separate LIDAR systems 24 of a decentralized system 72. Atmospheric data from adjacent and/or up-wind LIDAR systems 24 can improve measurement resolution, measurement accuracy, and turbulence or wind shear estimation of other LIDAR systems 24, perhaps in conjunction with weather modeling or forecasting software, or in conjunction with other sources of weather data. In a decentralized system 72, in addition to the individual map, model or database 62 local to a particular wind turbine 14, atmospheric data from the entire wind farm 12 can be compiled and a detailed large scale three dimensional wind power density, wind velocity, turbulence, density, molecular to aerosol scattering ratio and temperature maps can be generated. These maps can be maintained for historical purposes and for sale to others such as weather forecasters who could find the data beneficial in their enterprises. In addition to the information mentioned above, the LIDAR systems 24 are able to measure the extinction coefficient at their operational wavelength and the aerosol-to-molecular scattering ratio which could be used to locate the boundary layer interface 58 and estimate visibility.

As each new measurement is added to the map, model or database 62, it is compared to previous measurements to determine if the new measurement indicates significant changes in the current conditions. New measurements are compared to the mean and standard deviation that are calculated on a window of time history data. Deviations between the measured value and the expected value are indicative of changes, and if the deviation exceeds established limits, appropriate warnings are issued. In one example if the wind speed v suddenly decreases, one might want to prepare to tap stored energy to take up the slack. In another example, if the temperature data indicates thermal turbulence, then one might expect turbulence to strike the wind farm 12 or wind turbine 14 in the near future.

For example, referring to FIG. 2, each wind turbine 14 could incorporate an associated controller 80 for controlling the associated generator 82 and rotor 18 of the wind turbine 14, and for controlling the orientation of the rotor 18 relative to the local direction 50 of the wind 16, wherein the generators 82 are connected to the power grid 56 so as to provide for supplying electrical power thereto. In one mode of operation, the wind turbines 14 are controlled so as to generate the maximum amount of electrical power available from the wind, and atmospheric data from the atmospheric measurement system 10 is used to anticipate atmospheric conditions that could be potentially damaging to the wind turbine 14, or that could cause fatigue or extreme loading that would either weaken the wind turbine 14 or lead to subsequent damage thereto, so that the controller 80 can control the wind turbine 14—for example, by pitching the blades—so as to prevent damage to the elements thereof.

The map, model or database 62 can be used as direct input into a feedforward controller 80 to automatically compensate for wind gusts, shear, and turbulence.

In another mode of operation, the controller 80 can use the information of the wind power flux density $\overline{\psi}$ to anticipate the amount of electrical power that can be generated by the wind turbine 14, and responsive to a demand signal 84 from the power grid 56, possibly in cooperation or coordination with signals from other controllers 80 of the wind farm 12, then the controller 80 controls the elements of the wind turbine 14 so as to generate and supply the appropriate amount of electrical power to the power grid 56. Atmospheric data from the atmospheric measurement system 10, i.e. the associated map, model or database 62, can be provided to the power grid 56 so that the power grid 56 can anticipate the amount of electrical power that could potentially be available from the wind farm 12, for example, for peaking power if necessary.

Wind velocity $\overline{v}$ provides the information necessary to generate extended maps showing the location of a particular air mass with its temperature T, density $\rho$, and molecular-to-aerosol ratio. A spatial rather than the temporal view provides another independent method for examining data and projecting when the wind power will interact with the wind turbine 14. Knowing that a neighboring wind farm 12 or wind turbine 14 has just detected a wind change event is a strong indicator that the current wind farm 12 or wind turbine 14 might also experience that same event in the near future. It is highly unlikely that a wind gust could hit all the wind turbines 14 in an installation at the same time. It is more likely that some wind turbines 14 could be subjected to the disturbance before others.

Atmospheric data from the atmospheric measurement system 10 can be made commercially available to operators of wind farms 12, or for other purposes. For example, the atmospheric data, continuously gathered from various altitudes, can be used for weather forecasting. Instead of obtaining atmospheric profiles twice a day at sixty-nine sites throughout the continental United States under current practice, atmospheric data from the atmospheric measurement system 10 could be streamed continuously from thousands of LIDAR systems 24 distributed across the country, or across other countries or regions, which can lead to more accurate weather forecasts. For example, for an atmospheric measurement system 10 primarily developed for use by wind farms 12, available atmospheric data from associated LIDAR systems 24 having value for meteorological forecasts, could be included in the associated map, model or database 62. The atmospheric data could be used as input for an operational mesoscale numerical weather prediction model, such as the MM5 or other models. This additional data such as molecular to aerosol scattering ratio and extinction coefficient could be made commercially available to other interested parties. Furthermore, the atmospheric data may be further processed to establish visibility or other metrics that might be peculiar to weather forecasting.

Furthermore, atmospheric data from associated LIDAR systems 24 can be used to aid in astronomical observations. Clear-air turbulence in both the free atmosphere and in the boundary layer causes phase distortions to incoming electromagnetic wave fronts, resulting in motion, intensity fluctuations (scintillation), and blurring of images obtained by ground-based telescopes. Astronomical parameters that quantify these effects are generically referred to as seeing. Seeing improves or degrades with changes in the vertical location and strength of turbulence as quantified by profiles of the refractive index structure function $C_N^2$ (Nastrom and Eaton 1993). $C_N^2$ fluctuations usually occur at scales that are too small for routine direct measurement, but they can be parameterized from vertical gradients in wind 16, temperature T, and moisture in numerical weather prediction models responsive to measurements from the associated LIDAR systems 24. Seeing at a particular wavelength could then be calculated by vertically integrating the $C_N^2$ profile.

Global trend monitoring, for example, via cloud-based computing, can also be applied to analyzing climate change, pollution (dust, aerosols), weather patterns and volcanic events (particulates).

Predictive analytics and other learning-based software paradigms can be applied on an individual turbine, wind farm, or grid level to provide learning-based optimization through a learning module. The learning module consists of a processor, for example quad core computer combined with GPUS, that runs the predictive analytics software. On an individual turbine, the learning module collects data from the LIDAR as well as the turbine. As new data is collected, the predictive analytics software optimizes the control inputs to the turbine to minimize the effects of wind loading and maximize turbine health and lifetime. Over time, the learning module produces an optimal set of control system commands in response to the LIDAR atmospheric measurements, customized for the performance of each individual turbine. Effects such as turbulence and shear may differ for individual turbines and require different responses, depending on the type, size, and age of the turbine. Those effects are incorporated automatically into the learning module without the need for direct supervisory control. On a wind farm SCADA level, a learning module identifies trends in the overall health of each individual turbine that can be used to predict problems and optimize performance or maintenance schedules of a particular wind turbine or of other wind turbines within the wind farm.

The networking of LIDAR systems 24 allows the lifetime of each sensor to be extended. This is accomplished by turning off some sensors or placing them in a standby mode that minimizes the operational state or duty cycles of the components, thereby extending the sensor lifetime and reducing maintenance and repair requirements. One or more LIDAR systems 24 would remain in full operation and provide data to the other sensors in the atmospheric measurement system 10, thereby acting as sentries to warn of changing weather conditions. In one embodiment, most LIDAR systems 24 in the atmospheric measurement system 10 are placed in standby mode, with wind speeds averaging less than a certain value, for example one meter per second, over a period of time; one or more LIDAR systems 24 in a atmospheric measurement system 10 of sensors remain in full operation, monitoring wind speeds; when average wind speeds over a period of time exceed a certain value, for example two meters per second, some or all of the other sensors in the atmospheric measurement system 10 are placed in full operational mode again.

Using the same approach, the reliability of the entire atmospheric measurement system 10 is increased since a failure with one of the LIDAR systems 24 can be mitigated by sending data from other sensors in the atmospheric measurement system 10 to that node, essentially introducing multiple levels of redundancy and backup into the atmospheric measurement system 10. In one embodiment, a LIDAR system 24 being used for turbine control fails, but within a short time period, data from the other sensors in the atmospheric measurement system 10 is used to replace the function of the failed sensor, ensuring the continual safe operation of the turbine.

A measurement of water vapor—for example, using a Raman-based receiver incorporated with the LIDAR system 24—alone or in combination with other atmospheric measurements can provide for predicting and monitoring conditions that may cause or lead to the formation of ice on the blades of the wind turbine. In one embodiment, a Raman-based receiver incorporated with the LIDAR system 24.

The aforementioned U.S. application Ser. No. 12/780,895 filed on 15 May 2010, entitled Range imaging LIDAR illustrate various embodiments of LIDAR systems 24 and associated platforms that may be incorporated in the atmospheric measurement system 10.

Referring to FIG. 6a, in accordance with a first aspect, a range-imaging LIDAR system 24', $24^i$ incorporated in a first aspect of an atmospheric measurement system $10^i$ incorporates a light source 11 that provides for generating at least substantially monochromatic light 13, which is projected into the atmosphere 20 as a beam of light 28 through and by associated source optics 15. For example, the source optics 15 may comprise a lens assembly 15' that provides for the width and divergence of the beam of light 28, and a suitable location of the associated beam waist thereof, so as to illuminate an interaction region 17 within the atmosphere 20 that is detectable by the range-imaging LIDAR system 24', $24^i$, wherein the beam width within the interaction region 17 establishes the associated transverse spatial resolution limit of the range-imaging LIDAR system 24', $24^i$. For example, referring to FIG. 6b, the source optics 15 may be configured so as to provide for a pencil-like beam of light $28^P$ having a limited width w and depth d, for example, of circular or elliptical cross-section, so as to limit the associated width w and depth d of the associated interaction region 17. As another example, referring to FIG. 6c, the source optics 15 may be configured so as to provide for a sheet-like beam of light $28^S$—for example, using source optics 15 comprising cylindrical optics—having a limited depth d but an extended width w, for example, so as provide for an associated interaction region 17 with a corresponding extended width w, so as to provide for probing extending regions of the atmosphere 20.

A set of receive optics 32, for example, a telescope 32', laterally offset from the beam of light 28, provides for imaging a portion of the beam of light 28 onto an intermediate image plane 19, so as to provide for a one-to-one mapping of measurement volumes 52 within the beam of light 28 and corresponding associated regions or points 21 in the intermediate image plane 19. More particularly, the beam of light 28 illuminates molecules 20' or aerosols 20" of the atmosphere 20, or a combination thereof, within the interaction region 17, which in turn scatter the monochromatic light 13 of the beam of light 28. The resulting scattered light 30 within the field-of-view 54 of the receive optics 32 is collected thereby and imaged onto the intermediate image plane 19. The receive optics 32 is laterally offset from and points towards the beam of light 28, so that the optic axis 23 of the receive optics 32 is inclined relative to the optic axis 25 of the beam of light 28 at an associated parallax angle $\theta$. Accordingly, each measurement volume 52 of the beam of light 28 imaged onto a corresponding region or point 21 on the intermediate image plane 19 corresponds to a different nominal range R from the intermediate image plane 19 to a point 27 on the optic axis 25 of the beam of light 28 associated with the corresponding measurement volume 52. Accordingly, each region or point 21 on the intermediate image plane 19, corresponding to the measurement volume 52 of the beam of light 28 within the field-of-view 54 of the receive optics 32, corresponds to a different nominal range R. Accordingly, different regions or points 21 of the intermediate image 29 in the intermediate image plane 19 correspond to different nominal ranges R to the beam of light 28, and therefore correspond to different nominal ranges R to the associated measurement volumes 52 thereof within the interaction region 17. For example, as illustrated in FIG. 6a, a closest measurement volume 52.1 of the beam of light 28 within the field-of-view 54 of the receive optics 32 located at a closest nominal range $R_{MIN}$ from the intermediate image plane 19 is imaged as a corresponding first region or point 21.1 on the intermediate image plane 19, and a farthest measurement volume 52.2 of the beam of light 28 within the field-of-view 54 of the receive optics 32 located at a farthest nominal range $R_{MAX}$ from the intermediate image plane 19 is imaged as a corresponding second region or point 21.2 on the intermediate image plane 19. Furthermore, scattered light 30 from different measurement volumes 52 is imaged onto the intermediate image plane 19 at corresponding different angles of incidence relative thereto. The range R to the interaction region 17 is defined by the geometry of the associated beam of light 28 and the corresponding receive optics 32. The receive optics 32 can be in focus for one of a plurality of different ranges to the beam of light 28, so that for measurement volumes 52 of the beam of light 28 not in focus, the corresponding images thereof in the intermediate image plane 19, i.e. the corresponding regions or points 21 thereon, will be unfocused and therefore blurred. The range R within the interaction region 17 can optionally be further resolved with associated temporal range gating, or range-resolved imaging, of the associated scattered light 30 if desired or necessary for a particular application.

Figure 7:
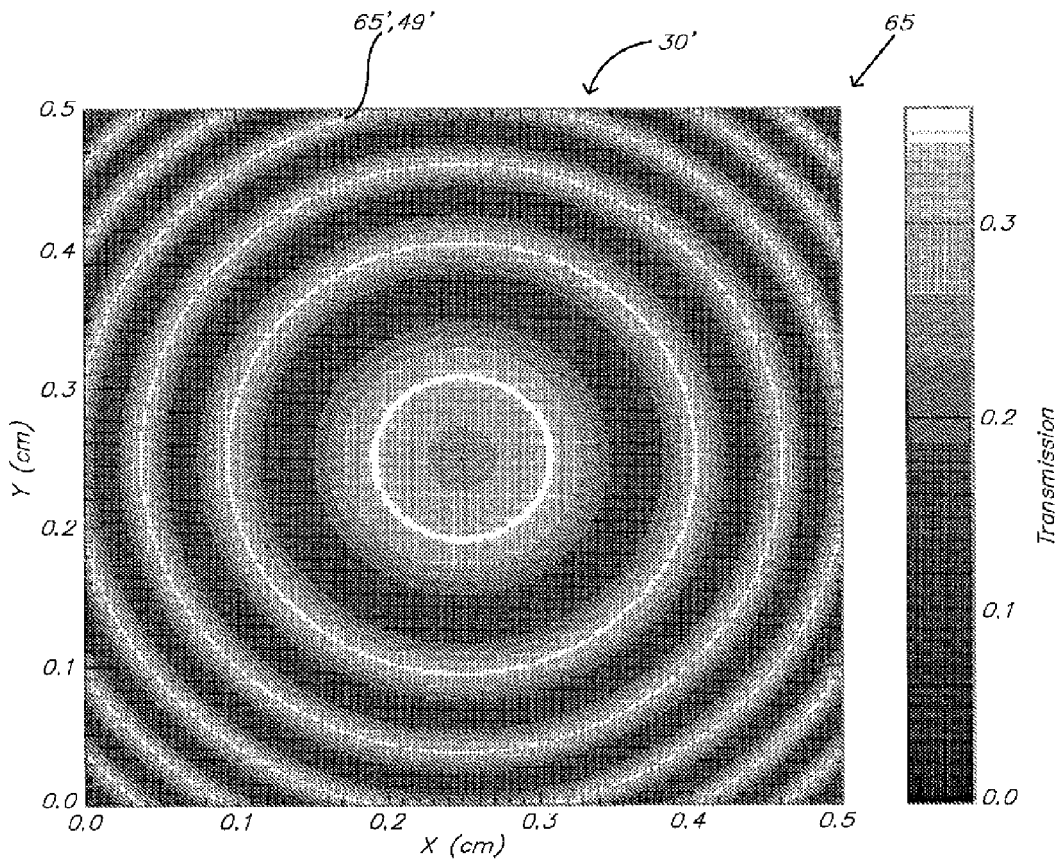
FIG. 7 illustrates a half-tone image of fringes from a fully illuminated Fabry-Pérot etalon.

The range-imaging LIDAR system 24', 24$^i$ further comprises an interferometer 31, for example, in accordance with a first aspect, a Fabry-Pérot interferometer 31' having an input focal plane 31.1' and an output focal plane 31.2'. The input focal plane 31.1' is collocated with the intermediate image plane 19 so as to receive scattered light 30 therefrom, which is then processed by the Fabry-Pérot interferometer 31' and imaged onto a detection system 34 located at the output focal plane 31.2'. Between the input 31.1' and output 31.2' focal planes, the Fabry-Pérot interferometer 31' comprises a collimating lens 33, a Fabry-Pérot etalon 35, and imaging optics 37 spaced along an associated common optic axis 39, wherein the input focal plane 31.1' is a focal plane of the collimating lens 33, the output focal plane 31.2' is a focal plane of the imaging optics 37, and scattered light 30 at the input focal plane 31.1' entering the collimating lens 33 is substantially collimated thereby, then processed by the Fabry-Pérot etalon 35, and finally imaged onto the detection system 34 by the imaging optics 37. The Fabry-Pérot etalon 35 of the Fabry-Pérot interferometer 31' comprises first 41 and second 43 partially-reflective surfaces that are parallel to one another and separated by a fixed gap 45. The angles at which the scattered light 30 is passed through the Fabry-Pérot etalon 35 is dependent upon the optical frequency of the scattered light 30 and the length of the gap 45, resulting in an associated scatter fringe pattern 47 comprising a plurality of concentric arcuate fringes 49'—also known as Haidinger fringes—in the output focal plane 31.2' of the Fabry-Pérot interferometer 31', for example, as illustrated in FIG. 7 for a fully illuminated Fabry-Pérot interferometer 31'. The scatter fringe pattern 47 is imaged onto the detection system 34 that generates a scatter electronic image signal 51 responsive thereto which is then processed as described hereinbelow by an associated data processor 53 so as to generate a corresponding set of atmospheric data 36 from information in the scatter fringe pattern 47.

For example, in one embodiment, the Fabry-Pérot etalon 35 comprises a pair of planar optical windows 55—for example, constructed of either optical glass or fused quartz—aligned parallel to and facing one another, and spaced apart from one another by the gap 45, wherein, for example, the first 41 and second 43 partially-reflective surfaces—e.g. partially-silvered surfaces or other partially-reflective surfaces—are on separate facing surfaces of the planar optical windows 55. Alternatively, the first 41 and second 43 partially-reflective surfaces could be on the outside opposing faces of the planar optical windows 55, or one of the first 41 and second 43 partially-reflective surfaces could be on a inner facing surface of one of the planar optical windows 55, and the other of the first 41 and second 43 partially-reflective surfaces could be on a outer facing surface of the other of the planar optical windows 55. In one embodiment, the gap 45 is substantially fixed, whereas in other embodiments, the gap 45 is moveable, e.g. adjustable, for example, using an etalon control actuator 57 responsive to a controller 71 operatively associated with or a part of the data processor 53, so as to provide for a tunable Fabry-Perot etalon 35.

Figure 6D:
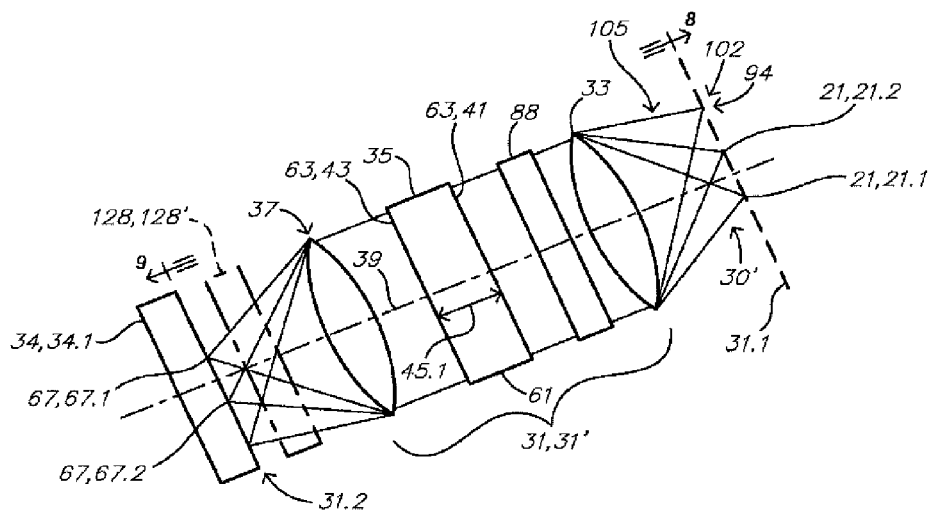
FIG. 6d illustrates a second aspect of a Fabry-Pérot interferometer of a range-imaging LIDAR system.

Referring to FIG. 6d, alternatively, the Fabry-Pérot etalon 35 could comprise a solid optical element 61—for example, constructed of either optical glass or fused quartz—with planar parallel faces 63 comprising first 41 and second 43 partially-reflective surfaces separated by a gap 45.1 constituting the length of the solid optical element 61.

Referring to FIG. 7, for a fully-illuminated Fabry-Pérot etalon 35, the resulting associated circular fringe pattern 65 is in the form of closed concentric circular fringes 65' centered about the optic axis 39 of the imaging optics 37. For example, a typical circular fringe pattern 65 is illustrated in FIG. 7 for an associated scattered light signal 30' that has been source thermally broadened by a medium comprising both aerosols and molecules. The light scattered from the molecules is spread over the shaded regions of the circular fringe pattern 65 in FIG. 7, and the light scattered from the heavy, slow moving aerosols is contained in the narrow white rings. The associated atmospheric state variables affect the circular fringe pattern 65 in different ways. Wind induced Doppler shifts change the diameter of the rings, and the constant that determines Doppler shift is dependent upon temperature. Atmospheric (molecular) temperature affects the width of molecular rings. Aerosol density controls the intensity of the narrow white rings and molecular density increases the brightness of the shaded regions in FIG. 7. Accordingly, wind velocity, density, and temperature can be determined directly from the circular fringe pattern 65.

Figure 8:
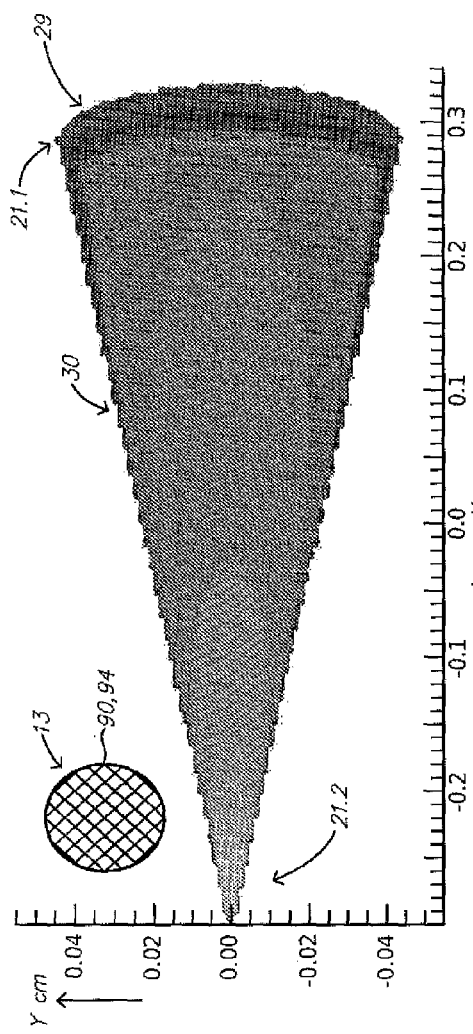

For example, referring to FIG. 8, a simulated image in the intermediate image plane 19 is illustrated for a beam of light 28 having a beam radius of 0.1 centimeters (cm) and a half-angle of divergence of 0.05 milliradians, and for receive optics 32 having an aperture radius of 2.5 centimeter and a focal length of 15 cm, separated from the beam of light 28 by 35 cm, for which the range R to beam of light 28 within the field-of-view 54 of the receive optics 32 ranged from $R_{MIN}$=8 meters to the closest measurement volume 52.1 to $R_{MAX}$=500 meters to the farthest measurement volume 52.2, respectively, with the receive optics 32 focused at the farthest measurement volume 52.2. Accordingly, as illustrated in FIG. 8, the second region or point 21.2 in the intermediate image plane 19 corresponding to the farthest measurement volume 52.2 is most sharply focused, and the first region or point 21.1 in the intermediate image plane 19 corresponding to the closest measurement volume 52.1 is the most blurred, with the amount of blurring and therefore the associated size of regions or points 21 in the intermediate image plane 19 therebetween increasing with decreasing corresponding associated nominal range R from the second region or point 21.2 to the first region or point 21.1, thereby giving the associated intermediate image 29 of the interaction region 17 of the beam of light 28 a wedge-shaped profile.

Absent the Fabry-Pérot etalon 35, the associated collimating lens 33 and imaging optics 37 provide for imaging the intermediate image plane 19 onto the output focal plane 31.2' that is detected by the detection system 34. Accordingly, the first 21.1 and second 21.2 regions or points on the intermediate image plane 19—corresponding to the closest 52.1 and farthest 52.2 measurement volumes of the beam of light 28 within the field-of-view 54 of the receive optics 32—are imaged as corresponding first 67.1 and second 67.2 regions or points on the output focal plane 31.2'. More generally, there is a one-to-one correspondence between regions or points 67 on the output focal plane 31.2' and corresponding measurement volumes 52 of the beam of light 28, and therefore, there is a one-to-one correspondence between regions or points 67 on the output focal plane 31.2' and the corresponding nominal range R thereto, given the parallax angle θ between the optic axes 23, 25 of the receive optics 32 and the beam of light 28, respectively, so that the nominal range R associated with any region or point 67 on the output focal plane 31.2'—or in the associated corresponding scatter electronic image signal 51 detected by the detection system 34—can be inferred from the location of that region or point 67 on the output focal plane 31.2'. With the Fabry-Pérot etalon 35 present, the arcuate fringes 49' of the scatter fringe pattern 47 are present for those regions or points 67 for which the associated frequency or wavelength of the associated scattered light 30 in cooperation with the gap 45 of the Fabry-Pérot etalon 35 provide for constructive interference, whereas arcuate nulls 69 in the scatter fringe pattern 47 are present for those regions or points 67 for which the associated frequency or wavelength of the associated scattered light 30 in cooperation with the gap 45 of the Fabry-Pérot etalon 35 provide for destructive interference. Locations of the arcuate fringes 49' are determined by the frequency or wavelength of the associated scattered light 30, the gap 45 of the Fabry-Pérot etalon 35 and the angle of incidence in the Fabry-Pérot etalon 35.

Figure 9:
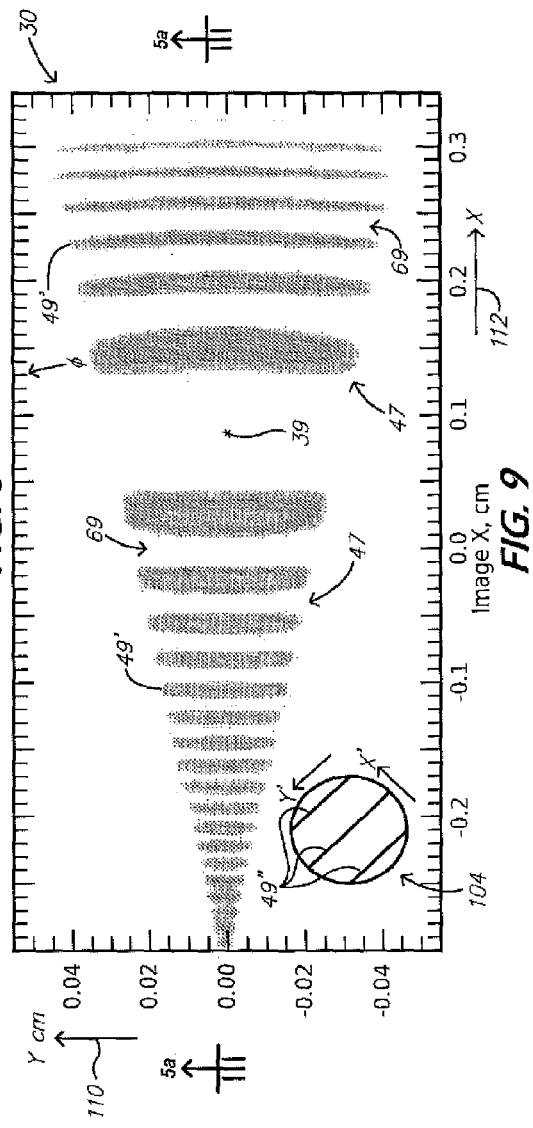
FIG. 9 illustrates an example of an image of a fringe pattern output from the Fabry-Perot interferometer, and the input to an associated detection system, of the first aspect of the range-imaging LIDAR system illustrated in FIG. 6a, processing the image illustrated in FIG. 8.

For example, for the conditions described hereinabove for FIG. 8, FIG. 9 illustrates a simulation of a resulting scatter fringe pattern 47 for a solid Fabry-Pérot etalon 35 having a thickness, or gap 45.1, of 0.7 cm and an associated reflectivity of 0.85. As with the associated intermediate image 29, with the receive optics 32 in focus at the farthest nominal range $R_{MAX}$, the arcuate fringes 49' associated with relatively closer measurement volumes 52 of the beam of light 28 are transversely broadened relative to those associated with relatively farther measurement volumes 52, so that the scatter fringe pattern 47 exhibits a wedge-shaped profile similar to that of the intermediate image 29, wherein the radial size of the associated arcuate nulls 69 decreases with increasing fringe order relative to the optic axis 39 of the Fabry-Pérot interferometer 31'. FIG. 10*a* illustrates a plot of the intensity of the scatter fringe pattern 47 along a section thereof through the optic axis 39 as a function of distance in the output focal plane 31.2', which is transformed in FIG. 10*b* to a plot of the intensity of the scatter fringe pattern 47 as a function of nominal range R. The nominal range R for which the intermediate image 29 and the associated scatter fringe pattern 47 are in focus can be set to improve the sharpness of the associated range resolution at any particular nominal range R, for example, either using an associated fixed focal setting, or using a focus control actuator 86 responsive to a signal from the controller 71.

The locations of the arcuate fringes 49' and associated arcuate nulls 69 can be changed by either changing the gap 45 of the Fabry-Pérot etalon 35, for example, by the etalon control actuator 57 responsive to a signal from the controller 71, or by tilting the Fabry-Pérot etalon 35. For example, the gap 45 of the Fabry-Pérot etalon 35 could be repeatedly scanned by the etalon control actuator 57 responsive to a signal from the controller 71 so as to repeatedly generate associated sets of scatter fringe pattern 47 collectively having arcuate fringes 49' associated with all nominal ranges R to the beam of light 28 within the field-of-view 54 of the receive optics 32, so as to directly provide for associated atmospheric data 36 at any particular nominal range R within the range of associated nominal ranges R from $R_{MIN}$ to $R_{MAX}$.

The range-imaging LIDAR system 24', 24$^i$ provides for directly detecting light scattered off of either molecules 20' of the atmosphere, aerosols 20" in the atmosphere, or a combination of the two, and provides for directly measuring the density and temperature of the atmosphere 20, and the velocity thereof in the direction of the optic axis 23 of the receive optics 32. For example, relatively short wavelength light is scattered by molecules 20' of the atmosphere in accordance with Rayleigh scattering. Light can also be scattered by aerosols 20" in the atmosphere in accordance with Mie scattering. Rayleigh scattering generally refers to the scattering of light by either molecules or particles having a size less than about $\frac{1}{10}^{th}$ the wavelength of the light, whereas Mie scattering generally refers to scattering of light by particles greater than $\frac{1}{10}^{th}$ the wavelength of the light. Being responsive to Rayleigh scattering, the range-imaging LIDAR system 24', 24$^i$ is therefore responsive to the properties—e.g. velocity, density and temperature—of those molecules 20' in the atmosphere giving rise to the associated scattering of the light detected by the range-imaging LIDAR system 24', 24$^i$. Furthermore, the range-imaging LIDAR system 24', 24$^i$ can provide for operation in clean air, i.e. in an atmosphere with no more than a negligible amount of aerosols 20", depending substantially upon only molecular scatter. If scattered from a moving molecule 20' or aerosol 20", the frequency scattered light 30 is Doppler shifted, which for a given gap 45 in the associated Fabry-Pérot etalon 35 thereby causes the associated arcuate fringes 49' of the scatter fringe pattern 47 from the Fabry-Perot interferometer 31' to be shifted to a location for which an associated constructive interference condition is satisfied for the corresponding rays of scattered light 30 entering the Fabry-Pérot interferometer 31' at a given angle from a corresponding given nominal range R. Accordingly, the Doppler shift in the frequency of the scattered light 30 will depend upon the local velocity of the atmosphere 20 within the interaction region 17 interacting with the beam of light 28, and for different amounts of Doppler shift, arcuate fringes 49' associated with corresponding different nominal ranges R will be generated by the Fabry-Pérot interferometer 31', thereby causing the arcuate fringes 49' to shift within the scatter fringe pattern 47—possibly relative to one another depending upon the distribution of velocity of the atmosphere 20 within the interaction region 17.

The range-imaging LIDAR system 24', 24$^i$ further incorporates a filter system 88 to filter the scattered light 30 received by the receive optics 32 so as to prevent background light from being detected by the detection system 34. For example, referring to FIGS. 6*a*, 6*d* and 11, in one set of embodiments, the filter system 88 is located within the Fabry-Pérot interferometer 31' between the collimating lens 33 and the Fabry-Pérot etalon 35. For example, referring to FIG. 11, in one embodiment, the filter system 88 incorporates eight bandpass filter mirrors 88' having associated filter pass bands centered about the operating frequency of the light source 11 The filter system 88 exhibits high out-of-band rejection, as well as low in-band attenuation, and the bandwidth of the filter system 88 is sufficiently narrow so as to substantially filter or remove components of solar radiation or stray light in the collected scattered light 30, yet sufficiently broad so as to be substantially larger than the bandwidth of the thermally-broadened spectrum in combination with the largest expected associated Doppler shift. For example, in one embodiment, the filter system 88 is adapted so as to provide for maximum filtering of light frequencies that are outside the frequency band of interest, e.g. greater than about 2 nanometers (nm) above or below the nominal center frequency of the light source 11.

Figure 11:
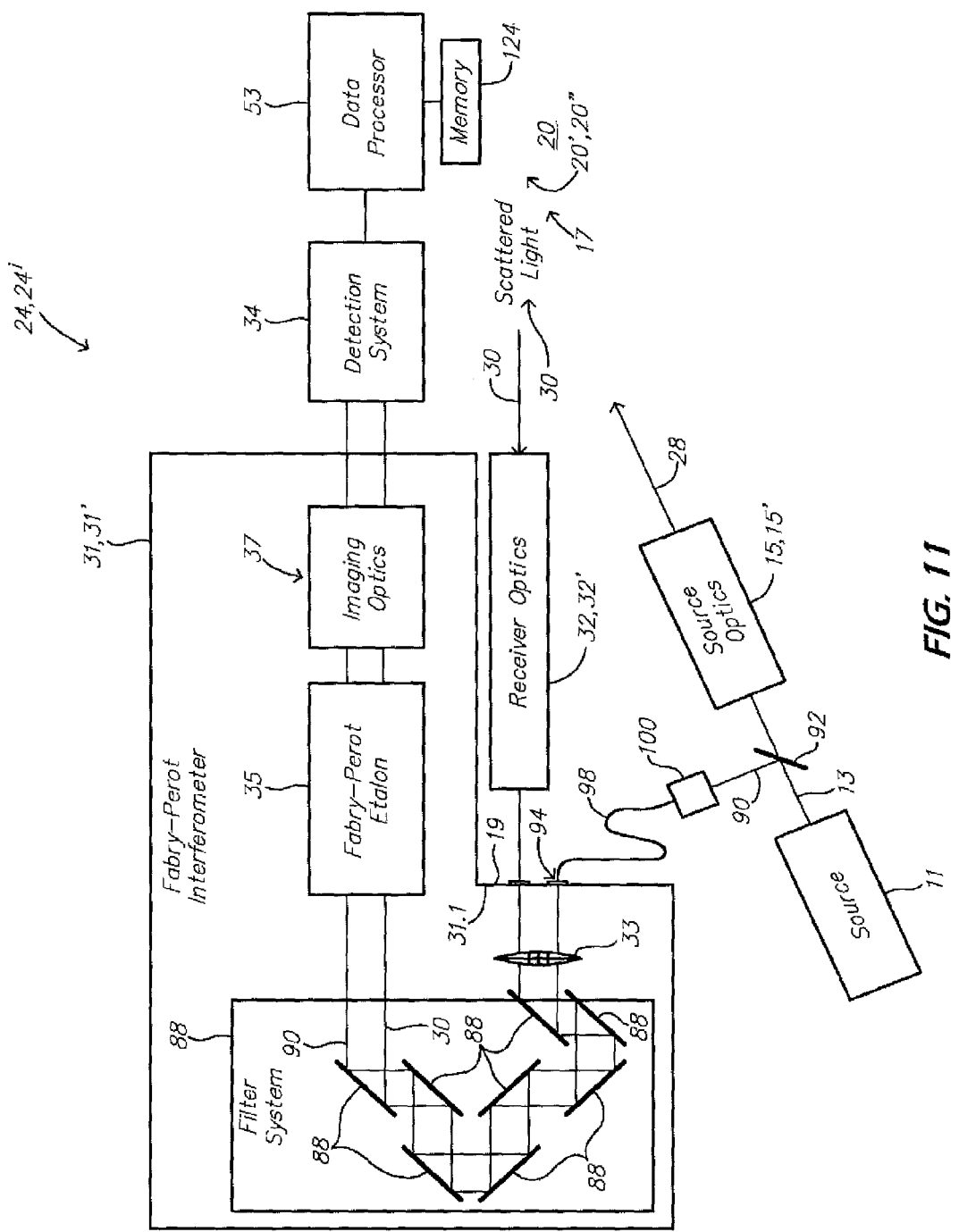
FIG. 11 illustrates a third aspect of a Fabry-Pérot interferometer of a range-imaging LIDAR system.

The Fabry-Pérot interferometer 31' is subject to mechanical defects and thermally induced drift that can be compensated through calibration using a reference beam portion 90 of the substantially monochromatic light 13 extracted from the light source 11 with a beam splitter optic 92 and then input to the Fabry-Pérot interferometer 31' at the intermediate image plane 19 as a reference source 94. For example, referring to FIG. 6a, in accordance with a first embodiment, the reference source 94 from the beam splitter optic 92 is directed into the Fabry-Pérot interferometer 31' with a mirror 96. Referring to FIG. 11, in accordance with a second embodiment, the reference beam portion 90 of the monochromatic light 13 extracted from the light source 11 with a beam splitter optic 92 as the reference source 94 is input to fiber optic 98, for example, using a graded index (GRIN) lens 100, the output of which is located at the intermediate image plane 19 so as to illuminate the collimating lens 33 of the Fabry-Pérot interferometer 31' therefrom. Accordingly, for either embodiment, the reference source 94 is input to the Fabry-Pérot interferometer 31' from a location 102 on the intermediate image plane 19/input focal plane 31.1' that is distinct from the intermediate image 29 of the scattered light 30, and is processed by the Fabry-Pérot interferometer 31' so as to generate a corresponding reference fringe pattern 104 comprising one or more associated arcuate fringes 49" at a corresponding location on the output focal plane 31.2', which is then detected by the detection system 34 so as to generate a corresponding reference electronic image signal 106 responsive thereto, which is then processed as described hereinbelow by the associated data processor 53 together with the scatter electronic image signal 51 associated with the scatter fringe pattern 47 from the scattered light 30.

The light source 11 provides for generating a sufficient amount of sufficiently narrow-band monochromatic light 13 so as to provide for a sufficient amount of scattered light 30 so that the resulting scatter fringe pattern 47 is detectable by the detection system 34 with a sufficient signal-to-noise ratio (SNR) so that the resulting atmospheric data 36 determined therefrom is accurate within a given accuracy threshold and provides for an information temporal bandwidth that is within a given temporal bandwidth threshold. For example, the light source 11 could comprise one or more lasers, light emitting diodes (LEDs), flash lamps, for example, xenon flash lamps, sodium lamps or mercury lamps. The light source 11 may be either continuous or pulsed, and need not necessarily be coherent. If the spectral bandwidth of the light source 11 is not inherently substantially less than the expected minimum Doppler shifts to be measured, then the output of the light source 11 may be filtered with a filter 108 so as to provide for generating sufficiently monochromatic light 13 so as to enable Doppler shifts in the scattered light 30 to be measured sufficiently accurately so as to provide for resolving velocity sufficiently accurately, i.e. less than a given threshold. The particular operating wavelength of the range-imaging LIDAR system 24', 24$^i$ is not limiting. For example, any optical wavelength that interacts with that which is being sensed in the associated interaction region 17 may be used.

For example, in one embodiment, the substantially monochromatic light 13 comprises ultraviolet (UV) laser light at a wavelength of about 266 nm that is generated using a laser light source 11. A wavelength of about 266 nm, being invisible to the human eye and substantially absorbed by the atmosphere, is beneficial for its stealth, eye safety and molecular scattering properties. There is relatively little natural background light at this frequency due to absorption of most natural 266 nm light by ozone and molecular oxygen. Ultraviolet light at about 266 nm is readily absorbed by glass and plastic, such as used in aircraft wind screens, which provides for improved eye safety. The particular operating wavelength of the range-imaging LIDAR system 24' is not limiting, and it should be understood that any optical wavelength that interacts with that which is being sensed in the associated interaction region 17 may be used.

For example, a Nd:YAG laser 11.1' can operate at relatively high power levels so as to provide sufficiently intense illumination so as to provide for relatively long range atmospheric sensing applications. An Nd:YAG laser 11.1' has a fundamental wavelength of 1064 nm, from which shorter wavelengths/higher frequencies may be generated using one or more harmonic generators operatively associated with or a part of the Nd:YAG laser 11.1'. For example, a second-harmonic generator could be used to convert the fundamental 1064 nm light to second-harmonic 532 nm light which could then be transformed with either a third- or fourth-harmonic generator to generate associated 355 nm or 266 nm light respectively. For example, these second-, third- and/or fourth-harmonic generators may be either incorporated in, free-space coupled to, or coupled with a fiber optic to the Nd:YAG laser 11.1'. Accordingly, alternative embodiments of the range-imaging LIDAR system 24', 24$^i$ incorporating a Nd:YAG laser 11.1' may be operated at frequencies other than 266 nm, for example, at either the second or third harmonics, respectively, for example, as described more fully hereinbelow.

The arcuate fringes 49', 49" of the scatter 47 and reference 104 fringe patterns are circumferentially ($\phi$) or transversely (Y) integrated either optically prior to detection, or electronically or by software during or following detection by the detection system 34, so as to provide for corresponding detected image signals I(X) and I$_0$(X), respectively, that representing the total radiometric counts as a function of radial distance through the corresponding scatter 47 and reference 104 fringe patterns. The resulting detected image signals I(X) and I$_0$(X) are then processed by the data processor 53 as described hereinbelow so as to generate one or more measures of the atmosphere 20 as a function of nominal range R, or at a particular nominal range R, within the interaction region 17.

Generally, depending upon how the resulting scatter 51 and reference 106 electronic image signals are processed, in accordance with a first aspect, the detection system 34 may comprise either one- or two-dimensional photodetector arrays, for example, either charge-coupled devices (CCDs) or charge injection devices (CIDs); or corresponding arrays of individual photodetectors, for example, photo-conductive, photo-voltaic, photo-emissive, bolometer, or thermopile photodetectors, i.e. generally any device that converts photons to a corresponding electrical signal. The particular detection system 34 may be adapted in cooperation with the associated light source 11 so as to provide for increasing the associated signal-to-noise ratio (SNR). For example, in cooperation with a continuous light source 11, a relatively high-sensitivity, low-noise, low-bandwidth detectors can be used, so as to provide for a higher signal-to-noise ratio (SNR) than possible with corresponding relatively higher-bandwidth detectors, so as to provide for relatively more precise associated measurements. Alternatively, the detection system 34 could comprise a camera with at least one array of concentric circular-segment photodetectors for each of the images being processed.

For example, in one embodiment, to process the scatter fringe pattern 47, the range-imaging LIDAR system 24', 24$^i$ incorporates a linear photodetector array or a linear array of photodetectors, wherein, referring to FIG. 9, each photodetector or photodetector element of the array is sufficiently broad in the Y-direction 110 of the output focal plane 31.2' so as to provide for accumulating all of the photons at a given associated X-position, and the each photodetector or photodetector element of the array is sufficiently narrow in the X-direction 112 of the output focal plane 31.2' so as to provide for generating a corresponding one-dimensional scatter electronic image signal 51 with sufficient resolution with respect to X to solve for the associated measurements with sufficient accuracy, i.e. accuracy within a given threshold, wherein the X dimension corresponds to nominal range R to the associated measurement volumes 52 of the atmosphere 20 being measured within the beam of light 28. Similarly, one embodiment adapted to process the reference fringe pattern 104, the range-imaging LIDAR system 24', 24$^i$ incorporates a similar linear photodetector array or a linear array of photodetectors, wherein each photodetector or photodetector element of the array is sufficiently broad in the Y'-direction 110 of the output focal plane 31.2' so as to provide for accumulating all of the photons at a given associated X'-position, and the each photodetector or photodetector element of the array is sufficiently narrow in the X'-direction 112 of the output focal plane 31.2' so as to provide for generating a corresponding one-dimensional reference electronic image signal 106 with sufficient resolution with respect to X' to characterize the Fabry-Pérot etalon 35 sufficiently accurately so as to provide for solving for the associated measurements with sufficient accuracy, i.e. accuracy within a given threshold.

As another example, in another embodiment, to process both the scatter 47 and reference 104 fringe patterns, the range-imaging LIDAR system 24', 24$^i$ incorporates a two-dimensional photodetector array or a two-dimensional array of photodetectors that provide for generating associated two-dimensional scatter 51 and reference 106 electronic image signals that; for example, can then be integrated either electronically; or by a process in the data processor 53, for example, as described hereinbelow.

Scattered light signal 30' from each of the associated interaction regions 17 are substantially simultaneously processed together with a reference light signal 105 from the reference fringe pattern 104 so as to provide for calibrating, and maintaining the calibration of, the range-imaging LIDAR system 24', and so as to provide for determining the associated air data products such as the speed, temperature and density of the atmosphere 20. This provides for an inherent self-calibration of the associated measurements or quantities derived therefrom. If wavelength drift of the light source 11 is not otherwise accounted for in the data, then errors can arise when making a measurement of the Doppler shift and resulting wavelength shift of the scattered light signal 30'. The range-imaging LIDAR system 24' provides for automatically compensating for wavelength drift of the light source 11 from the data because each measurement from a scattered light signal 30' is corrected using a corresponding measurement from the reference light signal 105 associated with the reference source 94.

In accordance with a first aspect, the associated detection system 34.1 provides for capturing an image 114 of the scatter 47 and reference 104 fringe patterns in the output focal plane 31.2' of the Fabry-Pérot interferometer 31'. For example, in one embodiment, the detection system 34.1 comprises an electronic camera, for example, a CCD detection system 34.1'.

Figure 12A:
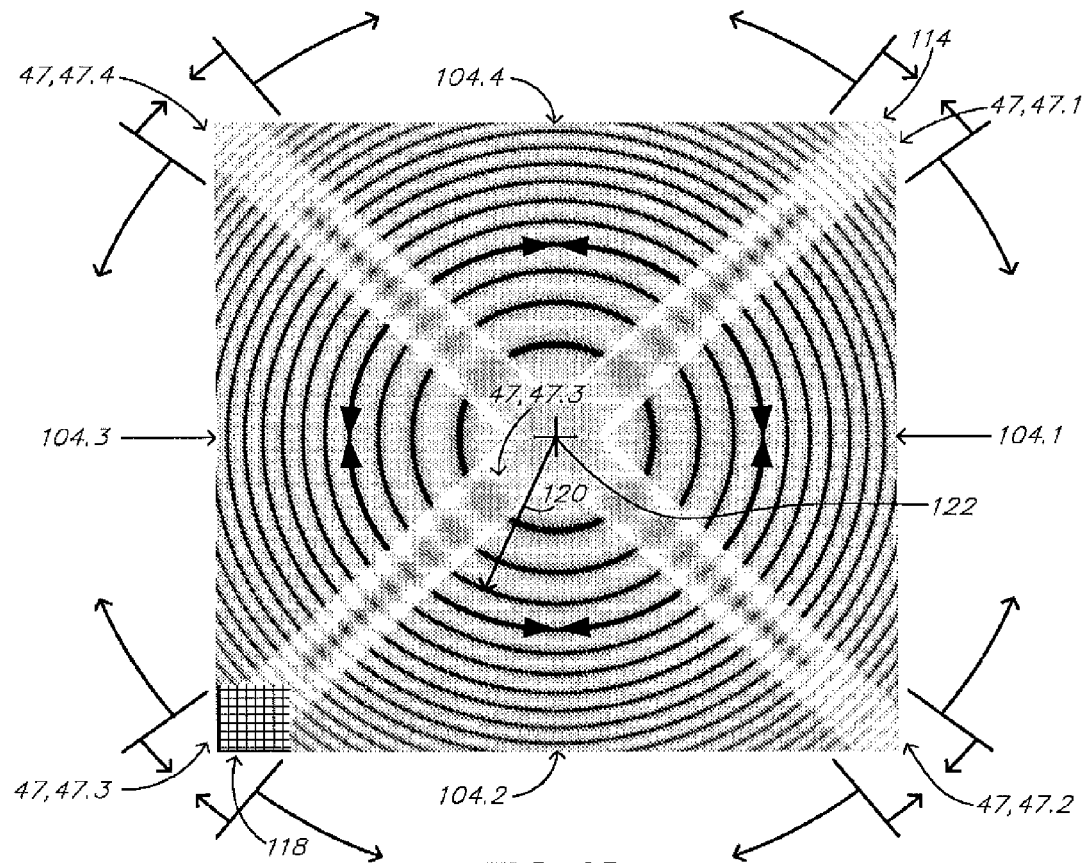
FIGS. 12a and 12b illustrate a circular image compression process operating on a fringe pattern from a Fabry-Pérot interferometer.
Figure 12B:
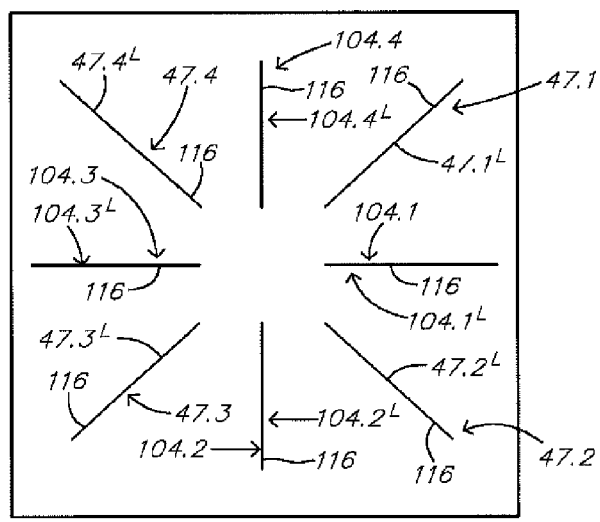

Referring to FIGS. 12a and 12b, this image 114 is then processed to azimuthally compress the associated scatter 47 and reference 104 fringe patterns into corresponding associated linear scatter 47$^L$ and reference 104$^L$ fringe patterns by an associated binning process to give corresponding linear sets of binned pixels 116 from which the corresponding atmospheric data 36 associated with each of the scattered light signals 30' is then determined by the data processor 53. For example, this process is illustrated in FIGS. 12a and 12b for a range-imaging LIDAR system 24', 24$^{viii}$ in accordance with an eighth aspect described hereinbelow, comprising four separate scatter fringe patterns 47, 47.1, 47.2, 47.3, 47.4 from four separate corresponding interaction regions 17, interleaved with a reference fringe pattern 104. In one embodiment, this is accomplished with a circular binning algorithm implemented in software on the associated data processor 53 operatively coupled to the associated CCD detection system 34.1' that provides for summing all pixels 118 at a particular radius 120 from the common center 122 of the associated circular fringe patterns 65 respectively corresponding to the first 47.1, second 47.2, third 47.3, and fourth 47.4 scatter fringe patterns and the reference fringe pattern 104 interleaved therewith divided into four separate corresponding referenCe fringe pattern portions 104.1, 104.2, 104.3, 104.4.

Each pixel 118 is read from the CCD detection system 34.1' and converted by an A/D conversion process. The ratio of signal to read noise can be enhanced by increasing the exposure time of the CCD detection system 34.1' between read cycles, although at the cost of reduced dynamic frequency response of the associated resulting air data products. After identifying the center 122 of the associated circular fringe patterns 65, the circular binning algorithm sums up the CCD charges (i.e. pixel values) for each pixel 118 at a particular radius from the center 122, for a particular circular fringe pattern 65, for each of the circular portions of the scatter fringe patterns 47.1, 47.2, 47.3, 47.4 and reference fringe pattern portions 104.1, 104.2, 104.3, 104.4, so as to provide a respective associated linear set of binned pixels 116 for each of the respective scatter fringe patterns 47.1, 47.2, 47.3, 47.4 and reference fringe pattern portions 104.1, 104.2, 104.3, 104.4.

Figure 13:
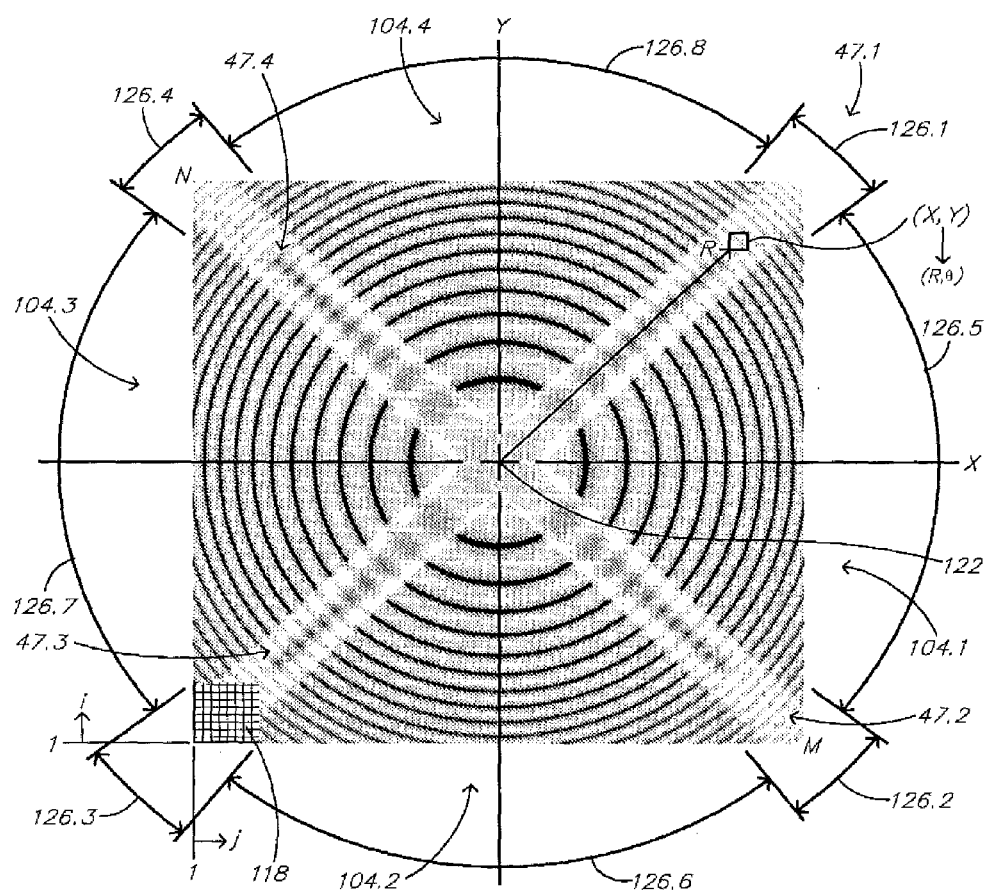
FIG. 13 illustrates an image of a set of circular fringe patterns and regions of interest associated with a circular binning process.

Referring to FIG. 13, the image 114 of the set of scatter fringe patterns 47.1, 47.2, 47.3, 47.4 and reference fringe pattern portions 104.1, 104.2, 104.3, 104.4 comprises an array of N rows by M columns of pixels 118, each of which is captured by the CCD detection system 34.1' and stored in a memory 124 of the associated data processor 53 of the range-imaging LIDAR system 24'. The image 114 comprises eight regions of interest (ROI) 126.1-126.8, each comprising one of the corresponding scatter fringe patterns 47.1, 47.2, 47.3, 47.4 and reference fringe pattern portions 104.1, 104.2, 104.3, 104.4, and located about the common center 122 of associated circular fringe patterns 65, wherein the center 122 of the associated circular fringe patterns 65 is determined upon initial calibration or subsequent recalibration of the associated range-imaging LIDAR system 24', and is assumed to be stationary during the operation thereof. For example, the center 122 may be determined by recording a substantial number, e.g. thousands, of circular fringe patterns 65 and determining the location of the center 122—by either iteration starting with an initial guess, or least squares or correlation with the coordinates of the center 122 as unknowns to be determined—that provides for a best fit of the recorded circular fringe patterns 65 with a corresponding circular model thereof centered at the center 122 of the circular fringe patterns 65.

Figure 14A:
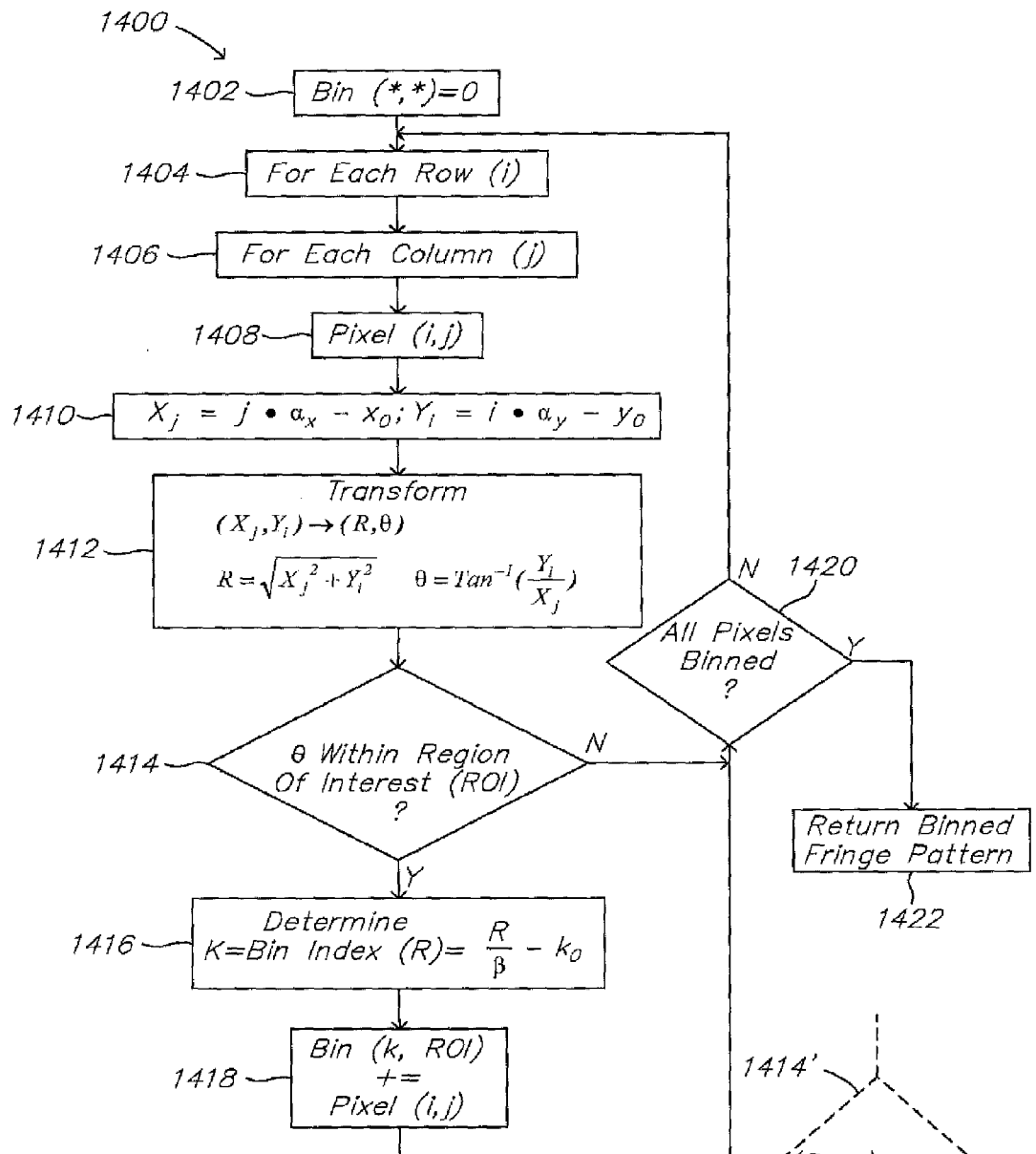
FIG. 14a illustrates a flow chart of a first aspect of a circular binning process.

Referring to FIG. 14a, in accordance with a first embodiment of a circular binning process 1400, in step (1402) a K×NROI bin array BIN(*,*) is defined with storage for NROI vectors of K elements each to hold the circumferentially-binned values for each of the NROI=8 portions of associated circular fringe patterns 65, and each value thereof is initialized to zero. Then, in steps (1404) and (1406), for each row i of the N rows, and for each column j of the M columns, of the pixels 118 in the image 114, the value Pixel(i,j) of the pixel 118 is read from the image 114 in step (1408), and in step (1410), the corresponding X and Y locations thereof are calculated respectively as follows:

$$x_j = j \cdot \alpha_X - x_0$$

$$y^i = i \cdot \alpha_y - y_0 \tag{14}$$

wherein $\alpha_X$ and $\alpha_Y$ are the distances per pixel in the X and Y directions, respectively, and $x_0$ and $y_0$ are the coordinates of the center 122 relative to Pixel(1,1) at the lower left corner of the image 114. Then, in step (1412), the Cartesian coordinates $(x_j, y_i)$ from step (1410) are transformed to cylindrical coordinates $(R, \theta)$, as follows:

$$R = \sqrt{x_j^2 + y_i^2} \tag{15}$$

$$\theta = \text{Tan}^{-1}\left(\frac{y_i}{x_j}\right)$$

Then, in step (1414), if the angle $\theta$ is within a region of interest (ROI) 126.1-126.8, the associated region of interest ROI 126 is identified, and in step (1416), the radial bin index k is given by:

$$k = \frac{R}{\beta} - k_0 \tag{16}$$

where $\beta$ is the distance per pixel in the radial direction, and $k_0$ is the number of pixels 118 between the center 122 and the closest portion of the circular fringe pattern 65 closest thereto. Then, in step (1418), the associated value Pixel(i,j) of the associated pixel 118 is added to the bin element BIN(k,ROI) of the bin array BIN(*,NROI) as follows:

$$\text{BIN}(k,\text{ROI}) = \text{BIN}(k,\text{ROI}) + \text{Pixel}(i,j) \tag{17}$$

Then, or otherwise from step (1414), in step (1420), if all of the pixels 118 have been circumferentially binned, then, in step (1422), the circumferentially-binned values for each portion of the associated circular fringe patterns 65 are returned in the associated bin array BIN(*,NROI). Otherwise, the process repeats with steps (1404) and (1406) for each of the rows and columns of pixels 118 until all of the portions of the associated circular fringe patterns 65 are binned.

Figure 14B:
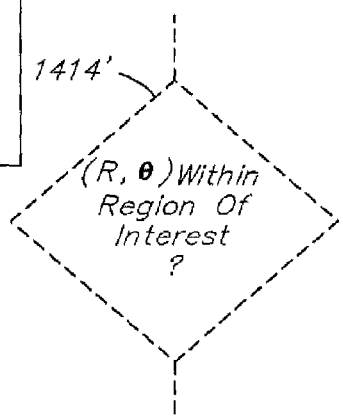

Referring to FIGS. 13 and 14b, alternatively, regions of interest (ROI) 126.1'-126.8' may be defined by the corresponding respective boundaries of the respective portions of the associated circular fringe patterns 65, in which case, step (1414) of the circular binning process 1400 would be replaced by step (1414'), whereby the test as to whether a particular pixel 118 was in a particular regions of interest (ROI) 126.1'-126.8' would depend upon both cylindrical coordinates $(R, \theta)$ of the particular pixel 118.

Figure 15:
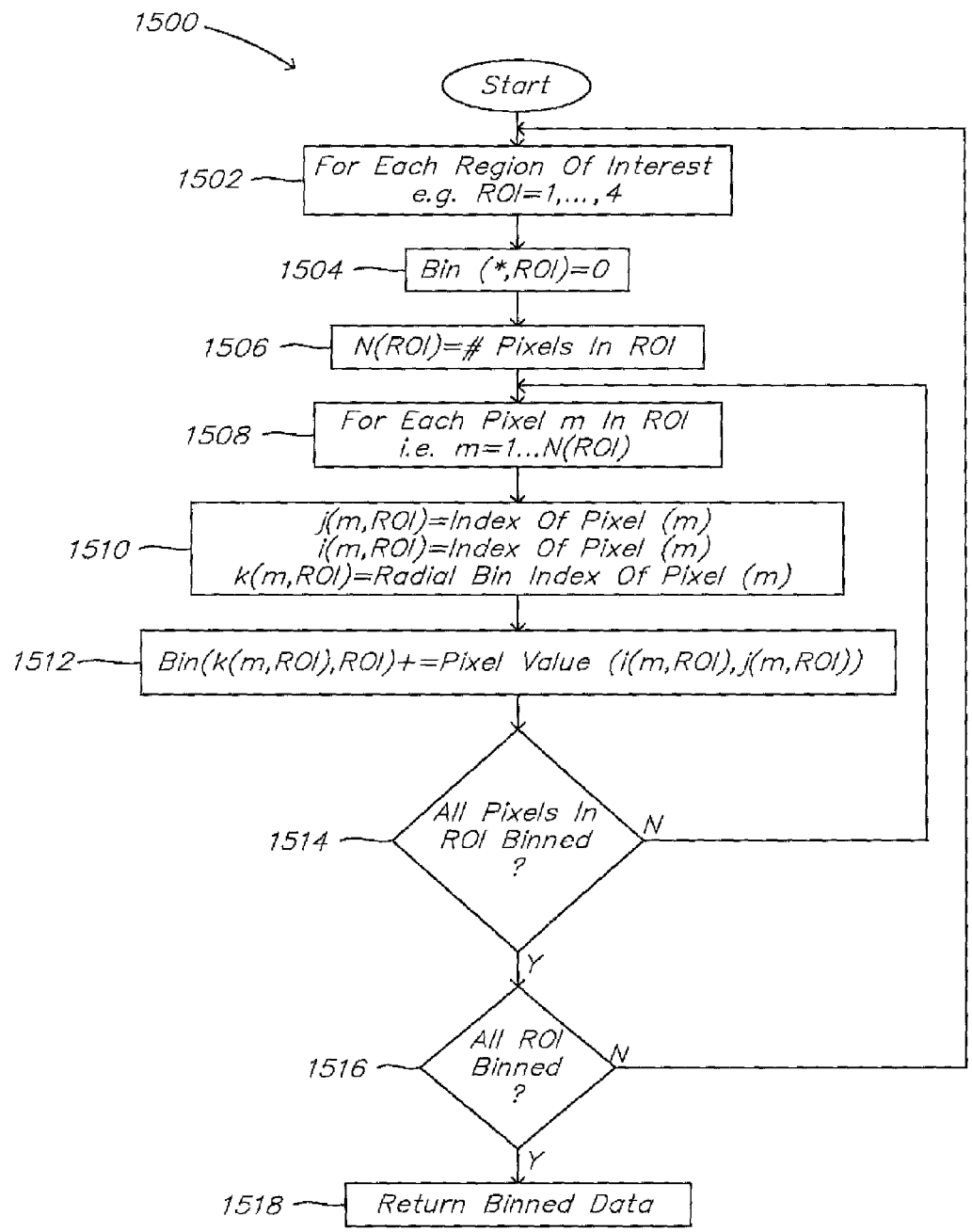
FIG. 15 illustrates a flow chart of a second aspect of a circular binning process.

Referring to FIG. 15, in accordance with a second embodiment of a circular binning process 1500, rather than processing every pixel 118 of the image 114, only those pixels 118 in predefined regions of interest (ROI) 126.1'-126.8' are processed, wherein, for example, the regions of interest (ROI) 126.1'-126.8' are defined by the corresponding respective circular boundaries of the respective portions of the associated circular fringe patterns 65. Beginning with step (1502), for each region of interest (ROI) 126.1'-126.8', in step (1504) the associated bin elements BIN(*,ROI) are initialized to zero. Then, in step (1506), the number of pixels 118 in the particular region of interest (ROI) 126.1'-126.8' is given by the predetermined value of N(ROI). Then in step (1508), for pixel m of the N(ROI) pixels 118 in the particular region of interest (ROI) 126.1'-126.8', the corresponding column j and row i indexes for the particular pixel 118, corresponding to the associated X and Y locations thereof, are given in step (1510) by predetermined values from predetermined index arrays j(m,ROI) and i(m,ROI) respectively, and the corresponding element k of the associated bin array BIN(*,ROI) into which the particular pixel 118 is to be binned is given by the predetermined index array k(m,ROI). Accordingly, in step (1512), the $m^{th}$ pixel 118 is binned into the $k^{th}$ element of the bin array BIN(*,ROI) as follows:

$$\text{BIN}(k(m,\text{ROI}),\text{ROI}) = \text{BIN}(k(m,\text{ROI}),\text{ROI}) + \text{Pixel}(i(m,\text{ROI}),j(m,\text{ROI})) \tag{18}$$

Then, in step (1514), if all of the pixels in in the particular region of interest (ROI) 126.1'-126.8' have not been binned, then the process continues with step (1508). Otherwise, in step (1516), if all of the regions of interest (ROI) 126.1'-126.8' have not been binned, then the process continues with step (1502). Otherwise, in step (1518), the circumferentially-binned values for each of the portions of/the associated circular fringe patterns 65 are returned in the associated bin array BIN(*,NROI).

In one embodiment, the scatter fringe patterns 104.1, 104.2, 104.3, 104.4 associated with the reference fringe pattern 104 are binned into a single common linear reference fringe pattern 104$^L$, whereas in other embodiments the scatter fringe patterns 104.1, 104.2, 104.3, 104.4 associated with the reference fringe pattern 104 are either binned into separate associated linear reference fringe pattern 104$^L$, 104.1$^L$, 104.2$^L$, 104.3$^L$, 104.4$^L$, or partially combined into a fewer number of associated linear reference fringe patterns 104$^L$.

As yet another example, in yet another embodiment, the range-imaging LIDAR system 24', 24$^i$ incorporates a plurality of circle-to-line interferometer optic (CLIO) elements 128 that provide for optically integrating the scatter 47 and reference 104 fringe patterns so as to generate corresponding linearly distributed associated fringe patterns that can then be detected with corresponding linear photodetector arrays or linear arrays of photodetectors, for example, as described hereinabove. For example, a separate circle-to-line interferometer optic (CLIO) element 128 would be used for each scatter fringe pattern 47.1, 47.2, 47.3, 47.4 and reference fringe pattern portion 104.1, 104.2, 104.3, 104.4 on diametrically opposing portions of the Fabry-Pérot interferometer 31' relative to the optic axis 39, wherein each circle-to-line interferometer optic (CLIO) element 128 may be constructed and operated in accordance with the teachings of U.S. Pat. No. 4,893,003, which is incorporated herein by reference in its entirety, and in accordance with the teachings of U.S. Pat. No. 7,495,774, from line 22 at column 8 through line 50 at column 10 with reference to FIGS. 8 through 15b inclusive therein, and line 54 at column 29 through line 41 at column 30 with reference to FIGS. 35 through 39 inclusive therein, all of which is incorporated by reference.

As yet another example, in yet another embodiment, the range-imaging LIDAR system 24', 24$^i$ incorporates a holographic optical element 128' adapted to transform the arcuate fringes 49', 49" into corresponding linear distributions of light, for example, in accordance with the teachings of U.S. Pat. No. 6,313,908, which is incorporated herein by reference in its entirety, but adapted so that the arcuate fringes 49' associated with the scatter fringe pattern 47 are transformed to a first linear distribution of light and the arcuate fringes 49'' associated with the reference fringe pattern 104 are transformed to a second linear distribution of light, wherein the first and second linear distributions are distinct, and detected by corresponding first and second linear photodetector arrays or linear arrays of photodetectors of the associated detection system 34, for example, as described hereinabove.

The reference 106 and scatter 51 electronic image signals are transmitted to the data processor 53, which processes the reference electronic image signal 106 to characterize the Fabry-Pérot etalon 35, and which then determines one or more range-dependent measures of the atmosphere 20—at one or more given ranges, or as a function of range—from the scatter electronic image signal 51 associated with arcuate fringes 49', wherein each arcuate fringes 49' corresponds to a different associated nominal range R and is analyzed separately. More particularly, the scatter electronic image signal 51 provides the information sufficient to determine the following measures of the atmosphere 20: aerosol counts A, molecular counts M, velocity u, temperature t, and background counts B, wherein molecular counts M provides for generating a measure of atmospheric density. As described more fully hereinbelow, data from each arcuate fringe 49' is analyzed separately, so as to determine one or more of the measures: aerosol counts A, molecular counts M, velocity u, temperature t, and background counts B either at a given nominal range R or set of nominal ranges R, or as a function of nominal range R. The measures are determined by non-linearly fitting the measured reference electronic image signal 106 with a parameterized model of the Fabry-Pérot etalon 35, parameterized with respect to the measures so as to characterize the Fabry-Pérot etalon 35, and then non-linearly fitting the measured scatter electronic image signal 51 associated with different arcuate fringes 49' to the parameterized model of the Fabry-Pérot etalon 35, parameterized with respect to the measures to be determined, i.e. with respect to aerosol counts A, molecular counts M, velocity u, temperature t, and background counts B, so as to determine values for those measures at the nominal range R associated with that particular arcuate fringe 49'.

Figure 16A:
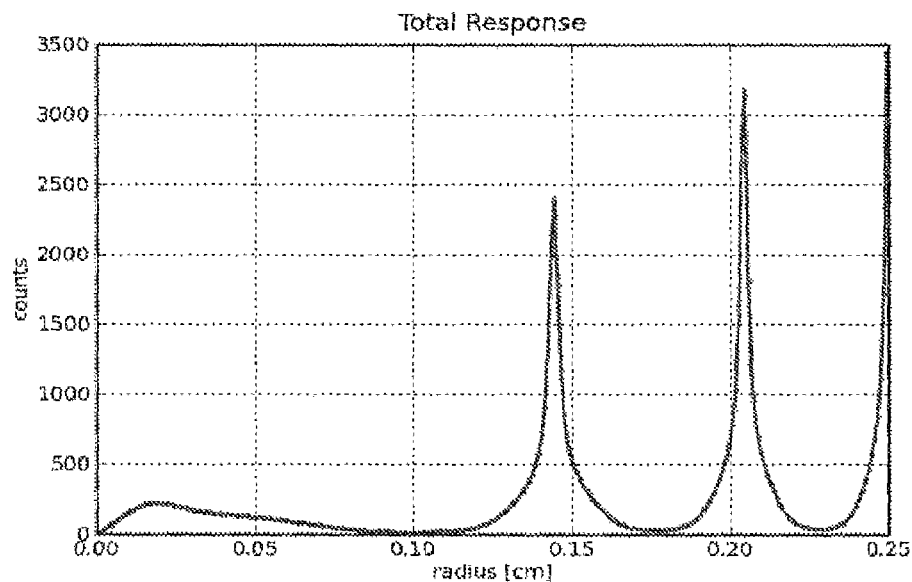
FIG. 16a illustrates a radial cross-section of an intensity distribution of a set of fringes from a Fabry-Pérot interferometer.
Figure 16B:
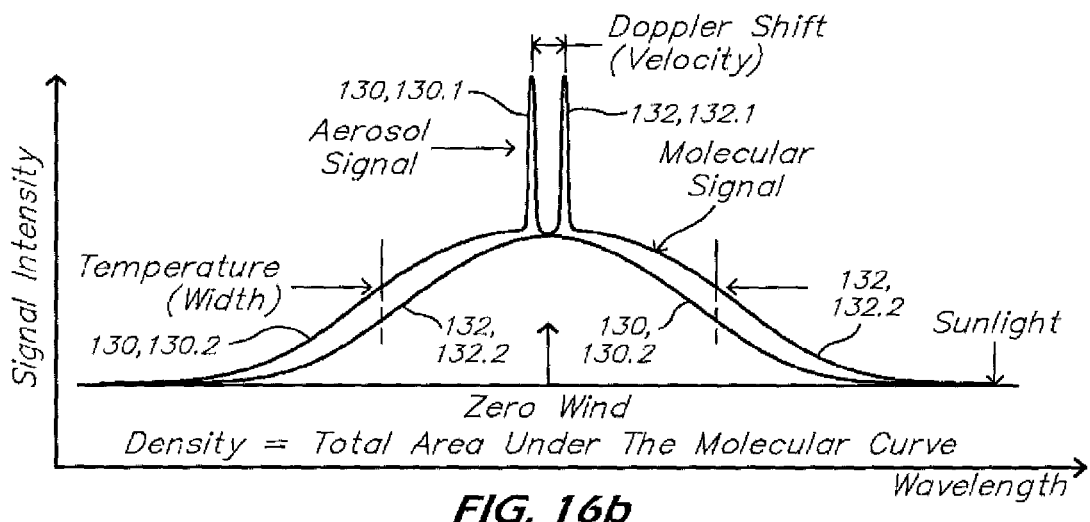
FIG. 16b illustrates fringes from the Fabry-Pérot interferometer from two scattered signals associated with different velocities.

A radial plot of the intensity of the circular fringe pattern 65 is illustrated in FIG. 16a. Referring to FIG. 16b, illustrating an expanded view of a radial cross-section of the intensity of a single circular fringe 65' of the circular fringe pattern 65, a first fringe 130 corresponds to a zero-wind, i.e. zero-velocity condition, and a second fringe 132 corresponds to a non-zero wind condition, wherein both the first 130 and second 132 fringes are illustrated as exhibiting both an aerosol signal component 130.1, 132.1 and a molecular signal component 130.2, 132.2 respectively. The reference light signal 105 also provides for a zero wind condition, but does not contain either molecular or background components, and accordingly would exhibit only the aerosol signal component 130.1 illustrated in FIG. 16b.

Figure 16C:
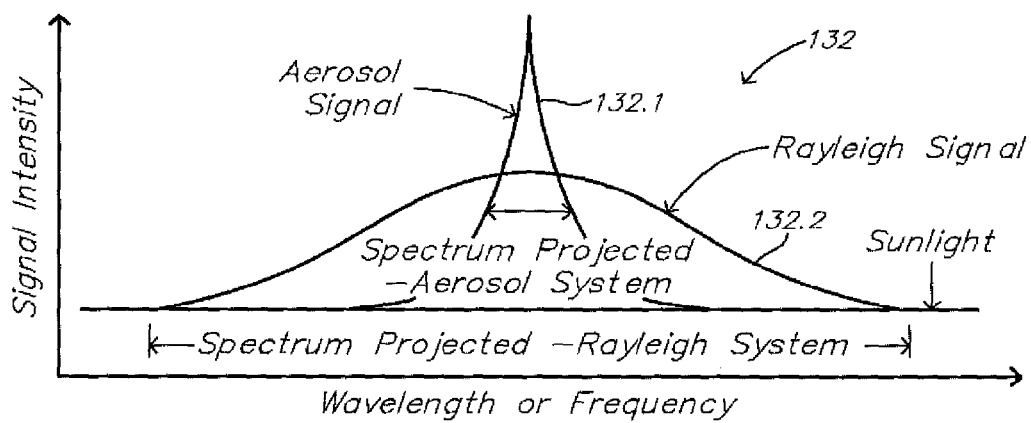
FIG. 16c illustrates a fringe associated with a scatter signal channel processed by the Fabry-Pérot etalon, wherein the fringe comprises aerosol (Mie), molecular (Rayleigh) and background signal components.

The spectral shape of the scattered light signal 30' processed by the Fabry-Pérot etalon 35, for a single associated fringe to be modeled, has a qualitative form illustrated in FIG. 16c, wherein the molecular scattered light, i.e. the molecular signal component 132.2, exhibits a broadened spectral shape, while the aerosol scattered light, i.e. the aerosol signal component 132.1, produces a sharp peak which is nearly identical to the shape of the transmitted laser light. Underlying these two components is a background signal from scattered sunlight, which at the scale of FIG. 16c forms a relatively flat continuum. By way of comparison, the corresponding spectral shape of the light of the reference light signal 105 processed by the Fabry-Pérot etalon 35 is substantially the same as that of the aerosol signal component 132.1.

The range-imaging LIDAR system 24' provides for directly detecting laser energy scattered off of either molecules 20' of the atmosphere, aerosols 20'' in the atmosphere, or a combination of the two, provides for directly measuring the associated velocity and direction, density, and temperature of the atmosphere, and provides for deriving other measurements therefrom, for example, a set of air data products. For example, relatively short wavelength laser energy is scattered by molecules of the atmosphere in accordance with Rayleigh scattering. Laser energy can also be scattered by aerosols in the atmosphere in accordance with Mie scattering. Rayleigh scattering generally refers to the scattering of light by either molecules or particles having a size less than about $1;10^{th}$ the wavelength of the light, whereas Mie scattering generally refers to scattering of light by particles greater than $1/10^{th}$ the wavelength of the light. Being responsive to Rayleigh scattering, the range-imaging LIDAR system 24' is therefore responsive to the properties—e.g. velocity, density and temperature—of those molecules in the atmosphere giving rise to the associated scattering of the light detected by the range-imaging LIDAR system 24'. Accordingly, the range-imaging LIDAR system 24' provides for operation in clean air, i.e. in an atmosphere with no more than a negligible amount of aerosols 20'', depending substantially only upon molecular scatter.

Figure 17:
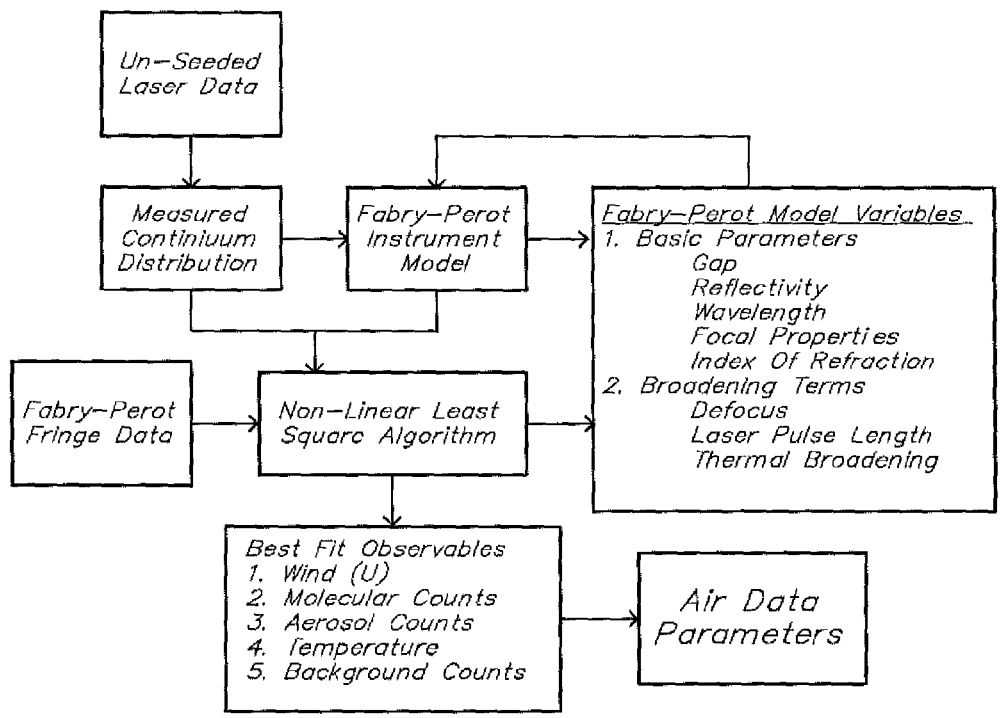
FIG. 17 illustrates a block diagram of a data analysis process used to determine atmospheric measurements from signals from a Fabry-Pérot interferometer.

Referring to FIG. 17, the image 114 of the scatter fringe pattern 47 generated by the range-imaging LIDAR system 24' is modeled use non-linear least square techniques. The distribution of the stray light and background radiation is provided by measurements of a scatter fringe pattern 47 either with an associated laser seeder 208 turned off when used in cooperation with a Nd:YAG laser 11.1' so as to enable the Nd:YAG laser 11.1' to lase over a relatively wider range of wavelengths that provides for simulating background radiation, or with the Fabry-Pérot etalon 35 removed from the Fabry-Pérot interferometer 31'. The scatter fringe patterns 47 are otherwise measured with the laser seeder 208 turned on if used in cooperation with a Nd:YAG laser 11.1' so as to provide for substantially single-frequency operation. The instrument functions and derivatives used in the algorithm are formed from analytic representations of the Fabry-Pérot interferometer 31' and include the necessary broadening functions to account for defects of the Fabry-Pérot etalon 35, e.g. the associated solid optical element 61, as well as temperature-dependent line shape broadening from molecular scatter. Empirical data for the illumination pattern is also used so that the correct light distribution of the fringes is accurately represented in the models.

Figure 18:
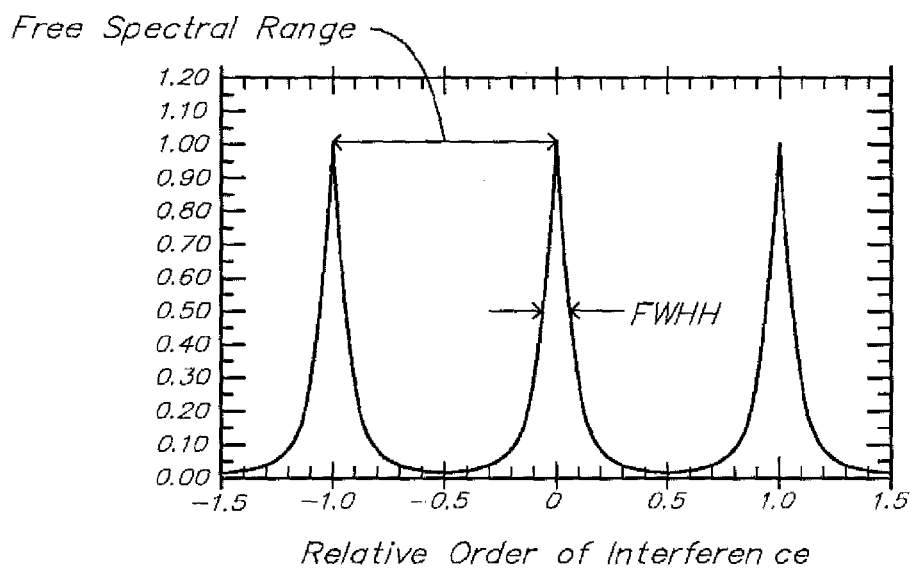
FIG. 18 illustrates a periodic transmission function of a Fabry-Pérot interferometer.

The transmission T, of a perfect Fabry-Pérot etalon 35 is given by the Airy function as follows, and as described in Hernandez, G., *Fabry-Pérot interferometers*, Cambridge: Cambridge University Press, 1986, and Vaughan, J. M., *The Fabry-Pérot Interferometer: History, Theory, Practice and Applications*, Bristol, England: A. Hilger, 1989, both of which documents are incorporated herein by reference:

$$T(M) = \frac{\left(1 - \frac{L}{1-R}\right)^2 (1-R)^2}{1 - 2R\cos 2\pi M + R^2} \tag{19}$$

where L is the loss per plate (absorption and scattering), R is the plate reflectivity, and M is the order of interference. Equation (19) describes a periodic transmission function, which is illustrated in FIG. 18. The separation between peaks is known as the free spectral range and depends inversely on the gap 45, 45.1 between the first 41 and second 43 partially-reflective surfaces, so that a relatively large spacing results in a relatively small free spectral range. The resolution of a Fabry-Pérot interferometer 31' is determined by the full width at half height (FWHH) of a fringe, which in turn determines the Rayleigh resolving power of the Fabry-Pérot interferometer 31'. The finesse of the Fabry-Pérot interferometer 31' is a unitless quantity that is defined as the ratio of the Free Spectral Range (FSR) to the FWHH. Finesse defines the number of resolvable elements that can fit in between two resonance peaks, and represents the sensitivity of the Fabry-Pérot interferometer 31'. In the absence of any defects, the finesse is related primarily to the reflectivity. For example, a reflectivity of 0.80 gives a finesse of 14, and a reflectivity of 0.90 gives a finesse of 30. In the presence of defects, both the finesse and the peak transmittance are reduced. Unless careful attention is given to defects when a Fabry-Pérot system is designed, the finesse and throughput can be substantially less than anticipated and can adversely bias the measured results. In order to incorporate defects into the instrument model equation (19) can be written in the equivalent series form, as follows:

$$T(M) = \left(1 - \frac{L}{1-R}\right)^2 \left(\frac{1-R}{1+R}\right)\left(1 + 2\sum_{n=1}^{\infty} R^n \cos 2\pi n M\right) \quad (20)$$

Equation (20) is a useful form of the Airy function since it provides for relatively easy convolutions with broadening functions.

The order of interference M is given by:

$$M = 2\mu t v \cos\theta \quad (21)$$

where μ is the index of refraction of the material between the first 41 and second 43 partially-reflective surfaces, t is the effective gap 45, 45.1, v is the wavenumber of light, and θ is the angle of incidence in the Fabry-Pérot etalon 35 which is responsive to the focal length of the imaging optics 37 and the size of the detection system 34. Perturbations of t, v and θ from a set of standard conditions and normal incidence, can be modeled as follows:

$$t = t_0 + \Delta t \quad (22)$$

$$v = v_0 + \Delta v \quad (23)$$

$$\cos\theta = 1 - \frac{\theta^2}{2} \quad (24)$$

The order of interference can then be written as follows:

$$M = 2\mu t_0 v_0 + 2\mu t_0 \Delta v + 2\mu v_0 \Delta t - 2\mu t_0 v_0 \frac{\theta^2}{2} \quad (25)$$

where only the first order terms have been retained, and can be further expressed as follows:

$$M = M_o + \Delta M \quad (26)$$

where $$M_0 = 2\mu t_0 v_0 \quad (27)$$

And $$\Delta M = 2\mu t_0 \Delta v + 2\mu v_0 \Delta t - 2\mu t_0 v_0 \frac{\theta^2}{2} \quad (28)$$

The quantity ½μt₀ is the change in wavenumber required to change the order of interference by one, and is defined as the free spectral range, $\Delta v_{FSR}$, which results in:

$$\Delta M = \frac{\Delta v}{\Delta v_{FSR}} - \frac{v_0}{\Delta v_{FSR}} \frac{\theta^2}{2} + 2\mu v_0 \Delta t \quad (29)$$

Without loss of generality $M_0$ can be an integer and therefore $T(M) = T(\Delta M)$.

Real instruments have defects which influence the behavior thereof and can be accounted for by broadening functions in the models used to characterize the device. These broadening functions are well known and are represented by a set of probability functions which can be convolved with the basic Fabry-Pérot Airy function to give the general result:

$$T(\Delta v, \theta) = \quad (30)$$

$$\left(1 - \frac{L}{1-R}\right)^2 \left(\frac{1-R}{1+R}\right)\left[1 + 2\sum_{n=1}^{\infty} R^n D_n \cos 2\pi n \left(\frac{\Delta v}{\Delta v_{FSR}} - \frac{v_0}{\Delta v_{FSR}} \frac{\theta^2}{2}\right)\right]$$

wherein the broadening function $D_n$ filters the transmission T depending upon the magnitude of the defect or broadening process, and is calculated from the following product:

$$D_n = \prod_{q=1}^{N_q} d_n^q \quad (31)$$

wherein $d_n^q$ is the $n^{th}$ element of the convolution of the $q^{th}$ broadening function $G_q$—described hereinbelow—with the instrument model of equation (20). The convolution integral is defined as follows:

$$d_n^q = \int_{-\infty}^{\infty} G_q(\delta')^* T(M(n) - \delta') d\delta' \quad (32)$$

where $T(M(n)-\delta')$ is the Fabry-Pérot infinite series term.

A simplified notation can be used to provide for a more compact representation, wherein $$A_n = \left(1 - \frac{L}{1-R}\right)^2 \left(\frac{1-R}{1+R}\right) \text{ for } n = 0 \quad (33)$$

$$= 2\left(1 - \frac{L}{1-R}\right)^2 \left(\frac{1-R}{1+R}\right) R^n D_n \text{ for } n > 0$$

so that the Airy function can be written as follows:

$$T(\Delta v, \theta) = \sum_{n=0}^{\infty} A_n \cos 2\pi n \left( \frac{\Delta v}{\Delta v_{FSR}} - \frac{v_0}{\Delta v_{FSR}} \frac{\theta^2}{2} \right) \quad (34)$$

The broadening functions $G_q$ account for broadening resulting from each of Doppler shift, laser width, scattering broadening, and turbulent motion, respectively, as given hereinbelow, for $N_q=3$ in equation (31).

Doppler Broadening:

The Doppler shift due to the mean air motion is given by:

$$\Delta v = v_1 \frac{2U_h \sin\phi}{c} \quad (35)$$

where $\Delta v$ is the Doppler shift, $v_1$ is the laser wavenumber, $U_h$ is the horizontal wind speed in the direction of viewing, and $\phi$ is the angle from the zenith made by the beam of light 28 as it passes through the atmosphere 20, wherein $U_h \sin\phi$ the line-of-sight relative wind velocity U. Accordingly, equation (35) provides the relationship between line-of-sight relative wind velocity U and the Doppler shift $\Delta v$.

Laser Spectral Width Broadening:

The spectral shape of the laser is assumed to be of Gaussian form, as follows:

$$G_{laser}(\Delta v, \Delta v_1) = \frac{1}{\sqrt{\pi}\, \Delta v_1} e^{-\frac{\Delta v^2}{\Delta v_1^2}} \quad (36)$$

where $\Delta v_1$ is the 1/e width of the laser, wherein the shorter the duration a laser pulse, the broader the associated broadening function, which results in lowered finesse for the Fabry-Pérot etalon 35.

Scattering Broadening:

The affect on the transmission T of a Fabry-Pérot interferometer 31' due to broadening induced by molecular scattering is different from that induced by aerosol scattering. Accordingly, different broadening functions $G_q$ are used to account for molecular and aerosol scattering, respectively, in respective corresponding models for the molecular $T_{Mol}$ and aerosol $T_{Aero}$ components of transmission T of the Fabry-Pérot interferometer 31'.

The molecular scattering media broadens the signal due to associated random motions. The molecules have a Gaussian broadening function, as follows:

$$G_{molecules}(\Delta v, \Delta v_G) = \frac{1}{\sqrt{\pi}\, \Delta v_G} e^{-\frac{\Delta v^2}{\Delta v_G^2}} \quad (37)$$

where $\Delta v_G$ is the 1/e width and is given by:

$$\Delta v_G = \frac{v_l}{c}\left(\frac{2k \cdot \text{Temp}}{m}\right)^{\frac{1}{2}} \quad (38)$$

or $$\Delta v_G = 4.30 \times 10^{-7} v_l \left(\frac{\text{Temp}}{\overline{M}}\right)^{\frac{1}{2}} \quad (39)$$

where k is Boltzmann's constant, m is the mean mass of a molecule in the atmosphere, Temp is the static absolute temperature in degrees Kelvin, and $\overline{M}$ is the mean molecular weight ($\overline{M}=28.964$).

The aerosol broadening function has a Lorentzian form as follows, for example, as described in Fiocco, G., and DeWolf, J. B., "Frequency spectrum of laser echoes from atmospheric constituents and determination of aerosol content of air," *Journal of Atmospheric Sciences*, v. 25, n3, May 1968, pp. 488-496; and Benedetti-Michelangeli, G., Congeduti, F., and Fiocco, G., "Measurement of aerosol motion and wind velocity in the lower troposphere by Doppler optical radar," *Journal of the Atmospheric Sciences*, v. 29, n5, July 1972, pp. 906-910, both of which references are incorporated herein by reference:

$$L_{aerosol}(\Delta v, \alpha_A) = \frac{1}{\pi} \frac{\alpha_A}{\alpha_A^2 + \Delta v^2} \quad (40)$$

where the half width $\alpha_A$ is given by:

$$\alpha_A = \frac{2\pi v^2 D}{c} \quad (41)$$

The spectral width of the aerosol-induced broadening component is extremely narrow compared to the molecular-induced broadening component, and in most cases are much narrower than the laser pulse, so that aerosol scattering essentially acts as a delta function and is not dependent on temperature.

Turbulent Motion Broadening:

In addition to random motions of molecules and aerosols, the model allows for random motions of bulk parcels, i.e. turbulence, wherein this broadening is represented by a relatively simple Gaussian shape, as follows:

$$G_{turbulence} = (\Delta v, \Delta v_T) = \frac{1}{\sqrt{\pi}\, \Delta v_T} e^{-\frac{\Delta v^2}{\Delta v_T^2}}, \quad (42)$$

where $$\Delta v_T = \frac{v_1}{c} U_T, \quad (43)$$

and $U_T$ is a characteristic turbulent velocity, which is a predefined constant that is independent of the line-of-sight relative wind velocity U. In some embodiments, this term is ignored because it is indistinguishable from temperature, so that the affects of equations (37) and (42) are indistinguishable from one another.

Other broadening functions $G_q$ can also be utilized in addition to those described hereinabove, for example, so as to account for a defocus of the imaging optics 37.

The values of the linear sets of binned pixels 116 for the reference light signal 105 and scattered light signals 30', respectively, provide a corresponding transmission measure T' of the Fabry-Pérot interferometer 31' for the corresponding reference light signal 105 and scattered light signals 30', respectively. Each transmission measure T' is an N-element vector, wherein each element n of the vector corresponds to a different wavelength or corresponding order of interference. The element values are in units of measurement counts; for example, with one measurement count being equal to one photo-electron captured by the detection system 34. The transmission measure T' is a measure of data from the Fabry-Pérot interferometer 31' that can be modeled as described hereinabove in accordance with equations (19) through (43), as represented by FIGS. 16c and 18, wherein FIG. 16c illustrates a finer scale of detail of each fringe illustrated in FIG. 18. Accordingly, the transmission measure T', in units of total counts of binned values from the detection system 34, can be modeled as the sum of associated molecular, aerosol and background counts, as follows:

$$T = T_{Mol}(\text{Temp}, U) \cdot \text{MolCounts} + T_{Aero}(U) \cdot \text{AeroCounts} + T_{Back} \cdot \text{BackCounts} \qquad (44)$$

where $T_{Mol}(\text{Temp}, U) \cdot \text{MolCounts}$ is the component of transmission T of the Fabry-Perot interferometer 31' resulting from molecular scatter, which is a function of temperature and line-of-sight relative wind velocity U; $T_{Aero}(U) \cdot \text{AeroCounts}$ is the component of transmission T of the Fabry-Pérot interferometer 31' resulting from aerosol scatter, which is not affected by temperature but is dependent upon the line-of-sight relative wind velocity U; and $T_{Back} \cdot \text{BackCounts}$ is the component of transmission T of the Fabry-Pérot interferometer 31' resulting from stray light and background wherein $T_{Back}$ is the continuum distribution or illumination profile through the instrument that is measured during calibration of the instrument from the response of the Fabry-Pérot interferometer 31' with the laser seeder 208 turned off, which is representative of the associated spectral distribution from the Fabry-Pérot interferometer 31' that would result from background illumination. During operation of the range-imaging LIDAR system 24', the continuum distribution $T_{Back}$ is obtained from pre-measured values that are stored in memory, and the components $T_{Mol}$ and $T_{Aero}$ are calculated from equation (34) using the appropriate associated broadening terms. Each of the above-described components of transmission T of the Fabry-Pérot interferometer 31' is in units of counts resulting from the charge collected by the elements of the detection system 34. The distributions $T_{Mol}(\text{Temp}, U)$, $T_{Aero}(U)$ are evaluated with equation (34) using broadening functions that are appropriate for the molecular and aerosol components of scatter, respectively. In practice, when evaluating equation (34), the associated infinite series is truncated to ignore higher-order terms of relatively insignificant value, wherein the level of truncation is either predetermined, or determined during the accumulation of the elements of the series.

Accordingly, the transmission T of the Fabry-Pérot interferometer 31' is modeled with a non-linear model of equation (44) that is parameterized by a first set (or vector) of parameters P that characterize a particular measurement, i.e. which characterize a particular transmission measure T'; and a second set of parameters Q which are assumed constant during operation of the Fabry-Pérot interferometer 31', the values of which are determined during calibration. Referring to FIG. 17, the first set of parameters P, referred to as observables P, include the following elements: line-of-sight relative wind velocity U, static temperature Temp, molecular counts MolCounts, aerosol counts AeroCounts, and scatter counts BackCounts. The second set of parameters Q includes the gap 45, 45.1 (*t*), index of refraction μ (1 for an air gap) and reflectivity R of the Fabry-Perot etalon 35, the nominal wavenumber ν (or wavelength λ) of the monochromatic light 13 from the light source 11, the focal properties of the imaging optics 37 (i.e. θ in equation (21)), and the continuum distribution $T_{Back}$.

The observables P can be determined as the values of the parameters P that minimize the following $\chi^2$ merit function:

$$\chi^2(P, Q) = \sum_{n=1}^{N} \frac{[T'(n) - T(M(n); P, Q)]^2}{\sigma^2(n)} \qquad (45)$$

using, for example, a Levenberg-Marquardt method of a non-linear least square process which provides for varying smoothly between an inverse-Hessian method and a steepest descent method, as described, along with other suitable non-linear methods, by W. H. Press, S. A. Teukolsky, W. T Veterling, and B. P. Flannery in *Numerical Recipes in C, The Art of Scientific Computing, Second Edition*, Cambridge University Press, 1992, pp. 656-661 and 681-706 which is incorporated herein by reference. In equation (45), T'(n) is the value of the $n^{th}$ binned pixel 116', and T(M(n),P,Q) is the value of the transmission model T from equation (44).

Accordingly, for the range-imaging LIDAR system 24', the transmission model T is overdetermined in the sense that the number of elements N of the detection system 34, i.e. the number of binned pixels per channel, is of a higher dimension than the number of observables P. For the range-imaging LIDAR system 24' embodiment described herein, there are 5 observables P.

In the inverse Hessian method, the gradient of $\chi^2$ is given by:

$$\beta_k = \frac{\partial \chi^2}{\partial P_k} = -2 \sum_{n=1}^{N} \frac{[T'(n) - T(M(n); P, Q)]}{\sigma^2(n)} \frac{\partial T(M(n); P, Q)}{\partial P_k} \qquad (46)$$

and the Hessian is approximated by:

$$\alpha_{kl} = \frac{\partial^2 \chi^2}{\partial P_k \partial P_l} = 2 \sum_{n=1}^{N} \frac{\partial T(M(n); P, Q)}{\partial P_k} \frac{\partial T(M(n); P, Q)}{\partial P_l} \qquad (47)$$

where k=1 to 5 for the 5 observables P.

The observables P are then solved by solving the set of linear equations:

$$\sum_{l=1}^{5} \alpha_{kl} \delta P_l = \beta_k \qquad (48)$$

where $\delta P_l$ is an vector increment that is to be added to a current approximation for the observable vector $P_l$. This system of equations can be represented as:

$$A \cdot \delta P = B \qquad (49)$$

where A is the Hessian matrix, δP is a vector of increments to the observables P that are to be added to a current approximation for the observable P, and B is the gradient vector. This system of equations can be solved as follows:

$$\delta P = A^{-1} \cdot B \qquad (50)$$

where $A^{-1}$ is the inverse Hessian matrix.

The inverse Hessian method is suitable when the $\chi^2$ merit function can be locally approximated by a quadratic form. If a quadratic form is a relatively poor local approximation, then the steepest descent formula can be used to find the increment δP of the observable P as follows:

$$\delta P_l = \text{constant} \times \beta_k \quad (51)$$

The Levenberg-Marquardt method provides for a combination of the inverse Hessian and steepest descent methods, wherein the Hessian matrix in equation (48) is replaced with:

$$\alpha'_{kk} = \alpha_{kk} \cdot (1 + \lambda) \quad (52)$$
$$\alpha'_{jk} = \alpha_{jk}$$
$$(j \neq k)$$

and both equations (48) and (51) are replaced with the following:

$$\sum_{l=1}^{5} \alpha'_{kl} \delta P_l = \beta_k \quad (53)$$

the solution of which is given by:

$$\delta P = A'^{-1} \cdot B \quad (54)$$

where the elements of A' are given by $\alpha'_{jk}$.

The Levenberg-Marquardt method commences with an initial guess for the observable vector P, after which $\chi^2(P,Q)$ is calculated, and an initial value of λ is chosen (e.g. λ=0.001). An iterative process then commences with the solution for δP of equation (44), and the evaluation of $\chi^2(P+\delta P, Q)$. If $\chi^2(P+\delta P, Q) \geq \chi^2(P,Q)$, then λ is increased, e.g. by a factor of 10, and the iteration is repeated. Otherwise, if $\chi^2(P+\delta P, Q) < \chi^2(P,Q)$, then λ is decreased, e.g. by a factor of 10, and the iteration is repeated. The iterations on the observable vector P are continued until a stopping criteria is satisfied, for example, on the first or second occasion when $\chi^2$ decreases by a negligible amount, and with the final solution, the method converses towards the inverse Hessian method.

The components of the gradient of the transmission model T used in calculating the gradient of $\chi^2$ and the Hessian matrix are given as follows, and are calculated numerically:

$$\frac{\partial T(U, \text{MolCounts}, \text{AeroCounts}, \text{Temp}, \text{BackCounts})}{\partial U} = \quad (55)$$
$$\frac{\partial}{\partial U}(T_{Mol}(\text{Temp}, U) \cdot \text{MolCounts} + T_{Aero}(U) \cdot \text{AeroCounts})$$

$$\frac{\partial T(U, \text{MolCounts}, \text{AeroCounts}, \text{Temp}, \text{BackCounts})}{\partial \text{MolCounts}} = \quad (56)$$
$$T_{Mol}(\text{Temp}, U)$$

$$\frac{\partial T(U, \text{MolCounts}, \text{AeroCounts}, \text{Temp}, \text{BackCounts})}{\partial \text{AeroCounts}} = T_{Aero}(U) \quad (57)$$

$$\frac{\partial T(U, \text{MolCounts}, \text{AeroCounts}, \text{Temp}, \text{BackCounts})}{\partial \text{Temp}} = \quad (58)$$
$$\frac{\partial}{\partial \text{Temp}} T_{Mol}(\text{Temp}, U)$$

$$\frac{\partial T(U, \text{Mol}, \text{Aero}, \text{Temp}, \text{BackCounts})}{\partial \text{BackCounts}} = T_{Back} \quad (59)$$

When processing the reference light signal 105, the observables MolCounts and BackCounts are assumed to be zero valued, and the partial derivatives with respect to MolCounts, BackCounts and Temp of equations (46), (59) and (58), respectively, are also assumed to be zero.

The $\sigma^2(n)$ weighing term in the $\chi^2$ merit function is the associated variance of the $n^{th}$ measurement channel (i.e. interference order or wavelength), which includes variance of the collected signal in combination with the variance associated with the noise from the detection system 34. The collected photons exhibit Poisson noise statistics. Accordingly, for Signal(n) photons/counts/photo-electrons collected on a single channel, the associated variance is equal to the signal level, as follows:

$$\sigma_{Signal}^2(n) = \text{Signal}(n) \quad (60)$$

wherein Signal(n) is the sum of the molecular, aerosol and background components, i.e.:

$$\text{Signal}(n) = \text{Molecular}(n) + \text{Aerosol}(n) + \text{Background}(n) \quad (61)$$

so that Signal(n) is the predicted value from equation (44). The total variance is the combination of the signal variance and the variance of the detector, as follows:

$$\sigma^2(n) = \text{Signal}(n) + \text{Noise}_{Detector}(n)^2 \quad (62)$$

wherein, for a CCD detection system 34.1, the detector noise is the associated read noise on each detector channel.

Alternatively, the observables P could be estimated using other non-linear modeling or non-linear programming techniques, or other techniques such as non-linear estimation or Kalman filtering.

Figure 19:
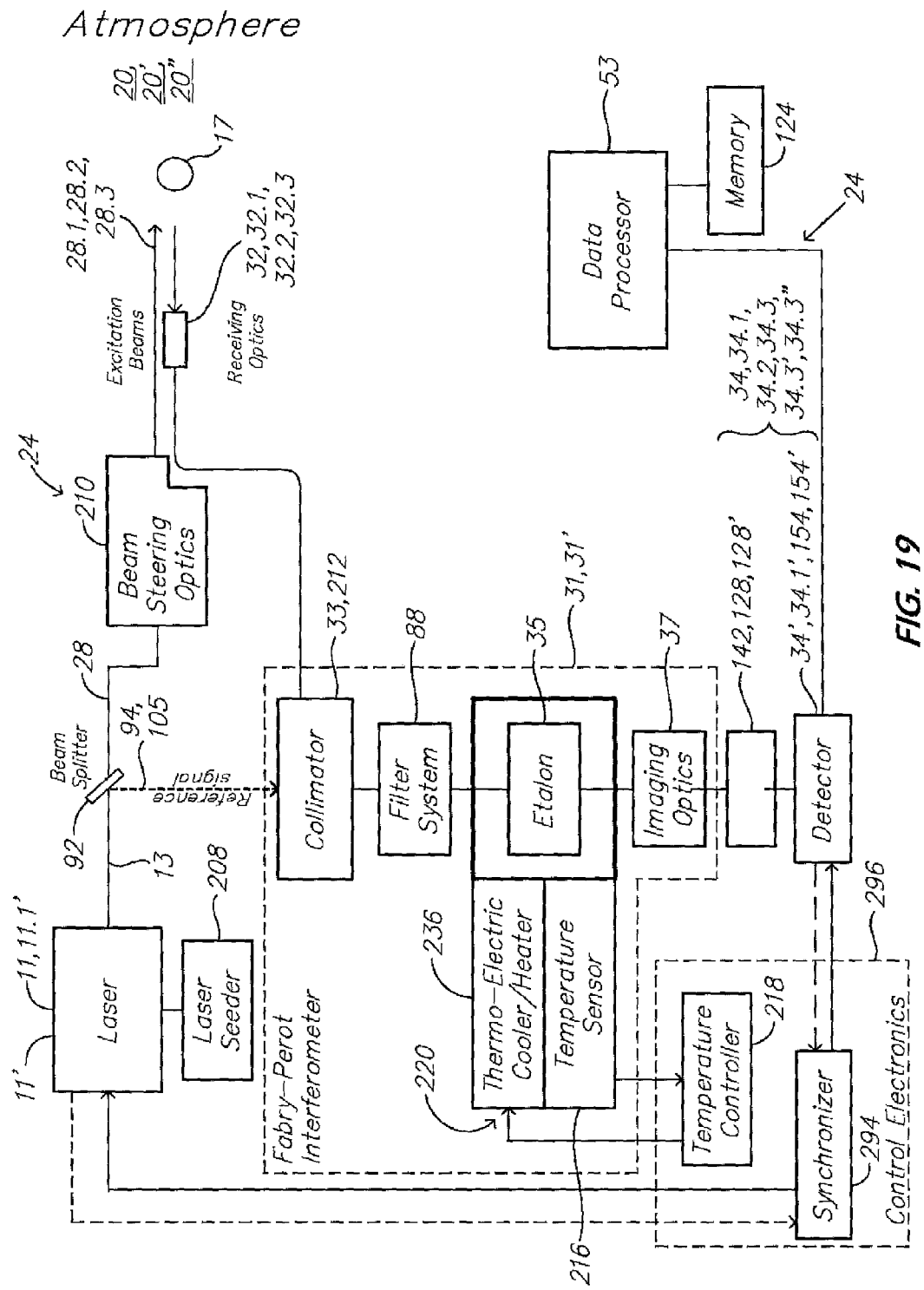
FIG. 19 illustrates a block diagram of various aspects of a range-imaging LIDAR system.
Figure 20:
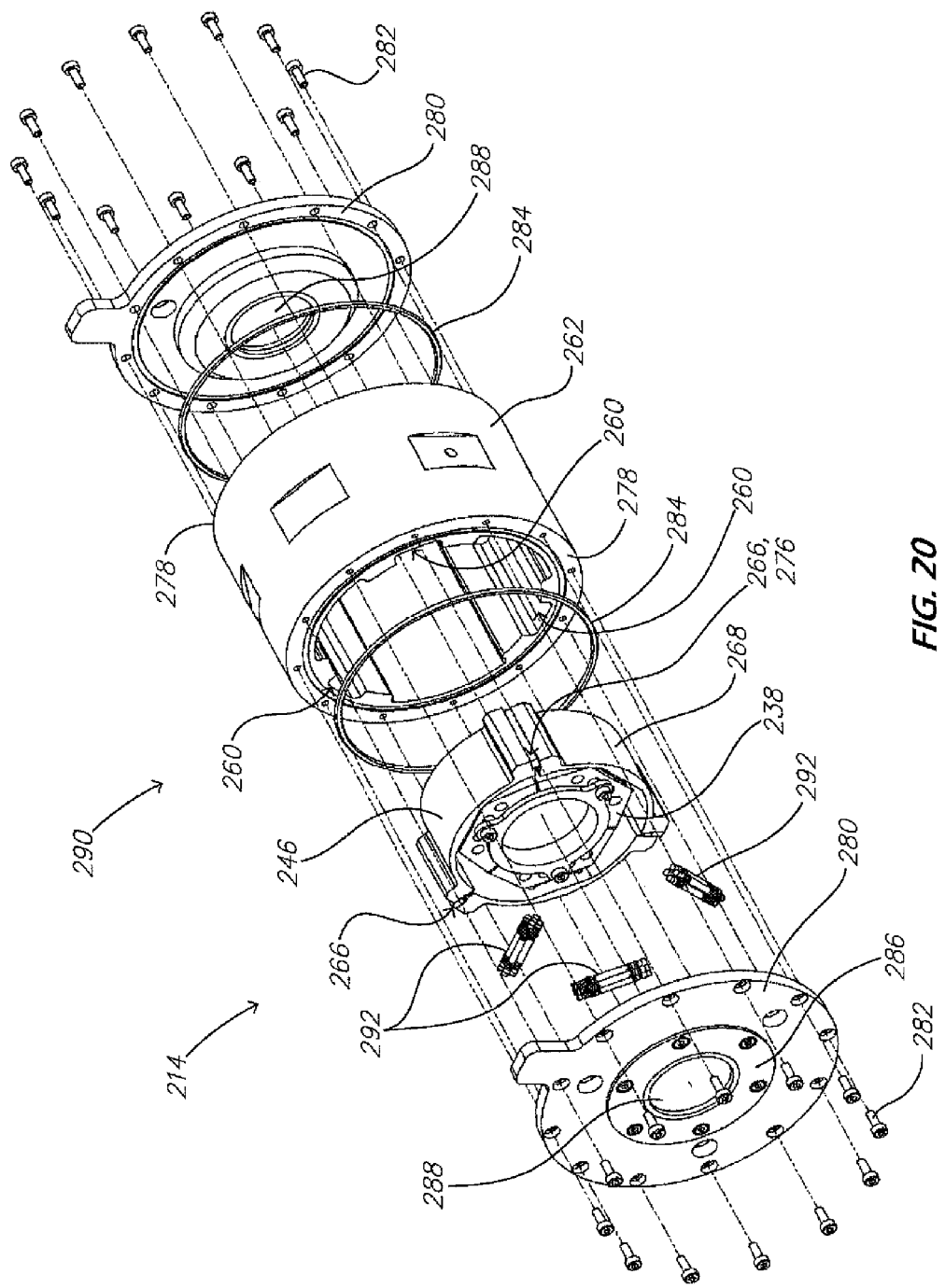
FIG. 20 illustrates an exploded view of thermal chamber assembly enclosing a Fabry-Pérot etalon.

Referring to FIG. 19, in accordance with other embodiments, the range-imaging LIDAR system 24' comprises a laser 11' as the light source 11, for example, in one embodiment, a Nd:YAG laser 11.1', which operates in a pulsed mode, and which is operatively associated with a laser seeder 208, for example, a laser diode that provides for seeding the cavity of the pulsed Nd:YAG laser 11.1' with photons via an associated light coupling system, wherein the photons are injected from the laser seeder 208 into the cavity of the Nd:YAG laser 11.1' prior to the build-up of the laser pulse associated of the light source 11, causing the frequency thereof to substantially match that of the laser seeder 208, so as to provide for substantially single-frequency operation. For example, in one embodiment, the laser seeder 208 is adapted in cooperation with the Nd:YAG laser 11.1' so that the bandwidth of the light source 11 is as narrow or narrower than the bandwidth of the associated Fabry-Pérot interferometer 31', wherein the bandwidth of the Fabry-Perot interferometer 31' is related to the finesse thereof.

The substantially monochromatic light 13 from the laser 11' is divided by a beam splitter optic 92 into a reference source 94 and the beam of light 28, the latter of which in some embodiments may be further divided into a plurality of beams of light 28 by beam steering optics 210, for example, incorporating beam splitting mirrors, prisms, a combination thereof, or some other type of beam splitter, each different beam of light 28 directed in a different direction into the atmosphere 20. The scattered light signals 30' and reference source 94 are each first collimated by a collimator 212, e.g. a collimating lens 33, then filtered by a filter system 88 as described hereinabove, and then processed by an associated Fabry-Pérot etalon 35, the output of which is imaged by associated imaging optics 37 as portions of associated circular fringe patterns 65 onto the associated detection system 34. The associated optical components are adapted for the frequency and power levels of operation. For example, for a range-imaging LIDAR system 24' incorporating a Nd:YAG laser 11.1' operating at 355 nanometers, the optical elements would incorporate UV-grade fused silica substrates and standard anti-reflection coatings tuned for 355 nanometers.

The geometry of the circular fringe patterns 65 from the Fabry-Pérot etalon 35 is responsive to the operative gap 45, 45.1 thereof, which would vary with temperature if the associated material or materials controlling the length of the gap 45, 45.1 were to exhibit a non-zero coefficient of thermal expansion. Although the reference source 94 simultaneously processed by the Fabry-Pérot etalon 35 provides for compensating for thermal drift affecting all portions of the Fabry-Pérot etalon 35 equally, it is beneficial if the temperature of the Fabry-Pérot etalon 35 can be controlled or maintained at a constant level so as to prevent a thermal expansion or contraction thereof during the operation thereof. Accordingly, in accordance with one aspect of the range-imaging LIDAR system 24', the Fabry-Pérot etalon 35 is thermally stabilized by enclosure in a thermally-controlled enclosure 214 so as to prevent thermally-induced drift of the circular fringe pattern 65.

In accordance with one aspect, the thermally-controlled enclosure 214 is passive, for example, with the Fabry-Pérot etalon 35 enclosed, i.e. thermally insulated or isolated, using a material or materials with a very low thermal conductance to increase the thermal time constant and to prevent any substantial thermal shock from reaching the Fabry-Pérot etalon 35. In accordance with another embodiment, or in combination therewith, the thermally-controlled enclosure 214 is constructed from a combination of materials adapted so that there is negligible net coefficient of thermal expansion in the portions of the structure surrounding the Fabry-Pérot etalon 35 that affect the length of the gap 45, 45.1.

Referring to FIGS. 20-23, in accordance with another aspect, a temperature of the thermally-controlled enclosure 214 is actively controlled responsive to at least one associated temperature sensor 216 using a temperature controller 218 incorporating a feedback control system 220 to control a heater, chiller or a combination heater and chiller—depending upon the temperature of the thermally-controlled enclosure 214 in relation to that of its environment. For example, referring to FIGS. 21 and 22, the Fabry-Pérot etalon 35 comprises a solid optical element 61—for example, constructed from high purity UV grade fused silica—enclosed within a etalon mount 222 comprising a cylindrical sleeve constructed from a material with a coefficient of thermal expansion that closely matches that of the solid optical element 61 so as to provide for preventing or substantially eliminating unwanted thermally induced radial stress in the solid optical element 61. The etalon mount 222 in turn is surrounded by a plurality, e.g. three, heat sink segments 224, each having a relatively high thermal conductance—for example, constructed of copper— each comprising an inner cylindrical face 226 that abuts an outside surface 228 of the etalon mount 222, and an outer face 230 incorporating a recess 232 adapted to receive and abut a first surface 234 of a thermo-electric heat pump 236, for example, what is known as a thermoelectric cooler (TEC). Upon assembly, the heat sink segments 224 collectively constitute an inner enclosure 238 that extends around and surrounds the etalon mount 222, the latter of which incorporates a flange 240 that abuts a set of first faces 242 on one side of the heat sink segments 224, and is fastened thereto with a plurality of fasteners 244, e.g. cap screws. The inner enclosure 238 is surrounded by an outer enclosure 246 comprising a plurality, e.g. three, heat conducting outer ring segments 248, e.g. constructed on aluminum, each of which incorporates an inside face 250 with an associated recess 252 that is adapted to receive and abut a second surface 254 of the thermo-electric heat pump 236. Each of the outer ring segments 248 incorporate associated flanges 256 at both ends, one side 258 of which are adapted to cooperate with internal grooves 260 in an outer shell 262 of the thermally-controlled enclosure 214, the other side 264 of which are adapted to cooperate with an outer ring retainer wedge 266 that operates between corresponding sides 264 of adjacent flanges 256 of adjacent outer ring segments 248 when the outer ring segments 248 are assembled to form the outer enclosure 246 surrounding the inner enclosure 238.

The inner 238 and outer 246 enclosures are assembled together to form a core assembly 268, as follows. The solid optical element 61 Fabry-Pérot etalon 35 is bonded inside a bore 270 of the etalon mount 222 with a thermal epoxy which provides for thermal conduction therebetween, wherein the inside diameter of the bore 270 is adapted so as to provide for a non-interfering fit with the solid optical element 61. The flange 240 of the etalon mount 222 is attached with fasteners 244 to the first faces 242 of the three heat sink segments 224 assembled around the outside surface 228 of the etalon mount 222. Three thermo-electric heat pumps 236 are sandwiched between respective recesses 232, 252 in a corresponding outer face 230 of each heat sink segment 224 and a corresponding inside face 250 of each outer ring segment 248, so that the first 234 and second 254 surfaces of the thermo-electric heat pumps 236 abut and are in thermal communication with the corresponding associated heat sink segment 224 and outer ring segment 248 respectively. The core assembly 268 further comprises a plurality, e.g. three, temperature sensors 216, e.g. thermistors, resistive temperature devices, or thermocouples—each of which is inserted in a corresponding hole 272 in a second face 274 of each heat sink segment 224, so as to provide for monitoring the temperature thereof, and so as to provide in cooperation with the associated temperature controller 218 and the associated thermo-electric heat pump 236, for controlling the temperature thereof.

The core assembly 268 is inserted in the outer shell 262 so that the flanges 240 of the outer ring segments 248 mate with the corresponding internal grooves 260 of the outer shell 262, and the outer ring retainer wedges 266 are inserted in the gaps 276 between the facing sides 264 of the flanges 240 so as to wedge the opposing sides 258 of the flanges 240 against associated internal grooves 260 of the outer shell 262, thereby providing for retaining the core assembly 268 within the outer shell 262, and providing for thermal communication therebetween. The ends 278 of the outer shell 262 are closed with associated end cap assemblies 280 secured thereto with associated fasteners 282 and sealed therewith with associated seals 284, e.g. gaskets or o-rings. The end cap assemblies 280 incorporate associated window assemblies 286 fastened thereto and incorporating optical windows 288, e.g. constructed from UV grade fused silica substrates with standard anti-reflection coatings, which provide for transmission of the associated scattered 30' and reference 105 light signals. The resulting assembly constitutes a thermally stabilized etalon assembly 290 incorporating a thermally-controlled enclosure 214. The thermally stabilized etalon assembly 290 further comprises a plurality of electrical connectors 292 therein which provide for connecting the thermo-electric heat pumps 236 and the temperature sensors 216 with the associated temperature controller 218. The temperature controller 218 uses the temperature sensors 216 to monitor the temperature of the core assembly 268, and controls the heating or cooling thereof relative to the environment using the associated thermo-electric heat pumps 236 so as to maintain the temperature of the core assembly 268 at a specified set-point. The outer enclosure 246 in thermal communication with the outer shell 262 provides for either supplying heat to or rejecting heat from the inner enclosure 238 responsive to the thermal effort of the thermo-electric heat pumps 236 as needed to maintain a particular set-point temperature. For example, in one embodiment, the set-point temperature is adapted so as to minimize the energy needed to maintain that temperature, while also maintaining a sufficient offset so as to operate the thermo-electric heat pumps 236 most efficiently. For example, for a thermo-electric heat pump 236 that operates most efficiently when heating, the set-point temperature might be 5 to 10 degrees Celsius above the nominal environmental temperature, e.g. 5 to 10 degrees Celsius above room temperature.

Referring to FIG. 19, in one embodiment, the firing of the Nd:YAG laser 11.1' is, for example, controlled with an associated Q-switch in cooperation with a synchronizer 294, so as to provide for synchronization with the acquisition of associated images by the detection system 34, thereby precluding the need for an electronic shutter that would otherwise provide for gating scattered 30' and reference 105 light signals to the detection system 34, although, alternatively, an electronic shutter could also be used or could be used without a synchronizer 294, for example, so as to preclude subsequent imaging during the process of reading image data if using a CCD detection system 34.1'. The synchronizer 294, if used, could be incorporated in a control electronics assembly 296, e.g. which could also incorporate the associated temperature controller 218 and/or the associated data processor 53. The synchronizer 294 could be adapted to either generate a master timing signal for controlling both the laser 11' and the detection system 34, or could be adapted to relay a timing pulse generated by either one of the laser 11' and detection system 34 to the other of the detection system 34 and laser 11'.

The range-imaging LIDAR system 24' can take advantage of aerosols when present, but does not rely upon their presence. The reference light signal 105 and the scattered light signals 30' of the range-imaging LIDAR system 24' can be used to directly measure velocity, true airspeed, vertical speed, angle of attack, angle of sideslip, static density, static temperature, and aerosol to total scattering ratio (ASR). From these data products the following quantities can be directly calculated: calibrated airspeed, Mach number, static pressure, total pressure, dynamic pressure, pressure altitude, air density ratio, total temperature, angle of attack, pressure differential, and angle-of-sideslip pressure differential. Wind velocity, density, and temperature are directly calculated using the fringe data from the Fabry-Pérot interferometer 31'. The other air data products are derived from these three basic measurements, in view of the knowledge of the associated geometry of the beam steering optics 210. The molecular signal yields a measure of air density that can be related to pressure. The aerosol to total scattering ratio is also directly derived from the results.

As used herein, the term relative wind is intended to refer to the relative motion between the atmosphere—included molecules and aerosols—and the range-imaging LIDAR system 24'. In addition to frequency—which, responsive to associated Doppler shift, provides for measuring associated velocity—the algorithm determines the contribution to the fringe pattern from molecular and aerosol scatter, the background radiation, and the temperature of the atmosphere 20 for each particular associated direction associated with each corresponding measurement volume 52 as viewed by the associated receive optics 32.

Figure 24:
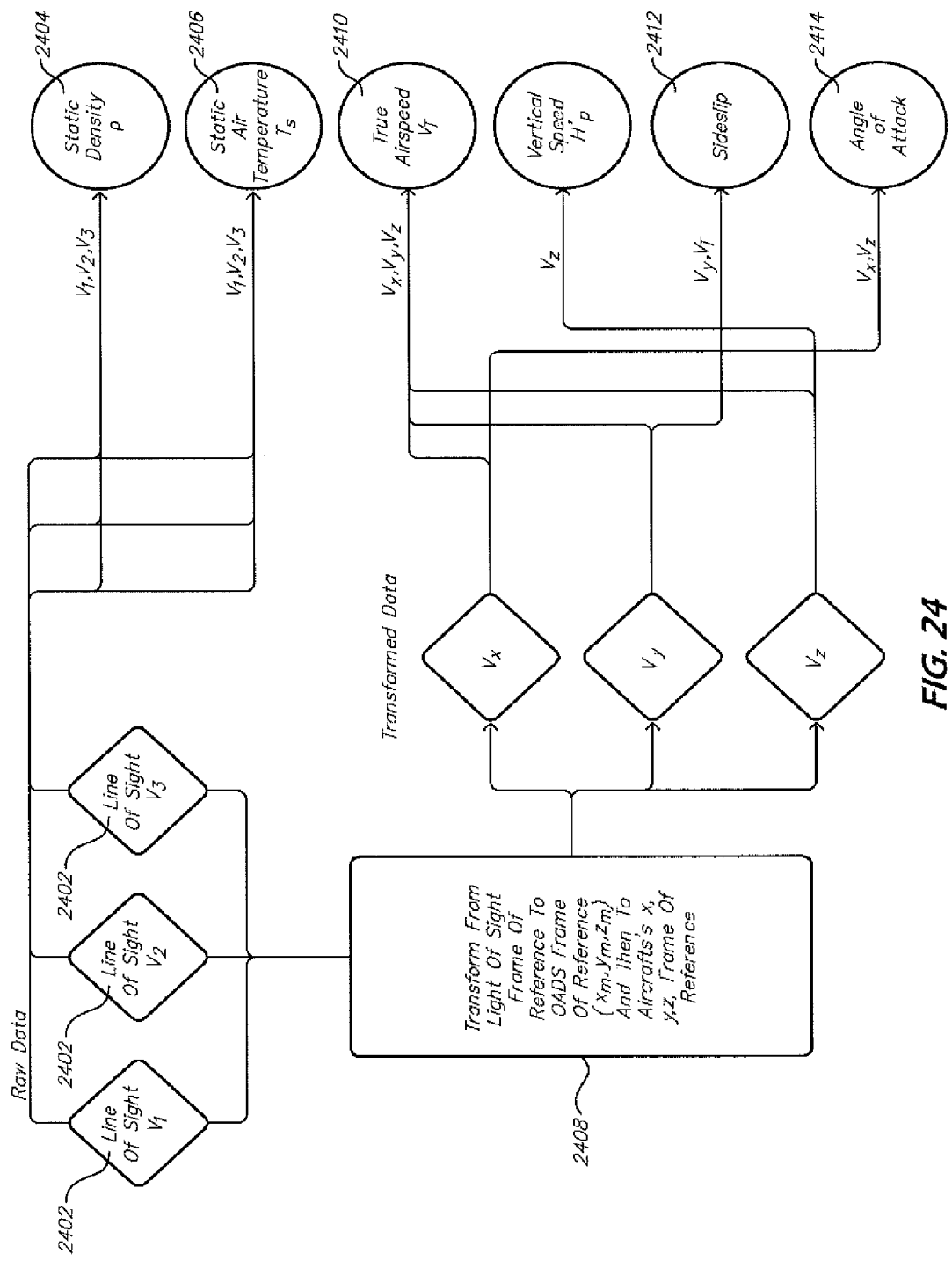
FIG. 24 illustrates a flow chart of a process for determining measured air data products with a range-imaging LIDAR system.

For example, referring to FIGS. 16b and 24, in accordance with a first measurement process 2402, the relative wind velocity $V_i$ is determined along a corresponding direction from a difference between the centroids of the associated scatter fringe pattern 47 associated with a corresponding scattered light signal 30' in comparison with that of the circular fringe pattern 65 associated with the reference light signal 105. The fringe position relative to the optic axis 39 is directly related to wavelength. Accordingly, a difference in wavelength between the circular fringe patterns 65 associated with a scattered light signal 30' and that of the circular fringe pattern 65 associated with the reference light signal 105 is a direct measure of the molecular/aerosol Doppler shift in the scattered light 30 from the atmosphere 20 responsive to either molecular or aerosol scattering. The relative wind velocity $V_i$ for each associated scattered light signal 30' is calculated by subtracting the associated line-of-sight velocity U observable from the corresponding "line-of-sight velocity U" observable of the reference light signal 105, similarly so solved, so as to provide an associated calibrated relative wind velocity $V_i$.

Referring to FIGS. 16b and 24, in accordance with a second measurement process 2404, the air density, i.e. static density $\rho$, is determined from an integral of the molecular signal component 130.2, 132.2 of the circular fringes 65' of the associated circular fringe patterns 65 associated with the scattered light signal 30'. The density of the atmosphere 20 is related to molecular density, not aerosol density. Accordingly, the Rayleigh scatter is separated from the Mie scatter by spectrally resolving the scattered light and de-convolving the spectrum into associated molecular and aerosol contributions, which provides for determining the density of the atmosphere 20 from the associated molecular component responsive to the total number of photons therein, i.e. responsive to an integral of the molecular signal component in accordance with Rayleigh scattering theory. The denser the air is, the more molecules are present to scatter light 30 back to the telescope 32' for detection by the associated detection system 34. The observables MolCounts and AeroCounts inherently provides for a deconvolution of the spectrum into the associated molecular and aerosol contributions, i.e. MolCounts is responsive to the integral of the molecular contribution, and AeroCounts is responsive to the integral of the aerosol contribution. Accordingly, static density is given by $\rho = C \cdot \text{MolCounts}$, wherein C is an empirically determined constant that depends upon the parameters that define the range-imaging LIDAR system 24', i.e. the laser power, interaction region, the transmission of the system, the gain of the detectors, the size of the telescope 32', and the coefficient of scatter from the atmospheric molecules 20'.

Referring to FIGS. 16b and 24, in accordance with a third measurement process 2406, the absolute temperature, i.e. static temperature $T_S$, of the atmosphere 20 is determined from a width of the molecular signal component 130.2, 132.2 of the circular fringes 65' of the associated circular fringe patterns 65 associated with the scattered light signal 30'. The temperature of the atmosphere 20 affects the random thermal motions of the constituent molecules, which causes an associated thermal broadening—referred to as "Doppler broadening" in the field of spectroscopy because of the random velocities in all directions of an ensemble of molecules—of the spectrum of the associated scattered radiation, thereby increasing the associated signal bandwidth which produces correspondingly wider fringes in the associated circular fringe patterns 65 from the Fabry-Pérot interferometer 31'. The absolute temperature of the atmosphere 20 is directly related to this signal bandwidth, and is directly determined as the observable temperature t.

Figure 25:
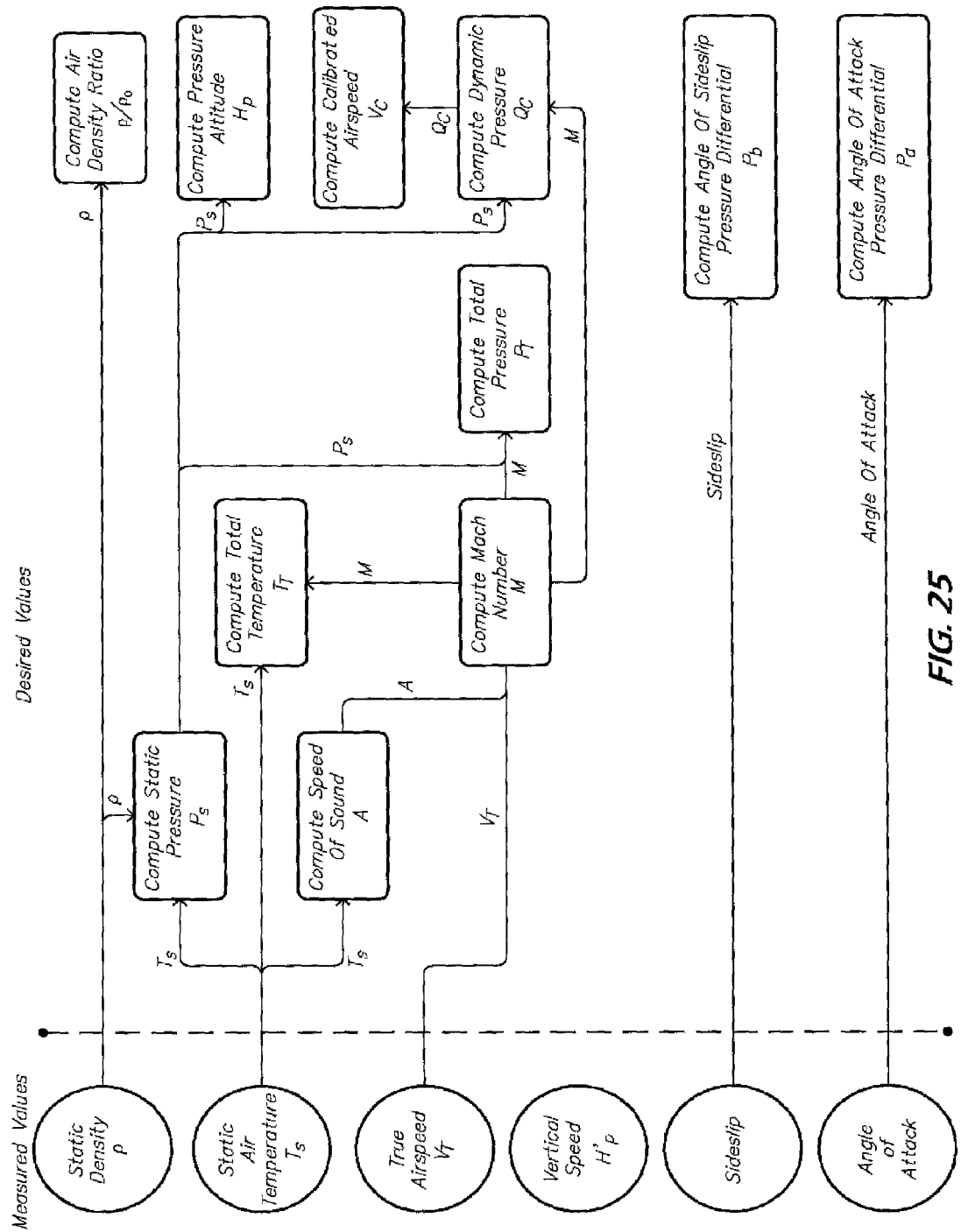
FIG. 25 illustrates a flow chart of a process for determining derived air data products with a range-imaging LIDAR system.

Referring to FIG. 24, for the example of an air data system in an aircraft 400, various other measured air data products may be calculated as follows: In accordance a fourth measurement process 2408, the relative wind velocities $V_i$ determined by the first measurement process 2402 along corresponding associated directions are first transformed from a line-of-sight frame of reference to a frame of reference ($x_m$, $y_m$ and $z_m$) of the range-imaging LIDAR system 24', and then to a frame of reference (x, y, z) of the aircraft 400 using known transformations, so as to provide the relative wind velocities $V_X$, $V_Y$ and $V_Z$ in the frame of reference (x, y, z) of the aircraft 400, from which the true airspeed $V_T$ may be calculated from the relative wind velocities $V_X$, $V_Y$ and $V_Z$ in accordance with a fifth measurement process 2410. The vertical speed $H'_P$ is given by the Z-component of relative wind velocity $V_Z$. The sideslip may be calculated from the Y-component of relative wind velocity $V_Y$ and the true airspeed $V_T$ in accordance with a sixth measurement process 2412. The angle of attack may be calculated from the X and Z-components of relative wind velocity $V_X$ and $V_Z$ in accordance with a seventh measurement process 2414. The Aerosol-to-Total Scattering Ratio (ASR) may also be calculated as the ratio of the observable AeroCounts to the sum of the observables MolCounts, AeroCounts and BackCounts. Referring to FIG. 25, the measured values of static density ρ, static temperature $T_S$, true airspeed $V_T$, sideslip and angle of attack may then be used to compute the following derived values using associated known relations and processes: air density ratio, static pressure, total pressure, pressure altitude, total temperature, speed of sound, Mach number, dynamic pressure, calibrated airspeed, angle of sideslip pressure differential, and angle of attack pressure differential.

Figure 26:
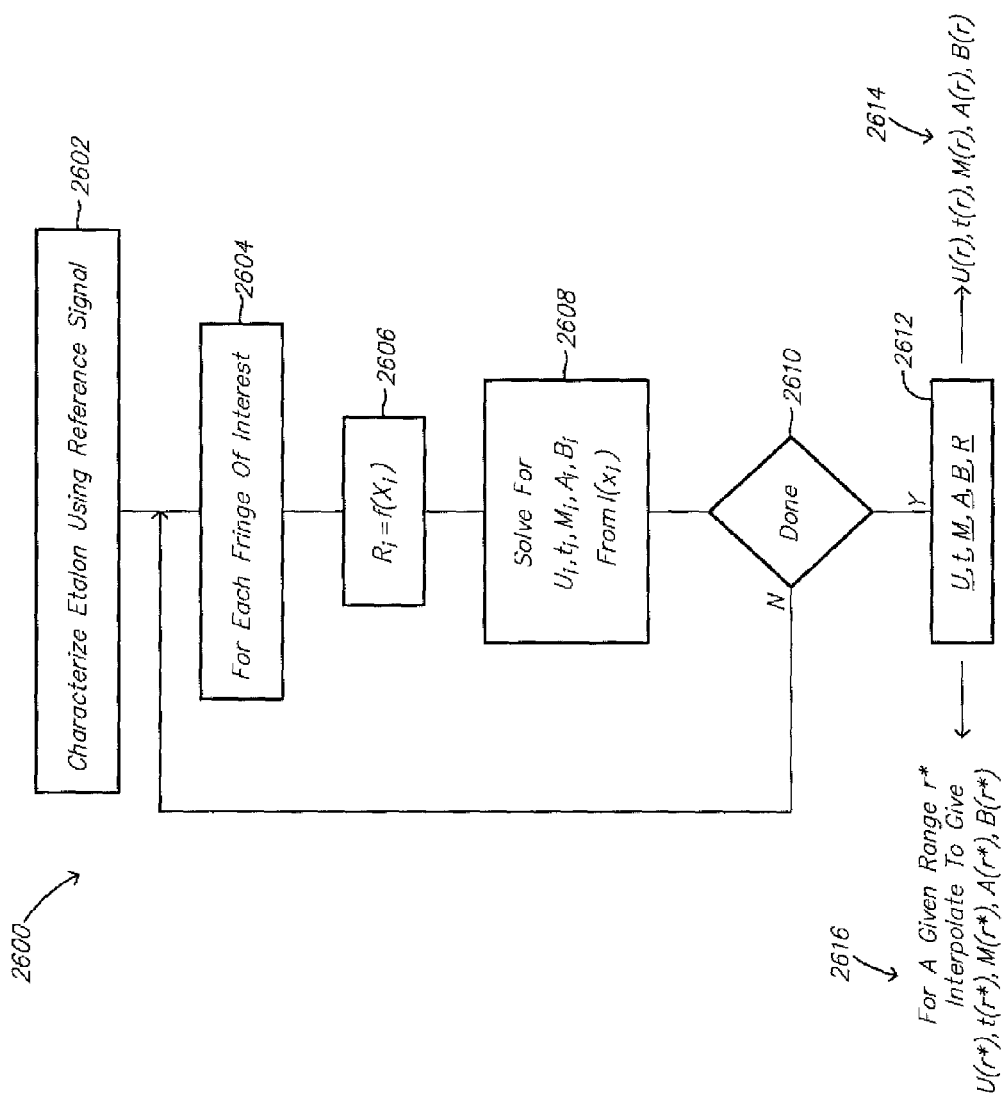
FIG. 26 illustrates a flow chart of a process for determining atmospheric measurements using a range-imaging LIDAR system.

More particularly, referring to FIG. 26, in accordance with a process 2600 for determining measures of atmosphere from the scatter electronic image signal 51, in step (2602), the Fabry-Pérot etalon 35 is characterized using the reference electronic image signal 106, wherein the velocity u, molecular counts M and background counts B are all assumed to be zero, as are the partial derivatives with respect to molecular counts M, background counts B and temperature t. Then, beginning with step (2604), for each arcuate fringe 49', $I(X_i)$ of interest, in step (2606), the associated nominal range $R_i$ is given from a pre-determined function or table given the location in the output focal plane 31.2' of the arcuate fringes 49', $I(X_i)$ being analyzed. Then, in step (2608), given the measurement vector $I(X_i)$ of the arcuate fringe 49', one or more of the atmospheric measures: aerosol counts A, molecular counts M, velocity u, temperature t, and background counts B is solved as described hereinabove. Then, in step (2610), if all of the arcuate fringes 49', $I(X_i)$ of interest have not been analyzed, then the above process repeats with step (2604). Otherwise, in step (2612), vectors $\underline{U}$, $\underline{t}$, $\underline{M}$, $\underline{A}$, and/or $\underline{B}$ of the one or more measures for each of the arcuate fringes 49', $I(X_i)$ analyzed in step (2608) are returned, together with a nominal range vector $\underline{R}$ of associated nominal ranges R, wherein the nominal ranges $R_i$ of the nominal range vector will depend upon the associated velocities $U_i$ (responsive to Doppler shift), and the gap 45 of the Fabry-Pérot etalon 35. These vectors can then be used to either determine functions of one or more measures U(r), t(r), M(r), A(r*) or B(r) as a function of nominal range R, as indicated by step (2614), or to interpolate values one or more measures U(r*), t(r*), M(r*), A(r*) or B(r*) at a particular nominal range R*, as indicated by step (2616). Alternatively, the nominal range vector $\underline{R}$ may be fixed, i.e. associated with a set of predetermined nominal ranges R, by adjusting the gap 45 of the Fabry-Pérot etalon 35 responsive to Doppler shift, for example, with the etalon control actuator 57, so that the associated arcuate fringes 49' being analyzed remain at substantially fixed locations regardless of the conditions of the atmosphere 20.

Figure 27:
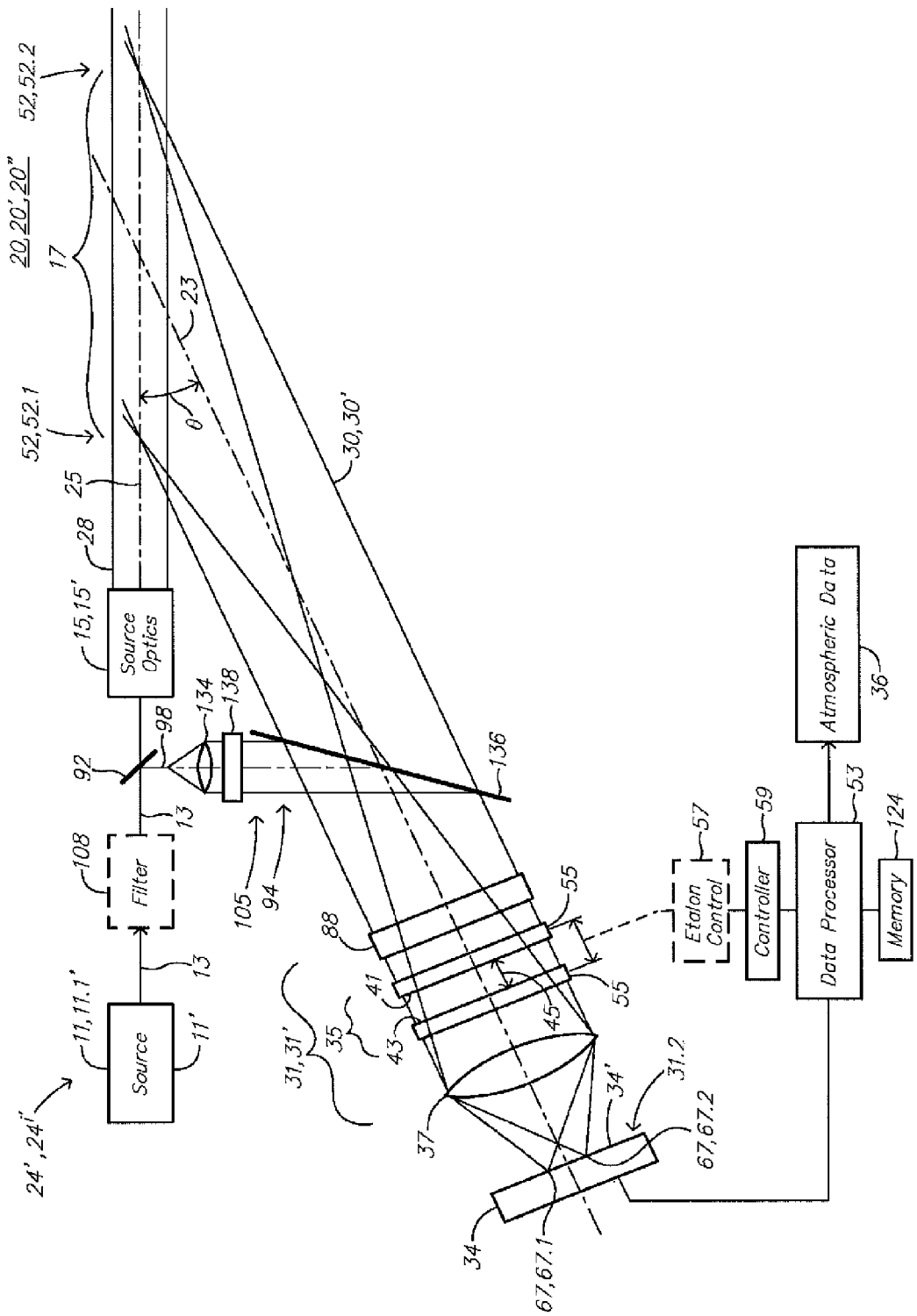
FIG. 27 illustrates a second embodiment of the first aspect of the range-imaging LIDAR system, incorporating a Fabry-Pérot interferometer without an associated collimating lens.

Referring to FIG. 27, in accordance with a second embodiment of the first aspect, the range-imaging LIDAR system 24', 24$^i$ may be built without the collimating lens 33 and input telescope 32'. With the detector of the detection system 34 located in the output focal plane 31.2' of the imaging optics 37—which is where the circular fringes 65' produced by the Fabry-Pérot etalon 35 are sharpest—when the scattered light signal 30' is relatively close to the sensor, the resulting image 114 of the scatter fringe pattern 47 will be out of focus, but the pertinent information is still present in the image. The geometry between the source beam of light 28 and the field-of-view 54 of the receive optics 32 is essentially the same as the system with the input telescope 32' and collimating lens 33.

A reference beam portion 90 of the substantially monochromatic light 13 from the light source 11 is reflected from a first beam splitter optic 92 so as to generate an associated third embodiment of a reference source 94 which is coupled into an associated fiber optic 98 that routes the signal to where it is needed. The output from the fiber optic 98 is divergent and is subsequently collimated by an associated lens 134 and then combined with the scattered light 30 using a second beam splitter optic 136 that reflects a relatively small portion of the substantially monochromatic light 13 from the reference source 94 into the Fabry-Pérot interferometer 31' as the associated reference light signal 105 while transmitting a substantial portion of the scattered light 30 therethrough into the Fabry-Pérot interferometer 31' as the scattered light signal 30'.

The position of the fiber optic 98 in the image plane of the lens 134 determines where the associated image 114 of the reference light signal 105 will appear on the detection system 34. In one embodiment, the image 114 of the reference light signal 105 is positioned so as to not overlap the associated scattered light signal 30' in the output focal plane 31.2' of the Fabry-Pérot interferometer 31'. In another embodiment, in accordance with the eighth aspect of the range-imaging LIDAR system 24', 24$^{viii}$ described more fully herein below, the image 114 of the reference light signal 105 is positioned so as to overlap the associated scattered light signal 30', with the portion of the reference light signal 105 overlapping the scattered light signal 30' blocked by an associated mask 138 between the lens 134 and the second beam splitter optic 136.

The associated optics can be designed so that the reference light signal 105 will be sufficient to determine the center of the interference pattern produced by the Fabry-Pérot interferometer 31' as well as the location of the associated arcuate fringes 49', 49".

Figure 28:
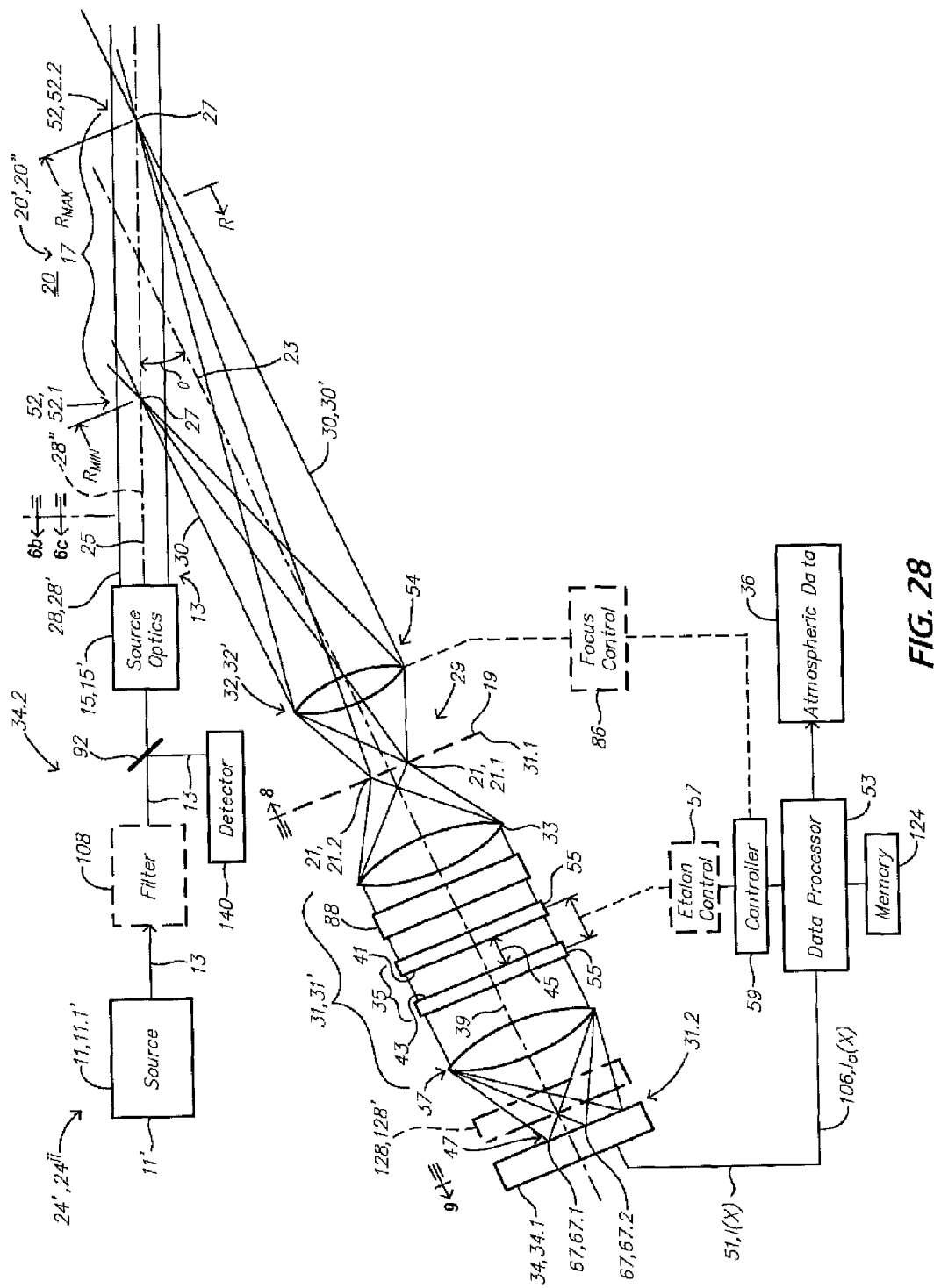
FIG. 28 illustrates an embodiment of a second aspect of range-imaging LIDAR system incorporating a second aspect of an associated detection system, suitable for determining atmospheric measurements that are not dependent upon relative wind velocity.

Referring to FIG. 28, in accordance with a second aspect, the range-imaging LIDAR system 24', 24$^{ii}$ may be adapted in accordance with a second aspect of an associated detection system 34.2 to measure the overall intensity of a fourth embodiment of a reference source 94 with a detector 140, rather than processing the reference beam through the Fabry-Pérot interferometer 31', for example, so as to provide for either reducing the total number of signals processed with the Fabry-Pérot interferometer 31'. Such an arrangement would be suitable when the associated atmospheric data 36 being measured therewith are not dependent upon relative wind velocity, the latter of which measure is calibrated responsive to a measure of frequency shift of the reference light signal 105 using the Fabry-Pérot interferometer 3P. For example, the range-imaging LIDAR system 24', 24$^{ii}$ illustrated in FIG. 28 would be suitable for measuring either or both of static density ρ and static temperature $T_S$, or to provide for deriving therefrom one or more of static air pressure, total air temperature, speed of sound, air density ratio or pressure altitude.

Figures 29A, 29B:
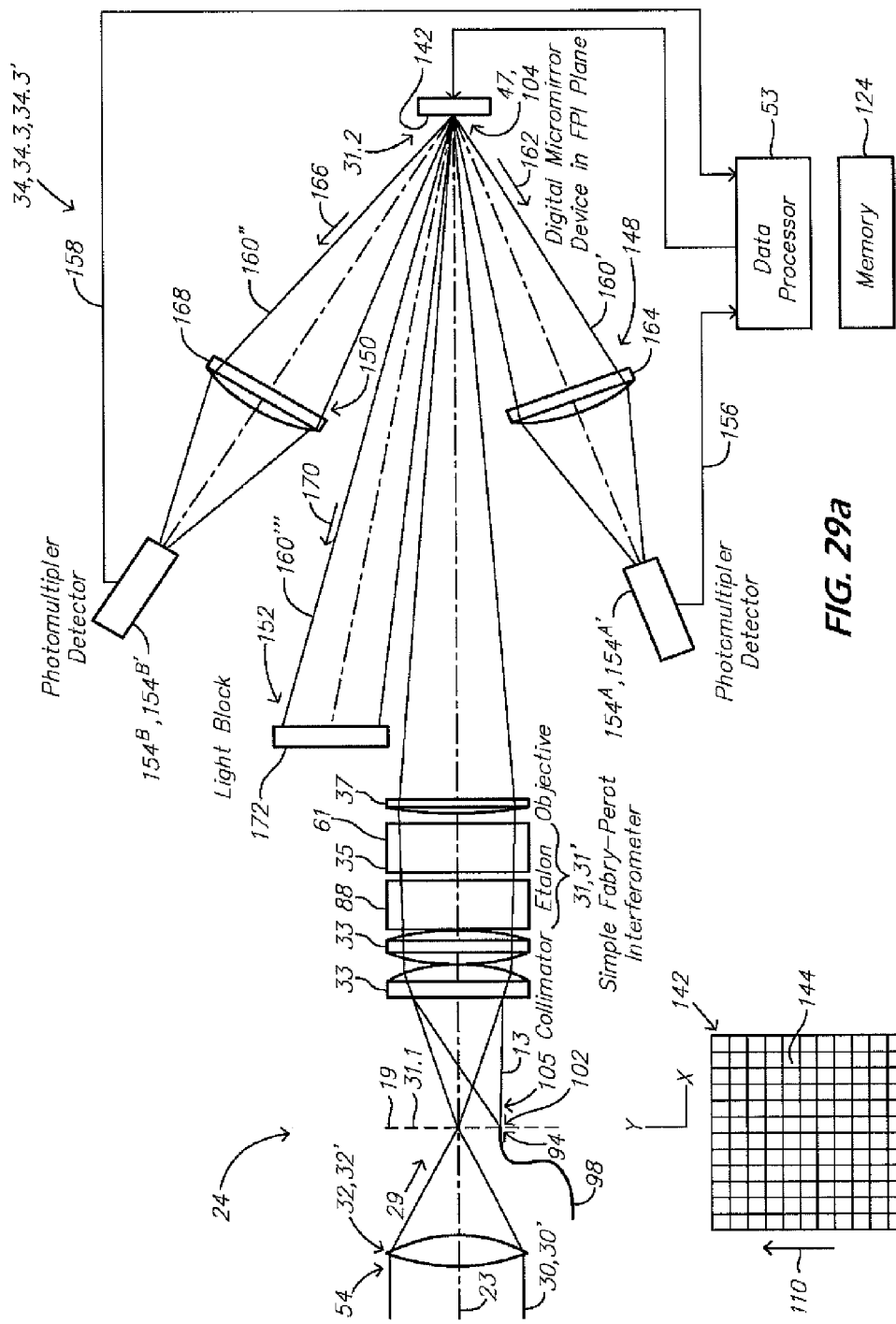

Referring to FIGS. 29a and 29b, a first embodiment of a third aspect of an associated detection system 34, 34.3 of a range-imaging LIDAR system 24' incorporates a digital micromirror device (DMD) 142 comprising an array—for example, a Cartesian array of N rows and M columns—of associated micromirrors 144, each of which constitutes a controllable pixel 146 that is individually addressable and controllable to one of at least three possible associated pixel mirror rotational states 148, 150, 152. The digital micromirror device (DMD) 142 is located in the output focal plane 31.2' of the imaging optics 37 of the Fabry-Pérot interferometer 31' so as to receive the scatter 47 and reference 104 fringe patterns processed by the Fabry-Pérot interferometer 31', portions of which, when processed, are selectively reflected onto a pair of photodetectors $154^A$, $154^B$, for example, photomultiplier detectors $154^{A'}$, $154^{B'}$, from which complementary signals 156, 158 detected thereby are processed by the data processor 53 so as to provide for determining the associated measures of the atmosphere 20 therefrom as a function of nominal range R.

The micromirrors 144 of the associated array of micromirrors 144 of the digital micromirror device (DMD) 142 in the first pixel mirror rotational state 148 cause first portions 160' of either the scatter fringe pattern 47 or the reference fringe pattern 104 from the Fabry-Pérot interferometer 31' impinging thereupon to be reflected in a first direction 162 to an associated first objective lens 164, and to be directed thereby to the a first photomultiplier detector $154^{A'}$. Similarly, micromirrors 144 of the associated array of micromirrors 144 of the digital micromirror device (DMD) 142 in the second pixel mirror rotational state 150 cause second portions 160" of either the scatter fringe pattern 47 or the reference fringe pattern 104 from the Fabry-Pérot interferometer 31' impinging thereupon to be reflected in a second direction 166 to an associated second objective lens 168, and to be directed thereby to the a second photomultiplier detector $154^{B'}$. Finally, micromirrors 144 of the associated array of micromirrors 144 of the digital micromirror device (DMD) 142 in the third pixel mirror rotational state 152 cause third portions 160''' of either the scatter fringe pattern 47 or the reference fringe pattern 104 from the Fabry-Pérot interferometer 31' impinging thereupon to be reflected in a third direction 170 to the light block 172 that provides for absorbing light impinging thereupon. For example, in one embodiment, the third pixel mirror rotational state 152 corresponds to a state of substantially no rotation of the associated micromirrors 144, which may be achieved, for example, by applying a common voltage to the associated micromirror 144 and it associated mirror address electrodes and yoke address electrodes, so as to create an equal state of electrostatic repulsion between all associated pairs of electrodes associated with the micromirror 144, thereby maintaining the micromirror 144 in a substantially unrotated condition.

The micromirrors 144 of the digital micromirror device (DMD) 142 are relatively efficient, with overall efficiency approaching 90% in one set of embodiments. Accordingly, the digital micromirror device (DMD) 142 provides for digitally isolating light impinging thereupon into two disjoint sets for the portion of the light being analyzed, and for masking a remaining portion of the light. More particularly, the digital micromirror device (DMD) 142 is used to interrogate portions the scatter 47 and reference 104 fringe patterns from the Fabry-Pérot interferometer 31', and in cooperation with the associated first $154^{A'}$ and second $154^{B'}$ photomultiplier detectors, to provide for generating associated one or more pairs of, associated complementary signals 156, 158, each responsive to the number of photons in the associated two disjoint sets of light reflected by the digital micromirror device (DMD) 142 resulting from a particular pattern of pixel mirror rotational states to which the associated array of micromirrors 144 of the digital micromirror device (DMD) 142 are set for a particular set of measurements, wherein the associated first $154^{A'}$ and second $154^{B'}$ photomultiplier detectors provide for counting the corresponding number of photons associated with each of the disjoint sets of light reflected by the digital micromirror device (DMD) 142.

Figure 30:
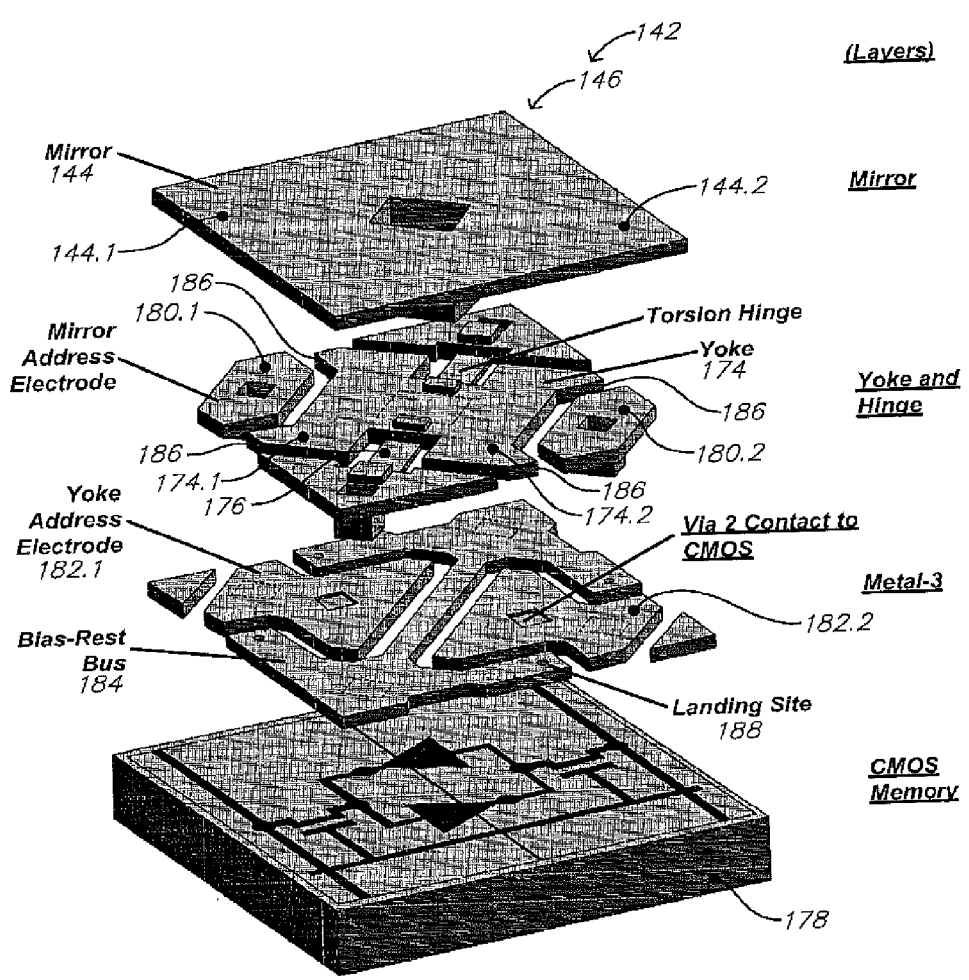
FIG. 30 illustrates a pixel element of a digital micromirror device.
Figure 31:
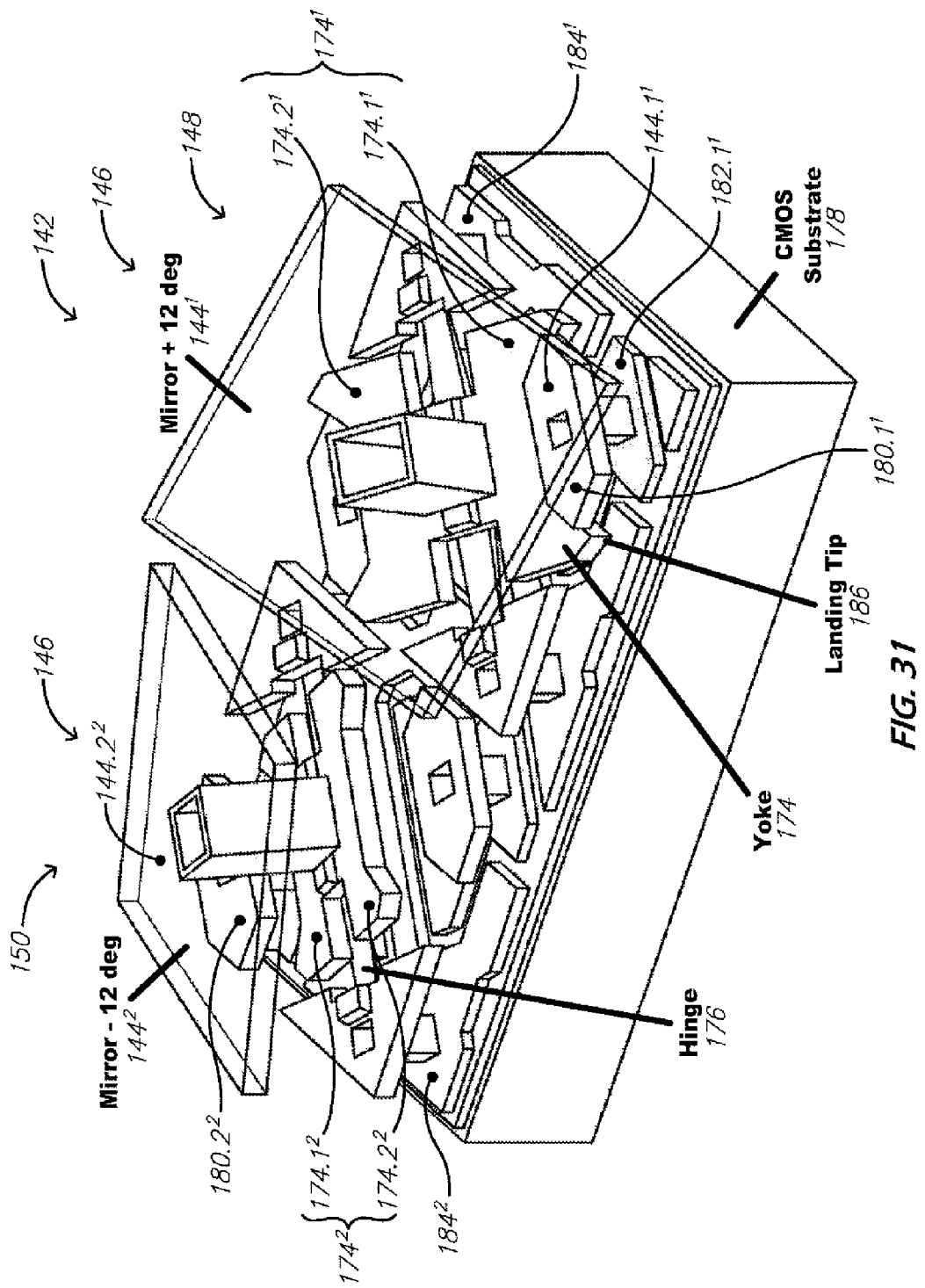
FIG. 31 illustrates two adjacent pixel elements of a digital micromirror device, each in a different pixel mirror rotational state.

For example, referring also to FIGS. 30 and 31, in accordance with the teachings of U.S. Pat. No. 5,535,047, and with the publication entitled "The Digital Micromirror Device: A Historic Mechanical Engineering Landmark", published by Texas Instruments Inc. and the American Society of Mechanical Engineers on 1 May 2008 with 20 pages, both of which references are incorporated herein by reference, one embodiment of the digital micromirror device (DMD) 142 comprises an array of 16 micron square movable micromirrors 144 on 17 micron centers, each micromirror 144 of which is mechanically supported by a yoke 174 suspended from a pair of compliant torsion hinges or flexures 176 operatively coupled to a common CMOS substrate 178. Each micromirror 144 is rotatable into one of two stable pixel mirror rotational states responsive to electrostatic attraction between a corner portion 144.1, 144.2 of the micromirror 144 and one of two associated elevated mirror address electrodes 180.1, 180.2, and responsive to electrostatic attraction between a corresponding on of two opposed portions 174.1, 174.2 of the yoke 174 and one of two associated yoke address electrodes 182.1, 182.2. The micromirror 144 is rotated to one of the two stable pixel mirror rotational states by applying a first voltage to the micromirror 144 and yoke 174 via a bias-reset bus 184 in electrical connection therewith, and applying a second voltage to one of the mirror address electrodes 180.1, 180.2, and a corresponding one of the yoke address electrodes 182.1, 182.2, wherein first corresponding mirror 180.1 and yoke 182.1 address electrodes are electrically connected with one another, second corresponding mirror 180.2 and yoke 182.2 address electrodes are electrically connected with one another, and the first and second voltages are set so as to provide for attraction between the first or second mirror 180.1, 180.2 and yoke 182.1, 182.2 address electrodes and corresponding portions 144.1, 144.2, 174.1, 174.2 of the micromirror 144 and yoke 174.

For example, referring to FIG. 31, with the first voltage applied to a first micromirror $144^1$ and associated yoke $174^1$ via the associated bias-reset bus $184^1$, a second voltage applied to the associated first mirror address electrode $180.1^1$ and to the associate first yoke address electrode $182.1^1$, causes the first corner portion $144.1^1$ of the first micromirror $144^1$ to be electrostatically attracted to the associated first mirror address electrode $180.1^1$, and causes the first opposed portion $174.1^1$ of the associated yoke $174^1$ to be electrostatically attracted to the associated first yoke address electrode $182.1^1$, thereby causing the first micromirror $144^1$ to rotate to the first pixel mirror rotational state 148, which for example, is illustrated in FIG. 31 as +12 degrees for a particular commercial embodiment, wherein the first and second voltages are adapted to provide for an electrostatically attractive force therebetween. Similarly, with the first voltage applied to a second micromirror $144^2$ and associated yoke $174^2$ via the associated bias-reset bus $184^2$, a third voltage applied to the associated second mirror address electrode $180.2^2$ and to the associate second yoke address electrode $182.2^2$, causes the second corner portion $144.2^2$ of the second micromirror $144^2$ to be electrostatically attracted to the associated second mirror address electrode $180.2^2$, and causes the second opposed portion 174.2² of the associated yoke 174² to be electrostatically attracted to the associated second yoke address electrode 182.2², thereby causing the second micromirror 144² to rotate to the second pixel mirror rotational state 150, which for example, is illustrated in FIG. 31 as −12 degree's for the particular commercial embodiment, wherein the first and third voltages are adapted to provide for an electrostatically attractive force therebetween. The tips 186 of the yoke 174 contact corresponding landing sites 188 on the associated bias-reset bus 184, and the landing sites 188 may be passivated so as to prevent or reduce stiction, so as to provide for reducing the voltage needed to either reset the micromirror 144 to a flat state, or to rotate the micromirror 144 to the other pixel mirror rotational state. Another commercial embodiment, for example, provides for mirror rotational states of +/−10 degrees. In the rest state, the micromirror 144 is flat, but this state is not addressable for individual pixels in one set of commercial embodiments.

Commercial digital micromirror devices (DMD) 142 comprise arrays of micromirrors 144 ranging from an array of 640×480 micromirrors 144 containing approximately a half million micromirrors 144 in total, to an array of 2048×1080 micromirrors 144 containing over two million micromirrors 144 in total. Each micromirror 144 of the array represents one pixel 146 of a pattern 190 of associated pixel mirror rotational states 148, 150, 152, wherein each pixel is independently controllable or programmable responsive to a signal from the data processor 53.

The scattered light signal 30' of the associated scattered light signal 30' received from the interaction region 17 associated with the field-of-view 54 of the telescope 32' is processed by the Fabry-Pérot interferometer 31' to generate an associated scatter fringe pattern 47 that is then separated by the digital micromirror device (DMD) 142 into disjoint portions 47', 47" that are then detected by the corresponding associated first 154$^{A'}$ and second 154$^{B'}$ photomultiplier detectors. The reference light signal 105 is processed by the same Fabry-Pérot interferometer 31', either simultaneously or sequentially, to generate an associated reference fringe pattern 104 that is then separated by the digital micromirror device (DMD) 142 or a separate corresponding digital micromirror device (DMD) (not illustrated) into disjoint portions 104', 104" that are then detected by the corresponding associated first 154$^{A'}$ and second 154$^{B'}$ photomultiplier detectors, or by a separate set of first and second photomultiplier detectors (not illustrated). The resulting complementary signals 156, 158 associated with the reference light signal 105 are used to provide for calibrating atmospheric measurements associated with the scattered light signal 30'. Accordingly, the range-imaging LIDAR system 24' uses the Fabry-Pérot interferometer 31' to directly detect information from the scattered laser energy, wherein the scatter 30' and reference 105 light signals are each detected separately, and information from the reference light signal 105 can then be used to calibrate the associated scattered light signal 30'. The detection process is responsive to an incoherent Doppler shift of the laser light scattered by molecules and aerosols in the atmosphere 20 responsive to Rayleigh and Mie scattering respectively.

The response of a Fabry-Pérot interferometer 31' is well documented in the literature, for example, as described by P. B. Hays and R. G. Roble in "A Technique for Recovering Doppler Line Profiles from Fabry-Pérot Interferometer Fringes of very Low Intensity", *Applied Optics*, 10,193-200, 1971, which is incorporated herein by reference. The ideal intensity distribution of a the fringe pattern for a single wavelength transmitted through a Fabry-Pérot interferometer 31' by a LIDAR system without optical defects is given by $$H_{ideal}(\varphi) = \frac{T^2}{1 + R^2 - 2R\cos(\varphi)} \quad (63.1)$$

where $$\varphi = \frac{4\pi\mu d}{\lambda}\left(1 - 2\frac{u}{c}\right)\cos(\theta) \quad (63.2)$$

wherein T is the transmissivity, R is the reflectivity, μ is the refractive index of the Fabry-Pérot etalon 35, d is the thickness of the gap 45, 45.1 of the Fabry-Pérot etalon 35, λ is the wavelength of the source, θ is the angle of transmission through the Fabry-Pérot etalon 35, c is the speed of light, and u is the line-of-sight air velocity. Hence, the Doppler shift is 2 u/c. In the presence of a source distribution including many wavelengths and optical defects it is advantageous to use the Fourier cosine series expansion of the response. The distribution of intensity transmitted per molecular weight (of the scattering species) is given by:

$$H(\phi, m) = \frac{T^2}{1 - R^2}\left(1 + 2\sum_{n=1}^{\infty} R^n \exp\left(-\frac{n^2}{4}G^2(t)\right)\prod_k D_{n,k}\cos(n\phi)\right) \quad (64.1)$$

where $$G(t) = \frac{4\pi\mu d}{\lambda c}\sqrt{\frac{2A_0 kt}{m}} \quad (64.2)$$

where t is the atmospheric temperature, k is the Boltzmann constant, $A_0$ is Avogadro's number, m is the molecular mass of the scattering species, and the convolution effects of the optical defects are represented by associated defect coefficients $D_{n,k}$.

If there were no optical defects, then each of the defect coefficients $D_{n,k}$ would be identically equal to one. However, in a system with optical defects, these may be accounted for in various ways. For example, in accordance with a first method, the defect coefficients $D_{n,k}$ are calibrated using a reference source 94 that does not interact with the atmosphere 20. As long as the range-imaging LIDAR system 24' stays calibrated then these defect coefficients $D_{n,k}$ may be used directly in the inversion of data to recover atmospheric state variables. As another example, in accordance with a second method, a signal from the reference light signal 105 is periodically collected together with one or more associated signals from the corresponding one or more scattered light signals 30', and the effect of the defect coefficients $D_{n,k}$ is computed by de-convolving the ideal signal, $H_{ideal}$,—for example, $H_{ideal}$ as given by equation (63.1),—from the recovered data using the Fourier transform of the ideal signal, $H_{ideal}$, for example, as given by equations (73.1), (73.2) and (74) described hereinbelow. The function G(t) approximates the effect of thermal broadening of a source by a low density gas, which effects are more precisely accounted for by Rayleigh-Brillouin scattering, although that level of detail is not essential to the practice of the range-imaging LIDAR system 24'.

For an atmosphere 20 containing both aerosols and molecules, and for the range-imaging LIDAR system 24' adapted to sample the entire circular fringe pattern 65, the associated total response is given by:

$$I(\varphi) = AH(\varphi, m_A) + MH(\varphi, m_M) + \frac{T^2}{1-R^2}B \quad (65)$$

where I is the total number of photons reaching the photodetector 154, A is the number of photons that have been scattered by aerosols, M is the number of photons that have been scattered by molecules, B is the number of background photons transmitted to the range-imaging LIDAR system 24' by the ambient atmosphere 20, $m_A$ is the molecular mass of an aerosol particle (for example, a very large number on the order of 1.0e5), and $m_M$ is the molecular mass of air (about 28.92). Given this model, the sensitivity of the system to the atmospheric variables A, M, u, t and B is respectively given by respectively taking partial derivatives of equation (65) with respect to each respective variable, as follows:

$$\frac{\partial I}{\partial A} = H(\varphi, m_A) \quad (66.1)$$

$$\frac{\partial I}{\partial M} = H(\varphi, m_M) \quad (66.2)$$

$$\frac{\partial I}{\partial u} = \left(A\frac{\partial}{\partial \varphi}H(\varphi, m_A) + M\frac{\partial}{\partial \varphi}H(\varphi, m_M)\right)\frac{\partial \varphi}{\partial u} \quad (66.3)$$

$$\frac{\partial I}{\partial t} \approx M\frac{\partial}{\partial t}H(\varphi, m_M), \quad (66.4)$$

and $$\frac{\partial I}{\partial B} = \frac{T^2}{1-R^2} \quad (66.5)$$

where $$\frac{\partial \varphi}{\partial u} = -2\frac{4\pi\mu d}{\lambda c}\cos(\theta). \quad (66.6)$$

Figure 32:
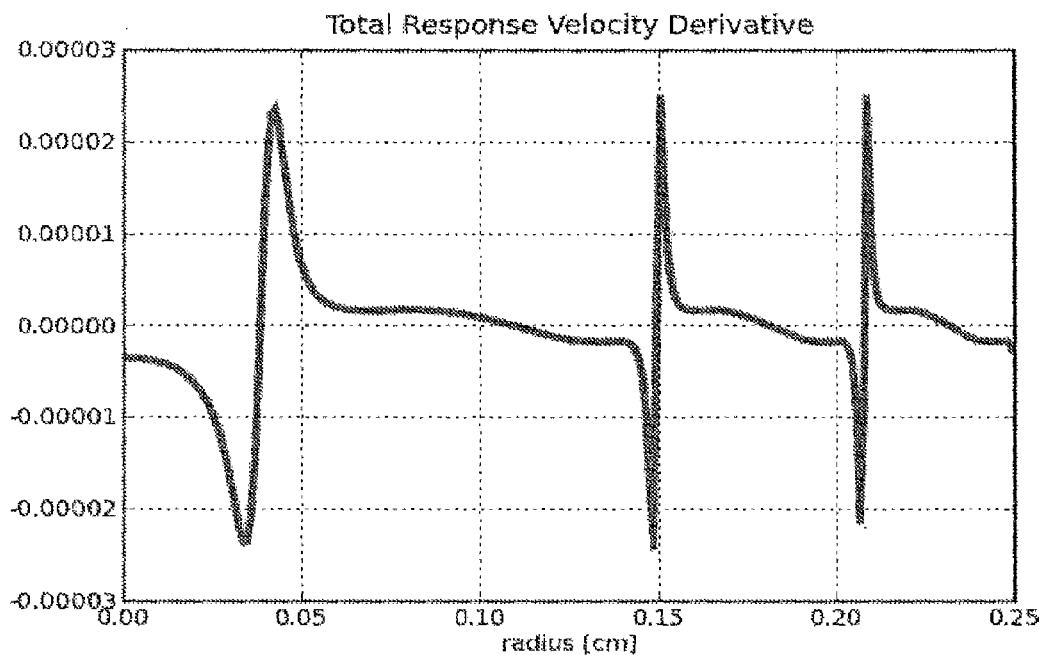
Figure 33:
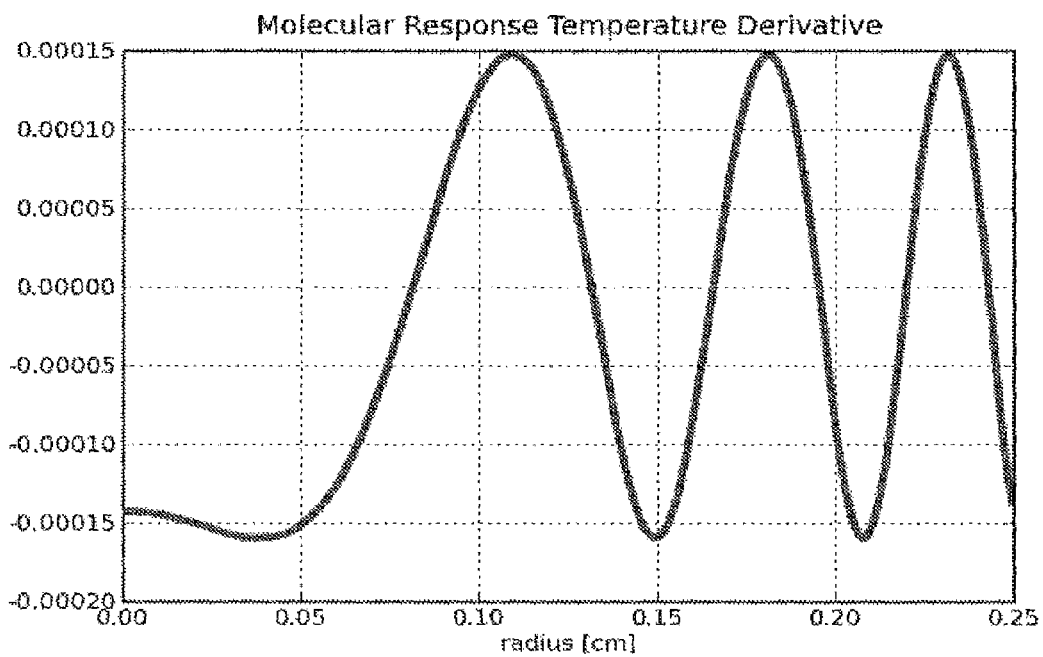

For example, FIG. 16a illustrates total fringe response I from equation (65) as a function of radius through the circular fringe pattern 65, and FIGS. 32 and 33 respective illustrate the corresponding partial derivatives thereof with respect to velocity u and temperature t, respectively, as given by equations (66.3) and (66.4), respectively.

The separate influence of molecules and aerosols is evident in the partial derivative of the total fringe response I with respect to velocity u illustrated in FIG. 32, wherein the aerosol contributions 192 are relatively narrow, with relatively sharp dipole-like features in the middle of each associated pattern; and the molecular contributions 194 are the relatively wide regions outside of the narrow aerosol contributions 192. Variations in the aerosol contributions 192 cause the centers 196 thereof to expand and contract as the density of aerosols changes, as illustrated in FIG. 16b. The temperature derivative illustrated in FIG. 33 is not affected by aerosol density, but an unknown variation in aerosol content will confuse the determination of temperature. Accordingly, the mutual influences of temperature t, velocity u, aerosol counts A, molecular counts M, and background counts B upon one another can be accounted for by simultaneously or contemporaneously measuring or determining all of the variables that exhibit mutual dependencies upon one another.

Generally, the range-imaging LIDAR system 24' provides for sampling, collecting and integrating separate portions, for example, disjoint portions 47', 47", 104', 104", of the scatter 47 and reference 104 fringe patterns, and then using the resulting associated signals, for example complementary signals 156, 158, for each of a set of different disjoint portions 47', 47", 104', 104", to determine the values of the variables or parameters characterizing the associated scatter fringe pattern 47. The scatter 47 and reference 104 fringe patterns are sampled by the digital micromirror device (DMD) 142, with the pixel mirror rotational states 148, 150, 152 of the associated micromirrors 144 controlled according to a particular pattern 190, so that the micromirrors 144 in the first pixel mirror rotational state 148 provide for reflecting light from a first disjoint portion 47', 104' of the scatter 47 or reference 104 fringe pattern to the first objective lens 164, which focuses the light onto the first photomultiplier detector $154^{A'}$ that provides for integrating the light from the first disjoint portion 47', 104' of the scatter 47 or reference 104 fringe pattern so as to generate a first complementary signal 156; and so that the micromirrors 144 in the second pixel mirror rotational state 150 provide for simultaneously reflecting light from a second disjoint portion 47", 104" of the scatter 47 or reference 104 fringe pattern to the second objective lens 168, which focuses the light onto the second photomultiplier detector $154^{B'}$ that provides for integrating the light from the second disjoint portion 47", 104" of the scatter 47 or reference 104 fringe pattern so as to generate a second complementary signal 158. This process is repeated for each different set of N different sets of disjoint portions 47', 47" of the scatter fringe pattern 47, and for one set of disjoint portions 104', 104" of the reference fringe pattern 104, so as to provide for generating N corresponding sets of complementary signals 156, 158, from which up to N different variables or parameters can be characterized.

For example, in accordance with a first aspect, the scatter fringe pattern 47 is characterized with respect to the following N=5 variables: aerosol counts A, molecular counts M, velocity u, temperature t, and background counts B as provided by equations (64.1), (64.2) and (65) hereinabove, using a corresponding N=5 different patterns 190 of pixel mirror rotational states 148, 150, 152 of the micromirrors 144 of the digital micromirror device (DMD) 142, wherein each of the associated patterns 190 is chosen in advance based upon the expected sensitivity of the optical response with respect to each of these variables. For example, in on embodiment, the pattern 190 of pixel mirror rotational states 148, 150, 152 for each of the N=5 variables are chosen responsive to the sign of the partial derivatives of the total fringe response I(φ) with respect to that variable, i.e. responsive to the sign of equations (66.1)-(66.5), subject to a fixed offset, respectively. For example, FIGS. 34-38 are examples of patterns 190 of pixel mirror rotational states 148, 150, 152 of the micromirrors 144 of the digital micromirror device (DMD) 142 for determining measures of aerosol counts A, molecular counts M, velocity u, temperature t, and background counts B, respectively, as given by the sign of equations (66.1)-(66.5), respectively, wherein the black regions in FIGS. 34-38 are where the value of the corresponding equations (66.1)-(66.5), plus an offset, are negative, for which the associated digital micromirror device (DMD) 142 are controlled to a first pixel mirror rotational state 148; and the white regions in FIGS. 34-38 are where the value of the corresponding equations (66.1)-(66.5), plus an offset, are positive, for which the associated digital micromirror device (DMD) 142 are controlled to a second pixel mirror rotational state 150. FIGS. 39a-e illustrate radial cross-sections through the corresponding patterns illustrated in FIGS. 34-38, respectively, from the center of each pattern 190 of pixel mirror rotational states 148, 150, 152, outwards.

More particularly, FIG. 34 illustrates an example of the pattern 190, 190.1 of pixel mirror rotational states 148, 150, 152 of the micromirrors 144 of the digital micromirror device (DMD) 142, based upon the sign of the value of equation (66.1), used to obtain a corresponding first set of complementary signals 156.1, 158.1 responsive to a measure of aerosol counts A, wherein the a radial cross-section through the pattern 190, 190.1 of pixel mirror rotational states illustrated in FIG. 34, from the center thereof outwards, is illustrated in FIG. 39a. Furthermore, FIG. 35 illustrates and example of the pattern 190, 190.2 of pixel mirror rotational states 148, 150, 152 of the micromirrors 144 of the digital micromirror device (DMD) 142, based upon the sign of the value of equation (66.2), used to obtain a corresponding second set of complementary signals 156.2, 158.2 responsive to a measure of molecular counts M, wherein the a radial cross-section through the pattern 190, 190.2 of pixel mirror rotational states illustrated in FIG. 35, from the center thereof outwards, is illustrated in FIG. 39b. Yet further, FIG. 36 illustrates and example of the pattern 190, 190.3 of pixel mirror rotational states 148, 150, 152 of the micromirrors 144 of the digital micromirror device (DMD) 142, based upon the sign of the value of equation (66.3), used to obtain a corresponding third set of complementary signals 156.3, 158.3 responsive to a measure of velocity u, wherein the a radial cross-section through the pattern 190, 190.3 of pixel mirror rotational states 148, 150, 152 illustrated in FIG. 36, from the center thereof outwards, is illustrated in FIG. 39c. Yet further, FIG. 37 illustrates and example of the pattern 190, 190.4 of pixel mirror rotational states 148, 150, 152 of the micromirrors 144 of the digital micromirror device (DMD) 142, based upon the sign of the value of equation (66.4), used to obtain a corresponding fourth set of complementary signals 156.4, 158.4 responsive to a measure of temperature t, wherein the a radial cross-section through the pattern 190, 190.4 of pixel mirror rotational states 148, 150, 152 illustrated in FIG. 37, from the center thereof outwards, is illustrated in FIG. 39d. Yet further, FIG. 38 illustrates and example of the pattern 190, 190.5 of pixel mirror rotational states 148, 150, 152 of the micromirrors 144 of the digital micromirror device (DMD) 142, based upon the sign of the value of equation (66.5), used to obtain a corresponding fifth set of complementary signals 156.5, 158.5 responsive to a measure of temperature t, wherein the a radial cross-section through the pattern 190, 190.5 of pixel mirror rotational states 148, 150, 152 illustrated in FIG. 38, from the center thereof outwards, is illustrated in FIG. 39e.

It should be noted that the pattern 190, 190.1 of pixel mirror rotational states 148, 150, 152 used for the measure of aerosol counts A is a subset of the pattern 190, 190.2 of pixel mirror rotational states 148, 150, 152 used for the measure of molecular counts M, and that each of the patterns 190, 190.1-190.5 of pixel mirror rotational states 148, 150, 152 is mathematically independent of the others, so that none of these patterns 190, 190.1-190.5 may be constructed by superposition of the other patterns 190, 190.1-190.5 of pixel mirror rotational states 148, 150, 152. Accordingly, the five sets of complementary signals 156.1-156.5, 158.1-158.5 from the first 154$^A$ and second 154$^B$ photodetectors for the circular fringe pattern 65 from the scattered light signal 30' provides sufficient information as necessary to determine aerosol counts A, molecular counts M, velocity u, temperature t, and background counts B therefrom.

Generally, any collection of patterns 190 of pixel mirror rotational states 148, 150, 152 that are spatially independent will work however, not all patterns 190 of pixel mirror rotational states 148, 150, 152 provide the same expected error. The optimum selection of patterns 190 of pixel mirror rotational states 148, 150, 152 depends on the variables of interest in the remote sensing problem at hand and also on the state of the solution being sought. In accordance with the first aspect, the patterns 190 of pixel mirror rotational states 148, 150, 152 are chosen in view of an associated model of the optical response of the range-imaging LIDAR system 24', wherein the derivatives of the optical response provide for resulting associated complementary signals 156, 158 that are sensitive to changes in the associated variables of interest. From the partial derivatives of the total fringe response I with respect to aerosol counts A, molecular counts M, velocity u, temperature t, and background counts B as given by equations (66.1)-(66.5), the associated regions of interest are relatively broad and well defined. For example, referring to FIGS. 32 and 33, there are clear zones where the partial derivative is positive and others that where the partial derivative is negative. These zones explicitly map how the velocity u and temperature t information, respectively, is contained in the fringe pattern.

Figure 40:
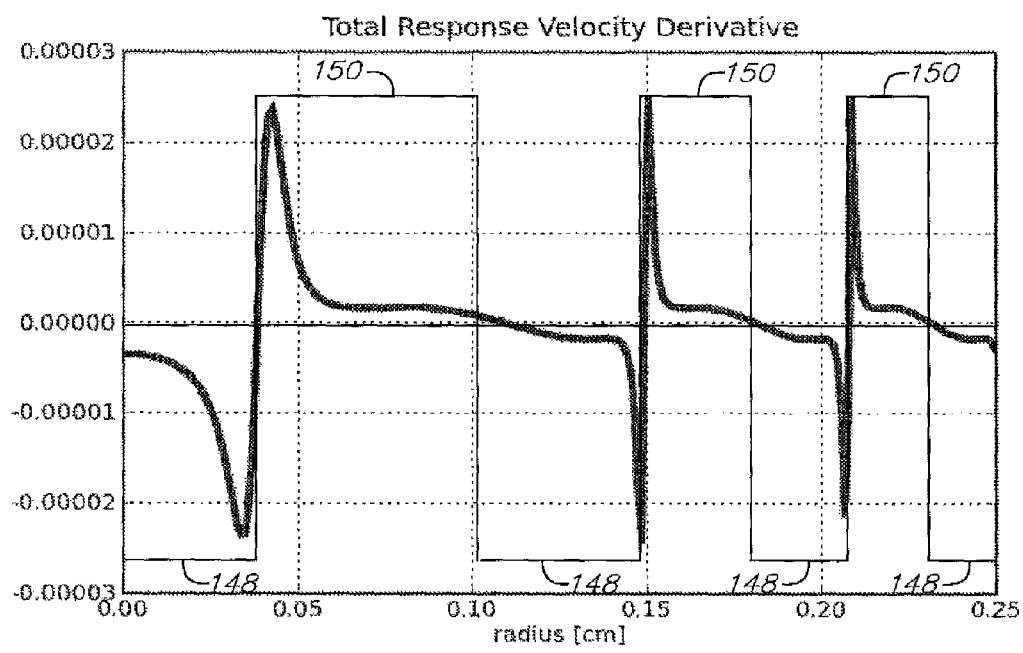
FIG. 40 illustrates a partial derivative with respect to velocity of the intensity distribution of FIG. 16a as in FIG. 32, upon which is superimposed a corresponding radial cross-section of a first set of associated complementary reflection patterns of a digital micromirror device programmed to gather associated complementary velocity signal components, for a first value of a velocity threshold that distinguishes the complementary components of the associated complementary reflection patterns.
Figure 41:
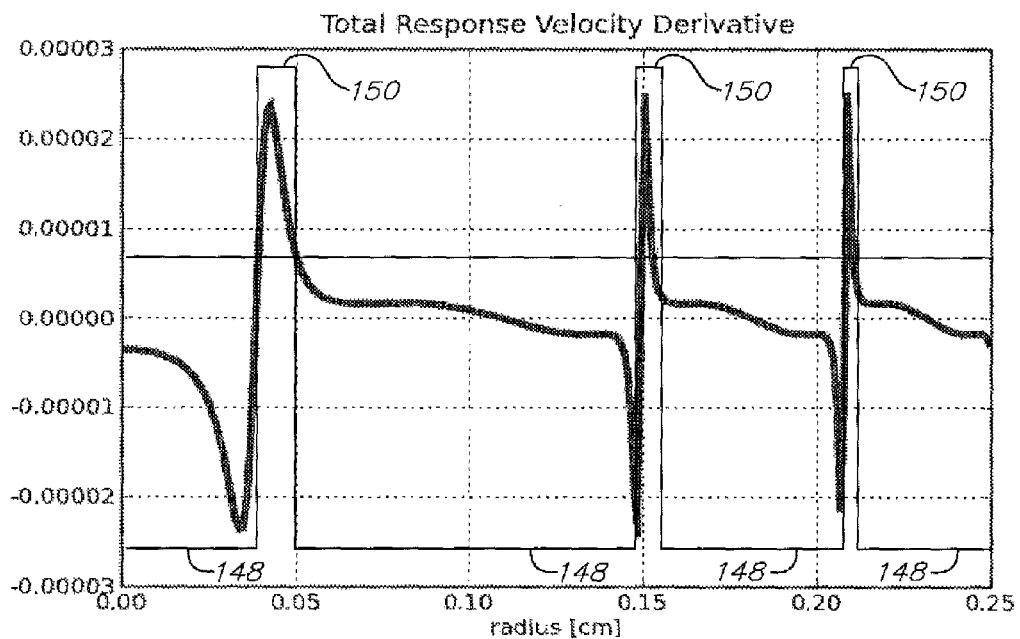
FIG. 41 illustrates a partial derivative with respect to velocity of the intensity distribution of FIG. 16a as in FIG. 32, upon which is superimposed a corresponding radial cross-section of a second set of associated complementary reflection patterns of a digital micromirror device programmed to gather associated complementary velocity signal components, for a second value of a velocity threshold that distinguishes the complementary components of the associated complementary reflection patterns.

In accordance with a second aspect, the patterns 190 may be adapted as with the first aspect, but with the use of an associated threshold when mapping the results of equations (66.1)-(66.5) to the corresponding patterns 190, wherein the patterns 190 are then given responsive whether or not the value of the associated derivative is either greater or less than a chosen threshold, for example, as shown in FIGS. 40 and 41 for two different threshold values—zero and +30% of signal amplitude, respectively—as applied to equation (66.3) for partial derivative with respect to velocity u. More particularly, FIG. 40 illustrates a pattern 190, 190.3 of pixel mirror rotational states 148, 150, 152 for determining a measure of velocity u superimposed upon the partial derivative of the total fringe response I with respect to velocity u as given by equation (66.3), for a circular fringe pattern 65 with three orders on the photodetector, and for a threshold of zero, wherein the corresponding pattern 190, 190.3 of pixel mirror rotational states 148, 150, 152 illustrated in FIG. 39c has three positive regions and four negative regions, so that three complete rings of micromirrors 144 would be tilted in a first pixel mirror rotational state 148 towards the first photodetector 154$^A$ and four complete rings would be tilted in a second pixel mirror rotational state 150 toward the second photodetector 154$^B$. The incomplete rings illustrated in FIG. 36 would not be illuminated by the optical source. A different value for the threshold would cause some of the regions would grow and others to shrink, for example, as shown in FIG. 41 which illustrates the pattern 190, 190.3 of pixel mirror rotational states 148, 150, 152 for a threshold setting of 0.3 times the associated peak amplitude. For the pattern 190, 190.5 of pixel mirror rotational states 148, 150, 152 associated with background counts B, the partial derivative is a constant, so the associated pattern 190, 190.5 of pixel mirror rotational states 148, 150, 152 is chosen to be spatially independent of the others. For example, a pattern 190, 190.5 of pixel mirror rotational states 148, 150, 152 associated with the measure of background counts B could simply divide the radial domain in two by a parameterized proportionality threshold such that all radii above the threshold are imaged onto the first photodetector 154$^A$ and radii below the threshold onto the second photodetector 154$^B$. Patterns 190.1, 190.2 and 190.4, respectively, for aerosol counts A, molecular counts M, and temperature t, respectively, can be determined in a similar fashion.

The programmability of the digital micromirror device (DMD) 142 allows the regions being selected to be varied dynamically as the measurement conditions vary. For example: in the case of a LIDAR, the pattern 190, 190.3 of pixel mirror rotational states 148, 150, 152 for velocity u is most sensitive when its divisions coincide with the fringe peaks (which move with velocity dependent Doppler shifts). Accordingly, real time accuracy can be improved if the pattern 190, 190.3 of pixel mirror rotational states 148, 150, 152 for velocity u were adapted in real time to account for this shift. This ability to adapt the observations can be beneficial in a highly variable natural environment. Similarly, the temporal duration of exposure for each pattern 190 of pixel mirror rotational states 148, 150, 152 may be adjusted within a sample set, i.e. the duration of measurement may be different for different patterns 190 of pixel mirror rotational states 148, 150, 152, so as to provide for re-balancing the sensitivity of the range-imaging LIDAR system 24' to increase accuracy in the state variable or state variables of greatest interest.

The choice of temporal exposure weighting and patterns 190 of pixel mirror rotational states 148, 150, 152 depend on the present environmental state and a ranking of the parameters of interest. One approach for examining potential systems is by a Monte-Carlo simulation. Another is by a non-linear optimization technique such as the Broyden Fletcher-Goldfarb-Shanno (BFGS) method, a quasi-Newton, variable metric method, for example, as described by J. Nocedal and, S. Wright, *Numerical Optimization*, Springer-Verlag New York, Inc., 1999, pages 194-201, which is incorporated herein by reference. In these cases one may design a cost function based on the covariance of the minimum variance unbiased estimate for example, as described by D. Luenberger in "*Optimization by Vector Space Methods*", John Wiley & Sons, Inc. (1969) on page 15, which is incorporated herein by reference—using the system dynamics from the model response and expected environmental noise, for example, as given by equation (83) hereinbelow. At which point Monte-Carlo can be employed to understand how the distribution of solutions vary with respect to the system design, or descent-based schemes can by employed to find a best candidate according to ones rankings of state variable accuracy.

Once a scheme for generating patterns 190 of pixel mirror rotational states 148, 150, 152 is established, the associated thresholds and temporal weighting fractions can then be mathematically optimized. The resulting optimal set of parameters will be referred to as a solution to the optimization problem. Given a pattern 190 of pixel mirror rotational states 148, 150, 152, the system partial derivatives (Jacobean Matrix) and the expected measurement covariance, one can estimate the inversion errors that would occur in using that system. In particular the Jacobean derivative, J, is given $$J = \left[\frac{\partial I}{\partial A}, \frac{\partial I}{\partial M}, \frac{\partial I}{\partial u}, \frac{\partial I}{\partial t}, \frac{\partial I}{\partial B}\right] \qquad (67)$$

which allows the intensity at any phase point, $\phi$, to be approximated as $$I \approx I_0 + J[\Delta A, \Delta M, \Delta u, \Delta t, \Delta B]^T \qquad (68)$$

The expected covariance of the noise in intensity is given by Q. In the case of a shot noise limited system this covariance would be a diagonal matrix of the counts collected in each measurement. The matrix of dynamics, W, is formed by integrating the Jacobean over each pattern 190 of pixel mirror rotational states 148, 150, 152 and applying the corresponding temporal weighting, factor. Let $\Omega_A$, $\Omega_M$, $\Omega_u$, $\Omega_t$, $\Omega_B$ represent the patterns 190 of pixel mirror rotational states 148, 150, 152 that send light to the first photodetector, and $\tilde{\Omega}_A$, $\tilde{\Omega}_M$, $\tilde{\Omega}_u$, $\tilde{\Omega}_t$, $\tilde{\Omega}_B$ be the complements of these patterns 190 of pixel mirror rotational states 148, 150, 152 which send light to the second photodetector, then one can form a 10×5 matrix where the $k^{th}$ row is given by cycling $\Omega_k$ through the set $\{\Omega_A, \tilde{\Omega}_A, \Omega_M, \tilde{\Omega}_M, \Omega_u, \tilde{\Omega}_u, \Omega_t, \tilde{\Omega}_t, \Omega_B, \tilde{\Omega}_B\}$ and similarly for the temporal weighting fractions $p_k$ through $\{p_A, p_A, p_M, p_M, p_u, p_u, p_t, p_t, p_B, p_B\}$.

$$W[k,:] = p_k \left[ \int_{\Omega_k} \int \frac{\partial I}{\partial A} d\Omega, \int_{\Omega_k} \int \frac{\partial I}{\partial M} d\Omega, \right. \qquad (69)$$
$$\left. \int_{\Omega_k} \int \frac{\partial I}{\partial u} d\Omega, \int_{\Omega_k} \int \frac{\partial I}{\partial t} d\Omega, \int_{\Omega_k} \int \frac{\partial I}{\partial B} d\Omega \right]$$

This equation (69) is valid for any set of patterns 190 of pixel mirror rotational states 148, 150, 152 (such as those shown in FIGS. 39a-e, 45 or 46). Similarly, for a shot noise limited system with expected intensity, $I_0$, the covariance is $$Q[k,:] = p_k \delta_{ik} \int_{\Omega_k} \int I_0 d\Omega \qquad (70)$$

At this point one may compute the standard deviation of the errors expected in each measured parameter through the minimum variance unbiased estimator as $$\sigma = \sqrt{\mathrm{diag}([W^T Q^{-1} W]^{-1})} \qquad (71)$$

Figure 42:
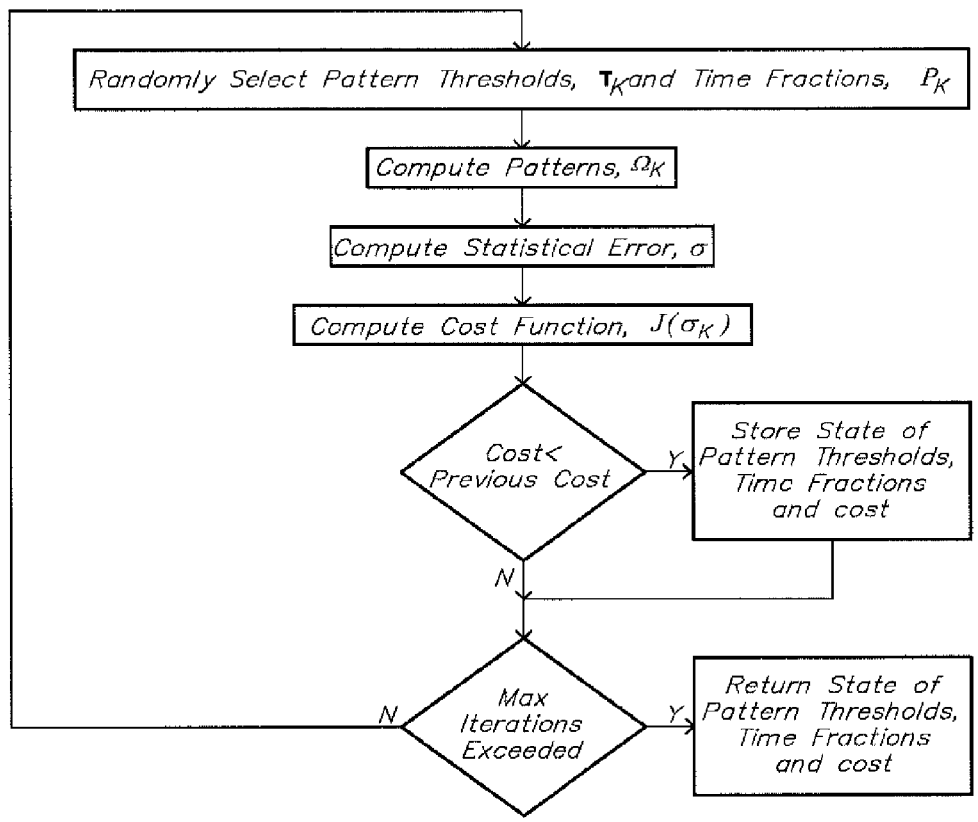
FIG. 42 illustrates a flowchart of a Monte Carlo simulation process.

Each element of the $\sigma$ vector represents the expected error in A,M,u,t,B respectively. With this ability to estimate the errors in each parameter of the system, one may perform a Monte-Carlo analysis to vary the associated thresholds and temporal weighting factors to see how the parameters affect the accuracy of the system, for example, in accordance with the Monte-Carlo procedure is illustrated in FIG. 42.

Figure 43:
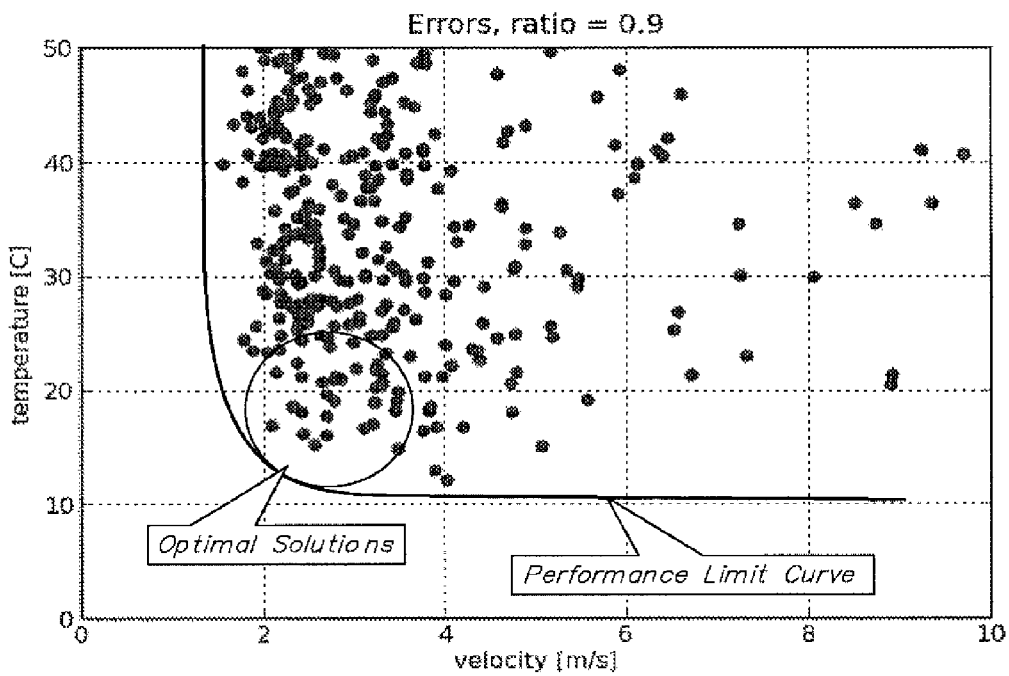
FIG. 43 illustrates the results from a Monte Carlo simulation used to optimize parameters associated with the complementary reflection patterns used to program a digital micromirror device for gathering signals used to determine atmospheric measurements from a fringe pattern output from a Fabry-Pérot interferometer.

The distribution of the solution space can be understood by viewing the Monte-Carlo results, for example, such as those shown in FIG. 43, where each point (solution) corresponds to a choice of temporal weightings and pattern thresholds. Such results can aid in choosing a cost function for a descent-based optimization. The simplest form of cost function is a dot product of weights with the standard deviations, $J(\sigma)=\langle \omega, \sigma \rangle$, where $\omega_k$ is a vector of length 5 whose entries magnitude reflect the relative importance of each variable that are particular to one's interest. Note that the effects of the selected thresholds and temporal weighting factors are embedded in the calculation of $\sigma$. Other more elaborate cost functions may be constructed as well by using any non-negative functional form (such as a Gaussian or logarithmic) such as:

Example Linear Cost functional $$J(\sigma) = \langle \omega, \sigma \rangle = \sum_k \omega_k \sigma_k \qquad (72.1)$$

Example Gaussian multivariate functional $$J(\sigma) = B\exp\left(-\frac{1}{2}\sigma^T A \sigma\right) \qquad (72.2)$$

Example Logarithmic functional $$J(\sigma) = \log(\langle \omega, \sigma \rangle^n + \gamma) \qquad (72.3)$$

FIG. 43 shows that there is a trade-off between accurately measuring velocity or temperature. The horizontal axis shows the expected error in velocity and the vertical axis shows the expected error in temperature. Some solutions work well for velocity determination and others for temperature. Normally, the best solution for velocity is not the best solution for temperature and one must compromise. The curve in FIG. 43 labeled "Performance Limit Curve" indicates the performance limit achievable by the system. There are many different solutions (weighting schemes and thresholds) in the knee of the curve identified by the circle labeled "Optimal Solutions" which will provide useful answers with expected errors as small as possible. In some cases it may be worthwhile to alternate between several system solutions in order to take turns giving answers that are best for each state of interest.

Figure 44:
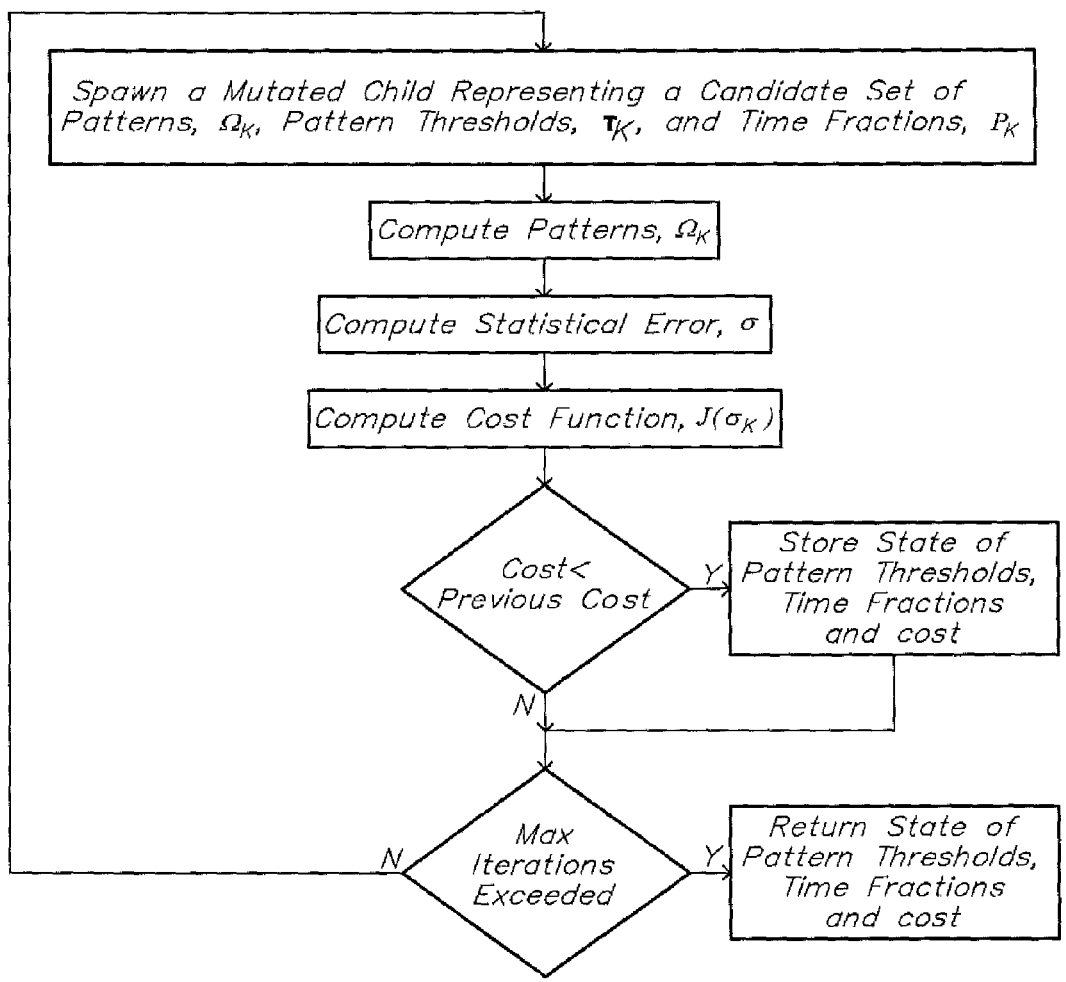
FIG. 44 illustrates a flowchart of a Genetic Algorithm process.
Figure 45:
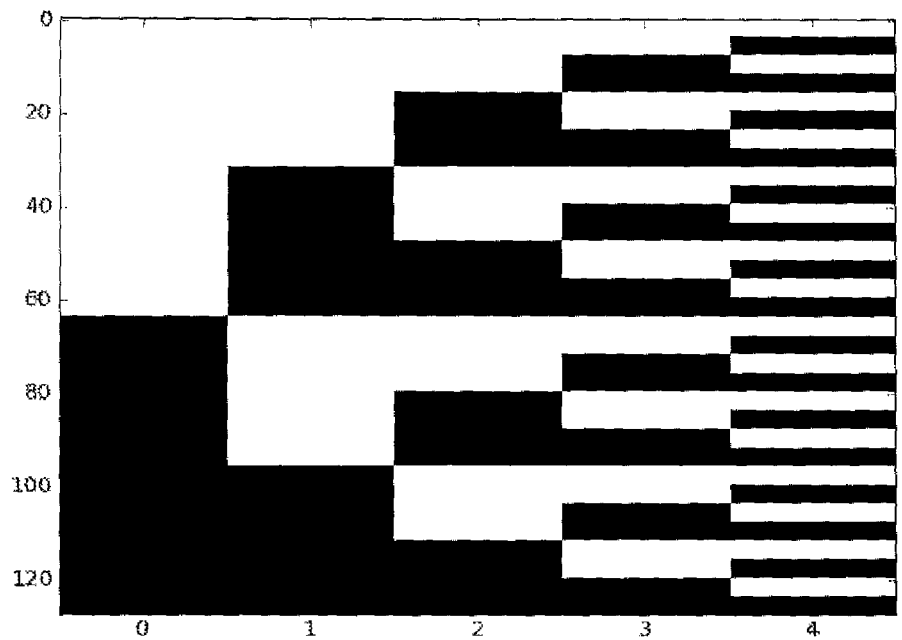
FIG. 45 illustrates a composite of radial cross-sections through a first alternative set of complementary reflection patterns.

Alternatively, any number of schemes could be used to find patterns 190 of pixel mirror rotational states 148, 150, 152 which optimize a cost function. For example, in a Genetic algorithm procedure, the first step of FIG. 42 is changed from "Randomly select pattern thresholds" to "spawn a mutated child representing a candidate set of patterns 190 of pixel mirror rotational states 148, 150, 152 (or thresholds) and time fractions", as illustrated in FIG. 44.

It is an interesting point that the patterns 190 of pixel mirror rotational states 148, 150, 152 used with the Fabry-Pérot interferometer 31' are not required to be generated without regard to the expected fringe pattern. In fact, the only requirement is that the patterns 190 of pixel mirror rotational states 148, 150, 152 are algebraically independent, such that no pattern 190 of pixel mirror rotational states 148, 150, 152 can be constructed as a linear combination of the other patterns 190 of pixel mirror rotational states 148, 150, 152 in the set Referring to FIG. 45, as one example, an alternative set of patterns 190 of pixel mirror rotational states 148, 150, 152 can be generated by dyadic divisions in the radii, similar to a wavelet decomposition.

Figure 46:
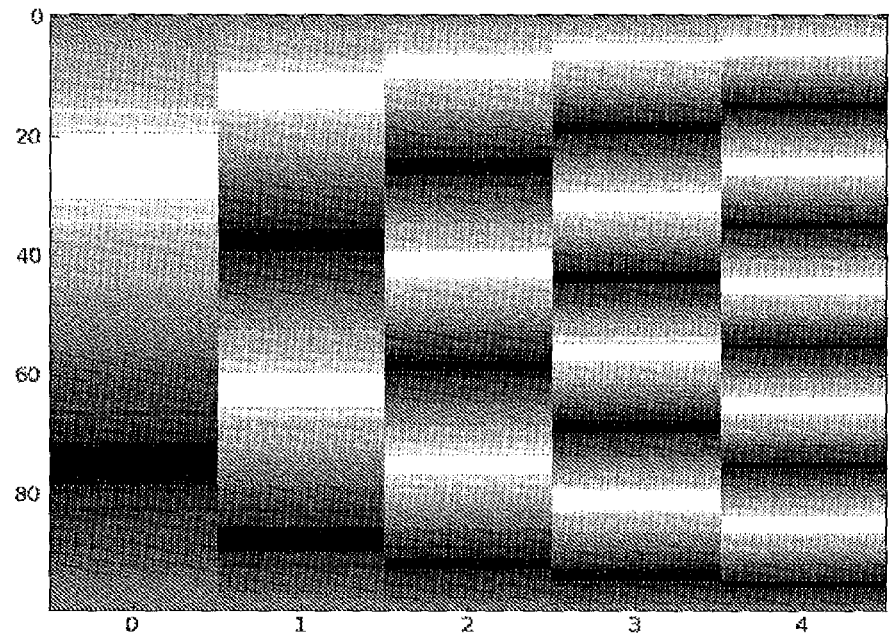
FIG. 46 illustrates a composite of radial cross-sections through a second alternative set of complementary reflection patterns.

Furthermore, the patterns 190 of pixel mirror rotational states 148, 150, 152 do not necessarily have to be radially symmetric. Although the information content of a Fabry-Pérot interferometer 31' is circularly symmetric, if circular symmetry of the selected patterns 190 of pixel mirror rotational states 148, 150, 152 is broken then one may consider the value of the pattern 190 of pixel mirror rotational states 148, 150, 152 for that specific radii to be the fraction (or probability) of pixels in either the first 148 or second 150 pixel mirror rotational states. Such a pattern 190 of pixel mirror rotational states 148, 150, 152 is shown in FIG. 46 where the gray values connote probabilities between 0 and 1.

The set of measurements of the complementary signals 156, 158 for the corresponding set of patterns 190 of pixel mirror rotational states 148, 150, 152 can then be used to estimate the parameters or measurements from the range-imaging LIDAR system 24'. All routines must account for the optical defects in the system as in equations (64.1-64.2). These defects typically have a convolution type response such as a defocus-blurring or an etalon wedge defect. In a Fabry-Pérot imaging system one can usually acquire a reference fringe pattern of the laser before it has interacted with the atmosphere. This response will contain all the information necessary to model the system's optical defects and any changes to the Fabry-Pérot etalon 35. For example changes in the temperature of a solid Fabry-Pérot etalon 35 will change its refractive index thereby changing the systems response to velocity and temperature. This information is readily accessible by comparing the Fourier Transform of the reference to the Fourier transform of the ideal signal. Term by term (i.e. per mode) division reveals the defect coefficients (in a noise free environment), for example, as described by T. L. Killeen and P. B. Hays in "Doppler line profile analysis for a multichannel Fabry-Pérot interferometer," *Applied Optics* 23, 612 (1984), which is incorporated herein by reference. These can be applied to the forward model of the Fabry-Pérot response as discussed earlier. As such, the Fourier expansion of an ideal signal, $H_{ideal} = H_0(\phi)$, and the reference signal, $H_{ref}(\phi)$, is $$H_0(\phi) = \frac{T^2}{1-R^2}\left(1 + 2\sum_{n=1}^{\infty} R^n \cos(n\phi)\right) = \sum_{n=0}^{\infty} \hat{H}_0[n] \times \cos(n\phi) \quad (73.1)$$

and $$H_{ref}(\phi) = \frac{T^2}{1-R^2}\left(1 + 2\sum_{n=1}^{\infty} R^n D_n \cos(n\phi)\right) = \sum_{n=0}^{\infty} \hat{H}_{ref}[n] \times \cos(n\phi), \quad (73.2)$$

where the $\hat{H}[n]$ terms are the Fourier coefficients of the normalized responses. The orthogonality of the cosine basis implies that the nth coefficient of the optical defects can be obtained from $$D_n = \frac{\hat{H}_{ref}[n]}{\hat{H}_0[n]}. \quad (74)$$

These are the terms to be computed in the calibration of the instrument. The reference signal is also used to track the intensity of the beam and any phase shifts in response due to drift of the gap 45, 45.1 of the Fabry-Pérot etalon 35. The refractive index of the Fabry-Pérot etalon 35 may be obtained by independently monitoring the temperature of the Fabry-Pérot etalon 35. This tracking is accomplished in an iterative process using measurements akin to equation (69). Starting with the matrix of dynamics $$W_{ref}[k,:] = p_k\left[\int_{\Omega_k}\int \frac{\partial I}{\partial A} d\Omega, \int_{\Omega_k}\int \frac{\partial I}{\partial u} d\Omega, \int_{\Omega_k}\int \frac{\partial I}{\partial B} d\Omega\right] \quad (75)$$

and the vector of measurements $$M[k] = p_k \delta_{ik} \int_{\Omega_k}\int I_0 d\Omega \quad (76)$$

then the change in those measurements is expected to be driven by changes in the state of the system. Hence the measurements at time j+1 are given by the previous measurements, j, and the system dynamics existing at the time of the jth measurement:

$$M_{j+1} = M_j + W_j \delta x \quad (77)$$

where $\delta x = [\delta A, \delta u, \delta B]^T$. Recall that the phase is given by $$\varphi = \frac{4\pi\mu d}{\lambda}\left(1 - 2\frac{u}{c}\right)\cos(\theta) \quad (78)$$

The velocity term should be zero, however changes in length d of the gap 45, 45.1 of the Fabry-Pérot etalon 35, will have a similar impact as velocity, namely $\delta d = -2 \, d\delta u/c$. Because the reference signal has not been broadened its response is exactly the same as the scatter signal from aerosols. As such, the aerosol term will be used to track the change in laser power. Equation (774) is then solved for the updates $[\delta A, \delta d, \delta B]^T$. These updates then define the normalization and phase changes necessary to consider for inversion of the total scatter signal. The reference state may be computed with each scattered signal, or as often as necessary to capture the rate at which the optical system changes (for example, with temperature). If one can guarantee thermal stability via a temperature controlled Fabry-Pérot etalon 35 and housing then it may only be necessary to evaluate the reference periodically or on system initialization.

A similarly related technique is to divide the Fourier Transform coefficients of the reference fringe from the fringe pattern produced by the scattered atmospheric response. The remaining response reveals a phase shift (linearly correlated to the velocity via the expected Doppler shift) and broadening function related to the thermal effects. This method is very sensitive to noise in the collected data. More than the five patterns 190.1-190.5 of pixel mirror rotational states 148, 150, 152 already described would be used in order to recover the defect coefficients. One generally requires at least as many patterns 190 of pixel mirror rotational states 148, 150, 152 states as Fourier coefficients that one needs to faithfully represent the signal. In a rich aerosol environment this could be anywhere from 45 to 100 coefficients thus requiring the same number or more of independent measurements. One simple method gaining these measurements is to create a pattern 190 of pixel mirror rotational states 148, 150, 152 of rings which sweep outward from the center. These measurements may be made periodically within normal system operation and post-processed later to produce the analytical representation of the reference fringe. Alternatively, a large enough digital micromirror device (DMD) 142 could simultaneously image the atmospheric response with one set of patterns 190 of pixel mirror rotational states 148, 150, 152 and a reference fringe pattern with another set of patterns 190 of pixel mirror rotational states 148, 150, 152.

One method for estimating the parameters of the atmospheric state from the scattered signal is the classic Levenberg-Marquardt nonlinear least squares method which provides for varying smoothly between an inverse-Hessian method and a steepest descent method, as described, along with other suitable non-linear methods, by W. H. Press, S. A. Teukolsky, W. T Vetterling, and B. P. Flannery in *Numerical Recipes in C, The Art of Scientific Computing, Second Edition*, Cambridge University Press, 1992, pp. 656-661 and 681-706 which is incorporated herein by reference. This method works by iteratively minimizing the mean square error of a set of acquired samples against the output of a forward model (such as the model for the Fabry-Pérot transmitted fringe pattern). It only requires the system dynamics equation given in equation (69) for any given state of the parameters. It operates by performing Quasi-Newton decent type steps toward the parameter state which minimizes the residual (mean square error of the difference between the data and the model). The algorithm works as follows:

Consider the measurements made with each pattern 190 of pixel mirror rotational states 148, 150, 152 to be the vector:

$$M[k] = p_k \delta_{ik} \int_{\Omega_k} \int I_0 d\Omega. \tag{79}$$

Let $$Y[k] = p_k \delta_{ik} \int_{\Omega_k} \int I_{model}(A, M, u, t, B) d\Omega \tag{80}$$

be the estimates of return signal given the model described in equations (63-65). As described in equation (69), the Jacobean of this model is:

$$W[k, :] = p_k \left[ \int_{\Omega_k} \int \frac{\partial I}{\partial A} d\Omega, \int_{\Omega_k} \int \frac{\partial I}{\partial M} d\Omega, \int_{\Omega_k} \int \frac{\partial I}{\partial u} d\Omega, \int_{\Omega_k} \int \frac{\partial I}{\partial t} d\Omega, \int_{\Omega_k} \int \frac{\partial I}{\partial B} d\Omega \right] \tag{81}$$

such that, given a state vector, $x=(A, M, u, t, B)$ and another nearby state, $x_0$, the measured response is approximately:

$$Y(x) \approx Y(x_0) + W \cdot (x - x_0) \tag{82}$$

One can form a cost functional for the mismatch of the model to the data:

$$F(x) = \|(Y(x) - M)\|_{\sigma}^2 = \Sigma_k (Y[k] - M[k])^2 / \sigma_k^2 = (Y-M)^T Q^{-1} (Y-M) \tag{83}$$

Where $\sigma_k$ is the standard deviation (in counts) of the $k^{th}$ measurement, namely $\sqrt{M[k]}$ and Q is defined in equation (70).

One selects a candidate solution for x and then seeks to update it in a fashion that minimizes the cost functional. One method of minimizing this is via steepest descent iteration. A steepest descent step simply updates the guess using some fraction of the gradient, $x_{j+1} = x_j - \Delta t \cdot \nabla F(x_j)$. The gradient of the cost functional given in equation (81) is simply $$\nabla F(x) = W^T Q^{-1} (Y(x_0) - M + W \cdot (x - x_0)) \tag{84}$$

The Levenberg-Marquardt algorithm extends this to handle quasi Newton steps by adding a curvature dependent regularization term and iteratively solving:

$$(W^T Q^{-1} W + \lambda \cdot \text{diag}(W^T Q^{-1} W)) \cdot \delta = W^T Q^{-1} (M - Y(x_0)) \tag{85}$$

where $$\delta = (x_{j+1} - x_j), \tag{86}$$

and the regularization parameter is updated via $$\lambda = \begin{cases} \lambda/\varepsilon, & \varepsilon > 1: F \text{ decreasing} \\ \lambda \cdot \varepsilon, & \varepsilon > 1: F \text{ increasing} \end{cases} \tag{87}$$

In the case of a velocity only solution, one may correlate the phase shift of the acquired data against the response of the model. A normalized correlation operation will produce a maximum for the correct response when swept through a sequence of parameters. This may be efficiently implemented by Fast Fourier Transforms. Correlation has a long history of utilization in Radar applications. This concept may be extended to solve for temperature and aerosol and molecular density.

One advantage of the range-imaging LIDAR system 24' is that the associated ring or pattern parameters can be reconfigured rapidly. The micromirrors 144 of the digital micromirror device (DMD) 142 can be reconfigured in about 10 microseconds. This allows the instrument to adapt as the environment changes. One other advantage of this type of system is that there is no read noise from the pixels like there is with an imaging photodetector such as a CCD. The only noise is from the first $154^{A'}$ and second $154^{B'}$ photomultiplier detectors which when cooled produces very low background signals. Also, the range-imaging LIDAR system 24' uses the molecular response as well as the strong aerosol response which has a very high signal to noise ratio and effectively reduces the system error due to noise; the range-imaging LIDAR system 24' can account for and exploit the known effects due to thermal broadening; the range-imaging LIDAR system 24' can simultaneously measure velocity, temperature, aerosol and molecular components, and the range-imaging LIDAR system 24' can adapt to the changing environment in order to always produce measurements based on the highest sensitivity.

However, this is subject to several limitations, the first being the relatively low quantum efficiency of the first $154^{A'}$ and second $154^{B'}$ photomultiplier detectors and the second being the fact that only two of the patterns 190 of pixel mirror rotational states 148, 150, 152 or "ring sets" are being monitored at any given time. However, there is need to cycle amongst all of the patterns 190 of pixel mirror rotational states 148, 150, 152 with equal temporal resolution. The knowledge of aerosol content might only be required infrequently to provide a reasonable measurement of the Ratio parameter. Temperature is not always required and again could be provided only at infrequent intervals. Accordingly, the basic advantage of the edge type of detection can be achieved with the range-imaging LIDAR system 24', and most of the limitations associated with the simple edge detection can be eliminated.

The range-imaging LIDAR system 24' can be employed utilized for any optical remote sensing scenario. Every remote sensing problem is solved by fitting a model for the system response to the data observed while accounting for the expected deviations in the data. In a Fabry-Pérot interferometer 31' system this response is a collection of fringes for which exists a wealth of phenomenological models. The range-imaging LIDAR system 24' incorporates a digital micromirror device (DMD) 142 in cooperation with a Fabry-Pérot interferometer 31' to segment the optical response between two fast photodetectors. These segmented measurements are made using patterns 190 of pixel mirror rotational states 148, 150, 152 based on the derivatives of the model with respect to each parameter to be estimated thereby granting the highest sensitivity possible. An optimization with respect to segmentation thresholds and timing exposure resolution is performed to minimize the covariance of the minimum variance unbiased estimator of the system. Cost functions based on this covariance may be formed to allow trade-offs to be computed automatically with nonlinear optimization techniques such as BFGS or the Nelder-Mead Simplex algorithm. The ability to use fast photodetectors allows one to apply the range-imaging LIDAR system 24' to problems where one wishes to measure state variable with a fine spatial resolution.

There are future possibilities for improving the range-imaging LIDAR system 24' when digital micromirror devices (DMD) 142 become available having more than two programmable angle states. In this case one could step the digital micromirror device (DMD) 142 through a range of angles and, by using an array of photomultiplier detectors 154', observe many more patterns 190 of pixel mirror rotational states 148, 150, 152 at one time. The patterns 190 of pixel mirror rotational states 148, 150, 152 producing these observations could be optimized in much the same way as described here by simply increasing the number of threshold states used for each derivative.

In operation of the third aspect of an associated detection system 34.3 of a range-imaging LIDAR system 24' first calibrates the Fabry-Pérot etalon 35 by analyzing the reference fringe pattern 104, and then generates measures of aerosol counts A, molecular counts M, velocity u, temperature t, and background counts B from the scatter 47 and reference 104 fringe patterns at one or more particular nominal ranges R, or as a function of nominal range R, by parsing the scatter fringe pattern 47 in accordance with the process illustrated in FIG. 26 and described hereinabove and illustrated in FIGS. 32-46 and 17, so as to separately analyze each arcuate fringe 49' of interest using the hereinabove methodology to analyze the selected portions of the scatter 47 and reference 104 fringe patterns by successively setting the associated patterns 190, 190.1, 190.2, 190.3, 190.4, 190.5 of pixel mirror rotational states 148, 150 for the subset of micromirrors 144 illuminated by the selected portions of the scatter 47 and reference 104 fringe patterns being analyzed at any given time, and setting the remaining micromirrors 144 to the third pixel mirror rotational state 152 so as to preclude that portion of the scatter 47 and reference 104 fringe patterns from being detected, so as to determine the measures of aerosol counts A, molecular counts M, velocity u, temperature t, and background counts B responsive thereto, wherein the final results are processed in accordance with steps (2612)-(2616) of FIG. 26 as described hereinabove. More particularly, when analyzing the reference fringe pattern 104, the micromirrors 144 not illuminated thereby are set to the third pixel mirror rotational state 152 so that only light from the reference fringe pattern 104 is then processed as described hereinabove, and the remaining light is reflected to the light block 172 so as to be blocked from detection by the photodetectors $154^A$, $154^B$. Furthermore, when analyzing the scatter fringe pattern 47, the micromirrors 144 not illuminated by the particular arcuate fringe 49' being analyzed at a particular time are set to the third pixel mirror rotational state 152 so that only light from that particular arcuate fringe 49' is then processed as described hereinabove, and the remaining light is reflected to the light block 172 so as to be blocked from detection by the photodetectors $154^A$, $154^B$.

Figure 47:
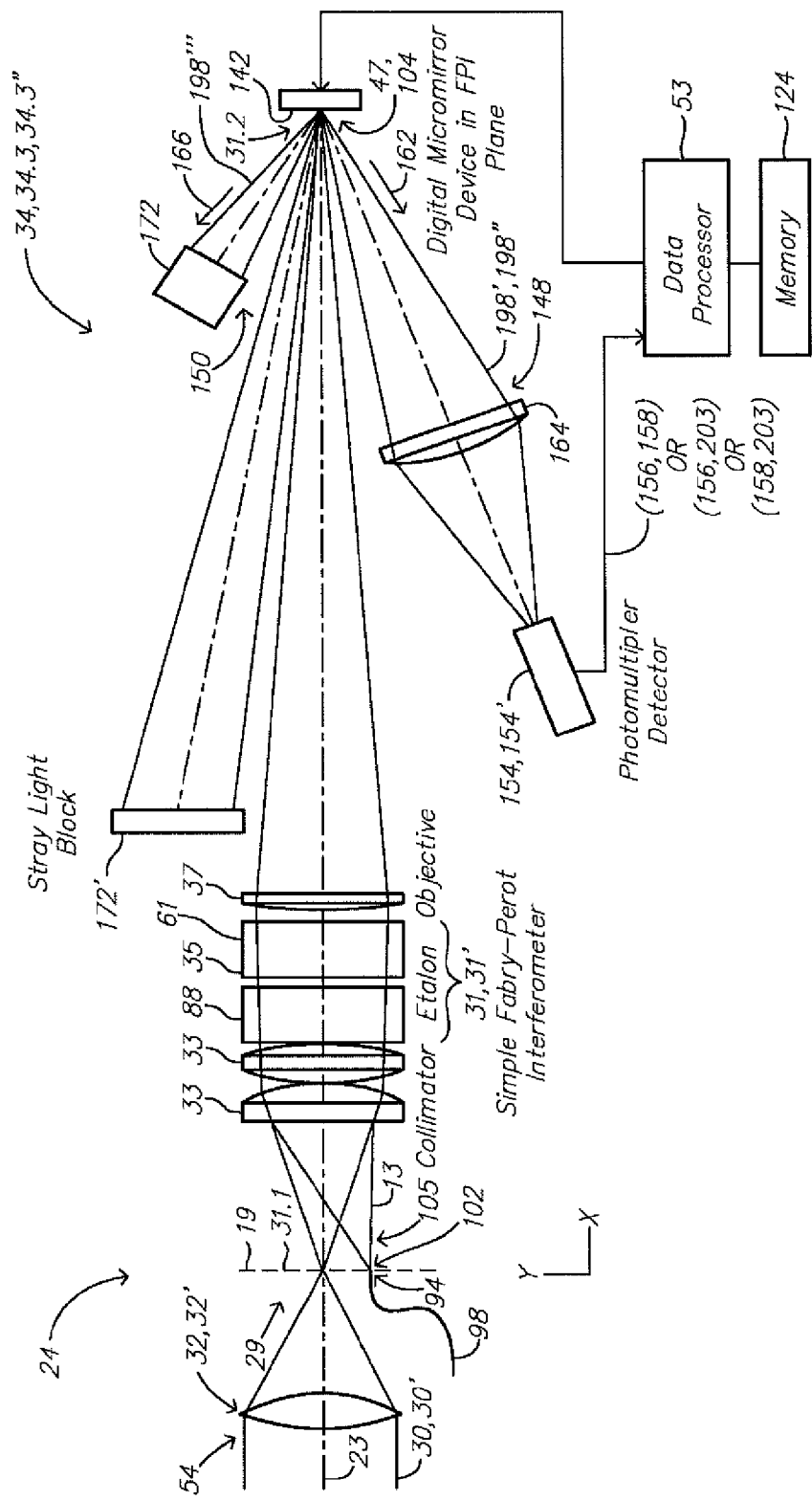
FIG. 47 illustrates a second embodiment of the third aspect of an associated detection system of a range-imaging LIDAR system.

Referring to FIG. 47, a second embodiment of a third aspect of an associated detection system 34.3, 34.3" is the same as for the first embodiment the third aspect of the associated detection system 34.3, 34.3' except that the associated digital micromirror device (DMD) 142 is adapted so that the associated micromirrors 144 thereof are individually addressable and controllable to one of at least two possible associated pixel mirror rotational states 148, 150. The micromirrors 144 of the associated array of micromirrors 144 of the digital micromirror device (DMD) 142 in the first pixel mirror rotational state 148 cause first 198' and second 198" portions of either the scatter fringe pattern 47 or the reference fringe pattern 104 from the Fabry-Pérot interferometer 31' impinging thereupon to be reflected in the first direction 162 to the associated first objective lens 164, and to be directed thereby to the a photodetector 154, for example, a photomultiplier detector 154', wherein the first 198' and second 198" portions are sequentially reflected using different associated pixel mirror rotational states 148, 150 of the associated array of micromirrors 144 of the digital micromirror device (DMD) 142 at different times. Corresponding associated signals 200, 202 are sampled sequentially, rather than simultaneously in contradistinction with the first embodiment the third aspect of the associated detection system 34.3, 34.3' for which the associated complementary signals 156, 158 are sampled simultaneously. The micromirrors 144 of the associated array of micromirrors 144 of the digital micromirror device (DMD)

142 in the second pixel mirror rotational state 150 cause third portions 198''' of either the scatter fringe pattern 47 or the reference fringe pattern 104 from the Fabry-Pérot interferometer 31' impinging thereupon to be reflected in the second direction 166 to a light block 172 that provides for absorbing light impinging thereupon.

In accordance with a first aspect of signal processing associated with the second embodiment of a third aspect of an associated detection system 34.3, 34.3'', the first 198' and second 198'' portions are sequentially reflected using different associated pixel mirror rotational states 148, 150 of the associated array of micromirrors 144 of the digital micromirror device (DMD) 142 at different times, wherein the first 198' and second 198'' portions are relatively disjoint as for the first embodiment the third aspect of the associated detection system 34.3, 34.3', so that the resulting signals 200, 202 correspond to the complementary signals 156, 158 that would otherwise be sampled by the first embodiment the third aspect of the associated detection system 34.3, 34.3'. Accordingly, for each and every parameter, the micromirrors 144 of the digital micromirror device (DMD) 142 associated with the first disjoint portion 47' of the scatter fringe pattern 47, or the first disjoint portion 104' of the reference fringe pattern 104, within the region being processed are set to the first pixel mirror rotational state 148 at a first point in time to measure the first complementary signal 156, and the micromirrors 144 of the digital micromirror device (DMD) 142 associated with the second disjoint portion 47'' of the scatter fringe pattern 47, or the second disjoint portion 104'' of the reference fringe pattern 104, within the region being processed are set to the first pixel mirror rotational state 148 at a second point in time to measure the second complementary signal 158. During both the first and second points in time, the micromirrors 144 of the associated array of micromirrors 144 of the digital micromirror device (DMD) 142 outside of the region being processed are set to the second pixel mirror rotational state 150 so as to cause the remaining portion of either the scatter fringe pattern 47 or the reference fringe pattern 104 from the Fabry-Pérot interferometer 31' impinging thereupon to be reflected in the second direction 166 to a stray light block 172' that provides for absorbing light impinging thereupon. An additional stray light block 172' is provided to receive stray light reflected from the digital micromirror device (DMD) 142. This process is repeated for each of the parameters being detected. Accordingly, a total of 2N measurements are needed in order to identify N parameters using the first aspect of signal processing associated with the second aspect of the second embodiment of a third aspect of an associated detection system 34.3, 34.3''.

In accordance with a second aspect of signal processing associated with the second embodiment of a third aspect of an associated detection system 34.3, 34.3'', only N+1 measurements are needed within each region of the scatter 47 or reference 104 fringe patterns to identify N parameters associated with that region, wherein one of the measurements is of the light from the entire region, and the remaining N measurements are for one of the disjoint portions 47', 104' or 47'', 104'' associated with each of the parameters. Then, either the signals associated with the remaining disjoint portions 47'', 104'' or 47', 104' are then found for each parameter by subtracting the corresponding measurement for the one of the disjoint portions 47', 104' or 47'', 104'' from the corresponding measurement of the total signal 203 for the entire region, or the N parameters are identified by solving a system of equations based upon the N+1 measurements directly, rather than the corresponding 2N complementary signals.

Accordingly, the measurement of the total signal 203 for the entire region is made by setting the associated micromirrors 144 of the digital micromirror device (DMD) 142 to the first pixel mirror rotational state 148 at a first point to make a measurement of the total signal 203 from the light of that entire region as one of the first 200 and second 202 signals. Then, for each parameter, as corresponding distinct points in time, the micromirrors 144 of the digital micromirror device (DMD) 142 associated with either the first 47', 104' or second 47'', 104'' disjoint portion within the region being processed is set to the first pixel mirror rotational state 148 at that point in time to measure the other of the first 200 and second 202 signals corresponding to the first 156 or second 158 complementary signal. While these measurements are being made, the micromirrors 144 of the associated array of micromirrors 144 of the digital micromirror device (DMD) 142 outside of the region being processed are set to the second pixel mirror rotational state 150 so as to cause the remaining portion of either the scatter fringe pattern 47 or the reference fringe pattern 104 from the Fabry-Pérot interferometer 31' impinging thereupon to be reflected in the second direction 166 to a light block 172 that provides for absorbing light impinging thereupon. The remaining second 158 or first 156 complementary signal is then found by subtracting the measured first 156 or second 158 complementary signal from the total signal 203, for each of the N different parameters, or the first 200 and second 202 signals are used directly to solve for the N parameters.

The method of processing the disjoint portions 47', 47'', 104', 104'' of the associated scatter 47 and reference 104 fringe patterns, or one of the disjoint portions 47', 47'', 104', 104'' in combination with the corresponding total signal 203, can also be applied in cooperation with other systems that provide for generating the associated disjoint portions 47', 47'', 104', 104'' similar to that provided for by one or more digital micromirror devices (DMD) 142 as described hereinabove, but without requiring a digital micromirror device (DMD) 142.

For example, in one embodiment, a Liquid Crystal Device (LCD), could be used to generate the associated disjoint portions 47', 47'', 104', 104'' that are extracted from the associated underlying scatter 47 or reference 104 fringe pattern by controlling the pattern of transmission of associated pixels of the LCD provide for transmitting corresponding selected disjoint portions 47', 47'', 104', 104'' at any given time. For example, this can be accomplished by replace one of the polarizers normally used in the LCD with a polarization selective beam splitter, wherein the beam splitter provides for a transmission of one polarization while reflecting the other polarization. The output of the LCD would then consist of the selected disjoint pattern and its compliment, one transmitted and the other reflected.

As another example, a Holographic Optical Element (HOE), could be fabricated that would direct the light from disjoint regions onto individual areas. A Holographic Optical Element (HOE) could be constructed that would focus the light from a ring for example onto a single small area where a detector could be located. Separate disjoint areas would direct the light to different detectors which would then be used to detect the light in each disjoint pattern.

As yet another example, micro-machined mirrors could be fabricated to focus the light in a selected pattern onto a particular region. Detectors located at those regions would then convert the light to an electrical signal that would be measured and processed.

As yet another example, individual masks could be moved into position to generate the disjoint patterns. These masks could be configured around the edge of a disk and the individual masks rotated into position or the masks could be arranged in a linear or two dimensional array, and either a linear or a pair of linear actuators could be used to move the selected masks into position.

Alternatively, the disjoint portions 47', 47", 104', 104" can be extracted from an electronically captured image 114 of the scatter 47 or reference 104 fringe pattern that—or the corresponding regions thereof to be processed corresponding to the associated scattered 30' and reference 105 light signals—is subsequently compressed by using electronic or software integration or binning as described hereinabove. For example, the image 114 may be captured using the first aspect of the associated detection system 34.1, for example, using an electronic camera, for example, a CCD detection system 34.1', from which the corresponding linear scatter $47^L$ and reference $104^L$ fringe patterns are for example formed in accordance with the methodology described hereinabove and illustrated in FIGS. 12a-15, or using a circle-to-line interferometer optic (CLIO) elements 128 or a holographic optical element 128' as described hereinabove. The associated disjoint portions 47', 47", 104', 104" of the corresponding linear scatter $47^L$ and reference $104^L$ fringe patterns are then extracted electronically or by software, and then processed in accordance with the methodology described hereinabove and illustrated in FIGS. 32-46 and 17, for example, so as to provide for determining the corresponding atmospheric data 36 for each of the associated scattered light signals 30'.

Figure 48:
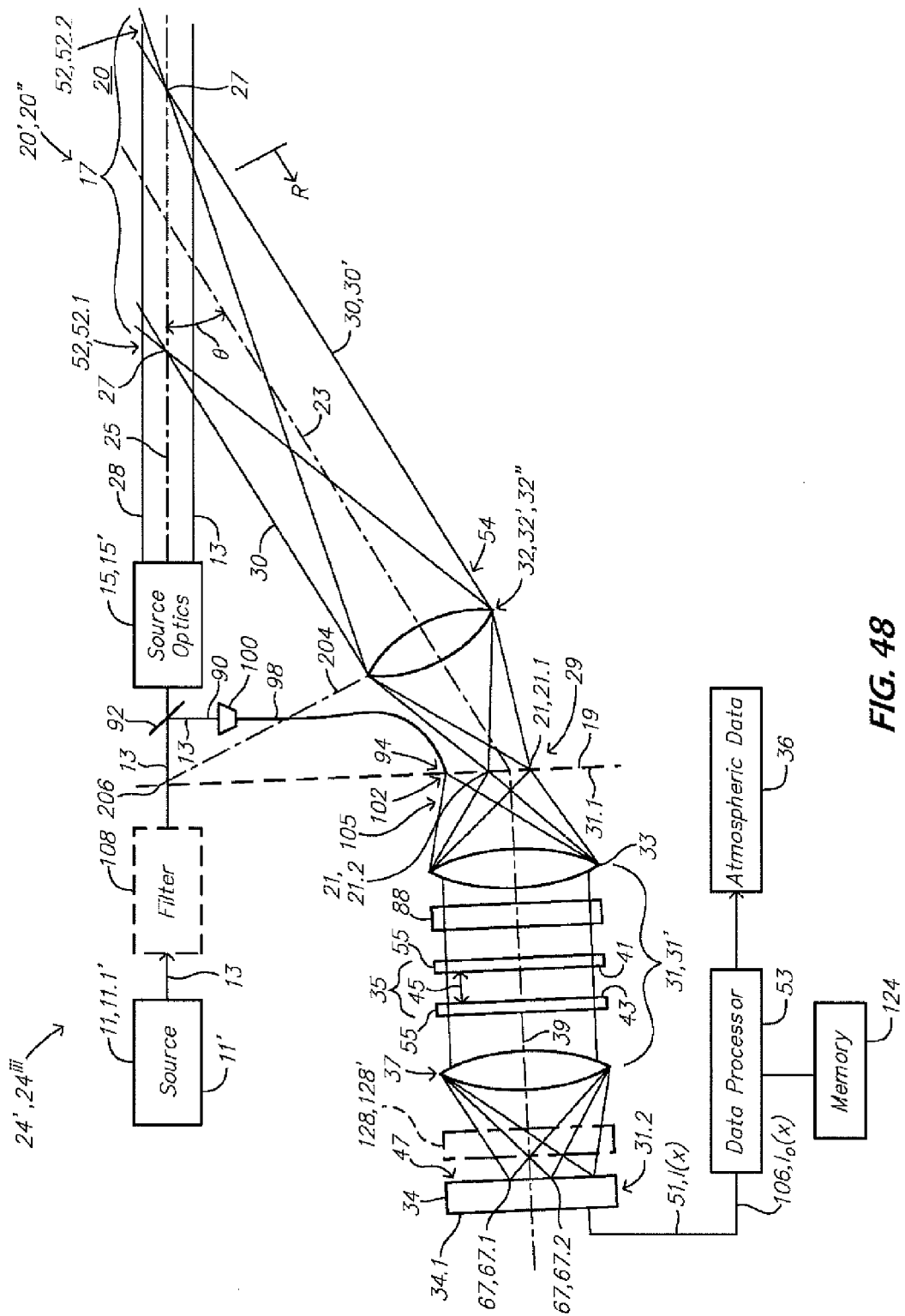
FIG. 48 illustrates an embodiment of a third aspect of a range-imaging LIDAR system.

Referring to FIG. 48, in accordance with a third aspect, the range-imaging LIDAR system 24', $24^{iii}$ is substantially the same as the first aspect of the range-imaging LIDAR system 24', $24^i$ except that the near-range blur in the intermediate image 29 can be reduced by orienting the Fabry-Pérot interferometer 31', and particularly, the collimating lens 33 thereof, in relation to the receive optics 32 so that the intermediate image plane 19 satisfies the Scheimpflug condition, whereby the optic axis 25 of the beam of light 28, the plane 204 of the effective lens 32" of the receive optics 32 and the intermediate image plane 19 all interest at a common point of intersection 206, also known as a Scheimpflug intersection. Reducing the blur in the intermediate image 29 provides for reducing the breadth of the scatter fringe pattern 47 in the Y-direction 110 in the output focal plane 31.2', thereby simplifying the requirements of the associated detection system 34, for example, so as to enable the use of a linear photodetector array or a linear array of photo detectors.

Figure 49:
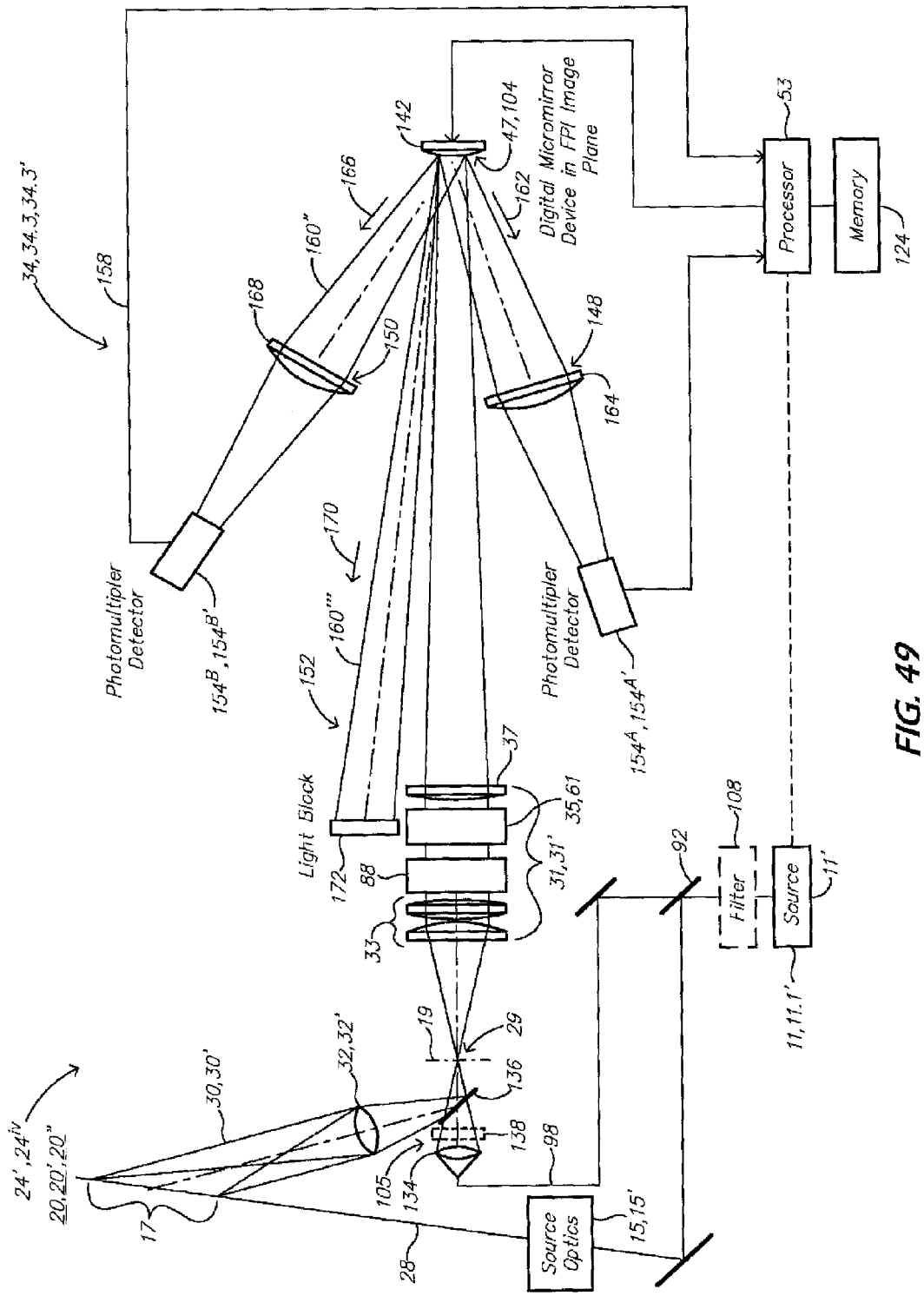
FIG. 49 illustrates and embodiment of a fourth aspect of a range-imaging LIDAR system.

Referring to FIG. 49, in accordance with a fourth aspect, a range-imaging LIDAR system 24', $24^{iv}$ is similar to the second embodiment of the first aspect of the range-imaging LIDAR system 24', $24^{ii}$ illustrated in FIG. 27 but incorporating the first embodiment of the third aspect of an associated detection system 34.3, 34.3' illustrated in FIG. 29a, a collimating lens 33 in cooperation with the Fabry-Pérot interferometer 31', an input telescope 32' for receiving the scattered light 30, and with the scattered light 30 and reference source 94 juxtaposed relative to the associated second beam splitter optic 136. A substantial portion of the scattered light 30 is reflected from the second beam splitter optic 136, and the reference light signal 105 from the reference source 94 is transmitted through the second beam splitter optic 136, wherein the reference source 94 is embodied substantially the same as illustrated and described in accordance with the second embodiment of the first aspect of the range-imaging LIDAR system 24', $24^{ii}$.

In one embodiment, the image 114 of the reference light signal 105 is positioned so as to not overlap the associated scattered light signal 30' in the output focal plane 31.2' of the Fabry-Pérot interferometer 31'. In another embodiment, in accordance with the eighth aspect of the range-imaging LIDAR system 24', $24^{viii}$ described more fully herein below, the image 114 of the reference light signal 105 is positioned so as to overlap the associated scattered light signal 30', with the portion of the reference light signal 105 overlapping the scattered light signal 30' blocked by an associated mask 138 between the lens 134 and the second beam splitter optic 136. In yet another embodiment, the light source 11 is pulsed, for example, a pulsed Nd:YAG laser 11.1', and the associated detection system 34—for example, using a fast CCD detection system 34.1' instead of the relatively slower DVD-based detection system 34.3 as illustrated—is sampled in synchronism with the light source 11 so as to provide for initially capturing the reference light signal 105 prior to receiving the scattered light signal 30', and to then receive the process the scattered light signal 30' thereafter.

Figure 50:
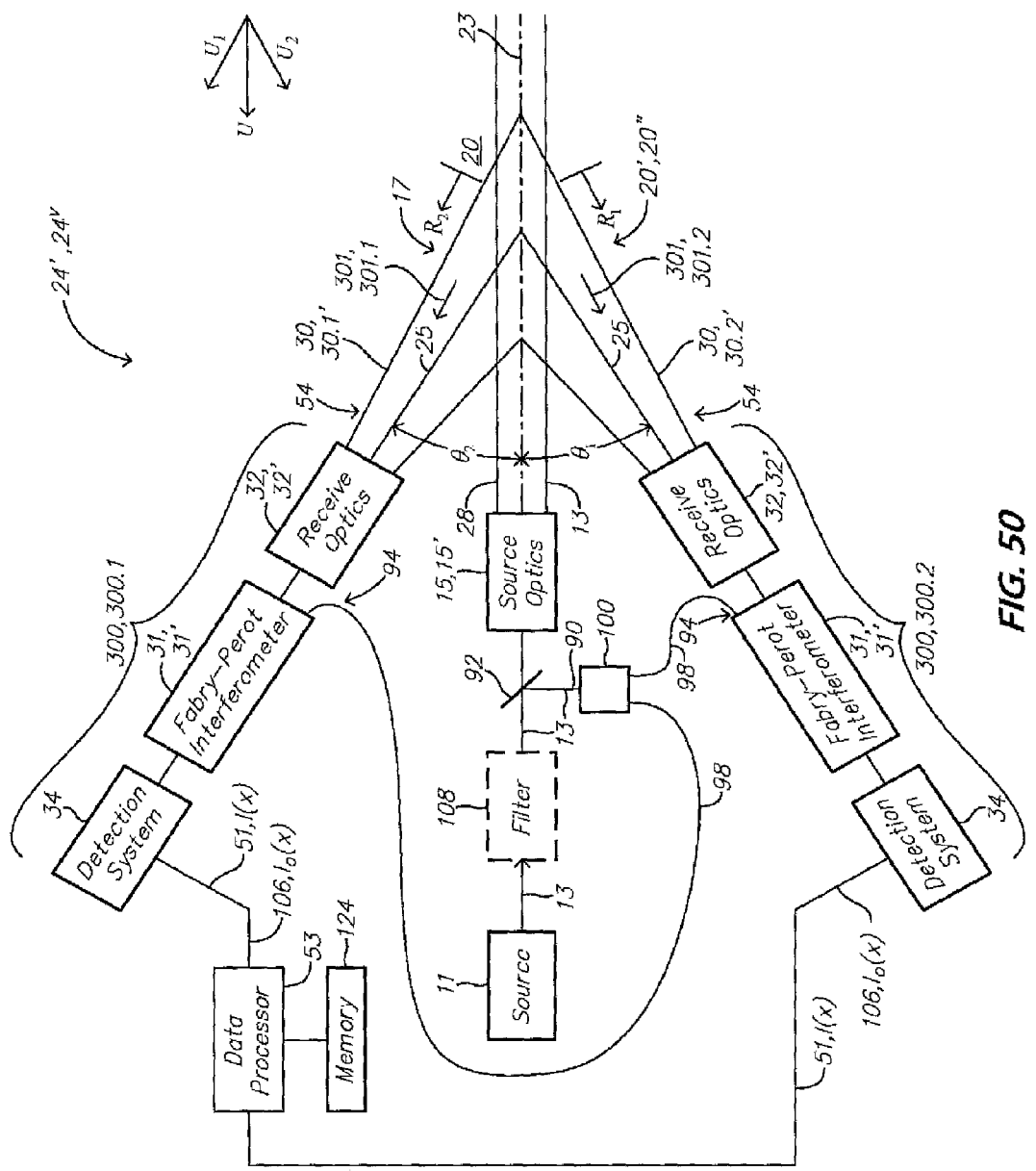
FIG. 50 illustrates an embodiment of a fifth aspect of a range-imaging LIDAR system.

Referring to FIG. 50, in accordance with a fifth aspect of a range-imaging LIDAR system 24', $24^v$, a plurality of separate receivers 300, 300.1, 300.2 are adapted to cooperate with a common beam of light 28, wherein each receiver 300, 300.1, 300.2 comprises an associated combination of receive optics 32, a Fabry-Pérot interferometer 31' and a detection system 34 constructed and operated in accordance with any of the above-described aspects of the range-imaging LIDAR systems 24' described hereinabove, wherein the reference source 94 associated with each receiver 300, 300.1, 300.2 is obtained from a common beam of light 28. The scatter 51 and reference 106 electronic image signals from the receivers 300, 300.1, 300.2 are separately processed by the data processor 53 in accordance with any of the above-described aspects of the range-imaging LIDAR systems 24' described hereinabove, and in accordance with the process 2600 illustrated in FIG. 26, so as to provide for generating a set of one or more measures of aerosol counts A, molecular counts M, velocity u, temperature t, and background counts B at one or more selected nominal ranges R, or as a function of nominal range R, for each of the receivers 300, 300.1, 300.2. More particularly, in one embodiment, separate measures of velocity u, $u_1$, $u_2$ at one or more selected nominal ranges R, or as a function of nominal range R, are generated for each receiver 300, 300.1, 300.2, wherein the associated Doppler shift to the frequency of the common beam of light 28 is dependent upon the velocity a of the atmosphere 20 in the direction 301, 301.1, 301.2 of the receiver 300, 300.1, 300.2. The separate measures of velocity u, $u_1$, $u_2$ in combination then provide for determining a measure of a velocity vector U at one or more selected nominal ranges R, or as a function of nominal range R, so as to provide for determining a velocity field within the atmosphere 20. For example, the fifth aspect of a range-imaging LIDAR system 24', $24^v$ could be used in a wind tunnel to provide for probing the velocity field of the flow field therein without perturbing that flow field.

Figure 51:
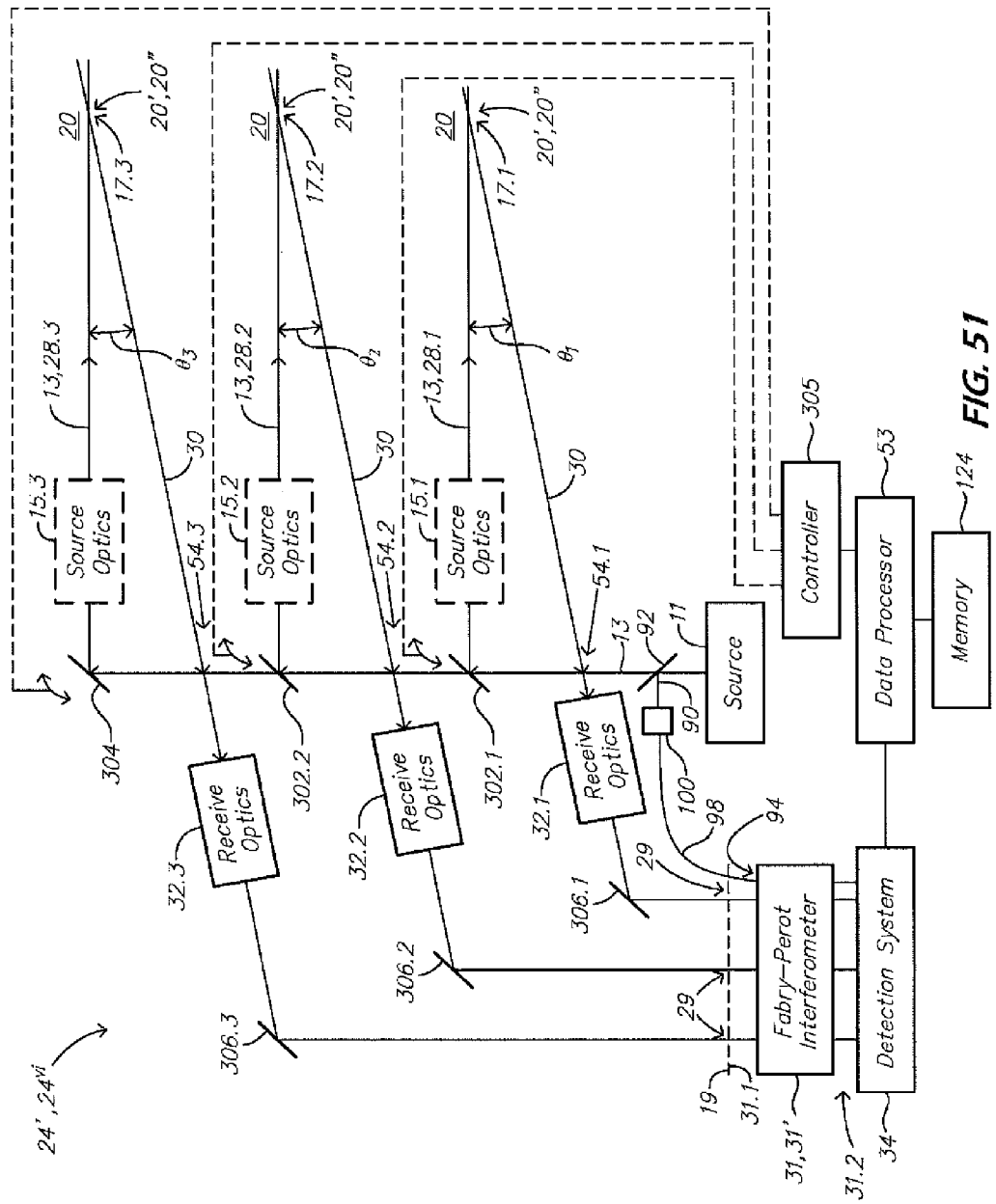
FIG. 51 illustrates an embodiment of a sixth aspect of a range-imaging LIDAR system.

Referring to FIG. 51, in accordance with a sixth aspect of a range-imaging LIDAR system 24', $24^{vi}$, a plurality of beams of light 28, 28.1, 28.2, 28.3 are generated from a common light source 11 that is distributed thereto by a corresponding set of beam splitters 302.1, 302.2 and a mirror 304. For example, different beams of light 28, 28.1, 28.2, 28.3 may be directed in different directions or at different locations into the atmosphere 20, for example, so as to provide for either probing different portions of the atmosphere, or so as to provide for a velocity vector U of the range-imaging LIDAR system 24', $24^{vi}$ relative to the atmosphere 20, for example, with the range-imaging LIDAR system 24', $24^{vi}$ used as an optical air data system in a vehicle, for example, an aircraft. For example, in one set of embodiments, the attitude or position of one or more of the beam splitters 302.1, 302.2 and mirror 304 may be controlled by a controller 305 operatively associated with or a part of the data processor 53 so as to provide for controlling the position or orientation of one or more of the associated beams of light 28, 28.1, 28.2, 28.3. In some embodiments, the range-imaging LIDAR system 24', $24^{vi}$ may incorporate one or more sets of source optics 15, 15.1, 15.2, 15.3 associated with one or more of the corresponding beams of light 28, 28.1, 28.2, 28.3 so as to provide for shaping the one or more beams of light 28, 28.1, 28.2, 28.3 and setting the size and divergence thereof. A plurality of receive optics 32, 32.1, 32.2, 32.3 are adapted to receive scattered light 30 from corresponding interaction regions 17, 17.1, 17.2, 17.3 of the one or more of the corresponding beams of light 28, 28.1, 28.2, 28.3 within the corresponding fields-of-view 54, 54.1, 54.2, 54.3 of the associated receive optics 32, 32.1, 32.2, 32.3, wherein each receive optics 32, 32.1, 32.2, 32.3 is oriented at a corresponding parallax angle $\theta$, $\theta_1$, $\theta_2$, $\theta_3$ with respect to the corresponding beam of light 28, 28.1, 28.2, 28.3, so that the associated interaction regions 17, 17.1, 17.2, 17.3 span a substantial range of nominal ranges R. Each set of receive optics 32, 32.1, 32.2, 32.3 is adapted to image the corresponding interaction region 17, 17.1, 17.2, 17.3 at different locations on a common intermediate image plane 19 that is located at the input focal plane 31.1' of a common Fabry-Pérot interferometer 31'. For example, scattered light 30 from the receive optics 32, 32.1, 32.2, 32.3 is reflected onto the intermediate image plane 19 by an associated set of mirrors 306.1, 306.2, 306.3. Furthermore, a reference beam portion 90 of the substantially monochromatic light 13 is extracted from the light source 11 with a beam splitter optic 92 and then input as a reference source 94 at a location on the intermediate image plane 19 that is distinct from the locations of the intermediate images 29 from each of the receive optics 32, 32.1, 32.2, 32.3. The reference source 94 is processed by the Fabry-Pérot interferometer 31' to generate a corresponding reference fringe pattern 104, and the intermediate images 29 from each of the receive optics 32, 32.1, 32.2, 32.3 are processed by the Fabry-Pérot interferometer 31' to generate corresponding scatter fringe patterns 47, 47.1, 47.2, 47.3.

Referring to FIG. 52, in accordance with a seventh aspect, the range-imaging LIDAR system 24', $24^{vii}$ is adapted to provide for interleaving the scattered 30' and reference 105 light signals in the associated image 114 at the output focal plane 31.2' of the Fabry-Pérot interferometer 31', for example, as illustrated in FIGS. 12a and 13 for four separate associated scatter fringe patterns 47, 47.1, 47.2, 47.3, 47.4, although the range-imaging LIDAR system 24', $24^{vii}$ illustrated in FIG. 52 would provide only two of the four scatter fringe patterns 47, 47.1, 47.2, 47.3, 47.4. The seventh aspect of the range-imaging LIDAR system 24', $24^{vii}$ incorporates a second aspect of a reference source 94' that is used in the eighth aspect of the range-imaging LIDAR system 24', $24^{viii}$ that is more fully described hereinbelow. Generally, the second aspect of a reference source 94' uses a rotating diffuser 308—driven by a motor 309—in cooperation with an integrating sphere 310 so as to provide for substantial angular diversity of the associated reference light signal 105. A second beam splitter optic 136 interleaves the reference light signal 105 with associated scattered light signals 30', wherein portions of the reference light signal 105 that would otherwise overlay the scattered light signals 30' are blocked by a first mask 138 prior to combination with the scattered light signals 30' by the second beam splitter optic 136 so that the reference light signal 105 and scattered light signals 30' are disjoint with respect to one another in the resulting image 114.

The seventh aspect of the range-imaging LIDAR system 24', $24^{vii}$ comprises a pyramidal image combiner 312 that provides for separating the scattered light signals 30' from one another in the image 114, for example, uniformly separating the scattered light signals 30' from one another as illustrated in FIGS. 12a and 13. More particularly, the pyramidal image combiner 312 comprises a plurality of reflective faces 314, each of which provides for reflecting a different scattered light signal 30' into a second mask 316 that is configured to block portions of the scattered light signal 30' that would otherwise overlap the reference light signal 105. More particularly, the range-imaging LIDAR system 24', $24^{vii}$ incorporates associated beam steering optics 210 comprising a third beam splitter optic 318 that divides the beam of light 28 from the light source 11 into first 28.1 and second 28.2 beams of light that are directed into separate regions of the atmosphere 20 by a series of associated mirrors 320. The range-imaging LIDAR system 24', $24^{vii}$ further incorporates first 32.1 and second 32.1 receive optics with associated first 23.1 and second 23.2 optic axes directed at separate first 17.1 and second 17.2 interaction regions along the first 28.1 and second 28.2 beams of light within the atmosphere 20, that provide for receiving corresponding associated first 30.1 and second 30.2 scattered light therefrom that is directed to the corresponding first 314.1 and second 314.2 reflective faces of the pyramidal image combiner 312 by a plurality of associated mirrors 322. In one embodiment the reflective faces 314 are flat, whereas in another embodiment the reflective faces 314 are conical circle-to-line interferometer optic (CLIO) elements 128 that also provide for azimuthally compressing the associated resulting scatter fringe patterns 47, 47.1, 47.2.

Figure 53:
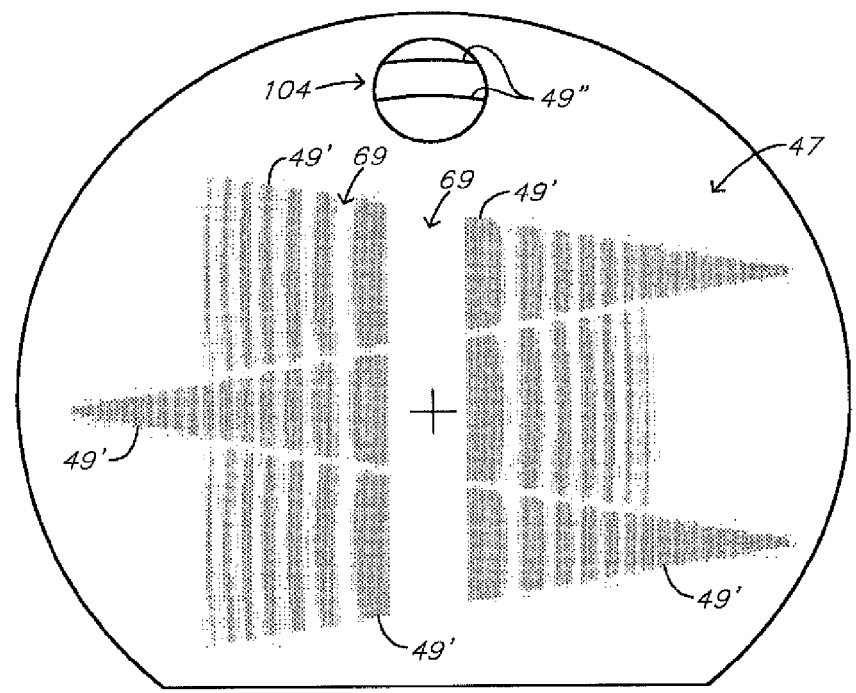
FIG. 53 illustrates a first aspect of plural fringe patterns generated by the sixth aspect of a range-imaging LIDAR system illustrated in FIG. 51.
Figure 54:
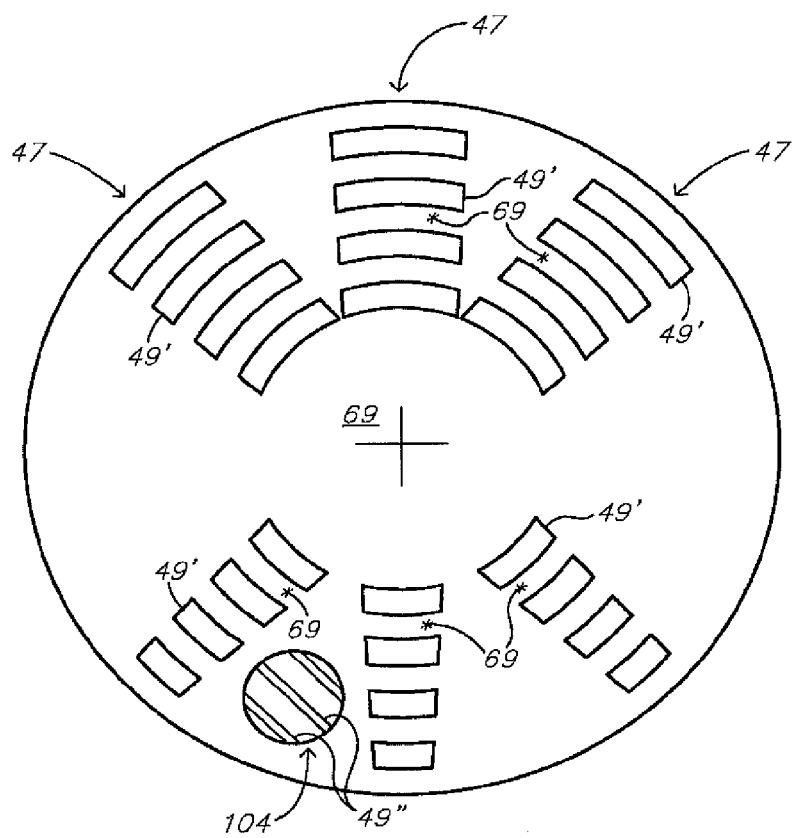
FIG. 54 illustrates a second aspect of plural fringe patterns generated by the sixth aspect of a range-imaging LIDAR system illustrated in FIG. 51.

Referring to FIG. 53, in accordance with a first aspect, the plural scatter fringe patterns 47, 47.1, 47.2, 47.3 generated by the sixth aspect of a range-imaging LIDAR system 24', $24^{vi}$ illustrated in FIG. 51 are translated with respect to one another in the output focal plane 31.2' 31.2" of the Fabry-Pérot interferometer 31', whereas referring to FIG. 54, in accordance with a second aspect, the plural scatter fringe patterns 47, 47.1, 47.2, 47.3 generated by the sixth aspect of a range-imaging LIDAR system 24', $24^{vi}$ illustrated in FIG. 51 are rotated with respect to one another relative to the optic axis 39 of the Fabry-Pérot interferometer 31'. The separate arcuate fringes 49' of each of the scatter fringe patterns 47, 47.1, 47.2, 47.3 are separately processed by the data processor 53 in accordance with any of the above-described methods so as to provide for generating a set of one or more measures of aerosol counts A, molecular counts M, velocity u, temperature t, and background counts B at one or more selected nominal ranges R, or as a function of nominal range R, for each of the interaction region 17, 17.1, 17.2, 17.3 within the associated fields-of-view 54, 54.1, 54.2, 54.3 of the associated receive optics 32, 32.1, 32.2, 32.3.

Referring to FIG. 55a, in accordance with a first embodiment of an eighth aspect, the range-imaging LIDAR system 24', $24^{viii'}$ is similar to the third aspect of the range-imaging LIDAR system 24', $24^{iii}$ illustrated in FIG. 48 but instead incorporating the second aspect of the reference source 94' and explicitly incorporating the first aspect of the associated detection system 34.1. In accordance with the second aspect of the reference source 94', the reference beam portion 90 emanating from the first beam splitter optic 92 is directed therefrom to a reference illuminator 324, for example, comprising an associated rotating diffuser 308 in combination with an integrating sphere 310 relatively located behind and illuminating the mask 138, 138.1. The rotating diffuser 308 produces the phase diversity necessary to reduce the speckle in the reference beam thus providing uniform illumination.

Accordingly, the reference illuminator 324 provides for generating a uniform and diffuse reference beam 90', for example, as illustrated in FIG. 55b, which is then directed through a first aspect of a mask 138, 138.1 that blocks a portion of the uniform and diffuse reference beam 90' from transmission therethrough, resulting in a corresponding first embodiment of a masked reference beam 90", 90.1" that is then reflected of a partially reflective surface 136.1 of a second beam splitter optic 136, then through and collimated by the collimating lens 33 of the Fabry-Pérot interferometer 31', through the associated filter system 88, then through the associated Fabry-Pérot etalon 35, and finally through the associated imaging optics 37 of the Fabry-Pérot interferometer 31'. The scattered light signal 30' is transmitted through the second beam splitter optic 136, then through and collimated by the collimating lens 33 of the Fabry-Pérot interferometer 31', through the associated filter system 88, then through the associated Fabry-Pérot etalon 35, and finally through the associated imaging optics 37 of the Fabry-Pérot interferometer 31'. In the absence of the Fabry-Pérot etalon 35, the imaging optics 37 in cooperation with the collimating lens 33 provides for generating an image 114", 114.1" of the masked reference beam 90", 90.1" in the output focal plane 31.2' 31.2" of the Fabry-Pérot interferometer 31', wherein a corresponding image of the mask 138, 138.1 is illustrated in FIG. 55c. Similarly, in the absence of the Fabry-Pérot etalon 35, the imaging optics 37 in cooperation with the collimating lens 33 provides for generating an image 114' of the scattered light signal 30' in the output focal plane 31.2' 31.2" of the Fabry-Pérot interferometer 31'. Referring to FIG. 55c, in accordance with the first aspect, the mask 138, 138.1 comprises an opaque region 138' and a remaining transparent region 138", wherein the opaque region 138' is sized so as to correspond in profile—in the output focal plane 31.2' 31.2" of the Fabry-Pérot interferometer 31'—to the image 114' of the associated scattered light signal 30'. Referring to FIG. 55d, a hypothetical image in the output focal plane 31.2' 31.2" of the Fabry-Pérot interferometer 31' absent the associated Fabry-Pérot etalon 35 illustrates the disjoint regions 326, 328 therein of the image 114' of the scattered light signal 30' and the image 114", 114.1" of the masked reference beam 90", 90.1", respectively.

The mask 138, 138.1 is configured and aligned so as to provide for masking all of the light from the uniform and diffuse reference beam 90' for which the image thereof at the output focal plane 31.2' of the Fabry-Pérot interferometer 31' would otherwise overlap the corresponding image 114' of the scattered light signal 30'. Accordingly, within the output focal plane 31.2' of the Fabry-Pérot interferometer 31', the light within the region 326 associated with the image 114' of the scattered light signal 30' is exclusively from the scattered light 30, and light associated with the remaining region 328 of the output focal plane 31.2' is exclusively from the uniform and diffuse reference beam 90'.

The reference illuminator 324 that provides for illuminating the mask 138 could be implemented in various ways. For example, in one embodiment, the rotating diffuser 308 may be replaced with a scanning mirror that would scan a narrow laser beam across the inside of the integrating sphere 310. In another embodiment, the integrating sphere 310 could be replaced by either single or multiple diffusers. In yet another embodiment, optics could be employed to provide for a uniform illumination of the mask 138.

Referring to FIG. 55e, with the Fabry-Pérot etalon 35 in place, the Fabry-Pérot interferometer 31' generates two sets of fringes in the output focal plane 31.2', i.e. focal plane, of the imaging optics 37 as follows: a first set of fringes 330 of an associated reference fringe pattern 104 in the region 328 associated with the uniform and diffuse reference beam 90', and a second set of fringes 332 of a scatter fringe pattern 47 in the region 326 associated with the scattered light signal 30', wherein each set of fringes 330, 332 is generated responsive to a transmission function of the Fabry-Pérot etalon 35. The uniform and diffuse reference beam 90' provides an illumination pattern that is uniform and sufficient in extent so as to fully illuminate the first set of fringes 330 that fall on the detection system 34, 34.1. Otherwise, the first 330 and second 332 sets of fringes are processed as described hereinabove in accordance with any of the above-described aspects of the range-imaging LIDAR system 24'.

The range-imaging LIDAR system 24', $24^{viii}$ may be expanded with additional sets of receive optics 32, either with one or more associated beams of light 28, in cooperation with a common Fabry-Pérot interferometer 31',—for example, similar to the fifth through seventh aspects of the range-imaging LIDAR system 24', $24^{v-vii}$ illustrated in FIGS. 50-52, but using the reference illuminator 324, mask 138 and second beam splitter optic 136 of the first embodiment of an eighth aspect of range-imaging LIDAR system 24', $24^{viii}$ as illustrated in FIG. 55a. For the example of such an range-imaging LIDAR system 24', $24^{viii}$ with three scattered light signals 30.1', 30.2', 30.3' resulting in a corresponding three distinct second sets of fringes 332.1, 332.2, 332.3 associated with three distinct scatter fringe patterns 47, 47.1, 47.2, 47.3, referring to FIGS. 56a-58b, the scatter fringe patterns 47, 47.1, 47.2, 47.3 and the associated opaque regions $138^{i'}$, $138^{ii'}$ and $138^{iii'}$ of the associated mask 138, 138.1 can be arranged in various orientations relative to one for processing by the Fabry-Pérot interferometer 31'.

For example, FIG. 56a illustrates an example of a mask 138, $138.1^a$ with three opaque regions $138^{i'}$, $138^{ii'}$ and $138^{iii'}$ used with a range-imaging LIDAR system 24', $24^{viii.a}$ with three scatter signal channels for which, referring to FIG. 56b, the associated three distinct scatter fringe patterns 47, 47.1, 47.2, 47.3 are translated with respect to one another, and with one of the scatter fringe patterns 47.2 flipped with respect to the other two scatter fringe patterns 47.1, 47.3, in the output focal plane 31.2' of the Fabry-Pérot interferometer 31', wherein relative to the first embodiment of the eighth aspect of the range-imaging LIDAR system 24', $24^{viii}$ illustrated in FIG. 55a, FIG. 56a corresponds in location to FIG. 55c and FIG. 56b corresponds in location to FIG. 55e. The mask 138, $138.1^a$ is configured (i.e. sized and shaped) and aligned so as to provide for masking all of the light from the uniform and diffuse reference beam 90' for which the image thereof at the output focal plane 31.2' of the Fabry-Pérot interferometer 31' would otherwise overlap the corresponding image 114' of the scattered light signals 30.1', 30.2', 30.3'. Accordingly, within the output focal plane 31.2' of the Fabry-Pérot interferometer 31', the light within the region 326 of the image 114' of the scattered light signals 30.1', 30.2', 30.3' is exclusively from the associated scattered light 30 thereof, and light associated with the remaining region 328 of the output focal plane 31.2' is exclusively from the uniform and diffuse reference beam 90'.

As another example, FIG. 57a illustrates an example of a mask 138, $138.1^b$ with three opaque regions $138^{i'}$, $138^{ii'}$ and $138^{iii'}$ used with a range-imaging LIDAR system 24', $24^{viii.b}$ with three scatter signal channels for which, referring to FIG. 57b, the associated three distinct scatter fringe patterns 47, 47.1, 47.2, 47.3 are rotated with respect to one another and intersecting one another so that each spans a substantial portion of the diametrical image space in the output focal plane 31.2' of the Fabry-Pérot interferometer 31', wherein relative to the first embodiment of the eighth aspect of the range-imaging LIDAR system 24', $24^{viii}$ illustrated in FIG. 55a, FIG. 57a corresponds in location to FIG. 55c and FIG. 57b corresponds in location to FIG. 55e. The mask 138, $138.1^b$ is configured (i.e. sized and shaped) and aligned so as to provide for masking all of the light from the uniform and diffuse reference beam 90' for which the image thereof at the output focal plane 31.2' of the Fabry-Pérot interferometer 31' would otherwise overlap the corresponding image 114' of the scattered light signals 30.1', 30.2', 30.3'. Accordingly, within the output focal plane 31.2' of the Fabry-Pérot interferometer 31', the light within the region 326 of the image 114' of the of the scattered light signals 30.1', 30.2', 30.3' is exclusively from the associated scattered light 30 thereof, and light associated with the remaining region 328 of the output focal plane 31.2' is exclusively from the uniform and diffuse reference beam 90'.

As yet another example, FIG. 58a illustrates an example of a mask 138, $138.1^c$ with three opaque regions $138^{ii'}$, $138^{ii'}$ and $138^{iii'}$ used with a range-imaging LIDAR system 24', $24^{viii.c}$ with three scatter signal channels for which, referring to FIG. 58b, the associated three distinct scatter fringe patterns 47, 47.1, 47.2, 47.3 are rotated with respect to one another, each separated from one another, extending radially outwards from the optic axis 39 of the imaging optics 37, wherein relative to the first embodiment of the eighth aspect of the range-imaging LIDAR system 24', $24^{viii}$ illustrated in FIG. 55a, FIG. 58a corresponds in location to FIG. 55c and FIG. 58b corresponds in location to FIG. 55e. The mask 138, $138.1^c$ is configured (i.e. sized and shaped) and aligned so as to provide for masking all of the light from the uniform and diffuse reference beam 90' for which the image thereof at the output focal plane 31.2' of the Fabry-Pérot interferometer 31' would otherwise overlap the corresponding image 114' of the scattered light signals 30.1', 30.2', 30.3'. Accordingly, within the output focal plane 31.2' of the Fabry-Pérot interferometer 31', the light within the region 326 of the image 114' of the of the scattered light signals 30.1', 30.2', 30.3' is exclusively from the associated scattered light 30 thereof, and light associated with the remaining region 328 of the output focal plane 31.2' is exclusively from the uniform and diffuse reference beam 90'.

For each of the embodiments illustrated in FIGS. 56a-58b, the separate arcuate fringes 49' of each of the scatter fringe patterns 47, 47.1, 47.2, 47.3 are separately processed by the data processor 53 in accordance with the multichannel variations of the eighth aspect of the range-imaging LIDAR system 24', $24^{viii.a-c}$ described hereinabove so as to provide for generating a set of one or more measures of line-of-sight relative wind velocity U, static temperature Temp, molecular counts MolCounts, aerosol counts AeroCounts, and background counts BackCounts at one or more selected nominal ranges R, or as a function of nominal range R, for each of the interaction regions 17, 17.1, 17.2, 17.3 within the associated fields-of-view 54 of the associated receive optics 32.

Referring to FIGS. 59a-e, there is illustrated a second embodiment of the eighth aspect of the range-imaging LIDAR system 24', $24^{viii''}$, that is the same as the second embodiment illustrated in FIGS. 55a-e except that the associated detection system 34 is in accordance with the first embodiment of the third aspect of the detection system 34.3 illustrated in FIGS. 29a and 49. Accordingly, the associated resulting first 330 and second 332 sets of fringes are processed in accordance with the methodology described hereinabove associated with FIGS. 32-46, 17 and 24-26.

Referring to FIGS. 60a-e, there is illustrated a third embodiment of the eighth aspect of the range-imaging LIDAR system 24', $24^{viii'''}$, that is substantially the same as the second embodiment of the eighth aspect of the range-imaging LIDAR system 24', $24^{viii''}$ described hereinabove, except that the third embodiment of the eighth aspect of the range-imaging LIDAR system 24', $24^{viii'''}$ incorporates second aspect of a mask 138, 138.2 comprising a programmable mask 138.2 that replaces the mask 138, 138.1 of the second embodiment of the eighth aspect of the range-imaging LIDAR system 24', $24^{viii'}$, wherein the programmable mask 138.2 comprises a second digital micromirror device (DMD) 334 and an associated second light block 336. The second digital micromirror device (DMD) 334 is oriented relative to the reference illuminator 324 and to the second beam splitter optic 136 so that when the associated micromirrors 144 of the second digital micromirror device (DMD) 334 are in a first pixel mirror rotational state 338, light from the uniform and diffuse reference beam 90' incident thereupon is reflected towards the second beam splitter optic 136 and is reflected from the partially reflective surface 136.1 of a second beam splitter optic 136 into to the Fabry-Pérot interferometer 31', and when the associated micromirrors 144 of the second digital micromirror device (DMD) 334 are in a second pixel mirror rotational state 340, light from the uniform and diffuse reference beam 90' incident thereupon is reflected towards the second light block 336 and is substantially absorbed thereby. Accordingly, the micromirrors 144 of the second digital micromirror device (DMD) 334 that would coincide in location with the opaque region 138' of the first aspect of the mask 138, 138.1 used in the first and second embodiments of the eighth aspect of the range-imaging LIDAR system 24', $24^{viii'}$, $24^{viii''}$ are set to the second pixel mirror rotational state 340 so as to block the corresponding portions of the uniform and diffuse reference beam 90', and the remaining micromirrors 144 of the second digital micromirror device (DMD) 334 are set to the first pixel mirror rotational state 338 so as to generate a masked reference beam 90'', 90.2'' that corresponds to the masked reference beam 90'', 90.1'' of the first and second embodiments of the eighth aspect of the range-imaging LIDAR system 24', $24^{viii'}$, $24^{viii''}$. Otherwise, the third embodiment of the eighth aspect of the range-imaging LIDAR system 24', $24^{viii'''}$ functions the same as the second embodiment of the eighth aspect of the range-imaging LIDAR system 24', $24^{viii''}$, with FIGS. 60b-e corresponding to FIGS. 59b-e, respectively.

Figure 61:
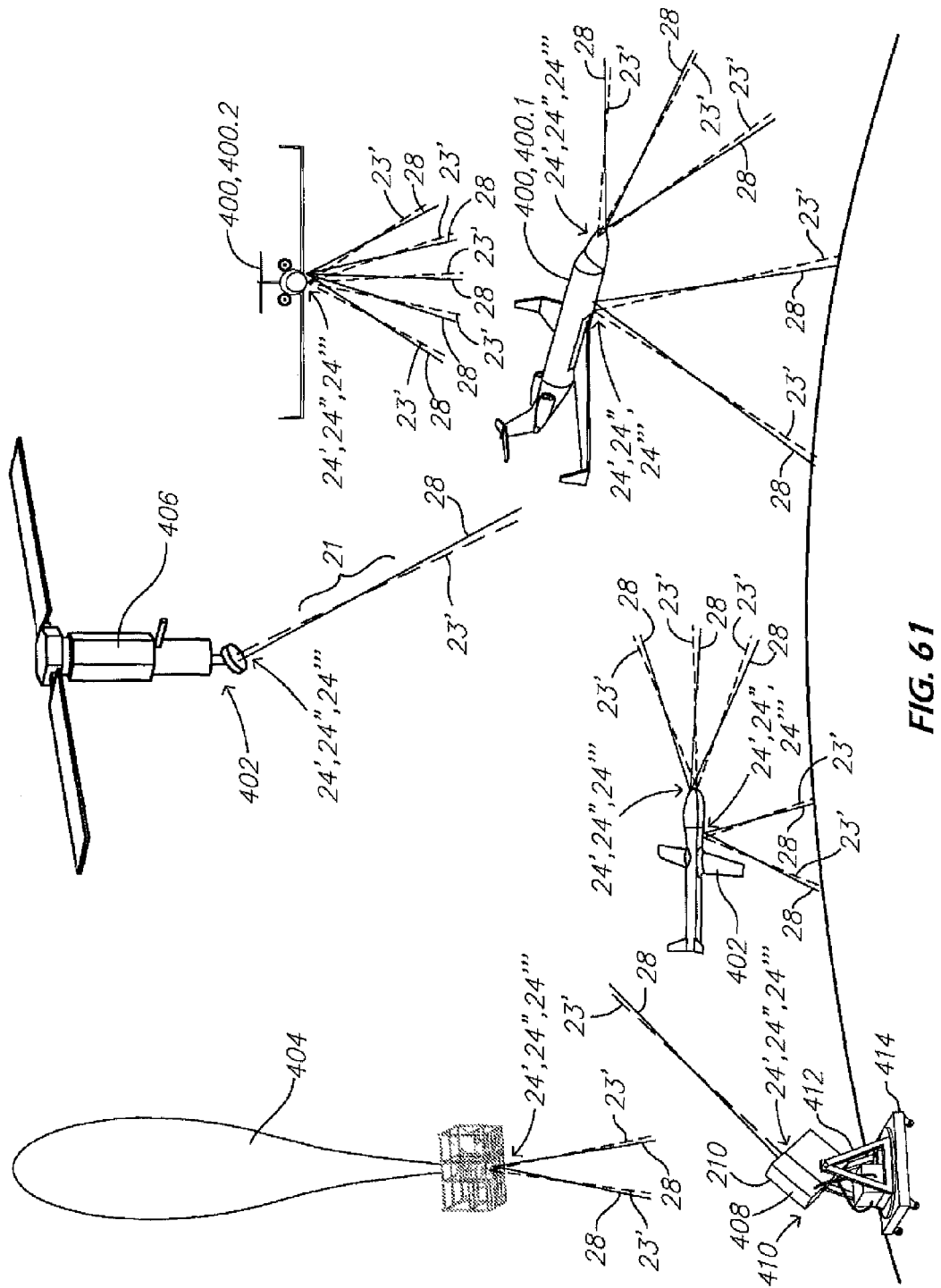
FIG. 61 illustrates various applications of a range-imaging LIDAR system.

Referring to FIG. 61, the various aspects of the range-imaging LIDAR system 24', $24^i$-$24^{viii}$ can be used in a variety of applications, including flight control or flight data monitoring, for example, for an aircraft 400 or UAV 402; or monitoring atmospheric or weather conditions from an aircraft 400.1, 400.2, UAV 402, balloon 404, satellite 406, or ground-based LIDAR system 408.

For example, the aircraft 400, 400.1 and UAV 402 illustrated in FIG. 61 each incorporate a range-imaging LIDAR system 24' that incorporates three lines-of-sight 23' so as to provide for measuring an associated relative wind vector in addition to other air data products, wherein each line-of-sight 23' is along the associated optic axis of the corresponding associated receive optics 32. Generally the range-imaging LIDAR system 24' can be adapted for airframe applications which, for example, might otherwise incorporate a pitot-static tube for measuring air speed. In addition to air speed, the range-imaging LIDAR system 24' provides for optically measuring, or calculating from optical measurements, a substantial quantity of air data products, and can be adapted to detect wind shear, wake vortices, clear air turbulence, and engine stall (unstart) conditions. Common air data products include, but are not limited to, Mach number, true airspeed, calibrated airspeed, vertical speed, static density, static air temperature, sideslip, angle of attack, pressure altitude, and dynamic pressure. The air data products can be used directly by an aircraft flight computer for flight control purposes. The range-imaging LIDAR system 24' provides for an airframe-independent design that can be flush-mounted to the skin of the airframe, e.g. without protrusions that otherwise might increase the airframe's radar cross section and drag, so as to provide for relatively low observability and drag. The range-imaging LIDAR system 24' can operate at substantial angles of attack. For example, a properly-configured range-imaging LIDAR system 24' can operate at a 90 degree angle of attack. The range-imaging LIDAR system 24' can be adapted to a variety of airframes, for example, including highly maneuverable aircraft and hoverable aircraft. The range-imaging LIDAR system 24' provides for an airframe-independent design that can be relatively inexpensive to calibrate, recalibrate or service.

As another example, the aircraft 400, 400.1, 400.2, UAV 402, and balloon 404 illustrated in FIG. 61 each incorporate an range-imaging LIDAR system 24' adapted with a plurality of lines-of-sight 23', so as to provide for substantially simultaneously measuring air data products from one or more interaction regions 17 along each of the associated lines-of-sight 23'. For example, the first aircraft 400.1 incorporates two lines-of-sight 23' distributed transversely with respect to the associated direction of travel thereof, and the second aircraft 400.2 incorporates five lines-of-sight 23' distributed transversely with respect to the associated direction of travel thereof, so as to provide for automatically acquiring a substantial amount of atmospheric data (e.g. density, temperature and wind velocity) that can be used for either monitoring or predicting weather, or for monitoring particular emissions into the atmosphere. In accordance with another embodiment, the UAV 402 is illustrated with lines-of-sight 23' substantially along the direction of travel thereof, which can provide for automatically acquiring a substantial amount of atmospheric data (e.g. density, temperature and wind velocity) that, for example, can be used for either monitoring or predicting weather dynamics, or for monitoring the dynamics of particulate emissions into the atmosphere. Generally, the orientation of the plurality of lines-of-sight 23' relative to the associated vehicle or the associated direction of travel thereof is not limiting, i.e. either other orientations or a combination of orientations may be used.

As yet another example, the satellite 406 and the ground-based LIDAR system 408 illustrated in FIG. 61 each incorporate an range-imaging LIDAR system 24' adapted with a line-of-sight 23' that is directed respectively downwards or upwards into the atmosphere so as to provide for measuring air data products from one or more interaction regions 17 along each of the associated one or more lines-of-sight 23', for example, so as to provide for automatically acquiring a substantial amount of atmospheric data (e.g. density, temperature and wind velocity) that can be used for either monitoring or predicting weather, or for monitoring particular emissions into the atmosphere.

As yet another example, the ground-based LIDAR system 408 and associated range-imaging LIDAR system 24' may be operatively associated with a gimbal mechanism 410 comprising an azimuthally-rotatable platform 412 which is adapted to pivotally support associated beam steering optics 210 so as to provide for an elevational rotation thereof relative a base 414 to which the azimuthally-rotatable platform 412 is operatively associated. Accordingly, the azimuthally-rotatable platform 412 is adapted to rotate relative to the base 414, for example, responsive to an associated motor drive system, so as to define an associated azimuth angle of the beam steering optics 210, and the beam steering optics 210 is adapted to rotate relative to the azimuthally-rotatable platform 412, for example, responsive to an associated motor drive system, so as to define an associated elevation angle of the beam steering optics 210.

Figure 62:
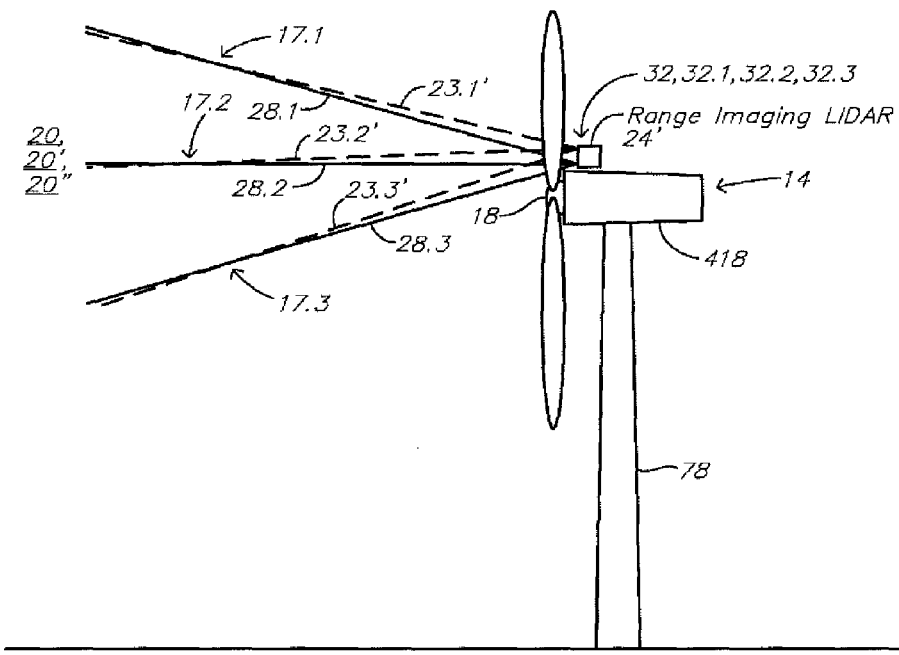
FIG. 62 illustrates a first embodiment a range-imaging LIDAR system in cooperation with a wind turbine.
Figure 63:
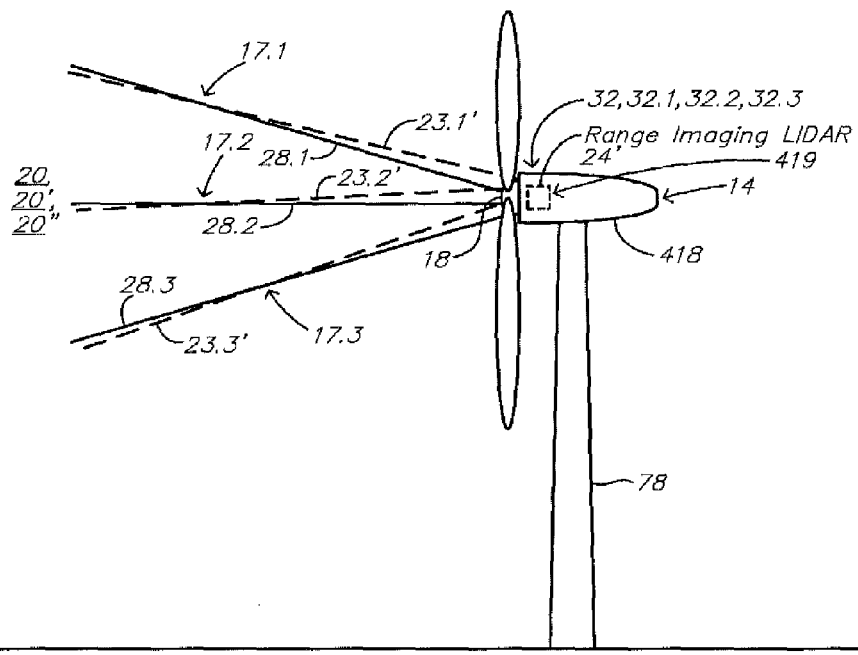
FIG. 63 illustrates a first embodiment a range-imaging LIDAR system in cooperation with a wind turbine.

Referring to FIGS. 62 and 63, a range-imaging LIDAR system 24' in accordance with any of the above-described aspects is illustrated in cooperation with an associated wind turbine 14 so as to provide for measuring atmospheric data 36 associated with the operation of the wind turbine 14, for example, a plurality of velocity, temperature or density measurements at a plurality of ranges R from the wind turbine 14, so as to provide for assessing both immediate and near term atmospheric conditions, the atmospheric data 36 of which can be used to control the wind turbine 14 so as to provide for optimizing the electrical power generated thereby or to prevent wind-caused damage thereto. For example, FIG. 62 illustrates a first embodiment for which the associated range-imaging LIDAR system 24' is attached to the housing or nacelle 418 of the wind turbine 14, and FIG. 62 illustrates a second embodiment wherein the associated range-imaging LIDAR system 24' is mounted withing the housing or nacelle 418 of the wind turbine 14 and is operative from within or through a rotatable portion of the wind turbine 14, for example, from within or through a hollow axle 419 of the wind turbine 14. For example, in both the first and second embodiments, the range-imaging LIDAR system 24' comprise a plurality of beams of light 28.1, 28.2, 28.3 in a corresponding plurality of different directions, and a corresponding plurality of receive optics 32, 32.1, 32.2, 32.3 with a corresponding plurality of lines-of-sight 23.1', 23.2', 23.3' that in cooperation with the corresponding associated beams of light 28.1, 28.2, 28.3 provide for a plurality of associated interaction regions 17.1, 17.2, 17.3, each spanning a range of ranges R, and which collectively provide for measuring a different regions of the atmosphere 20. In the first and second embodiments illustrated in FIGS. 62 and 63, the associated range-imaging LIDAR systems 24' are relatively fixed with respect to the wind turbine 14. Alternatively, the associated interaction regions 17.1, 17.2, 17.3 could be scanned within the atmosphere 20. For example, in the second embodiment of the range-imaging LIDAR systems 24 illustrated in FIG. 63, the associated beams of light 28.1, 28.2, 28.3 and associated receive optics 32, 32.1, 32.2, 32.3 could be configured to rotate with the wind turbine 14 and thereby scan the associated interaction regions 17.1, 17.2, 17.3 over one or more conical surface paths. Alternatively or additionally, a ground-based LIDAR system 408 could be used in cooperation with the wind turbine 14 to similarly provide associated atmospheric data 36.

Referring to FIG. 64, in accordance with a ninth aspect, a LIDAR system 24''', 241$^{ix}$ incorporated in a second aspect of an atmospheric measurement system 10$^{ii}$ incorporates a light source 11, for example, a laser 11', that generates a first beam of light 420, of substantially monochromatic light 13, which is split into a reference beam portion 90 and one or more second beams of light 28 by a beam splitter optic 92 in an optical head 422. The optical head 422 provides for directing the one or more second beams of light 28 into an atmosphere 20 within sight thereof, and further incorporates a corresponding one or more telescopes 32', each associated with one of the one or more second beams of light 28, wherein each of the telescopes 32' provides for receiving scattered light 30 that is scattered by the atmosphere 20 from a corresponding interaction region 17 therein defined by the intersection of the associated second beam of light 28 with an associated field-of-view 54 of the corresponding telescope 32'.

Figures 65A, 65B:
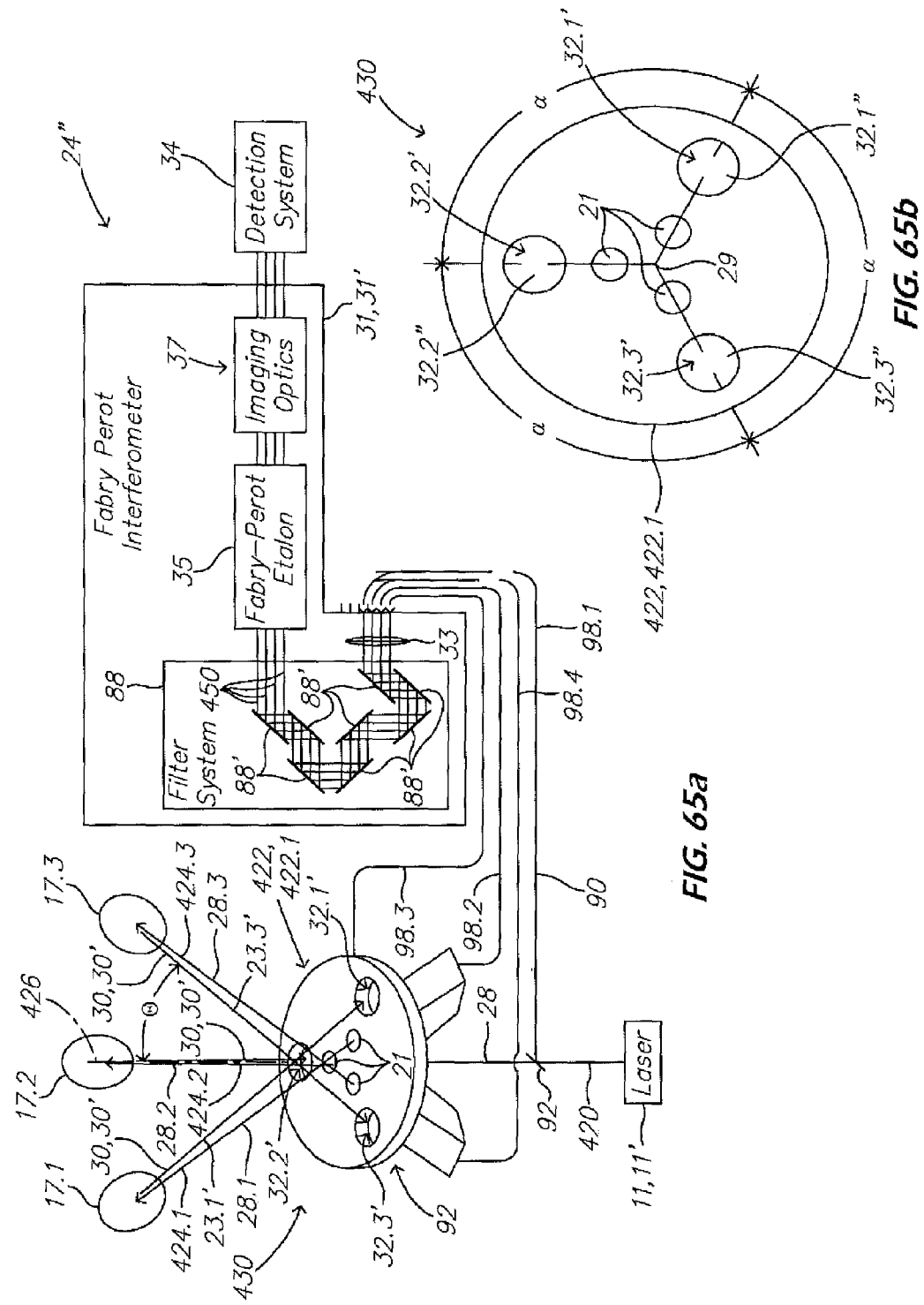
FIG. 65a illustrates several opto-mechanical elements of an optical air data system.
FIG. 65b illustrates a geometry of an embodiment of an optical head of a LIDAR system.

Referring to FIGS. 65a and 65b, the optical head 422 provides for directing the outgoing one or more second beams of light 28, as well as collecting the scattered signal, i.e. scattered light 30, utilizing the corresponding associated separate telescopes 32'. The optical head 422 can be custom-configured. For example, as illustrated in FIGS. 65a and 65b, proximate to the center of the optical head 422, the first beam of light 420 is divided using a beam splitter optic 92 into three separate second beams of light 28.1, 28.2 and 28.3, and then directed along three associated lines of projection 424: 424.1, 424.2 and 424.3, each spaced 120 degrees from each other and 30 degrees from a central axis 426. Scattered light signals 30' are then collected by each telescope 32' of an array of three telescopes 32' built into the optical head 422. Plural channels oriented in different directions provide for calculating a wind or airspeed vector from the associated scattered light signals 30', in addition to scalar properties of the atmosphere 20 in the associated interaction regions 17 along associated lines-of-sight 23'.

Each second beam of light 28 and its associated telescope 32' define a channel, and neither the number of channels, nor the geometry of the channels in relation to each other, is limiting. For example, although the embodiment illustrated in FIGS. 65a and 65b incorporates three channels, spaced 120 degrees apart from each other, other angles may be used to calculate a wind or airspeed vector. In addition, although three channels are necessary to calculate a wind or airspeed vector in 3-D space, the system may have extra redundant channels, dual channels to measure wind or airspeed in a particular plane, or single channels to measure the speed or properties of the atmosphere 20 along a specific line-of-sight 23' of the associated telescope 32'.

The LIDAR system 24" is a laser remote sensing instrument that senses within the volume of the interaction region 17. The range R to the interaction region 17 is defined by the geometry of the associated second beam of light 28 and the corresponding telescope 32' as embodied in the optical head 422. The range R within the interaction region 17 can optionally be further resolved with associated temporal range gating, or range-resolved imaging, of the associated scattered light signals 30' if desired or necessary for a particular application.

The LIDAR system 24" is responsive substantially only to scattering from the interaction region 17 where the field-of-view 54 of the detecting telescope 32' and the second beam of light 28 overlap, and the geometry of the optical head 422 can be adapted to locate the interaction region 17 at substantially any distance, e.g. near or far, from the optical head 422 provided there is sufficient scattered light 30 to be subsequently processed. For example, with the optical head 422 adapted to locate the interaction region 17 relatively far from the optical head 422, e.g. so as to be substantially not influenced by any turbulence proximate thereto, there would be substantially no signal from the associated near-field region 428 relatively proximate to the optical head 422 that might otherwise be affected, e.g. adversely, by a turbulent air stream therein.

Referring to FIGS. 64, 65a, 65b and 66, in accordance with a first aspect, each channel of the optical head 422.1 is adapted as a biaxial system 430 wherein, for a given channel, the associated second beam of light 28 and telescope 32' do not share a common axis. For example, at the optical head 422.1, the respective optic axes 25, 23 of the second beam of light 28 and telescope 32' are separated by an offset distance 432, and the optic axes 25, 23 are oriented at a relative angle 434 and directed so that the second beam of light 28 intersects the field-of-view 54 of the telescope 32' so as to define the associated interaction region 17. The length 436 of the interaction region 17 is defined between an entrance 438 where the second beam of light 28 enters the field-of-view 54 of the telescope 32', and an exit 440 where the second beam of light 28 exits the field-of-view 54 of the telescope 32', wherein the interaction region 17 is bounded by the second beam of light 28 between the associated entrance 438 and exit 440.

Figure 67:
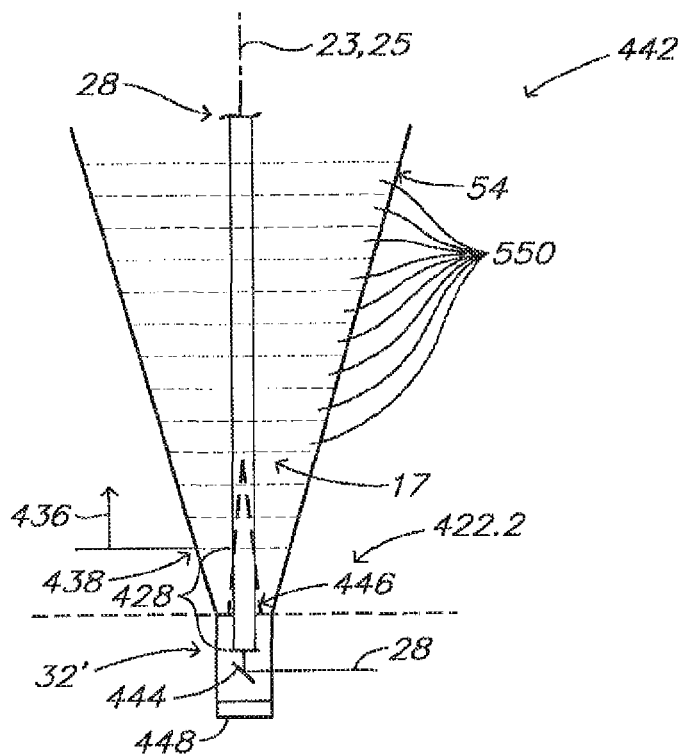
FIG. 67 illustrates an optical head of a coaxial system.

Referring to FIG. 67, in accordance with a second aspect, the optical head 422.2 is adapted as a coaxial system 442 wherein, for a given channel, the associated second beam of light 28 and telescope 32' substantially share a common optic axis 23, 25. For example, a mirror 444 located within a portion, e.g. a central portion, of the field-of-view 54 of the telescope 32'. The second beam of light 28 is reflected off the mirror 444, and the mirror 444 is oriented so as to substantially align the optic axis 25 of the second beam of light 28 reflected from the mirror 444, with the optic axis 23 of the telescope 32'. The mirror 444 partially obstructs the field-of-view 54 of the telescope 32', which provides for a near-field region 428 in the shadow 446 of the mirror 444 within which the second beam of light 28 is not visible to the telescope 32' and therefore outside the interaction region 17, thereby providing for substantially preventing any signal return from a prospective turbulent region proximate to the optical head 422. The interaction region 17 extends from an entrance 438 where the size of second beam of light 28 exceeds the size of the shadow 446 in the near-field region 428, and therebeyond the interaction region 17 remains within the field-of-view 54 of the telescope 32'. The interaction region 17 can then be tuned by adjusting the size of the central obstruction, the field-of-view 54 of the telescope 32', the divergence angle of the second beam of light 28, and by translating a final light-collecting element 448 of the telescope 32' along the optic axis 23 thereof so as to effectively change the field-of-view 54 of the telescope 32' and the focal plane for the final light-collecting element 448.

Each telescope 32' comprises an effective lens 32", and the scattered light signal 30' collected thereby is collected by the final light-collecting element 448 thereof into a fiber optic 98 that directs the returned photons to associated portions of a Fabry-Pérot interferometer 31' and an associated detection system 34 for processing thereby. The reference beam portion 90 from the laser 11' and beam splitter optic 92 is directed to a separate portion of the Fabry-Pérot interferometer 31' and an associated detection system 34 for simultaneous processing thereby.

The reference beam portion 90 and the scattered light signal 30' from the effective lens 32" are each collimated by a collimating lens 33 of the Fabry-Pérot interferometer 31' and then filtered by a filter system 88 which, for example, as illustrated in FIG. 65a, incorporates eight bandpass filter mirrors 88' having associated filter pass bands centered about the operating frequency of the laser 11'—e.g. about 266 nm for the above-described embodiment—which provides for filtering out associated background light. The filter system 88 exhibits high out-of-band rejection, as well as low in-band attenuation, and the bandwidth of the filter system 88 is sufficiently narrow so as to substantially filter or remove components of solar radiation or stray light in the collected scattered light signals 30', yet sufficiently broad so as to be substantially larger than the bandwidth of the thermally-broadened spectrum in combination with the largest expected associated Doppler shift. For example, in one embodiment, the filter system 88 is adapted so as to provide for maximum filtering of light frequencies that are outside the frequency band of interest, e.g. greater than about 2 nanometers above or below the nominal center frequency of the first beam of light 420.

Referring to FIGS. 64, 65*a*, 68, 69*a* and 69*b* the light signals 450 from the filter system 88 are input to a Fabry-Pérot etalon 35 of the Fabry-Pérot interferometer 31', which provides for generating a fringe pattern 452 responsive to the optical frequency of the associated light signals 450, which optical frequency can exhibit a Doppler shift responsive to a relative velocity of the atmosphere 20 within the interaction region 17 from which the associated scattered light 30 is scattered. The Fabry-Pérot etalon 35 of the Fabry-Pérot interferometer 31' comprises first 41 and second 43 partially-reflective surfaces—either of separate planar optical windows 55 or of a corresponding solid optical element 61—which are parallel to one another and separated by a fixed gap 45, and located between the collimating lens 33 and associated imaging optics 37. Light 454 at a front focal plane 33.1 of the collimating lens 33 is substantially collimated thereby, and the angles at which the light 454 is passed through the Fabry-Pérot etalon 35 is dependent upon the optical frequency of the light 454, which, referring to FIG. 69*a*, becomes imaged as a circular fringe pattern 65—also known as Haidinger fringes—comprising a plurality of concentric circular fringes 65' in the rear focal plane 37.2 of the imaging optics 37. Referring to FIG. 69*a*, for a fully-illuminated Fabry-Pérot etalon 35, the resulting circular fringe pattern 65 is in the form of closed concentric circles centered about the optic axis 39 of the imaging optics 37.

Figure 68:
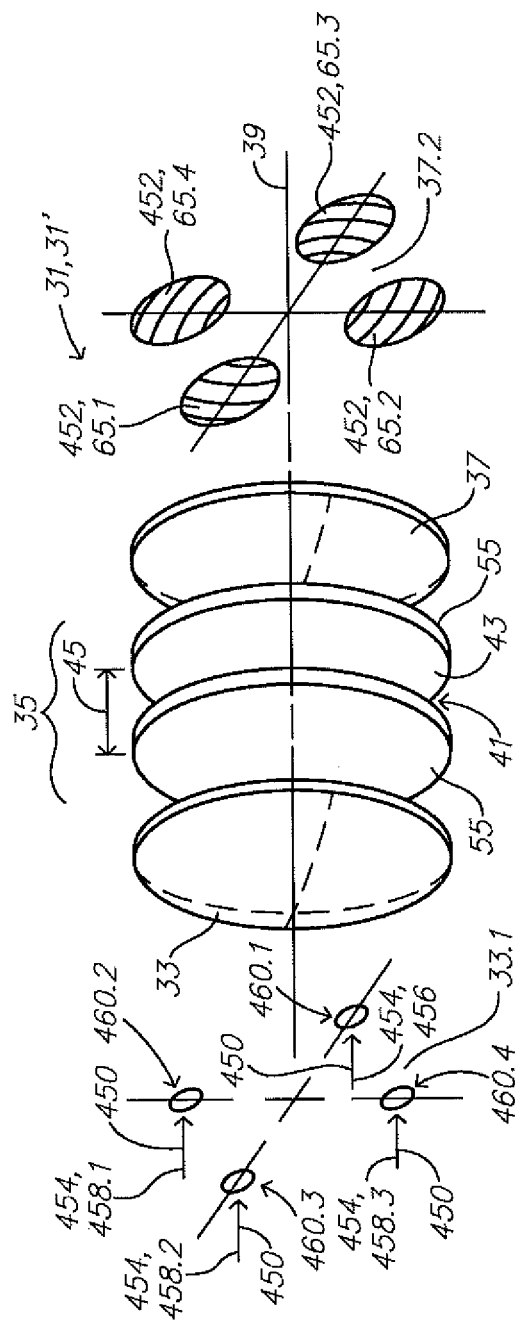
FIG. 68 illustrates an isometric view of a Fabry-Pérot interferometer.

Referring to FIG. 68, the LIDAR system 24" provides for an efficient use of the Fabry-Pérot etalon 35 by simultaneously processing a plurality of different channels of light 454 with a single, common Fabry-Pérot etalon 35. In one embodiment, a single Fabry-Pérot etalon 35 is used with four channels of light 454, i.e. a reference channel 456 from the reference beam portion 90, and three scatter signal channels 458.1, 458.2 and 458.3 from the associated three effective lenses 32.1", 32.2" and 32.3" associated with each of three telescopes 32.1', 32.2' and 32.3' having respectively three different lines-of-sight 23.1', 23.2' and 23.3'. Referring also to FIG. 65*a*, respective fiber optics 98.1, 98.2, 98.3 and 98.4 receive light from the reference beam portion 90 and from each of the effective lenses 32.1", 32.2" and 32.3", respectively, and illuminate corresponding portions of the Fabry-Pérot etalon 35 from respective off-axis locations 460.1, 460.2, 460.3 and 460.4 in the focal plane 33.1 of the collimating lens 33, producing associated images of partial circular fringe patterns 65.1, 65.2, 65.3 and 65.4, for example, as illustrated in FIGS. 68 and 69*b*.

The off-axis illumination of the Fabry-Pérot etalon 35 provides for increasing the geometric etendue of the LIDAR system 24" than would result otherwise, wherein geometric etendue G characterizes the ability of an optical system to accept light. Geometric etendue G is defined as a product of the area A of the emitting source and the solid angle $\Omega$ into which the light therefrom propagates, i.e. $(G=A*\Omega)$. Geometric etendue G is a constant of the optical system, and is determined by the least optimized portion thereof. For a fixed divergence and aperture size of the associated fiber optic 98, for a given value of geometric etendue G, the area A of the emitting source (i.e. that of the fiber optic 98)—and the associated diameter of the optical system—may be reduced by increasing the solid angle $\Omega$, i.e. the divergence of the associated optical system, so as to provide for reducing the size of the associated optical system without sacrificing performance. Alternatively, for a given area A and associated diameter of the optical system, the geometric etendue G of the optical system may be increased by increasing the solid angle $\Omega$. For a Fabry-Pérot interferometer 31', increasing the angular divergence, i.e. solid angle $\Omega$, of the associated optical system provides for a greater fraction and/or number of circular fringes 65'. The LIDAR system 24" simultaneously processes a reference channel 456 and one or more scatter signal channels 458.1, 458.2 and 458.3 using a common Fabry-Pérot etalon 35, each channel 456, 458.1, 458.2 and 458.3 occupying a separate portion of the Fabry-Pérot etalon 35, the collection of channels 456, 458.1, 458.2 and 458.3 thereby necessitating a larger-diameter Fabry-Pérot etalon 35 than would be required otherwise if only a single channel 456, 458.1, 458.2 or 458.3 were to be processed thereby. Accordingly associated respective off-axis locations 460.1, 460.2, 460.3 and 460.4 of the respective fiber optics 98.1, 98.2, 98.3 and 98.4 provides for both simultaneously accommodating the plurality of fiber optics 98.1, 98.2, 98.3 and 98.4 input to the common Fabry-Pérot etalon 35, and provides for increasing the associated angular divergence through the optical system which provides for either relatively, increasing the geometric etendue G and associated light gathering capability of the associated optical system for a given-sized optical system, or for relatively decreasing the size (i.e. diameter) of the optical system for a given geometric etendue G thereof.

Signals from the scatter signal channel 458.1, 458.2 or 458.3 for each of the associated interaction regions 17 are substantially simultaneously processed together with a signal from the reference channel 456 so as to provide for calibrating, and maintaining the calibration of, the LIDAR system 24", and so as to provide for determining the associated air data products such as the speed, temperature and density of the atmosphere 20. This provides for an inherent self-calibration of the associated measurements or quantities derived therefrom. If wavelength drift of the first beam of light 420 is not otherwise accounted for in the data, then errors can arise when making a measurement of the Doppler shift and resulting wavelength shift of the scatter signal channels 458.1, 458.2 and 458.3. The LIDAR system 24" provides for automatically compensating for wavelength drift of the first beam of light 420 from the data because each measurement from a scatter signal channel 458.1, 458.2 or 458.3 is corrected using a corresponding measurement from the reference channel 456 associated with the reference beam portion 90.

Referring to FIG. 70, in one embodiment, a quad circle-to-line interferometer optic 462 (quad-CLIO 462) is used to transform the four channels 456, 458.1, 458.2 and 458.3 of circular fringe patterns 65.1, 65.2, 65.3 and 65.4 into four associated linear fringe patterns 464.1, 464.2, 464.3 and 464.4, forming a cross pattern 466. The quad-CLIO 462 comprises four circle-to-line interferometer optic 468 (CLIO 468) elements, each associated with a different one of the four channels 456, 458.1, 458.2 and 458.3 of circular fringe patterns 65.1, 65.2, 65.3 and 65.4.

Figure 72:
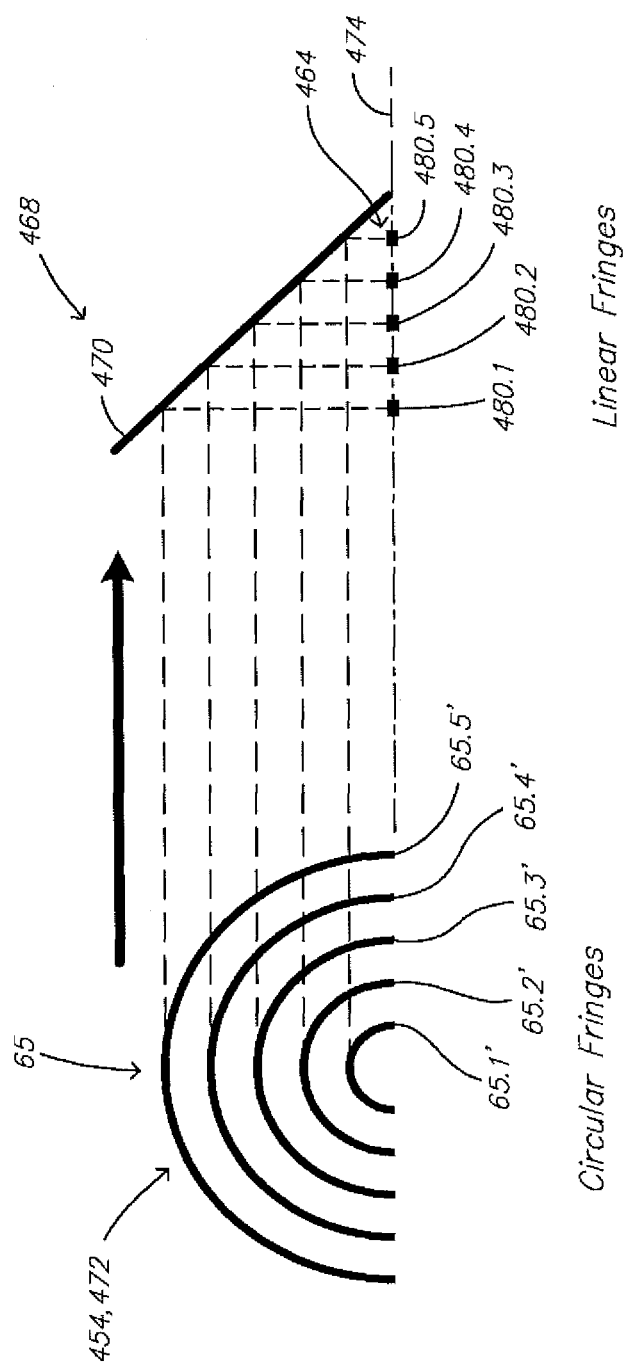
FIG. 72 illustrates the operation of a circle-to-line interferometer optic (CLIO)
Figure 76:
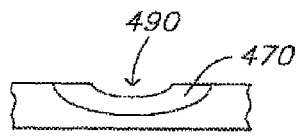
FIG. 76 illustrates a fragmentary end view of a concave conical reflector on a face of the first pyramidal shaped optic element illustrated in FIGS. 73 and 74, wherein the direction of the end view is substantially parallel to the face of the first pyramidal shaped optic element.
Figure 73:
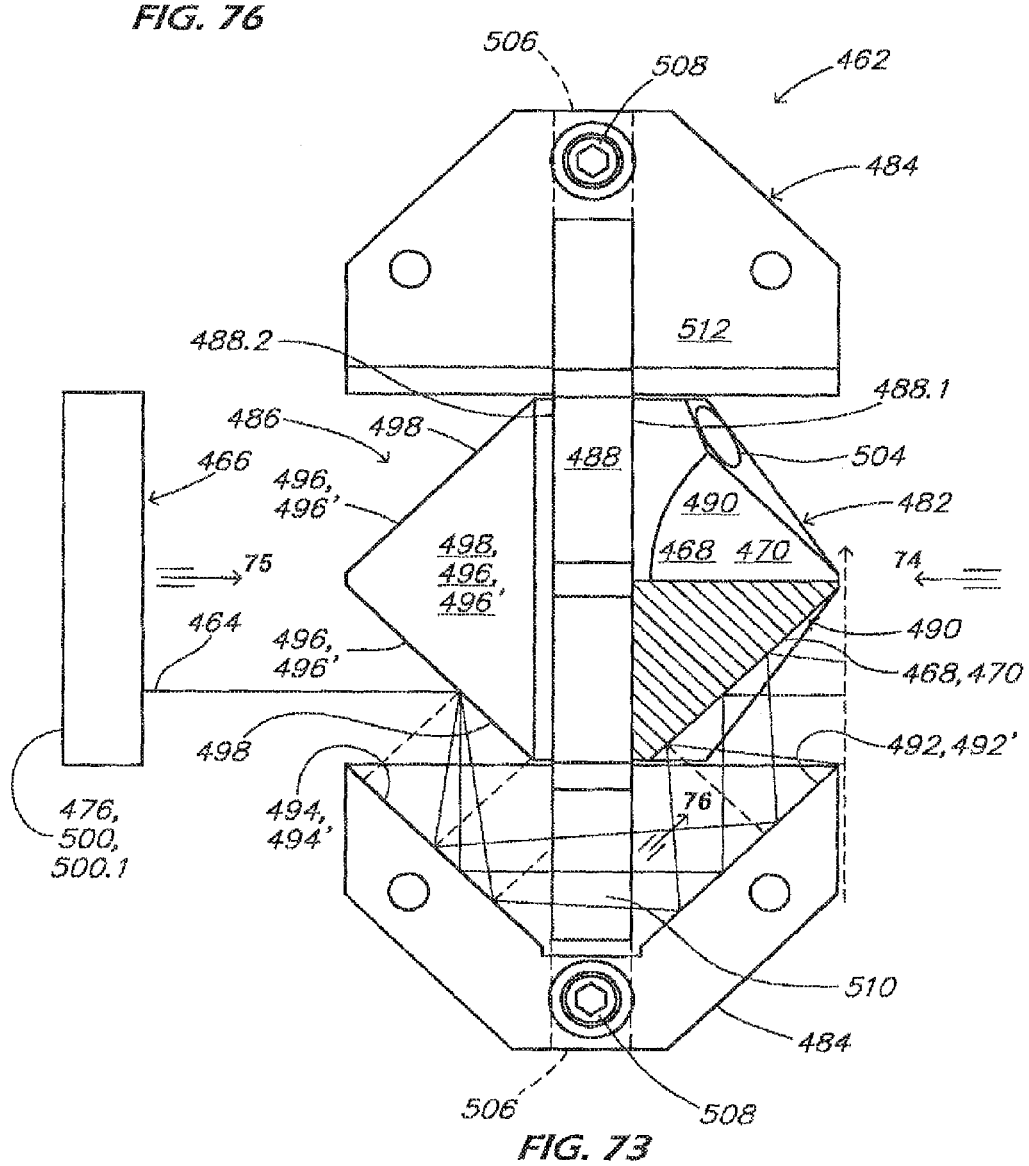
FIG. 73 illustrates a side view of a quad-CLIO element and an associated detector.
Figure 74:
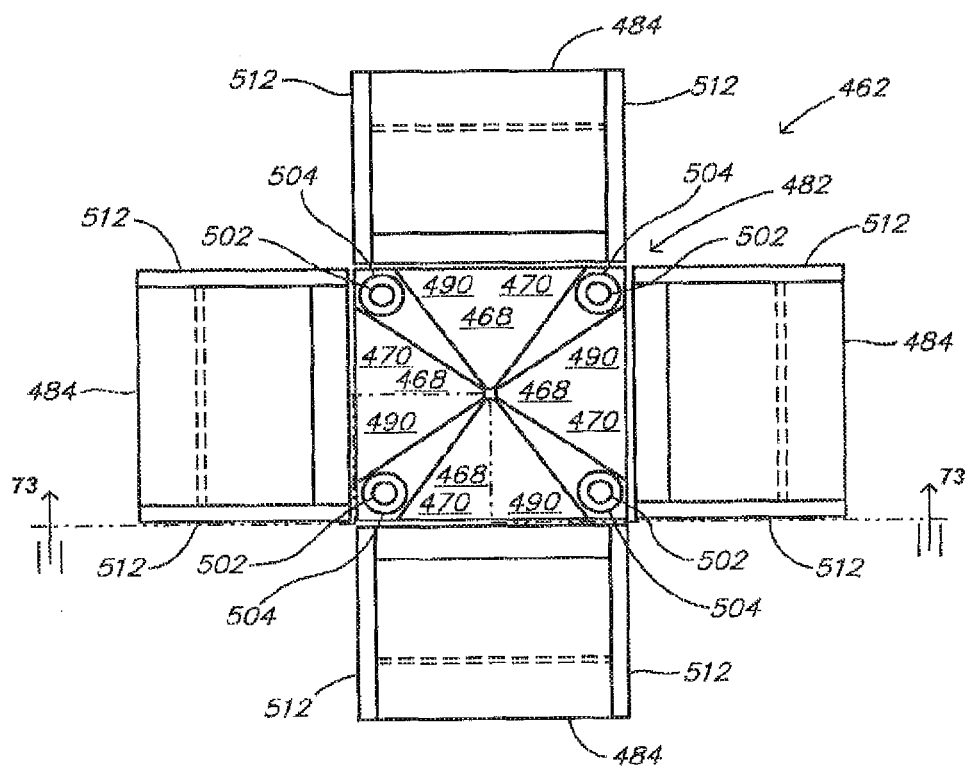
FIG. 74 illustrates a plan view of the quad-CLIO element illustrated in FIG. 73, viewed from the side of an associated first pyramidal shaped optic element.
Figure 75:
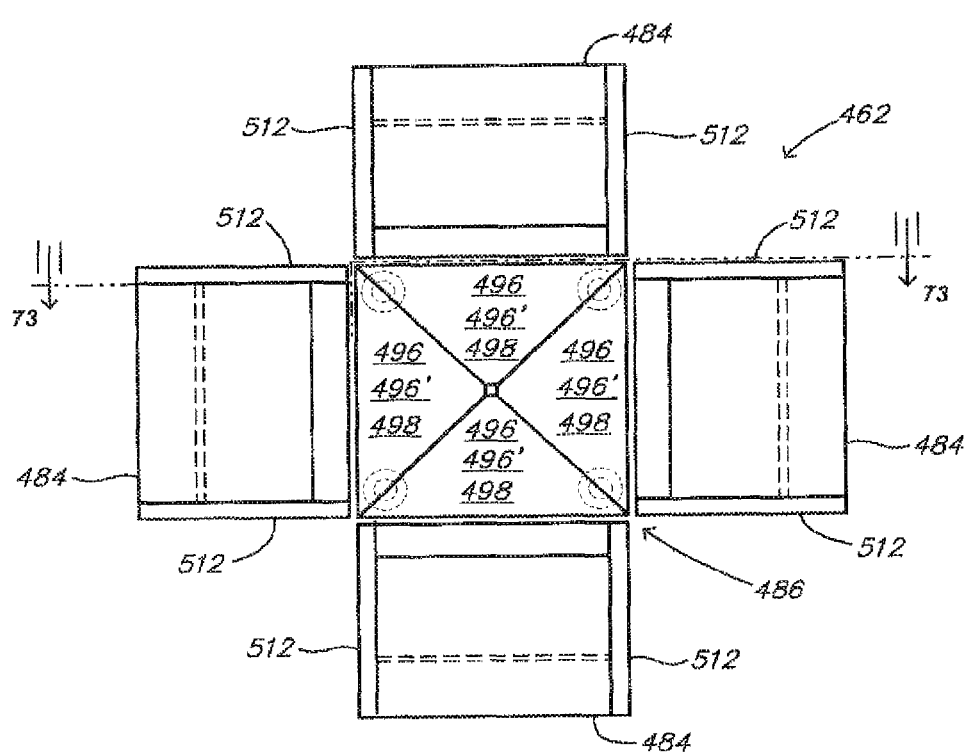
FIG. 75 illustrates a plan view of the quad-CLIO element illustrated in FIG. 73, viewed from the side of an associated second pyramidal shaped optic element.

Referring to FIG. 71, a circle-to-line interferometer optic 468 (CLIO 468), described in U.S. Pat. No. 4,893,003, the entire content of which is incorporated herein by reference, comprises a concave conical reflector 470, the surface of which is a conical segment constituting a section of the underlying conical surface. Electromagnetic energy 472 from the Fabry-Pérot interferometer 31'—constituting the circular fringe pattern 65 to be transformed—is propagated substantially parallel to the conical axis 474 of the underlying conical surface, and is reflected and focused by the concave conical reflector 470 substantially onto a linear detector 476 substantially along or proximate to the conical axis 474. In one embodiment, the apex 478 of the underlying conical surface is situated where the conical axis 474 intersects the rear focal plane 37.2 of the circular fringe pattern 65. Referring to FIG. 72, the CLIO 468 transforms each circular fringe 65', e.g. 65.1', 65.2', 65.3', 65.4' and 65.5', into a corresponding spot 480, e.g. 480.1, 480.2, 480.3, 480.4 and 480.5 of an associated linear fringe pattern 464, thereby concentrating the associated electromagnetic energy 472 so as to improve the associated signal to noise ratio of the associated detection process by the associated linear detector 476. Accordingly, each CLIO 468 provides for transforming a circular fringe pattern 65 into a corresponding linear fringe pattern 464 substantially along the associated conical axis 474 so as to provide for using a linear detector 476 array—for example, a charge-coupled device (CCD), e.g. as used in spectroscopic analysis—to detect the light of the linear fringe pattern 464.

Referring to FIGS. 73-76, for example, in one embodiment, the quad-CLIO 462, comprises a first pyramidal shaped optic element 482 which cooperates with a plurality of corner reflector optic elements 484, which in turn cooperate with a second pyramidal shaped optic element 486, all of which are operatively coupled to an associated base plate 488. Each side face 490 of the first pyramidal shaped optic element 482 incorporates an associated concave conical reflector 470 adapted to receive an associated circular fringe pattern 65.1, 65.2, 65.3 and 65.4 from the Fabry-Pérot interferometer 31', wherein different concave conical reflectors 470 are adapted to receive different respective circular fringe patterns 65.1, 65.2, 65.3 and 65.4. A light signal 450 of the circular fringe pattern 65.1, 65.2, 65.3, 65.4 is reflected from the corresponding concave conical reflector 470 onto a first reflective surface 492 of a corresponding corner reflector optic element 484, and then reflected therefrom onto a second reflective surface 494 of the corresponding corner reflector optic element 484, and then reflected therefrom onto a third reflective surface 496 on a side face 498 of the second pyramidal shaped optic element 486, and finally reflected therefrom onto an associated detector 500, for example, an associated array of linear detectors 476. For example, in one embodiment, the first 492, second 494 and third 496 reflective surfaces comprise corresponding planar reflective surfaces 492, 494' and 496'. The first 482 and second 486 pyramidal shaped optic elements are secured to and aligned with one another on opposite faces 488.1, 488.2 of the base plate 488, for example, with fasteners 502, e.g. machine screws, extending through associated counterbores 504 in the first pyramidal shaped optic element 482, through the base plate 488, and into the second pyramidal shaped optic element 486. The corner reflector optic elements 484 are fastened to tongue portions 506 of the base plate 488 with associated fasteners 508, which provide for a rotational adjustment of the corner reflector optic elements 484. The base plate 488 is adapted with a plurality of openings 510 so as to provide for optical communication between the first 492 and second 494 reflective surfaces. Each corner reflector optic element 484 incorporates a pair of side plates 512 which provide for shielding stray light and for improved structural integrity. In another embodiment, one or more corner reflector optic elements 484 could be replaced with separate elements for each of the associated first 492 and second 494 reflective surfaces. The first 482 and second 486 pyramidal shaped optic elements and the corner reflector optic elements 484 can be constructed from a variety of materials—including, but not limited to, aluminum, stainless steel, copper-nickel alloy, glass or fused quartz—that can be adapted to incorporate associated reflective surfaces or coatings.

Accordingly, the quad-CLIO 462 comprises a tele-kaleidoscope having a predetermined arrangement of mirrors adapted to provide for compressing the azimuthal angular extent of the partial circular fringe patterns 65.1, 65.2, 65.3 and 65.4 into associated linear fringe patterns 464.1, 464.2, 464.3 and 464.4 forming a cross pattern 466. The circular fringe patterns 65.1, 65.2, 65.3 and 65.4 generated by the Fabry-Pérot interferometer 31' are transformed by the quad-CLIO 462 into a linear cross pattern 466 which is then imaged onto a detector 500. For example, the detector 500 may comprise one or more charge-coupled devices (CCD), i.e. a CCD detector 500.1, a set of linear arrays, one or more photomultiplier tubes, a plurality of avalanche photo diodes, or any other multi-element detection device that converts photons to electrons. For example, a CCD detector 500.1 can be adapted to be low-light sensitive, and can provide for provide a low noise image readout. A quad-CLIO 462, although not essential, can provide for enhancing the associated signal to noise ratio, and by providing for detection using readily-available linear-based detectors such as a linear array or CCD, can provide for improving the overall efficiency and simplicity of the signal detection process.

Figures 77A, 77B:
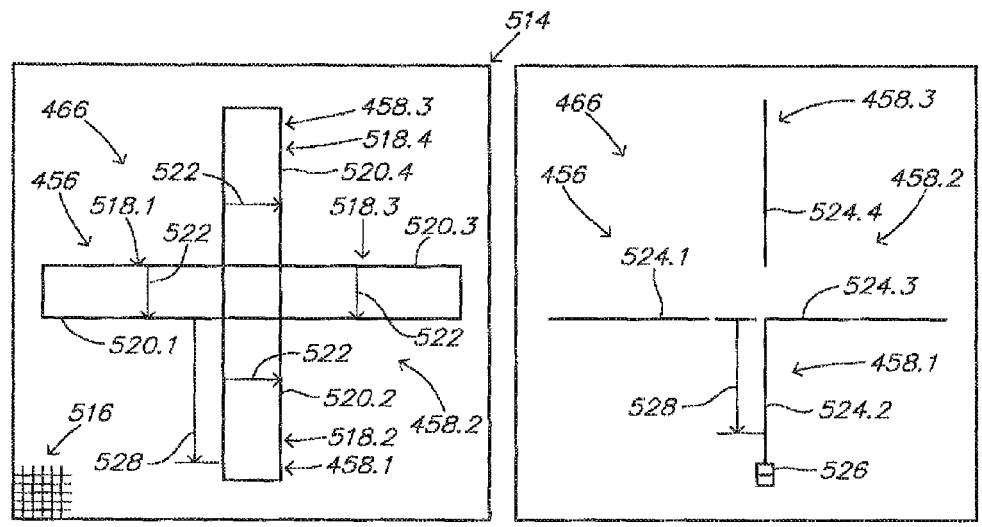
FIGS. 77a and 77b illustrate a cross-binning process operating on a cross-pattern from a quad-CLIO element.

Referring to FIGS. 77a and 77b, the detector 500 generates an image signal 514 of the cross pattern 466 transformed by the quad-CLIO 462, wherein the image signal 514 comprises an array of pixels 516. The efficiency of the detection process can be increased by binning the image signal 514 during the associated detection process, wherein the plurality pixel values of a plurality of adjacent pixels 516 are replaced with a single sum of the plurality of pixel values. For example, for a Cartesian array of pixels 516, generally the binning process can operate in either of the associated Cartesian directions, or in both directions. For example, binning is a standard process for use with CCD devices wherein pixel charges are summed together on chip, so as to provide for reducing the relative amount of read-noise associated with the analog-to-digital conversion (A/D) process that occurs when pixel charges are read off of the CCD detector 500.1, for example, by summing a plurality of rows of pixels 516 together so as to limit the number of rows or columns undergoing an A/D conversion.

Referring to FIGS. 77a and 77b, in accordance with a first embodiment, a LIDAR system 24" incorporates a quad-CLIO 462 and a custom-binning pattern is utilized to efficiently detect the associated cross pattern 466, using a cross-binning process that provides for multi-axis binning within selected sub-regions of interest on the CCD detector 500.1. For the cross-binning algorithm, respective regions of interest 518.1, 518.2, 518.3 and 518.4 are defined for each respective channel 456, 458.1, 458.2 and 458.3 comprising one leg 520.1, 520.2, 520.3, 520.4 of the associated cross pattern 466. Photo-electric generated charges collected on the CCD detector 500.1 within each region of interest 518.1, 518.2, 518.3, 518.4 are binned, i.e. summed, by the CCD detector 500.1 for each channel 456, 458.1, 458.2 and 458.3 along the width 522 of the corresponding leg 520.1, 520.2, 520.3, 520.4 of the associated cross pattern 466, so as to compress the array of pixels 516 associated with each leg 520.1, 520.2, 520.3, 520.4 of the associated cross pattern 466 into a corresponding line of binned pixels 524.1, 524.2, 524.3, 524.4 of the same length as the corresponding leg 520.1, 520.2, 520.3, 520.4, but only one binned pixel 526 wide, with the value of each binned pixel 526 equal to the sum of the values of the corresponding pixels 516 across the corresponding leg 520.1, 520.2, 520.3, 520.4 at a position 528 along the leg 520.1, 520.2, 520.3, 520.4 corresponding to the position 528 of the corresponding binned pixel 526 along the corresponding line of binned pixels 524.1, 524.2, 524.3, 524.4, thereby providing for reducing the overall read noise associated with reading the lines of binned pixels 524.1, 524.2, 524.3, 524.4 relative to that associated with reading a greater number of pixels 516 in the original legs 520.1, 520.2, 520.3, 520.4 of the associated cross pattern 466, because of the reduction in the number of pixels being read and the greater value of each binned pixel 526 relative to that of the corresponding pixels 516 of the original image signal 514.

Figures 78A, 78B:
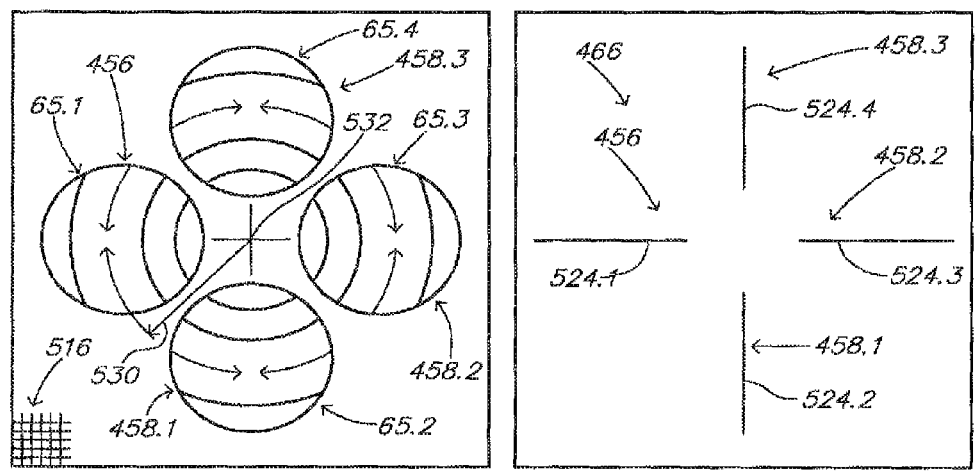
FIGS. 78a and 78b illustrate a circular process operating on a fringe pattern from a Fabry-Pérot interferometer.

Referring to FIGS. 78a and 78b, in accordance with a second embodiment, the LIDAR system 24" is adapted so as to provide for directly processing the associated circular fringe patterns 65.1, 65.2, 65.3 and 65.4 from the Fabry-Pérot interferometer 31' without utilizing an associated quad-CLIO 462, whereby the circular fringe patterns 65.1, 65.2, 65.3 and 65.4 are imaged directly upon the associated CCD detector 500.1, and a circular binning algorithm then, sums all pixels 516 at a particular radius 530 from the common center 532 of the circular fringe patterns 65.1, 65.2, 65.3 and 65.4. For example, the circular binning algorithm could be implemented by a data processor 53—for example, in software therein—operatively coupled to the associated CCD detector 500.1, or to an associated plurality of CCD detectors 500.1, each adapted to detect one or more of the associated circular fringe patterns 65.1, 65.2, 65.3 and 65.4. After identifying the center 532 of the circular fringe patterns 65.1, 65.2, 65.3 and 65.4, the circular binning algorithm sums up the CCD charges (i.e. pixel values) for each pixel 516 at a particular radius from the center 532, for a particular circular fringe pattern 65.1, 65.2, 65.3, 65.4, for each of the circular fringe patterns 65.1, 65.2, 65.3 and 65.4, so as to provide a respective associated line of binned pixels 524.1, 524.2, 524.3, 524.4 for each of the respective circular fringe patterns 65.1, 65.2, 65.3 and 65.4. Compared with the first embodiment operative with a quad-CLIO 462 and an associated cross-binning process operative within the CCD detectors 500.1, wherein the charges for pixels 516 to be binned are summed before readout of the resulting corresponding binned pixel 526, the circular binning process of the second embodiment provides for reading the pixels 516 before binning, whereby each pixel 516 is read from the CCD detector 500.1 and converted by an A/D conversion process, which results in a greater amount of overall read noise than would occur with the first embodiment, although the overall noise level can be kept to within acceptable levels by using a relatively low-noise CCD detector 500.1. The ratio of signal to read noise can be enhanced by increasing the exposure time of the CCD detector 500.1 between read cycles, although at the cost of reduced dynamic frequency response of the associated resulting air data products.

Figure 79:
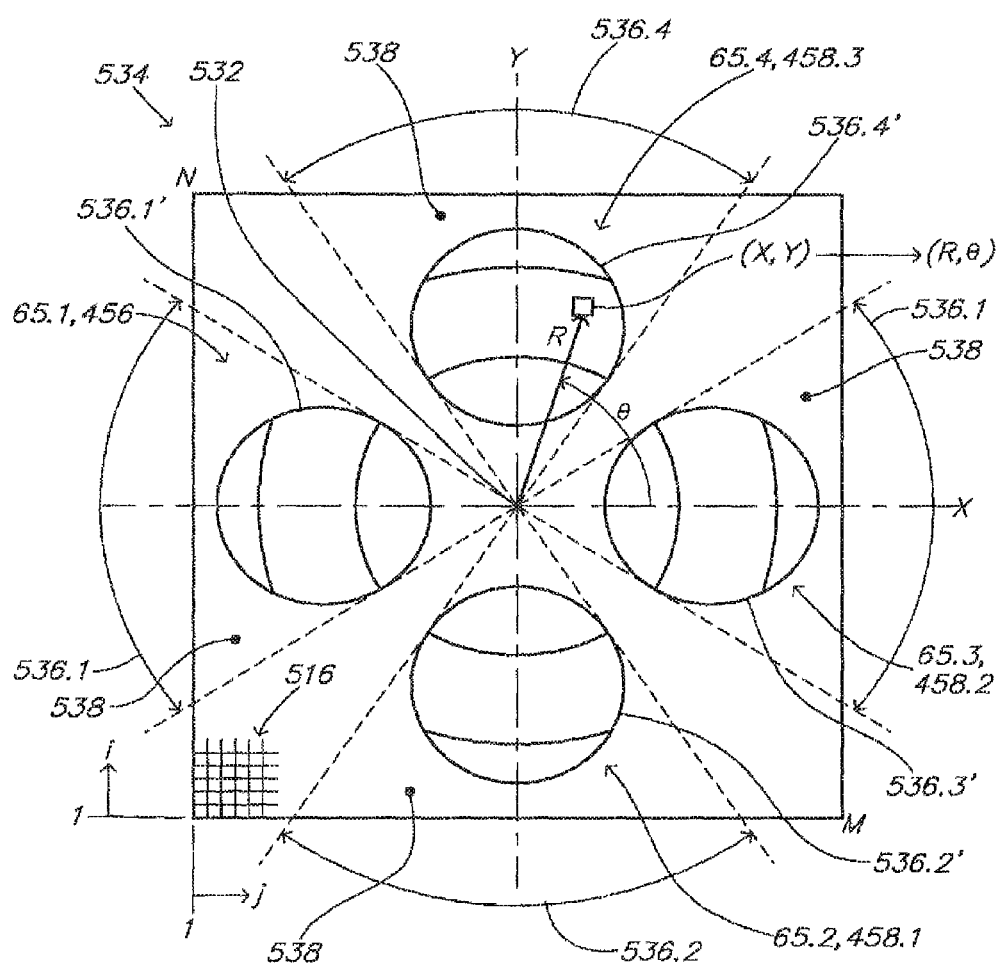
FIG. 79 illustrates an image of a set of circular fringe patterns and regions of interest associated with a circular binning process.

Referring to FIG. 79, an image 534 of a set of circular fringe patterns 65.1, 65.2, 65.3 and 65.4 comprises an array of N rows by M columns of pixels 516, each of which is captured by an associated detector 500 and stored in a memory 124 of the associated data processor 53 of the LIDAR system 24". The image 534 comprises four regions of interest (ROI) 536.1, 536.2, 536.3 and 536.4, each comprising a segment 538 containing an associated circular fringe pattern 65.1, 65.2, 65.3 and 65.4, and centered about the common center 532 of the circular fringe patterns 65.1, 65.2, 65.3 and 65.4, wherein the center 532 of the circular fringe patterns 65.1, 65.2, 65.3 and 65.4 is determined upon initial calibration or subsequent recalibration of the associated LIDAR system 24", and is assumed to be stationary during the operation thereof. For example, the center 532 may be determined by recording a substantial number, e.g. thousands, of circular fringe patterns 65.1, 65.2, 65.3 and 65.4 and determining the location of the center 532—by either iteration starting with an initial guess, or least squares or correlation with the coordinates of the center 532 as unknowns to be determined—that provides for a best fit of the recorded circular fringe patterns 65.1, 65.2, 65.3 and 65.4 with a corresponding circular model thereof centered at the center 532 of the circular fringe patterns 65.1, 65.2, 65.3 and 65.4.

Referring to FIGS. 80-83, in accordance with several other embodiments, the LIDAR system 24" comprises a laser 11' that generates a first beam of light 420 which is divided into a reference beam portion 90 and a second beam of light 28 by a first beam splitter optic 92.1. The second beam of light 28 is directed into an optical head 422 incorporating associated beam steering optics 210 which divide the second beam of light 28 into a plurality of second beams of light 28.1, 28.2 and 28.3, each directed in a different direction, e.g. line of projection 424: 424.1, 424.2, 424.3, into the atmosphere 20. For example, the beam steering optics 210 comprise second 92.2 and third 92.3 beam splitter optics, wherein the second beam splitter optic 92.2 reflects the first portion 28.1, e.g. about one third, of the second beam of light 28, and transmits a fourth portion 28.4, e.g. about two thirds, thereof; and the third beam splitter optic 92.3 transmits the second portion 28.2, e.g. about one half, of the fourth portion 28.4 of the second beam of light 28, and reflects the remaining third portion 28.3 of the second beam of light 28. The first portion 28.1 of the second beam of light 28 reflected from the second beam splitter optic 92.2 is directed along a first line of projection 424.1 by a first mirror 540, e.g. a front-surface mirror, the second portion 28.2 of the second beam of light 28 is transmitted through the third beam splitter optic 92.3 along a second line of projection 424.2, and the third portion 28.3 of the second beam of light 28 reflected from the third beam splitter optic 92.3 is directed along a third line of projection 424.3 by a second mirror 542, e.g. a front-surface mirror. For example, the associated front-surface first 540 and second 542 mirrors may each incorporate dielectric or metallic coatings (e.g. silver), or may comprise a long-wave-pass dichroic beam splitter optic. The optical head 422 further incorporates a plurality of respective telescopes 32.1', 32.2' and 32.3' each associated with a different of the respective second beams of light 28.1, 28.2 and 28.3 directed along or in cooperation with respective lines of projection 424.1, 424.2 and 424.3, each aimed at an associated respective interaction region 17.1, 17.2, 17.3 of the respective second beams of light 28.1, 28.2 and 28.3 projected into the atmosphere 20, and each adapted to collect the associated scattered light signals 30' from each of the respective interaction regions 17.1, 17.2, 17.3.

Each telescope 32' comprises an effective lens 32", and the scattered light signal 30' collected thereby is collected by the final light-collecting element 448 thereof into a corresponding fiber optic 98.2, 98.3, 98.4 that directs the returned photons to associated portions of a Fabry-Pérot interferometer 31' and an associated detection system 34 for processing thereby. The reference beam portion 90 from the laser 11' and beam splitter optic 92 is separately collected by a separate light-collecting element 544 into a fiber optic 98.1 directed to a separate portion of the Fabry-Pérot interferometer 31' and an associated detection system 34 for simultaneous processing thereby. For example, the final light-collecting elements 448 of the telescopes 32.1', 32.2' and 32.3', and the light-collecting element 544 for collecting the reference beam portion 90, may comprise either a GRIN lens or an aspheric lens. In one embodiment, the associated fibers of the four fiber optics 98.1, 98.2, 98.3 and 98.4 are bundled together in a fiber-optic bundle 99 which operatively couples the laser 11' and optical head 422 to the Fabry-Pérot interferometer 31'. The use of fiber optics 98.1, 98.2, 98.3 and 98.4 and/or a fiber-optic bundle 99 provides for simplifying the alignment of the Fabry-Pérot interferometer 31' with the telescopes 32.1', 32.2' and 32.3' and with the reference beam portion 90 from the laser 11'. Furthermore a separate fiber optic 546 may be used to operatively couple the laser 11' to the optical head 422, either directly from the output of the laser 11' to the optical head 422—the latter of which could be adapted in an alternate embodiment of an optical head 422' to incorporate the first beam splitter optic 92.1,—or from the first beam splitter optic 92.1 to the optical head 422, or both, so as to provide for flexibility in packaging the optical head 422 in relation to the laser 11', so as to provide for mounting the laser 11' in a relatively benign and stable environment. A fiber optic 546 interconnecting the laser 11' with the optical head 422 also provides for precise alignment of the associated first beam of light 420 with the optical head 422, and simplifies associated installation and maintenance of the associated components thereof.

The associated fiber optics 98.1, 98.2, 98.3, 98.4 and 546 can be adapted as necessary to incorporate non-solarizing fibers so as to mitigate against degradation from relatively high-energy UV laser light which might otherwise solarize the associated fibers and thereby degrade associated fiber-optic transmission. Furthermore, the fiber optic 546 from the laser 11' to the optical head 422 may comprise a bundle of associated fibers, each adapted to transmit a portion of the total light to be transmitted to the optical head 422, so as to reduce the energy density within each fiber of the bundle and thereby mitigate against the degradation thereof. For example, a beam expander may be used to enlarge the first beam of light 420 so as to distribute the associated energy thereof amongst the plurality of associated fibers.

Figure 81:
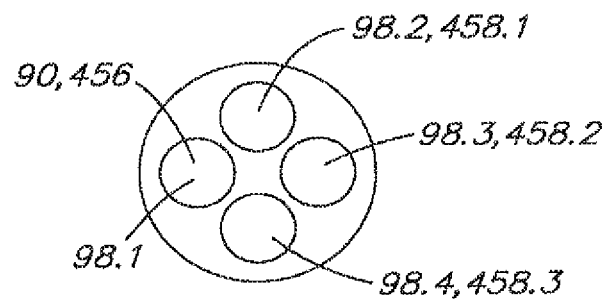
FIG. 81 illustrates an end view of a fiber-optic assembly connected to the input of the Fabry-Pérot interferometer illustrated in FIG. 80.
Figure 82:
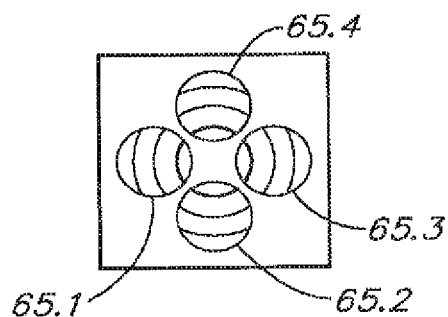
FIG. 82 illustrates a view of a set of circular fringe patterns imaged onto the detector of the optical air data system illustrated in FIG. 80 for an embodiment that does not incorporate a quad-CLIO.
Figure 83:
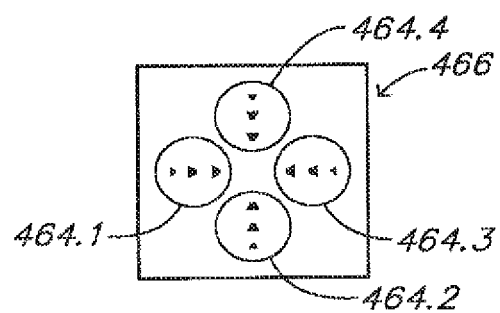
FIG. 83 illustrates a view of a set of substantially linear fringe patterns imaged onto the detector of the optical air data system illustrated in FIG. 80 for an embodiment that incorporates a quad-CLIO.
Figure 84:
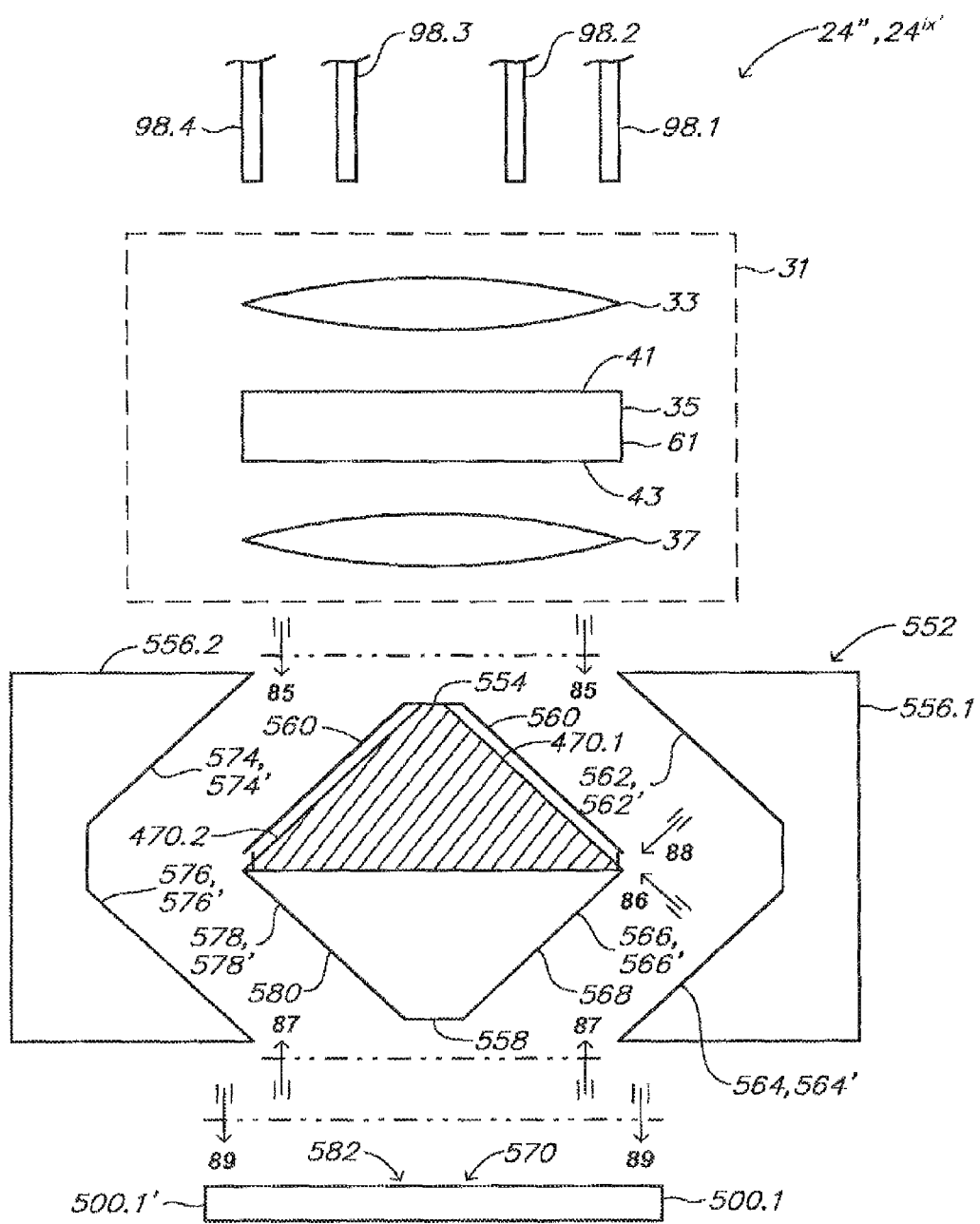
FIG. 84 illustrates a side-view of a signal processor of an optical air data system, including a bi-CLIO element, adapted to provide for measuring wavelength as a function of range.
Figure 85:
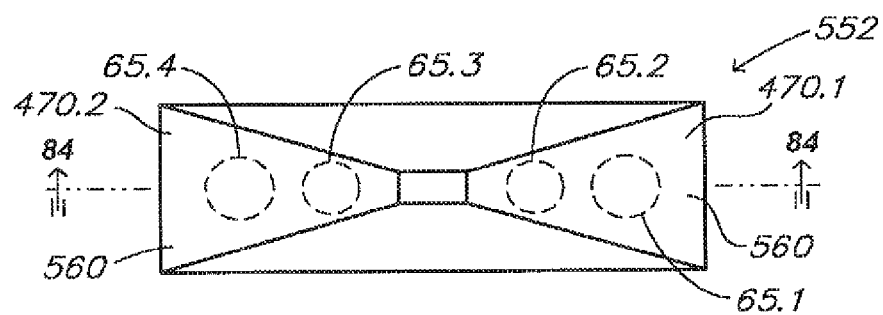
FIG. 85 illustrates a plan view of the bi-CLIO element illustrated in FIG. 84, viewed from the perspective of an associated first pyramidal shaped optic element.
Figure 86:
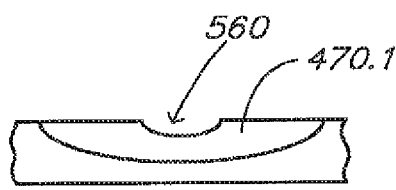
FIG. 86 illustrates a fragmentary end view of a concave conical reflector on a face of the first pyramidal shaped optic element of the bi-CLIO element illustrated in FIGS. 84 and 36, wherein the direction of the end view is substantially parallel to the face of the first pyramidal shaped optic element.
Figure 87:
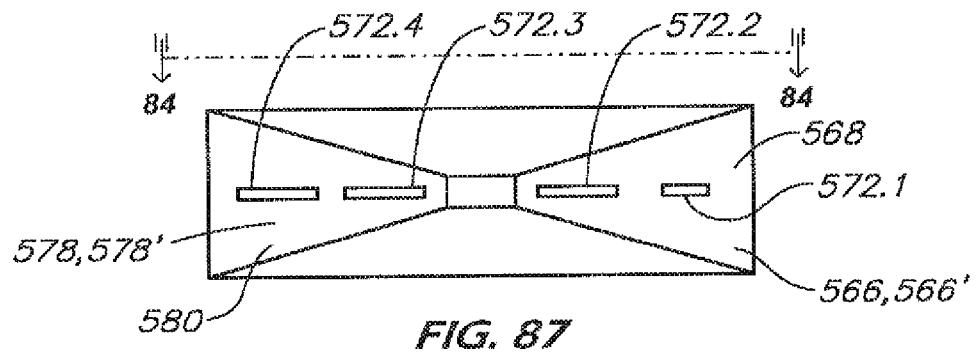
FIG. 87 illustrates a plan view of the bi-CLIO element illustrated in FIG. 84, viewed from the perspective of an associated second pyramidal shaped optic element.
Figure 88:
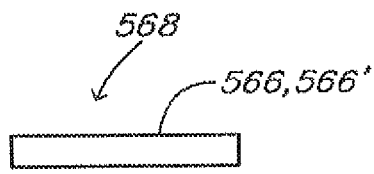
FIG. 88 illustrates a fragmentary end view of a reflective surface on a face of the first second shaped optic element of the bi-CLIO element illustrated in FIGS. 84 and 87, wherein the direction of the end view is substantially parallel to the face of the second pyramidal shaped optic element.

The scattered light signals 30' collected by each of the telescopes 32.1', 32.2' and 32.3', and the reference beam portion 90, are transmitted to the Fabry-Pérot interferometer 31' by the associated fiber optics 98.1, 98.2, 98.3 and 98.4 and are each simultaneously processed by a separate portion of a Fabry-Pérot interferometer 31', wherein the scattered light signals 30' and reference beam portion 90 passing through the Fabry-Pérot interferometer 31' are arranged with respect to one another in "cloverleaf" pattern, as illustrated in FIG. 81. The scattered light signals 30' and reference beam portion 90 are each collimated by a collimating lens 33, then filtered by a filter system 88 as described hereinabove, and then processed by the associated Fabry-Pérot etalon 35, the output of which is imaged by associated imaging optics 37 as associated circular fringe patterns 65.1, 65.2, 65.3 and 65.4 either directly onto a detector 500 as illustrated in FIG. 82, or into a quad-CLIO 462 which, as illustrated in FIG. 83, transforms the circular fringe pattern 65.1, 65.2, 65.3 and 65.4 into a cross pattern 466 which is then imaged onto the detector 500. The image 534 from the detector 500 is then processed by a data processor 53 which provides for determining the associated air data products therefrom. The Fabry-Pérot interferometer 31' and the associated detection system 34 may be mounted within a common housing 548.

Figure 80:
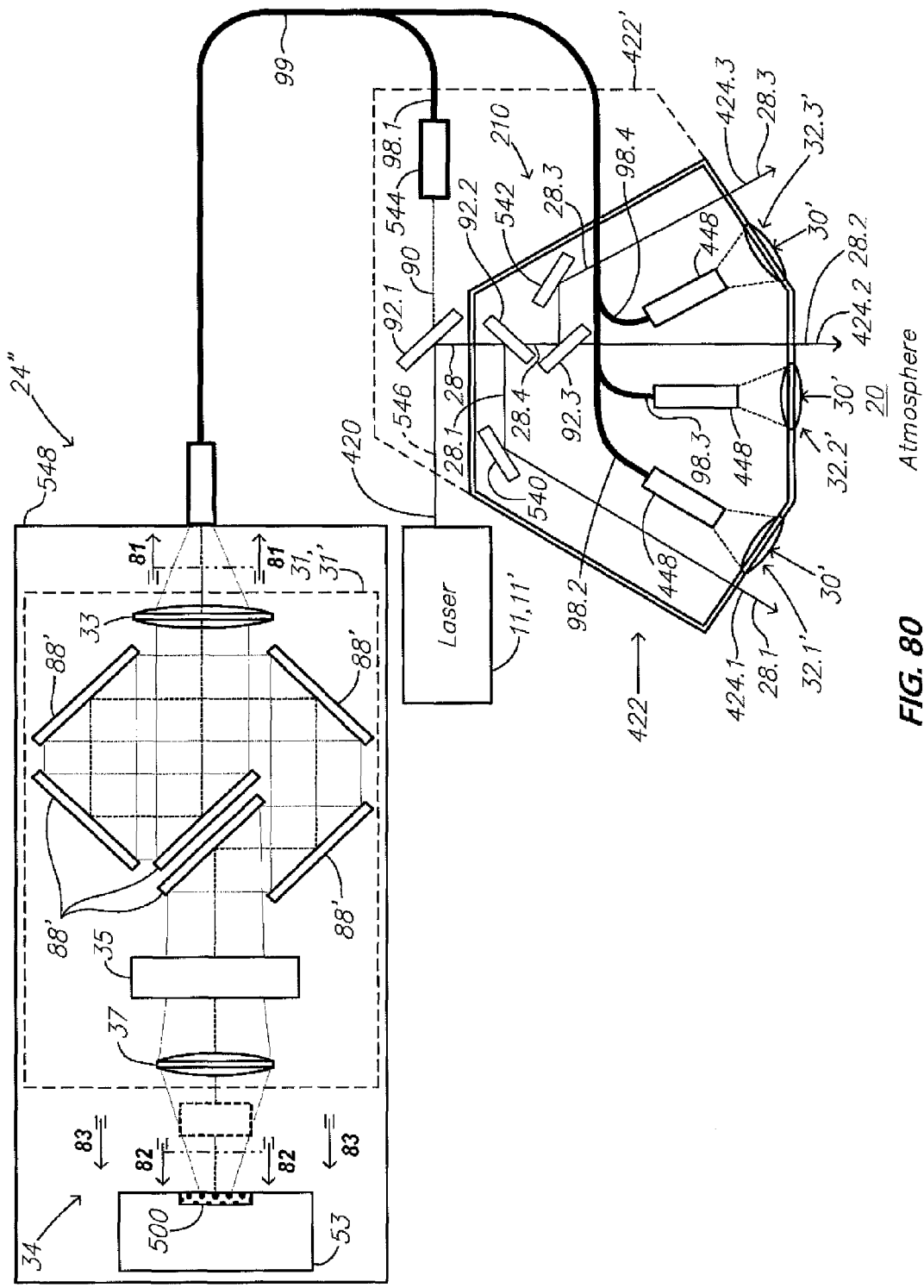
FIG. 80 illustrates a physical layout of various LIDAR system embodiments.

Referring again to FIGS. 66 and 67, the LIDAR system 24'' of FIG. 80, either with an optical head 422.1 incorporating a biaxial system 430 (also known as a bistatic system) as illustrated in FIG. 66, or with an optical head 422.2 incorporating a coaxial system 442 as illustrated in FIG. 67, may be adapted as either a non-ranging system or a ranging system. In the non-ranging embodiment, the measurement volume consists of one region that spans the entire interaction region within the field-of-view 54 of the associated telescope 32.1', 32.2', 32.3' along the line of projection 424: 424.1, 424.2, 424.3 of the associated second beam of light 28.1, 28.2 and 28.3.

Accordingly, referring also to FIGS. 84-91, in accordance with another aspect, a LIDAR system 24'', 24$^{ix'}$, either with an optical head 422.1 incorporating a biaxial system 430 or with an optical head 422.2 incorporating a coaxial system 442 (also known as a monostatic system), may be adapted so as to provide for air data products as a function of range R. In the ranging embodiment, a sufficiently fast CCD detector 500.1 is responsive to the time of flight of each laser pulse, thereby providing for multiple range-separated measurement volumes 550 extending out along the line of projection 424: 424.1, 424.2, 424.3 of the associated telescope 32.1', 32.2', 32.3', so as to provide for mapping the air data products as they vary along the line of projection 424: 424.1, 424.2, 424.3 extending out from the optical head 422.1, 422.2.

Referring to FIGS. 84-89, the LIDAR system 24'', 24$^{ix'}$ incorporates a bi-CLIO 552, for example, comprising a first pyramidal shaped optic element 554 which cooperates with first 556.1 and second 556.2 corner reflector optic elements, which in turn cooperate with a second pyramidal shaped optic element 558. Two of the opposing side faces 560 of the first pyramidal shaped optic element 554 incorporate associated first 470.1 and second 470.2 concave conical reflectors adapted to receive an associated circular fringe patterns 65.1 and 65.2, and 65.3 and 65.4, respectively, from the Fabry-Pérot interferometer 31', wherein the associated fiber optics 98.1, 98.2, 98.3 and 98.4 inputting to the Fabry-Pérot interferometer 31' are arranged substantially in-line with a center of the first 554 and second 558 pyramidal shaped optic elements. The first concave conical reflector 470.1 is adapted to receive a first two circular fringe patterns 65.1, 65.2, and the second concave conical reflector 470.2 is adapted to receive the remaining two circular fringe patterns 65.3 and 65.4.

Light signals 450 of the first two circular fringe patterns 65.1, 65.2 are reflected from the first concave conical reflector 470.1 onto a first reflective surface 562 of the corresponding first corner reflector optic element 556.1, and then reflected therefrom onto a second reflective surface 564 of the corresponding first corner reflector optic element 556.1, and then reflected therefrom onto a third reflective surface 566 on a first side face 568 of the second pyramidal shaped optic element 558, and finally reflected therefrom onto a first portion 570 an associated CCD detector 500.1 as corresponding first 572.1 and second 572.2 linear fringe patterns. Similarly, light signals 450 of the remaining two circular fringe patterns 65.3 and 65.4 are reflected from the second concave conical reflector 470.2 onto a fourth reflective surface 574 of a corresponding second corner reflector optic element 556.2, and then reflected therefrom onto a fifth reflective surface 576 of the corresponding second corner reflector optic element 556.2, and then reflected therefrom onto a sixth reflective surface 578 on a second side face 580 of the second pyramidal shaped optic element 558, and finally reflected therefrom onto a second portion 582 an associated CCD detector 500.1 as corresponding third 572.3 and fourth 572.4 linear fringe patterns. For example, in one embodiment, the first 562, second 564, third 566, fourth 574, fifth 576 and sixth 578 reflective surfaces comprise corresponding planar reflective surfaces 562', 564', 566', 574', 576', 578'. The first 554 and second 558 pyramidal shaped optic elements and the first 556.1 and second 556.2 corner reflector optic elements can be constructed from a variety of materials—including, but not limited to, aluminum, stainless steel, copper-nickel alloy, glass or fused quartz—that can be adapted to incorporate associated reflective surfaces or coatings. Furthermore, one or both of the first 556.1 and second 556.2 corner reflector optic elements could be replaced with separate elements for each of the associated first 562, second 564, fourth 574 and fifth 576 reflective surfaces.

Figure 89:
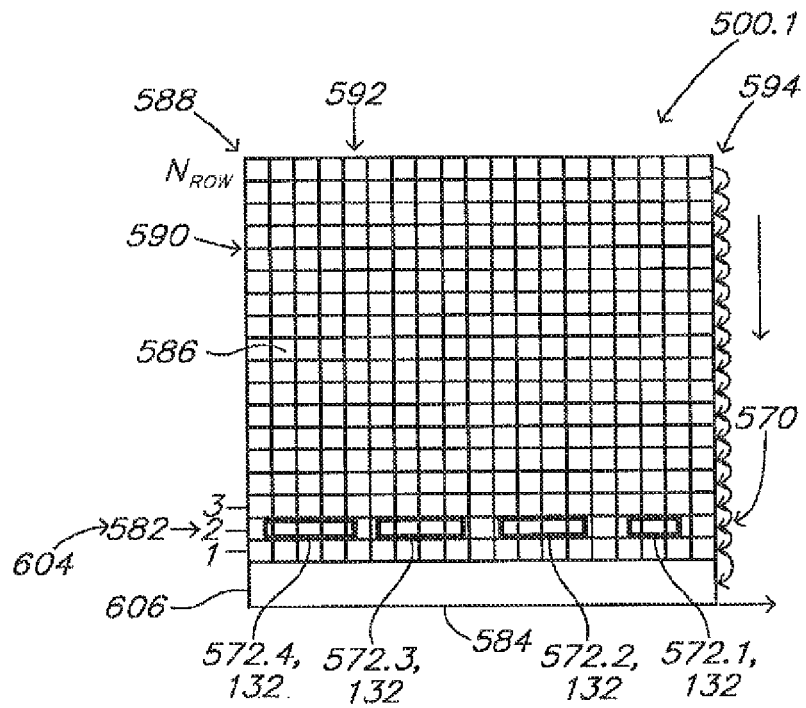
FIG. 89 illustrates a plan view of a CCD detector illustrated in FIG. 84, and an associated imaging process.
Figure 90:
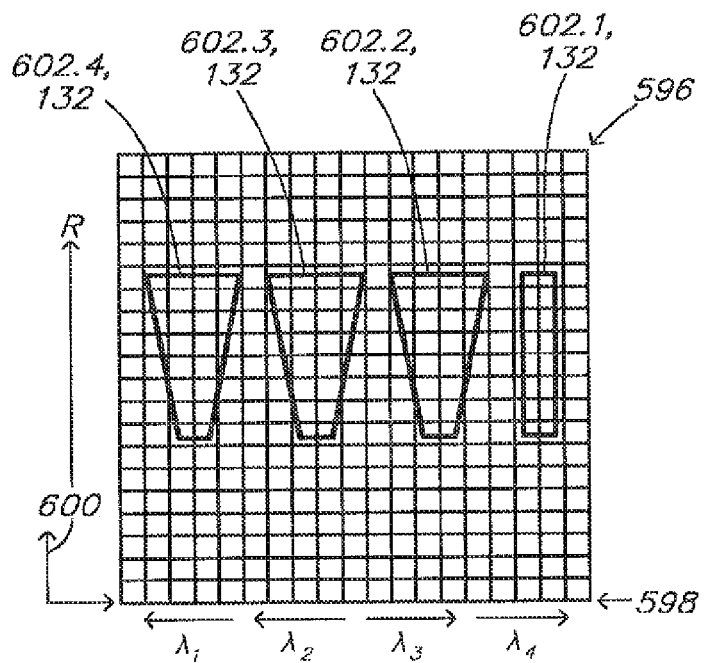
FIG. 90 illustrates an image from the CCD detector illustrated in FIG. 89.

Referring to FIGS. 89 and 90, the first 572.1, second 572.2, third 572.3 and fourth 572.4 linear fringe patterns are projected onto the associated first 570 and second 582 portions of the CCD detector 500.1 located proximate to an associated serial register 584 thereof, and the remaining photosites 586 of the CCD detector 500.1 are masked from receiving light. The CCD detector 500.1 comprises an array 588 of photosites 586 organized as a plurality of rows 590, each row comprising a plurality of columns 592. Upon exposure to light, each of the photosites 586 accumulates charge in proportion to the amount of light impinging thereon. In a normal process of recording a 2-dimensional image, the entire array 588 is simultaneously exposed to an entire image, e.g. by the opening of an associated shutter or by the activation of the laser 11' illumination source. Then, with the shutter closed or the laser 11' off after the scattered light signals 30' have been received, the 2-dimensional image is read from the array 588, one row 590 at a time, by successively shifting the charges from each row 590 successively downwards, for example, by first shifting the charges from row #1 into the serial register 584, then shifting the charges from row #2 into row #1, then row #3 into row #2, and so on until the charges from row #N is shifted into row #N−1. The contents of the serial register 584 are then A/D converted and communicated to an associated processor for subsequent processing. Afterwards, this process repeats on rows #1 to #N−1, and so on until the last row 590 of recorded photosites 586 has been transferred to the serial register 584, and then to the associated processor for subsequent processing.

The LIDAR system 24", $24^{ix'}$ takes advantage of the normal process by which the CCD detector 500.1 is read to provide for continuously recording the first 572.1, second 572.2, third 572.3 and fourth 572.4 linear fringe patterns over time so that each subsequent row 590 of photosites 586 passing by first 570 and second 582 portions of the CCD detector 500.1 during the process of reading the CCD detector 500.1 captures the associated first 572.1, second 572.2, third 572.3 and fourth 572.4 linear fringe patterns at a corresponding subsequent point in time with data associated with a corresponding range R from the optical head 422.1, 422.2. More particularly, the process of reading the CCD detector 500.1 commences simultaneously with the generation of an associated light pulse from the laser 11'. Light signals 450 are continuously processed by the Fabry-Perot interferometer 31' and associated bi-CLIO 552 so as to illuminate the first 570 and second 582 portions of the CCD detector 500.1 with corresponding first 572.1, second 572.2, third 572.3 and fourth 572.4 linear fringe patterns. In the CCD detector 500.1 illustrated in FIG. 89, the first 570 and second 582 portions of the CCD detector 500.1 are aligned with row #2 thereof. After the charges from row #2 are transferred to row #1 during a charge transfer cycle 594, row #2 is replaced with the blank contents of row #3, which then becomes exposed to the light signals 450 from the first 572.1, second 572.2, third 572.3 and fourth 572.4 linear fringe patterns at that time. This process repeats with a fresh row of blank photosites 586 replacing the contents of row #2 with each subsequent charge transfer cycle 594 until all of the rows 590 have been read. During each charge transfer cycle 594, the contents of row #1 are shifted into the serial register 584, and then transferred to the data processor 53 where the corresponding values are stored in memory 124 as pixels 516 of an associated image 596, beginning from the bottom 598 of the image 596, and progressing upwards 600 until the entire image 596 has been recorded, as illustrated in FIG. 90, whereupon the image 596 records each of the first 572.1, second 572.2, third 572.3 and fourth 572.4 linear fringe patterns in corresponding range-resolved fringe patterns 602.1, 602.2, 602.3 and 602.4, with range R (R) increasing upwards 600 in the associated image 596. The range resolution of the image 596 is dependent upon the time required for each charge transfer cycle 594, i.e. the time required to transfer the associated charges from one row to the next. For example, for a CCD detector 500.1 with 512 rows and a row shift rate of 375 nanoseconds per row, the range resolution would be 56.25 meters (i.e. $3.0 \times 10^8$ m/s*½*375× $10^{-9}$ s) and the maximum range for the CCD detector 500.1 would be 28.8 Kilometers (i.e. 512*56.25). The frame transfer/streaking process/range acquisition takes only a relatively short time, e.g. for 512 rows at a streak rate of 375 ns/row it takes 192 micro-seconds to resolve the full range on the CCD detector 500.1. For a 200 Hz refresh rate a frame is acquired every 5 milliseconds (½₀₀), so there are 0.00500−0.000192=0.004808 seconds for reading the image out of the readout registers and transferring to disk in accordance with an associated process of acquiring image frames from the CCD detector 500.1 at an associated refresh rate thereof, e.g. in frames per second.

Figure 91:
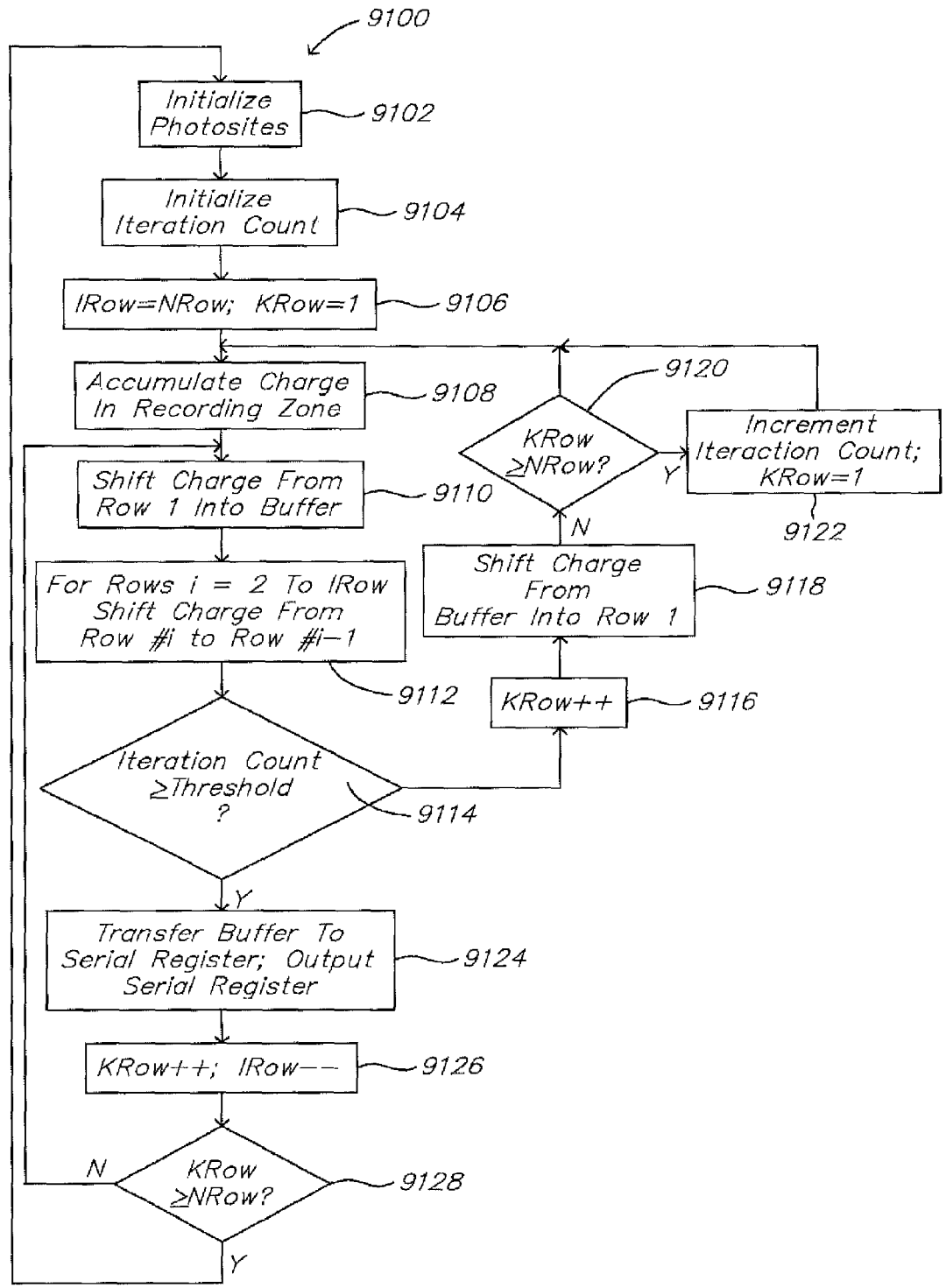
FIG. 91 illustrates a flow chart of a first imaging process for generating range-resolved images.

Referring to FIG. 91, in accordance with a first imaging process 9100 for generating a range-resolved image, for example, operative in cooperation with the CCD detector 500.1 illustrated in FIG. 89 to generate an associated image 596, e.g. as illustrated in FIG. 90, in step (9102), the array 588 of photosites 586 of the CCD detector 500.1 is initialized, e.g. to substantially zero charge. Then, in step (9104), in synchronism with the lasing of the second beams of light 28 from the laser 11', for a pulsed laser 11', an iteration count is initialized, e.g. to a value of zero, wherein the iteration count is used to record the number of times the array 588 of photosites 586 has been processed in subsequent steps. Then, in step (9106), a first row counter IRow is initialized to a value of NRow, where NRow is the number of rows in the array 588 of photosites 586; and a second row counter KRow is initialized to a value of 1. Then, in step (9108), an iterative process commences, wherein charge is accumulated in the photosites 586 in a recording zone 604 comprising the first 570 and second 582 portions of the CCD detector 500.1 that are aligned with a particular row of the array 588 of photosites 586 and which receive scattered light 30 of the first 572.1, second 572.2, third 572.3 and fourth 572.4 linear fringe patterns from the associated fiber optics 98.1, 98.2, 98.3 and 98.4. Then, in step (9110), the charges in the photosites 586 of row #1 are shifted into a buffer row 606, and then, in step (9112), the charges in row ##2 to IRow are shifted into row ##1 to IRow−1, respectively. Then, in step (9114), if the iteration count is less than a threshold, then in step (9116), the second row counter KRow is incremented, and, in step (9118), the charges in the buffer row 606 are shifted into Row #NRow. Then, in step (9120), if the value of the second row counter KRow is greater than or equal to the number of rows NRow, then, in step (9122), the iteration count is incremented and the second row counter KRow is initialized to a value of 1. Then, from step (9122), or otherwise from step (9120), the process of steps (9108) through (9112) is repeated until, in step (9114), the iteration count is greater than or equal to the threshold, in which case, in step (9124), the charges are transferred from the buffer row 606 to the serial register 584 and then output so as to generate the image 596. Then, in step (9126), the second row counter KRow is incremented and the first row counter IRow is decremented. If, in step (9128), the value of the second row counter KRow is less than the number of rows NRow, then the process repeats with step (9110) until the entire image 596 has been transferred from the array 588 of photosites 586; otherwise, the process of recording and outputting an image 596 repeats with step (9102). Accordingly, the second row counter KRow provides for determining whether each row of the array 588 of photosites 586 has been recorded, the iteration count provides for repetitively recording the entire array 588 of photosites 586 so as to accumulate additional charge within each of the photosites 586, thereby improving the associate ratio of charge (signal) to read noise, and the first row counter IRow provides for efficiently reading the array 588 of photosites 586.

Referring to FIGS. 92a-e, a second embodiment of a CCD detector 500.1' comprises an imaging region 608 and a masked, frame-transfer region 610, wherein the frame-transfer region 610 provides for buffering the image 596 so as to facilitate transfer thereof from the CCD detector 500.1' via a relatively slow serial register 584. Both the imaging region 608 and the frame-transfer region 610 contain similar photosites 586 that are adapted to store photo-generated charges, the difference being that the frame-transfer region 610 is masked from light, and thereby unable to generate photo-generated charges. Although the second embodiment of the CCD detector 500.1' is suitable for use in any of the above-described embodiments of the LIDAR system 24", $24^{ix'}$, it will now be described with particularity in cooperation with the LIDAR system 24", $24^{ix'}$ illustrated in FIGS. 84-91, for example, in cooperation with a second imaging process 9300 illustrated in FIG. 93.

Figure 93:
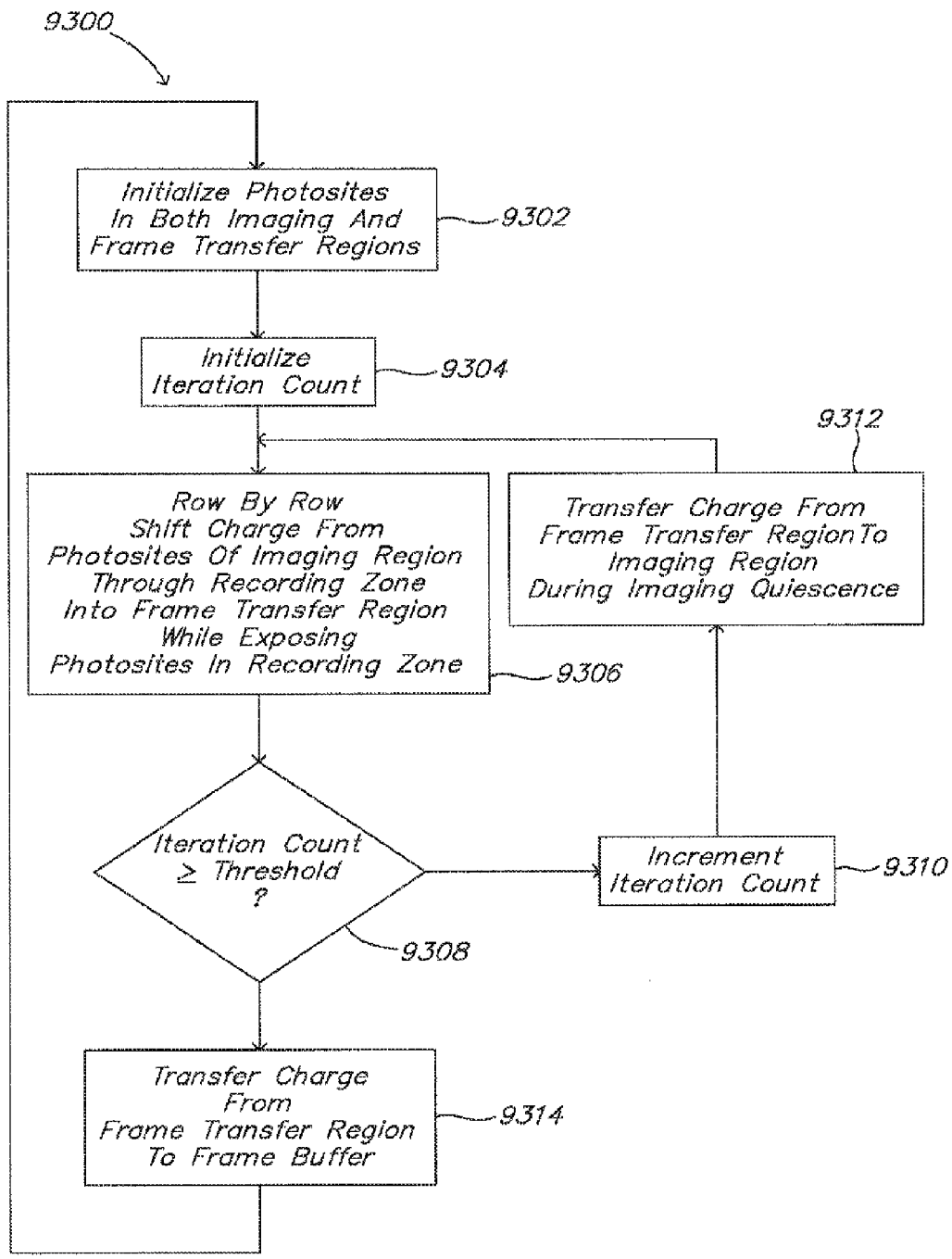
FIG. 93 illustrates a flow chart of a second imaging process for generating range-resolved images.

Referring to FIGS. 92a and 93, in step (9302), the photosites 604 in both the imaging region 608 and the frame-transfer region 610 of the CCD detector 500.1' are initialized, for example, to a condition of substantially zero charge, for example, as may result from an associated read process of the CCD detector 500.1'. Then, in step (9304), in synchronism with the second beams of light 28 from the laser 11', for a pulsed laser 11', an iteration count is initialized, e.g. to a value of zero, wherein the iteration count is used to record the number of times the imaging region 608 has been recorded in subsequent steps. Then, in step (9306), the charges in the array 588 of photosites 586 are shifted downwards, row by row, from the imaging region 608 into the frame-transfer region 610, through the recording zone 604 therebetween, wherein the photosites 586 in the recording zone 604 are exposed to the first 572.1, second 572.2, third 572.3 and fourth 572.4 linear fringe patterns, the light of which causes charges to be generated within the associated photosites 586, which charges are then subsequently shifted downwards. For example, FIG. 92b illustrates a beginning stage of an image recording cycle, at which time the lowest row of photosites 586 of the imaging region 608 are recorded; FIG. 92c illustrates an intermediate stage of the image recording cycle at which time a portion of the photosites 586 of the imaging region 608 have been recorded and the charges therefrom have been shifted into the frame-transfer region 610, and FIG. 92d illustrates a final stage of the image recording cycle at which time all of the photosites 586 of the imaging region 608 have been recorded and the charges therefrom have been shifted into the frame-transfer region 610. Then, in step (9308), if the iteration count is less than a threshold, then, in step (9310), the iteration count is incremented, and, in step (9312), the charges are transferred from the frame-transfer region 610 back to the imaging region 608 of the CCD detector 500.1', after which the process repeats with step (9306) until, in step (9308), the iteration count is greater than or equal to the threshold, after which, in step (9314), the charges are transferred from the frame-transfer region 610 to a frame buffer 612 via a serial register 584 operatively associated with the frame-transfer region 610 of the CCD detector 500.1', as illustrated in FIG. 92e, and then the process repeats with step (9302). Accordingly, the iteration count provides for repetitively recording the imaging region 608 so as to accumulate additional charge within each of the photosites 586 thereof, thereby improving the associate ratio of charge (signal) to read noise. The cumulative recording process is illustrated by the portions of the range-resolved fringe patterns 602.1, 602.2, 602.3 and 602.4 in FIGS. 92b and 92c with dashed outlines.

The range-resolved fringe patterns 602.1, 602.2, 602.3 and 602.4 in the images 596 illustrated in FIGS. 90 and 92e are simulations of measurements from a high-altitude or space-based LIDAR system 24", $24^{ix'}$ looking down on the atmosphere 20, wherein each range-resolved fringe patterns 602.1, 602.2, 602.3 and 602.4 comprises a single fringe 132. For the range-resolved fringe patterns 602.2, 602.3 and 602.4 associated with the scatter signal channels 458.1, 458.2 and 458.3, the width and amplitude of the range-resolved fringe patterns 602.1, 602.2, 602.3 and 602.4, i.e. the molecular signal component 132.2 thereof, increases with increasing range R corresponding to an increase in density and temperature with decreasing altitude in the atmosphere 20, whereas the range-resolved fringe pattern 602.1 associated with the reference channel 456 exhibits a substantially constant width.

Figure 94:
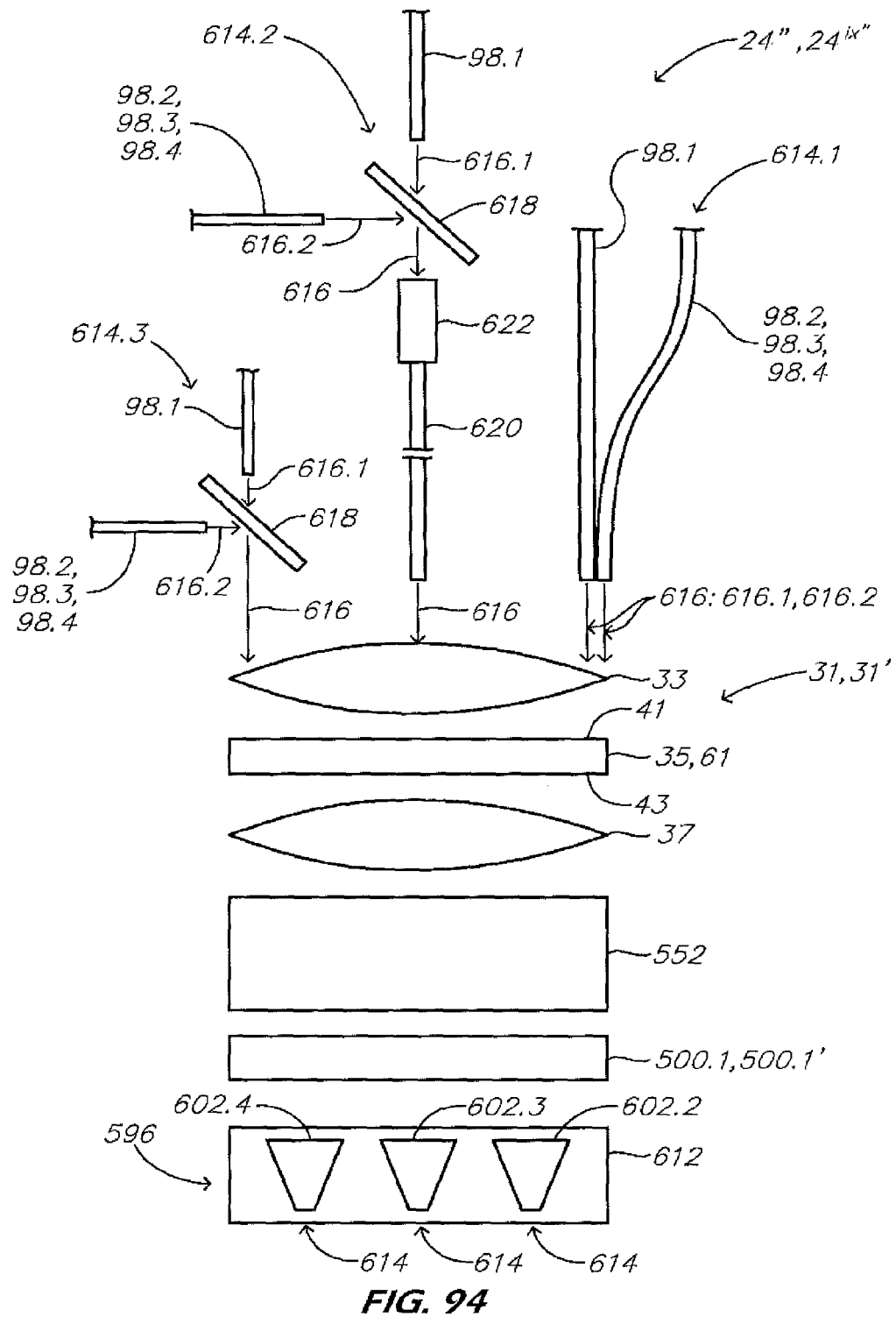
FIG. 94 illustrates various embodiments for multiplexing reference and signal channels for a range-resolved optical air data system.

Referring to FIG. 94, in accordance with an alternative embodiment of a LIDAR system 24", $24^{ix''}$, the reference channel 456 can be multiplexed with one or more scatter signal channels 458.1, 458.2 and 458.3 so as to provide for eliminating the separate and distinct processing of the reference channel 456 by the LIDAR system 24", $24^{ix''}$. For example, in accordance with a first embodiment of an optical multiplexer 614.1, the fiber optic 98.1 of the reference channel 456 is bunched together with the fiber optic 98.2, 98.3, 98.4 of one of the scatter signal channels 458.1, 458.2 or 458.3 so that the light 616.1, 616.2 from the reference 456 and scatter signal 458.1, 458.2, 458.3 channels illuminates a common region of the Fabry-Pérot interferometer 31' as a multiplexed beam of light 616. As another example, in accordance with a second embodiment of an optical multiplexer 614.2, light 616.1 from the fiber optic 98.1 of the reference channel 456 is combined with light 616.2 from a fiber optic 98.2, 98.3, 98.4 of one of the scatter signal channels 458.1, 458.2 or 458.3 using a beam splitter 618 so as to form a multiplexed beam of light 616, which is then collected into a fiber optic 620 by a light-collecting element 622, for example, a GRIN lens or an aspheric lens, and directed therethrough to the Fabry-Pérot interferometer 31'. As yet another example, in accordance with a third embodiment of an optical multiplexer 614.3, light 616.1 from the fiber optic 98.1 of the reference channel 456 is combined with light 616.2 from a fiber optic 98.2, 98.3, 98.4 of one of the scatter signal channels 458.1, 458.2 or 458.3 using a beam splitter 618 so as to form a multiplexed beam of light 616, which is directed via an associated optical path to the Fabry-Pérot interferometer 31', either directly, or indirectly using one or more associated mirrors.

The multiplexed beam of light 616 is processed by the Fabry-Pérot interferometer 31', transformed into an associated linear fringe pattern 572.2, 572.3 or 572.4 by the associated bi-CLIO 552, and imaged onto an associated CCD detector 500.1, 500.1' which provides for generating an associated range-resolved fringe pattern 602.2, 602.3 or 602.4, wherein the information associated with the zero or near-zero range portion thereof corresponds to the reference channel 456, and the remaining information corresponds to the associated scatter signal channel 458.1, 458.2 or 458.3. Although FIG. 94 illustrates three multiplexed channels, so as to illustrate the three different associated optical multiplexers 614.1, 614.2 and 614.3, it should be understood that the LIDAR system 24", $24^{ix''}$ can function using only one optical multiplexer 614.1, 614.2 or 614.3 to provide the information from the reference channel 456.

Figure 66:
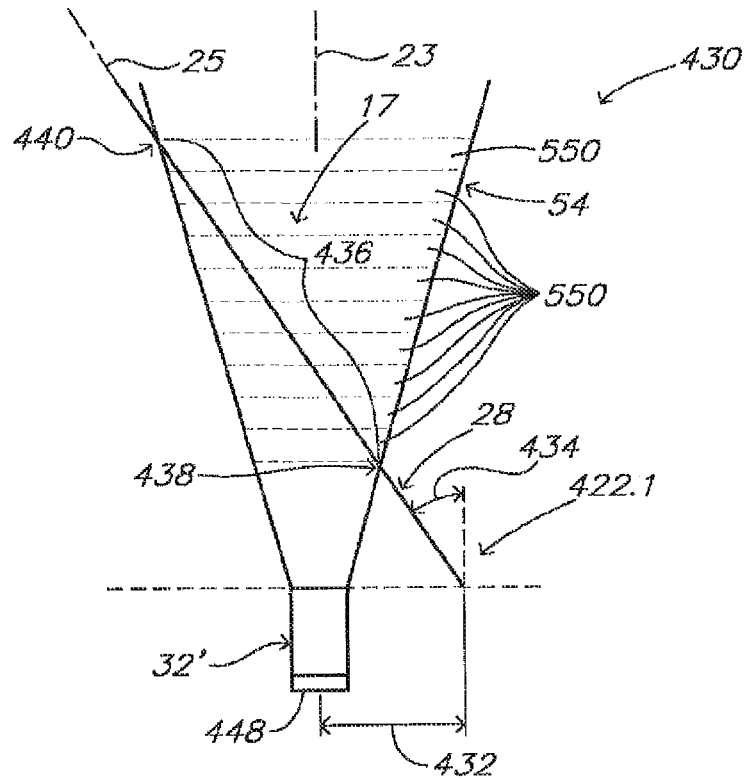
FIG. 66 illustrates an optical head of a biaxial system.

Referring to FIGS. 66 and 67, the LIDAR systems 24", $24^{ix'}$, $24^{ix''}$ that provide for range-resolved imaging and associated range-resolved air data products can be adapted to incorporate or cooperate with either a biaxial system 430, e.g. as illustrated in FIG. 66, or a coaxial system 442, e.g. as illustrated in FIG. 67, wherein different rows in the image 596 of the range-resolved fringe patterns 602.2, 602.3 and 602.4 are associated with different range-separated measurement volumes 550 within the associated interaction regions 17.

Figure 95:
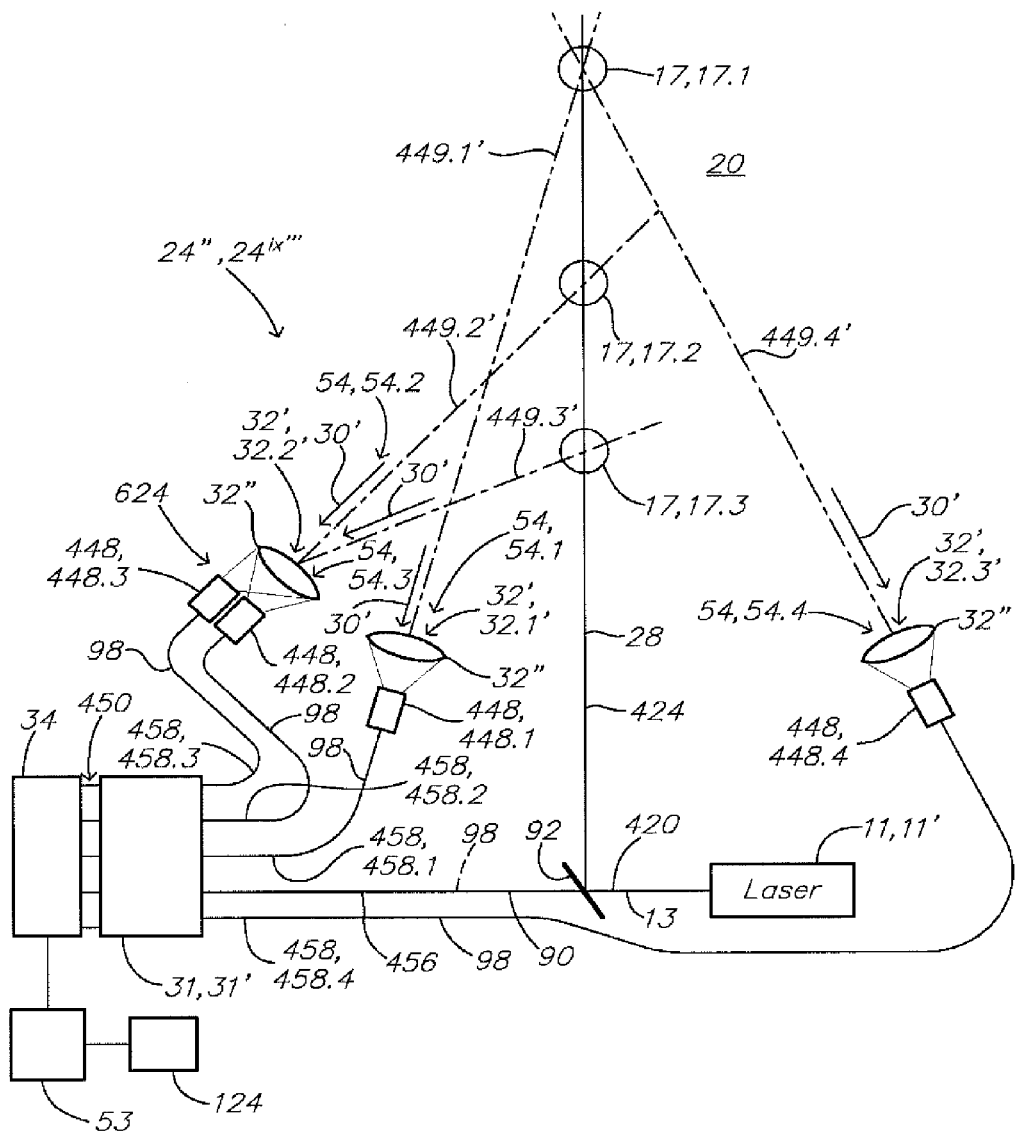
FIG. 95 illustrates various interaction regions associated with a common line-of-sight of a second laser beam.

Referring to FIG. 95, in accordance with alternative embodiments, a LIDAR system 24", $24^{ix'''}$ in a biaxial system 430 configuration may be adapted with a plurality of different fields-of-view 54, each of which cooperates with a common line of projection 424 of an associated second beam of light 28. A telescope 32' and an associated final light-collecting element 448 is adapted for each associated field-of-view 54 to collect associated scattered light signals 30' scattered from associated interaction regions 17 defined by the intersection of the associated field-of-view 54 with the second beam of light 28 along the line of projection 424. Each of the scattered light signals 30' associated with the different fields-of-view 54 are then processed by an associated Fabry-Pérot interferometer 31', detection system 34, and data processor 53 as separate scatter signal channels 458, together with an associated reference channel 456 of an associated reference beam portion 90, as described hereinabove for the previously described embodiments.

In accordance with one aspect, the different fields-of-view 54 may be associated with corresponding different ranges along the line of projection 424. For example, for a line of projection 424 spanning a range of altitudes, each different field-of-view 54 provides for measuring an associated set of air data products at a corresponding different altitude. In one embodiment, for example, a first final light-collecting element 448.1 in cooperation with a first telescope 32.1' aligned with a first axis 449.1 associated with a first field-of-view 54.1 provides for collecting scattered scattered light signals 30' from a first interaction region 17.1 located at a first range from the beam splitter optic 92 from which the second beam of light 28 originates. A second final light-collecting element 448.2 at a first light-collecting location in cooperation with a second telescope 32.2' aligned with a second axis 449.2 associated with a second field-of-view 54.2 provides for collecting scattered scattered light signals 30' from a second interaction region 17.2 located at a second range from the beam splitter optic 92. A third final light-collecting element 448.3 at a second light-collecting location in cooperation with the second telescope 32.2' aligned with a third axis 449.3 associated with a third field-of-view 54.3 provides for collecting scattered scattered light signals 30' from a third interaction region 17.3 located at a third range from the beam splitter optic 92. For example, in one embodiment, the first and second light-collecting locations associated with the second telescope 32.2' are transversely offset from one another in the focal plane 624 of the associated effective lens 32" of the second telescope 32.2', the first and second light-collecting locations thereby defining the corresponding associated second 54.2 and third 54.3 fields-of-view. It should be understood that the particular plurality of final light-collecting element 448 associated with a particular telescope 32' is not limiting, i.e. the actual number being limited by the physical size of the final light-collecting elements 448 and the size of the associated effective lens 32".

In accordance with another aspect, the different fields-of-view 54 may be associated with a common interaction region 17 along the line of projection 424, for example, so as to provide for measuring different line-of-sight relative wind velocities U in different directions relative to a common region of the atmosphere 20, so that relative to an inertial frame of reference, each measurement is affected by substantially the same wind velocity of the atmosphere relative to the inertial frame of reference, so as to improve the accuracy of an associated relative wind vector calculated from the associated line-of sight-relative wind velocities U. In one embodiment, for example, a first final light-collecting element 448.1 in cooperation with a first telescope 32.1' aligned with a first axis 449.1 associated with a first field-of-view 54.1 provides for collecting scattered scattered light signals 30' from a first interaction region 17.1, and a fourth final light-collecting element 448.4 in cooperation with a third telescope 32.3' aligned with a fourth axis 449.4 associated with a fourth field-of-view 54.4 also provides for collecting scattered scattered light signals 30' from the first interaction region 17.1, but from a different direction, so that the scattered light signals 30' from the first 448.1 and fourth 448.4 final light-collecting elements provide for measuring line-of-sight relative wind velocities U in different directions so as to provide for measuring an associated relative wind vector. The first 448.1 and fourth 448.4 final light-collecting elements in the embodiment illustrated in FIG. 95 provide for determining an associated 2-D relative wind vector in the plane defined by the first 449.1 and fourth 449.4 axes. An additional out-of-plane final light-collecting element 448 in cooperation with an associated telescope 32' having an associated field-of-view 54 also aligned with the first interaction region 17.1 may be used to provide for determining an associated 3-D relative wind vector.

Figure 96:
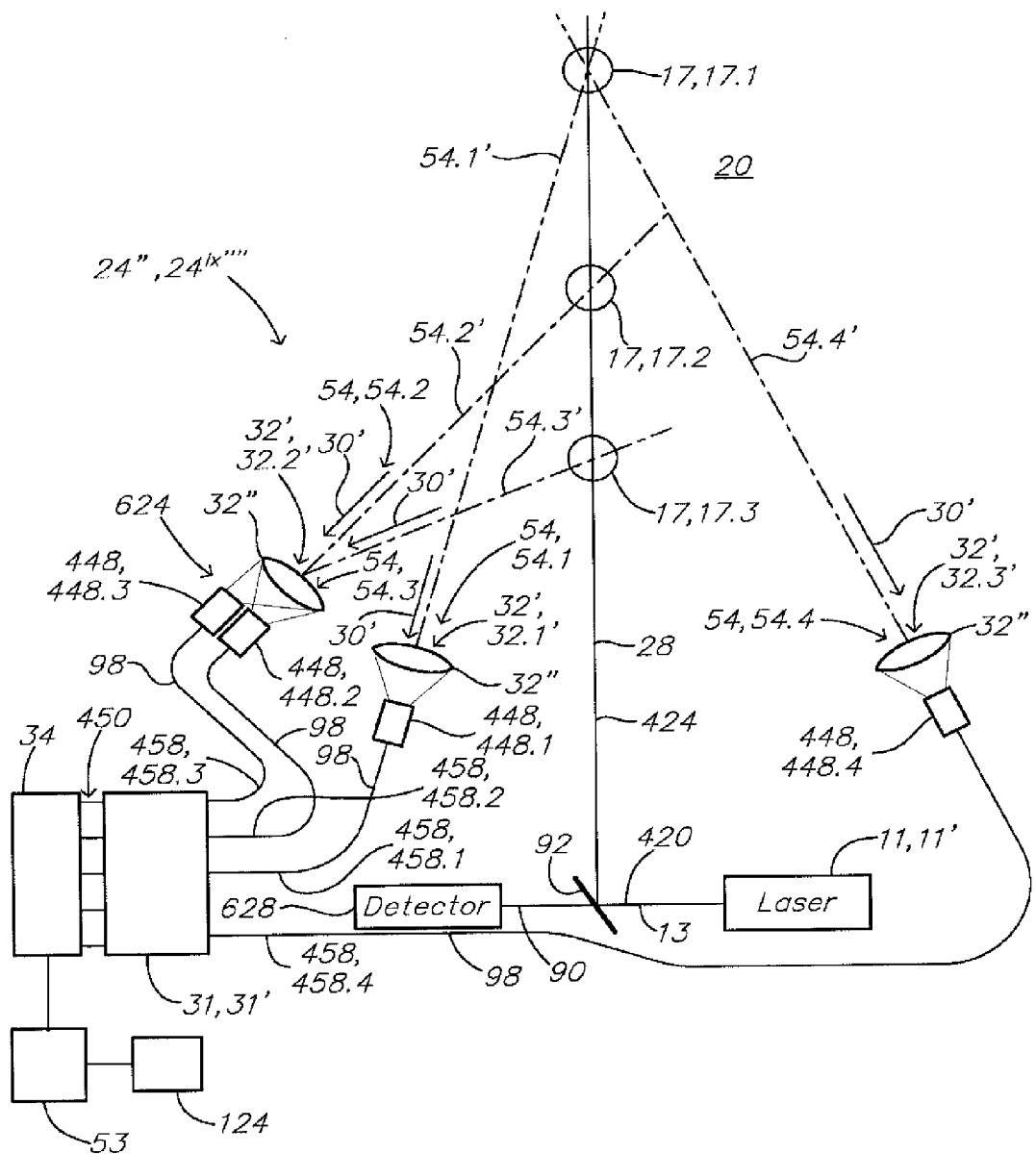
FIG. 96 illustrates an alternative to the various embodiments illustrated in FIG. 95, suitable for determining air data products that are not dependent upon relative wind velocity.

Referring to FIG. 96, a LIDAR system 24", $24^{ix''''}$ may be adapted to measure the overall intensity of the reference beam portion 90 with a detector 628, rather than processing the reference beam through the Fabry-Pérot interferometer 31', so as to provide for either reducing the total number of channels processed with the Fabry-Pérot interferometer 31', or so as to provide for processing an additional scatter signal channel 458 therewith. Such an arrangement would be suitable when the associated air data products being measured therewith are not dependent upon relative wind velocity, the latter of which measure is calibrated responsive to a measure of frequency shift of the reference channel 456 using the Fabry-Pérot interferometer 31'. For example, the LIDAR system 24", $24^{ix''''}$ illustrated in FIG. 96 would be suitable for measuring either or both of static density ρ and static temperature $T_S$, or to provide for deriving therefrom one or more of static air pressure, total air temperature, speed of sound, air density ratio or pressure altitude.

Heretofore the laser 11' has been assumed to be a generic device capable of providing sufficiently narrow-band photonic radiation at an operative frequency so as to provide for an operative LIDAR system 24", $24^{ix'}$, $24^{ix''}$, $24^{ix'''}$, $24^{ix''''}$. For example, a Nd:YAG laser 11.1' can operate at relatively high power levels so as to provide sufficiently intense illumination so as to provide for relatively long range atmospheric sensing applications. An Nd:YAG laser 11.1' has a fundamental wavelength of 1064 nanometers (nm), from which shorter wavelengths/higher frequencies may be generated using one or more harmonic generators operatively associated with or a part of the Nd:YAG laser 11.1'. For example, a second-harmonic generator could be used to convert the fundamental 1064 nm light to second-harmonic 532 nm light which could then be transformed with either a third- or fourth-harmonic generator to generate associated 355 nm or 266 nm light respectively. Heretofore these second-, third- and/or fourth-harmonic generators would be either incorporated in, or free-space coupled to, the laser 11' generally or, more particularly, the Nd:YAG laser 11.1'.

As noted hereinabove, ultraviolet light—e.g. 266 nm or 355 nm light that can be generated as described hereinabove—can be suitable for atmospheric sensing applications. One problem associated with ultraviolet light when transmitted or distributed through associated fiber optics 98 of the LIDAR system 24", 24$^{ix'}$, 24$^{ix''}$, 24$^{ix'''}$, 24$^{ix''''}$ is the resulting degradation of the associated fiber optics 98, for example, that can occur as a result of a power per unit area therein exceeding a damage threshold, e.g. at a focal point within the fiber optics 98, or a solarization of the fiber optics 98. However, the fiber optics 98 provide for locating relatively sensitive portions of the LIDAR system 24", 24$^{ix'}$, 24$^{ix''}$, 24$^{ix'''}$, 24$^{ix''''}$, e.g. the laser 11', Fabry-Pérot interferometer 31', and detection system 34, at a relatively secure location that may be relatively remote from the associated optical head 422 containing the associated beam splitter optics 92, beam steering optics 210, and telescope(s) 32', by providing for efficiently transmitting the associated first 420 and/or second 28 beams of light, and/or the reference beam portion 90 to the optical head 422, and for transferring the received scattered light signals 30' from the optical head 422 to the Fabry-Pérot interferometer 31'.

Figure 97:
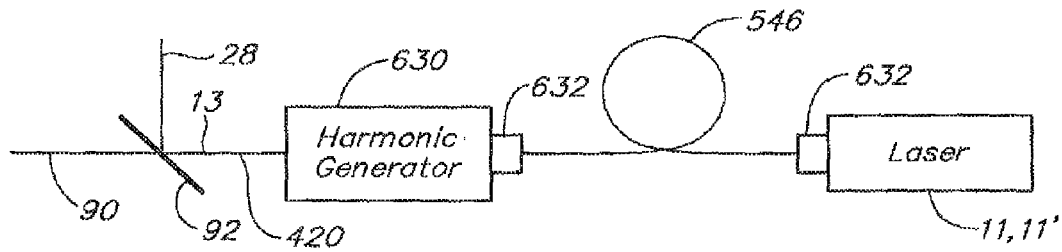
FIG. 97 illustrates a laser coupled with a fiber optic to an associated harmonic generator, the output of which is then propagated in free space.

Referring to FIG. 97, a LIDAR system 24", 24$^{ix'}$, 24$^{ix''}$, 24$^{ix'''}$, 24$^{ix''''}$ may be adapted to operate at ultraviolet frequencies without the ill affects of associated solarization or power-induced damage of an associated fiber optic 546 coupling the relatively high-power first beam of light 420 operating at a fundamental harmonic to the associated optical head 422 by transmitting relatively long-wavelength laser light from the laser 11' through a fiber optic 546 to an associated harmonic generator 630, generating relatively shorter-wavelength light with the harmonic generator 630, and then transmitting through free space the relatively shorter-wavelength light from the harmonic generator 630 to the beam splitter optic 92 of the optical head 422. The harmonic generator 630 could be incorporated in the optical head 422 so as to provide for optical alignment therewith and ruggedization of the associated harmonic generator 630. Accordingly, this arrangement provides for operation at ultraviolet frequencies and the use of fiber optics 546, 98 to mechanically isolate of the laser 11', Fabry-Pérot interferometer 31', and detection system 34 from the optical head 422, without a substantial prospect of solarization-induced degradation of the fiber optic 546 carrying the relatively high-power laser light from the laser 11' to the optical head 422.

Figure 98A:
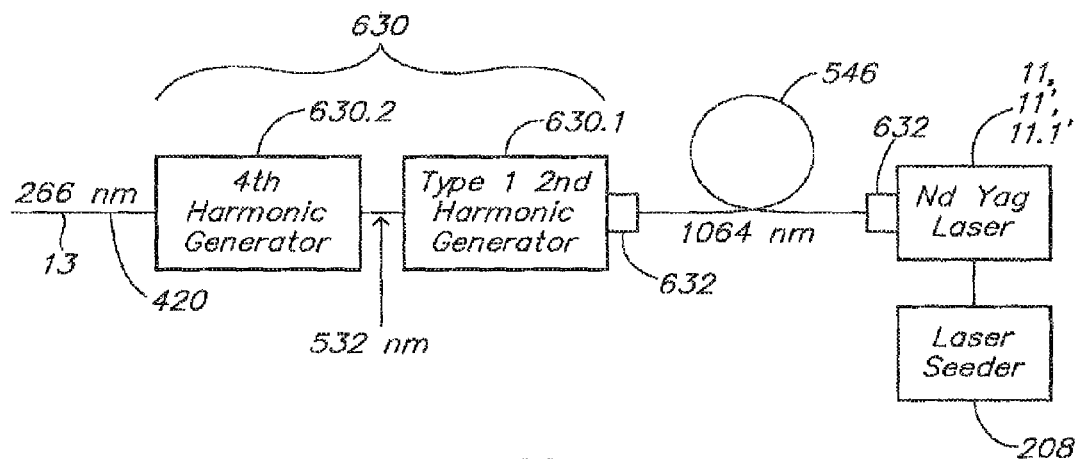

For example, referring to FIG. 98a, in accordance with a first embodiment, a Nd:YAG laser 11.1' is operatively coupled to a Type 1 second-harmonic generator 630.1 with a fiber optic 546, wherein the Type 1 second-harmonic generator 630.1 provides for converting the 1064 nm laser light from the Nd:YAG laser 11.1' to 532 nm light, which is then operatively coupled over free space to a fourth-harmonic generator 630.2 that provides for converting the 532 nm light from the Type 1 second-harmonic generator 630.1 to 266 nm light of the first beam of light 420. The Type 1 second-harmonic generator 630.1 and the fourth-harmonic generator 630.2 comprise crystals, for example, BBO, KDP and LBO, the selection of which depends upon the manufacturer and various factors, e.g. pulse energy. The crystal used in the Type 1 second-harmonic generator 630.1 is cut in accordance with what is known as a Type 1 cut so as to provide for two photons of 532 nm light to be doubled to 266 nm light by the fourth-harmonic generator 630.2. For example, in one embodiment, the Nd:YAG laser 11.1' can be a model 8030 manufactured by Continuum, which operates in cooperation with a Continuum Part No. 617-8000 Type 1 second-harmonic generator 630.1 and a Continuum Part No. 617-8140 fourth-harmonic generator 630.2. The Nd:YAG laser 11.1' can be either flash-lamp pumped or diode-pumped.

Figure 98B:
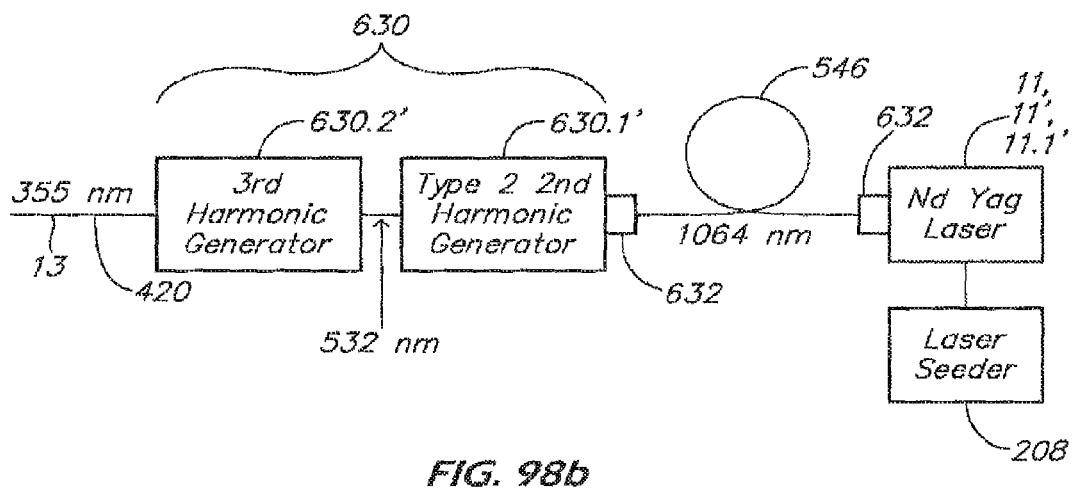

As another example, referring to FIG. 98b, in accordance with a second embodiment, a Nd:YAG laser 11.1' is operatively coupled to a Type 2 second-harmonic generator 630.1' with a fiber optic 546, wherein the Type 2 second-harmonic generator 630.1' provides for converting the 1064 nm laser light from the Nd:YAG laser 11.1' to 532 nm light, which is then operatively coupled over free space to a third-harmonic generator 630.2' that provides for converting the 532 nm light from the Type 2 second-harmonic generator 630.1' to 355 nm light of the first beam of light 420. The Type 2 second-harmonic generator 630.1' and the third-harmonic generator 630.2' comprise crystals, for example, BBO, KDP and LBO, the selection of which depends upon the manufacturer and various factors, e.g. pulse energy. The crystal used in the Type 2 second-harmonic generator 630.1' is cut in accordance with what is known as a Type 2 cut so as to provide for one photon of 532 nm light to be mixed with one photon of 1064 nm light by the third-harmonic generator 630.2' so as to generate a corresponding photon of 355 nm light. For example, in one embodiment, the Nd:YAG laser 11.1' can be a model 8030 manufactured by Continuum, which operates in cooperation with a Continuum Part No. 617-9100 Type 2 second-harmonic generator 630.1' and a Continuum Part No. 617-8020 third-harmonic generator 630.2'. The Nd:YAG laser 11.1' can be either flash-lamp pumped or diode-pumped.

Accordingly, in the first and second embodiments illustrated in FIGS. 98a and 98b respectively, the fundamental 1064 nm laser light from the Nd:YAG laser 11.1' is transmitted via a fiber optic 546 to harmonic generators 630.1, 630.2 or 630.1', 630.2' that can be located remotely relative to the Nd:YAG laser 11.1', for example, in the optical head 422, and ultraviolet light generated by the harmonic generators 630.2 or 630.2' is thereafter transmitted through free space. The 1064 nm laser light transmitted through the fiber optic 546 does not result in any substantial degradation thereof.

As yet another example, referring to FIG. 98c, in accordance with a third embodiment—a modification of either the first or second embodiments,—the Nd:YAG laser 11.1' is operatively coupled to the associated Type 1 630.1 or Type 2 630.1' second-harmonic generator with a first fiber optic 546.1, and the Type 1 630.1 or Type 2 630.1' second-harmonic generator is operatively coupled to the associated fourth— 630.2 or third— 630.2' harmonic generator, respectively, with a second fiber optic 546.2, so that the first fiber optic 546.1 transmits fundamental 1064 nm laser light, and the second fiber optic 546.2 transmits 532 nm laser light, neither of which results in any substantial degradation of the associated first 546.1 or second 546.2 fiber optics.

As yet another example, referring to FIG. 98d, in accordance with a fourth embodiment—a modification of either the first or second embodiments,—the Nd:YAG laser 11.1' is operatively coupled to the associated Type 1 630.1 or Type 2 630.1' second-harmonic generator via free space, and the Type 1 630.1 or Type 2 630.1' second-harmonic generator is operatively coupled to the associated fourth— 630.2 or third— 630.2' harmonic generator, respectively, with a fiber optic 546, so that the fiber optic 546 transmits 532 nm laser light which does not result in any substantial degradation thereof. For example, the Type 1 630.1 or Type 2 630.1' second-harmonic generator could be either attached to, located within, or otherwise a part of the Nd:YAG laser 11.1'.

The fiber optics 546, 546.1, 546.2 used in the first through fourth embodiments of FIGS. 98a-d may comprise either single optical fibers or bundles of optical fibers. An optics assembly 632 operatively associated at each end of the associated fiber optics, i.e. at each of the entrance and exit ends, provides for focusing and/or collimating and/or otherwise shaping the associated beam of laser light into or out of the associated fiber optics 546, 546.1, 546.2 so as to provide for efficiently transferring light from the laser 11', 11.1' to the associated first beam of light 420. The optics assembly 632 may or may not be integrated with the associated fiber optics 546, 546.1, 546.2, and may or may not be hermetically sealed at the associated fiber interface.

Referring to FIG. 61, various LIDAR systems 24", 24$^{ix'}$, 24$^{ix''}$, 24$^{ix'''}$, 24$^{ix''''}$ can be used in a variety of applications, including flight control or flight data monitoring, for example, for an aircraft 400 or UAV 402; or monitoring atmospheric or weather conditions from an aircraft 400.1, 400.2, UAV 402, balloon 404, satellite 406, or ground-based LIDAR system 408, For example, the aircraft 400, 400.1 and UAV 402 illustrated in FIG. 61 each incorporate a LIDAR system 24" that incorporates three lines-of-sight 23' so as to provide for measuring an associated relative wind vector in addition to other air data products. Generally the LIDAR system 24" can be adapted for airframe applications which, for example, might otherwise incorporate a pitot-static tube for measuring air speed. In addition to air speed, the LIDAR system 24" provides for optically measuring, or calculating from optical measurements, a substantial quantity of air data products, and can be adapted to detect wind shear, wake vortices, clear air turbulence, and engine stall (unstart) conditions. Common air data products include, but are not limited to, Mach number, true airspeed, calibrated airspeed, vertical speed, static density, static air temperature, sideslip, angle of attack, pressure altitude, and dynamic pressure. The air data products can be used directly by an aircraft flight computer for flight control purposes. The LIDAR system 24" provides for an airframe-independent design that can be flush-mounted to the skin of the airframe, e.g. without protrusions that otherwise might increase the airframe's radar cross section and drag, so as to provide for relatively low observability and drag. The LIDAR system 24" can operate at substantial angles of attack. For example, a properly-configured LIDAR system 24" can operate at a 90 degree angle of attack. The LIDAR system 24" can be adapted to a variety of airframes, for example, including highly maneuverable aircraft and hoverable aircraft. The LIDAR system 24" provides for an airframe-independent design that can be relatively inexpensive to calibrate, recalibrate or service.

As another example, the aircraft 400, 400.1, 400.2, UAV 402, and balloon 404 illustrated in FIG. 61 each incorporate a LIDAR system 24" adapted with a plurality of lines-of-sight 23', so as to provide for substantially simultaneously measuring air data products from one or more interaction regions 17 along each of the associated lines-of-sight 23'. For example, the first aircraft 400.1 incorporates two lines-of-sight 23' distributed transversely with respect to the associated direction of travel thereof, and the second aircraft 400.2 incorporates five lines-of-sight 23' distributed transversely with respect to the associated direction of travel thereof, so as to provide for automatically acquiring a substantial amount of atmospheric data (e.g. density, temperature and wind velocity) that can be used for either monitoring or predicting weather, or for monitoring particular emissions into the atmosphere. In accordance with another embodiment, the UAV 402 is illustrated with lines-of-sight 23' substantially along the direction of travel thereof, which can provide for automatically acquiring a substantial amount of atmospheric data (e.g. density, temperature and wind velocity) that, for example, can be used for either monitoring or predicting weather dynamics, or for monitoring the dynamics of particulate emissions into the atmosphere. Generally, the orientation of the plurality of lines-of-sight 23' relative to the associated vehicle or the associated direction of travel thereof is not limiting, i.e. either other orientations or a combination of orientations may be used.

As yet another example, the satellite 406 and the ground-based LIDAR system 408 illustrated in FIG. 61 each incorporate a LIDAR system 24" adapted with a line of projection 424 that is directed respectively downwards or upwards into the atmosphere so as to provide for measuring air data products from one or more interaction regions 17 along each of the associated one or more lines-of-sight 23', for example, so as to provide for automatically acquiring a substantial amount of atmospheric data (e.g. density, temperature and wind velocity) that can be used for either monitoring or predicting weather, or for monitoring particular emissions into the atmosphere.

Figure 99:
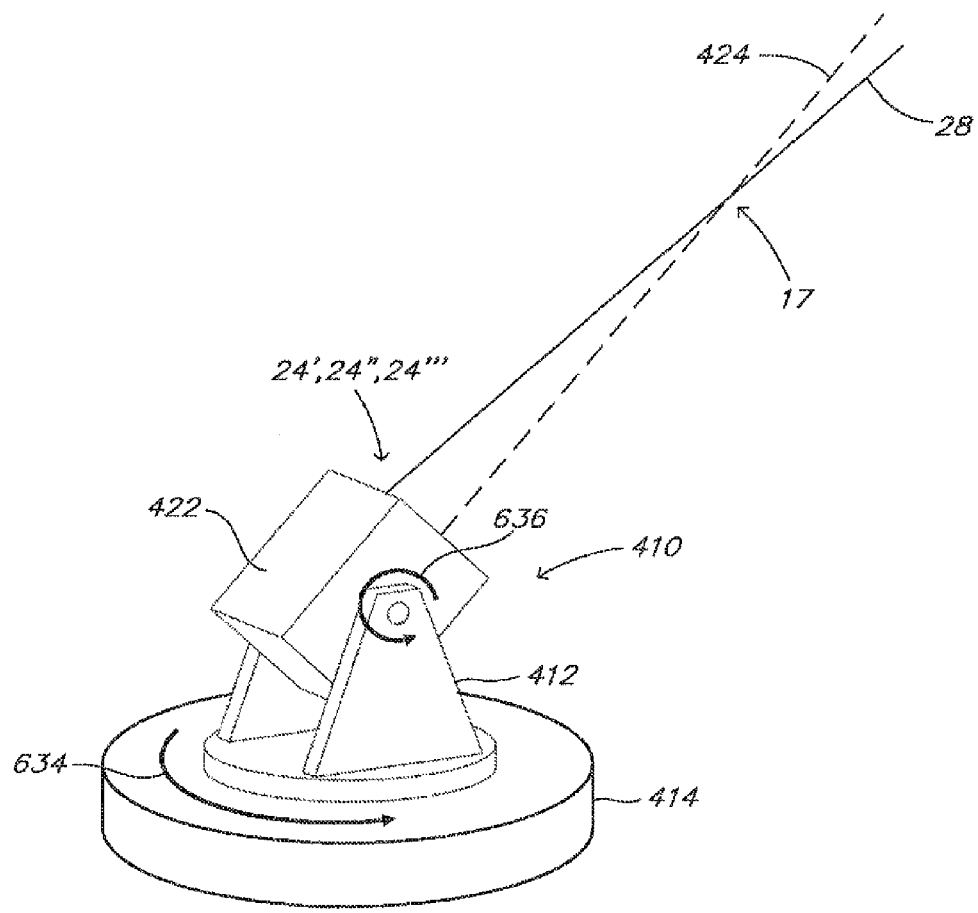

Referring to FIG. 99, and as illustrated in FIG. 61 for the satellite 406 and the ground-based LIDAR system 408, the LIDAR system 24" may be operatively associated with a gimbal mechanism 410 comprising an azimuthally-rotatable platform 412 which is adapted to pivotally support an optical head 422 so as to provide for an elevational rotation thereof relative a base 414 to which the azimuthally-rotatable platform 412 is operatively associated. Accordingly, the azimuthally-rotatable platform 412 is adapted to rotate relative to the base 414, for example, responsive to an associated motor drive system, so as to define an associated azimuth angle 634 of the optical head 422, and the optical head 422 is adapted to rotate relative to the azimuthally-rotatable platform 412, for example, responsive to an associated motor drive system, so as to define an associated elevation angle 636 of the optical head 422. Accordingly, coordinated rotations of the optical head 422 in both azimuth 634 and elevation 636 angle provide for acquiring associated optical air data from associated interaction regions 17 of an associated spherical shell of the atmosphere 20. The LIDAR system 24" may provide for a plurality or range of interaction regions 17 associated with the associated second beam of light 28 so as to provide for sampling optical air data from a corresponding plurality of spherical shells. Referring to FIG. 61, in one embodiment illustrated in cooperation with the ground-based LIDAR system 408, the laser 11', Fabry-Pérot interferometer 31' and detection system 34 of the LIDAR system 24" may be mounted on the associated azimuthally-rotatable platform 412 so as to rotate therewith, wherein the laser 11' and Fabry-Pérot interferometer 31' are operatively coupled to the associated optical head 422 with an associated fiber-optic bundle 99. The base 414 of the gimbal mechanism 410 of the ground-based LIDAR system 408 is adapted to provide for mobile operation thereof. The base 414 of the gimbal mechanism 410 of the satellite 406 is operatively coupled to the satellite 406 so as to provide for scanning the optical head 422, for example, as the satellite 406 travels in its orbit.

It should be understood that any of the LIDAR systems 24', 24" illustrated in FIG. 61 can be operatively associated with any of the associated platforms (i.e. aircraft 400.1, 400.2, UAV 402, balloon 404, satellite 406, or ground-based LIDAR system 408) or other platforms. For example, the satellite 406 could incorporate a LIDAR system 24" comprising a plurality of lines-of-sight 23' arranged transverse to the direction of travel. For example, in one embodiment, eight lines-of-sight 23' are contemplated. As another example, the balloon 404 could incorporate a LIDAR system 24" with a single line of projection 424, possibly operatively associated with a gimbal mechanism 410. As another example, an optical head 422 operatively associated with a gimbal mechanism 410 could incorporate a plurality of lines-of-sight 23' and could provide for either range-resolved imaging or a plurality of interaction regions 17 and a plurality of associated scattered light signals 30' associated with a given line of projection 424.

The aforementioned International Application Serial No. PCT/US10/31965 filed on 21 Apr. 2010, entitled Atmospheric measurement system illustrates additional embodiments of LIDAR systems 24 that may be incorporated in the atmospheric measurement system 10.

Figure 100:
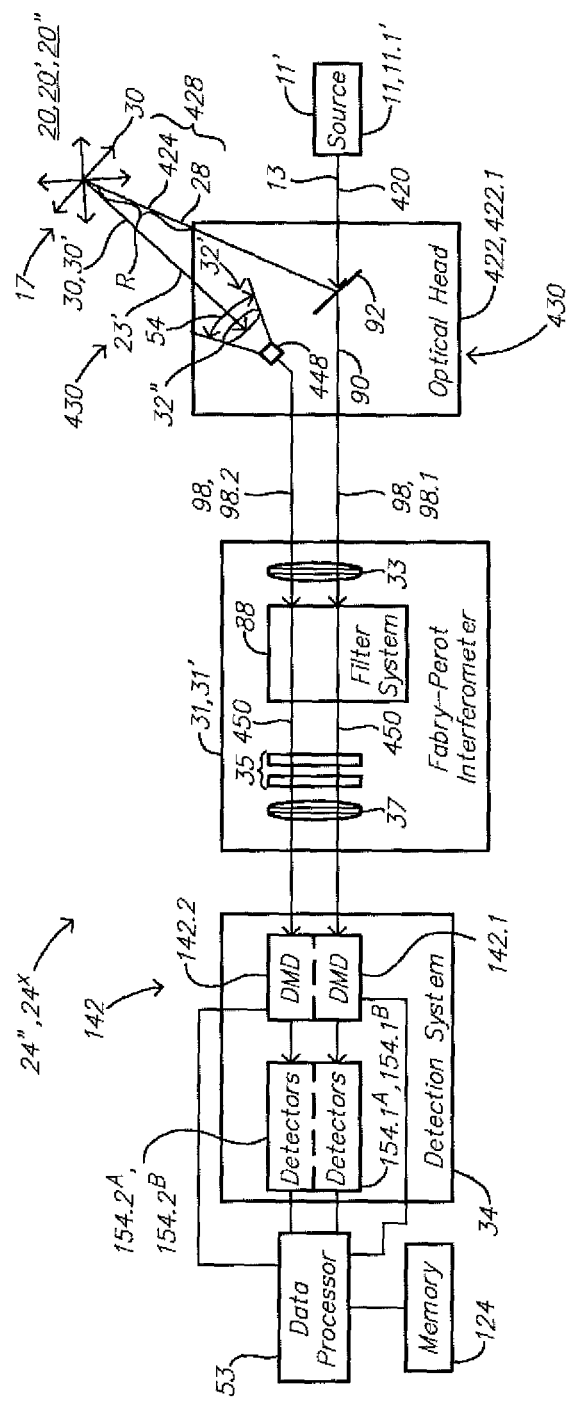

Referring to FIG. 100, in accordance with a tenth aspect, a LIDAR system 24", 24$^x$ incorporates a light source 11, for example, a laser 11', that generates a first beam of light 420, of substantially monochromatic light 13, which is split into a reference beam portion 90 and one or more second beams of light 28 by a beam splitter optic 92 in an optical head 422. The optical head 422 provides for directing the one or more second beams of light 28 into an atmosphere 20 within sight thereof, and further incorporates a corresponding one or more telescopes 32', each associated with one of the one or more second beams of light 28, wherein each of the telescopes 32' provides for receiving scattered light 30 that is scattered by the atmosphere 20 from a corresponding interaction region 17 therein defined by the intersection of the associated second beam of light 28 with an associated field-of-view 54 of the corresponding telescope 32'. Each second beam of light 28 and its associated telescope 32' define a channel, and neither the number of channels, nor the geometry of the channels in relation to each other, is limiting.

For example, in one embodiment, the first 420 and second 28 beams of light comprise ultraviolet (UV) laser light at a wavelength of about 266 nm that is emitted into the atmosphere 20 by one or more associated second beam of light 28, and the associated one or more telescopes 32' provide for detecting the return from scattering of the one or more second beams of light 28 by atmospheric molecules and aerosols. A wavelength of about 266 nm, being invisible to the human eye and substantially absorbed by the atmosphere, is beneficial for its stealth, eye safety and molecular scattering properties. There is very little natural background light due to absorption of most natural 266 nm light by ozone and molecular oxygen. Ultraviolet light at about 266 nm is readily absorbed by glass and plastic, such as used in aircraft wind screens, which provides for improved eye safety. The particular operating wavelength of the LIDAR system 24" is not limiting, and it should be understood that any optical wavelength that interacts with that which is being sensed in the associated interaction region 17 may be used. For example, any of the above described light sources 11 may be used.

The LIDAR system 24" is a laser remote sensing instrument that senses within the volume of the interaction region 17. The range R to the interaction region 17, e.g. the distance thereof from the optical head 422, is defined by the geometry of the associated second beam of light 28 and the corresponding telescope 32' as embodied in the optical head 422. The range R within the interaction region 17 can optionally be further resolved with associated temporal range gating, or range-resolved imaging, of the associated scattered light signals 30' if desired or necessary for a particular application.

The LIDAR system 24" is responsive substantially only to scattering from the interaction region 17 where the field-of-view 54 of the detecting telescope 32' and the second beam of light 28 overlap, and the geometry of the optical head 422 can be adapted to locate the interaction region 17 at substantially any distance, e.g. near or far, from the optical head 422 provided there is sufficient scattered light 30 to be subsequently processed. For example, with the optical head 422 adapted to locate the interaction region 17 relatively far from the optical head 422, e.g. so as to be substantially not influenced by any turbulence proximate thereto, there would be substantially no signal from any associated near-field region 428 relatively proximate thereto.

In accordance with a first aspect, each channel of the optical head 422, 422.1 is adapted as a biaxial system 430 in accordance with that illustrated in FIG. 66 and described hereinabove, wherein, for a given channel, the associated second beam of light 28 and telescope 32' do not share a common axis.

The telescope 32' comprises an effective lens 32", and the scattered light signal 30' collected thereby is collected by the final light-collecting element 448 thereof into a fiber optic 98 that directs the returned photons to associated portions of a Fabry-Pérot interferometer 31' and an associated detection system 34 for processing thereby. The reference beam portion 90 from the laser 11' and beam splitter optic 92 is directed to a separate portion of the Fabry-Pérot interferometer 31' and an associated detection system 34 for simultaneous processing thereby.

The reference beam portion 90 and the scattered light signal 30' from the effective lens 32" are each collimated by a collimating lens 33 of the Fabry-Pérot interferometer 31' and then filtered by a filter system 88 which, for example, as illustrated in FIG. 65a, incorporates eight bandpass filter mirrors 88' having associated filter pass bands centered about the operating frequency of the laser 11'—e.g. about 266 nm for the above-described embodiment—which provides for filtering out associated background light. The filter system 88 exhibits high out-of-band rejection, as well as low in-band attenuation, and the bandwidth of the filter system 88 is sufficiently narrow so as to substantially filter or remove components of solar radiation or stray light in the collected scattered light signals 30', yet sufficiently broad so as to be substantially larger than the bandwidth of the thermally-broadened spectrum in combination with the largest expected associated Doppler shift. For example, in one embodiment, the filter system 88 is adapted so as to provide for maximum filtering of light frequencies that are outside the frequency band of interest, e.g. greater than about 2 nanometers above or below the nominal center frequency of the first beam of light 420.

Referring to FIGS. 100, 65a, 68, 69a and 69b the light signals 450 from the filter system 88 are input to a Fabry-Pérot etalon 35 of the Fabry-Pérot interferometer 31', which provides for generating a fringe pattern 452 responsive to the optical frequency of the associated light signals 450, which optical frequency can exhibit a Doppler shift responsive to a relative velocity of the atmosphere 20 within the interaction region 17 from which the associated scattered light 30 is scattered. The Fabry-Pérot etalon 35 of the Fabry-Pérot interferometer 31' comprises first 41 and second 43 partially-reflective surfaces either of separate planar optical windows 55 or of a corresponding solid optical element 61—which are parallel to one another and separated by a fixed gap 45, and located between the collimating lens 33 and associated imaging optics 37. Light 454 at a focal plane 33.1 of the collimating lens 33 is substantially collimated thereby, and the angles at which the light 454 is passed through the Fabry-Pérot etalon 35 is dependent upon the optical frequency of the light 454, which, referring to FIG. 69a, becomes imaged as a circular fringe pattern 65—also known as Haidinger fringes—comprising a plurality of concentric circular fringes 65' in the rear focal plane 37.2 of the imaging optics 37.

Referring to FIG. 69a, for a fully-illuminated Fabry-Pérot etalon 35, the resulting circular fringe pattern 65 is in the form of closed concentric circles centered about the optic axis 39 of the imaging optics 37.

Referring to FIG. 68, the LIDAR system 24" provides for an efficient use of the Fabry-Pérot etalon 35 by simultaneously processing a plurality of different channels of light 454 with a single, common Fabry-Pérot etalon 35. In accordance with the tenth aspect of the LIDAR system 24", $24^x$ illustrated in FIG. 100, a single Fabry-Pérot etalon 35 is used with two channels of light 454, i.e. a reference channel 456 from the reference beam portion 90, and a scatter signal channel 458 from the final light-collecting element 448, each via a corresponding respective fiber optic 98, 98.1, 98.2 that receive light from the reference beam portion 90 and from each of the effective lens 32", respectively, and illuminate corresponding portions of the Fabry-Pérot etalon 35 from respective off-axis locations 460.1 and 460.3 in the focal plane 33.1 of the collimating lens 33, producing associated images of partial circular fringe patterns 65.1 and 65.3, for example, as illustrated in FIGS. 68 and 69b.

As described hereinabove, the signal from the scatter signal channel 458 is substantially simultaneously processed together with a signal from the reference channel 456 so as to provide for calibrating, and maintaining the calibration of, the LIDAR system 24", and so as to provide for determining the associated air data products such as the speed, temperature and density of the atmosphere 20. This provides for an inherent self-calibration of the associated measurements or quantities derived therefrom. If wavelength drift of the first beam of light 420 is not otherwise accounted for in the data, then errors can arise when making a measurement of the Doppler shift and resulting wavelength shift of the scatter signal channel 458. The LIDAR system 24" provides for automatically compensating for wavelength drift of the first beam of light 420 from the data because each measurement from the scatter signal channel 458 is corrected using a corresponding measurement from the reference channel 456 associated with the reference beam portion 90.

The scattered light signal 30' collected by the telescope 32', and the reference beam portion 90, are transmitted to the Fabry-Pérot interferometer 31' by the associated fiber optics 98.1 and 98.2 and are each simultaneously processed by a separate portion of a Fabry-Pérot interferometer 31', wherein the scattered light signals 30' and reference beam portion 90 passing through the Fabry-Pérot interferometer 31'. The scattered light signal 30' and reference beam portion 90 are each collimated by a collimating lens 33, then filtered by a filter system 88 as described hereinabove, and then processed by the associated Fabry-Pérot etalon 35, the output of which is imaged by associated imaging optics 37 as associated circular fringe patterns 65.1 and 65.2 onto a corresponding digital micromirror device (DMD) 142.1, 142.2 of an associated detection system 34, each under control of a data processor 53 incorporating or in communication with an associated memory 124, which provide for selectively reflecting portions of the associated circular fringe patterns 65.1 and 65.2 onto corresponding pair of associated photodetectors $154.1^A$, $154.1^B$, $154.2^A$, $154.2^B$. The signals from the photodetectors $154.1^A$, $154.1^B$, $154.2^A$, $154.2^B$ are then processed by the data processor 53, which provides for the data processor 53 to determine the associated atmospheric data 36 therefrom as described hereinabove in accordance with FIGS. 24a-41, wherein the separate circular fringe patterns 65.1 and 65.2 of the reference 456 and scatter signal 458 channels are separately detected by corresponding separate pairs of photodetectors $154.1^A$, $154.1^B$ and, $154.2^A$, $154.2^B$. The Fabry-Pérot interferometer 31' and the associated detection system 34 may be mounted within a common housing.

Figure 101:
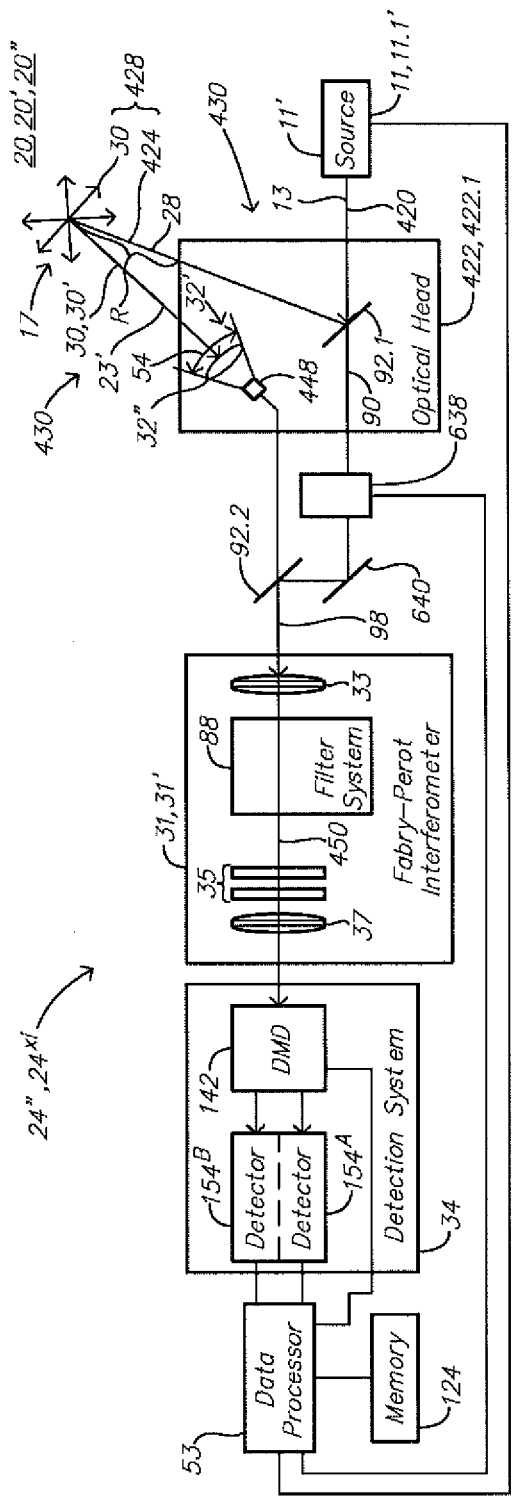

Referring to FIG. 101, an eleventh aspect of a LIDAR system 24", $24^{xi}$ incorporates a light source 11, for example, a laser 11', that generates a first beam of light 420, of substantially monochromatic light 13, which is split into a reference beam portion 90 and one or more second beams of light 28 by a first beam splitter optic 92.1 in an optical head 422. The optical head 422 provides for directing the one or more second beams of light 28 into an atmosphere 20 within sight thereof, and further incorporates a corresponding one or more telescopes 32', each associated with one of the one or more second beams of light 28, wherein each of the telescopes 32' provides for receiving scattered light 30 that is scattered by the atmosphere 20 from a corresponding interaction region 17 therein defined by the intersection of the associated second beam of light 28 with an associated field-of-view 54 of the corresponding telescope 32'. Each second beam of light 28 and its associated telescope 32' define a channel, and neither the number of channels, nor the geometry of the channels in relation to each other, is limiting.

As with the tenth aspect, the range R to the interaction region 17, e.g. the distance thereof from the optical head 422, is defined by the geometry of the associated second beam of light 28 and the corresponding telescope 32' as embodied in the optical head 422, and the range R within the interaction region 17 can optionally be further resolved with associated temporal range gating, or range-resolved imaging, of the associated scattered light signals 30' if desired or necessary for a particular application. Furthermore, the associated optical head 422, 422.1, 422.2 may be adapted either in accordance with the above-described first or second aspects thereof.

The LIDAR system 24", $24^{xi}$ is responsive substantially only to scattering from the interaction region 17 where the field-of-view 54 of the detecting telescope 32' and the second beam of light 28 overlap, and the geometry of the optical head 422 can be adapted to locate the interaction region 17 at substantially any distance, e.g. near or far, from the optical head 422 provided there is sufficient scattered light 30 to be subsequently processed.

The telescope 32' comprises a effective lens 32", and the scattered light signal 30' collected thereby is collected by the final light-collecting element 448 thereof into a fiber optic 98 that directs the returned photons of the associated scatter signal channel 458 through a second beam splitter optic 92.2 into a Fabry-Pérot interferometer 31', or an associated portion thereof, for subsequent detection by an associated detection system 34.

For at least one scatter signal channel 458, the reference beam portion 90 from the light source 11 and first beam splitter optic 92.1 is directed through a shutter 638 and reflected off a first surface mirror 640 and then off the second beam splitter optic 92.2 and into the Fabry-Pérot interferometer 31', or the same portion thereof as the corresponding scatter signal channel 458, for detection by the associated detection system 34. The shutter 638 is controlled by the data processor 53, which also control the light source 11 or a shutter associated therewith, so as to provide for time multiplexing the reference 456 and scatter signal 458 channels through the Fabry-Pérot interferometer 31' and associated detection system 34, for at least one scatter signal channel 458. Accordingly, in operation, the light source 11, or an associated shutter, is periodically activated so as to cause the associated first beam of light 420 to be emitted thereby, a portion of which is reflected as at least one second beam of light 28 into the atmosphere 20 by the first beam splitter optic 92.1, a remaining portion of which forms the associated reference beam portion 90. The shutter 638 is activated by the data processor 53 in synchronism with the light source 11, or shutter associated therewith, so as to provide for immediately directing the reference beam portion 90 into the Fabry-Pérot interferometer 31' and associated detection system 34. The shutter 638 is then later deactivated by the data processor 53 before the scattered light signal 30' of the scatter signal channel 458 reaches the second beam splitter optic 92.2. For example, for a interaction region 17 about 300 meters from the optical head 422, the shutter 638 would be gated on for about one microsecond, during which time the detection system 34 would provide for detecting the reference channel 456, after which, the detection system 34 would provide for detecting the corresponding scatter signal channel 458.

Referring to FIGS. 102a-102c, there is illustrated a twelfth aspect of a LIDAR system 24", 24$^{xii}$ that is substantially the same as the tenth aspect of the LIDAR system 24", 24$^{xii}$ illustrated in FIG. 100, as described hereinabove, except that the twelfth aspect of the LIDAR system 24", 24$^{xii}$ incorporates a plurality of scattered light signals 30' from a plurality of associated final light collecting elements 448, 448.1, 448.2. In the embodiment illustrated in FIGS. 102a-102c, two scattered light signals 30', 30.1', 30.2' from corresponding separate final light collecting elements 448, 448.1, 448.2 associated with two separate telescopes 32', 32.1', 32.2' along corresponding associated lines-of-sight 23.1', 23.2' are directed to the Fabry-Pérot interferometer 31' by corresponding fiber optics 98, 98.1, 98.2 as associated scatter signal channels 458, 458.1, 458.2 that are imaged in two corresponding regions 642.1, 642.2 at the output focal plane 31.2' of the Fabry-Pérot interferometer 31' corresponding to the associated images 114' of the associated scattered light signals 30', 30.1', 30.2'. The Fabry-Pérot interferometer 31' generates a first scatter fringe patterns 47.1 at the output focal plane 31.2' of the of the Fabry-Pérot interferometer 31' from the first scattered light signal 30.1', and generates a second scatter fringe pattern 47.2 at the output focal plane 31.2' of the of the Fabry-Perot interferometer 31' from the second scattered light signal 30.2'. Similarly, the reference beam portion 90 is also directed to the Fabry-Pérot interferometer 31' as a reference light signal 105 by corresponding fiber optic 98, 98.3 as an associated reference channel 456 that is imaged in a corresponding region 642.3 at the output focal plane 31.2' of the Fabry-Pérot interferometer 31' corresponding to an associated image 114" of the associated reference light signal 105, wherein the Fabry-Pérot interferometer 31' generates a reference fringe pattern 104 at the output focal plane 31.2' of the of the Fabry-Pérot interferometer 31' from the reference light signal 105.

For example, FIG. 102b illustrates the images of the scattered light signals 30', 30.1', 30.2' and the reference light signal 105 at the imaging plane 31.2$^{i'}$ of the of the Fabry-Pérot interferometer 31' absent the Fabry-Pérot interferometer 31', and FIG. 102c illustrates the resulting associated first 47.1 and second 47.2 scatter fringe patterns and the reference fringe pattern 104 with the Fabry-Pérot interferometer 31' in place.

In accordance with the twelfth aspect, the LIDAR system 24", 24$^{xii}$ first calibrates the Fabry-Pérot etalon 35 by analyzing the reference fringe pattern 104, and then generates measures of line-of-sight relative wind velocity U, static temperature Temp, molecular counts MolCounts, aerosol counts AeroCounts, and background counts BackCounts from the scatter 47.1, 47.2 and reference 104 fringe patterns, as described hereinabove for the tenth aspect of the LIDAR system 24", 24$^x$ to determine the measures of line-of-sight relative wind velocity U, static temperature Temp, molecular counts MolCounts, aerosol counts Aero Counts, and background counts BackCounts responsive thereto for each separate scatter fringe pattern 47.1, 47.2, in accordance with either the first or second embodiments of the third aspect of the associated detection system 34.3, 34.3', 34.3".

More particularly, when analyzing the reference fringe pattern 104, the micromirrors 144 not illuminated thereby are set to the third pixel mirror rotational state 152 so that only light from the reference fringe pattern 104 is then processed according to the methodology described and illustrated hereinabove, either in accordance with either the first or second embodiments of the third aspect of the associated detection system 34.3, 34.3', 34.3". Furthermore, when analyzing the first scatter fringe pattern 47.1, the micromirrors 144 not illuminated thereby are set to the third pixel mirror rotational state 152 so that only light from that particular first scatter fringe pattern 47.1 is then processed according to the methodology described and illustrated hereinabove, either in accordance with either the first or second embodiments of the third aspect of the associated detection system 34.3, 34.3', 34.3". Finally, when analyzing the second scatter fringe pattern 47.2, the micromirrors 144 not illuminated thereby are set to the third pixel mirror rotational state 152 so that only light from that particular second scatter fringe pattern 47.2 is then processed according to the methodology described and illustrated hereinabove, either in accordance with either the first or second embodiments of the third aspect of the associated detection system 34.3, 34.3', 34.3".

The method of processing the disjoint portions 104', 104"; 47', 47" of the associated reference 104 and scatter 47 fringe patterns for associated reference 456 and scatter signal 458 channels can also be applied in cooperation with other systems that provide for generating the associated disjoint portions 104', 104"; 47', 47" similar to that provided for by one or more digital micromirror devices (DMD) 142 as described hereinabove, but without requiring a digital micromirror device (DMD) 142, as described hereinabove.

For example, the disjoint portions 104', 104"; 47', 47" can be extracted by electronic or software integration of the associated disjoint portions 104', 104"; 47', 47" of the corresponding regions of the reference 104 and scatter 47 fringe patterns to be processed, corresponding to the associated reference 456 and scatter signal 458 channels.

For example, referring to FIGS. 103a-103e, a thirteenth aspect of a LIDAR system 24", 24$^{xiii}$ is substantially the same as the twelfth aspect of the LIDAR system 24", 24$^{xii}$ illustrated in FIG. 102a, except for the incorporation of an additional of scatter signal channel 458 so as to provide for processing an additional scattered light signals 30', 30.3' from an additional interaction region 17, 17.3 within the atmosphere 20, for example, with all the a single common second beam of light 28 projected into the atmosphere 20. More particularly, a first interaction region 17.1 is defined by the intersection of the second beam of light 28 with a first field-of-view 54.1 of an associated first telescope 32.1' having a first effective lens 32.1" in cooperation with a first final light collecting element 448.1 that provides for looking along a first line-of-sight 23.1' at the second beam of light 28; a second interaction region 17.2 is defined by the intersection of the second beam of light 28 with a second field-of-view 54.2 of an associated second telescope 32.2' having a second effective lens 32.2" in cooperation with a second final light collecting element 448.2 that provides for looking along a second line-of-sight 23.2' at the second beam of light 28; and a third interaction region 17.3 is defined by the intersection of the second beam of light 28 with a third field-of-view 54.3 of the second telescope 32.2' and second effective lens 32.2″ in cooperation with a third final light collecting element 448.3 that provides for looking along a third line-of-sight 23.3′ at the second beam of light 28, wherein the third final light collecting element 448.3 is displaced from the associated second final light collecting element 448.2 within the focal plane of the second telescope 32.2′.

A first fiber optic 98.1 directs the returned photons from the first final light collecting element 448.1 as a first scattered light signal 30.1′ to a first location 644.1 in a front focal plane 33.1 of the collimating lens 33; a second fiber optic 98.2 directs the returned photons from the second final light collecting element 448.2 as a second scattered light signal 30.2′ to a second location 644.2 in the front focal plane 33.1 of the collimating lens 33; a third fiber optic 98.3 directs the returned photons from the third final light collecting element 448.3 as a third scattered light signal 30.3′ to a third location 644.3 in the front focal plane 33.1 of the collimating lens 33, and a fourth fiber optic 98.4 directs the returned photons from the reference beam portion 90, for example, as input thereto from an associated graded index (GRIN) lens 100, as a corresponding reference light signal 105 to a fourth location 644.4 in the front focal plane 33.1 of the collimating lens 33, wherein the first 644.1, second 644.2, third 644.3 and fourth 644.4 locations are at different arbitrary radial and aziumthal locations relative to the optic axis of the imaging optics 37 of the Fabry-Pérot interferometer 31′. The Fabry-Pérot interferometer 31′ generates a first scatter fringe patterns 47.1 at the output focal plane 31.2′ of the of the Fabry-Pérot interferometer 31′ from the first scattered light signal 30.1′, generates a second scatter fringe pattern 47.2 at the output focal plane 31.2′ of the of the Fabry-Pérot interferometer 31′ from the second scattered light signal 30.2′, and generates a third scatter fringe pattern 47.3 at the output focal plane 31.2′ of the of the Fabry-Pérot interferometer 31′ from the third scattered light signal 30.3′ Similarly, the Fabry-Pérot interferometer 31′ generates a reference fringe pattern 104 at the output focal plane 31.2′ of the of the Fabry-Pérot interferometer 31′ from the reference light signal 105.

For example, FIG. 103*b* illustrates the images of the scattered light signals 30′, 30.1′, 30.2′, 30.3′ and the reference light signal 105 at the imaging plane 31.2$^{i″}$ of the of the Fabry-Pérot interferometer 31′ absent the Fabry-Pérot interferometer 31′, and FIG. 103*c* illustrates the resulting associated first 47.1, second 47.2 and third 47.3 scatter fringe patterns and the reference fringe pattern 104 with the Fabry-Pérot interferometer 31′ in place, at corresponding respective regions 642.1, 642.2, 642.3 and 642.4 in the at the output focal plane 31.2′ of the Fabry-Pérot interferometer 31′ corresponding to the associated images 30″ of the associated scattered light signals 30′, 30.1′, 30.2′, 30.3′ and an associated image 114″ of the associated reference light signal 105, respectively.

The detection system 34 of the thirteenth aspect of the LIDAR system 24‴, 24$^{xiii}$ comprises a CCD detection system 34.1′—generally an electronic image capture device—that provides for capturing an image 646 of the first 47.1, second 47.2 and third 47.3 scatter fringe patterns and the reference fringe pattern 104 from the imaging plane 31.2$^{i″}$ of the Fabry-Pérot interferometer 31′. For example, the image 646 may then processed as described hereinabove in accordance with any of the processes illustrated in FIGS. 42*a*-45.

Alternatively, the first 47.1, second 47.2 and third 47.3 scatter fringe patterns and the reference fringe pattern 104 from a associated circular fringe patterns 65 may be physically azimuthally compressed into the corresponding linear fringe patterns 464.1, 464.2, 464.3 and 464.4 prior to image capture by the associated detection system 34 by using circle-to-line interferometer optic (CLIO) elements 128, 468 for each of the first 47.1, second 47.2 and third 47.3 scatter fringe patterns and reference fringe pattern 104 to be compressed, for example, as described hereinabove and illustrated in FIGS. 70-77*b* and FIGS. 84-88.

Further alternatively, a holographic optical element 128′ may be adapted to transform the arcuate fringes 49′ into corresponding linear distributions of light, for example, in accordance with the teachings of U.S. Pat. No. 6,613,908, which is incorporated herein by reference in its entirety.

Each telescope 32′ comprises a effective lens 32″, and the scattered light signal 30′ collected thereby is collected by the final light-collecting element 448 thereof into a corresponding fiber optic 98.2, 98.3, 98.4 that directs the returned photons to associated portions of a Fabry-Pérot interferometer 31′ and an associated detection system 34 for processing thereby. The reference beam portion 90 from the light source 11 and beam splitter optic 92 is separately collected by a separate final light-collecting element 448 into a fiber optic 98.1 directed to a separate portion of the Fabry-Pérot interferometer 31′ and an associated detection system 34 for simultaneous processing thereby. For example, the final light-collecting elements 448 of the telescopes 32.1′, 32.2′ and 32.3′ may comprise either a graded index (GRIN) lens 100 or an aspheric lens. In one embodiment, the associated fibers of the four fiber optics 98.1, 98.2, 98.3 and 98.4 are bundled together in a fiber-optic bundle 99 which operatively couples the light source 11 and optical head 422 to the Fabry-Pérot interferometer 31′. The use of fiber optics 98.1, 98.2, 98.3 and 98.4 and/or a fiber-optic bundle 99 provides for simplifying the alignment of the Fabry-Pérot interferometer 31′ with the telescopes 32.1′, 32.2′ and 32.3′ and with the reference beam portion 90 from the light source 11. Furthermore a separate fiber optic 98 may be used to operatively couple the light source 11 to the optical head 422, either directly from the output of the light source 11 to the optical head 422—the latter of which could be adapted in an alternative embodiment of an optical head 422′ to incorporate the first beam splitter optic 92.1,—or from the first beam splitter optic 92.1 to the optical head 422, or both, so as to provide for flexibility in packaging the optical head 422 in relation to the light source 11 so as to provide for mounting the light source 11 in a more benign and stable environment within the aircraft. A fiber optic 98 interconnecting the light source 11 with the optical head 422 also provides for precise alignment of the associated first beam of light 420 with the optical head 422, and simplifies associated installation and maintenance of the associated components thereof.

Referring to FIG. 104, a fourteenth aspect of a LIDAR system 24‴, 24$^{xiv}$ incorporated in a third aspect of an atmospheric measurement system 10$^{iii}$ incorporates a light source 11 that provides for generating light 648 that is projected into the atmosphere 20 as a beam of light 28 through and by associated source optics 15. For example, the source optics 15 may comprise a lens assembly 15′ that provides for the width and divergence of the beam of light 28, and a suitable location of the associated beam waist thereof, so as to illuminate an interaction region 17 within the atmosphere 20 that is detectable by the LIDAR system 24‴, wherein the beam width within the interaction region 17 establishes the associated transverse spatial resolution limit of the LIDAR system 24‴. For example, referring to FIG. 1*b*, the source optics 15 may be configured so as to provide for a pencil-like beam of light 28$^P$ having a limited width w and depth d, for example, of circular or elliptical cross-section, so as to limit the associated width w and depth d of the associated interaction region 17. As another example, referring to FIG. 1c, the source optics 15 may be configured so as to provide for a sheet-like beam of light 28$^S$—for example, using source optics 15 comprising cylindrical optics—having a limited depth d but an extended width w, for example, so as provide for an associated interaction region 17 with a corresponding extended width w, so as to provide for probing extending regions of the atmosphere 20.

A set of receive optics 32, for example, a telescope 32', laterally offset from the beam of light 28, provides for imaging a portion of the beam of light 28 onto an image plane 650, so as to provide for a one-to-one mapping of measurement volumes 52 within the beam of light 28 and corresponding associated regions or points 21 in the image plane 650. More particularly, in accordance with one aspect, the beam of light 28 illuminates molecules 20' or aerosols 20" of the atmosphere 20, or a combination thereof, within the interaction region 17, which in turn scatter the light 648 of the beam of light 28. The resulting scattered light 30 within the field-of-view 54 of the receive optics 32 is collected thereby and imaged onto the image plane 650. The receive optics 32 is laterally offset from and points towards the beam of light 28, so that the optic axis 23 of the receive optics 32 is inclined relative to the optic axis 25 of the beam of light 28 at an associated parallax angle θ. Accordingly, each measurement volume 52 of the beam of light 28 imaged onto a corresponding region or point 21 on the image plane 650 corresponds to a different nominal range R from the image plane 650 to a point 27 on the optic axis 25 of the beam of light 28 associated with the corresponding measurement volume 52. Accordingly, different regions or points 21 on the image plane 650 correspond to different nominal ranges R to the beam of light 28, and therefore correspond to different nominal ranges R to the associated measurement volumes 52 thereof within the interaction region 17. For example, as illustrated in FIG. 104, a closest measurement volume 52.1 of the beam of light 28 at a first interaction region 17.1 within the field-of-view 54 of the receive optics 32 located at a closest nominal range $R_{MIN}$ from the image plane 650 is imaged as a corresponding first region or point 21.1 on the image plane 650, a farthest measurement volume 52.2 of the beam of light 28 at a second interaction region 17.2 within the field-of-view 54 of the receive optics 32 located at a farthest nominal range $R_{MAX}$ from the image plane 650 is imaged as a corresponding second region or point 21.2 on the image plane 650, and an intermediate measurement volume 52.3 of the beam of light 28 at a third interaction region 17.3 within the field-of-view 54 of the receive optics 32 located at an intermediate range $R_{MID}$ from the image plane 650 is imaged as a corresponding third region or point 21.3 on the image plane 650. Furthermore, scattered light 30 from different measurement volumes 52, 52.1, 52.2, 52.3 is imaged onto the image plane 650 at corresponding different angles of incidence relative thereto. With different regions or points 21, 21.1, 21.2, 21.3 in the image plane 650 corresponding to different associated nominal ranges R, the image plane 650 is oriented relative to the receive optics 32 in accordance with the Scheimpflug condition—whereby the optic axis 25 of the beam of light 28, the plane 204 of the effective lens 32" of the receive optics 32 and the image plane 650 all interest at a common point of intersection 206, also known as a Scheimpflug intersection—so that each different region or point 21, 21.1, 21.2, 21.3 in the image plane 650 is in best focus. Although three measurement volumes 52, 52.1, 52.2, 52.3 and associated regions or points 21, 21.1, 21.2, 21.3 in the image plane 650 are illustrated in FIG. 104, it should be understood that the number of different measurement volumes 52 and associated regions or points 21 in the image plane 650 is not limiting, and can be of any value greater than or equal to one.

The LIDAR system 24''' incorporates a fourth aspect of a detection system 34, 34.4 comprising a plurality of photodetectors 652, 652.1, 652.2, 652.3 in one-to-one relationship with the regions or points 21, 21.1, 21.2, 21.3 in the image plane 650 associated with the corresponding measurement volumes 52, 52.1, 52.2, 52.3 of the beam of light 28 to be detected within the field-of-view 54 of the receive optics 32, wherein each photodetector 652 is either located at the image plane 650 to receive scattered light 30 directly from the receive optics 32 for the associated measurement volume 52, or indirectly via an associated fiber optic 98, 98.1, 98.2, 98.3 that conducts the scattered light 30 from the each region or point 21, 21.1, 21.2, 21.3 in the image plane 650 to the corresponding photodetector 652, 652.1, 652.2, 652.3. Each photodetector 652 transduces the associated scattered light 30 to a corresponding electronic signal 654, 654.1, 654.2, 654.3 suitable for subsequent processing by either associated signal processing circuitry 656 or an associated signal processor 658. Depending upon the type of light source 11, examples of various possible photodetectors 652 include, but are not limited to, a photo-multiplier tube (PMT), a PIN diode, and avalanche photo diode (APD), a PN junction photodetector, and a photovoltaic photodetector, a charge-coupled device (CCD) or charge injection device (CID); a corresponding arrays of individual photodetectors, for example, photo-conductive, photo-voltaic, photo-emissive, bolometer, or thermopile photodetectors, i.e. generally any device that converts photons to a corresponding electrical signal. The particular detection system 34, 34.4 may be adapted in cooperation with the associated light source 11 so as to provide for increasing the associated signal-to-noise ratio (SNR). For example, in cooperation with a continuous light source 11, a relatively high-sensitivity, low-noise, low-bandwidth detectors can be used, so as to provide for a higher signal-to-noise ratio (SNR) than possible with corresponding relatively higher-bandwidth detectors, so as to provide for relatively more precise associated measurements.

The amplitude or intensity of the light 648 from the light source 11 is modulated either directly by the light source 11, or by a separate light modulator 660, responsive to a modulation signal 662, for example, either an oscillatory 662.1 or repetitive pulse 662.2 signal, for example, either from a separate local oscillator 664, or inherent in the light source 11 Accordingly, the intensity of the beam of light 28 is modulated by the modulation signal 662, and this modulation signal 662 is embedded within, i.e. impressed upon or carried by, the beam of light 28, and by any scattered light 30 that is scattered therefrom upon interaction of the atmosphere 20, or an object therein, therewith. Depending upon the type of light source 11, examples of various possible light modulators 660 include an acousto-optic (AO) modulator and an electro-optic (EO) modulator. Examples of light sources 11 that can be modulated directly include, but are not limited to, a mode-locked laser 11', a Q-switched laser 11', a diode laser 11', and a light-emitting diode (LED).

In accordance with one aspect, LIDAR system 24''' provides for directly detecting scattered light 30 that is scattered off of either molecules 20' of the atmosphere 20, aerosols 20" in the atmosphere 20, or a combination of the two, and for determining from subsequent processing of the associated resulting electronic signals 654, 654.1, 654.2, 654.3, the velocity of the associated molecules 20' or aerosols 20" of the atmosphere 20 in the direction of the optic axis 23 of the receive optics 32. For example, relatively short wavelength light is scattered by molecules 20' of the atmosphere in accordance with Rayleigh scattering. Light can also be scattered by aerosols 20" in the atmosphere in accordance with Mie scattering. Rayleigh scattering generally refers to the scattering of light by either molecules or particles having a size less than about $\frac{1}{10}^{th}$ the wavelength of the light, whereas Mie scattering generally refers to scattering of light by particles greater than $\frac{1}{10}^{th}$ the wavelength of the light. Being responsive to Rayleigh scattering, the LIDAR system 24''' is therefore responsive to the velocity of those molecules 20' in the atmosphere giving rise to the associated scattering of the light detected by the LIDAR system 24'''. Furthermore, the LIDAR system 24''' can provide for operation in clean air, i.e. in an atmosphere with no more than a negligible amount of aerosols 20", depending substantially upon only molecular scatter. If scattered from a moving molecule 20' or aerosol 20", the frequency scattered light 30 is Doppler shifted, which results in a corresponding shift of frequency or phase of the associated modulation signal 662' embedded within the scattered light 30. Accordingly, the Doppler, shift in the frequency or phase of the of the associated modulation signal 662 embedded within the scattered light 30 will depend upon the local velocity of the atmosphere 20 within the interaction region 17 interacting with the beam of light 28, so that the velocity of the associated molecules 20' or aerosols 20" of the atmosphere 20 in the direction of the optic axis 23 of the receive optics 32 can be detected by detecting associated Doppler shift in the frequency or phase of the associated modulation signal 662' embedded within the scattered light 30. The corresponding nominal range R is determined by triangulation apriori from the geometry of the corresponding region or point 21 in the image plane 650, and the relative orientation of the optic axes 23, 25 of the receive optics 32 and beam of light 28 respectively, wherein each region or point 21, 21.1, 21.2, 21.3 in the image plane 650 corresponds to a distinct range bin 26, 26.1, 26.2, 26.3 associated with corresponding measurement volumes 52 of the beam of light 28 within the field-of-view 54 of the receive optics 32.

The light source 11 provides for generating a sufficient amount of light 648 so as to provide for a sufficient amount of scattered light 30, that when imaged by the receive optics 32, is detectable by the detection system 34, 34.4 with a sufficient signal-to-noise ratio (SNR) so that the resulting atmospheric data 36, i.e. velocity, determined therefrom is accurate within a given accuracy threshold and provides for an information temporal bandwidth that is within a given temporal bandwidth threshold. For example, the light source 11 could comprise one or more lasers, broadband optical sources such as light emitting diodes (LEDs), flash lamps, for example, xenon flash lamps, sodium lamps or mercury lamps, or white light sources that can be modulated with internal or external modulation. The light source 11 may be either continuous or pulsed, and need not necessarily be coherent. The particular operating wavelength of the LIDAR system 24''' is not limiting. For example, any optical wavelength that interacts with that which is being sensed in the associated interaction region 17 may be used.

For example, in one embodiment, the light 648 comprises ultraviolet (UV) laser light at a wavelength of about 266 nm that is generated using a laser 11' light source 11. A wavelength of about 266 nm, being invisible to the human eye and substantially absorbed by the atmosphere, is beneficial for its stealth, eye safety and molecular scattering properties. There is relatively little natural background light at this frequency due to absorption of most natural 266 nm light by ozone and molecular oxygen. Ultraviolet light at about 266 nm is readily absorbed by glass and plastic, such as used in aircraft wind screens, which provides for improved eye safety. For example, a Nd:YAG laser 11.1' can operate at relatively high power levels so as to provide sufficiently intense illumination so as to provide for relatively long range atmospheric sensing applications. An Nd:YAG laser 11.1' has a fundamental wavelength of 1064 nm, from which shorter wavelengths/higher frequencies may be generated using one or more harmonic generators operatively associated with or a part of the Nd:YAG laser 11.1'. For example, a second-harmonic generator could be used to convert the fundamental 1064 nm light to second-harmonic 532 nm light which could then be transformed with either a third- or fourth-harmonic generator to generate associated 355 nm or 266 nm light respectively. For example, these second-, third- and/or fourth-harmonic generators may be either incorporated in, free-space coupled to, or coupled with a fiber optic to the Nd:YAG laser 11.1'. Accordingly, alternative embodiments of the LIDAR system 24''' incorporating a Nd:YAG laser 11.1' may be operated at frequencies other than 266 nm, for example, at either the second or third harmonics, respectively, for example, as described hereinabove. Generally, near infrared or infrared wavelengths may be used for the detection of scattering from aerosols 20" in the atmosphere 20, and visible or ultraviolet wavelengths may be used for the detection of scattering from either aerosols 20" or molecules 20' in or of the atmosphere 20.

Generally, either the light source 11 or the light 648 therefrom is needs to be modulated by an amount sufficient to allow separation of the modulation signal 662' in the scattered light 30 from associated background light 668 that may be received by the receive optics 32. For example, lasers 11', or the light 648 therefrom, can be readily modulated and collimated. A laser 11', if used, need not be a single mode laser, nor does the LIDAR system 24''' even require a high level of spectral purity. Sources with relatively broad spectral characteristics could be used, however, the broader the source, the wider the frequency range and the greater the magnitude of background light 668 that must be accommodated. Accordingly, a light source 11 having a spectral width less than 1 nanometer can be beneficial.

The WAR system 24''' further incorporates a bandpass filter 670, for example, a narrow-band interference filter 670', to filter the scattered light 30 received by the receive optics 32 so as to limit the amount of background light 668 that is detected by the detection system 34, 34.4. The bandpass filter 670 exhibits high out-of-band rejection, as well as low in-band attenuation, and the bandwidth of the bandpass filter 670 is sufficiently narrow so as to substantially filter or remove components of solar radiation or stray light in the collected scattered light 30, yet sufficiently broad so as to be substantially larger than the largest expected associated Doppler shift. For example, in one embodiment, the bandpass filter 670 is adapted so as to provide for maximum filtering of light frequencies that are outside the frequency band of interest, e.g. greater than about 2 nanometers (nm) above or below the nominal center frequency of the light source 11.

The electronic signal 654 from each photodetector 652 is amplified and electronically filtered by an associated amplifier/filter 672, and then processed by associated signal processing circuitry 656 or an associated signal processor 658 that provides for demodulating the modulation signal 662' embedded within the electronic signal 654 detected from the scattered light 30, and generating an associated output signal 674 representative of the velocity of the aerosols 20" or molecules 20' in or of the atmosphere 20, or of some other object from which the scattered light 30 is scattered. The scattered light 30 is modulated by the modulation signal 662' to be detected, whereas the background light 668. Accordingly, an electronic filter 672' portion of the amplifier/filter 672, for example, a bandpass filter 672", provides for extracting the scattered light signal 30'/modulation signal 662' component of the electronic signal 654, and rejecting the background light 668 component of the electronic signal 654, wherein the associated frequency band of the bandpass filter 672" is, for example, adapted to pass a sufficient range of frequencies so as to provide for subsequent demodulation of the associated modulation signal 662'. Shot noise contributed by the background light 668 within the frequency band of the modulation signal 662' will however pass through the amplifier/filter 672 and will accordingly affect the resulting output signal 674. The relevance of this depends upon the associated signal-to-noise ratio (SNR) of the associated electronic signal 654. Whereas the background light 668 can contribute noise within the frequency range of the modulation signal 662' that can affect performance, this contribution will typically be small in comparison with the signal level of the modulation signal 662'. The frequency of the modulation signal 662 in relation to the volume or size of the associated measurement volumes 52 can also affect the resulting output signal 674, wherein the level of the modulation signal 662' can decrease if the size of the measurement volumes 52 that contribute to the associated scattered light 30 are too large in relation to the wavelength of the modulation signal 662.

Then, for each photodetector 652, the signal processing circuitry 656 or associated signal processor 658 compares the amplified and filtered electronic signal 654 to an associated modulation reference signal 676 that is either generated from a separate detector 678 that receives a portion of the modulated light 648' from a beam splitter optic 92 following the light modulator 660 (if present), or extracted directly from the modulation signal 662 used to modulate either the light modulator 660 (if present) or the light source 11 directly, so as to generate a measure of the associated Doppler frequency or phase shift which is then converted to a corresponding speed or velocity measurement for the corresponding range bin 26, 26.1, 26.2, 26.3.

If the atmosphere 20 in the interaction region 17 is not moving relative to the LIDAR system 24''', then the modulation signal 662' within the scattered light 30 will have the same frequency as the modulation signal 662 within the beam of light 28. If the atmosphere 20 is moving relative to the LIDAR system 24''' then the modulation signal 662' within the scattered light 30 will be shifted in frequency relative to the modulation signal 662 within the beam of light 28, wherein the Doppler frequency shift is responsive to the speed of the atmosphere 20 in the associated line-of-sight 23'.

The frequency of the modulation signal 662 is subject to counterbalancing considerations. On the one hand, a high frequency provides for a more accurate or highly resolved measurement of associated velocity because for a given velocity being measured, the magnitude of the associated Doppler frequency shift is directly related to the associated frequency of the modulation signal 662. On the other hand, the wavelength of the modulation signal 662 should be substantially larger than the size of the measurement volume 52 associated with the observed range bin 26. For example, a measurement volume 52/range bin 26 having a size that is $\frac{1}{20}^{th}$ of the wavelength of the modulation signal 662 will provide a reasonable signal return. Accordingly, under this condition, for a LIDAR system 24''' with a measurement volume 52/range bin 26 having a size of 1 meter, the associated modulation signal 662 would have a wavelength of 20 meters, which corresponds to a frequency of 15 MHz. The particular modulation frequency is one parameter to be optimized along with the selection of the other associated design parameters, including but not limited to the wavelength of the light source 11, the bandwidth of the bandpass filter 670, the size and divergence of the beam of light 28, the type of photodetectors 652, and the associated modulation and demodulation techniques.

For example, a velocity of 1 meter per second will produce a Doppler frequency shift of 0.05 Hz. Although this Doppler shift is relatively small, it can be measured many times a second so as to provide for an adequate associated SNR. Frequency measurements may be made at a rate that exceeds the inverse signal period by using the concept of instantaneous frequency or using the relationship between phase and frequency, wherein a constant change in phase versus time is equivalent to a frequency shift. For example, a shift in phase of 18 degrees per second is equivalent to a frequency change of 0.05 Hz in one second. There are a number of ways to measure phase between two signals, and the technique used would be selected based on the particular set of parameters of the LIDAR system 24'''. Digital techniques can be used and may be beneficial, but simple analog techniques may provide a less expensive alternative.

For example, in accordance with a first embodiment of a LIDAR system 24''', the light source 11 comprises either a continuous wave (CW) laser 11' or a pulsed laser 11' that is operated at a relatively high pulse repetition rate relative to the frequency of the modulation signal 662. The light 648 from the laser 11' is amplitude modulated with a constant frequency sinusoidal modulation signal 662 using an Acousto-Optic (AO) light modulator 660. The associated photodetector(s) 652 is/are selected so as to have a bandwidth sufficient to respond at the modulation frequency. Referring to FIG. 105a, a first embodiment of the associated signal processing circuitry 656.1 incorporates a first embodiment of an analog phase detector 680.1, wherein the electronic signal 654 from the amplifier/filter 672 is first limited in amplitude by a limiter circuit 682 and then mixed with the modulation reference signal 676 by a mixer 684 that generates sum and difference frequency components, the later of which are selected by a low pass filter 686 that outputs the output signal 674 from which the associated velocity measurement of the atmosphere 20 is determined. For example, the limiter circuit 682 may be embodied by an ANALOG DEVICES® AD606 integrated circuit, which comprises a logarithmic amplifier with limiter output. The ANALOG DEVICES® AD606 combines successive-detection gain stages that are followed by a hard limiter that acts more like a comparator than a clipper or automatic gain control (AGC), and which provides for maintaining the phase relationship between the input signal and the output signal substantially independent of input amplitude. FIG. 105b illustrates the relationship between the phase 688 of the output signal 674 to the corresponding phase 690 of the electronic signal 654 being demodulated for the first embodiment of the analog phase detector 680.1, and illustrates a corresponding linear region 692 at which the analog phase detector 680.1 is intended to be operated. Referring to FIG. 106a, a second embodiment of the associated signal processing circuitry 656.2 incorporates a second embodiment of an analog phase detector 680.2, wherein the electronic signal 654 from the amplifier/filter 672 is first limited in amplitude by a limiter circuit 682 and then processed by a first zero-crossing detector 694.1 that generates a first pulse or edge 696.1 at each point in time at which the electronic signal 654 (and associated modulation signal 662') crosses zero voltage. Similarly, the modulation reference signal 676 is processed by a second zero-crossing detector 694.2 that generates a second pulse or edge 696.2 at each point in time at which the modulation reference signal 676 crosses zero voltage. The first 696.1 and second 696.2 pulse or edge signals are respectively input to the set S and reset R inputs of a RS flip-flop 698, the output of which is input to a low pass filter 686 that outputs the output signal 674 from which the associated velocity measurement of the atmosphere 20 is determined. FIG. 106b illustrates the relationship between the phase 688 of the output signal 674 to the corresponding phase 690 of the electronic signal 654 being demodulated for the second embodiment of the analog phase detector 680.2, and illustrates a corresponding linear region 692 at which the analog phase detector 680.2 is intended to be operated As another example, in accordance with a second embodiment of a LIDAR system 24''', for a light source 11 operating at a wavelength selected to interact with that being measured (e.g. either the atmosphere 20 or some other object or medium being measured), the light 648 therefrom is amplitude modulated with a modulation signal 662 comprising a waveform that is either a sinusoidal, pulsed, or something therebetween, using an Electro-Optic (AO) light modulator 660. The associated photodetector(s) 652 comprise photon detectors, and the resulting electronic signal 654 from the amplifier/filter 672 is digitally demodulated/detected by the signal processing circuitry 656 in accordance with the teachings of either of U.S. Pat. No. 4,569,078 or 4,636,719, each of which is incorporated herein by reference in its entirety. FIG. 107 illustrates the relationship between the phase 688 of the output signal 674 to the corresponding phase 690 of the electronic signal 654 being for digital demodulation/detection by the signal processing circuitry 656 in accordance with the teachings of either of U.S. Pat. No. 4,569,078 or U.S. Pat. No. 4,636,719, illustrating linearity over the entire range of operation.

As yet another example, in accordance with a third embodiment of a LIDAR system 24''', the light source 11 comprises a mode-locked laser 11' capable of amplitude modulation at the mode-lock frequency and at the frequency of the modulation signal 662, operating at either a near infrared (IR) or an infrared (IR) wavelength suitable for responding to aerosols 20" in the atmosphere 20. The associated photodetector(s) 652 comprise PN junction or photovoltaic devices, and the resulting electronic signal 654 from the amplifier/filter 672 is digitally demodulated/detected by the signal processing circuitry 656 using what is known as a Digital Costas Loop (DCL), for example, as described in INTERSIL® Data Sheet FN3652.5 dated Jul. 2, 2008 for an HSP50210 device, which is incorporated herein by reference in its entirety.

As yet another example, in accordance with a fourth embodiment of a LIDAR system 24''', the light source 11 comprises a Q-switched laser 11' capable of amplitude modulation at the Q-switch frequency and at the frequency of the modulation signal 662, operating at a visible or ultraviolet (UV) wavelength suitable for responding to either molecules 20' or aerosols 20" in the atmosphere 20. The associated photodetector(s) 652 comprise photo-multiplier tubes (PMT), and the resulting electronic signal 654 from the amplifier/filter 672 may digitally demodulated/detected by the signal processing circuitry 656, for example, using the above-described Digital Costas Loop (DCL). Light 648 from the Q-switched laser 11' can have significant energy in the sidebands, and the particular modulation technique may be selected on the basis of a Modulation Form Factor $S(\omega)$ as described hereinbelow.

As yet another example, in accordance with a fifth embodiment of a LIDAR system 24''', the light source 11 comprises a relatively broad-band optical source, for example, a light-emitting diode (LED), which can be amplitude modulated directly responsive to the associated drive current, and the associated photodetector(s) 652 comprise PIN diodes.

As yet another example, in accordance with a sixth embodiment of a LIDAR system 24''', the light source 11 comprises a white light optical source, using either internal or external modulation, and the associated photodetector(s) 652 comprise avalanche photodiodes (APD).

As yet another example, in accordance with a seventh embodiment of a LIDAR system 24''', the light source 11 has no particular line width requirements, with the associated photodetector(s) 652 dependent upon the associated wavelength of the light source 11.

The Modulation Form Factor, $S(\omega)$, is a normalized parameter describing the relative magnitude of the AC component of the modulation signal 662 to the average DC level. $S(\omega)$ is computed by normalizing the $n^{th}$ harmonic component of the Fourier power spectrum, as shown in the following equation:

$$S(\omega) = \frac{\left(\frac{1}{T}\int_{-\frac{T}{2}}^{\frac{T}{2}} p(t)e^{-jn\omega_1 t} dt\right)^2}{\left(\frac{1}{T}\int_{-\frac{T}{2}}^{\frac{T}{2}} p(t) dt\right)^2} \tag{88}$$

Where $S(\omega)$=Modulation Form Factor n=Number of harmonic of interest

T=Period of the modulation $\omega_1$=Angular frequency of the desired harmonic p(t)=Modulated beam power waveform The numerator in equation (89) computes the modulated waveform Fourier power spectrum coefficient for the harmonic of interest that affects the detector output current, and the denominator normalizes $S(\omega)$ with respect to the waveform's average dc level. $S(\omega)$ must be multiplied by a factor of 2 in the SNR equation to account for the selected harmonic's positive and negative frequency components.

If the LIDAR system 24''' uses a sinusoidal drive, then, to a first approximation, the power waveform of the light source 11 is given by:

$$p(t) = 1 + \cos(\omega \cdot t) \tag{89}$$

$$\text{Let } T = \frac{2 \cdot \pi}{\omega}. \tag{90}$$

The integral in the denominator of the $S(\omega)$ equation is evaluated below $$\frac{1}{T}\int_{-\frac{T}{2}}^{\frac{T}{2}} p(t) dt = \frac{\omega}{2 \cdot \pi}\int_{-\frac{\pi}{\omega}}^{\frac{\pi}{\omega}} (1 + \cos(\omega \cdot t)) dt = \tag{91}$$

$$\frac{\omega}{2 \cdot \pi}(t + \sin(\omega \cdot t))\Big|_{-\frac{\pi}{\omega}}^{\frac{\pi}{\omega}} = \frac{\omega}{2 \cdot \pi}\left(\frac{\pi}{\omega} + \frac{\pi}{\omega} + \sin(\pi) - \sin(-\pi)\right) = 1$$

One squared is one, and therefore, the denominator of the equation for $S(\omega)$ is one.

The numerator evaluation follows.

$$\frac{1}{T}\int_{-\frac{T}{2}}^{\frac{T}{2}} p(t)e^{-jn\omega_1 t}dt = \frac{\omega}{2\cdot\pi}\int_{-\frac{\pi}{\omega}}^{\frac{\pi}{\omega}}(1+\cos(\omega\cdot t))e^{-j\omega t}dt = \qquad (92)$$

$$\frac{\omega}{2\cdot\pi}\int_{-\frac{\pi}{\omega}}^{\frac{\pi}{\omega}}(e^{-j\omega t}+e^{-j\omega t}\cdot\cos(\omega\cdot t))dt$$

$$=\frac{\omega}{2\cdot\pi}\int_{-\frac{\pi}{\omega}}^{\frac{\pi}{\omega}}e^{-j\omega t}+e^{-j\omega t}\left(\frac{e^{j\omega t}+e^{-j\omega t}}{2}\right)dt = \qquad (93)$$

$$\frac{\omega}{2\cdot\pi}\int_{-\frac{\pi}{\omega}}^{\frac{\pi}{\omega}}\left(e^{-j\omega t}+\frac{1}{2}+\frac{e^{-j2\omega t}}{2}\right)dt$$

$$=\frac{\omega}{2\cdot\pi}\left(\frac{e^{-j\omega t}}{-j\omega}+\frac{t}{2}+\frac{e^{-j2\omega t}}{-j4\omega}\right)\Big|_{-\frac{\pi}{\omega}}^{\frac{\pi}{\omega}} = \qquad (94)$$

$$\frac{\omega}{2\cdot\pi}\left(\frac{e^{-j\pi}-e^{j\pi}}{-j\pi}+\frac{\pi}{\omega}+\frac{e^{-j2\pi}+e^{j2\pi}}{-j4\pi}\right)$$

$$=\frac{\omega}{2\cdot\pi}\left(\frac{2}{\omega}\sin(\pi)+\frac{\pi}{\omega}+\frac{1}{2\cdot\omega}\sin(2\cdot\pi)\right)=\frac{1}{2} \qquad (95)$$

The value of the integral of the numerator of the equation for S(ω) is ½ squared or ¼, and therefore for a sinusoidal modulation, S(ω) is 0.25. Other waveforms may be evaluated by computing the Modulation Form Factor using the equation for S(ω) as the example shown above illustrates.

The LIDAR system 24''' may be adapted with plural sets of receive optics 32 and associated detection systems 34 so as to provide for imaging a common interaction region 17 with a common set of associated measurement volumes 52 associated with a common beam of light 28, so as to provide for measuring a plurality of vector velocity components for each measurement volume 52 and to determine therefrom a corresponding velocity vector, for example, as illustrated herinabove in FIGS. 1, 2, 4, 50, 95, 96 and 104.

Furthermore, the LIDAR system 24''' may be adapted with plural sets of source optics 15, associated receive optics 32 and associated detection systems 34 so as to provide for imaging a plurality of different interaction regions 17 associated with one or more, corresponding beams of light 28, so as to provide for measuring the velocity of the atmosphere 20 at a plurality of different locations, for example, as illustrated hereinabove in FIGS. 1-4, 19, 51, 52, 61-63, 65a, 66, 67, 80, 95, 96, 102a, 103a.

It is convenient to package the light source 11 and associated detection system 34 of a given LIDAR system 24 either together or in relatively close proximity to one another, particularly for the first and second aspects of LIDAR systems 24', 24'' that incorporate an associated interferometer 31 that is calibrated using a reference beam portion 90 as described hereinabove.

Alternatively, one or more LIDAR systems 24 could each be configured strictly as a LIDAR receiver 700 that incorporates associated receive optics 32 and a corresponding detection system 34, without an associated light source 11 as the source of scattered light 30 that is received and detected by the receive optics 32 and corresponding detection system 34—possibly in cooperation with an associated interferometer 31 therebetween—but which would detect scattered light 30 that is generated by a light source 11 either of another LIDAR system 24 located relatively remotely with respect to the LIDAR receiver 700, or by a remotely located light source 11 located relatively remotely with respect to the LIDAR receiver 700 without a co-located set of associated receive optics 32 and detection system 34. Accordingly, the LIDAR receiver 700 is part of an effective LIDAR system 24', 24'', 24''' for which the associated light source 11 is located relatively remotely with respect to the associated receive optics 32 and corresponding detection system 34.

For example, a first aspect of the LIDAR receiver $700^i$ comprises the fourth aspect of the detection system 34, 34.4 that is adapted to cooperate with a remotely located light source 11 associated with the fourteenth aspect of the LIDAR system 24''', $24^{xiv}$, for example, as illustrated in FIG. 104, or a corresponding system adapted to sense only a single interaction region 17.

As another example, a second aspect of the LIDAR receiver $700^{ii}$ comprises any of the first, second or third aspects of the detection system 34, 34.1, 34.2, 34.3 that cooperates with an associated interferometer 31 that is pre-calibrated so as to not require an associated reference beam portion 90 for continuous in situ calibration as described hereinabove.

As yet another example, a third aspect of the LIDAR receiver $700^{iii}$ comprises any of the first or third aspects of the detection system 34, 34.1, 34.3 that cooperates with an associated interferometer 31 that also uses an associated reference beam portion 90 for continuous in situ calibration as described hereinabove, and which is transmitted from the associated light source 11 to the interferometer 31 of the relatively remotely located LIDAR receiver $700^{iii}$, for example, via a fiber optic 98.

Further alternatively, one or more LIDAR systems 24 could each be configured as a hybrid LIDAR system 702 that incorporates at least one light source 11 and at least one set of associated receive optics 32 and corresponding detection system 34—possibly in cooperation with an associated interferometer 31 therebetween—adapted to receive and detect scattered light 30 from that light source 11, in combination with at least one set of associated receive optics 32 and corresponding detection system 34—possibly in cooperation with an associated interferometer 31 therebetween—adapted to receive and detect scattered light 30 that is generated by a light source 11 either of another LIDAR system 24 located relatively remotely with respect to the hybrid LIDAR system 702, or by a remotely located light source 11 located relatively remotely with respect to the hybrid LIDAR system 702 without a co-located set of associated receive optics 32 and detection system 34. Accordingly, the hybrid LIDAR system 702 comprises a combination of at least one LIDAR system 24', 24'', 24''' with at least one LIDAR receiver 700, $700^i$, $700^{ii}$, $700^{iii}$ in accordance either the first, second or third aspects thereof.

Referring to FIG. 108, in accordance with a fourth aspect of an atmospheric measurement system $10^{iv}$ there is illustrated a group of three LIDAR sub-systems 24.1, 24.2, 24.3 in cooperation with one another so as to provide for generating three different measures of wind velocity $\bar{v}_1$, $\bar{v}_2$, $\bar{v}_3$ from three corresponding different measurement volumes 52.1, 52.2, 52.3, substantially independent of spatial and temporal variations of the associated wind field 16'. More particularly, each of the LIDAR systems 24.1, 24.2, 24.3 comprises a corresponding respective hybrid LIDAR systems 702.1, 702.2, 702.3 that respectively project a corresponding respective first 28.1', second 28.2' and third 28.3' beams of light into the respective corresponding measurement volume 52.1, 52.2, 52.3 substantially in front of the each corresponding respective LIDAR system 24.1, 24.2, 24.3. Each LIDAR system 24.1, 24.2, 24.3 incorporates a corresponding first set of receive optics 32.1, 32.2, 32.3 having associated fields-of-view 54.1', 54.2', 54.3' that intersect the respective corresponding respective first 28.1', second 28.2' and third 28.3' beams of light within the respective corresponding measurement volumes 52.1, 52.2, 52.3 so as to provide for measuring respective corresponding first components of wind speed $v_{1.1}, v_{1.2}, v_{1.3}$ therewithin along respective corresponding first directions 46.1', 46.2', 46.3' along corresponding lines-of-sight 23'.

The hybrid LIDAR system 702.1 of the first LIDAR system 24.1 comprises a second LIDAR receiver 700.1", for example, in accordance with either the first 700$^i$ or second 700$^{ii}$ aspects, that incorporates a second set of receive optics 32.1" having an associated field-of-view 54.1" that intersects the second 28.2' and third 28.3' beams of light within the second 52.2 and third 52.3 measurement volumes, respectively, so as to provide for measuring respective corresponding second components of wind speed $v_{2.2}$, $v_{2.3}$ therewithin along a corresponding second direction 46.1". For example, in accordance with the fourteenth aspect of the LIDAR system 24''', 24$^{xiv}$, the measurements from the second 52.2 and third 52.3 measurement volumes can be distinguished from one another either by timing the generation and detection of the second 28.2' and third 28.3' beams of light so as to occur at predetermined and distinct intervals of time, or by using different corresponding modulation signals 662 that can be distinguished during the associated demodulation processes.

The hybrid LIDAR system 702.2 of the second LIDAR system 24.2 comprises a second LIDAR receiver 700.2", for example, in accordance with either the first 700$^i$ or second 700$^{ii}$ aspects, that incorporates a second set of receive optics 32.2" having an associated field-of-view 54.2" that intersects the first beam of light 28.1' within the first measurement volume 52.1 so as to provide for measuring a corresponding second component of wind speed $v_{2.1}$ therewithin along a corresponding second direction 46.2". Furthermore, hybrid LIDAR system 702.2 of the second LIDAR system 24.2 also comprises a third LIDAR receiver 700.2''', for example, in accordance with either the first 700$^i$ or second 700$^{ii}$ aspects, that incorporates a third set of receive optics 32.2''' having an associated field-of-view 54.2''' that intersects the third beam of light 28.3' within the third measurement volume 52.3 so as to provide for measuring a corresponding third component of wind speed $v_{3.3}$ therewithin along a corresponding third direction 46.2'''.

The hybrid LIDAR system 702.3 of the third LIDAR system 24.3 also comprises a second LIDAR receiver 700.3", for example, in accordance with either the first 700$^i$ or second 700$^{ii}$ aspects, that incorporates a second set of receive optics 32.3" having associated fields-of-view 54.3" that intersect the second 28.2' and first 28.1' beams of light within the second 52.2 and first 52.1 measurement volumes, respectively, so as to provide for measuring respective corresponding third components of wind speed $v_{3.2}$, $v_{3.1}$ therewithin along a corresponding second direction 46.3".

The associated beams of light 28.1', 28.2', 28.3' and LIDAR receivers 700.1", 700.2", 700.2''', 700.3" are configured so that the associated directions 46.1', 46.2" and 46.3" are linearly independent (i.e. not all in the same plane) within the first measurement volume 52.1, the associated directions 46.2', 46.1" and 46.3" are linearly independent (i.e. not all in the same plane) within the second measurement volume 52.2, and the associated directions 46.3', 46.1" and 46.2''' are linearly independent (i.e. not all in the same plane) within the third measurement volume 52.3, so as to provide for determining a first measure of wind velocity $\bar{v}_1$, from the first $v_{1.1}$, second $v_{2.1}$ and third $v_{3.1}$ components of wind speed within the first measurement volume 52.1, determining a second measure of wind velocity $\bar{v}_2$ from the first $v_{1.2}$, second $v_{2.2}$ and third $V_{3.2}$ components of wind speed within the second measurement volume 52.2, and determining a third measure of wind velocity $\bar{v}_3$ from the first $v_{1.3}$, second $v_{2.3}$ and third $v_{3.3}$ components of wind speed within the third measurement volume 52.3.

Referring to FIG. 109, a fifth aspect of an atmospheric measurement system 10$^v$ is substantially the same as the fourth aspect of an atmospheric measurement system 10$^{iv}$ illustrated in FIG. 108, except that the associated LIDAR receivers 700.1", 700.2", 700.2''', 700.3" are each in accordance with the third aspect of the LIDAR receiver 700$^{iii}$, further comprising a plurality of fiber optics 98 that extend from each LIDAR system 24.1, 24.2, 24.3 to each other LIDAR system 24.1, 24.2, 24.3, for example, so as to provide for transmitting a first reference beam portion 90.1 associated with the first beam of light 28.1' to each of the second 24.2 and third 24.3 LIDAR systems, so as to provide for transmitting a second reference beam portion 90.2 associated with the second beam of light 28.2' to each of the first 24.1 and third 24.3 LIDAR systems, and so as to provide for transmitting a third reference beam portion 90.3 associated with the third beam of light 28.3' to each of the first 24.1 and second 24.2 LIDAR systems. For example, the first reference beam portion 90.1 is used by the second LIDAR receiver 700.2" of the second LIDAR system 24.2 and by the second LIDAR receiver 700.3" of the third LIDAR system 24.3 to provide for calibrating the associated interferometers 31 when measuring scattered light 30 from the first beam of light 28.1' within the first measurement volume 52.1. Similarly, the second reference beam portion 90.2 is used by the second LIDAR receiver 700.1" of the first LIDAR system 24.1 and by the second LIDAR receiver 700.3" of the third LIDAR system 24.3 to provide for calibrating the associated interferometers 31 when measuring scattered light 30 from the second beam of light 28.2' within the second measurement volume 52.2. Finally, the third reference beam portion 90.3 is used by the second LIDAR receiver 700.1" of the first LIDAR system 24.1 and by the third LIDAR receiver 700.2''' of the second LIDAR system 24.2 to provide for calibrating the associated interferometers 31 when measuring scattered light 30 from the third beam of light 28.3' within the third measurement volume 52.3.

For example, the third and fourth aspects illustrated in FIGS. 108 and 109 are each representative of the measurement volumes 52$^{iv}$, 52$^v$ associated with the third 24.3, fourth 24.4 and fifth 24.5 LIDAR systems illustrated in FIGS. 1 and 2.

Referring to FIGS. 110a-110e, a fifteenth aspect of a LIDAR system 24", 24$^{xv'}$ incorporated in the second aspect of an atmospheric measurement system 10, 10$^{ii}$ incorporates an at least substantially monochromatic light source 11 that provides for generating a first beam of light 420 of substantially monochromatic light 13, which is split by a first beam splitter optic 92 into a reference beam portion 90 and a second beam of light 28, wherein the second beam of light 28 is then projected into the atmosphere 20 through and by associated source optics 15. For example, the reference beam portion 90 is formed by the transmission of a first portion of the first beam of light 420 from the light source 11 through the first beam splitter optic 92, and the second beam of light 28 is formed from the reflection of a second portion of the first beam of light 420 from the light source 11 from a first surface of the first beam splitter optic 92. Furthermore, the source optics 15 may comprise a lens assembly 15' that provides for determining the width and divergence of the second beam of light 28, and a suitable location of the associated beam waist thereof, so as to illuminate an interaction region 17 within the atmosphere 20 therewith, wherein the interaction region 17 is defined by the intersection of the second beam of light 28 with a field-of-view 54 of an associated telescope 32' looking along an associated direction 46 at the second beam of light 28 and the associated transverse spatial resolution limit of the LIDAR system 24", $24^{xv'}$ is dependent upon the beam width of the second beam of light 28 within the interaction region 17. Scattered light 30 scattered from molecules 20' or aerosols 20" in the interaction region 17 of the atmosphere 20 is received by the associated telescope 32', and transmitted therefrom to a first collimating lens $33^A$ of an associated Fabry-Pérot interferometer 31'.

For example, in various embodiments, the light source 11 comprises a laser 11', for example, a Nd:YAG laser 11.1' that provides for generating ultraviolet (UV) laser light at a wavelength of about 266 nm, and the associated telescope 32' provides for detecting the return from scattering of the second beam of light 28 by atmospheric molecules 20' and aerosols 20". A Nd:YAG laser 11.1' has a fundamental wavelength of 1064 nm, from which shorter wavelengths/higher frequencies may be generated using one or more harmonic generators operatively associated with or a part of the Nd:YAG laser 11.1'. For example, a second-harmonic generator could be used to convert the fundamental 1064 nm light to second-harmonic 532 nm light which could then be transformed with either a third- or fourth-harmonic generator to generate associated 355 nm or 266 nm light respectively. For example, these second-, third- and/or fourth-harmonic generators may be either incorporated in, free-space coupled to, or coupled with a fiber optic to the Nd:YAG laser 11.1'. Accordingly, alternative embodiments of the LIDAR system 24", $24^{xv'}$ incorporating a Nd:YAG laser 11.1' may be operated at frequencies other than 266 nm, for example, at either the second or third harmonics, respectively, for example, as described more fully hereinabove. The particular operating wavelength of the light source 11 is not limiting, and it should be understood that any optical wavelength that interacts with that which is being sensed in the associated interaction region 17 may be used.

The telescope 32' comprises an associated effective lens 32", and in accordance with one aspect, the scattered light 30 received thereby is collected by a final light collecting element 448 thereof as an associated scattered light signal 30' into a first end 98' of a corresponding fiber optic 98 that directs the returned photons therethrough to a second end 98" thereof located at a front focal plane $33.1^A$ of the first collimating lens $33^A$. The first collimating lens $33^A$ provides for collimating the associated scattered light signal 30' for illumination of an associated portion of the Fabry-Pérot interferometer 31' and then an associated detection system 34 for processing thereby. For example, the final light collecting element 448 of the telescopes 32' may comprise either a GRIN lens or an aspheric lens. The use of a fiber optic 98 provides for mechanically decoupling the telescope 32' from the Fabry-Pérot interferometer 31' and thereby provides for simplifying the alignment of the scattered light signal 30' with the Fabry-Pérot interferometer 31'.

The scattered light signal 30' from the fiber optic 98 is projected onto and through the first collimating lens $33^A$ of the Fabry-Pérot interferometer 31', then through a second beam splitter optic 136, then through an associated filter system 88, then through an associated Fabry-Pérot etalon 35, and finally through an associated imaging optics 37. In the absence of the Fabry-Pérot etalon 35, the imaging optics 37 in cooperation with the first collimating lens $33^A$ provides for generating an image 114 of the scattered light signal 30' in the imaging plane $31.2^{i'}$ of the Fabry-Pérot interferometer 31'. For example, in one embodiment, the filter system 88 comprises a plurality of bandpass mirrors from which light entering the Fabry-Pérot interferometer 31' is successively reflected, for example, as described hereinabove and illustrated in FIG. 11.

The reference beam portion 90 emanating from the first beam splitter optic 92 is directed therefrom to a reference illuminator 324, for example, comprising an associated rotating diffuser 308 in combination with an integrating sphere 310 relatively located behind and illuminating a mask 138, 138.3. The rotating diffuser 308 produces the phase diversity necessary to reduce the speckle in the reference beam thus providing uniform illumination. Accordingly, the reference illuminator 324 provides for generating a uniform and diffuse reference beam 90', for example, as illustrated in FIG. 110b, which is then directed through the mask 138, 138.3 that blocks a portion of the uniform and diffuse reference beam 90' from transmission therethrough, resulting in a corresponding first embodiment of a masked reference beam 90", 90.3" that is then directed through a second collimating lens $33^B$ of the Fabry-Pérot interferometer 31', then reflected off a first surface 640.1 of a first surface mirror 640 onto a partially reflective surface 136.1 of the second beam splitter optic 136, through the associated filter system 88, then through the associated Fabry-Pérot etalon 35, and finally through the associated imaging optics 37 of the Fabry-Pérot interferometer 31'. In the absence of the Fabry-Pérot etalon 35, the imaging optics 37 in cooperation with the second collimating lens $33^B$ provides for generating an image 114", 114.3" of the masked reference beam 90", 90.3" in the imaging plane $31.2^{i'}$ of the Fabry-Pérot interferometer 31'.

The reference illuminator 324 that provides for illuminating the mask 138 could be implemented in various ways. For example, in one embodiment, the rotating diffuser 308 may be replaced with a scanning mirror that would scan a narrow laser beam across the inside of the integrating sphere 310. In another embodiment, the integrating sphere 310 could be replaced by either single or multiple diffusers. In yet another embodiment, optics could be employed to provide for a uniform illumination of the mask 138.

Both the scattered light signal 30' and the masked reference beam 90", 90.3" entering the Fabry-Pérot interferometer 31' are each first separately collimated by an associated collimation system 704, which in accordance with a first aspect 704' comprises the combination of the first $33^A$ and second $33^B$ collimating lenses. For example, in one embodiment, the rear focal planes $33.2^A$, $33.2^B$ of the first $33^A$ and second $33^B$ collimating lenses and the front focal plane 37.1 of the imaging optics 37 are coincident with one another, and the optic axes $33^{A'}$, $33^{B'}$, 39 of the first $33^A$ and second $33^B$ collimating lenses and the imaging optics 37 are all aligned with one another within the Fabry-Pérot interferometer 31'. Accordingly, the combination of the first collimating lens $33^A$ and the imaging optics 37 provides for imaging the second end 98" of the fiber optic 98, and scattered light signal 30' emanating therefrom, in the imaging plane $31.2^{i'}$ of the Fabry-Pérot interferometer 31' at the rear focal plane 37.2 of the imaging optics 37. Similarly, the combination of the second collimating lens $33^B$ and the imaging optics 37 provides for also imaging the masked reference beam 90", 90.3" in the imaging plane $31.2^{i'}$ of the Fabry-Pérot interferometer 31', wherein the mask 138, 138.3 is configured and aligned so as to provide for masking all of the light from the uniform and diffuse reference beam 90' for which the image thereof at the rear focal plane 37.2 of the imaging optics 37 would otherwise overlap the corresponding image 114 of the second end 98" of the fiber optic 98, and scattered light signal 30' emanating therefrom. Accordingly, within the imaging plane $31.2^{i'}$ of the Fabry-Pérot interferometer 31', the light within the region 326 associated with the image of the second end 98" of the fiber optic 98 is exclusively from the scattered light signal 30', and light associated with the remaining region 328 of the imaging plane 31.2$^{i'}$ is exclusively from the uniform and diffuse reference beam 90'.

For example, referring to FIG. 110c, in accordance with a first aspect, the mask 138, 138.3 comprises an opaque circular region 138', 138.3' and a remaining transparent region 138", wherein the opaque circular region 138', 138.3' is sized so as to correspond in the imaging plane 31.2$^{i'}$ of the Fabry-Pérot interferometer 31' to the second end 98" of the fiber optic 98. Referring to FIG. 110d, a hypothetical image in the imaging plane 31.2$^{i'}$ of the Fabry-Pérot interferometer 31' absent the associated Fabry-Pérot etalon 35 illustrates the mutually exclusive regions 326, 328 therein of the image 114 of the scattered light signal 30' together with the image 114", 114.3" of the masked reference beam 90", 90.3".

The Fabry-Pérot etalon 35 of the Fabry-Pérot interferometer 31' comprises first 41 and second 43 partially-reflective surfaces that are parallel to one another and separated by a fixed gap 45, and located between the collimating lens 33$^A$, 33$^B$ and associated imaging optics 37 of the Fabry-Pérot interferometer 31'. For example, the Fabry-Pérot etalon 35 may be constructed either of separate planar optical windows or of a solid optical element, as described hereinabove. For example, as illustrated in FIG. 110a, the Fabry-Pérot etalon 35 could comprise a solid optical element 61—for example, constructed of either optical glass or fused quartz—with planar parallel faces 35.1, 35.2 comprising first 41 and second 43 partially-reflective surfaces separated by the gap 45 constituting the length of the solid optical element 61.

Light 454 at a rear focal plane 33.2$^A$, 33.2$^B$ of the collimating lens 33$^A$, 33$^B$ is substantially collimated thereby, and the angles at which the light 454 is passed through the Fabry-Pérot etalon 35 are dependent upon the optical frequency of the light 454 and the length of the gap 45. Referring to FIG. 110e, with the Fabry-Pérot etalon 35 in place, the Fabry-Pérot interferometer 31' generates two sets of fringes in the imaging plane 31.2$^{i'}$, i.e. focal plane, of the imaging optics 37 as follows: a first set of fringes 330 of an associated reference fringe pattern 104 in the region 328 associated with the uniform and diffuse reference beam 90', and a second set of fringes 332 of a scatter fringe pattern 47 in the region 326 associated with the scattered light signal 30', wherein each set of fringes 330, 332 is generated responsive to a transmission function of the Fabry-Perot etalon 35, for example, as described hereinabove. The first 330 and second 332 sets of fringes—each also known as Haidinger fringes—comprising respective pluralities of concentric circular 65' or arcuate 49', 49" fringes in the rear focal plane 37.2 of the imaging optics 37 centered about the optic axis 39 of the imaging optics 37. The respective patterns of the first 330 and second 332 sets of fringes are responsive to the optical frequency of the associated respective uniform and diffuse reference beam 90' and scattered light signal 30', respectively. For example, the optical frequency of the scattered light signal 30' can exhibit a Doppler shift responsive to a relative velocity of the atmosphere 20 within the interaction region 17 from which the associated second beam of light 28 is backscattered, relative to the LIDAR system 24", 24$^{xv'}$. The uniform and diffuse reference beam 90' provides an illumination pattern that is uniform and sufficient in extent so as to fully illuminate the first set of fringes 330 that fall on the detection system 34.

The LIDAR system 24", 24$^{xv'}$ provides for directly detecting light scattered off of either molecules 20' of the atmosphere 20, aerosols 20" in the atmosphere 20, or a combination of the two, and provides for directly measuring the density and temperature of the atmosphere 20, and the velocity thereof in the direction 46 of the telescope 32'. For example, relatively short wavelength light is scattered by molecules 20' of the atmosphere 20 in accordance with Rayleigh scattering. Light can also be scattered by aerosols 20" in the atmosphere in accordance with Mie scattering. Rayleigh scattering generally refers to the scattering of light by either molecules or particles having a size less than about $\frac{1}{10}^{th}$ the wavelength of the light, whereas Mie scattering generally refers to scattering of light by particles greater than$/1;10^{th}$ the wavelength of the light. Being responsive to Rayleigh scattering, the LIDAR system 24", 24$^{xv'}$ is therefore responsive to the properties—e.g. velocity, density and temperature—of those molecules 20' in the atmosphere giving rise to the associated scattering of the light detected by the LIDAR system 24", 24$^{xv'}$. Furthermore, the LIDAR system 24", 24$^{xv'}$ can provide for operation in clean air, i.e. in an atmosphere with no more than a negligible amount of aerosols 20", depending substantially upon only molecular backscatter. If scattered from a moving molecule 20' or aerosol 20", the frequency of the resulting scattered light 30 is Doppler shifted, which for a given gap 45 in the associated Fabry-Pérot etalon 35 thereby causes the associated arcuate fringes 49' of the second set of fringes 332 from the Fabry-Pérot interferometer 31' to be shifted to a location for which an associated constructive interference condition is satisfied for the corresponding rays of scattered light 30 entering the Fabry-Pérot interferometer 31' at a given angle from a corresponding given nominal range R.

In accordance with a first aspect of a detection system 34, the respective images 114", 114.3", 114' in the imaging plane 31.2$^{i'}$ of the Fabry-Pérot interferometer 31' of the masked reference beam 90", 90.3" and the scattered light signal 30', respectively, are captured by a detection system 34, for example, a camera 34.1", for example, incorporating a two-dimensional array of photodetectors 34.1''', for example, either charge-coupled devices (CCDs) or charge injection devices (CIDs); or corresponding arrays of individual photo-detectors, for example, photo-conductive, photo-voltaic, photo-emissive, bolometer, or thermopile photodetectors, i.e. generally any device that converts photons to a corresponding electrical signal. The particular detection system 34 may be adapted in cooperation with the associated light source 11 so as to provide for increasing the associated signal-to-noise ratio (SNR). For example, in cooperation with a continuous light source 11, a relatively high-sensitivity, low-noise, low-bandwidth detectors can be used, so as to provide for a higher signal-to-noise ratio (SNR) than possible with corresponding relatively higher-bandwidth detectors, so as to provide for relatively more precise associated measurements.

Alternatively, the camera 34.1" could comprise at least one array of concentric circular-segment photodetectors 34.1"" for each of the images 114", 114.3", 114' being processed. The camera 34.1" is operatively coupled to and controlled by an associated data processor 53 under control of a stored program in associated memory 124, which also provides for processing the associated images 114", 114.3", 114' of the first 330 and second 332 sets of fringes from the Fabry-Pérot interferometer 31'.

Each of the first 330 and second 332 sets of fringes is first compressed into a one-dimensional radial fringe distribution, either by integrating the associated signals from the two-dimensional array of photodetectors 34.1''', or, for a detection system 34 comprising at least one array of concentric circular-segment photodetectors 34.1"", directly or by combination of signals from corresponding concentric circular-segment photodetectors 34.1"" for the same circular 65' or arcuate 49', 49" fringes, and respectively transformed into an reference electronic image signal 106 and an scatter electronic image signal 51, respectively, also referred to as detected image signals I(X) and I0(X), respectively representing the total radiometric counts as a function of radial distance through the corresponding scatter 47 and reference 104 fringe patterns. The resulting detected image signals I(X) and I0(X) are then processed by the data processor 53 as described hereinbelow so as to generate one or more measures of the atmosphere 20 within the interaction region 17.

For example, for a detection system 34 comprising a two-dimensional array of photodetectors 34.1''', the first 330 and second 332 sets of fringes are each separately integrated—for example, using a circular integration process as described hereinabove—along circular paths centered about the optic axis 39 of the of the imaging optics 37 for a given radial distance therefrom, for plurality of different radial distances, so as to transform the associated circular first 330 or second 332 set of fringes to the corresponding electronic image signal 106, 51 responsive to the corresponding intensity of the first 330 or second 332 set of fringes, for each of the first 330 and second 332 sets of fringes, so as to generate the reference electronic image signal 106 from the first set of fringes 330 responsive to the uniform and diffuse reference beam 90', and to generate the scatter electronic image signal 51 from the second set of fringes 332 responsive to the scattered light signal 30'.

The reference 106 and scatter 51 electronic image signals are then used in conjunction with the transmission function of the Fabry-Pérot etalon 35 to solve for the associated detectable observables P, for example, line-of-sight relative wind velocity U, static temperature Temp, molecular counts Mol-Counts, aerosol counts Aero Counts, and background counts BackCounts, and possibly for associated measures derived therefrom, collectively known as atmospheric data 36, as described hereinabove.

Accordingly, the masked reference beam 90", 90.3" provides for increasing the amount of energy in the first set of fringes 330 associated with the reference beam 90, and for more fully utilizing the available area of the Fabry-Pérot etalon 35, so as to provide for a higher signal-to-noise ratio in the information associated with the reference beam 90, and so as to provide for a more complete set of concentric circular 65' or arcuate 49', 49" fringes in the rear focal plane 37.2 of the imaging optics 37 centered about the optic axis 39 of the imaging optics 37 that provides for more accurately locating the optic axis 39 and thereby more accurately integrating both the first 330 and second 332 sets of fringes prior to subsequent detection of the associated observables P from the associated effective linear radial fringe intensity signals.

The light source 11 provides for generating a sufficient amount of sufficiently narrow-band monochromatic light in the first beam of light 420 so as to provide for a sufficient amount of scattered light 30 so that the resulting second set of fringes 332 is detectable by the detection system 34 with a sufficient signal-to-noise ratio (SNR) so that the resulting atmospheric data 36 determined therefrom is accurate within a given accuracy threshold and provides for an information temporal bandwidth that is within a given temporal bandwidth threshold. For example, the light source 11 could comprise one or more lasers, light emitting diodes (LEDs), flash lamps, for example, xenon flash lamps, sodium lamps or mercury lamps. The light source 11 may be either continuous or pulsed, and need not necessarily be coherent. If the spectral bandwidth of the light source 11 is not inherently substantially less than the expected minimum Doppler shifts to be measured, then the output of the light source 11 may be filtered with a filter 108 so as to provide for generating a sufficiently monochromatic first beam of light 420 so as to enable Doppler shifts in the scattered light 30 to be measured sufficiently accurately so as to provide for resolving velocity sufficiently accurately, i.e. less than a given threshold. The particular operating wavelength of the LIDAR system 24", 24$^{xv'}$ is not limiting. For example, any optical wavelength that interacts with that which is being sensed in the associated interaction region 17 may be used.

Referring to FIGS. 111a-111e, a second embodiment of the fifteenth aspect of a LIDAR system 24", 24$^{xv'}$ incorporated in the second aspect of an atmospheric measurement system is the substantially the same as the first embodiments of the fifteenth aspect of the LIDAR system 24", 24$^{xv'}$ illustrated in FIG. 110a, except for the incorporation of a second aspect 704" of an associated collimation system 704 for which the first 33$^A$ and second 33$^B$ collimating lenses ahead of the second beam splitter optic 136 in the first embodiment of the LIDAR system 24", 24$^{xv'}$ are replaced with a single, common collimating lens 33 behind the second beam splitter optic 136, for example, with both the second end 98" of the fiber optic 98 and the mask 138, 138.3 located one focal distance of the collimating lens 33 in front thereof, and the optic axis 33' of the collimating lens 33 aligned with the optic axis 39 of the imaging optics 37 of the Fabry-Pérot interferometer 31'. Otherwise, the second embodiment of the fifteenth aspect of the of a LIDAR system 24", 24$^{xv''}$ functions the same as the corresponding first embodiment, for example, with the operations illustrated in FIGS. 111b-111e respectively corresponding to those illustrated in FIGS. 110b-110e, respectively. In general, the first 704' and second 704" aspects of the collimation system 704 can be used interchangeably.

Referring to FIGS. 112a-112e, a first embodiment of a sixteenth aspect of a LIDAR system 24", 24$^{xvi'}$, is the substantially the same as the second embodiment of the fifteenth aspect of a of the LIDAR system 24", 24$^{xv''}$ illustrated in FIG. 111a, except for the incorporation of a plurality of scattered light signal 30' channels so as to provide for simultaneously processing a plurality of scattered light signals 30' from a plurality of different interaction regions 17 within the atmosphere 20. For example, in FIG. 112a there is illustrated a plurality of interaction regions 17.1, 17.2, 17.3 displaced from one another along a single common second beam of light 28 projected into the atmosphere 20. More particularly, a first interaction region 17.1 is defined by the intersection of the second beam of light 28 with a first field-of-view 54.1 of an associated first telescope 32.1' having a first effective lens 32.1" in cooperation with a first final light collecting element 448.1 that provides for looking along a first direction 46.1 at the second beam of light 28; a second interaction region 17.2 is defined by the intersection of the second beam of light 28 with a second field-of-view 54.2 of an associated second telescope 32.2' having a second effective lens 32.2" in cooperation with a second final light collecting element 448.2 that provides for looking along a second direction 46.2 at the second beam of light 28; and a third interaction region 17.3 is defined by the intersection of the second beam of light 28 with a third field-of-view 54.3 of the second telescope 32.2' and second effective lens 32.2" in cooperation with a third final light collecting element 448.3 that provides for looking along a third direction 46.3 at the second beam of light 28, wherein the third final light collecting element 448.3 is displaced from the associated second final light collecting element 448.2 within the focal plane of the second telescope 32.2'. A first fiber optic 98.1 directs the returned photons from the first final light collecting element 448.1 as a first scattered light signal 30.1' to a first location 644.1 in a front focal plane 33.1 of the collimating lens 33; a second fiber optic 98.2 directs the returned photons from the second final light collecting element 448.2 as a second scattered light signal 30.2' to a second location 644.2 in the front focal plane 33.1 of the collimating lens 33; and a third fiber optic 98.3 directs the returned photons from the third final light collecting element 448.3 as a third scattered light signal 30.3' to a third location 644.3 in the front focal plane 33.1 of the collimating lens 33, wherein the first 644.1, second 644.2 and third 644.3 locations are at different arbitrary radial and aziumthal locations relative to the optic axis 39 of the imaging optics 37 of the Fabry-Pérot interferometer 31'.

In operation, referring to FIG. 112b, as with the first and second embodiments of the fifteenth aspect of the LIDAR system 24", $24^{xv'}$, $24^{xv''}$, the reference illuminator 324 provides for generating the uniform and diffuse reference beam 90', which is then directed through a mask 138, 138.4 illustrated in FIG. 112c that blocks a portion of the uniform and diffuse reference beam 90' from transmission therethrough in associated first $138.4^{i'}$, second $138.4^{ii'}$ and third $138.4^{iii'}$ opaque circular regions corresponding in size and location to the first 30.1', second 30.2' and third 30.3' scattered light signals and associated images of the second ends 98.1", 98.2", 98.3" of the first 98.1, second 98.2 and third 98.3 fiber optics, resulting in a corresponding second embodiment of a masked reference beam 90", 90.4", a corresponding image 114", 114.4" of which is illustrated in FIG. 112d together with images of the associated first 30.1', second 30.2' and third 30.3' scattered light signals in the imaging plane $31.2^{i'}$ of the Fabry-Pérot interferometer 31' with the associated Fabry-Pérot etalon 35 hypothetically absent. Accordingly, the mask 138, 138.4 is configured and aligned so that within the imaging plane $31.2^{i'}$ of the Fabry-Pérot interferometer 31', the light within the regions 326.1, 326.2, 326.3 associated with the images of the second end 98.1", 98.2", 98.3" of the first 30.1', second 30.2' and third 30.3' scattered light signals is exclusively from the associated first 30.1', second 30.2' and third 30.3' scattered light signals, and light associated with the remaining region 328 of the imaging plane 31.2" is exclusively from the uniform and diffuse reference beam 90'.

Referring to FIG. 112e, with the Fabry-Pérot etalon 35 in place, the Fabry-Pérot interferometer 31' generates a first set of fringes 330 in the region 328 associated with the uniform and diffuse reference beam 90', and a plurality of second sets of fringes 332.1, 332.2, 332.3 in the regions 326.1, 326.2, 326.3 associated with the first 30.1', second 30.2' and third 30.3' scattered light signals, wherein each set of fringes 330, 332.1, 332.2, 332.3 is generated responsive to the transmission function of the Fabry-Pérot etalon 35 as described hereinabove. Each second set of fringes 332.1, 332.2, 332.3 is processed separately together with the first set of fringes 330 as described hereinabove so as to respectively solve for the corresponding associated detectable observables P.1, P.2, P.3, respectively, corresponding to the condition of the atmosphere 20 in each of the respective associated interaction regions 17.1, 17.2, 17.3. Accordingly, each of the second set of fringes 332.1, 332.2, 332.3 and the first set of fringes 330 are first separately integrated so as to provide for four corresponding separate effective linear radial fringe intensities that are then used to solve for the corresponding associated detectable observables P.1, P.2, P.3.

Referring to FIGS. 113a-113e, a second embodiment of the sixteenth aspect of a LIDAR system 24", $24^{xvi''}$ is the substantially the same as the first embodiment of the sixteenth aspect of a LIDAR system 24", $24^{xvi'}$ illustrated in FIGS. 112a-112e, except that the first 644.1, second 644.2 and third 644.3 locations of the first 30.1', second 30.2' and third 30.3' scattered light signals are all at a substantially equal radial location relative to the optic axis 39 of the imaging optics 37 of the Fabry-Pérot interferometer 31', so as to each be substantially radially aligned with a common set of fringes of the Fabry-Pérot interferometer 31'.

More particularly, in FIG. 112e, the scattered light signals 30.1', 30.2' and 30.3' are located on separate fringes 65', 49', 49" and the associated reference fringe pattern 104 is processed separately for each scattered light signal 30.1', 30.2', 30.3', whereas in FIG. 113e, all of the scattered light signals 30.1', 30.2' and 30.3' are located on a common fringe 65', 49', 49". The first embodiment of the sixteenth aspect of the LIDAR system 24", $24^{xvi'}$ provides a more precise reference from the reference fringe pattern 104 for each scattered light signal 30.1', 30.2', 30.3' than the second embodiment of the sixteenth aspect of the LIDAR system 24", $24^{xvi''}$, whereas the second embodiment of the sixteenth aspect of the LIDAR system 24", $24^{xvi''}$ provides for a single computation of a common reference from the reference fringe pattern 104 for all scattered light signals 30.1', 30.2' and 30.3', which speeds computation at the expense of a slightly reduced precision of the reference measurement. Overall system level design considerations will determine which approach is best for that particular application and scenario.

Referring to FIGS. 114a-114e, there is illustrated a seventeenth aspect of a LIDAR system 24", $24^{xvii}$ incorporated in the second aspect of an atmospheric measurement system 10, $10^{ii}$, that is the same the second embodiment of the fifteenth aspect of the LIDAR system 24", $24^{xv''}$ up through the imaging optics 37 of the Fabry-Pérot interferometer 31'—so that respective FIGS. 114b-114e correspond to FIGS. 111b-111e, respectively,—but instead incorporates a second aspect of a detection system 34.3, 34.3' comprising a digital micromirror device (DMD) 142 comprising an array—for example, a Cartesian array of N rows and M columns—of associated micromirrors 144, for example, as illustrated in FIG. 114f, each of which constitutes a controllable pixel 146 that is individually addressable and controllable to one of at least three possible associated pixel mirror rotational states 148, 150, 152. The digital micromirror device (DMD) 142 is located in the rear focal plane 37.2 of the imaging optics 37 of the Fabry-Pérot interferometer 31' so as to receive the scatter 47 and reference 104 fringe patterns processed by the Fabry-Pérot interferometer 31', portions of which, when processed, are selectively reflected onto a pair of photodetectors $154^A$, $154^B$, for example, photomultiplier detectors $154^{A'}$, $154^{B'}$, from which complementary signals 156, 158 detected thereby are processed by the data processor 53 so as to provide for determining the associated measures of the atmosphere 20 therefrom that are processed as described hereinabove.

In the first pixel mirror rotational state 148, the micromirrors 144 of the associated array of micromirrors 144 of the digital micromirror device (DMD) 142 cause first portions 160' of either the scatter fringe pattern 47 or the reference fringe pattern 104 from the Fabry-Pérot interferometer 31' impinging thereupon to be reflected in a first direction 162 to an associated first objective lens 164 and then directed thereby to a first photomultiplier detector $154^{A'}$. Similarly, in the second pixel mirror rotational state 150, micromirrors 144 of the associated array of micromirrors 144 of the digital micromirror device (DMD) 142 cause second portions 160" of either the scatter fringe pattern 47 or the reference fringe pattern 104 from the Fabry-Pérot interferometer 31' impinging thereupon to be reflected in a second direction 166 to an associated second objective lens 168 and to then directed thereby to a second photomultiplier detector $154^{B'}$. Finally, micromirrors 144 of the associated array of micromirrors 144 of the digital micromirror device (DMD) 142 in the third pixel mirror rotational state 152 cause third portions 160''' of either the scatter fringe pattern 47 or the reference fringe pattern 104 from the Fabry-Pérot interferometer 31' impinging thereupon to be reflected in a third direction 170 to a light block 172 that provides for absorbing light impinging thereupon. For example, in one embodiment, the third pixel mirror rotational state 152 corresponds to a state of substantially no rotation of the associated micromirrors 144, which may be achieved, for example, by applying a common voltage to the associated micromirror 144 and it associated mirror address electrodes and yoke address electrodes, so as to create an equal state of electrostatic repulsion between all associated pairs of electrodes associated with the micromirror 144, thereby maintaining the micromirror 144 in a substantially unrotated condition.

The micromirrors 144 of the digital micromirror device (DMD) 142 are relatively efficient, with overall efficiency approaching 90% in one set of embodiments. Accordingly, the digital micromirror device (DMD) 142 provides for digitally isolating light impinging thereupon into two disjoint sets for the portion of the light being analyzed, and for masking a remaining portion of the light. More particularly, the digital micromirror device (DMD) 142 is used to interrogate portions the scatter 47 and reference 104 fringe patterns from the Fabry-Pérot interferometer 31', and in cooperation with the associated first $154^{A'}$ and second $154^{B'}$ photomultiplier detectors, to provide for generating associated one or more pairs of associated complementary signals 156, 158, each responsive to the number of photons in the associated two disjoint sets of light reflected by the digital micromirror device (DMD) 142 resulting from a particular pattern of pixel mirror rotational states to which the associated array of micromirrors 144 of the digital micromirror device (DMD) 142 are set for a particular set of measurements, wherein the associated first $154^{A'}$ and second $154^{B'}$ photomultiplier detectors provide for counting the corresponding number of photons associated with each of the disjoint sets of light reflected by the digital micromirror device (DMD) 142.

In accordance with the second embodiment of the sixteenth aspect, the LIDAR system 24", $24^{xvi'''}$ first calibrates the Fabry-Pérot etalon 35 by analyzing the reference fringe pattern 104, and then generates measures of line-of-sight relative wind velocity U, static temperature Temp, molecular counts MolCounts, aerosol counts Aero Counts, and background counts BackCounts from the scatter 47 and reference 104 fringe patterns, but using the methodology described hereinabove to analyze the selected portions of the scatter 47 and reference 104 fringe patterns and to determine the measures of line-of-sight relative wind velocity U, static temperature Temp, molecular counts MolCounts, aerosol counts AeroCounts, and background counts BackCounts responsive thereto. More particularly, when analyzing the reference fringe pattern 104, the micromirrors 144 not illuminated thereby are set to the third pixel mirror rotational state 152 so that only light from the reference fringe pattern 104 is then processed according to the methodology as described hereinabove. Furthermore, when analyzing the scatter fringe pattern 47, the micromirrors 144 not illuminated thereby are set to the third pixel mirror rotational state 152 so that only light from that particular scatter fringe pattern 47 is then processed according to the methodology as described hereinabove.

Referring to FIGS. 115a-115e, there is illustrated an eighteenth aspect of a LIDAR system 24", $24^{xviii}$ incorporated in the second aspect of an atmospheric measurement system 10, $10^{ii}$, that is substantially the same as the seventeenth aspect of the LIDAR system 24", $24^{xvii}$ as described hereinabove, except that the eighteenth aspect of the LIDAR system 24", $24^{xviii}$ incorporates a plurality of scattered light signals 30' from a plurality of associated final light collecting elements 448. For example, FIG. 115a illustrates two scattered light signals 30', 30.1', 30.2' from separate final light collecting elements 448, 448.1, 448.2 associated with two separate telescopes 32', 32.1', 32.2' are directed to the Fabry-Pérot interferometer 31' by corresponding fiber optics 98, 98.1, 98.2. The mask 138, 138.5 of the eighteenth aspect of the LIDAR system 24", $24^{xviii}$ incorporates two opaque circular regions 138', $138.5^{i'}$, $138.5^{ii'}$ that provide for blocking light from the uniform and diffuse reference beam 90' within two corresponding regions 326.1, 326.2 in the imaging plane $31.2^{i'}$ of the Fabry-Pérot interferometer 31' corresponding to the associated images 114 of the associated scattered light signals 30', 30.1', 30.2', similar in operation and effect as for the eighteenth aspect of the LIDAR system 24", $24^{xviii}$, but for two scattered light signals 30' rather than three, wherein each of the scattered light signals 30', 30.1', 30.2', and the corresponding opaque circular regions 138', $138.5^{i'}$, $138.5^{ii'}$ of the mask 138, 138.5 are associated common circular 65' or arcuate 49', 49" fringes of the Fabry-Pérot interferometer 31'. The Fabry-Pérot interferometer 31' generates a first scatter fringe patterns 47.1 in the imaging plane $31.2^{i'}$ of the of the Fabry-Pérot interferometer 31' from the first scattered light signal 30.1', and generates a second scatter fringe pattern 47.2 in the imaging plane $31.2^{i'}$ of the of the Fabry-Pérot interferometer 31' from the second scattered light signal 30.2'.

In accordance with the eighteenth aspect, the LIDAR system 24", $24^{xviii}$ first calibrates the Fabry-Pérot etalon 35 by analyzing the reference fringe pattern 104, and then generates measures of line-of-sight relative wind velocity U, static temperature Temp, molecular counts MolCounts, aerosol counts AeroCounts, and background counts BackCounts from the scatter 47 and reference 104 fringe patterns, but using the methodology described hereinabove to analyze the selected portions of the scatter 47 and reference 104 fringe patterns and to determine the measures of line-of-sight relative wind velocity U, static temperature Temp, molecular counts MolCounts, aerosol counts AeroCounts, and background counts BackCounts responsive thereto for each separate scatter fringe pattern 47.1, 47.2. More particularly, when analyzing the reference fringe pattern 104, the micromirrors 144 not illuminated thereby are set to the third pixel mirror rotational state 152 so that only light from the reference fringe pattern 104 is then processed according to the methodology described hereinabove. Furthermore, when analyzing the first scatter fringe pattern 47.1, the micromirrors 144 not illuminated thereby are set to the third pixel mirror rotational state 152 so that only light from that particular first scatter fringe pattern 47.1 is then processed according to the methodology described hereinabove. Finally, when analyzing the second scatter fringe pattern 47.2, the micromirrors 144 not illuminated thereby are set to the third pixel mirror rotational state 152 so that only light from that particular second scatter fringe pattern 47.2 is then processed according to the methodology described hereinabove.

Referring to FIGS. 116a-116e, there is illustrated a nineteenth aspect of a LIDAR system 24", $24^{xix}$ incorporated in the second aspect of an atmospheric measurement system 10, $10^{ii}$, that is substantially the same as the eighteenth aspect as described hereinabove, except that the nineteenth aspect incorporates the second aspect of a mask system 138, 138.2 comprising a programmable mask 138.2 that replaces the mask 138, 138.5 of the eighteenth aspect of the LIDAR system 24", $24^{xviii}$, wherein the programmable mask 138.2 comprises a second digital micromirror device (DMD) 334 and an associated second light block 336. The second digital micromirror device (DMD) 334 is oriented relative to the reference illuminator 324 and to the second beam splitter optic 136 so that when the associated micromirrors 144 of the second digital micromirror device (DMD) 334 are in a first pixel mirror rotational state 338, light from the uniform and diffuse reference beam 90' incident thereupon is reflected towards the second beam splitter optic 136 and is reflected from the partially-reflective surface 136.1 into to the Fabry-Pérot interferometer 31', and when the associated micromirrors 144 of the second digital micromirror device (DMD) 334 are in a second pixel mirror rotational state 340, light from the uniform and diffuse reference beam 90' incident thereupon is reflected towards the second light block 336 and is substantially absorbed thereby. Accordingly, the micromirrors 144 of the second digital micromirror device (DMD) 334 that would coincide in location with the opaque circular regions 138', 138.5$^{i'}$, 138.5$^{ii'}$ of the mask 138, 138.5 of the eighteenth aspect of the LIDAR system 24", 24$^{xviii}$ are set to the second pixel mirror rotational state 340 so as to block the corresponding portions of the uniform and diffuse reference beam 90', and the remaining micromirrors 144 of the second digital micromirror device (DMD) 334 are set to the first pixel mirror rotational state 338 so as to generate a masked reference beam 90", 90.5" that corresponds to the masked reference beam 90", 90.5" of the eighteenth aspect of the WAR system 24", 24$^{xviii}$. Otherwise, the nineteenth aspect of the LIDAR system 24", 24$^{xix}$ functions the same as the eighteenth aspect of the LIDAR system 24", 24$^{xviii}$, with FIGS. 116b-116e corresponding to FIGS. 115b-115e, respectively.

Although the LIDAR systems 24', 24$^i$, 24$^{i'}$, 24$^{ii}$, 24$^{iii}$, 24$^{iv}$, 24$^v$, 24$^{vi}$, 24$^{vii}$, 24$^{viii}$, 24$^{viii'}$, 24$^{viii''}$, 24$^{viii'''}$, 24$^{viii.a}$, 24$^{viii.b}$, 24$^{viii.c}$, 24", 24$^{ix'}$, 24$^{ix''}$, 24$^{ix'''}$, 24$^{ix''''}$, 24$^x$, 24$^{xi}$, 24$^{xii}$, 24$^{xiii}$, 24$^{xv'}$, 24$^{xv''}$, 24$^{xvi'}$, 24$^{xvi''}$, 24$^{xvii}$, 24$^{xviii}$, 24$^{xix}$ described herein have each incorporated a Fabry-Pérot interferometer 31', it should be understood that any type of interferometer 31 could instead also be used, for example, including but not limited to either a Michelson interferometer and associated variations thereof, a Twyman-Green interferometer or a Fizeau interferometer.

For example, referring to FIG. 117, in accordance with a second aspect, the interferometer 31 comprises a tunable Michelson interferometer 31" comprising a collimating lens 33, a beam splitter 706, first 708.1 and second 708.2 planar mirrors, a positioner 710 operatively associated with one of the first 708.1 and second 708.2 planar mirrors—illustrated in FIG. 117 operatively associated with the first planar mirror 708.1—and associated imaging optics 37, wherein the tunable Michelson interferometer 31" can be substituted for the Fabry-Pérot interferometer 31' in any of the above described LIDAR systems 24', 24$^i$, 24$^{i'}$, 24$^{ii}$, 24$^{iii}$, 24$^{iv}$, 24$^v$, 24$^{vi}$, 24$^{vii}$, 24$^{viii}$, 24$^{viii'}$, 24$^{viii''}$, 24$^{viii'''}$, 24$^{viii.a}$, 24$^{viii.b}$, 24$^{viii.c}$, 24", 24$^{ix'}$, 24$^{ix''}$, 24$^{ix'''}$, 24$^{ix''''}$, 24$^x$, 24$^{xi}$, 24$^{xii}$, 24$^{xiii}$, 24$^{xv'}$, 24$^{xv''}$, 24$^{xvi'}$, 24$^{xvi''}$, 24$^{xvii}$, 24$^{xviii}$, 24$^{xix}$ while maintaining the relationships between the collimating lens 33 and the imaging optics 37 with the remainder of the elements of the LIDAR systems 24', 24$^i$, 24$^{i'}$, 24$^{ii}$, 24$^{iii}$, 24$^{iv}$, 24$^v$, 24$^{vi}$, 24$^{vii}$, 24$^{viii}$, 24$^{viii'}$, 24$^{viii''}$, 24$^{viii'''}$, 24$^{viii.a}$, 24$^{viii.b}$, 24$^{viii.c}$, 24", 24$^{ix'}$, 24$^{ix''}$, 24$^{ix'''}$, 24$^{ix''''}$, 24$^x$, 24$^{xi}$, 24$^{xii}$, 24$^{xiii}$, 24$^{xv'}$, 24$^{xv''}$, 24$^{xvi'}$, 24$^{xvi''}$, 24$^{xvii}$, 24$^{xviii}$, 24$^{xix}$ the same as for the Fabry-Pérot interferometer 31'. The collimating lens 33 having an associated optic axis 33' provides for transforming the scattered light signal 30' into a collimated beam of light 712 that propagates along the optic axis 33' to the beam splitter 706 located between the collimating lens 33 and the second planar mirror 708.2, and between the imaging optics 37 and the first planar mirror 708.1. A partially reflective surface 706' of the beam splitter 706, for example, with 50% reflectivity, is oriented at a substantially 45 degree angle with respect to the optic axis 33' of the collimating lens 33, and is oriented at a substantially 45 degree angle with respect to the optic axis 39 of the imaging optics 37, wherein the associated optic axes 33', 39 are substantially normal with respect to one another, the reflective surface 708.1' of the first planar mirror 708.1 is substantially normal to the optic axis 39 of the imaging optics 37, the reflective surface 708.2' of the second planar mirror 708.2 is substantially normal to the optic axis 33' of the collimating lens 33, and the planes of the partially reflective surface 706' and the first 708.1 and second 708.2 planar mirrors are each substantially normal to the Y-Z plane illustrated in FIG. 117

In operation, a first portion 712.1 of the collimated beam of light 712 is reflected from the partially reflective surface 706' of the beam splitter 706, towards the first planar mirror 708.1 along the optic axis 39 of the imaging optics 37 and is reflected back along the optic axis 39 by the reflective surface 708.1' of the first planar mirror 708.1, after which the first portion 712.1 of the collimated beam of light 712 propagates through the partially reflective surface 706' of the beam splitter 706, and then propogates to the imaging optics 37 along the optic axis 39 thereof. A second portion 712.2 of the collimated beam of light 712 propagates through the partially reflective surface 706' of the beam splitter 706 towards the second planar mirror 708.2 along the optic axis 33' of the collimating lens 33, and is reflected back along the optic axis 33' by the reflective surface 708.1' of the first planar mirror 708.1, and is then reflected from the partially reflective surface 706' of the beam splitter 706 to the imaging optics 37 along the optic axis 39 thereof. The first 712.1 and second 712.2 portions of the collimated beam of light 712 comprise plane waves 712' that are relatively coherent and interfere with one another when mixed following the respective transmission through or reflection from the partially reflective surface 706' of the beam splitter 706, wherein the resulting interference is dependent upon the optical path difference δ of the first 712.1 and second 712.2 portions of the collimated beam of light 712, given by:

$$\delta(z) = L_1(z) - L_2 \quad (97)$$

The resulting fringes of the associated interfering plane waves 712' are imaged by the imaging optics 37 at the focal plane 37.2 onto a photodetector 34.4' of an associated fourth aspect of a detection system 34, 34.4, and the intensity I(δ) of the resulting detected signal at a particular wave number σ for a particular optical path difference δ is given by:

$$I(\delta) = I(\sigma)[1 + e^{-j2\pi\sigma\delta}] \quad (98)$$

where I(σ) is the spectral distribution of the scattered light signal 30' with σ=1/λ, and δ is the optical path difference δ of the first 712.1 and second 712.2 portions of the collimated beam of light 712. The total intensity I(δ) is then given by integrating over all all wave numbers σ, as follows:

$$I(\delta) = \int_{-\infty}^{\infty} I(\sigma)d\sigma + \int_{-\infty}^{\infty} I(\sigma)e^{-j2\pi\sigma\delta}d\sigma = I_0 + F\{I(\sigma)\} \quad (99)$$

where $I_0$ is a constant, and $F\{I(\sigma)\}$ is the Fourier Transform of the spectral distribution I(σ) with respect to wave number σ. Accordingly, the spectral distribution I(σ) can be found from an Inverse Fourier Transform $F^{-1}\{I(\delta(z))\}$ of a series of measurements of total intensity I(δ(z)) measured over a range of optical path differences δ(z), as follows:

$$I(\sigma) = \int_{-\infty}^{\infty} I(\delta)e^{j2\pi\sigma\delta}d\delta = F^{-1}\{I(\delta)\} \quad (100)$$

For example, for the embodiment illustrated in FIG. 117, the series of measurements of total intensity I(δ(z)) are made by using the positioner 710, for example, a stepper motor 710', to scan the position of the first planar mirror 708.1 along the "Z" axis responsive to a signal from an associated data processor 53/controller 53', thereby adjusting the first path length $L_1(z)$, and the optical path difference $\delta(z)$ responsive thereto, and acquiring the associated total intensity $I(\delta)$ from the photodetector 34.4' at each scanned position. The resulting series of measurements of total intensity $I(\delta(z))$ is then transformed by the associated data processor 53 in accordance with equation (100), for example, using a Discrete Inverse Fourier Transform. The resulting spectral distribution $I(\sigma)$ may then be used to determine the associated atmospheric data 36 in accordance with a methodology similar to that described hereinabove for the Fabry-Pérot interferometer 31', wherein the transmission T of the Fabry-Pérot interferometer 31' is replaced with the transmission function of the tunable Michelson interferometer 31" which to a first order is represented by a Fourier transform, which can then be used with the same Levenberg-Marquardt nonlinear least squares method as described hereinabove, using the same broadening functions that account for Doppler, Laser Spectral Width, Scattering, and Turbulent Motion broadening in the inversion of the data from the tunable Michelson interferometer 31".

As another example, referring to FIG. 118, in accordance with a third aspect, the interferometer 31 comprises a Spatial Heterodyne Spectrometer (SHS) 31''' comprising a collimating lens 33, a beam splitter 706, first 714.1 and second 714.2 diffraction gratings, and associated imaging optics 37, wherein the Spatial Heterodyne Spectrometer (SHS) 31''' can be substituted for the Fabry-Pérot interferometer 31' in any of the above described LIDAR systems 24', $24^i$, $24^{i'}$, $24^{ii}$, $24^{iii}$, $24^{iv}$, $24^v$, $24^{vi}$, $24^{vii}$, $24^{viii}$, $24^{viii'}$, $24^{viii''}$, $24^{viii'''}$, $24^{viii.a}$, $24^{viii.b}$, $24^{viii.c}$, 24", $24^{ix'}$, $24^{ix''}$, $24^{ix'''}$, $24^{ix''''}$, $24^x$, $24^{xi}$, $24^{xii}$, $24^{xiii}$, $24^{xv'}$, $24^{xv''}$, $24^{xvi'}$, $24^{xvi''}$, $24^{xvii}$, $24^{xviii}$, $24^{xix}$ while maintaining the relationships between the collimating lens 33 and the imaging optics 37 with the remainder of the elements of the LIDAR systems 24', $24^i$, $24^{i'}$, $24^{ii}$, $24^{iii}$, $24^{iv}$, $24^v$, $24^{vi}$, $24^{vii}$, $24^{viii}$, $24^{viii'}$, $24^{viii''}$, $24^{viii'''}$, $24^{viii.a}$, $24^{viii.b}$, $24^{viii.c}$, 24", $24^{ix'}$, $24^{ix''}$, $24^{ix'''}$, $24^{ix''''}$, $24^x$, $24^{xi}$, $24^{xii}$, $24^{xiii}$, $24^{xv'}$, $24^{xv''}$, $24^{xvi'}$, $24^{xvi''}$, $24^{xvii}$, $24^{xviii}$, $24^{xix}$ the same as for the Fabry-Pérot interferometer 31'. The Spatial Heterodyne Spectrometer (SHS) 31''' is described in the following references, each of which is incorporated by reference it its entirety: U.S. Pat. No. 5,059,027 to Roesler et al. issued on 22 Oct. 1991; John M. Harlander, Fred L. Roesler, Joel G. Cardon, Christoph R. Englert, and Robert R. Conway, "SHIMMER: a spatial heterodyne spectrometer for remote sensing of Earth's middle atmosphere," *Applied Optics* 41, 1343-1352 (2002); John M. Harlander, Fred L. Roesler, Christoph R. Englert, Joel Cardon, and Jeff Wimperis, "Spatial Heterodyne Spectroscopy for High Spectral Resolution Space-Based Remote Sensing", *Optics & Photonics News,* 551, 46-51 (2004); Ian Powell and Pavel Cheben, "Modeling of the generic spatial heterodyne spectrometer and comparison with conventional spectrometer," *Applied Optics,* 36, 9079-9086 (2006); U.S. Pat. No. 7,535,572 B2 to Christoph P. Englert issued on 19 May 2009; and U.S. Patent Application Publication No. 2009/0231592 A1 to Harlander et al. published on 17 Sep. 2009.

The Spatial Heterodyne Spectrometer (SHS) 31''' is a two beam dispersive interferometer similar to a Michelson interferometer, but with the associated first 708.1 and second 708.2 planar mirrors replaced with corresponding first 714.1 and second 714.2 diffraction gratings, each tilted at the Litrow angle $\theta_L$ relative to the corresponding associated optic axes 33', 39 so as to provide for generating a Fizeau fringe pattern 716 in the imaging plane $31.2^{i'''}$ of the associated imaging optics 37, wherein the Fizeau fringe pattern 716 comprises a spatial Fourier Transform of the spectral distribution $I(\sigma)$ of the associated scattered light signal 30' that is input to the Spatial Heterodyne Spectrometer (SHS) 31'''—but without the moving parts of the tunable Michelson interferometer 31" described hereinabove—wherein all associated spectral components are processed simultaneously rather than over time.

More particularly, the collimating lens 33 having an associated optic axis 33' provides for transforming the scattered light signal 30' into a collimated beam of light 712 that propagates along the optic axis 33' to the beam splitter 706 located between the collimating lens 33 and the second diffraction grating 714.2, and between the imaging optics 37 and the first diffraction grating 714.1. A partially reflective surface 706' of the beam splitter 706, for example, with 50% reflectivity, is oriented at a substantially 45 degree angle with respect to the optic axis 33' of the collimating lens 33, and is oriented at a substantially 45 degree angle with respect to the optic axis 39 of the imaging optics 37, wherein the associated optic axes 33', 39 are substantially normal with respect to one another, and the plane of the partially reflective surface 706' is substantially normal to the Y-Z plane illustrated in FIG. 118a.

Referring to FIG. 118b, each diffraction grating 714 of the first 714.1 and second 714.2 diffraction gratings comprises a plurality of periodically-spaced grooves 718 having an associated grating pitch ∇, wherein an incident plane wave 720.1 incident at an angle $\theta_i$ relative to a normal 722 to the diffraction grating 714 is diffracted at a diffraction-order-dependent angle $\theta_r$ as an associated diffracted plane wave 720.2, wherein for operation in a medium having an index of refraction μ, the relationship between diffraction order m, wave number σ, grating pitch ∇ and the associated angles $\theta_i$, $\theta_r$ is given by the diffraction equation that provides for constructive interference between corresponding rays 724.1, 724.2 of the incident plane wave 720.1 upon diffraction from different periodically-spaced grooves 718 of the diffraction grating 714, as follows:

$$m\lambda = \frac{m}{\sigma} = \mu\Lambda(\sin\theta_i + \sin\theta_r) \tag{101}$$

wherein angles $\theta_i$, $\theta_r$ are positive when measured counter-clockwise from the normal 722. In a Littrow mode of operation, the incident plane wave 720.1 is diffracted back upon itself—but with phase changes across the diffraction grating 714,—with the angles of incidence $\theta_i$ and diffraction $\theta_r$ equal to one another at what is referred to as the Littrow angle $\theta_L$, i.e. $\theta_r=\theta_i=\theta_L$, which occurs at a corresponding wave number $\sigma=\sigma_L$ (referred to as the Littrow wave number $\sigma_L$) given as follows:

$$\sigma_L = \frac{1}{2\left(\frac{\mu\Lambda}{m}\right)\sin\theta_L}. \tag{102}$$

Referring again to FIG. 118a, the periodically-spaced grooves 718 of each of the first 714.1 and second 714.2 diffraction gratings are all oriented substantially parallel to the X axis, so as to provide for the wavefronts of the resulting diffracted plane waves 720.2 to be perpendicular to the Y-Z plane, and for diffraction-related rotations of the associated diffracted plane waves 720.2 to be about the X-axis.

In operation, a first portion 712.1 of the collimated beam of light 712 is reflected from the partially reflective surface 706' of the beam splitter 706, towards the first diffraction grating 714.1 along the optic axis 39 of the imaging optics 37 and is diffracted back along the optic axis 39 by the periodically-spaced grooves 718 of the first diffraction grating 714.1, after which the first portion 712.1 of the collimated beam of light 712 propagates through the partially reflective surface 706' of the beam splitter 706, and then propagates to the imaging optics 37 along the optic axis 39 thereof. A second portion 712.2 of the collimated beam of light 712 propagates through the partially reflective surface 706' of the beam splitter 706 towards the second diffraction grating 714.2 along the optic axis 33' of the collimating lens 33, and is diffracted back along the optic axis 33' by the periodically-spaced grooves 718 of the second diffraction grating 714.2, and is then reflected from the partially reflective surface 706' of the beam splitter 706 to the imaging optics 37 along the optic axis 39 thereof. The first 712.1 and second 712.2 portions of the collimated beam of light 712 comprise plane waves 712' that are relatively coherent and interfere with one another when mixed following the respective transmission through or reflection from the partially reflective surface 706' of the beam splitter 706. The reflected ray b1 of top-most ray b0 follows a shorter path than the corresponding transmitted ray b2, and the reflected ray a1 of bottom-most ray a0 follows a longer path than the corresponding transmitted ray a2, resulting in a phase shift across the associated resulting first 712.1' and second 712.2' plane waves.

For spectral components of the scattered light signal 30' at the Littrow wave number $\sigma_L$, the wavefronts of the resulting corresponding first 712.1' and second 712.2' plane waves will each be oriented substantially normal to the optic axis 39 of the imaging optics 37. However, spectral components of the scattered light signal 30' having different wave number σ will result in corresponding first 712.1' and second 712.2' plane waves that are each diffracted at an angle β relative to the associated corresponding optic axes 33', 39, so that the resulting wavefronts of the associated first 712.1' and second 712.2' plane waves are each at an angle β relative to the normal to the optic axis 39 of the imaging optics 37 and at an angle 2β relative to one another, as indicated in FIG. 118a. For small angles, angle β may be approximates as:

$$\beta = 2\tan(\theta_L)[(\sigma - \sigma_L)/\sigma], \quad (103)$$

for which equation (101)—the diffraction equation—may be expressed with respect to the Littrow angle $\theta_L$ and angle β as follows:

$$m\lambda = \frac{m}{\sigma} = \mu\Lambda(\sin\theta_L + \sin(\theta_L + \beta)). \quad (104)$$

The interference between the first 712.1' and second 712.2' plane waves with corresponding wavefronts oriented at an angle 2β relative to one another causes a Fizeau fringe pattern 716 having a spatial frequency given by:

$$f(\sigma) = 2\mu m\sigma \sin(\beta) \quad (105)$$

which, for small angle β can be approximated as:

$$f(\sigma) = \frac{2\mu m(\sigma_L - \sigma)}{\cos(\theta_L)\sigma_L} \quad (106)$$

The resulting Fizeau fringe pattern 716 is imaged by the imaging optics 37, for example, a pair of first 37' and second 37" relay lenses, onto an imaging detector 34.5' of an associated fifth aspect of a detection system 34, 34.5—for example, either a CCD detection system 34.1', a camera 34.1", or a two-dimensional array of photodetectors 34.1'''—located at the rear focal plane 37.2 of the imaging optics 37.

Referring to FIG. 119, the Spatial Heterodyne Spectrometer (SHS) 31''' illustrated in FIG. 118a may be modified with the addition of first 726.1 and second 726.2 field widening prisms,—for example, each constructed of an optical material, for example, glass or fused quartz—with the first field widening prism 726.1 located between the beam splitter 706 and the first diffraction grating 714.1 in the first arm 728.1 of the Spatial Heterodyne Spectrometer (SHS) 31''', and with the second field widening prism 726.2 located between the beam splitter 706 and the second diffraction grating 714.2 in the second arm 728.2 of the Spatial Heterodyne Spectrometer (SHS) 31''', wherein each of the first 726.1 and second 726.2 field widening prisms is configured so as to provide for refracting the respective first 712.1 and second 712.2 portions of the collimated beam of light 712 at the Litrow angle $\theta_L$, thereby providing for the associated first 714.1 and second 714.2 diffraction gratings to each be oriented substantially normal to the corresponding respective optic axes 39, 33'. In one embodiment, the second face 726" of each of the first 726.1 and second 726.2 field widening prisms is oriented substantially parallel to the corresponding associated first 714.1 and second 714.2 diffraction grating. The first 726.1 and second 726.2 field widening prisms provide for maintaining the phase of the associated first 712.1 and second 712.2 portions of the collimated beam of light 712 to be maintained over a substantially larger range of angles than possible without the first 726.1 and second 726.2 field widening prisms, thereby providing for using scattered light signals 30' over a substantially wider range of angles, thereby increasing the throughput and associated signal levels of this "field-widened" Spatial Heterodyne Spectrometer (SHS) 31''' relative to the Spatial Heterodyne Spectrometer (SHS) 31''' as illustrated in FIG. 118a, by correcting for the interference path difference that would otherwise be caused by off axis angles, thereby providing for a relatively large solid angle to be viewed coherently through the Spatial Heterodyne Spectrometer (SHS) 31'''.

Continuing to refer to FIG. 119, in accordance with a fourth aspect, the interferometer 31 comprises a Doppler Asymmetric Spatial Heterodyne Spectrometer 31''''—also referred to as a DASH Spectrometer 31''''—which comprises the above-described "field-widened" Spatial Heterodyne Spectrometer (SITS) 31''', but with the first 728.1 and second 728.2 arms of the DASH Spectrometer 31'''' having unequal optical path lengths $d_0$ and $d_0 + \Delta d$. Furthermore, an additional prism 730 of optical material—for example, constructed of an optical material, for example, glass or fused quartz—may be inserted in the longer arm 728 of the DASH Spectrometer 31'''' between the beam splitter 706 and the associated corresponding first 726.1 or second 726.2 field widening prism, so as to provide for compensating for the longer associated optical path length $d_0 + \Delta d$, thereby providing for the correct imaging of the first 714.1 and second 714.2 diffraction gratings on the imaging detector 34.5'. For example, this is illustrated in FIG. 119 with a parallel-faced prism 730' in the second arm 728.2 between the beam splitter 706 and the second field widening prism 726.2. Alternatively, instead of, or in addition to, the separate prism 730 in one of the first 728.1 or second 728.2 arms of the of the DASH Spectrometer 31'''', the associated first 726.1 or second 726.2 field widening prisms could be made with different thicknesses so as to provide a similar optical path length compensation.

The DASH Spectrometer 31'''' can be substituted for the Fabry-Pérot interferometer 31' in any of the above described LIDAR systems 24', 24$^i$, 24$^{i'}$, 24$^{ii}$, 24$^{iii}$, 24$^{iv}$, 24$^v$, 24$^{vi}$, 24$^{vii}$, 24$^{viii}$, 24$^{viii'}$, 24$^{viii''}$, 24$^{viii'''}$, 24$^{viii.a}$, 24$^{viii.b}$, 24$^{viii.c}$, 24'', 24$^{ix'}$, 24$^{ix''}$, 24$^{ix'''}$, 24$^{ix''''}$, 24$^x$, 24$^{xi}$, 24$^{xii}$, 24$^{xiii}$, 24$^{xv'}$, 24$^{xv''}$, 24$^{xvi'}$, 24$^{xvi''}$, 24$^{xvii}$, 24$^{xviii}$, 24$^{xix}$ while maintaining the relationships between the collimating lens 33 and the imaging optics 37 with the remainder of the elements of the LIDAR systems 24', 24$^i$, 24$^{i'}$, 24$^{ii}$, 24$^{iii}$, 24$^{iv}$, 24$^v$, 24$^{vi}$, 24$^{vii}$, 24$^{viii}$, 24$^{viii'}$, 24$^{viii''}$, 24$^{viii'''}$, 24$^{viii.a}$, 24$^{viii.b}$, 24$^{viii.c}$, 24'', 24$^{ix'}$, 24$^{ix''}$, 24$^{ix'''}$, 24$^{ix''''}$, 24$^x$, 24$^{xi}$, 24$^{xii}$, 24$^{xiii}$, 24$^{xv'}$, 24$^{xv''}$, 24$^{xvi'}$, 24$^{xvi''}$, 24$^{xvii}$, 24$^{xviii}$, 24$^{xix}$ the same as for the Fabry-Pérot interferometer 31'. The DASH Spectrometer 31'''' is described in the following references, each of which is incorporated by reference it its entirety: Christoph R. Englert, David D. Babcock, and John M. Harlander 'Doppler asymmetric spatial heterodyne spectroscopy (DASH): concept and experimental demonstration', *Applied Optics*, 29, 7297-7307, (2007); and U.S. Pat. No. 7,773,229 B2 to Harlander et al. issued on 10 Aug. 2010.

Referring to FIG. 120, there is illustrated an image of Fizeau fringe patterns 716 from either the Spatial Heterodyne Spectrometer (SHS) 31''' or the DASH Spectrometer 31'''' for two different scattered light signals 30', one substantially monochromatic, resulting in a corresponding first Fizeau fringe pattern 716.1, and the other slightly Doppler-shifted with respect thereto, as a function of optical path difference δ that varies with position across the imaging detector 34.5', for example, along the Z-direction as illustrated in FIGS. 118a and 119, resulting in a corresponding second Fizeau fringe pattern 716.2, illustrating the effect of a phase shift between the two fringe patterns having slightly different frequencies. As described more fully hereinbelow, the Fizeau fringe patterns 716 represent the Fourier transforms of the spectra of the associated scattered light signals 30', wherein light that is nearly monochromatic results in a sinusoidal Fizeau fringe patterns 716.

The optical path length difference Δd in optical path lengths $d_0$, $d_0+\Delta d$ of the first 728.1 and second 728.2 arms of the DASH Spectrometer 31'''' provides for enhancing or optimizing the difference between Doppler-shifted and non-Doppler-shifted Fizeau fringe patterns 716 from the DASH Spectrometer 31''''. For example, referring to FIG. 121, the Fizeau fringe pattern 716$^T$ for a purely temperature-broadened scattered light signal 30' having a Gaussian spectral line shape proportional to:

$$e^{-\frac{(\sigma-\sigma_L)^2}{2\sigma_D^2}} \quad (107)$$

with a width $\sigma_D$ of:

$$\sigma_D = \sigma_L\sqrt{\frac{kT}{Mc^2}} \quad (108)$$

is illustrated as a function of optical path difference δ, as is Fizeau fringe pattern 716$^{TD}$ for a slightly Doppler-shifted version thereof, where T is the temperature, M is the mass of the emitter, and k is the Boltzmann constant. The optimal optical path length difference $\Delta d_{OPT}$ that maximizes the envelope of the difference 732 of the Fizeau fringe patterns 716$^T$, 716$^{TD}$ is given by:

$$2\Delta d_{OPT} = \frac{1}{2\pi\sigma_D}. \quad (108)$$

When configured with the correct optical path length difference Δd, the DASH Spectrometer 31'''' provides for substantial Doppler-induced shifts in the frequency of the Fizeau fringe pattern 716 that can readily be detected by the imaging detector 34.5'. The intensity I(z) of the Fizeau fringe pattern 716 measured by the imaging detector 34.5', as a function of the position z on the imaging detector 34.5', is given by:

$$I(z) = \frac{1}{2}\int_0^\infty I(\sigma)\left[1+\cos\left\{2\pi[4(\sigma-\sigma_L)\tan\theta_L]\times\left[z+\frac{\Delta d}{2\tan\theta_L}\right]\right\}\right]d\sigma \quad (109)$$

which is a Fourier transform of the corresponding spectral distribution I(σ).

Referring to FIGS. 122a-122c, there is illustrated a Zemax model of an embodiment of the DASH Spectrometer 31'''$^i$, portions of which are otherwise shown schematically in FIG. 119, and which is configured so as to provide for processing a plurality of separate light signals including at least one scattered light signal 30', possibly in combination with a reference light signal 105, each of which is input to the DASH Spectrometer 31''''$^i$ from the focal plane 33.1 of the collimating lens 33 from a different position, different positions being separated from one another along a direction parallel to the periodically-spaced grooves 718 of the first 714.1 and second 714.2 diffraction gratings. For example, in the embodiment illustrated in FIGS. 122a and 122b, there is illustrated four separate scattered light signals 30.1', 30.2', 30.3', 30.4' and a reference light signal 105, each at different X-locations along the intersection of the focal plane 33.1 of the collimating lens 33 with an X-Z plane through the optic axis 33' of the collimating lens 33. The DASH Spectrometer 31''''$^i$ incorporates an anamorphic imaging element 734, for example, a bi-convex cylindrical lens 734' located between the imaging optics 37 and the imaging detector 34.5' as illustrated in FIGS. 122a and 122b, or incorporated in the imaging optics 37, that, as illustrated in FIG. 122c, provides for generating—at the imaging detector 34.5' along the X-direction—an image of the scattered light signals 30.1', 30.2', 30.3', 30.4' and the reference light signal 105 in the focal plane 33.1 of the collimating lens 33, without adversely affecting the resulting Fizeau fringe patterns 716$^i$, 716$^{ii}$, 716$^{iii}$, 716$^{iv}$, 716$^v$ generated by the DASH Spectrometer 31''''$^i$ for the scattered light signals 30.1', 30.2', 30.3', 30.4' and the reference light signal 105, respectively, that are imaged by the associated imaging optics 37 onto the imaging detector 34.5'. Accordingly, the anamorphic imaging element 734 provides for collecting and separating the light of the scattered light signals 30.1', 30.2', 30.3', 30.4' and the reference light signal 105 at the imaging detector 34.5', and the imaging optics 37 independently provide for imaging onto the imaging detector 34.5' the fringe patterns 716$^i$, 716$^{ii}$, 716$^{iii}$, 716$^{iv}$, 716$^v$ generated by the DASH Spectrometer 31''''$^i$. In the embodiment illustrated in FIGS. 122a and 122b, the bi-convex cylindrical lens 734' having an optic axis aligned with the Y-direction provides for magnifying power in the X-direction without any magnifying power in the Z-direction.

U.S. Pat. Nos. 5,59,027 and 7,535,572 B2, U.S. Patent Application Publication No. 2009/0231592 A1, and the publication by John M. Harlander, Fred L. Roesler, Christoph R. Englert, Joel Cardon, and Jeff Wimperis, "Spatial Heterodyne Spectroscopy for High Spectral Resolution Space-Based Remote Sensing", *Optics & Photonics News,* 551, 46-51 (2004), each referred to hereinabove and incorporated herein by reference, disclose various alternative aspects that can be used to provide for alternative embodiments of either the Spatial Heterodyne Spectrometer (SHS) 31''' or the DASH Spectrometer 31''''. For example, in accordance with the teachings of U.S. Pat. No. 5,59,027, the collimating lens 33 and imaging optics 37 may each be embodied with corresponding reflective elements rather than refractive elements. Furthermore, in accordance with the teachings of U.S. Pat. No. 7,535,572 and the above-identified 2004 publication of Harlander et al., either the Spatial Heterodyne Spectrometer (SHS) 31''' or the DASH Spectrometer 31'''' may be embodied in a monolithic element with the associated beam splitter 706, first 726.1 and second 726.2 field widening prisms, prism 730, and first 714.1 and second 714.2 diffraction gratings optically contacted with one another with fused silica spacers instead of being individually fixed in a mechanical structure, and, for example, each constructed of fused silica. Yet further, in accordance with the teachings of U.S. Patent Application Publication No. 2009/0231592 A1, each of the first 714.1 and second 714.2 diffraction gratings may each be replaced with a combination of a dispersing prism and a mirror.

The spectral distribution $I(\sigma)$ of the scattered light signal(s) 30' may be determined by inverse Fourier transformation of the measured intensity $I(z)$ from equation (109) of the Fizeau fringe pattern 716—for example, using a Discrete Inverse Fourier Transform,—and then used to determine the associated atmospheric data 36 in accordance with a methodology similar to that described hereinabove for the Fabry-Pérot interferometer 31', wherein the transmission T of the Fabry-Pérot interferometer 31' is replaced with the transmission function of either the Spatial Heterodyne Spectrometer (SHS) 31''' or the DASH Spectrometer 31'''' which to a first order is represented by a Fourier transform, which can then be used with the same Levenberg-Marquardt nonlinear least squares method as described hereinabove, using the same broadening functions that account for Doppler, Laser Spectral Width, Scattering, and Turbulent Motion broadening in the inversion of the data from either the Spatial Heterodyne Spectrometer (SHS) 31''' or the DASH Spectrometer 31''''.

Furthermore, the reference light signal 105 when used with either the Spatial Heterodyne Spectrometer (SHS) 31''' or the DASH Spectrometer 31'''' provides for correcting for small perturbations of the associated transmission function model used for signal processing. For example a slight change in the wavelength or frequency of the light source 11 may be accounted for in the data analysis instead of adding to associated measurement uncertainty. Any associated instrument drifts that are either slow when compared to the measurement interval or small enough to be absorbed by the algorithm will be accounted for in the data processing which allows one to accommodate wider tolerances on components while maintaining performance.

Referring to FIG. 123*a*, a twentieth aspect of a LIDAR system 24'', 24$^{xx}$ incorporated in a second aspect of an atmospheric measurement system 10$^{ii}$ incorporates a light source 11, for example, a laser 11', that generates a first beam of light 420, of substantially monochromatic light 13, which is split into a reference beam portion 90 and a second beam of light 28 by a first beam splitter optic 92.1. In one embodiment, the second beam of light 28 is shaped by source optics 15, for example, a lens assembly 15' that provides for the width and divergence of the second beam of light 28, and a suitable location of the associated beam waist thereof, so as to provide for illuminating an interaction region 17 within the atmosphere 20 that is detectable by the LIDAR system 24'', 24$^{xx}$, wherein the beam width within the interaction region 17 establishes the associated transverse spatial resolution limit of the LIDAR system 24'', 24$^{xx}$. In one embodiment, in accordance with a coaxial system 442, the second beam of light 28 is reflected off a first surface mirror 639 and then off a first surface 92.2' of a second beam splitter optic 92.2 and into the atmosphere 20 along a line-of-sight 23' that is coincident with an optic axis 23 of an associated set of receive optics 32, for example, a telescope 32'. The reference beam portion 90 is reflected off a second first surface mirror 640 and then of a second surface 92.2'' of the second beam splitter optic 92.2 and into the receive optics 32, for example, along the optic axis 23 thereof.

The light source 11 provides for generating a pulsed first beam of light 420 responsive a control signal 736 from an associated data processor 53. The receive optics 32 provides for receiving the reference beam portion 90 generated substantially simultaneously with the second beam of light 28, and the resulting scattered light 30 within the field-of-view 54 of the receive optics 32 that is scattered by the atmosphere 20 from the interaction region 17 some time after the second beam of light 28 is generated. The telescope 32' comprises a effective lens 32'', and both the reference beam portion 90 and the scattered light signal 30' collected thereby is collected by the final light-collecting element 448 thereof into the first end 98' of a fiber optic 98 that directs the returned photons to the collimating lens 33 of an interferometer 31 comprising, for example, either a Spatial Heterodyne Spectrometer (SHS) 31''' or a DASH Spectrometer 31'''', for example, with the second end 98'' of the fiber optic 98 located at the focal plane 33.1 of the collimating lens 33. The Spatial Heterodyne Spectrometer (SHS) 31''' or a DASH Spectrometer 31'''' further incorporates a filter system 88—similar to that described hereinabove—between the collimating lens 33 and the beam splitter 706 thereof.

Referring to FIG. 123*b*, the imaging optics 37 of the Spatial Heterodyne Spectrometer (SHS) 31''' or a DASH Spectrometer 31'''', alone or in combination with an associated anamorphic imaging element 734 such as a bi-convex cylindrical lens 734', is configured to compress the associated resulting Fizeau fringe pattern 716 generated by the Spatial Heterodyne Spectrometer (SHS) 31''' or a DASH Spectrometer 31'''' in the X-direction indicated FIG. 123*b*, so as to form the Fizeau fringe pattern line 716' along the Z-direction, in the imaging plane 31.2$^{i'''}$ 31.2$^{i''''}$ of the Spatial Heterodyne Spectrometer (SHS) 31''' or the DASH Spectrometer 31'''', respectively, which is then projected onto a sixth aspect of a detection system 34, 34.6 comprising either the fast CCD detector 500.1 or a second embodiment of the CCD detector 500.1' comprising an imaging region 608 and a masked, frame-transfer region 610, as described hereinabove in the context of FIGS. 89-93, so as to provide for initially recording the Fizeau fringe pattern 716 associated with the reference light signal 105 associated with the reference beam portion 90 and then continuing to record over time a range-dependent Fizeau fringe pattern 716 associated with the scattered light signal 30' with a monotonically increasing one-to-one relationship between time at which a particular Fizeau fringe pattern 716 is recorded by the CCD detector 500.1, 500.1' an the corresponding range R from which the associated scattered light 30 originated within the interaction region 17 along the second beam of light 28.

In operation, the light source 11 first generates a pulsed first beam of light 420, wherein the associated pulse width is substantially less than the time required for the second beam of light 28 to be generated and for scattered light 30' generated therefrom to reach the second beam splitter optic 92.2 from the closest measurement volume 52.1 along the associated interaction region 17. The first light received by the receive optics 32 is from the reference beam portion 90 reflected from the second beam splitter optic 92.2, and is processed by the Spatial Heterodyne Spectrometer (SHS) 31''' or a DASH Spectrometer 31'''' to generate a corresponding Fizeau fringe pattern 716 that is first recorded by the CCD detector 500.1, 500.1'. Thereafter, the receive optics 32 receives scattered light 30 over time from increasingly greater ranges R within the interaction region 17, and the resulting scattered light signals 30' are processed by the Spatial Heterodyne Spectrometer (SHS) 31''' or a DASH Spectrometer 31'''' to generate a corresponding Fizeau fringe pattern 716 over time that is then recorded over time by the CCD detector 500.1, 500.1'. Thereafter, the data processor 53 processes the recorded Fizeau fringe patterns 716, using the initially recorded Fizeau fringe pattern 716 as being representative of the reference light signal 105 when processing the remaining recorded Fizeau fringe patterns 716 in order to determine corresponding range-dependent atmospheric data 36. Accordingly, the twentieth aspect of the LIDAR system 24'', $24^{xx}$ provides for the reference 105 and scattered 30' light signals to be time-multiplexed over a common optical processing channel.

In an alternative embodiment, the LIDAR system 24'', $24^{xx}$ may be configured to provide for measuring light from an interaction region 17 comprising a single measurement volume 52 by eliminating the first first surface mirror 639, and instead projecting the second beam of light 28 directly into the atmosphere 20 into the interaction region 17 defined by the intersection of the second beam of light 28 with the field-of-view 54 of the receive optics 32, however, while continuing to time-multiplex the processing of the reference 105 and scattered 30' light signals. Further to this alternative embodiment, in accordance with a second alternative embodiment, the need for the second beam splitter optic 92.2 could be eliminated by instead reflecting the reference beam portion 90 from a side of the receive optics 32 facing the final light-collecting element 448, so as to use the receive optics 32 also as an inherent beam splitter.

Referring to FIG. 124a, there is illustrated a first embodiment of a twenty-first aspect of a LIDAR System 24'', $24^{xxi'}$ incorporated in a second aspect of an atmospheric measurement system $10^{ii}$, which is substantially the same as the ninth aspect of the LIDAR system 24'', $24^{ix}$ illustrated in FIG. 64, except for incorporating either a Spatial Heterodyne Spectrometer (SHS) 31''' or a DASH Spectrometer 31'''' as the interferometer 31 instead of a Fabry-Pérot interferometer 31' and associated circle-to-line interferometer optics 468, wherein the Spatial Heterodyne Spectrometer (SHS) 31''' or a DASH Spectrometer 31'''' further incorporates a filter system 88—similar to that described hereinabove—between the collimating lens 33 and the beam splitter 706 thereof.

More particularly, the receive optics 32 of the LIDAR System 24'', $24^{xvi'}$ provides for receiving scattered light 30 that is scattered by the atmosphere 20 from a corresponding interaction region 17 therein defined by the intersection of an associated second beam of light 28 with an associated field-of-view 54 of a corresponding telescope 32'. A reference light signal 105 from a reference beam portion 90 is directed by an associated first fiber optic 98.1 to the focal plane 33.1 of the collimating lens 33, and a scattered light signal 30' captured by a final light-collecting element 448 of the telescope 32' is directed by an associated second fiber optic 98.2 also to the focal plane 33.1 of the collimating lens 33 but at a separate location, for example, as illustrated in FIG. 122b and described hereinabove. Referring to FIG. 124b, thereafter the Spatial Heterodyne Spectrometer (SHS) 31''' or a DASH Spectrometer 31'''' provides for generating corresponding Fizeau fringe patterns $716^{i}$, $716^{Ref}$ associated with the scattered light signal 30' and reference light signal 105, that are detected by the associated imaging detector 34.5' of an associated fifth aspect of a detection system 34, 34.5—for example, either a CCD detection system 34.1', a camera 34.1'', or a two-dimensional array of photodetectors 34.1'''—located at the rear focal plane 37.2 of the imaging optics 37, from which the atmospheric data 36 associated with the interaction region 17 is determined by the data processor 53 as described hereinabove.

Referring to FIG. 125a, there is illustrated a first embodiment of a twenty-second aspect of a LIDAR System 24'', $24^{xxii'}$ incorporated in a second aspect of an atmospheric measurement system $10^{ii}$, which is substantially the same as the second embodiment of the fifteenth aspect of the LIDAR system 24'', $24^{xv''}$ illustrated in FIG. 110a, except for incorporating either a Spatial Heterodyne Spectrometer (SHS) 31''' or a DASH Spectrometer 31'''' as the interferometer 31 instead of a Fabry-Pérot interferometer 31', wherein the Spatial Heterodyne Spectrometer (SHS) 31''' or a DASH Spectrometer 31'''' further incorporates a filter system 88—similar to that described hereinabove—between the collimating lens 33 and the beam splitter 706 thereof.

More particularly, the receive optics 32 of the LIDAR System 24'', $24^{xvii'}$ provides for receiving scattered light 30 that is scattered by the atmosphere 20 from a corresponding interaction region 17 therein defined by the intersection of an associated second beam of light 28 with an associated field-of-view 54 of a corresponding telescope 32'. A scattered light signal 30' captured by a final light-collecting element 448 of the telescope 32' is directed by an associated second fiber optic 98.2 also to the front focal plane $33.1^{A}$ of a first collimating lens $33^{A}$ and then transmitted through the second beam splitter optic 136 and then the associated filter system 88, and processed by the Spatial Heterodyne Spectrometer (SHS) 31''' or a DASH Spectrometer 31'''' so as to generate a corresponding Fizeau fringe pattern $716^{i}$ as described hereinabove. In parallel with this, a reference illuminator 324 generates a uniform and diffuse reference beam 90'—for example, as illustrated in FIG. 125b—and that is directed through a mask 138, 138.6 illustrated in FIG. 125c that blocks a portion of the uniform and diffuse reference beam 90' from transmission therethrough in an associated opaque rectangular region 138.6' corresponding in size and location to the image of the scattered light signal 30' at the in the imaging plane $31.2^{i'''}$, $31.2^{i''''}$ of the Spatial Heterodyne Spectrometer (SHS) 31''' or the DASH Spectrometer 31'''', respectively, so as to generated a corresponding masked reference beam 90'', 90.6'' that is collimated by a second collimating lens $33^{B}$ and is then reflected off a first surface 640.1 of a first surface mirror 640 onto a partially reflective surface 136.1 of the second beam splitter optic 136, and then transmitted through the associated filter system 88, and processed by the Spatial Heterodyne Spectrometer (SHS) 31''' or a DASH Spectrometer 31'''' so as to generate a corresponding reference Fizeau fringe pattern $716^{Ref}$ as described hereinabove. Referring to FIG. 125d, the Fizeau fringe patterns $716^{i}$, $716^{Ref}$ from scattered light signal 30' and the masked reference beam 90'', 90.6'', respectively, are mutually exclusive in the imaging plane $31.2^{i'''}$ $31.2^{i''''}$ as a result of the mask 138, 138.6, and accordingly are separately detected by the associated imaging detector 34.5' of an associated fifth aspect of a detection system 34, 34.5—for example, either a CCD detection system 34.1', a camera 34.1", or a two-dimensional array of photo-detectors 34.1'''—located at the rear focal plane 37.2 of the imaging optics 37, from which the atmospheric data 36 associated with the interaction region 17 is determined by the data processor 53 as described hereinabove.

Referring to FIG. 126a, there is illustrated a second embodiment of the twenty-first aspect of a LIDAR System 24", 24$^{xxi'''}$ incorporated in a second aspect of an atmospheric measurement system 10$^{ii}$, which is substantially the same as the thirteenth aspect of the LIDAR system 24", 24$^{xiii}$ illustrated in FIG. 103a, except for incorporating either a Spatial Heterodyne Spectrometer (SHS) 31''' or a DASH Spectrometer 31'''' as the interferometer 31 instead of a Fabry-Pérot interferometer 31', wherein the Spatial Heterodyne Spectrometer (SHS) 31''' or a DASH Spectrometer 31'''' further incorporates a filter system 88—similar to that described hereinabove between the collimating lens 33 and the beam splitter 706 thereof. The second embodiment of the twenty-first aspect of a LIDAR System 24", 24$^{xxi'''}$ is also similar to the above-described first embodiment of the twenty-first aspect of the LIDAR System 24", 24$^{xxi'}$ illustrated in FIG. 124a, except for incorporating a plurality of telescopes 32.1', 32.2' and 32.3' that provide for receiving scattered light 30 from a plurality of different interaction regions 17, 17.1, 17.2, 17.3, wherein the separate corresponding resulting scattered light signals 30.1', 30.2', 30.3' input to the Spatial Heterodyne Spectrometer (SHS) 31''' or a DASH Spectrometer 31'''' at separate locations as illustrated in FIG. 122b, and separately simultaneously processed together with the associated reference light signal 105 to generate a plurality of corresponding Fizeau fringe patterns 716$^i$, 716$^{ii}$, 716$^{iii}$, 716$^{Ref}$, as illustrated in FIG. 126d, from which the atmospheric data 36 associated with each corresponding interaction region 17, 17.1, 17.2, 17.3 is determined by the data processor 53 from the corresponding Fizeau fringe patterns 716$^i$, 716$^{ii}$, 716$^{iii}$ together with the reference Fizeau fringe pattern 716$^{Ref}$ associated with the reference light signal 105, as described hereinabove.

Similarly, referring to FIG. 127a, there is illustrated a second embodiment of the twenty-second aspect of a LIDAR System 24", 24$^{xxii'''}$ incorporated in a second aspect of an atmospheric measurement system 10$^{ii}$, which is substantially the same as the sixteenth aspect of a LIDAR system 24", 24$^{xvi'}$, LIDAR system 24", 24$^{xvi'}$ illustrated in FIGS. 112a and 113a, except for incorporating either a Spatial Heterodyne Spectrometer (SHS) 31''' or a DASH Spectrometer 31'''' as the interferometer 31 instead of a Fabry-Pérot interferometer 31', wherein the Spatial Heterodyne Spectrometer (SHS) 31''' or a DASH Spectrometer 31'''' further incorporates a filter system 88—similar to that described hereinabove—between the collimating lens 33 and the beam splitter 706 thereof. The second embodiment of the twenty-second aspect of a LIDAR System 24", 24$^{xxii'''}$ is also similar to the above-described first embodiment of the twenty-second aspect of the LIDAR System 24", 24$^{xxii'}$ illustrated in FIG. 125a, except for incorporating a plurality of telescopes 32.1', 32.2' and 32.3' that provide for receiving scattered light 30 from a plurality of different interaction regions 17, 17.1, 17.2, 17.3, wherein the corresponding mask 138, 138.7 illustrated in FIG. 127c incorporates a plurality of opaque rectangular regions 138.7$^{i'}$, 138.7$^{ii'}$, 138.7$^{iii'}$ corresponding in size and location to the separate images of the associated scattered light signals 30.1', 30.2', 30.3' at the in the imaging plane 31.2$^{i'''}$ 31.2$^{i''''}$0 of the Spatial Heterodyne Spectrometer (SHS) 31''' or the DASH Spectrometer 31'''', respectively, so as to generated the corresponding masked reference beam 90", 90.7", wherein the scattered light signals 30.1', 30.2', 30.3' and the masked reference beam 90", 90.7" are both collimated by a common collimating lens 33. The separate corresponding resulting scattered light signals 30.1', 30.2', 30.3' input to the Spatial Heterodyne Spectrometer (SHS) 31''' or a DASH Spectrometer 31'''' at separate locations as illustrated in FIG. 122b, and separately simultaneously processed together with the associated masked reference beam 90", 90.7" so as to generate a plurality of corresponding Fizeau fringe patterns 716$^i$, 716$^{ii}$, 716$^{iii}$, 716$^{Ref}$ as illustrated in FIG. 127d, from which the atmospheric data 36 associated with each corresponding interaction region 17, 17.1, 17.2, 17.3 is determined by the data processor 53 from the corresponding Fizeau fringe patterns 716$^i$, 716$^{ii}$, 716$^{iii}$ together with the reference Fizeau fringe pattern 716$^{Ref}$ associated with the reference light signal 105, as described hereinabove.

Referring to FIG. 128a, there is illustrated a twenty-third aspect of a range-imaging LIDAR System 24', 24$^{xxiii'}$ incorporated in a first aspect of an atmospheric measurement system 10$^i$, which is substantially the same as the first embodiment of the eighth aspect of the range-imaging LIDAR system 24', 24$^{viii'}$ illustrated in FIG. 55a, except for incorporating either a Spatial Heterodyne Spectrometer (SHS) 31''' or a DASH Spectrometer 31'''' as the interferometer 31 instead of a Fabry-Pérot interferometer 31', wherein the Spatial Heterodyne Spectrometer (SHS) 31''' or a DASH Spectrometer 31'''' further incorporates a filter system 88—similar to that described hereinabove—between the collimating lens 33 and the beam splitter 706 thereof.

More particularly, the plane containing the respective optic axes 23, 25 of the receive optics 32 and the associated beam of light 28, respectively, is optically oriented substantially parallel to the X-axis of the Spatial Heterodyne Spectrometer (SHS) 31''' or a DASH Spectrometer 31'''' as illustrated in FIGS. 118a, 119 and 122a-c, so as to provide for a range-dependent Fizeau fringe pattern 716$^{Range}$ for which different portions of the scattered light signal 30' in the intermediate image 29 associated with different ranges R are transformed into corresponding different portions of the resulting range-dependent Fizeau fringe pattern 716$^{Range}$ by the Spatial Heterodyne Spectrometer (SHS) 31''' or a DASH Spectrometer 31'''', so that each separate portion of the resulting range-dependent Fizeau fringe pattern 716$^{Range}$ contains information about an associated corresponding measurement volume 52 in the atmosphere 20 at a corresponding range R from the range-imaging LIDAR System 24', 24$^{xxiii}$. The extent of the intermediate image 29 of the scattered light signal 30' along the X-direction thereof is scaled to use a portion of the corresponding extent of the Spatial Heterodyne Spectrometer (SHS) 31''' or a DASH Spectrometer 31'''', and the associated imaging detector 34.5' of an associated fifth aspect of a detection system 34, 34.5, and the remaining portion thereof is used to process a corresponding masked reference beam 90", 90.8", as illustrated in FIG. 128c, generated using a corresponding associated mask 138, 138.8 having an opaque rectangular region 138.8' corresponding in size and location to the image of the scattered light signal 30' at the imaging plane 31.2$^{1'''}$ 31.2$^{i''''}$ of the Spatial Heterodyne Spectrometer (SHS) 31''' or the DASH Spectrometer 31'''', so as to provide for generating a range-dependent Fizeau fringe pattern 716$^{Range}$ at the imaging plane 31.2$^{i'''}$ 31.2$^{i''''}$ of the Spatial Heterodyne Spectrometer (SHS) 31''' or the DASH Spectrometer 31'''' at locations where the mask 138, 138.8 is active, and so as to provide for generating a reference Fizeau fringe pattern 716$^{Ref}$ at the imaging plane 31.2$^{i'''}$ 31.2$^{i''''}$ of the Spatial Heterodyne Spectrometer (SHS) 31''' or the DASH Spectrometer 31'''' elsewhere, i.e. at locations where the mask 138, 138.8 is inactive, as illustrated in FIG. 128d. The data processor 53 then uses a particular Z-directed slice of the range-dependent Fizeau fringe pattern $716^{Range}$ at a particular X-location, together with the reference Fizeau fringe pattern $716^{Ref}$, to determine the atmospheric data 36 associated with a corresponding measurement volume 52 at a corresponding range R within the interaction region 17 in accordance with the process as described hereinabove.

Referring to FIG. 129a, there is illustrated a twenty-fourth aspect of a range-imaging LIDAR System 24', $24^{xxiv}$ incorporated in a first aspect of an atmospheric measurement system $10^i$, which is substantially the same as the seventh aspect of the range-imaging LIDAR system 24', $24^{vii}$ illustrated in FIG. 52, except for incorporating either a Spatial Heterodyne Spectrometer (SHS) 31''' or a DASH Spectrometer 31'''' as the interferometer 31 instead of a Fabry-Pérot interferometer 31', wherein the Spatial Heterodyne Spectrometer (SHS) 31''' or a DASH Spectrometer 31'''' further incorporates a filter system 88—similar to that described hereinabove—between the collimating lens 33 and the beam splitter 706 thereof.

More particularly, the plane containing the respective first optic axes 23.1, 25.1 of the first set of receive optics 32 and the associated first beam of light 28.1, respectively, and the plane containing the respective second optic axes 23.1, 25.1 of the second set of receive optics 32.2 and the associated second beam of light 28.2, respectively, are each optically oriented substantially parallel to the X-axis of the Spatial Heterodyne Spectrometer (SHS) 31''' or a DASH Spectrometer 31'''' as illustrated in FIGS. 118a, 119 and 122a-c for which different portions of the scattered light signals 30.1', 30.2' in the intermediate image 29 associated with different ranges R are transformed into corresponding different portions of the resulting range-dependent Fizeau fringe patterns $716^{Range1}$, $716^{Range2}$ by the Spatial Heterodyne Spectrometer (SHS) 31''' or a DASH Spectrometer 31'''', so that each separate portion of the resulting range-dependent Fizeau fringe patterns $716^{Range1}$, $716^{Range2}$ contains information about associated corresponding measurement volumes 52 in the atmosphere 20 within the associated corresponding interaction regions 17.1, 17.2 at a corresponding ranges R from the range-imaging LIDAR System 24', $24^{xxiv}$. The extent of the intermediate image 29 of the scattered light signals 30.1', 30.2' along the X-direction thereof is scaled to use a portion of the corresponding extent of the Spatial Heterodyne Spectrometer (SHS) 31''' or a DASH Spectrometer 31'''', and the associated imaging detector 34.5' of an associated fifth aspect of a detection system 34, 34.5, and the remaining portion thereof is used to process a corresponding masked reference beam 90'', 90.9'' generated using a corresponding associated mask 138, 138.9 having a plurality of opaque rectangular regions $138.9^{i'}$, $139^{ii'}$ corresponding in size and location to the image of the scattered light signal 30' at the imaging plane $31.2^{i'''}$ $31.2^{i''''}$ of the Spatial Heterodyne Spectrometer (SHS) 31''' or the DASH Spectrometer 31'''', so as to provide for generating range-dependent Fizeau fringe patterns $716^{Range1}$, $716^{Range2}$ at the imaging plane $31.2^{i'''}$ $31.2^{i''''}$ of the Spatial Heterodyne Spectrometer (SHS) 31''' or the DASH Spectrometer 31'''' at locations where the mask 138, 138.8 is active, and so as to provide for generating a reference Fizeau fringe pattern $716^{Ref}$ at the imaging plane $31.2^{i'''}$ $31.2^{i''''}$ of the Spatial Heterodyne Spectrometer (SHS) 31''' or the DASH Spectrometer 31'''' elsewhere, i.e. at locations where the mask 138, 138.8 is inactive, as illustrated in FIG. 129b. The data processor 53 then uses a particular Z-directed slice of the range-dependent Fizeau fringe patterns $716^{Range1}$, $716^{Range2}$ at a particular X-locations, together with the reference Fizeau fringe pattern $716^{Ref}$, to determine the atmospheric data 36 associated with corresponding measurement volumes 52 at a corresponding ranges R within the associated interaction regions 17.1, 17.2 in accordance with the process as described hereinabove.

Furthermore, as an alternative to the third aspect of the detection system 34.3, the associated digital micromirror device (DMD) 142 can be replaced with corresponding plurality fixed optical masks that provide for either transmitting or reflecting in accordance with the same patterns 190 described hereinabove in respect of pixel mirror rotational states 148, 150, 152. For example, each corresponding complementary signal 156, 158 detectable by one of the photodetectors $154^A$, $154^B$ for a given pattern 190 of pixel mirror rotational states 148, 150, 152 could alternatively be detected by a corresponding fixed optical mask in the position of the micromirrors 144 of the digital micromirror device (DMD) 142 in cooperation with a corresponding photodetector 154 that provides for detecting a either a transmitted or reflected corresponding complementary signal 156, 158, wherein two fixed masks would be used to provide for detecting both complementary signals 156, 158 associated with a given pattern. The various fixed optical masks would be moved into position one at a time for each measurement, for example, by linear or circular motion responsive to either a linear or rotary positioner, for example, by adapting either a mechanical translation stage or a filter wheel accordingly, with individual filters of the filter wheel replaced with the fixed optical masks, each corresponding to a different portion of the associated pattern 190. In another embodiment, in cooperation with fixed optical transmission masks in which the associated transmitted light is detected, a different photodetector 154 could be used for each of the reference 456 and signal 458 channels in cooperation with corresponding portions of the associated fixed optical masks so as to provide for reducing the total number of fixed optical masks and so as to provide for increasing the associated data processing throughput.

Generally, each LIDAR system 24 can provide for measuring atmospheric data 36 within a limited measurement volume 52 and with limited precision. The overall effective volume of the atmosphere 20 being measured may be increased by using a combination of a plurality of LIDAR systems 24 having corresponding distinct measurement volume 52 that are either overlapping or relatively proximal to in relation to one another. The precision of the measurement of the atmospheric data 36 within a given measurement volume 52 may be increased by increasing the duration over which the associated scattered light 30 is received and processed. The particular characteristic of a particular LIDAR system 24 may be adapted to the particular application of the associated atmospheric data 36, and measurements from different LIDAR systems 24 having differing characteristics may be combined so as to provide for atmospheric data 36 that is most useful for a particular application. For example, a LIDAR system 24 operating at a relatively short range relative to an associated wind turbine 14, and a relatively faster data sampling rate, may be appropriate for immediately controlling the wind turbine 14, for example, so as to provide for optimizing the capture of wind energy wile limiting fatigue and/or extreme loads; whereas a LIDAR system 24 operating at a relatively longer range and a relatively slower data sampling rate, may be appropriate for anticipating future wind conditions to provide for either controlling an associated power grid 56 to which the generator 82 of the wind turbine 14 is connected, or for controlling the wind turbine 14 responsive to anticipated demand from the associated power grid 56. Similarly, short and long range versions of associated LIDAR systems 24 can be used in combination to provide for wind farm site assessment or on operational wind farms, for example, to optimize coverage and measurement accuracy while minimizing cost.

Furthermore, referring to FIGS. 130-132, different LIDAR systems 24, each operating at a different wavelength, may be used in combination to sense either a common measurement volume 52, overlapping measurement volumes 52, or proximal measurement volumes 52, so as to provide for improved reliability through redundancy, for example, with respect to either all or a subset of associated atmospheric data 36, or so as to provide for either improved reliability or an extended operating lifetime by preferably operating at an infrared or visible wavelength if measurements responsive to aerosol scattering are possible and sufficient.

For example, referring to FIG. 130, first 14.1 and third 14.3 wind turbines of the wind farm 12 illustrated in FIG. 2 in accordance with a sixth aspect of an atmospheric measurement system $10^{vi}$ each cooperate with a pair of associated first LIDAR systems 24.1', 24.1" or third LIDAR systems 24.3', 24.3", respectively. For example, a first 24.1' of the pair of first LIDAR systems 24.1', 24.1" is configured to operate at a nominal first wavelength 738, for example, an infrared wavelength 738' or a visible wavelength 738", that provides for primarily only scattering from aerosols 20" in the atmosphere 20, for example, with not more than negligible scattering from molecules 20' in the atmosphere 20, whereas a second 24.1" of the pair of first LIDAR systems 24.1', 24.1" is configured to operate at a nominal second wavelength 740, for example, an ultraviolet wavelength 740', that provides for scattering both from aerosols 20" and molecules 20' in the atmosphere 20.

As one example, each of the first LIDAR systems 24.1', 24.1" emits a corresponding beam of light $28^{i'}$, $28^{i''}$ that emanates from a central region of the rotor 18 of the associated wind turbine 14.1—for example, from the hub 19 thereof—and that rotates therewith so that the respective associated beams of light $28^{i'}$, $28^{i''}$ sweep out corresponding conical surfaces of revolution 42.1', 42.1", wherein the associated conical surfaces of revolution 42.1', 42.1' are aligned with the rotor 18, wherein the associated beams of light $28^{i'}$, $28^{i''}$ are at least relatively proximate to one another and possibly at least partially overlapping one another. Each of the first LIDAR systems 24.1', 24.1" receives corresponding scattered light 30 from associated one or more measurement volumes 52 within an interaction region 17 along the corresponding beam of light $28^{i'}$, $28^{i''}$.

As another example, each of the third LIDAR systems 24.3', 24.3" is relatively fixed to the nacelle 44 of the third wind turbine 14.3 so as to emit corresponding a first pair of relatively fixed beams of light $28.1^{iii'}$, $28.1^{iii''}$ in a first direction $46.1^{iii}$, and so as to emit a second pair of relatively fixed beams of light $28.2^{iii'}$, $28.2^{iii''}$ in a second direction $46.2^{iii}$, wherein the beams of light $28.1^{iii'}$, $28.1^{iii''}$, $28.2^{iii'}$, $28.2^{iii''}$ along the associated directions $46.1^{iii}$, $46.2^{iii}$ turn with the nacelle 44 as the direction $48^{iii}$ of the nacelle 44 is changed to accommodate changes in the local direction 50 of the wind 16 as illustrated in FIG. 2, wherein the associated first pair of relatively fixed beams of light $28.1^{iii'}$, $28.1^{iii''}$ are at least relatively proximate to one another and possibly at least overlapping one another, and the associated second pair of relatively fixed beams of light $28.2^{iii'}$, $28.2^{iii''}$ are at least relatively proximate to one another and possibly at least partially overlapping one another. Each of the third LIDAR systems 24.3', 24.3" receives corresponding scattered light 30 from associated measurement volumes 52 associated interaction regions 17 along the corresponding beams of light $28.1^{iii'}$, $28.1^{iii''}$, $28.2^{iii'}$, $28.2^{iii''}$.

Referring to FIG. 131, there is illustrated a twenty-fifth aspect of a LIDAR System 24', 24", $24^{xxv}$ in accordance with an embodiment of the sixth aspect of the atmospheric measurement system $10^{vi}$, incorporating a light source 11 comprising first $11^{A'}$ and second $11^{B'}$ lasers selectively operated under control of a controller/data processor 53' so that at most only one of the first $11^{A'}$ and second $11^{B'}$ lasers is operated at any given time in cooperation with a common set of source optics 15, for example, a lens assembly 15', so as to provide for generating and projecting into the atmosphere 20 a common beam of light 28 containing substantially monochromatic light 13 from one of the first $11^{A'}$ and second $11^{B'}$ lasers.

For example, in one embodiment, in a first mode of operation, substantially monochromatic light $13^{A}$ at a nominal first wavelength 738 from the first laser $11^{A'}$ operated under control of the controller/data processor 53' is reflected by a first surface 742' of a mirror 742 in a first rotational position 744.1 so as to form the beam of light 28 that is then projected through the source optics 15 and into the atmosphere 20 along an associated optic axis 23; and in a second mode of operation, substantially monochromatic light $13^{B}$ at a nominal second wavelength 740 from the second laser $11^{B'}$ operated under control of the controller/data processor 53' is reflected by a second surface 742" of the mirror 742 in a second rotational position 744.2 so as to form the beam of light 28 that is then projected through the source optics 15 and into the atmosphere 20 along the associated optic axis 23, wherein the rotational position 744.1, 744.2 of the mirror 742 is controlled in synchronism with the operation of the first $11^{A'}$ and second $11^{B'}$ lasers by an associated angular positioner 746 under control of the controller/data processor 53'. In one embodiment, the first 742' and second 742" surfaces of the mirror 742 are one and the same surface of the mirror 742 and possibly one and the same; whereas for another embodiment, the first 742' and second 742" surfaces of the mirror 742 are different, for example, on opposite sides of the mirror 742, for example, implemented with coatings that are tuned to the particular wavelength 738, 740 being reflected.

As another example, in a second embodiment; the mirror 742 is oriented in a substantially fixed angular position and adapted to be translated transversely relative to the optic axis 23 of the beam of light 28 so that in a first position under the first mode of operation, substantially monochromatic light $13^{A}$ at a nominal first wavelength 738 from the first laser $11^{A'}$ operated under control of the controller/data processor 53' is reflected by the first surface 742' of the mirror 742 in the first rotational position 744.1 so as to form the beam of light 28 that is then projected through the source optics 15 and into the atmosphere 20 along an associated optic axis 23. However, in the second mode of operation, the mirror 742 is translated by an associated linear positioner 748 under control of the controller/data processor 53' so as to provide for the substantially monochromatic light $13^{B}$ at the nominal second wavelength 740 from the second laser $11^{B'}$ operated under control of the controller/data processor 53' to be transmitted directly to the source optics 15 without first interacting with the mirror 742.

The substantially monochromatic light 13 of the beam of light 28 projected into the atmosphere 20 is scattered by the aerosols 20" or molecules 20' of the atmosphere 20, and the resulting scattered light 30 from a particular interaction region 17 and associated one or more measurement volumes 52 is received by associated receive optics 32, for example, an associated telescope 32', along an associated optic axis 25, wherein the extent of the associated interaction region 17 is defined by the intersection of an associated field-of-view 54 of the receive optics 32 with the corresponding beam of light 28. The resulting scattered light signal 30' captured by the associated receive optics 32 is collimated by an associated collimating lens 33, filtered by an associated filter system 88 and processed by an associated interferometer 31 so as to generate an associated interference pattern, i.e. a scatter fringe pattern 47, that is detected by an associated detection system 34. The filter system 88 comprises a pair of first 88$^A$ and second 88$^B$ bandpass filters, for example, that are mechanically-selectable by action of an associated actuator 750 under control of the controller/data processor 53' so as to provide filtering the scattered light signal 30' with the first bandpass filter 88$^A$ in synchronism with the use of the first laser 11$^{A'}$ to generate the beam of light 28, and so as to provide filtering the scattered light signal 30' with the second bandpass filter 88$^B$ in synchronism with the use of the second laser 11$^{B'}$ to generate the beam of light 28. The signal from the detection system 34 is processed by the controller/data processor 53' so as to determine the atmospheric data 36 associated with the corresponding scattered light signal 30' representative of the state of the atmosphere 20 within the associated measurement volume 52. The interferometer 31 and associated detection system may be configured and operated in accordance with any of the above-described embodiments. A portion of the substantially monochromatic light 13 may be extracted from the beam of light 28 with an associated beam splitter optic 92 so as to provide for a reference beam portion 90 that can be processed by the interferometer 31 and detection system 34 simultaneously together with the scatter fringe pattern 47 so as to provide for compensating for associated defects in the interferometer 31 when determining the corresponding atmospheric data 36.

When operated in the first mode of operation, the above-described LIDAR systems 24.1', 24.3', 24$^{xxv}$ in accordance with the sixth aspect of the atmospheric measurement system 10$^{vi}$ provide for projecting substantially monochromatic light 13$^A$ at a nominal first wavelength 738—for example, either an infrared 738' or visible 738" wavelength—into the atmosphere 20, which primarily interacts with aerosols 20" therein, so that the resulting scattered light 30 and associated scattered light signal 30' are primarily a result of scattering by aerosols 20", which can provide for a detection of an associated velocity V of the aerosols 20 in the atmosphere 20, but which does not provide for detecting the corresponding temperature T or density ρ.

When operated in the second mode of operation, the above-described LIDAR systems 24.1', 24.3', 24$^{xxv}$ in accordance with the sixth aspect of the atmospheric measurement system 10$^{vi}$ provide for projecting substantially monochromatic light 13$^B$ at a nominal second wavelength 740—for example, an ultraviolet wavelength 740'—into the atmosphere 20, which interacts with both molecules 20' and aerosols 20" therein, so that the resulting scattered light 30 and associated scattered light signal 30' are a result of scattering by both molecules 20' and aerosols 20", which can provide for a detection of an associated velocity V of the molecules 20' and aerosols 20" in the atmosphere 20, and which provides for detecting the corresponding temperature T or density ρ of the molecules 20' of the atmosphere 20.

Although the second mode of operation provides for detecting temperature T or density ρ, operation of the sixth aspect of the atmospheric measurement system 10$^{vi}$ can provide for a longer lifetime and associated greater reliability when operated in accordance with the first mode of operation, i.e. at at either infrared 738' or visible 738" wavelengths, however, with the associated limitation of being able to measure only velocity V, and not temperature T or density ρ. However, in situations where velocity V alone is sufficient, then if aerosols 20" are present in sufficient amount in the atmosphere 20 so as to provide for a sufficiently strong scattered light signal 30' responsive to illumination by a beam of light 28 comprising infrared 738' or visible 738" wavelengths in accordance with the first mode of operation, then operation in accordance with the first mode of operation would provide for extending the lifetime of the associated atmospheric measurement system 10$^{vi}$ and thereby provide for improved reliability.

Referring to FIG. 132, when the measurement of velocity V alone is sufficient, the process 1320 of operating the sixth aspect of the atmospheric measurement system 10$^{vi}$ so as to provide for such enhanced lifetime and reliability commences with step (1320') after which in step (1321) the second laser 11$^{B'}$ light source 11 is turned OFF and the first laser 11$^{A'}$ light source 11 is turned ON, thereby commencing the first mode of operation. If operating a twenty-fifth aspect of the LIDAR system 24', 24", 24$^{xxv}$, in addition to controlling the first 11$^{A'}$ and second 11$^{B'}$ lasers accordingly, the controller/data processor 53' positions the mirror 742 and the filter system 88 in synchronism with this action. Then, in step (1322), the velocity V of the atmosphere 20 is measured with the associated LIDAR systems 24.1', 24.3', 24$^{xxv}$—as described herein above in detail for other corresponding LIDAR systems 24,—and the corresponding associated single-to-noise ratio SNR of this measurement is determined as described hereinbelow. In step (1323), if the single-to-noise ratio SNR exceeds a corresponding SNR threshold $SNR_{MIN}$—or a substantially equivalent test is satisfied, indicating that there is a sufficient amount of aerosols 20" present in the atmosphere 20 so as to provide for a valid measurement of velocity V—then the process repeats with step (1322) at the next sample in time.

Generally, measurement performance is ultimately limited by the ratio given by the level of signal energy divided by the level of noise energy. In practice, this is given by comparing the measurement of signal plus noise to the corresponding measurement of noise alone. The noise level N of the system may be obtained during a calibration period, or during operation of the system.

For example, with any of the above LIDAR systems 24.1', 24.3', 24$^{xxv}$, during a calibration process, one may simply measure the noise level N without providing for a scattered light signal 30' from the atmosphere 20. That noise level N could then be used to generate a simple ratio of the measurement of the scattered light signal 30' plus noise—since the measurement of the scattered light signal 30' would inherently include noise—divided by the measured noise level N. Accordingly, for a given uncorrupted signal level S, the measured corrupted signal level S divided by the noise level N would be given by:

$$R_M = \frac{S+N}{N} = \frac{S_M}{N} \tag{107}$$

from which the signal-to-noise ratio SNR would be given by:

$$SNR = \frac{S}{N} = R_M - 1 \tag{108}$$

A requirement that the single-to-noise ratio SNR exceeds the corresponding SNR threshold $SNR_{MIN}$ is equivalent to:

$$S_M > N \cdot (SNR_{MIN} + 1) \tag{109}$$

Accordingly, if the measured value of the noisy signal $S_M$—that provides a measure of the signal level S plus the noise level N—exceeds the threshold value from equation (109), then step (1323) repeats with step (1322). Otherwise, the process continues with step (1324) for operation responsive to molecular scattering.

Alternatively, the noise level N could be determined during operation of any of the above LIDAR systems $24.1'$, $24.3'$, $24^{xxv}$ by making noise measurements in a different spectral region than that of the scattered light signal $30'$, which is possible because noise would have nearly equal contribution to each spectral region, whereas the scattered light signal $30'$ would be limited to a relatively narrow spectral region, thereby provided for using measurements from the sufficiently disparate spectral regions to provide for a measure of the associated single-to-noise ratio SNR.

In step (1324), the first laser $11^{A'}$ light source 11 is turned OFF and the second laser $11^{B'}$ light source 11 is turned ON, thereby commencing the second mode of operation. If operating a twenty-fifth aspect of the LIDAR system $24'$, $24''$, $24^{xxv}$, in addition to controlling the first $11^{A'}$ and second $11^{B'}$ lasers accordingly, the controller/data processor $53'$ positions the mirror 742 and the filter system 88 in synchronism with this action. Then, in step (1325), at least the velocity V of the atmosphere 20 is measured and the aerosol-to-molecular scattering ratio AMR is calculated from the ratio of measured aerosol counts A to measured molecular counts M for measurements with the associated LIDAR systems $24.1''$, $24.3''$, $24^{xxv}$ as described herein above in detail for other corresponding LIDAR systems 24. The temperature T and density $\rho$ may also be measured at step (1325) as described hereinabove. Then if in step (1326), the aerosol-to-molecular scattering ratio AMR is less than a threshold—indicating that there is not a sufficient amount of aerosols $20''$ present in the atmosphere 20 to make measurements of velocity V from scattering by aerosols $20''$, then the process repeats with step (1325). Otherwise, from step (1326), if measurements of temperature T or density $\rho$ are not required, then the process returns to operation response to aerosol scattering by returning to step (1321).

Alternative to commencing with step (1320'), if measurements of temperature T or density $\rho$ are required, then process 1320 of operating the sixth aspect of the atmospheric measurement system $10^{vi}$ would commence with step (1320") which commences with operation responsive to molecular scattering beginning with step (1324), after which, in step (1325), measurements of one or both of temperature T or density $\rho$ would be make either alone or together with measurements of velocity V, depending upon the particular need at that time.

The above-described dual operating mode would provide for increasing the lifetime of the overall LIDAR system $24.1'$, $24.1''$, $24.3'$, $24.3''$, $24^{xxv}$ by reducing the duty cycle of operation during either the first or second modes of operation, particularly for the second mode of operation when using the second wavelength 740, e.g. ultraviolet wavelength $740'$ of substantially monochromatic light $13^B$, while providing for measurements of at least velocity V from either completely clear air, devoid of aerosols while using the second wavelength 740—e.g. an ultraviolet wavelength $740'$,—or from air containing sufficient aerosol content to use the first wavelength 738—e.g. an infrared $738'$ or visible $738''$ wavelength.

Different LIDAR systems $24.1'$, $24.1''$, $24.3'$, $24.3''$ could operate using different detection technologies, for example, using a mix of direct detection as described hereinabove, for one of the pair of LIDAR systems $24.1'$, $24.1''$, $24.3'$, $24.3''$, and heterodyne detection for the other of the pair of LIDAR systems $24.1'$, $24.1''$, $24.3'$, $24.3''$.

In an alternative embodiment of the LIDAR systems $24.1'$, $24.1''$, $24.3'$, $24.3''$ illustrated in FIG. 130, both the first $24.1'$, $24.3'$ and second $24.1''$, $24.3''$ LIDAR systems of each pair could be operated at the second wavelength 740—e.g. an ultraviolet wavelength $740'$—so as to provide for both redundant measurements of either aerosol $20''$ or molecular $20'$ scattering, but without the benefit of enhance lifetime and reduced duty cycle resulting from operation-where-possible at the first wavelength 738—e.g. an infrared $738'$ or visible $738''$ wavelength.

The atmospheric measurement system 10 can be used for assessing or prospecting the suitability of land for wind farm development. The information provided by the map, model or database 62, including wind velocity $\overline{v}$, temperature $7'$, density $\rho$, or combinations thereof, can be used in conjunction with recording equipment to determine statistics, such as average and standard deviation of associated measurement, over periods of time ranging from seconds to years. These statistics, together with derived measures, such as gusts and turbulent intensity, can be used to guide decision making processes for the size, type, and placement of wind turbines relative to the terrain and to each other, and to provide for estimating the expected energy output of the completed wind farm. Referring to FIG. 133, there is illustrated a seventh aspect of an atmospheric measurement system $10^{vii}$ comprising an associated LIDAR system 24 and located so as to provide for assessing a particular site for the suitability of producing power from the wind thereat. For purposes of comparison, there are also illustrated several meteorological towers 752, also referred to as MET towers 752, that the atmospheric measurement system $10^{vii}$ would replace or supplement, wherein the MET towers 752 provide for supporting one or more associated cup anemometers 754, weather vanes 756 or sonic anemometers 758 that provide for making associated localized measurements of wind speed and direction. The atmospheric measurement system 10 can be used to provide data over relatively larger volumes at relatively higher spatial resolution than is practical using MET towers 752 alone. For example, referring to FIG. 133, the LIDAR system 24 is adapted to scan a volume over both a range of azimuth 634 and elevation 636 angles, sweeping out a conical volume either by step-and-stare or continuous scanning over a range that may extend from hundreds of meters to many kilometers. For example, three separate measurements of wind speed $v_1$, $v_2$, $v_3$ can be measured with a common beam of light 28 at a corresponding three separate times and at a corresponding three separate angles, each separated by an angle $\theta$ from one another, so as to provide for determining a corresponding vector wind velocity $\overline{v}$. In another embodiment, at least three measurements of wind speed $v_1$, $v_2$, $v_3$ are measured simultaneously, so as to provide for determining a corresponding instantaneous measurement of vector wind velocity $\overline{v}$. Furthermore, the atmospheric measurement system $10^{vii}$ provides for acquiring the associated atmospheric data 36 without requiring a MET tower 752 that might otherwise perturb the associated wind field $16'$.

The resulting measurements of wind velocity $\overline{v}$, atmospheric density $\rho$, and atmospheric temperature T, can be used as inputs into various software program products, for example numerical weather prediction models, such as the Weather Research and Forecasting (WRF) model, MM5; equivalent physics-based models; computational fluid dynamics (CFD) models, such as AcuSim, WindSim, or Fluent; or wind turbine site assessment software, so as to provide for site assessment, turbine placement, turbine power curve validation, or wind farm forecasting applications. Turbulence and shear, caused by complex terrain, atmospheric conditions, or turbine wake effects, can also be measured more accurately using data from the map, model or database 62 gathered by one or more LIDAR systems 24 of one or more associated atmospheric measurement systems $10^{vii}$.

For example, a common tool for assessing the suitability of a site is the Wind Atlas Analysis and Application Program (WAsP). Long term time series of wind speed and direction are input into WAsP as a tab delimited file. Once input into WAsP, the wind data are converted into a Weibull fit and extended to the geostrophic wind layer. Using the additional inputs of topography and surface roughness, WAsP ultimately produces a Wind Resource Grid (WRG) file. The WRG is a text file containing the coordinates, height above ground level, estimated overall wind climate, and estimated power density or power production at each of a number of locations in a resource grid. Garrad Hassan's WindFarmer makes use of the frequency characteristics of the original data rather than relying on Weibull representations using a process known as "association." WindFarmer also includes modeling of the wake effects from turbines. Using either WAsP alone or an expanded model, such as WindFarmer, the result is a prediction of energy output from the potential wind farm site.

If adapted to utilize data from a map, model or database 62 based upon measurements from one or more LIDAR systems 24 of one or more associated atmospheric measurement systems $10^{vii}$, program products such as WAsP and WindFarmer, or other commercially available wind site assessment or wind farm design program products, could likely benefit from the relatively richer set of data that is possible to acquire using the one or more LIDAR systems 24 of one or more associated atmospheric measurement systems $10^{vii}$ so as to provide for improved results.

The map, model or database 62 can also be used in conjunction with mesoscale meteorological models, such as MM5, to model the associated wind field 16'. The substantial amount of data available from the atmospheric measurement system $10^{vii}$ can provide for improving the associated wind field model and as a result, provide for more accurately predicting the corresponding amount of energy that would be generated by each wind turbine 14.

The 3-D volumetric nature of the data produced by the atmospheric measurement system $10^{vii}$ can also be used in conjunction with computational fluid dynamics (CFD) software to improve the measurement of key wind turbine design parameters, for example, hub-height wind speed and turbulent intensity, so as to provide for a relatively more accurate assessment of the suitability of a particular wind turbine site, and so as to provide the information needed to design the wind farm 12 and the associated wind turbines 14 therein.

As described more fully hereinabove, the power available from the wind 16 is dependent upon both the associated velocity $\bar{v}$ and density $\rho$ thereof. As measurements of air pressure are not typically made on site, air density $\rho$ is typically calculated from temperature and elevation. Accordingly, many wind turbine site assessment models allow for input of elevation in addition to either temperature T or air density $\rho$. Temperature T varies nearly linearly with elevation above sea level over typical wind farm elevations. To convert between air temperature T and air density $\rho$, assumptions are normally made with respect to the profiles of each parameter throughout the atmosphere 20. For example, it may be assumed that air density $\rho$ decreases exponentially with elevation, implying an isothermal temperature profile.

However, the atmospheric measurement system $10^{vii}$ would provides for directly measuring air density $\rho$, thereby eliminating any need to calculate air density $\rho$ indirectly from temperature T and elevation. The atmospheric measurement system $10^{vii}$ provides for measuring density $\rho$ at a relatively high spatial resolution so as to enable calculating the power that could or should be generated by each turbine or potential turbine, either as part of a wind turbine site assessment, for example, as illustrated in FIG. 133; or for validation of the power generated by a wind turbine 14, for example, as illustrated in FIGS. 135 and 136. The relatively high spatial resolution of the air density $\rho$ measurements that are possible with the atmospheric measurement system $10^{vii}$ provide for more accurately determining the wind power that is available at a particular site or that is driving a particular wind turbine 14.

Referring to FIG. 134, in accordance with one embodiment of a wind turbine site assessment process 1340, commencing with step (1341), the wind velocity $\bar{v}$ and associated air density $\rho$ are directly measured in the atmosphere 20 at a plurality of measurement volumes 52 therein using one or more beams of light 28 projected into the atmosphere 20 from one or more LIDAR systems 24 of one or more associated atmospheric measurement systems $10^{vii}$ responsive to the resulting scattered light 30 received from the associated measurement volumes 52 within one or more associated interaction regions 17 along associated one or more beams of light 28 by the associated one or more LIDAR systems 24. For example, one or more associated beams of light 28 may be scanned over a range of azimuth 634 or elevation 636 angles, or a combination thereof; a plurality of simultaneously-generated beams of light 28, each oriented in a different direction, may be either fixed or scanned, or a combination thereof may be used. The one or more LIDAR systems 24 may be constructed and operated in accordance with any of the above-described embodiments. Atmospheric data 36, including at least velocity V and density $\rho$ is gathered by the one or more LIDAR systems 24 for the plurality of associated interaction regions 17 and measurement volumes 52 therein. Then, in step (1342), one or more average measures of or responsive to wind power flux density $\bar{\psi}$ are calculated at prospective wind turbine 14 locations, and in step (1343), the wind power P* that would be available for power generation is calculated, for example, using equations (1)-(3), and in step (1344) the corresponding associated electrical energy generating potential of a prospective one or more wind turbine(s) 14 is calculated at the prospective wind turbine 14 locations. Two or more of steps (1342)-(1344) could be combined and carried out in one or more of the above-described numerical weather prediction, wind turbine site assessment, or computational fluid dynamics (CFD) software program products, which could use the associated atmospheric data 36 directly, thereby providing for bypassing step (1342). The results of step (1344) provide for specifying in step (1345) the wind turbines 14 and associated locations thereof on the site being assessed.

Referring to FIGS. 135 and 136, first and second embodiments of the seventh aspect of an atmospheric measurement systems $10^{vii}$ are each illustrated in cooperation with a wind turbine 14 for use in validating the electrical power output of the wind turbine 14 in relation to the corresponding wind power P* to which the wind turbine 14 is exposed. The second embodiment of the seventh aspect of an atmospheric measurement systems $10^{vii}$ illustrated in FIG. 136 explicitly illustrates the used of a plurality of four simulataneously generated beams of light 28.1, 28.2, 28.3, 28.4—each oriented in a different direction—that provide for simultaneously sampling the atmosphere 20 at one or more measurement volumes 52 within each of one or more interaction regions 17.1, 17.2, 17.3, 17.4 along each of the corresponding beams of light 28.1, 28.2, 28.3, 28.4, for example, so as to provide for determining a corresponding instantaneous wind velocity $\bar{v}$ for each associated sample of the atmospheric data 36 from each of the one or more measurement volumes 52 within each of one or more interaction regions 17.1, 17.2, 17.3, 17.4. The set of the simulataneously generated beams of light 28.1, 28.2, 28.3, 28.4 may be scanned in azimuth and elevation over time so as to provide for increasing the extent over which the atmospheric data 36 is acquired.

Referring to FIG. 137, steps (1371) through (1375) of one embodiment of a wind turbine power validation process 1370 correspond to steps (1341) through (1344) of the above-described wind turbine site assessment process 1340 and provide for calculating the electrical energy generating potential of the one or more wind turbine(s) 14 being validated, wherein the corresponding atmospheric data 136 measured in step (1371) in a region of the atmosphere 20 upstream of the one or more wind turbine(s) 14 so as to provide for estimating in step (1373) the corresponding wind power P* to which the one or more wind turbines 14 are exposed. Simultaneous with step (1371), in step (1372) the actual power generated by the one or more wind turbine(s) 14 is measured, and then step (1376) provides for calculating the actual amount of electrical energy generated by the one or more wind turbine(s) 14, which in step (1377) is compared with the estimate from step (1375) of the corresponding energy generating potential determined from measurements of the associated wind field 16' so as to provide for validating the one or more wind turbine(s) 14 and the associated power curve(s) thereof that characterize the performance thereof. The results of the validation are then output in step (1378).

Referring to FIG. 138, the atmospheric measurement systems 10$^{vii}$ may also be used to characterize the wake flow behind a wind turbine 14, for example, by measuring the corresponding wind field 16' downstream thereof from measurements of the vector wind velocity $\bar{v}$ at a plurality of locations downstream of the wind turbine 14 and at a plurality of time, for example, with sufficient spatial and temporal resolution so as to provide for characterizing the resulting turbulent eddies 59 caused by the operation of the wind turbine 14.

The LIDAR systems 24', 24$^i$, 24$^{i'}$, 24$^{ii}$, 24$^{iii}$, 24$^{iv}$, 24$^v$, 24$^{vi}$, 24$^{vii}$, 24$^{viii}$, 24$^{viii'}$, 24$^{viii''}$, 24$^{viii.a}$, 24$^{viii.b}$, 24$^{viii.c}$, 24'', 24$^{ix}$, 24$^{ix'}$, 24$^{ix''}$, 24$^{ix'''}$, 24$^{ix''''}$, 24$^x$, 24$^{xi}$, 24$^{xii}$, 24$^{xiii}$, 24''', 24$^{xiv}$, 24$^{xv}$, 24$^{xv'}$, 24$^{xvi}$, 24$^{xvi'}$, 24$^{xvii}$, 24$^{xviii}$, 24$^{xix}$, 24$^{xx}$, 24$^{xxi'}$, 24$^{xxi''}$, 24$^{xxii'}$, 24$^{xxiii}$, 24$^{xxiv}$ can be adapted as LIDAR systems 24 or a LIDAR system 24 to measure air data products on a variety of platforms, for example, including, but not limited to, satellites 406, aircraft 400, UAVs 402, glide weapon systems, ground-based platforms (stationary or mobile), and watercraft. The LIDAR systems 24 can be adapted to measure air data products of a variety of atmospheres 20, for example, that of the Earth or other planetary or celestial bodies, or can be adapted to measure or map air data products of fields within a wind tunnel or surrounding an aerodynamic body during the operation thereof. Furthermore, although one embodiment uses ultraviolet (UV) laser light, the LIDAR system 24 can operate over a large range of wavelengths spanning from the visible down to the ultraviolet. The ultraviolet light provides additional stealth characteristics for the system because the light is quickly absorbed by the atmosphere 20, and is not otherwise easily detected from relatively long-range distances. However, the LIDAR system 24 can also operate in other wavelength regions, such as longer ultraviolet wavelengths or even visible wavelengths. For example, a variety of lasers 11' can be used, including, but not limited to: Ruby (694 nm); Neodymium-based lasers: Nd:YAG, Nd: Glass (1.062 microns, 1.054 microns), Nd:Cr: GSGG, Nd:YLF (1.047 and 1.053 microns), Nd:YVO (orthovanadate, 1.064 microns); Erbium-based lasers: Er:YAG and Er:Glass; Ytterbium-based lasers: Yb:YAG (1.03 microns); Holmium-based lasers: Ho:YAG (2.1 microns); Thulium-based lasers: Tm:YAG (2.0 microns); and tunable lasers: Alexandrite (700-820 nm), Ti:Sapphire (650-1100 nm), and Cr:LiSAF. The associated laser 11' can be either pulsed—at any Pulse Repetition Frequency (PRF)—or continuous wave (CW).

Any of the LIDAR systems 24', 24$^i$, 24$^{i'}$, 24$^{ii}$, 24$^{iii}$, 24$^{iv}$, 24$^v$, 24$^{vi}$, 24$^{vii}$, 24$^{viii}$, 24$^{viii'}$, 24$^{viii''}$, 24$^{viii'''}$, 24$^{viii.a}$, 24$^{viii.b}$, 24$^{viii.c}$, 24'', 24$^{ix}$, 24$^{ix'}$, 24$^{ix''}$, 24$^{ix'''}$, 24$^{ix''''}$, 24$^x$, 24$^{xi}$, 24$^{xii}$, 24$^{xiii}$, 24''', 24$^{xiv}$, 24$^{xv}$, 24$^{xv'}$, 24$^{xvi}$, 24$^{xvi'}$, 24$^{xvii}$, 24$^{xviii}$, 24$^{xix}$, 24$^{xx}$, 24$^{xxi'}$, 24$^{xxi''}$, 24$^{xxii'}$, 24$^{xxii''}$, 24$^{xxiii'''}$, 24$^{xxiv}$ in accordance with any of the above-described aspects can be used as a LIDAR system 24 for any optical remote sensing scenario to provide atmospheric data 36. For example, the LIDAR system 24 could be applied to the detection of Clear Air Turbulence, Optical Air Data systems, Atmospheric Aerosol Characterization, Smog detection and Chemical/Biological Agent detection. The LIDAR system 24 can be used to provide air data for Field Artillery Fire Direction Control, Small Arms Wind correction, Airport Turbulence Monitoring and Ship Navigation velocity/weather monitoring. The LIDAR system 24 can also be used to provide air data for predicting winds for any sporting events in which micro-scale airflow plays a significant role such as golf, football, baseball, etc. This LIDAR system 24 can also be used to provide air data for Wind Farm Site Prospecting, Assessment, and Optimization, Wind Farm Monitoring, Wake Effects Measurement and Analysis, Wind Turbine Control and Weather Forecasting for Wind Farms and Grid Management.

For example, in application to artillery, the LIDAR system 24 can be mounted on a vehicle or carried by an operator to a location from which artillery is to be fired. The LIDAR system 24 would then measure atmospheric parameters such as wind speed, wind direction, temperature, density, and pressure in the atmospheric volume through which the projectile will be fired. These are the standard inputs to contemporary fire direction control systems in use by the military, for example, as described in FM 6-40/MCWP 3-16.4 Tactics, Techniques, and Procedures for FIELD ARTILLERY MANUAL CANNON GUNNERY (Field Manual), which is incorporated herein by reference. By accounting for these atmospheric parameters along the projectile's flight path, the circular error probable (CEP) can be reduced and accuracy improved.

As another example, in application to sailing ships, the LIDAR system 24 can be used to provide measures of wind speed, wind direction, temperature, density, pressure, or the associated wind field around the ship, for ships that obtain their propulsion from the wind. For example, racing yachts such as used in the America's Cup, can benefit from knowing the winds near their ship as well as the winds near their competition. This information can be used to provide for trimming sails, deploying wings or aerodynamic propulsion devices, or planning trajectories so as to take maximum advantage of the current wind conditions. Recreational users can similarly use information about the winds blowing in the region near their craft.

As yet another example, in application to sporting events, the LIDAR system 24 can provide information about the local winds so as to enable participants to adapt accordingly. For example, a golf player can compensate for or take advantage of local winds, given information about how the wind is blowing over the entire flight path of the ball, or if a wind gust was approaching or would soon dissipate, so as to enable the golfer to either adjust their shot according, or to wait for better conditions. Even if the wind information is not available to the individual players, it would be of benefit to broadcasters in showing the viewing audience a graphic of the winds, a trajectory of the ball, and how the winds affected a particular shot. The LIDAR system 24 can also be of benefit in other sporting venues, such as baseball or football, for example, so as to enable broadcasters to illustrate how a baseball might have been held up by the winds in the stadium, or to show how winds had impacted a pass, punt or field goal in football, to as to enhance the viewing experience for fans. Given information about the winds in the stadium, players could adjust their actions accordingly, for example, when hitting a fly ball or kicking a field goal.

As yet another example, in application to the control of wind-induced building sway, the LIDAR system 24 can provide advance information about the wind field of a building so as to provide for wind-responsive or wind-anticipative control of tall buildings that are otherwise subject to sway in strong winds. Most modern tall buildings incorporate some form of damping to control how much the building sways in strong winds. The LIDAR system 24 can provide a predictive component (feed forward) to the associated control loops, so as to provide for improving the performance of these damping systems.

As yet another example, in application to road safety, the LIDAR system 24 can be used to monitor the wind fields that affect bridges, so as either to provide for an active control of the bridge structure responsive thereto, or to provide for controlling or limiting traffic over the bridge. Similarly, the LIDAR system 24 can be used to monitor wind conditions along roads in zones where high winds regularly pose a danger to travelers, and provide a real-time alert to motorists who are about to enter these zones. The LIDAR system 24 can be used to detect the presence of fog in fog-prone road zones, and to alert motorists of the presence of fog in advance of entering these zones.

As yet another example, in application to the control and/or dispersal of air pollution, the LIDAR system 24 can be used in a portable wind measuring system so as to enable responsible parties to more accurately predict where airborne pollution is headed as well as assisting in the assessment how much the pollution is being dispersed or diluted. Local wind mapping along with temperature and pressure measurements would provide input to models for prediction of the Nominal Hazard Zone even when there are no visible aerosols to define the plume.

As yet another example, the LIDAR system 24 can be used in a wind tunnel to provide for range resolved airflow measurements within the wind tunnel that can provide density and temperature as well as velocity of the air flow within the wind tunnel at a point, along a line, or within a volume of the wind tunnel, without perturbing the associated flow field, wherein the wind tunnel is used to measure how airflow interacts with the objects being tested therein.

As yet another example, the LIDAR system 24 can be used at an airport to enhance airport safety, for example, by providing for detecting clear air turbulence resulting from large aircraft taking off or landing, and to also provide measures of air temperature and density that can affect the lift, and hence performance, of aircraft operating at that airport.

As yet another example, the LIDAR system 24 can be used to enhance aircraft safety, for example, by providing for mapping the winds in the vicinity of an aircraft and thus providing the pilot with information that is difficult at best to obtain with other means. For example, in a roto-craft, the LIDAR system 24 can provide wind information outside of the rotor down wash so as to aid the pilot in maintaining hover in gusty wind conditions. In a conventional fixed-wing aircraft, the LIDAR system 24 can provide a measure of cross winds during landing or takeoff, and can be used to detect clear air turbulence during flight. In a sail-plane aircraft, the LIDAR system 24 can provide a measure of the wind field within which the aircraft is operating, and can provide assistance in locating updrafts in order to stay aloft. The LIDAR system 24 provides for measuring wind speed, air temperature and air density, which, for example, for purposes of landing, might not be otherwise be available at some airfields.

As yet another example, a LIDAR system 24 can be used support airdrops, for example, by either monitoring the wind field below from the aircraft making the drop so as to determine when to drop the payload, or by monitoring the wind field aloft with a LIDAR system 24 mounted on the payload so as to provide for adjusting the associated parachute during descent so as to provide for controlling the resulting drop location so that the payload is deposited closer to the desired drop zone than might otherwise be possible. Alternatively, the wind field could be monitored from above by an associated aircraft, and the resulting measurements could then be communicated to the payload to provide for controlling one or more associated parachutes or drag chutes accordingly so as to control the resulting drop location.

As yet another example, a LIDAR system 24 can be used to characterize the atmosphere 20. A LIDAR system 24 can be used to provide range resolved measures of velocity temperature, and density of the atmosphere 20 that can be used by meteorologists and/or by atmospheric scientists, for example, so as to provide for predicting or analyzing the weather.

As yet another example, a LIDAR system 24 can be used on ocean and lake buoys and other ocean platforms, for example, site assessment and optimization for off-shore wind farms, oil drilling and production platforms, so as to provide range resolved measures of wind speed and direction, for example, to provide for landing helicopters, to control the location of the platform on the ocean, or to provide a warning for general platform operations in advance of the occurrence of high winds or wind gusts.

The LIDAR system 24 is not limited to the detection of flow within or of the atmosphere 20. Generally, the LIDAR system 24 can be used to detect any object from which the beam of light 28 would scatter, or to detect the flow of any medium through which the associated beam of light 28 will propagate and from which the beam of light 28 will scatter. For example, depending upon the wavelength of the light source 11, the LIDAR system 24 could be used to detect the flow of other gases; or liquids, for example, water or liquid chemicals or solutions.

It should be understood that the LIDAR systems 24 can be used with any fluid medium that provides for generating detectable scattered light 30 when illuminated with a beam of light 28, including, but not limited to, non-atmospheric gases flowing in a pipe and liquids flowing in pipes, channels or sprays. For example, the LIDAR systems 24 could also be used to measure water flow in pipes or channels, or to provide for measuring the speed of a marine vehicle or the associated conditions of the water upon which or within which the marine vehicle operates.

Furthermore, although the LIDAR systems 24 described herein have been illustrated with associated geometries that provide for detecting backscattered scattered light 30, it should be understood that a LIDAR system 24 could also or alternatively incorporate an associated geometry that provides for detecting either transversely scattered light 30, or forward scattered light 30. Yet further, although the range-imaging LIDAR systems 24', 24$^i$-24$^{viii}$, 24$^{xxiii}$-24$^{xxiv}$ described herein have been illustrated as providing for range-responsive measurements responsive to a range R along the optic axis 23 of the receive optics 32, for example, a range R to the receive optics 32 or the detection system 34, the range-responsive measurements could also be characterized with respect to a range measured along the optic axis 25 of the beam of light 28, or any other axis, by geometric transformation.

The aforementioned U.S. patent application Ser. No. 11/460,603 filed on 27 Jul. 2006 that issued as U.S. Pat. No. 7,495,774 on 24 Feb. 2009, entitled Optical Air Data System illustrates additional embodiments of LIDAR systems 24 and associated platforms that may be incorporated in the atmospheric measurement system 10.

While specific embodiments have been described in detail in the foregoing detailed description and illustrated in the accompanying drawings, those with ordinary skill in the art will appreciate that various modifications and alternatives to those details could be developed in light of the overall teachings of the disclosure. It should be understood, that any reference herein to the term "or" is intended to mean an "inclusive or" or what is also known as a "logical OR", wherein the expression "A or B" is true if either A or B is true, or if both A and B are true. Furthermore, it should also be understood that unless indicated otherwise or unless physically impossible, that the above-described embodiments and aspects can be used in combination with one another and are not mutually exclusive. Accordingly, the particular arrangements disclosed are meant to be illustrative only and not limiting as to the scope of the invention, which is to be given the full breadth of the appended claims, and any and all equivalents thereof.

What is claimed is:

1. A method of remotely sensing an atmosphere, comprising:
   a. projecting one of a first beam of first light and a second beam of second light into an atmosphere at a first point in time so as to become scattered by said atmosphere, wherein said first light comprises a first wavelength configured for scattering from at least one of molecules and aerosols of said atmosphere, said second light comprises a second wavelength configured for scattering from said aerosols of said atmosphere, and a distribution of wavelengths of said one of said scattered first light and said scattered second light is responsive to at least one physical property of said atmosphere;
   b. receiving one of said scattered first light and said scattered second light scattered from said atmosphere;
   c. generating at least one first interference pattern responsive to said one of said scattered first light and said scattered second light based on said distribution of wavelengths of said one of said scattered first light and said scattered second light;
   d. detecting said at least one physical property of said atmosphere from said at least one first interference pattern;
   e. detecting at least one of a measure of signal-to-noise ratio and a measure of an aerosol-to-molecular ratio from said at least one first interference pattern based on a ratio of an amount of said scattered first light by said aerosols in said atmosphere to an amount of said scattered first light scattered by said molecules in said atmosphere;
   f. selecting one of said first beam of first light and said second beam of second light to be projected into said atmosphere at a second point in time after said first point in time, wherein the selecting said one of said first beam of first light and said second beam of second light to be projected at said second point in time is responsive to said at least one of said measure of signal-to-noise ratio and said measure of said aerosol-to-molecular ratio responsive to said first beam of first light; and
   g. projecting the selected one of said first and second beams.

2. A method of remotely sensing an atmosphere as recited in claim 1, wherein said at least one physical property comprises at least one of a measure responsive to a velocity of said atmosphere, a measure responsive to a temperature of said atmosphere and a measure responsive to a density of said atmosphere.

3. A method of remotely sensing an atmosphere as recited in claim 1, wherein when projected into said atmosphere said first beam of first light and said second beam of second light are each projected through a common set of source optics, further comprising selecting said one of said first beam of first light and said second beam of second light by positioning a mirror that provides for reflecting at least one of said first beam of first light and said second beam of second light from a corresponding source to said common set of source optics.

4. A method of remotely sensing an atmosphere as recited in claim 3, wherein the operation of positioning said mirror comprises:
   a. moving said mirror to a first position and reflecting with a first surface of said mirror when projecting said first beam of first light; and
   b. moving said mirror to a second position and reflecting with a second surface of said mirror when projecting said second beam of first light.

5. A method of remotely sensing an atmosphere as recited in claim 1, further comprising optically bandpass filtering said one of said scattered first light and said scattered second light prior to the operation of generating said at least one first interference pattern, wherein the operation of optically bandpass filtering comprises passing a range of wavelengths of said one of said scattered first light and said scattered second light spanning a wavelength of corresponding said first light or second light.

6. A method of remotely sensing an atmosphere as recited in claim 1, further comprising simultaneously generating a second interference pattern responsive to said one of said first light and said second light, wherein said at least one first interference pattern and said second interference pattern are generated by a common interferometer, and the operation of detecting said at least one physical property of said atmosphere is further responsive to said second interference pattern.

7. An atmospheric measurement system, comprising:
   a. a first light source, wherein said first light source provides for generating a first beam of first light, and said first light comprises a first wavelength that provides for scattering said first light from at least one of molecules and aerosols of an atmosphere;
   b. a second light source, wherein said second light source provides for generating a second beam of second light, said second light comprises a second wavelength that provides for scattering said first light substantially only from said aerosols of said atmosphere;
   c. at least one set of source optics in cooperation with said first and second light sources, wherein said at least one set of source optics provides for projecting at least one of said first beam of first light and said second beam of second light into said atmosphere so as to provide for one of said first light and said second light to become scattered by said atmosphere as a corresponding one of scattered first light and scattered second light, and a distribution of wavelengths of said one of said scattered first light and said scattered second light is responsive to at least one physical property of said atmosphere;

d. at least one light receiving system configured to receive either said scattered first light or said scattered second light from said atmosphere and for generating a corresponding at least one first interference pattern in response thereto;

e. at least one detection system, wherein said at least one detection system provides for detecting said at least one first interference pattern;

f. at least one processor, wherein said at least one processor in cooperation with said at least one detection system provides for detecting said at least one physical property of said atmosphere from said at least one first interference pattern, said at least one processor in cooperation with said at least one detection system provides for detecting at least one of a measure of signal-to-noise ratio and a measure of an aerosol-to-molecular ratio from said at least one first interference pattern, said aerosol-to-molecular ratio is responsive to a ratio of an amount of said scattered first light by said aerosols in said atmosphere to an amount of said scattered first light scattered by said molecules in said atmosphere, said at least one processor provides for selecting one of said first beam of first light and said second beam of second light to be projected into said atmosphere, and the operation of selecting said one of said first beam of first light and said second beam of second light to be projected into said atmosphere is responsive to said at least one of said measure of signal-to-noise ratio and said measure of said aerosol-to-molecular ratio responsive to said first beam of first light.

8. An atmospheric measurement system as recited in claim 7, wherein said at least one physical property comprises at least one of a measure responsive to a velocity of said atmosphere, a measure responsive to a temperature of said atmosphere and a measure responsive to a density of said atmosphere.

9. An atmospheric measurement system as recited in claim 7, said at least one processor provides for activating one of said first light source and said second light source responsive to said at least one of said measure of signal-to-noise ratio and said measure of said aerosol-to-molecular ratio responsive to said first beam of first light.

10. An atmospheric measurement system as recited in claim 7, further comprising:
a common set of source optics configured to cooperate with said first and second light sources;
a mirror that provides for said first and second light sources to cooperate with said common set of source optics; and
an actuator under control of said at least one processor that provides for positioning said mirror in one of two positions, wherein in a first position, said mirror provides for said first beam of first light from said first light source to be projected by said common set of source optics into said atmosphere, and in a second position, said mirror provides for said second beam of second light from said second light source to be projected by said common set of source optics into said atmosphere.

11. An atmospheric measurement system as recited in claim 7, further comprising at least one set of receive optics, wherein said at least one set of receive optics provide for receiving either said scattered first light or said scattered second light from said atmosphere prior to said at least one interferometer.

12. An atmospheric measurement system as recited in claim 7, further comprising first and second bandpass filters in cooperation with said at least one interferometer, wherein said first bandpass filter provides for passing said first wavelength in cooperation with said first light source, said second bandpass filter provides for passing said second wavelength in cooperation with said second light source.

13. An atmospheric measurement system as recited in claim 7, wherein said light receiving system includes at least one interferometer and said at least one interferometer comprises at least one Fabry-Perot interferometer.

14. An atmospheric measurement system as recited in claim 7, wherein said light receiving system includes at least one interferometer and said at least one interferometer comprises a spatial heterodyne spectrometer.

15. An atmospheric measurement system as recited in claim 7, wherein said light receiving system includes at least one interferometer and said at least one detection system comprises a direct detection system.

16. An atmospheric measurement system as recited in claim 7, wherein said at least one detection system comprises a heterodyne detection system.

17. A method of remotely sensing an atmosphere, comprising:

a. projecting one or more beams of substantially monochromatic light into an atmosphere over a first period of time from one or more locations, wherein each beam of said substantially monochromatic light of said one or more beams of said substantially monochromatic light is projected at one or more angles of azimuth and one or more angles of elevation, and said one or more angles of azimuth and said one or more angles of elevation are relative to a corresponding coordinate system centered about a corresponding location of said one or more locations;

b. for each said beam of said substantially monochromatic light of said one or more beams of said substantially monochromatic light:

receiving scattered light from one or more measurement volumes therein along said beam of substantially monochromatic light, wherein a distribution of wavelengths of said scattered light is responsive to at least one physical property of said atmosphere, and said at least one physical property of said atmosphere comprises at least one of a velocity of said atmosphere and a density of said atmosphere within said one or more measurement volumes therein;

generating at least one interference pattern responsive to said scattered light, wherein said at least one interference pattern is responsive to said distribution of wavelengths of said scattered light;

detecting said at least one physical property of said atmosphere within said one or more measurement volumes therein from said at least one interference pattern, wherein a total set of measurement volumes therein from which said scattered light is received, said at least one interference pattern is generated, and said at least one physical property is detected over said period of time is responsive to a total number of said one or more beams of substantially monochromatic light, a total number of said one or more angles of azimuth for each said beam, a total number of said one or more angles of elevation for each said beam, and a total number of said one or more measurement volumes therein along each said beam, and said total set of measurement volumes therein is sufficient to provide for determining at least one measure of wind power in said atmosphere at one or more measurement volumes therein;

c. selecting one or more of said beams of substantially monochromatic light to be projected into said atmosphere over a second period of time, wherein the selecting of said one or more of said beams of substantially monochromatic light to be projected over said second period of time is responsive to said detecting of at least one physical property of said atmosphere; and d. projecting the selected one or more of said beams of substantially monochromatic light.

18. A method of remotely sensing an atmosphere as recited in claim 17, further comprising scanning at least one beam of said one or more beams over at least one of a range of angles of azimuth and a range of angles of elevation within said period of time, wherein said at least one beam comprises a corresponding one or more interaction regions or measurement volumes therein, and the operations of receiving said scattered light, generating said at least one interference pattern, and detecting said at least one physical property of said atmosphere for each of said corresponding one or more measurement volumes therein of said at least one beam at a plurality of different times within said period of time.

19. A method of remotely sensing an atmosphere as recited in claim 18, wherein the operation of scanning said at least one beam comprises scanning an angular position of said at least one beam in at least one of azimuth and elevation while performing the operations of receiving said scattered light, generating said at least one interference pattern, and detecting said at least one physical property of said atmosphere for each of said corresponding one or more measurement volumes therein of said at least one beam.

20. A method of remotely sensing an atmosphere as recited in claim 19, wherein the operation of scanning said angular position includes one of stepping at each angular position and continuously sweeping through angular positions of said at least one beam.

21. A method of remotely sensing an atmosphere as recited in claim 17, wherein the operation of determining said at least one measure of wind power comprises:

determining at least one wind velocity vector of said atmosphere within one or more measurement volumes of said atmosphere within said period of time; and determining said at least one measure of wind power responsive to said at least one wind velocity vector and responsive to a measure of said density of said atmosphere within said one or more measurement volumes of said atmosphere within said period of time.

22. A method of remotely sensing an atmosphere as recited in claim 21, wherein the operation of determining said at least one wind velocity vector is responsive to said velocity of said atmosphere within said one or more interaction regions or measurement volumes therein from a plurality of at least three of said one or more beams, and each beam of said plurality of at least three of said one or more beams is oriented in a different direction.

23. A method of remotely sensing an atmosphere as recited in claim 22, wherein the operation of determining said at least one wind velocity vector is responsive to said velocity of said atmosphere within said one or more interaction regions or measurement volumes therein from at least one beam of said one or more beams, and said velocity of said atmosphere within said one or more interaction regions or measurement volumes therein is measured when said at least one beam is oriented in at least three different directions.

24. A method of remotely sensing an atmosphere as recited in claim 23, wherein said at least one beam is scanned over time, and said velocity of said atmosphere within said one or more interaction regions or measurement volumes therein is measured at a plurality of different times.

25. A method of remotely sensing an atmosphere as recited in claim 17, further comprising determining a suitability for power generation from wind within one or more regions of said atmosphere responsive to the operation of determining said at least one amount of or measure of wind power in said atmosphere at said one or more regions of said atmosphere.

26. A method of remotely sensing an atmosphere as recited in claim 17, further comprising determining a location of one or more wind turbines so as to provide for capturing wind power from wind within one or more regions of said atmosphere responsive to the operation of determining said at least one amount of or measure of wind power in said atmosphere at said one or more regions of said atmosphere.

27. A method of remotely sensing an atmosphere as recited in claim 17, further comprising comparing said at least one amount of or measure of wind power within one or more regions of said atmosphere with a corresponding measure of power actually generated by one or more wind turbines responsive to wind within said one or more measurement volumes of said atmosphere.

\* \* \* \* \*